US012583870B2

(12) United States Patent
Ma et al.

(10) Patent No.: US 12,583,870 B2
(45) **Date of Patent: *Mar. 24, 2026**

(54) AZAHETEROARYL COMPOUND AND APPLICATION THEREOF

(71) Applicant: SHANGHAI BLUERAY BIOPHARMA CO., LTD., Shanghai (CN)

(72) Inventors: Shichao Ma, Shanghai (CN); Zhongguo Zhang, Shanghai (CN); Song Zhang, Shanghai (CN); Wenjia Yuan, Shanghai (CN)

(73) Assignee: SHANGHAI BLUERAY BIOPHARMA CO., LTD., Shanghai (CN)

( * ) Notice: Subject to any disclaimer, the term of this patent is extended or adjusted under 35 U.S.C. 154(b) by 1059 days.

This patent is subject to a terminal disclaimer.

(21) Appl. No.: 17/637,010

(22) PCT Filed: Aug. 14, 2020

(86) PCT No.: PCT/CN2020/109232

§ 371 (c)(1),
(2) Date: Feb. 21, 2022

(87) PCT Pub. No.: WO2021/032004

PCT Pub. Date: Feb. 25, 2021

(65) Prior Publication Data

US 2023/0002414 A1 Jan. 5, 2023

(30) Foreign Application Priority Data

Aug. 22, 2019 (CN) ......................... 201910773333.0

(51) Int. Cl.
*C07D 519/00* (2006.01)
*C07D 471/04* (2006.01)
*C07D 487/04* (2006.01)

(52) U.S. Cl.
CPC ......... *C07D 519/00* (2013.01); *C07D 471/04* (2013.01); *C07D 487/04* (2013.01)

(58) Field of Classification Search
CPC .. A61K 2300/00; A61K 31/519; A61K 45/06; A61P 35/00; A61P 35/02; C07D 239/42; C07D 307/93; C07D 471/04; C07D 487/04; C07D 519/00
See application file for complete search history.

(56) References Cited

U.S. PATENT DOCUMENTS 11,013,745 B2 5/2021 Zhou et al.
11,207,325 B2 12/2021 Chan et al.
2007/0021443 A1 1/2007 Ohlmeyer et al.
2011/0237565 A1 9/2011 Borchardt et al.
2015/0218186 A1 8/2015 Burgdorf et al.
2019/0142837 A1 5/2019 Chan et al.
2024/0182492 A1* 6/2024 Ma ....................... C07D 213/79

FOREIGN PATENT DOCUMENTS

CN 102869666 A 1/2013
CN 107108637 A 8/2017
CN 110563722 A 12/2019
CN 110734436 A 1/2020
JP 2008534689 A 8/2008
JP 2013522222 A 6/2013
JP 2015529657 A 10/2015
JP 2018500342 A 1/2018
WO WO-2019062345 A1 4/2019
WO WO-2019062435 A1 * 4/2019 ........... A61K 31/519
WO WO-2019120276 A1 6/2019
WO WO-2019152419 A1 8/2019
WO WO-2019158019 A1 8/2019
WO WO-2019158025 A1 8/2019
WO WO-2020156479 A1 8/2020

OTHER PUBLICATIONS

Machine Translation of WO2019062435A1 (Year: 2019).*
Cecil Textbook of Medicine, 20th Ed., vol. 1 (Year: 1997).*
Wu et al., Small-molecule inhibitors, immune checkpoint inhibitors, and more: FDA-approved novel therapeutic drugs for solid tumors from 1991 to 2021; Journal of Hematology & Oncology, 15, 143 (Year: 2022).*
Mar. 31, 2023 Extended European Search Report issued in European Patent Application No. 20855529.2.
Mar. 22, 2023 First Office Action issued in Japanese Patent Application No. 2022-512467.
May 25, 2023 Second Office Action issued in Australian Patent Application No. 2020332462.
Jan. 25, 2023 First Office Action issued in Australian Patent Application No. 2020332462.

(Continued)

*Primary Examiner* — Jeffrey H Murray
*Assistant Examiner* — Daniel John Burkett
(74) *Attorney, Agent, or Firm* — Harness, Dickey & Pierce, P.L.C.

(57) ABSTRACT

Disclosed in the present disclosure are an azaheteroaryl compound, a pharmaceutically acceptable salt thereof, and a solvate thereof. The present disclosure also provides a method for preparing said compound, a composition containing said compound, and a use of said compound in the preparation of a drug for treating a disease or disorder related to the mechanism of action of an EED protein and/or a PRC2 protein complex. (Formula 1)

(I)

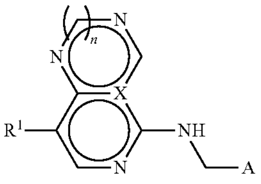

18 Claims, No Drawings

(56) References Cited

OTHER PUBLICATIONS

International Search Report dated Nov. 2, 2020 Issued in PCT application PCT/CN2020/109232.
Written Opinion of International Searching Authority dated Nov. 10, 2020 Issued in PCT application PCT/CN2020/109232.
The priority document of PCT/CN2020/109232.
RN 1314936-62-3, STN Registry, Aug. 4, 2011.
RN 1417360-98-5, STN Registry, Jan. 23, 2013.
RN 1951411-29-2, STN Registry, Jul. 13, 2016.
J. Chesterfield et al. "Pyrimidines. Part VIII. Halogeno- and Hydrazino-pyrimidines" Journal of the Chemical Society, Jan. 1, 1955.
Sep. 19, 2023 Written Opinion issued in Singaporean Patent Application No. 11202201686R.
Nov. 3, 2023 the First Office Action issued in Taiwanese Patent Application No. 109128326.
Dec. 8, 2023 Hearing Notice issued in Indian Patent Application No. 202217015315.
Aug. 2, 2022 1st OA issued in Indian counterpart application.
Jun. 13, 2024 the First Office Action issued in Korean Patent Application No. 10-2022-7009453.

* cited by examiner

AZAHETEROARYL COMPOUND AND APPLICATION THEREOF

CROSS-REFERENCE TO RELATED APPLICATIONS

The present application is a U.S. National Phase Application under 35 U.S.C. 371 of International Application No. PCT/CN2020/109232, filed on Aug. 14, 2020, which claims the benefit of Chinese patent application No. 201910773333.0, filed on Aug. 22, 2019. The entire disclosures of the above applications are incorporated herein by reference.

TECHNICAL FIELD

The present disclosure relates to a novel azaheteroaryl compound, a pharmaceutically acceptable salt, hydrate, prodrug, and stereoisomer thereof or a solvate thereof, and their isotopic labels. The present disclosure also provides a method for preparing said compound, a composition containing said compound, and the use as a drug for treating a disease related to the mechanism of action of an EED protein and/or a PRC2 protein complex.

BACKGROUND TECHNIQUE

PcG (Polycomb Group) protein is a class of important chromatin modifying enzymes. It regulates gene transcription by means of modifying chromatins and hence plays an important role in the growth, differentiation and long-term cell memory of stem cells. In mammalian cells, PcG proteins are mainly classified as two types of transcription inhibitory complexes: PRC1 (Polycomb Repressive Complex 1) and PRC2 (Polycomb Repressive Complex 2). Wherein, PRC2 inhibits the expression of related genes by means of methylated modification of the histone H3 on lysine 27 (H3K27) in the chromatin. The protein complex, PRC2, mainly consists of core proteins such as EZH2 (Enhancer of Zeste Homolog 2) (or a very similar homologous protein thereof, i.e., EZH1), EED (Embryonic ectoderm Development), and SUZ12 (Suppressor of Zeste 12). Wherein, EZH2 has an enzymatically catalytic activity and can transfer the methyl group of the substrate, SAM (S-adenosyl-L-methionine) to H3K27 via the SET (Su (var), E (Z), and Trithorax) protein domain, thereby achieving the mono-, di- and trimethylated modification of H3K27. The enzymatically catalytic activity of EZH2 also depends on other components of PRC2, such as the EED protein that belongs to the family of WD40 repeat domain proteins. The synergism of the EED and the trimethylated H3K27Me3 not only has strong allosteric potentiation effects on the enzymatically catalytic function of EZH2, but also can locate the PCR2 complex to the chromatin that needs to be modified. Dysfunction of PRC2, such as the over-expression or gain-of-function mutation of EZH2, is related to a variety of neoplastic diseases in clinic, including lung cancer, breast cancer, rectal cancer, prostate cancer, bladder cancer, pancreatic cancer, sarcoma, and lymphoma, etc. PRC2 also involves a variety of cellular immune functions, for example, EZH2 participates in the regulation of lymphocyte activation and, together with glycolysis, can collectively promote the response of T cells to tumor cells. Therefore, the research and development of small molecule inhibitors of PRC2 has important and broad drug development values.

The research and development concerning PRC2 inhibitors mainly focus on two strategies, EZH2 inhibitor development and EED inhibitor development. Currently, EZH2 inhibitors that have developed to the clinical stage comprise EPZ-6438 (Epizyme, clinical trial phase II study), GSK2816126 (GSK, clinical trial phase I study), CPI-1205 (Constellation, clinical trial phase I study), etc. Though many EZH2 inhibitors have developed to the clinical study phase, all these inhibitors contain one common pharmacophore of 2-pyridone. In addition, in clinical treatment with the existing EZH2 inhibitors, secondary mutations have begun to appear. EED inhibitors have allosteric inhibition effects on the enzymatic function of EZH2 and can achieve biological functions identical or similar to those of EZH2. Furthermore, not only are EED inhibitors well able to overcome the problem of drug resistance of EZH2, they can also be used in combination with EZH2 inhibitors to achieve better synergism. Therefore, the development of new EED inhibitors is of great significance.

CONTENT OF THE PRESENT INVENTION

The azaheteroaryl compound provided in the present disclosure is a brand new EED inhibitor, exhibits a very good inhibitory activity against tumor cells, and has broad prospects for drug development.

The present disclosure provides a compound as shown in formula (I), a pharmaceutically acceptable salt, hydrate, prodrug, and stereoisomer thereof, or a solvate thereof:

(I)

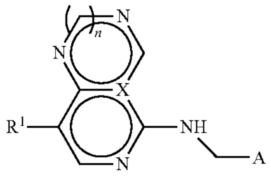

wherein

A is

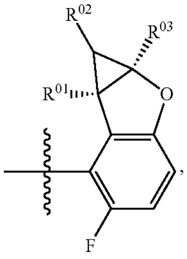
,
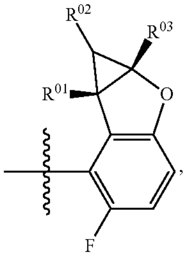
,
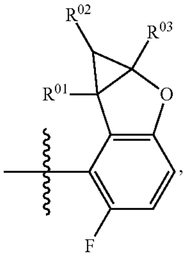
, or
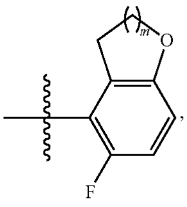
, $R^{01}$, $R^{02}$, and $R^{03}$ are each independently hydrogen or halogen (such as fluorine);

n is 0 or 1;

m is 1 or 2;

X is C or N;

$R^1$ is a bicyclic structure and is aromatic, and is preferably

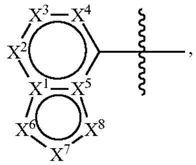
,
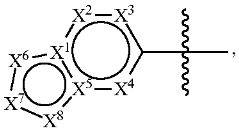
,
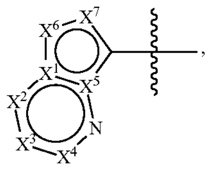
,
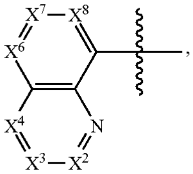
,
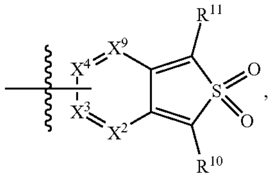
,
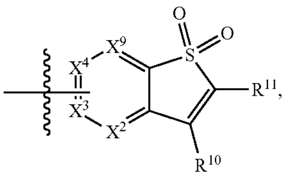
,
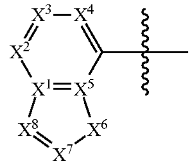
or
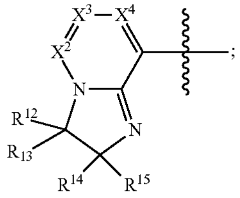
;

$X^1$ and $X^5$ are independently C or N;

$X^2$ is independently N or $CR^2$;

$X^3$ is independently N or $CR^3$;

$X^4$ is independently N or $CR^4$;

$X^6$ is independently $CR^6$, N, $NR^6$, O or S;

$X^7$ is independently $CR^7$, N, O or S;

$X^8$ is independently $CR^8$, N, O or S;

$X^9$ is independently N or $CR^9$;

$R^2$, $R^3$, $R^4$, $R^6$, $R^7$, $R^8$, $R^9$, $R^{10}$, $R^{11}$, $R^{12}$, $R^{13}$, $R^{14}$, and $R^{15}$ are independently H, halogen (such as fluorine, chlorine or bromine), —CN, $R^5$-substituted or unsubstituted amino, $R^5$-substituted or unsubstituted hydroxyl, $R^5$-substituted or unsubstituted $C_{1-4}$ alkyl (such as methyl), $R^5$-substituted or unsubstituted $C_{1-4}$ alkoxy, $R^5$-substituted or unsubstituted $C_{3-6}$ cycloalkyl (such as cyclopropyl), $R^5$-substituted or unsubstituted $C_{1-4}$ haloalkyl (such as trifluoromethyl), —(C═O)$R^{16}$, —$CO_2R^{16}$, —C(═O)$NR^{16}R^{17}$, —$SO_2R^{16}$, —$SO_2NR^{16}R^{17}$, —$POR^{16}R^{17}$, $R^5$-substituted or unsubstituted $C_{3-6}$ heterocycloalkyl, or $C_{3-6}$ heterospirocycloalkyl;

$R^5$ is independently $C_{1-4}$ alkoxy, —CN, $C_{1-4}$ alkoxy substituted with 1, 2 or 3 hydroxyl groups, $C_{1-4}$ alkyl (such as methyl), $C_{1-4}$ haloalkyl (such as trifluoromethyl), —$NR^{a1}R^{b1}$, halogen, hydroxyl, $C_{3-6}$ heterocycloalkyl, $C_{3-6}$ heterocycloalkyl, $C_{3-6}$ heterocycloalkyl substituted with 1, 2 or 3 $C_{1-4}$ alkyl groups, $C_{3-6}$ heterocycloalkyl substituted with 1, 2 or 3 $C_{3-6}$ heterocycloalkyl groups, $C_{6-18}$ aryl, $C_{1-5}$ heteroaryl, —C(═O)$NR^{16a}R^{17a}$, —$CO_2R^{16a}$, —O(C═O)$R^{16a}$, —NH(C═O)$R^{16a}$, or —(C═O)$R^{16a}$; $R^{a1}$ and $R^{b1}$ are independently H, $C_{1-4}$ alkyl, $C_{1-4}$ alkyl substituted with 1, 2 or 3 —$NR^{a2}R^{b2}$ groups, $C_{1-4}$ alkyl substituted with 1, 2 or 3 hydroxyl groups, or $C_{1-4}$ alkoxy substituted with 1, 2 or 3 hydroxyl groups; $R^{a2}$ and $R^{b2}$ are independently H or $C_{1-4}$ alkyl; each $R^{16a}$ and each $R^{17a}$ are independently H, $C_{1-4}$ alkyl, or $C_{3-6}$ heterocycloalkyl;

the number of $R^5$ is 1, 2, 3, 4, 5 or 6;

$R^{16}$ and $R^{17}$ are independently H, $C_{1-4}$ alkyl (such as methyl), $C_{1-4}$ haloalkyl (such as trifluoromethyl), or $C_{3-6}$ heterocycloalkyl;

the heteroatom in the $C_{3-6}$ heterocycloalkyl is selected from N, O and S, and the number of the heteroatom is 1, 2, 3 or 4; the heteroatom in the $C_{3-6}$ heterospirocycloalkyl is selected from N, O and S, and the number of the heteroatom is 1, 2, 3 or 4; the heteroatom in the $C_{1-15}$ heteroaryl is selected from N, O and S, and the number of the heteroatom is 1, 2, 3, 4, 5 or 6.

In certain embodiments, $R^2$, $R^3$, $R^4$, $R^7$, $R^8$, $R^9$, $R^{10}$, $R^{11}$, $R^{12}$, $R^{13}$, $R^{14}$, and $R^{15}$ are independently preferably H, halogen, —CN, —OH, —$NR^aR^b$, $C_{1-4}$ alkyl, $C_{1-4}$ alkyl substituted with 1, 2 or 3 $R^5$ groups, $C_{1-4}$ haloalkyl, $C_{1-4}$ haloalkyl substituted with 1, 2 or 3 $R^5$ groups, $C_{1-4}$ alkoxy, $C_{1-4}$ alkoxy substituted with 1, 2 or 3 $R^5$ groups, $C_{3-6}$ heterocycloalkyl, $C_{3-6}$ heterocycloalkyl substituted with 1, 2 or 3 $R^5$ groups, —(C═O)$R^{16}$, —$CO_2R^{16}$, —C(═O)$NR^{16}R^{17}$, —$SO_2R^{16}$, —$SO_2NR^{16}R^{17}$, —$POR^{16}R^{17}$, or $C_{3-6}$ heterospirocycloalkyl, wherein $R^a$ and $R^b$ are independently H or $C_{1-4}$ alkyl; $R^{16}$ and $R^{17}$ are independently H, $C_{1-4}$ alkyl, $C_{1-4}$ haloalkyl, or $C_{3-6}$ heterocycloalkyl;

each $R^5$ is independently —OH, —CN, $C_{1-4}$ alkyl, $C_{1-4}$ alkoxy, $C_{1-4}$ alkoxy substituted with 1, 2 or 3 hydroxyl groups, —$NR^{a1}R^{b1}$, $C_{3-6}$ heterocycloalkyl, $C_{3-6}$ heterocycloalkyl substituted with 1, 2 or 3 $C_{1-4}$ alkyl groups, $C_{3-6}$ heterocycloalkyl substituted with 1, 2 or 3 $C_3$-6 heterocycloalkyl groups, $C_{6-8}$ aryl, $C_{1-15}$ heteroaryl, —C(═O)$NR^{16a}R^{17a}$, —$CO_2R^{16a}$, —O(C═O)$R^{16a}$, —NH(C═O)$R^{16a}$, or —(C═O)$R^{16a}$; $R^{a1}$ and $R^{b1}$ are independently H, $C_{1-4}$ alkyl, $C_{1-4}$ alkyl substituted with 1, 2 or 3 —$NR^{a2}R^{b2}$ groups, or $C_{1-4}$ alkyl substituted with 1, 2 or 3 hydroxyl groups; $R^{a2}$ and $R^{b2}$ are independently H or $C_{1-4}$ alkyl; each $R^{16a}$ and $R^{17a}$ are independently H, $C_{1-4}$ alkyl, $C_{1-4}$ haloalkyl, or $C_{3-6}$ heterocycloalkyl;

the heteroatom in the $C_{3-6}$ heterocycloalkyl is selected from N, O and S, and the number of the heteroatom is 1, 2, 3 or 4; the heteroatom in the $C_{3-6}$ heterospirocycloalkyl is selected from N, O and S, and the number of the heteroatom is 1, 2, 3 or 4; the heteroatom in the $C_{1-15}$ heteroaryl is selected from N, O and S, and the number of the heteroatom is 1, 2, 3, 4, 5 or 6.

In certain embodiments, $R^2$ is preferably H, halogen, —CN, —$NR^aR^b$, $C_{1-4}$ alkyl, $C_{1-4}$ alkyl substituted with 1, 2 or 3 $R^5$ groups, $C_{1-4}$ haloalkyl, $C_{1-4}$ alkoxy, $C_{3-6}$ heterocycloalkyl, $C_{3-6}$ heterocycloalkyl substituted with 1, 2 or 3 $R^5$ groups, $C_{3-6}$ heterospirocycloalkyl, —$CO_2R^{16}$, —C(═O)$NR^{16}R^{17}$, or —$NR^aR^b$;

each $R^{16}$ and $R^{17}$ are independently H or $C_{1-4}$ alkyl;

$R^a$ and $R^b$ are independently H or $C_{1-4}$ alkyl;

each $R^5$ is independently —OH, $C_{1-4}$ alkyl, $C_{1-4}$ alkoxy, $C_{1-4}$ alkoxy substituted with 1, 2 or 3 hydroxyl groups, —$NR^{a1}R^{b1}$, $C_{3-6}$ heterocycloalkyl, $C_{3-6}$ heterocycloalkyl substituted with 1, 2 or 3 $C_{1-4}$ alkyl groups, $C_{3-6}$ heterocycloalkyl substituted with 1, 2 or 3 $C_{3-6}$ heterocycloalkyl groups, or $C_{1-5}$ heteroaryl; $R^{a1}$ and $R^{b1}$ are independently H, $C_{1-4}$ alkyl, $C_{1-4}$ alkyl substituted with 1, 2 or 3 —$NR^{a2}R^{b2}$ groups, or $C_{1-4}$ alkyl substituted with 1, 2 or 3 hydroxyl groups; $R^{a2}$ and $R^{b2}$ are independently H or $C_{1-4}$ alkyl;

the heteroatom in the $C_{3-6}$ heterocycloalkyl is selected from N, O and S, and the number of the heteroatom is 1, 2, 3 or 4; the heteroatom in the $C_{3-6}$ heterospirocycloalkyl is selected from N, O and S, and the number of the heteroatom is 1, 2, 3 or 4; the heteroatom in the $C_{1-15}$ heteroaryl is selected from N, O and S, and the number of the heteroatom is 1, 2, 3, 4, 5 or 6.

In certain embodiments, $R^2$ is further preferably H, —$CH_3$, —$CF_3$, —$OCH_3$,

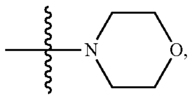 [SMILES: *N1CCOCC1]

—$N(CH_3)_2$,

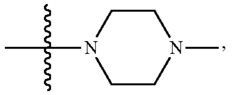

—$CH_2OCH_2C(CH_3)_2OH$, —$CH_2N(CH_3)_2$,

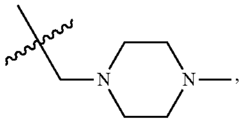 [SMILES: *CN1CCN(C)CC1]

—$CH_2NHCH_2C(CH_3)_2OH$,

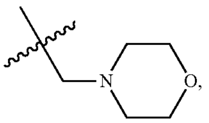
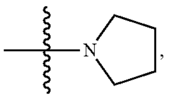
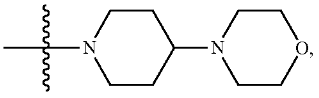
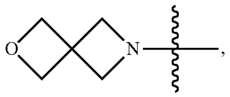

—$CH_2N(CH_3)CH_2CH_2N(CH_3)_2$,

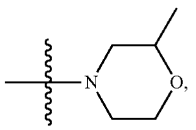
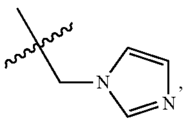

—$C(CH_3)_2OH$, —$CHF_2$, —$CO_2CH_3$, —$CH_2OH$, —$CON(CH_3)_2$, —$CH_2N(CH_3)_2$, —CN, or —Cl.

In certain embodiments, $R^3$ is preferably H, halogen, —CN, $C_{1-4}$ alkyl, $C_{1-4}$ alkoxy, $C_{1-4}$ haloalkyl, or —C(═O)$NR^{16}R^{17}$. $R^3$ is further preferably H, —$OCH_3$, —F, —CN, —Cl, —$CH_3$, —$CONH_2$, —$CF_3$, —$CONHCH_3$, or —$CON(CH_3)_2$.

In certain embodiments, $R^4$ is preferably H, halogen or $C_{1-4}$ alkyl; $R^4$ is further preferably H, —F or —$CH_3$.

In certain embodiments, $R^6$ is preferably H, halogen, —CN, $C_{1-4}$ alkyl, $C_{1-4}$ alkyl substituted with 1, 2 or 3 $R^5$ groups, —$CO_2R^{16}$, —C(═O)$NR^{16}R^{17}$, —(C═O)$R^{16}$, —$SO_2R^{16}$, or —$POR^{16}R^{17}$; each $R^{16}$ and each $R^{17}$ are independently H, $C_{1-4}$ alkyl, or $C_{3-6}$ heterocycloalkyl; each $R^5$ is independently —OH, —CN, —$NR^{a1}R^{b1}$, $C_{6-8}$ aryl, —C(═O)$NR^{16a}R^{17a}$, —$CO_2R^{16a}$, —O(C═O)$R^{16a}$, —NH(C═O)$R^{16a}$, or —(C═O)$R^{16a}$; $R^{a1}$ and $R^{b1}$ are independently H or $C_{1-4}$ alkyl; each $R^{16a}$ and $R^{17a}$ are independently H, $C_{1-4}$ alkyl or $C_{3-6}$ heterocycloalkyl.

In certain embodiments, $R^6$ is further preferably H, —$COOCH_2CH_3$, —COOH, —$CONH_2$, —$CH_3$, —$COCH_3$,

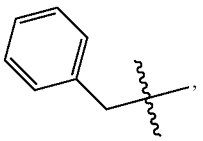 [SMILES: *Cc1ccccc1]

—$CH_2CH_3$, —F, —CN, —$CH(CH_3)_2$, —$CH_2CONH_2$, —$CH_2CH_2OH$, —$CH_2OH$, —$CH_2NH_2$, —$CH_2COOCH_3$, —$CH_2COOH$, —$CH_2CON(CH_3)_2$, —$CH_2CH_2OCOCH_3$, —$CH_2NHCOCH_3$, —$CON(CH_3)_2$, —CN,

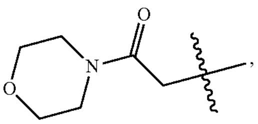
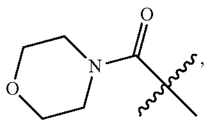

—$CONH_2$, —$CH_2CN$, —$SO_2Me$, or —$PO(CH_3)_2$.

In certain embodiments, $R^7$ is preferably H, —OH, —$NR^aR^b$, $C_{1-4}$ alkyl, $C_{1-4}$ alkyl substituted with 1, 2 or 3 hydroxyl groups, $C_{1-4}$ haloalkyl, —$CO_2R^{16}$, or —C(═O)$NR^{16}R^{17}$; $R^a$ and $R^b$ are independently H or $C_{1-4}$ alkyl; $R^{16}$ and $R^{17}$ are independently H, $C_{1-4}$ alkyl or $C_{1-4}$ haloalkyl. $R^7$ is further preferably H, —$NH(CH_3)$, —$N(CH_3)_2$, —$CH_3$, —$CF_3$, —OH, —$CH_2OH$, —$COOCH_2CH_3$, —COOH, —$CONH_2$, —$CON(CH_3)_2$, or —$NH_2$.

In certain embodiments, $R^8$ is preferably H or $C_{1-4}$ alkyl. $R^8$ is further preferably H.

In certain embodiments, $R^9$ is preferably H, halogen or $C_{1-4}$ alkyl. $R^9$ is further preferably H, —F, —Cl, or —$CH_3$.

In certain embodiments, $R^{10}$ is preferably H, halogen, $C_{1-4}$ alkyl, or $C_{1-4}$ alkyl substituted with 1, 2 or 3 $R^5$ groups; each $R^5$ is independently —$NR^{a1}R^1$; $R^{a1}$ and $R^{b1}$ are independently H or $C_{1-4}$ alkyl. $R^{10}$ is further preferably H, —$CH_3$, —$CH_2CH_2NH_2$, —F, or —Cl.

In certain embodiments, $R^{11}$ is preferably H, halogen or $C_{1-4}$ alkyl; $R^{11}$ is further preferably H, —$CH_3$ or —F.

In certain embodiments, $R^{12}$, $R^{13}$, $R^{14}$ and $R^{15}$ are preferably H.

In a preferred embodiment, $R^1$ is a bicyclic structure and is aromatic, and is preferably

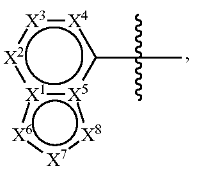
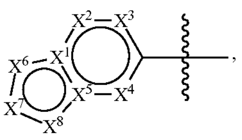

-continued

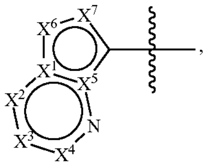
,
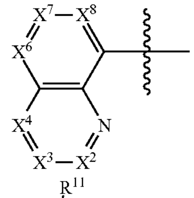
,
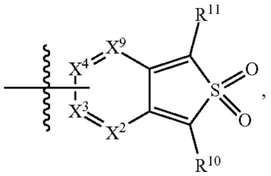
,
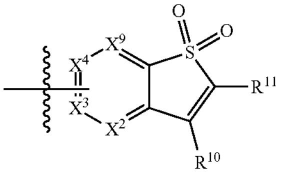
or
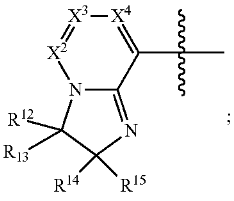
;

the definitions of the remaining letters and groups are as defined in the present disclosure.

In a preferred embodiment, in the compound as shown in formula (I), $R^2$, $R^3$, $R^4$, $R^6$, $R^7$, $R^8$, $R^9$, $R^{10}$, $R^{11}$, $R^{12}$, $R^{13}$, $R^{14}$, and $R^{15}$ are independently H, halogen (such as fluorine, chlorine or bromine), —CN, $R^5$-substituted or unsubstituted amino, $R^5$-substituted or unsubstituted hydroxyl, $R^5$-substituted or unsubstituted $C_{1-4}$ alkyl (such as methyl), $R^5$-substituted or unsubstituted $C_{3-6}$ cycloalkyl (such as cyclopropyl), $R^5$-substituted or unsubstituted $C_{1-4}$ haloalkyl (such as trifluoromethyl), —(C═O)$R^{16}$, —$CO_2R^{16}$, —C(═O)$NR^{16}R^{17}$, —$SO_2R^{16}$, or —$SO_2NR^{16}R^{17}$; the definitions of the remaining letters and groups are as defined in the present disclosure.

In a preferred embodiment, in the compound as shown in formula (I), $R^5$ is independently $C_{1-4}$ alkoxy, $C_{1-4}$ alkyl (such as methyl), $C_{1-4}$ haloalkyl (such as trifluoromethyl), amino, amino protected by an N protecting group (the protecting group can be

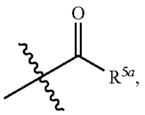
, wherein $R^{5a}$ is $C_{1-4}$ alkyl or $C_{1-4}$ alkoxy, for example,

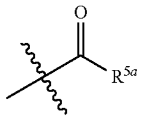

can be tertbutoxycarbonyl), fluorine, or hydroxyl; the definitions of the remaining letters and groups are as defined in the present disclosure.

In a preferred embodiment, in the compound as shown in formula (I), $R^{16}$ and $R^{17}$ are independently H, $C_{1-4}$ alkyl (such as methyl) or $C_{1-4}$ haloalkyl (such as trifluoromethyl); the definitions of the remaining letters and groups are as defined in the present disclosure.

In the present disclosure, "$R^5$-substituted or unsubstituted amino" is preferably —$NR^aR^b$; $R^a$ and $R^b$ are independently H or $C_{1-4}$ alkyl.

In certain embodiments, in the compound as shown in formula (I), n is 1, and the definitions of the remaining letters and groups are as defined in the present disclosure.

In certain embodiments, in the compound as shown in formula (I), X is N, and the definitions of the remaining letters and groups are as defined in the present disclosure.

In certain embodiments, in the compound as shown in formula (I), the moiety

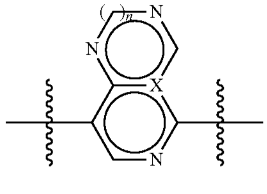

is

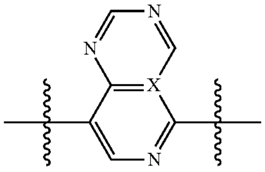
or
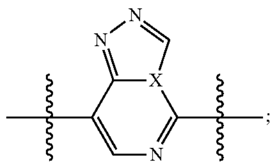
;

the definitions of the remaining letters and groups are as defined in the present disclosure.

In certain embodiments, the compound as shown in formula (I) is a compound as shown in formula I-A

I-A

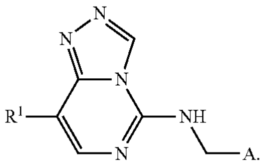

In certain embodiments, the A is:

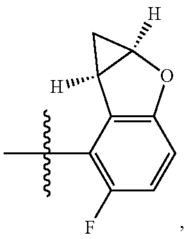
,
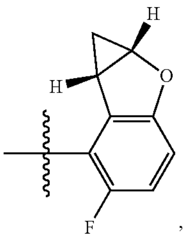
,
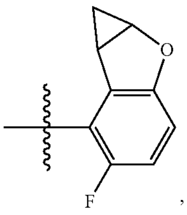
, or
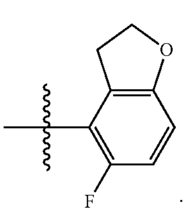
.

In certain embodiments, the moiety

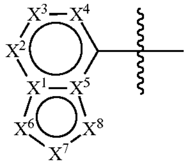

can be

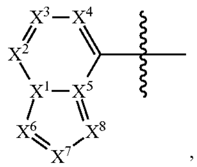
,
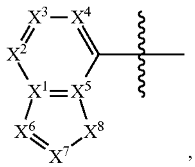
,
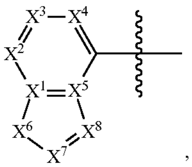
, or
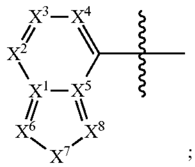
;

the definitions of $X^1$, $X^2$, $X^3$, $X^4$, $X^6$, $X^7$, and $X^8$ are as defined in the present disclosure.

In certain embodiments, the moiety

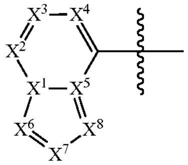

can be

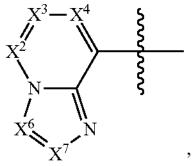
, wherein $X^6$ is independently $CR^6$ or N; $X^7$ is independently $CR^7$ or N; the definitions of $X^2$, $X^3$, $X^4$, $R^6$, and $R^7$ are as defined in the present disclosure.

In certain embodiments, the moiety

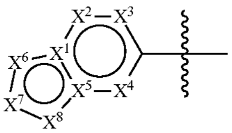

can be

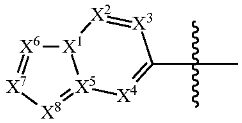
or
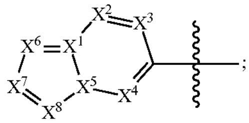
;

the definitions of $X^1$, $X^2$, $X^3$, $X^4$, $X^6$, $X^7$, and $X^8$ are as defined in the present disclosure.

In certain embodiments, the moiety

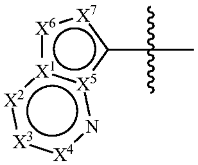

can be

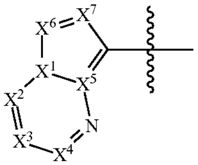
;

the definitions of $X^1$, $X^2$, $X^3$, $X^4$, $X^6$, and $X^7$ are as defined in the present disclosure.

In certain embodiments, the $R^1$ is any one of the following structures:

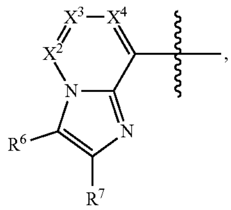
,
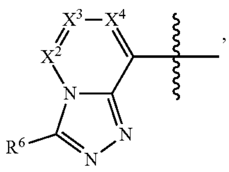
,
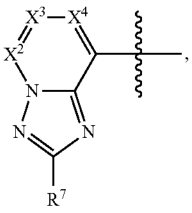
,
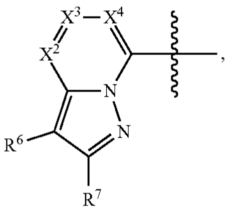
,
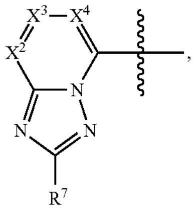
,
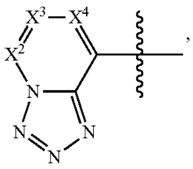
,

-continued
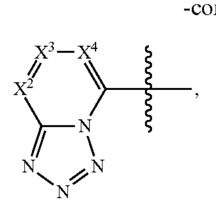
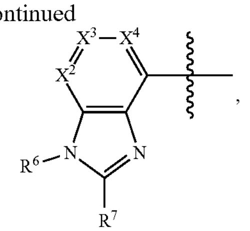
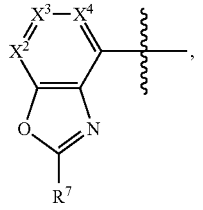
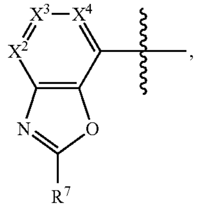
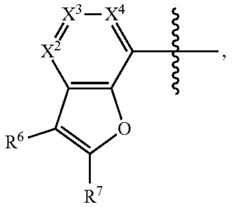
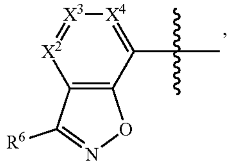
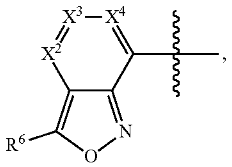
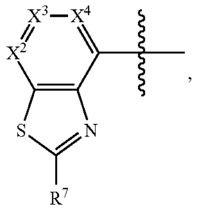
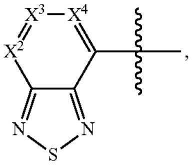
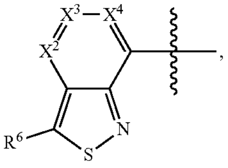
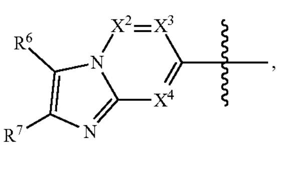
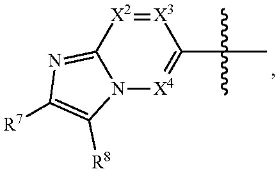
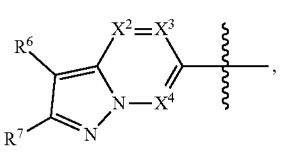
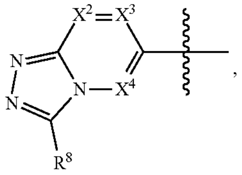
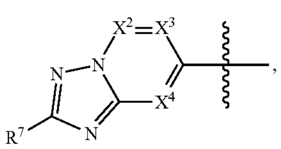
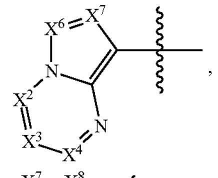
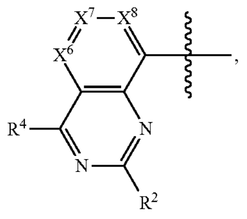
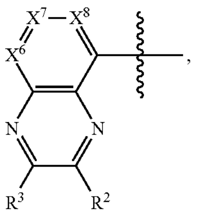
-continued
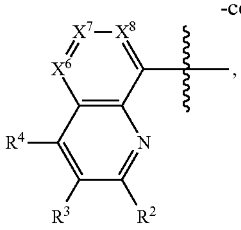
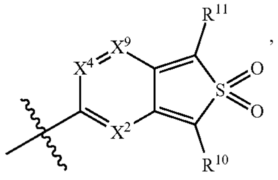
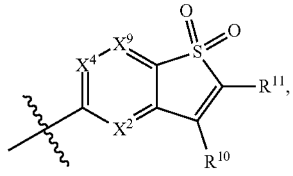
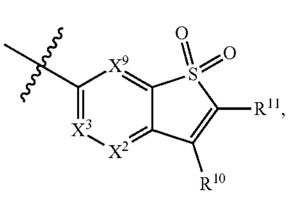
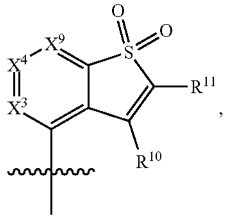
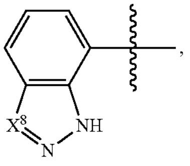
or
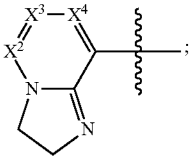
or $R^1$ is any one of the following structures:
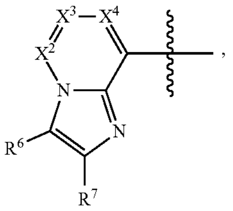
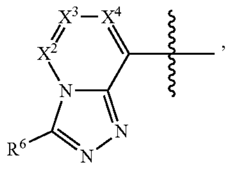
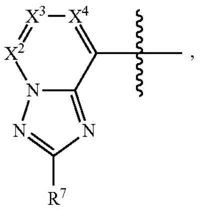
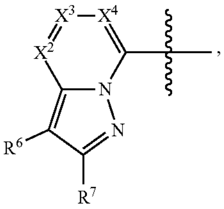
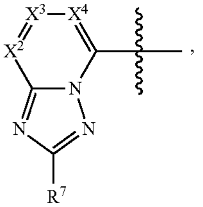
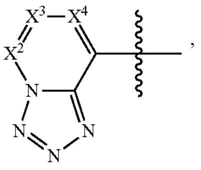
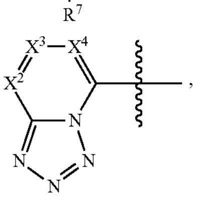
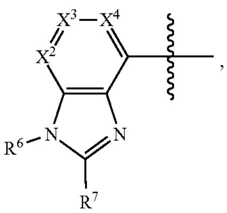

-continued
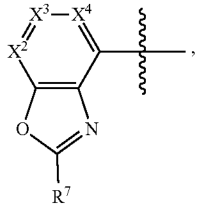
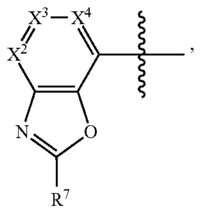
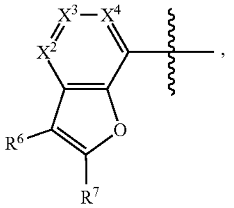
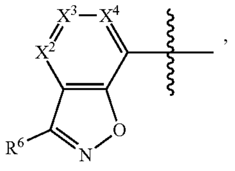
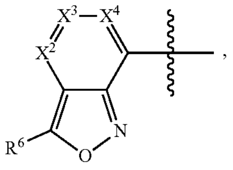
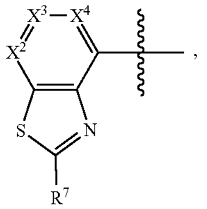
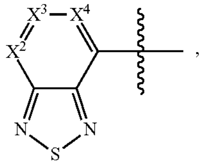
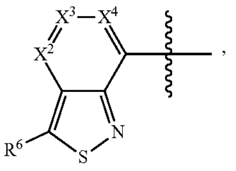
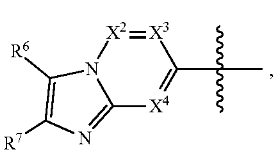
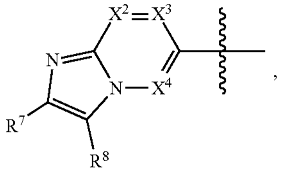
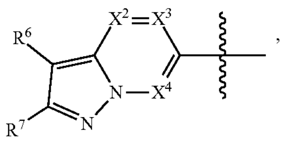
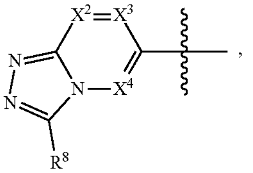
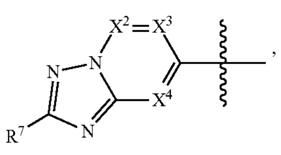
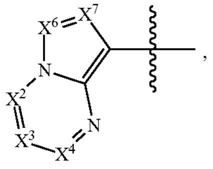
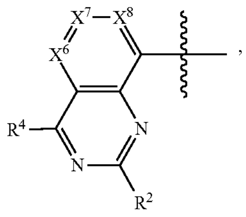
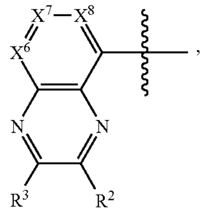
-continued
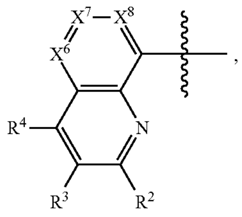
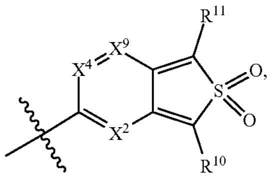
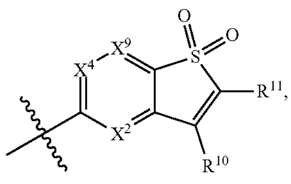
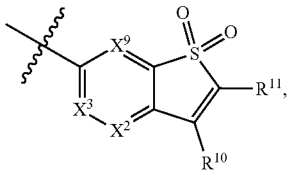
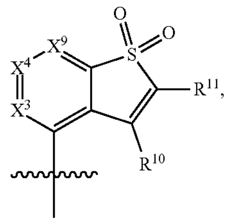
wherein the definitions of $X^2$, $X^3$, $X^4$, $X^6$, $X^7$, $X^8$, $R^2$, $R^3$, $R^4$, $R^6$, $R^7$, $R^8$, $R^9$, $R^{10}$, and $R^{11}$ are as described above.
In a preferred embodiment, $R^1$ is
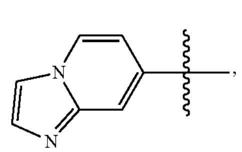
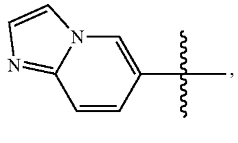
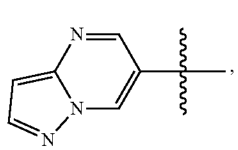
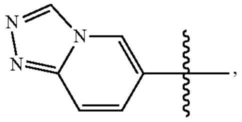
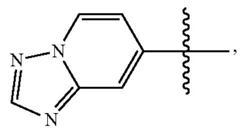
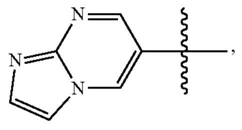
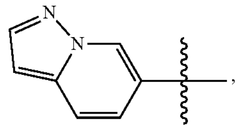
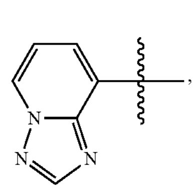
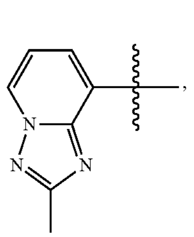
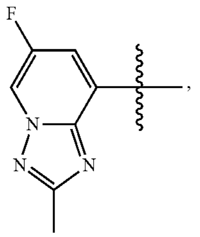

-continued
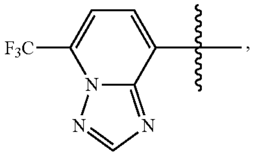, 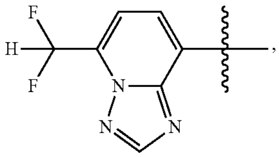,
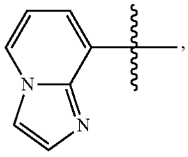, 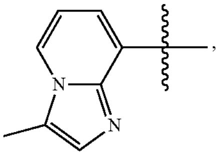,
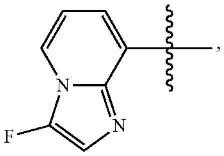, 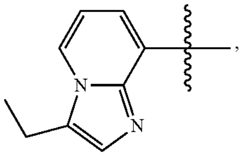,
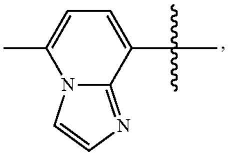, 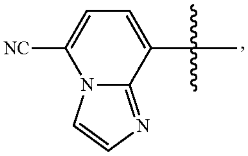,
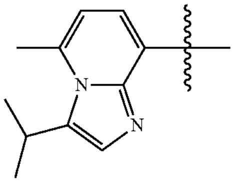, 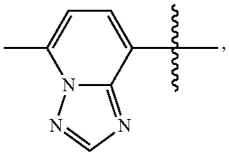,
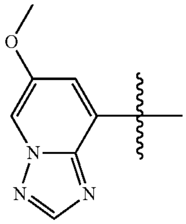, 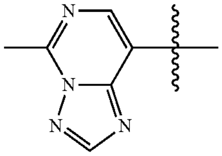,
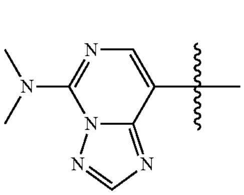, 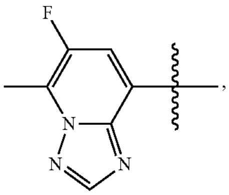,
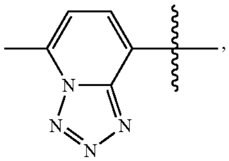, 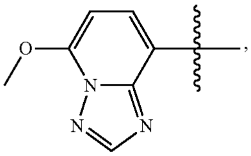,
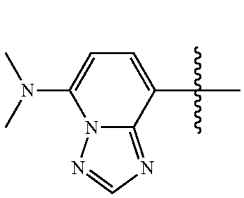, 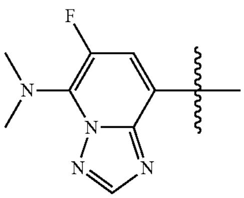,
-continued
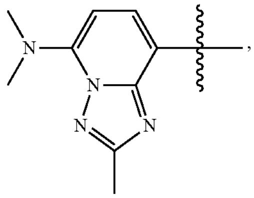, 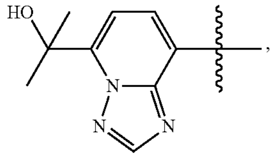,
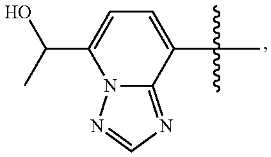,
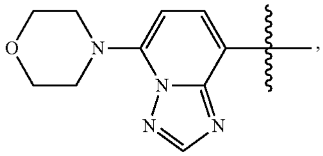,
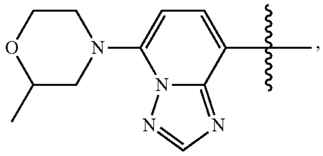,
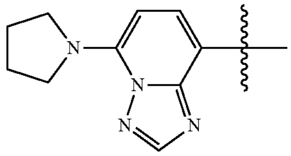,
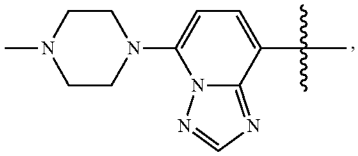,
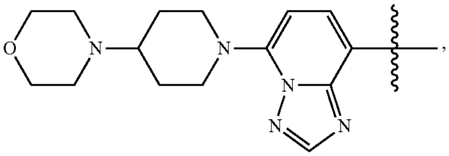,
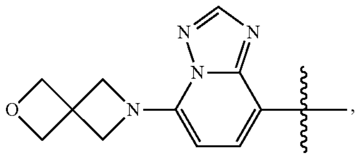,
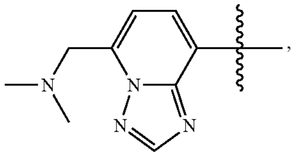,
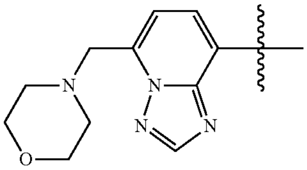, -continued
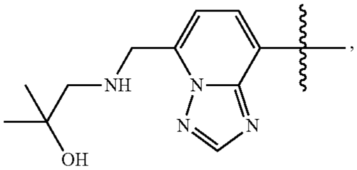,
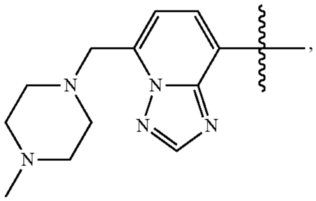,
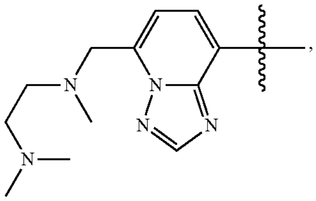,
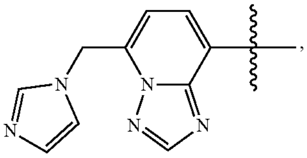, 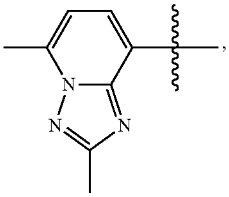,
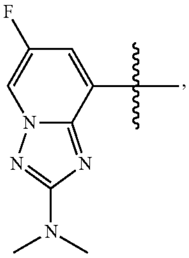, 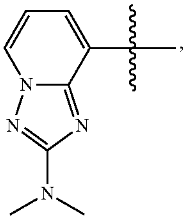,
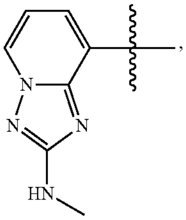, 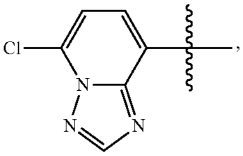,
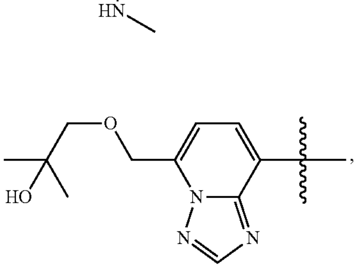, 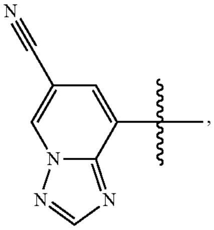,
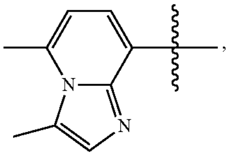, 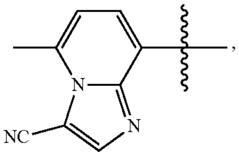,
-continued
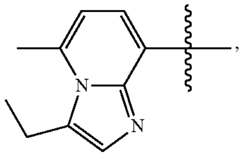, 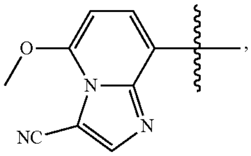,
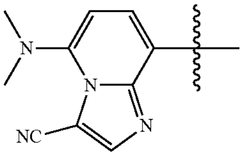,
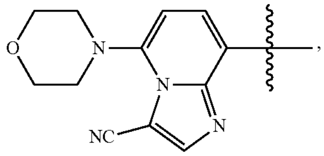,
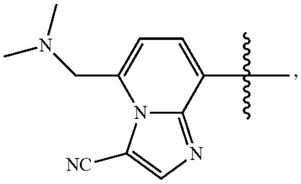, 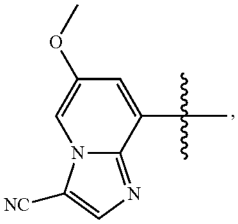,
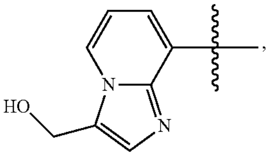, 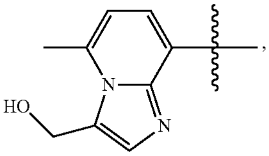,
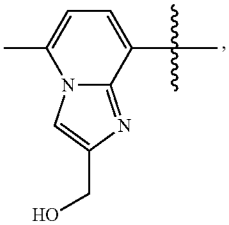, 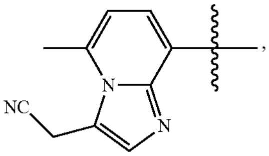,
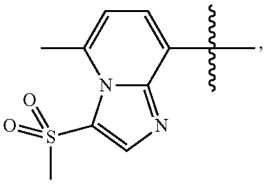, 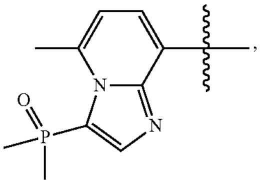,
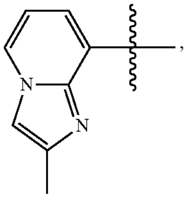, 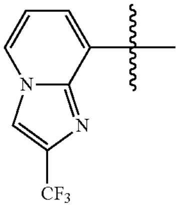,
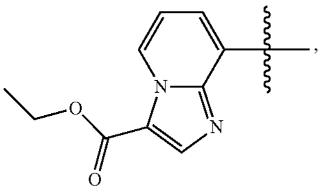, -continued
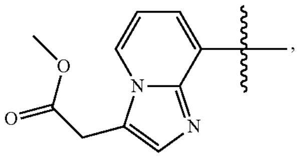,
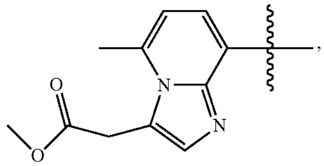,
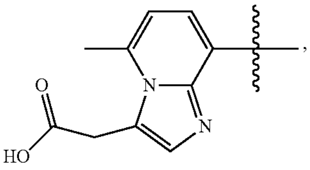,
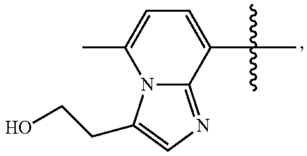,
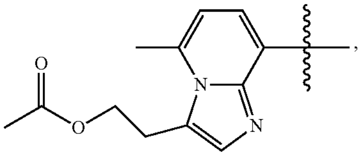,
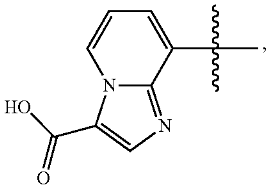, 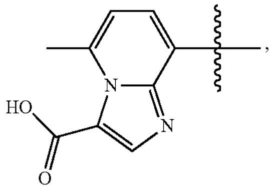,
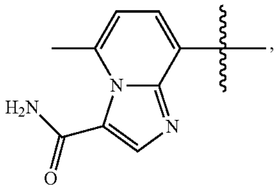, 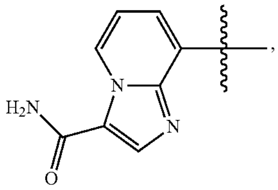,
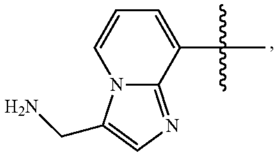, 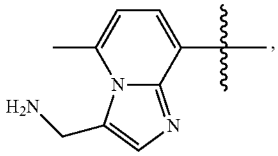,
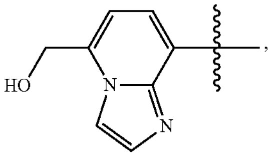, 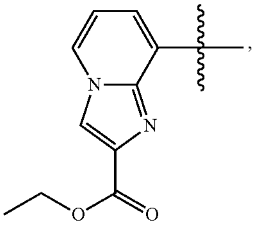
-continued
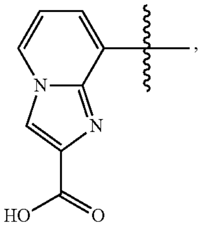, 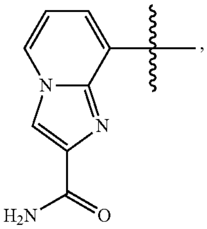,
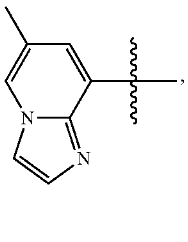, 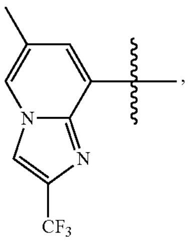, 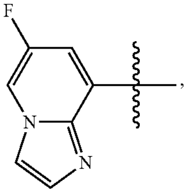,
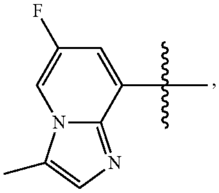, 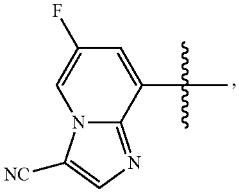,
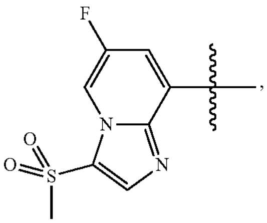, 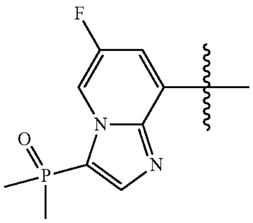,
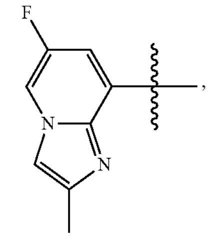, 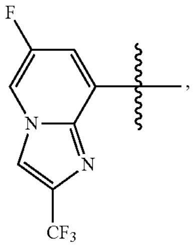,
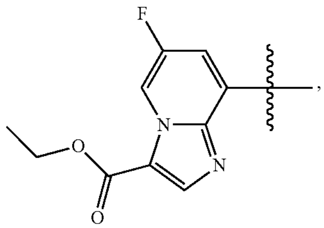,
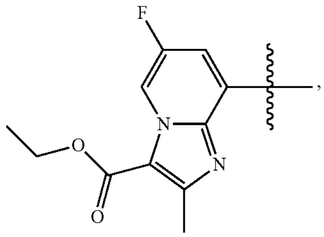, -continued
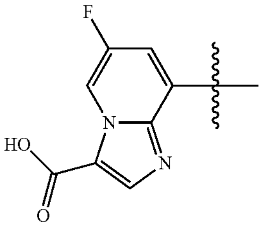,
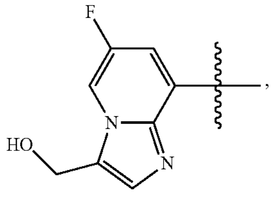,
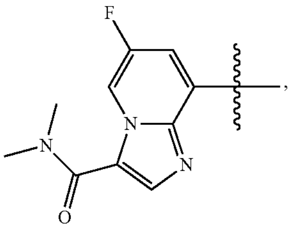,
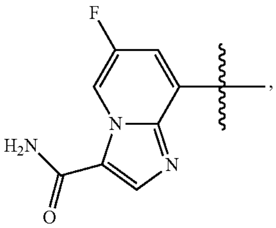,
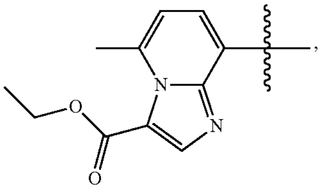,
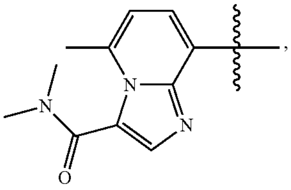,
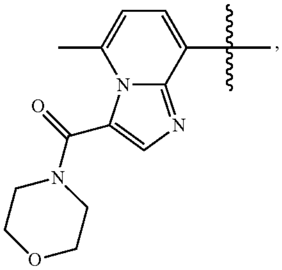,
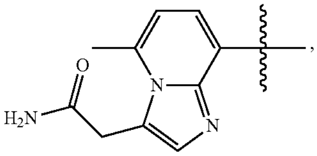,
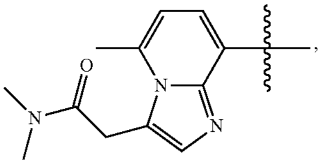,
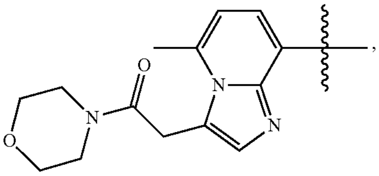,
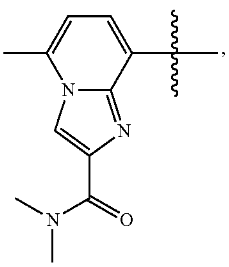,
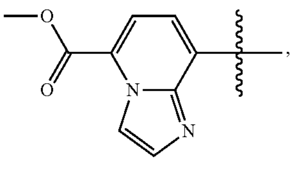,
-continued
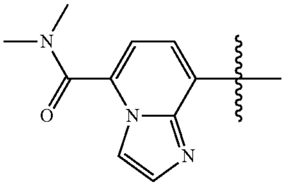,
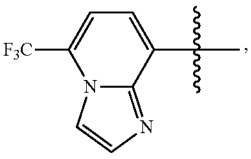,
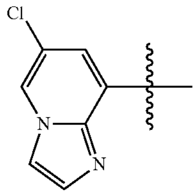,
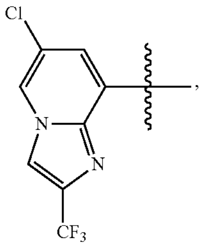,
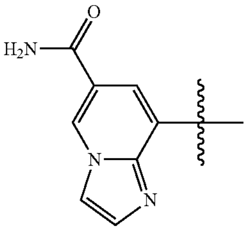,
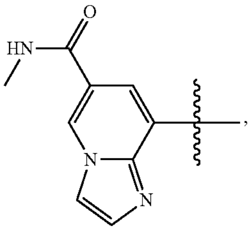,
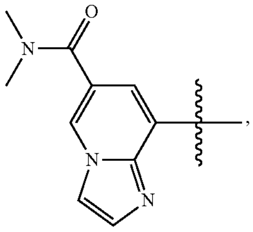,
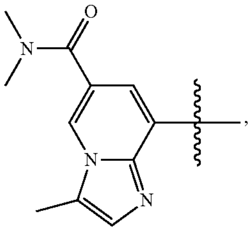,
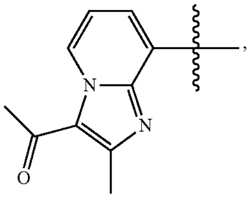,
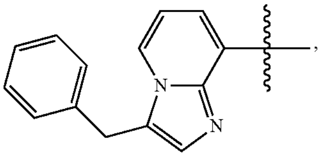,
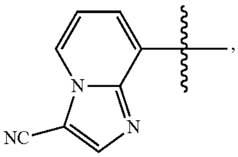,
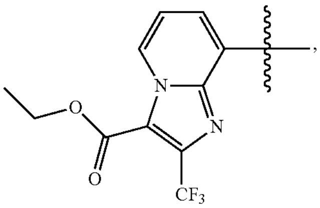,
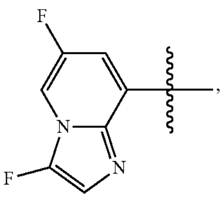,
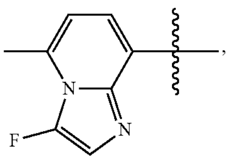,
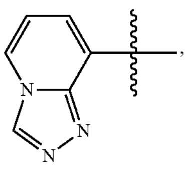,
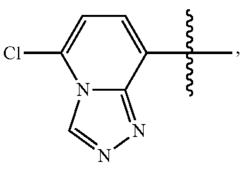, -continued
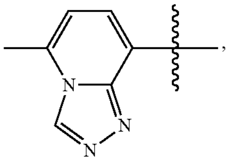, 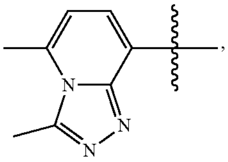,
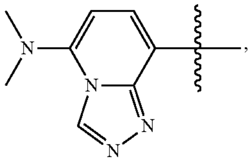, 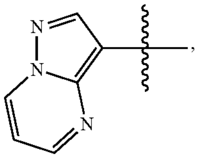,
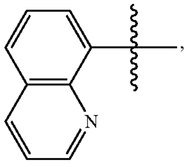, 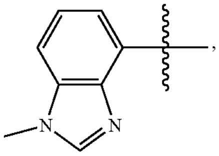,
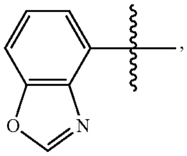, 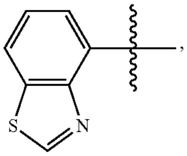,
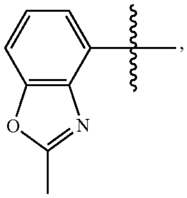, 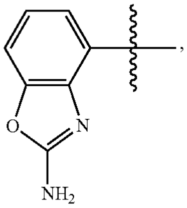,
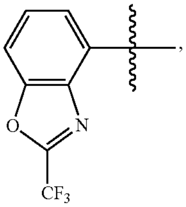, 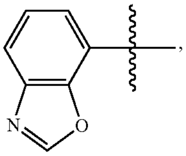,
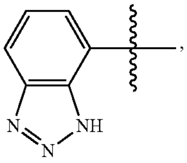, 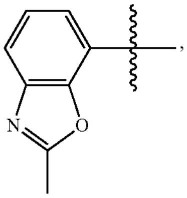,
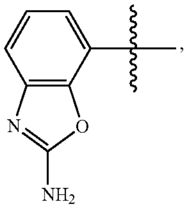, 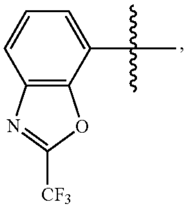,
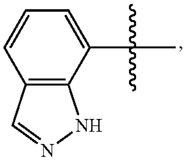, 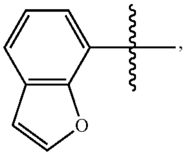,
-continued
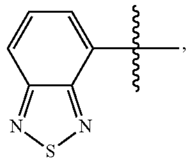, 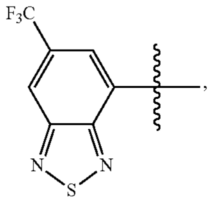,
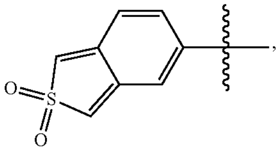, 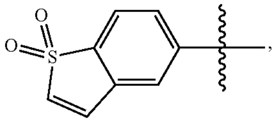,
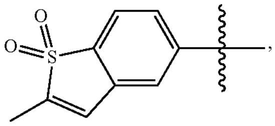, 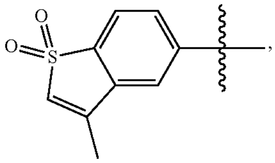,
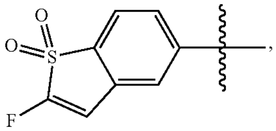, 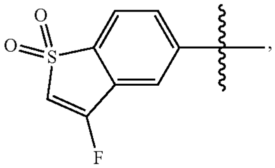,
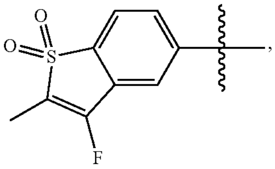, 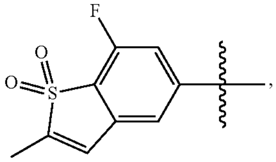,
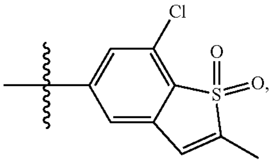, 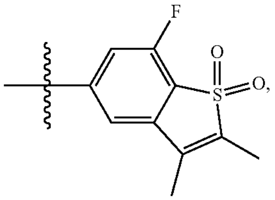,
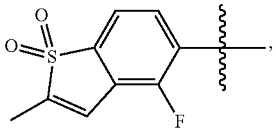, 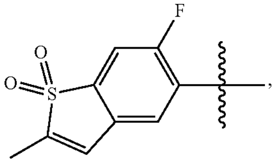,
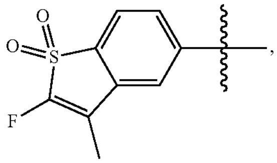, 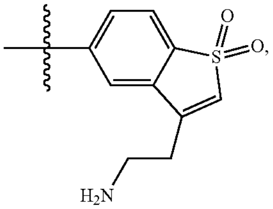,
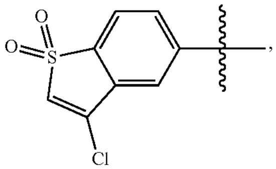, 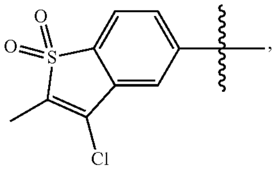, -continued
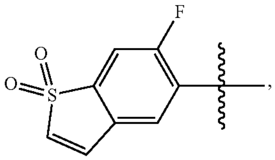
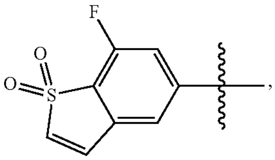
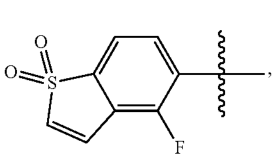
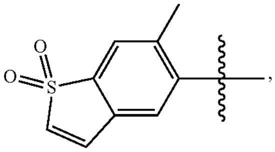
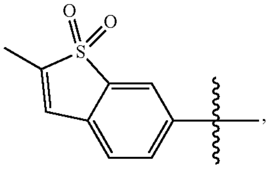
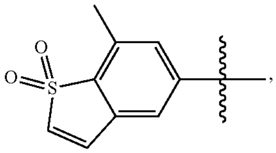
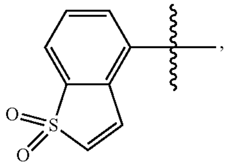
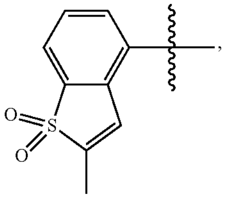
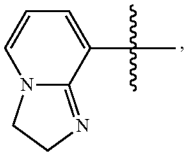
or
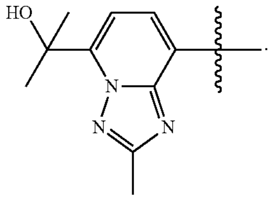
In another aspect, $R^1$ can be
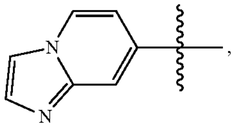
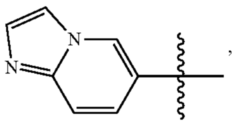
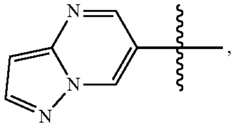
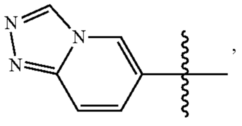
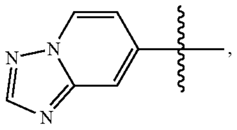
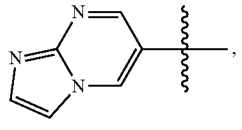
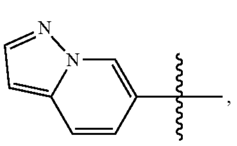
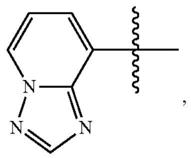
-continued
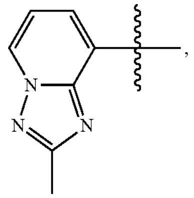
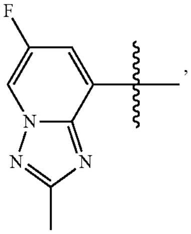
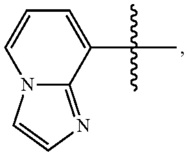
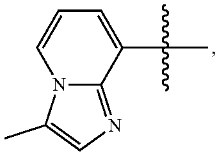
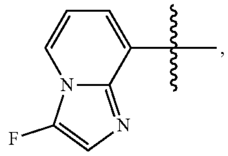
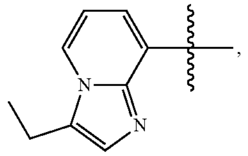
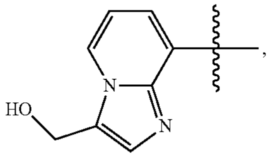
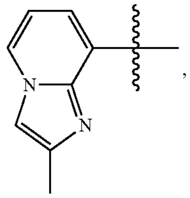
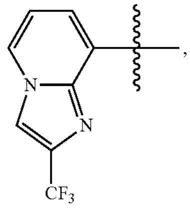
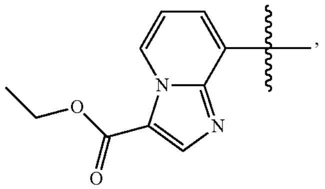
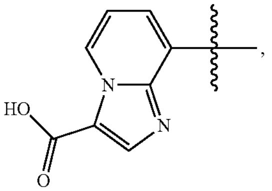
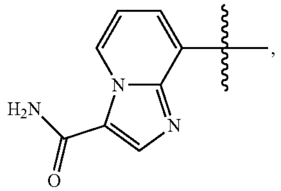
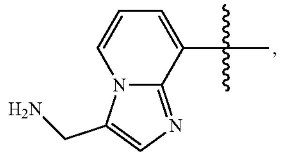
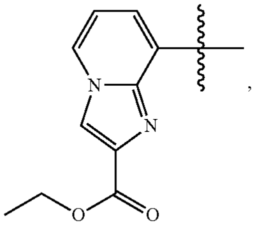
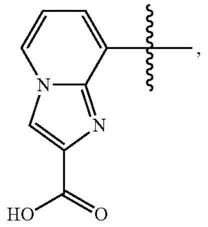
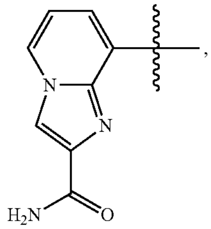

-continued
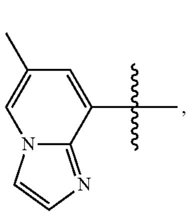,
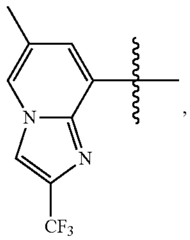,
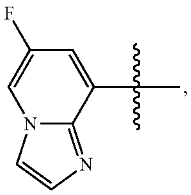,
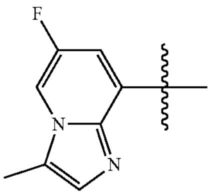,
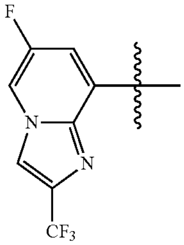,
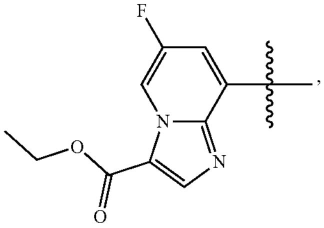,
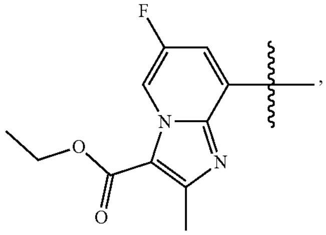,
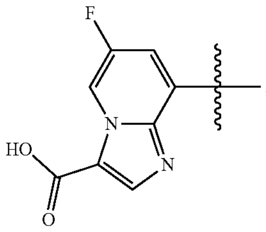,
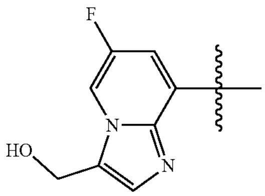,
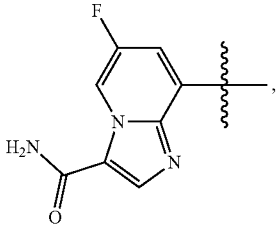,
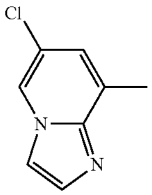,
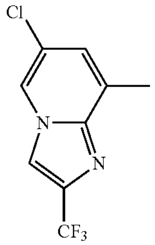,
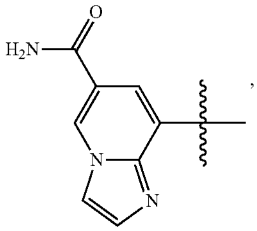,
-continued
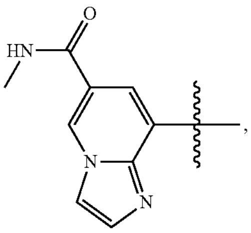,
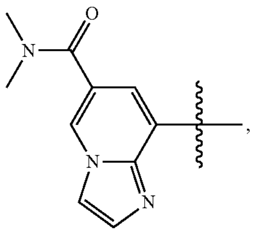,
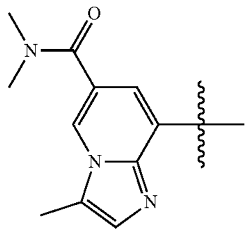,
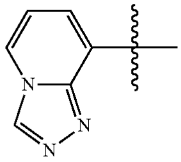,
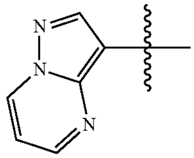,
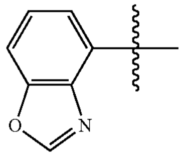,
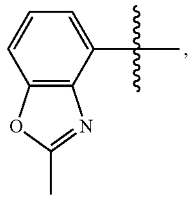,
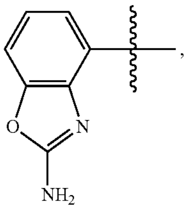,
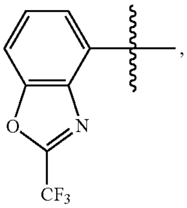,
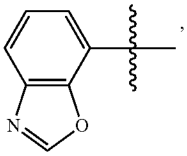,
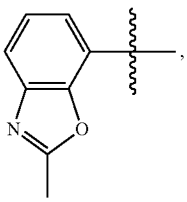,
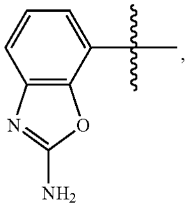,
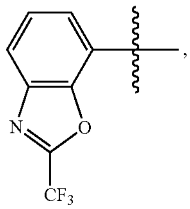,
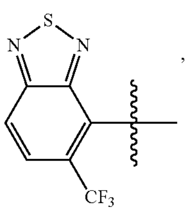,
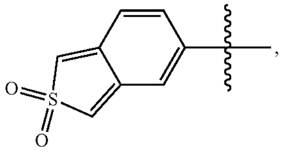,
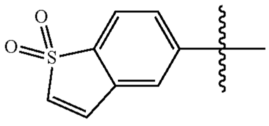, -continued
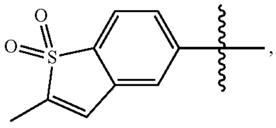,
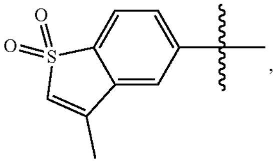,
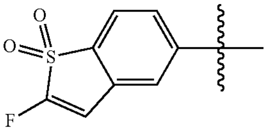,
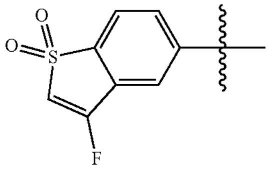,
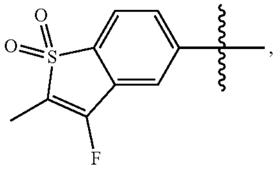,
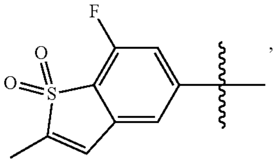,
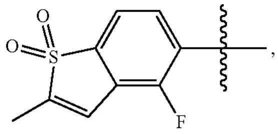,
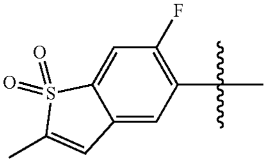,
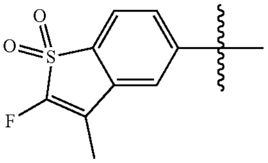,
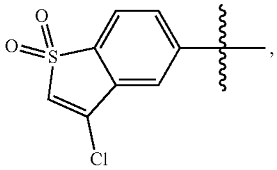,
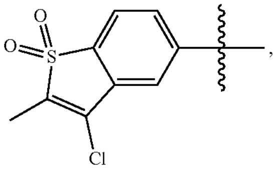,
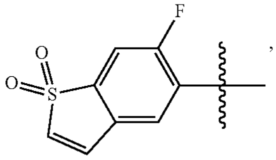,
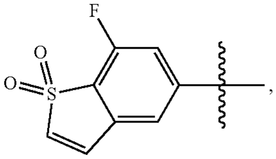,
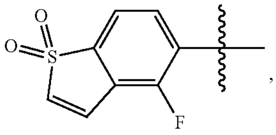,
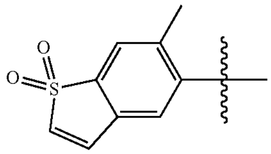,
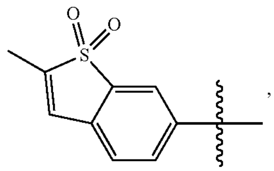,
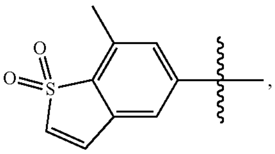,
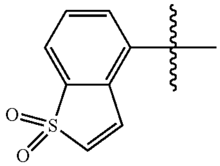,
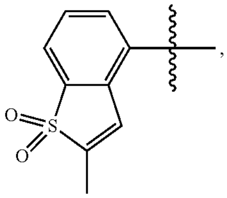,
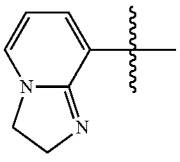.
In certain embodiments, the moiety
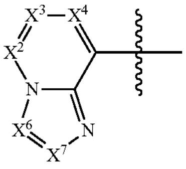
is preferably
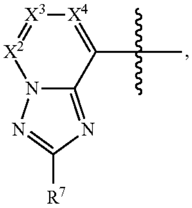, 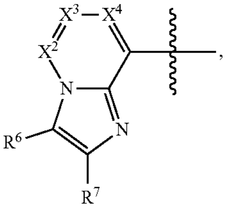,
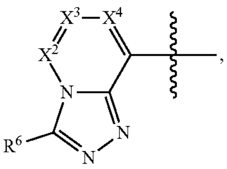, or 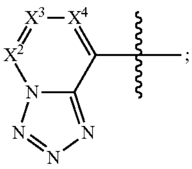;
the definitions of $X^2$, $X^3$, $X^4$, $R^6$, and $R^7$ are as defined in the present disclosure.
In certain embodiments, the moiety
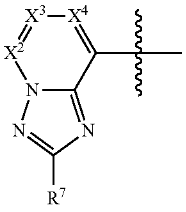
is preferably
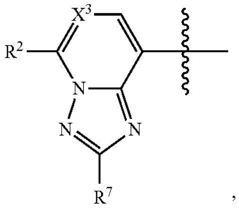,
wherein $X^3$ is N or $CR^3$; the definitions of $R^2$, $R^3$ and $R^7$ are as defined in the present disclosure.

In certain embodiments, in the moiety

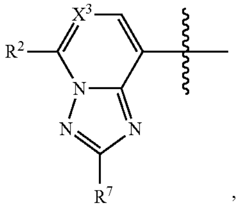

, the definition of $R^2$ is preferably as below, and the definitions of the remaining letters and groups are as defined in the present disclosure:

$R^2$ is H, $C_{1-4}$ alkyl, $C_{1-4}$ alkyl substituted with 1, 2 or 3 $R^{5-2-1}$ groups, $C_{1-4}$ haloalkyl, $C_{1-4}$ alkoxy, $C_{3-6}$ heterocycloalkyl, $C_{3-6}$ heterocycloalkyl substituted with 1, 2 or 3 $C_{1-4}$ alkyl groups, $C_{3-6}$ heterospirocycloalkyl, or —$NR^aR^b$;

$R^a$ and $R^b$ are independently H or $C_{1-4}$ alkyl;

each $R^{5-2-1}$ is independently —OH, $C_{1-4}$ alkyl, $C_{1-4}$ alkoxy, $C_{1-4}$ alkoxy substituted with 1, 2 or 3 hydroxyl groups, —$NR^{a1}R^{b1}$, $C_{3-6}$ heterocycloalkyl, or $C_{3-6}$ heterocycloalkyl substituted with 1, 2 or 3 $R^{5-2-2}$ groups; $R^{a1}$ and $R^{b1}$ are independently H, $C_{1-4}$ alkyl, $C_{1-4}$ alkyl substituted with 1, 2 or 3 —$NR^{a2}R^{b2}$ groups, or $C_{1-4}$ alkyl substituted with 1, 2 or 3 hydroxyl groups; $R^{5-2-2}$ is $C_{1-4}$ alkyl or $C_{3-6}$ heterocycloalkyl; $R^{a2}$ and $R^{b2}$ are independently H or $C_{1-4}$ alkyl;

wherein the heteroatom in the $C_{3-6}$ heterocycloalkyl is selected from N, O and S, and the number of the heteroatom is 1, 2, 3 or 4; the heteroatom in the $C_{3-6}$ heterospirocycloalkyl is selected from N, O and S, and the number of the heteroatom is 1, 2, 3 or 4;

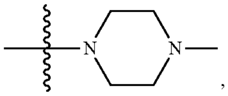 [SMILES: *N1CCN(C)CC1]

, preferably, each $R^{5-2-1}$ is independently —$OCH_2C(CH_3)_2OH$, —$N(CH_3)_2$, —$NHCH_2C(CH_3)_2OH$,

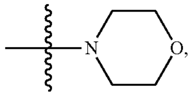 [SMILES: *N1CCOCC1]

—$N(CH_3)CH_2CH_2N(CH_3)_2$,

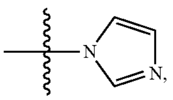

or —OH;

further preferably, $R^2$ is H, —$CH_3$, —$CF_3$, —$OCH_3$,

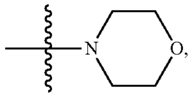 [SMILES: *N1CCOCC1]

—$N(CH_3)_2$,

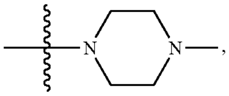

,

—$CH_2OCH_2C(CH_3)_2OH$, —$CH_2N(CH_3)_2$,

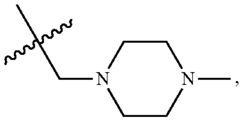 [SMILES: *CN1CCN(C)CC1]

,

—$CH_2NHCH_2C(CH_3)_2OH$,

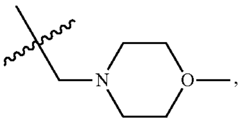

,

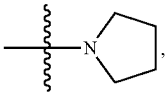

,

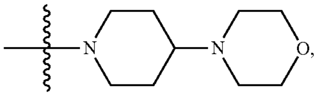

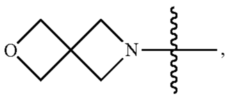

,

—$CH_2N(CH_3)CH_2CH_2N(CH_3)_2$,

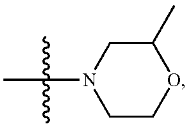

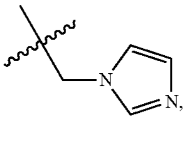

—$C(CH_3)_2OH$, or —$CHF_2$.

In certain embodiments, in the moiety

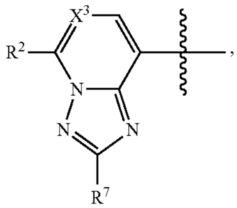

, when $X^3$ is $CR^3$, then the definition of $R^3$ is preferably as below, and the definitions of the remaining letters and groups are as defined in the present disclosure:

$R^3$ is H, halogen, $C_{1-4}$ alkoxy or —CN; further preferably, $R^3$ is H, —$OCH_3$, —F or —CN.

In certain embodiments, in the moiety

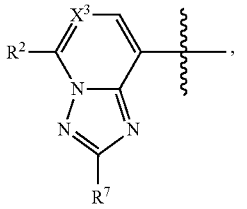

the definition of $R^7$ is preferably as below, and the definitions of the remaining letters and groups are as defined in the present disclosure:

$R^7$ is H, $C_{1-4}$ alkyl or —$NR^aR^b$; $R^a$ and $R^b$ are independently H or $C_{1-4}$ alkyl; further preferably, $R^7$ is H, —NH($CH_3$), —$N(CH_3)_2$, or —$CH_3$.

In certain embodiments, the moiety

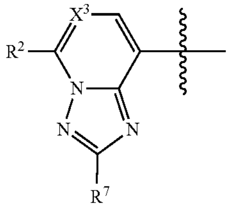

is preferably

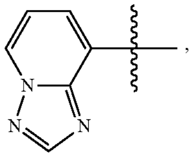

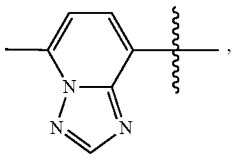

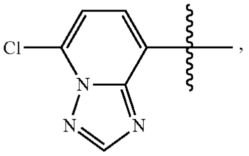

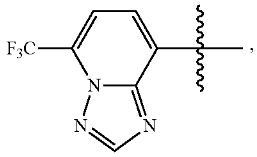

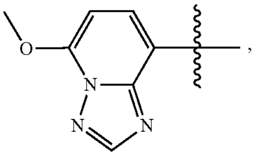

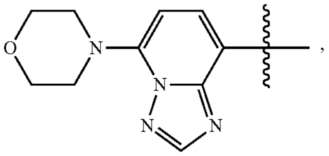

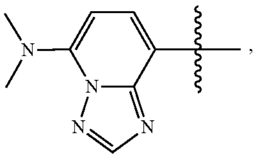

-continued

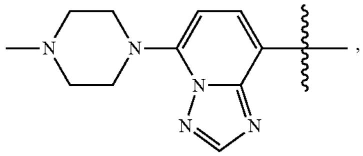

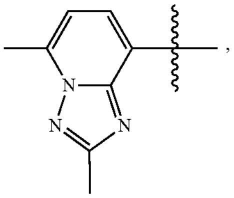

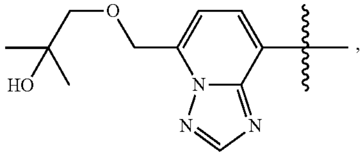

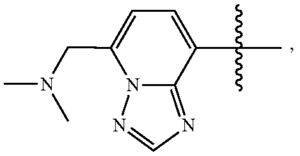

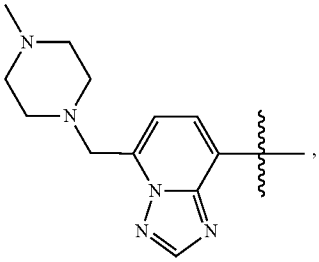

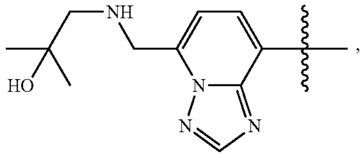

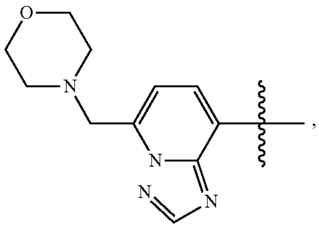

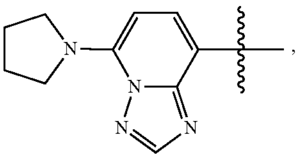

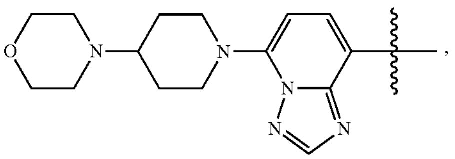

-continued
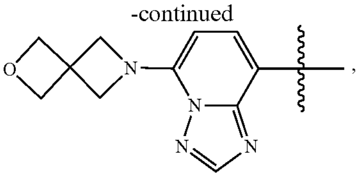
,
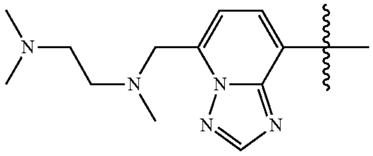
,
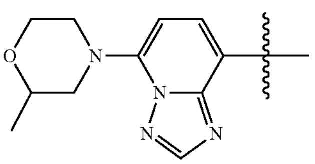
,
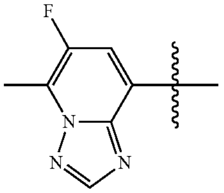
,
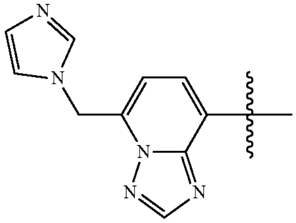
,
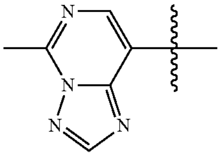
,
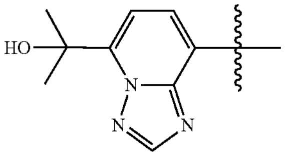
,
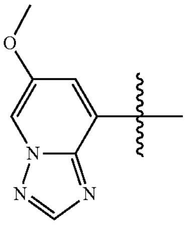
,
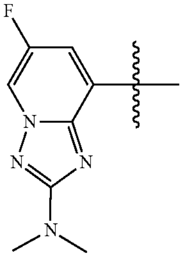
,
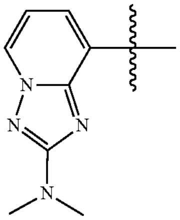
,
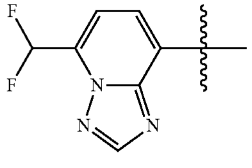
,
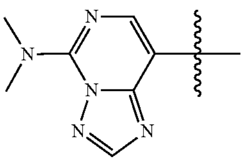
,
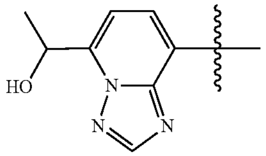
,
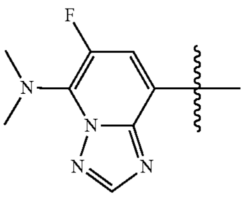
,
-continued
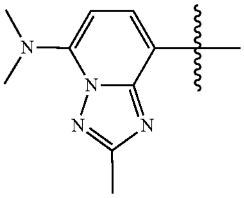
,
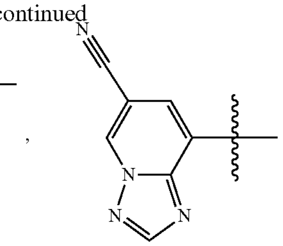
,
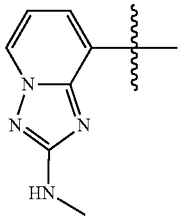
,
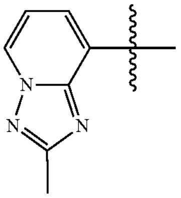
,
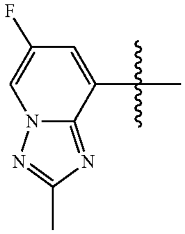
, or
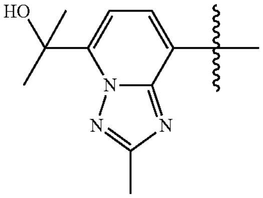
.
In certain embodiments, the moiety
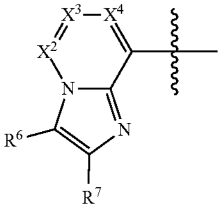
is preferably
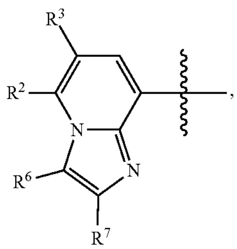
,
wherein the definitions of $R^2$ and $R^3$, $R^6$ and $R^7$ are as defined in the present disclosure.

In certain embodiments, in the moiety

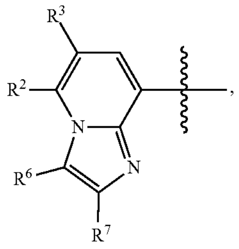

the definition of $R^2$ is preferably as below, and the definitions of the remaining letters and groups are as defined in the present disclosure:

$R^2$ is H, —CN, $C_{1-4}$ alkyl, $C_{1-4}$ alkyl substituted with 1, 2 or 3 $R^{5-2-3}$ groups, $C_{1-4}$ haloalkyl, $C_{1-4}$ alkoxy, —$CO_2R^{16}$, —C(═O)$NR^{16}R^{17}$, or —$NR^aR^b$, wherein each $R^{16}$ and $R^{17}$ are independently H or $C_{1-4}$ alkyl; each $R^{5-2-3}$ is independently —OH or —$NR^{a1}R^{b1}$; $R^{a1}$ and $R^{b1}$ are independently H or $C_{1-4}$ alkyl; each $R^{5-2-3}$ is preferably —OH or —$N(CH_3)_2$;

further preferably, $R^2$ is H, —$CH_3$, —$CO_2CH_3$, —$CH_2OH$, —$CON(CH_3)_2$, —$CF_3$, —$CH_2N(CH_3)_2$, —$OCH_3$, —$N(CH_3)_2$,

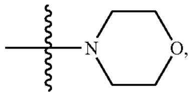 [SMILES: *N1CCOCC1]

or —CN.

In certain embodiments, in the moiety

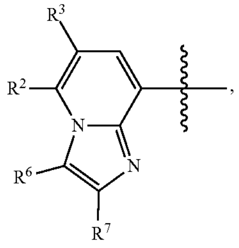

the definition of $R^3$ is preferably as below, and the definitions of the remaining letters and groups are as defined in the present disclosure:

$R^3$ is H, halogen, $C_{1-4}$ alkyl, $C_{1-4}$ alkoxy, or —C(═O)$NR^{16}R^{17}$; $R^{16}$ and $R^{17}$ are independently H or $C_{1-4}$ alkyl; further preferably, $R^3$ is H, —F, —Cl, —$CH_3$, —$OCH_3$, —$CONH_2$, —$CONHCH_3$, or —$CON(CH_3)_2$.

In certain embodiments, in the moiety

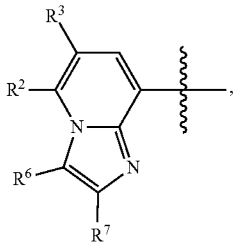

the definition of $R^6$ is preferably as below, and the definitions of the remaining letters and groups are as defined in the present disclosure:

$R^6$ is H, halogen, —CN, $C_{1-4}$ alkyl, $C_{1-4}$ alkyl substituted with 1, 2 or 3 $R^{5-6-1}$ groups, —$CO_2R^{16}$, —C(═O)$NR^{16}R^{17}$, —(C═O)$R^{16-1}$, —$SO_2R^{16}$, or —$POR^{16}R^{17}$; each $R^{16}$ and each $R^{17}$ are independently H or $C_{1-4}$ alkyl; $R^{16-1}$ is H, $C_{1-4}$ alkyl or $C_{3-6}$ heterocycloalkyl; each $R^{5-6-1}$ is independently $C_{6-8}$ aryl, —C(═O)$NR^{16a}R^{17a}$, —OH, —CN, —$CO_2R^{16a}$, —O(C═O)$R^{16a}$, —NH(C═O)$R^{16a}$, —(C═O)$R^{16a1}$, or —$NR^{a1}R^{b1}$; $R^{a1}$ and $R^{b1}$ are independently H or $C_{1-4}$ alkyl; each $R^{16a}$ and each $R^{17a}$ are independently H or $C_{1-4}$ alkyl; $R^{16a1}$ is $C_3$-$C_6$ heterocycloalkyl; for $R^{16-1}$ and $R^{16a1}$, the heteroatom in the $C_{3-6}$ heterocycloalkyl is selected from N, O and S, and the number of the heteroatom is 1, 2, 3 or 4 (such as

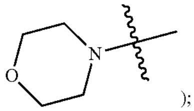 [SMILES: *N1CCOCC1]

);

further preferably, $R^6$ is H, —$COOCH_2CH_3$, —COOH, —$CONH_2$, —$CH_3$, —$COCH_3$,

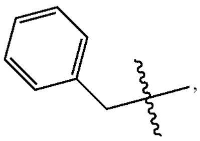 [SMILES: *Cc1ccccc1]

—$CH_2CH_3$, —F, —CN, —$CH(CH_3)_2$, —$CH_2CONH_2$, —$CH_2CH_2OH$, —$CH_2OH$, —$CH_2NH_2$, —$CH_2COOCH_3$, —$CH_2COOH$, —$CH_2CON(CH_3)_2$, —$CH_2CH_2OCOCH_3$, —$CH_2NHCOCH_3$, —$CON(CH_3)_2$, —CN,

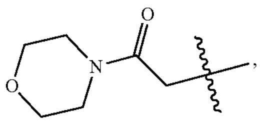

,

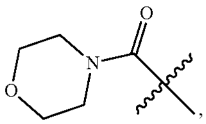

,

—$CONH_2$, —$CH_2CN$, —$SO_2Me$, or —$PO(CH_3)_2$.

In certain embodiments, in the moiety

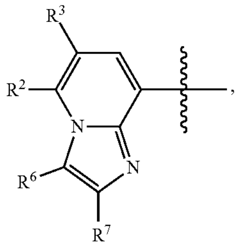

the definition of $R^7$ is preferably as below, and the definitions of the remaining letters and groups are as defined in the present disclosure:

$R^7$ is H, $C_{1-4}$ alkyl, $C_{1-4}$ alkyl substituted with 1, 2 or 3 hydroxyl groups, $C_{1-4}$ haloalkyl, —OH, —$CO_2R^{16}$, or —C(═O)$NR^{16}R^{17}$; $R^{16}$ and $R^{17}$ are independently H or $C_{1-4}$ alkyl;

further preferably, $R^7$ is H, —$CF_3$, —$CH_3$, —OH, —$CH_2OH$, —$COOCH_2CH_3$, —COOH, —$CONH_2$, or —$CON(CH_3)_2$.

In certain embodiments,

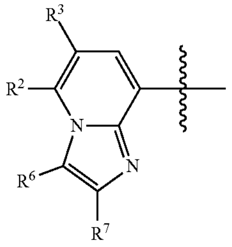

is preferably

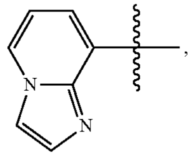,
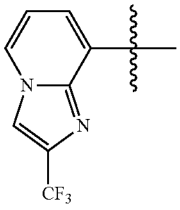,
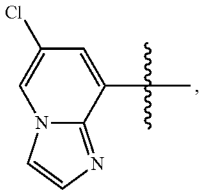,
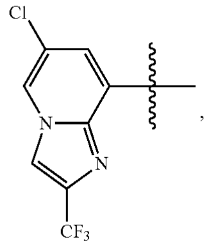,
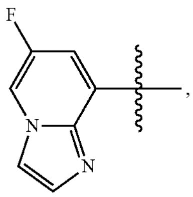,
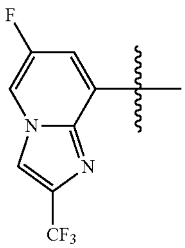,

-continued

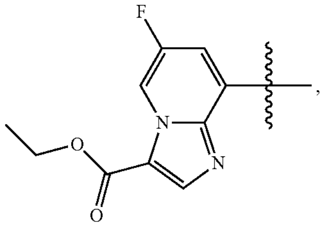,
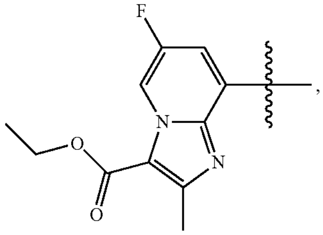,
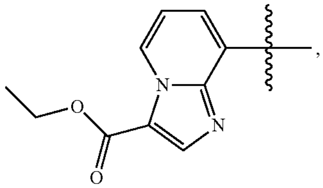,
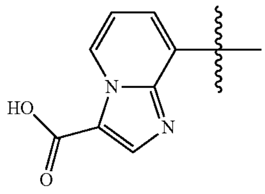,
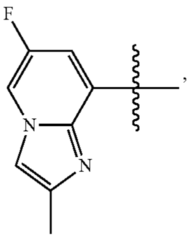,
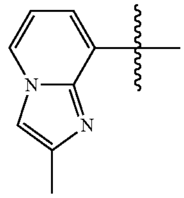,
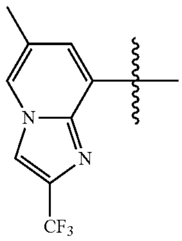,
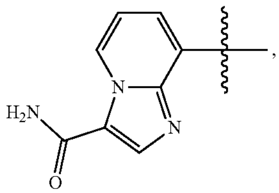,
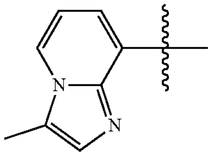,
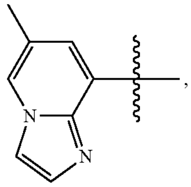,
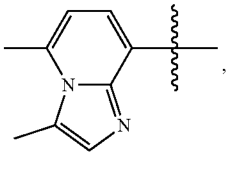,
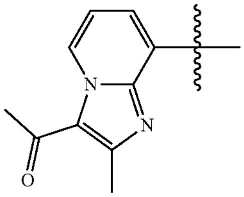, -continued
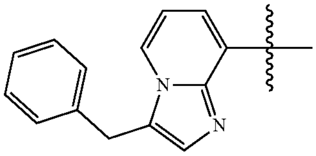,
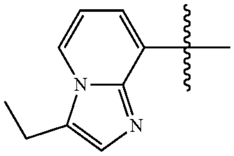, 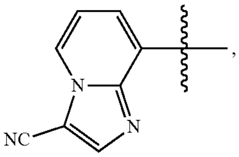,
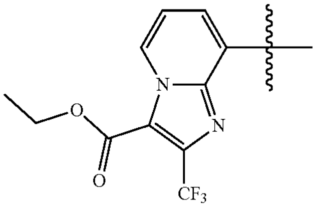,
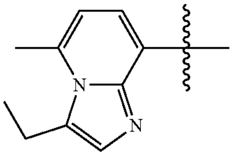, 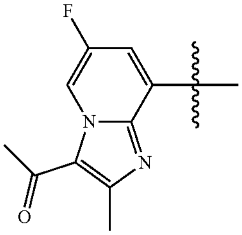,
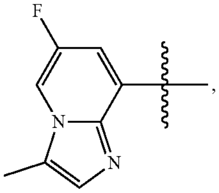, 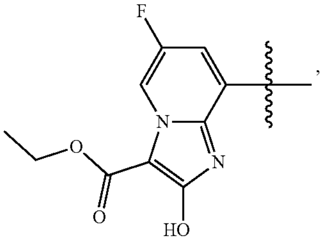,
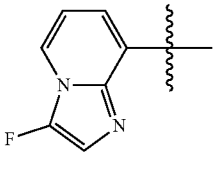, 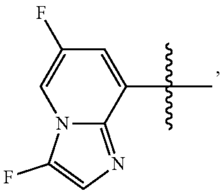,
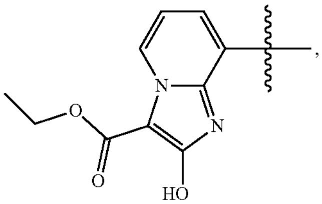,
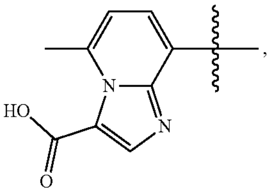, 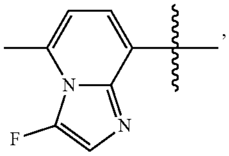,
-continued
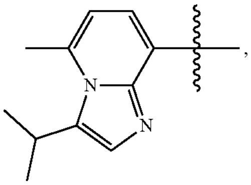, 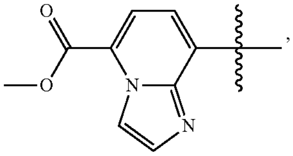,
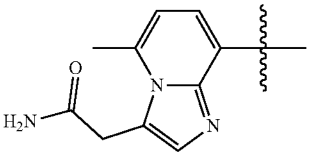,
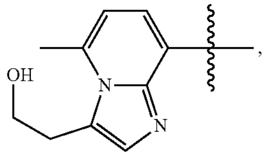,
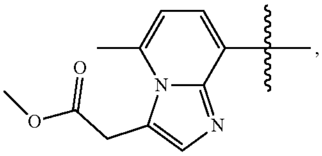,
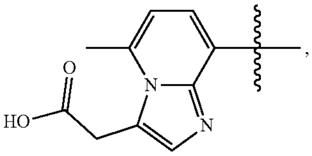,
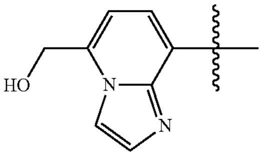,
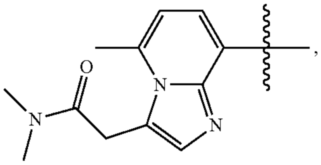,
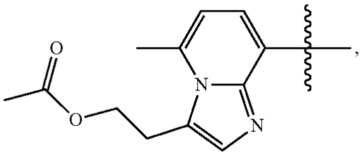,
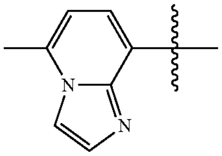,
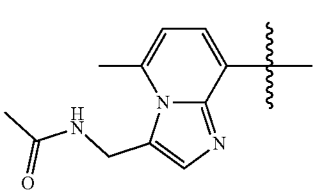, 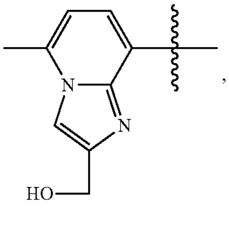, -continued
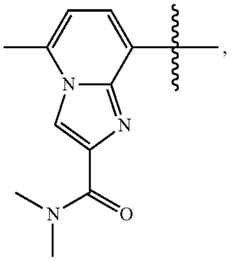
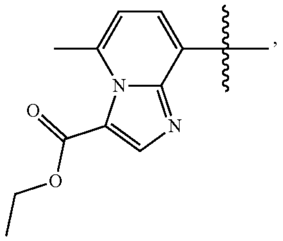
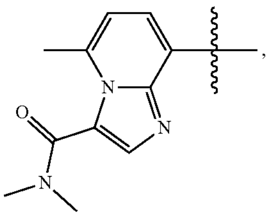
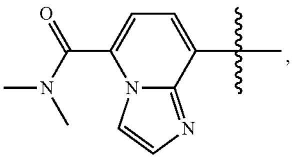
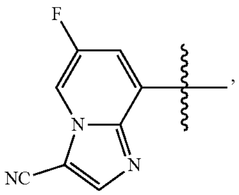
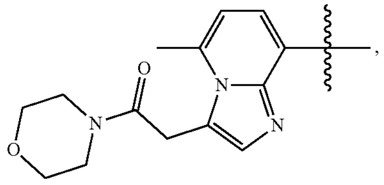
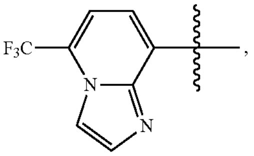
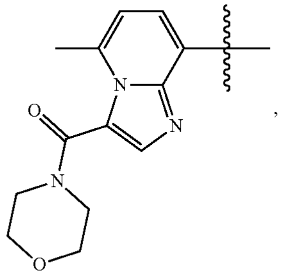
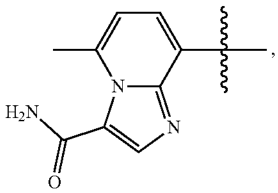
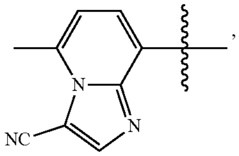
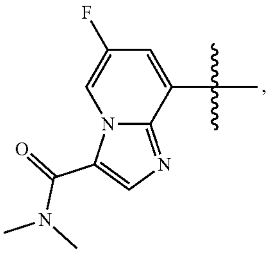
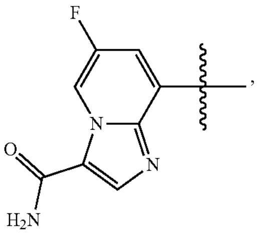
-continued
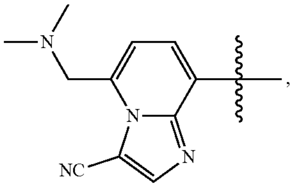
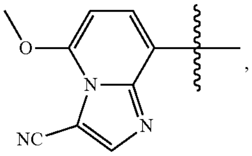
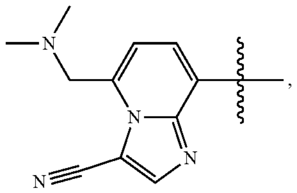
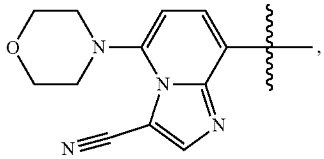
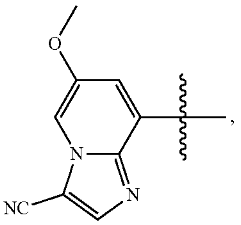
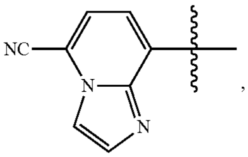
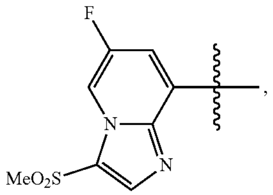
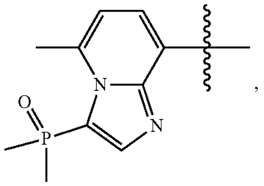
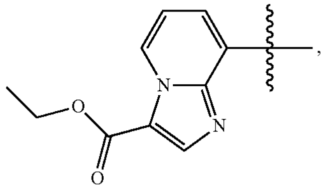
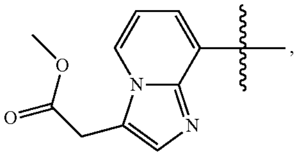
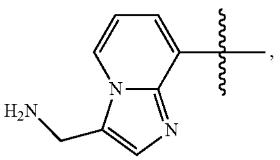
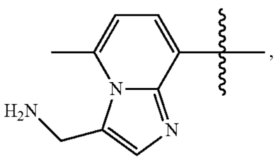
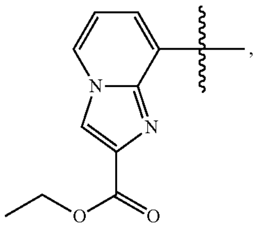
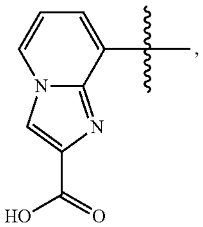

-continued

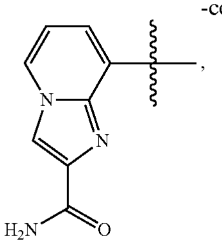

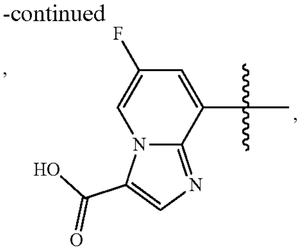

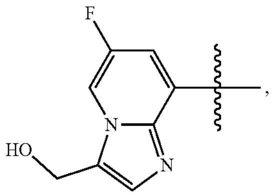

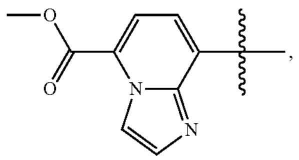

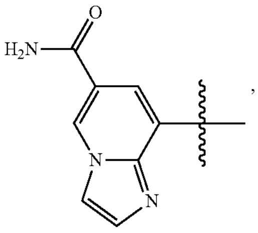

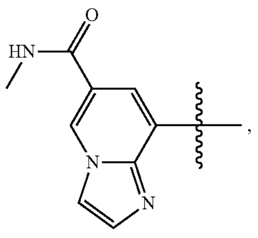

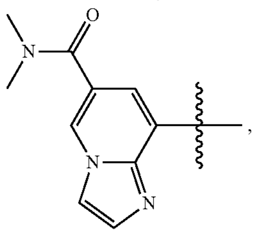

or

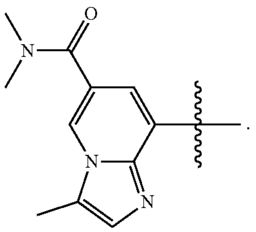 [SMILES: *c1cc(C(=O)N(C)C)cn2c(C)cnc12]

In certain embodiments, the moiety

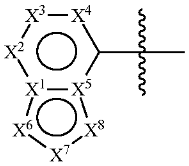

is preferably

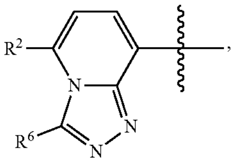

wherein the definitions of both $R^2$ and $R^6$ are as defined in the present disclosure.

In certain embodiments, in the moiety

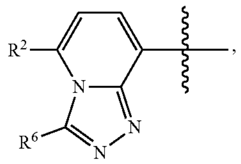

the definition of $R^2$ is preferably as below, and the definitions of the remaining letters and groups are as defined in the present disclosure:

$R^2$ is H, halogen, $C_{1-4}$ alkyl or $—NR^aR^b$; $R^a$ and $R^b$ are independently H or $C_{1-4}$ alkyl; further preferably, $R^2$ is H, —Cl, $—CH_3$, or $—N(CH_3)_2$.

In certain embodiments, in the moiety

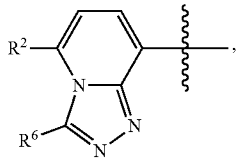

the definition of $R^6$ is preferably as below, and the definitions of the remaining letters and groups are as defined in the present disclosure:

$R^6$ is H or $C_{1-4}$ alkyl; further preferably, $R^6$ is H or $—CH_3$.

In certain embodiments,

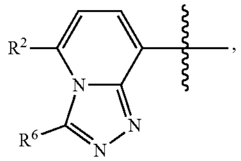

is preferably

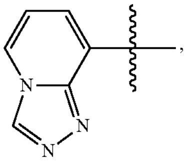

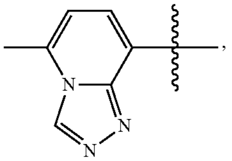

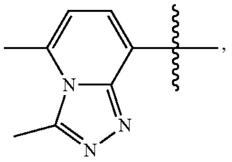

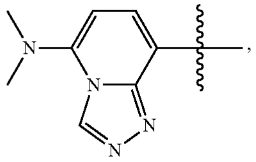

or

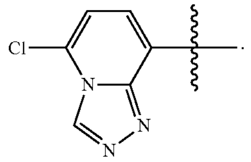

In certain embodiments,

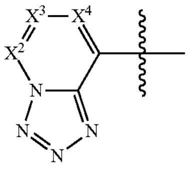

is preferably

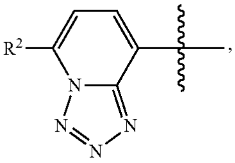, wherein $R^2$ is $C_{1-4}$ alkyl, such as

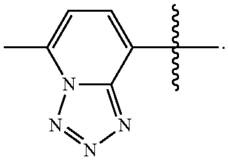 [SMILES: *c1ccc(C)n2nnnc12].

In certain embodiments, the moiety

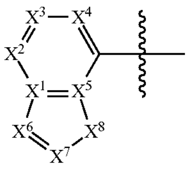

preferably

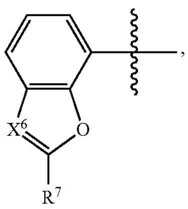, wherein $X^6$ is N or CH; $R^7$ is H, $C_{1-4}$ alkyl, $C_{1-4}$ haloalkyl, or —$NR^aR^b$; $R^a$ and $R^b$ are independently H or $C_{1-4}$ alkyl.

In certain embodiments, in the moiety

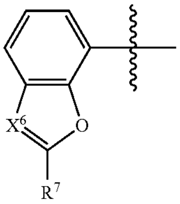, $R^7$ is H, —$CH_3$, —$NH_2$, or —$CF_3$.

In certain embodiments, the moiety

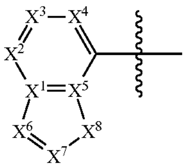

is preferably

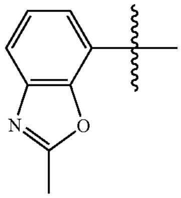, 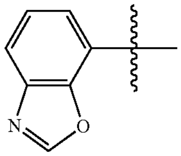,

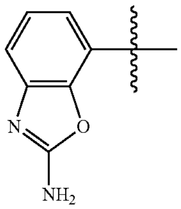, 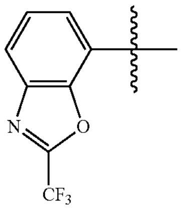, or

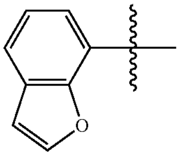.

In certain embodiments, the moiety

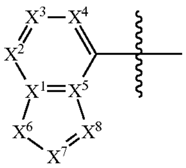

is preferably

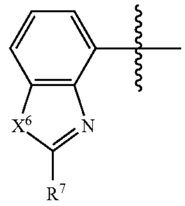

wherein $X^6$ is $NR^6$, O or S; $R^6$ is $C_{1-4}$ alkyl; $R^7$ is H, $C_{1-4}$ alkyl, $C_{1-4}$ haloalkyl, or —$NR^aR^b$; $R^a$ and $R^b$ are independently H or $C_{1-4}$ alkyl.

In certain embodiments, in the moiety

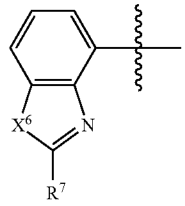

$X^6$ is —$NCH_3$, O or S.

In certain embodiments, in the moiety

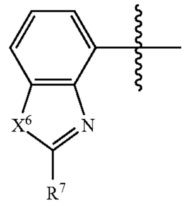

$R^7$ is H, —$CH_3$, —$NH_2$, or —$CF_3$.

In certain embodiments, the moiety

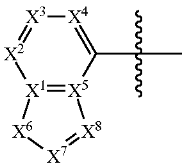

is preferably

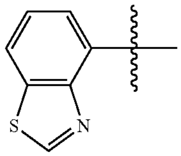 , 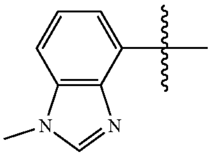 ,

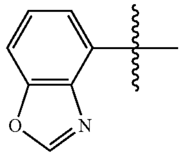 , 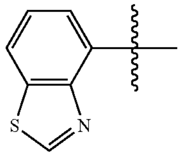 ,

-continued

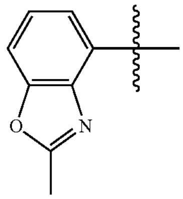 , 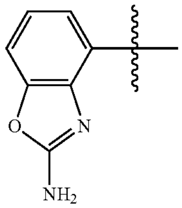 , or

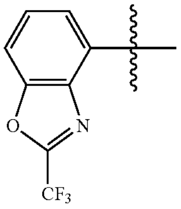 .

In certain embodiments, the moiety

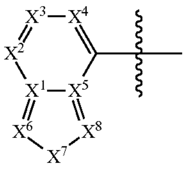

is preferably

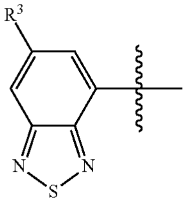 , $R^3$ is H or $C_{1-4}$ haloalkyl, such as

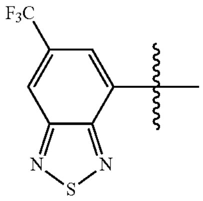 or 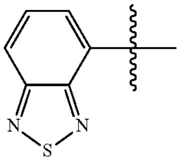 .

In certain embodiments, the moiety

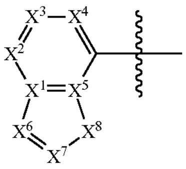

is preferably

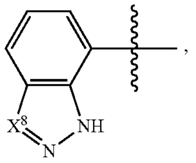

wherein $X^8$ is $CR^8$ or N; $R^8$ is H or $C_{1-4}$ alkyl, such as

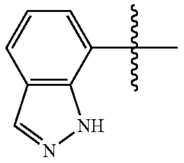
or
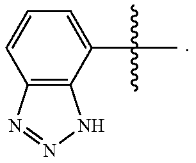

In certain embodiments, the moiety

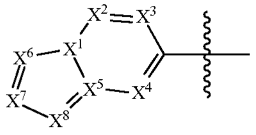

is preferably

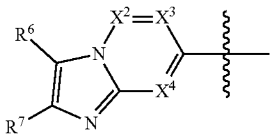
or
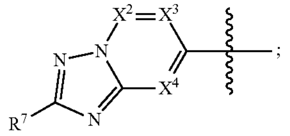

the definitions of $X^2$, $X^3$, $X^4$, $R^6$, and $R^7$ are as defined in the present disclosure.

In certain embodiments, the moiety

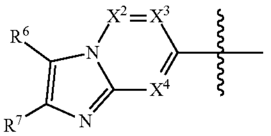

is preferably

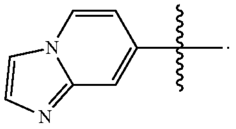 [SMILES: *c1ccn2ccnc2c1]

In certain embodiments, the moiety

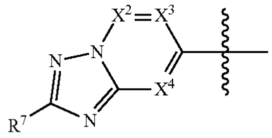

is preferably

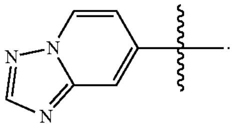 [SMILES: *c1ccn2ncnc2c1]

In certain embodiments, the moiety

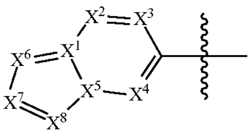

is preferably

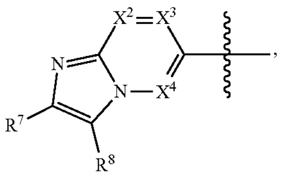

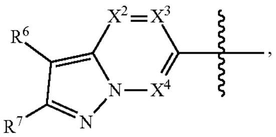
or
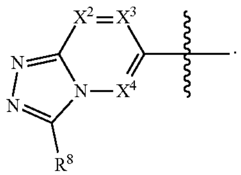

In certain embodiments, the moiety

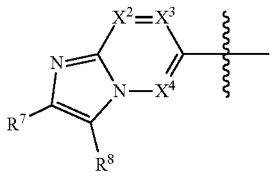

is preferably
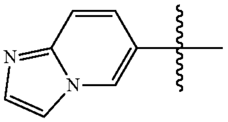
or
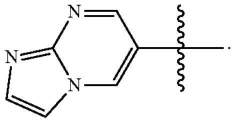
In certain embodiments, the moiety
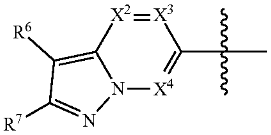
is preferably
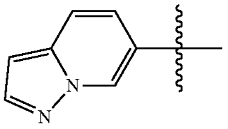
or
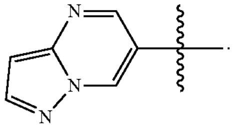
In certain embodiments, the moiety
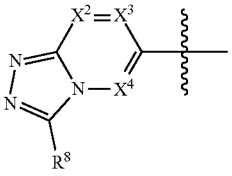
is preferably
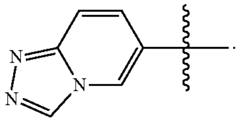 [SMILES: *c1ccc2nncn2c1]
In certain embodiments, the moiety
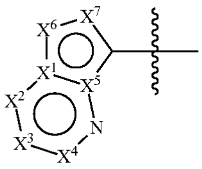
is preferably
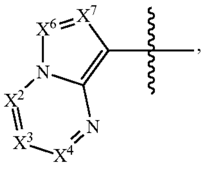
such as
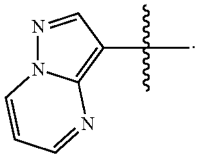 [SMILES: *c1cnn2cccnc12]
In certain embodiments, the moiety
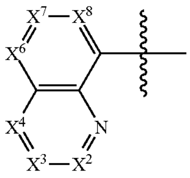
is preferably
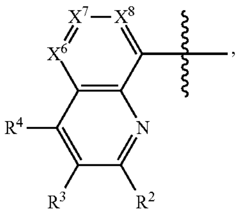
such as
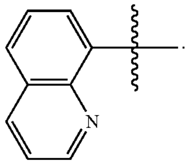 [SMILES: *c1cccc2cccnc12]
In certain embodiments, the moiety
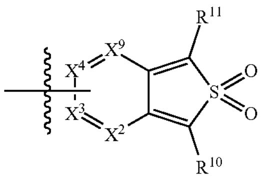

is preferably

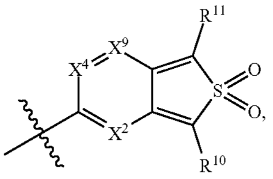

further preferably

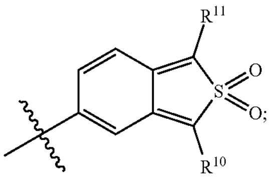

$R^{10}$ and $R^{11}$ are independently H or halogen (such as F), such as

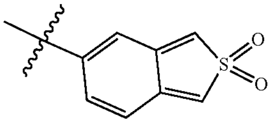

or

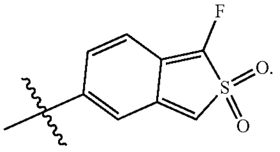

In certain embodiments, the moiety

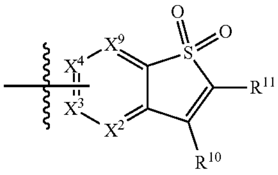

is preferably

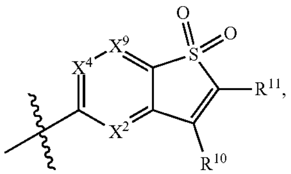

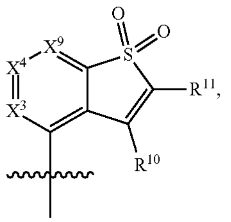

or

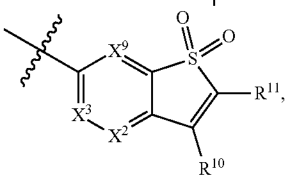

wherein the definitions of $X^2$, $X^3$, $X^4$, $X^9$, $R^{10}$ and $R^{11}$ are as defined in the present disclosure.

In certain embodiments, the moiety

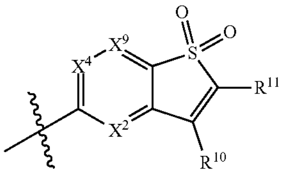

is preferably

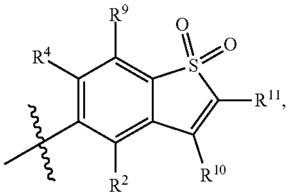

wherein the definitions of $R^2$, $R^4$, $R^9$, $R^{10}$, and $R^{11}$ are as defined in the present disclosure.

In certain embodiments, in the moiety

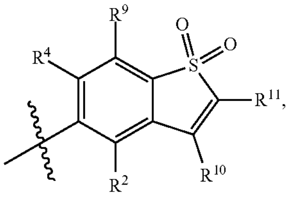

the definition of $R^2$ is preferably as below, and the definitions of the remaining letters and groups are as defined in the present disclosure:

$R^2$ is H or halogen; further preferably, $R^2$ is H or —F.

In certain embodiments, in the moiety

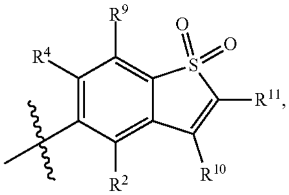

the definition of $R^4$ is preferably as below, and the definitions of the remaining letters and groups are as defined in the present disclosure:

$R^4$ is H, halogen or $C_{1-4}$ alkyl; further preferably, $R^4$ is H, —F or —$CH_3$.

In certain embodiments, in the moiety

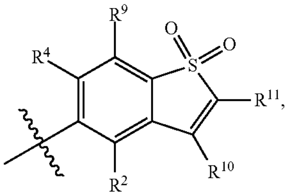

the definition of $R^9$ is preferably as below, and the definitions of the remaining letters and groups are as defined in the present disclosure:

$R^9$ is H, halogen or $C_{1-4}$ alkyl; further preferably, $R^9$ is H, —F, —Cl or —$CH_3$.

In certain embodiments, in the moiety

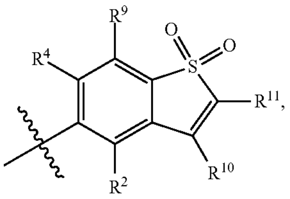

the definition of $R^{10}$ is preferably as below, and the definitions of the remaining letters and groups are as defined in the present disclosure:

$R^{10}$ is H, $C_{1-4}$ alkyl, $C_{1-4}$ alkyl substituted with 1, 2 or 3 amino groups, or halogen; further preferably, $R^{10}$ is H, —$CH_3$, —$CH_2CH_2NH_2$, —F or —Cl.

In certain embodiments, in the moiety

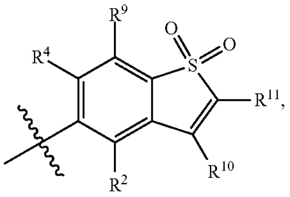

the definition of $R^{11}$ is preferably as below, and the definitions of the remaining letters and groups are as defined in the present disclosure:

$R^{11}$ is H, $C_{1-4}$ alkyl, or halogen; further preferably, $R^{11}$ is H, —$CH_3$ or —F.

In a preferred embodiment, the moiety

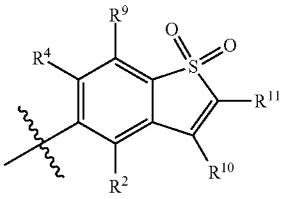

is preferably

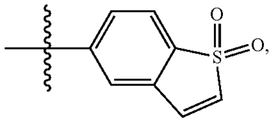 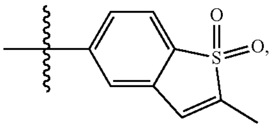

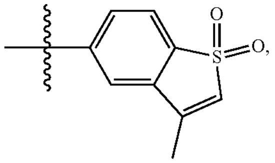 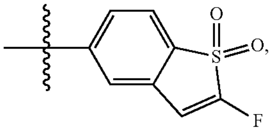

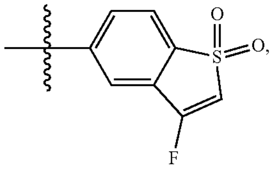 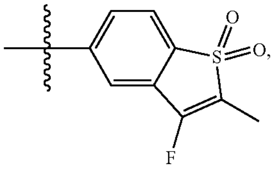

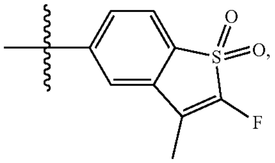 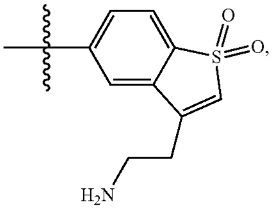

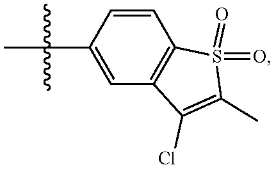 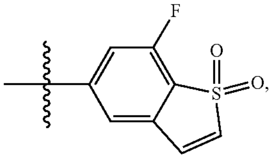

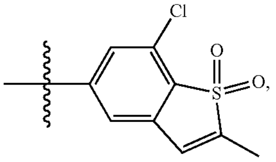 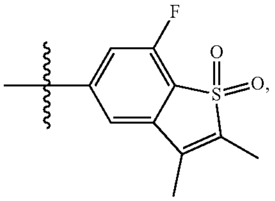

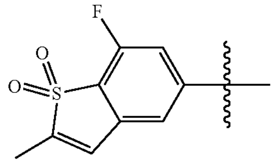 ,

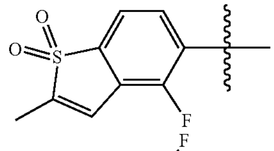 ,

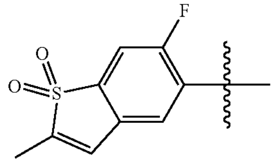 ,

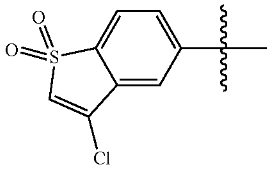 ,

-continued
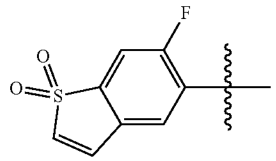
,
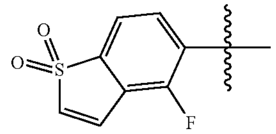
,
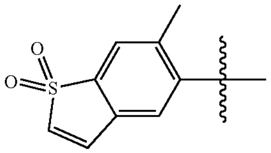
, or
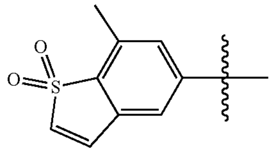
,
In a preferred embodiment, the moiety
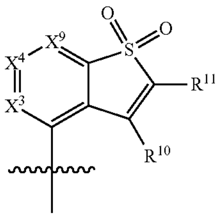
is preferably
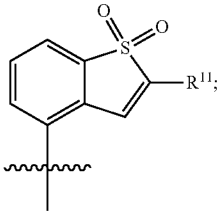
$R^{11}$ is H or $C_{1-4}$ alkyl (such as $—CH_3$), such as or
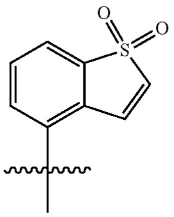
or
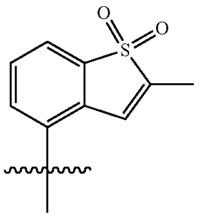
.
In a preferred embodiment, the moiety
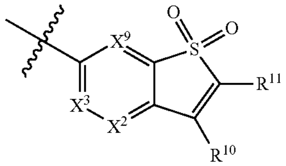
is preferably
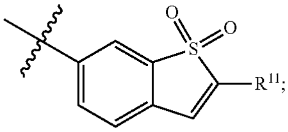
$R^{11}$ is H or $C_{1-4}$ alkyl (such as $—CH_3$), such as
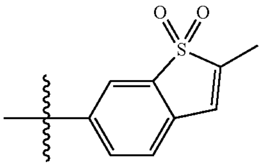
.
In a preferred embodiment, the moiety
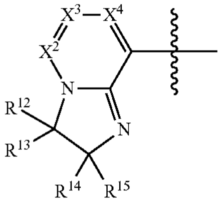
is preferably
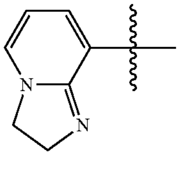
.
In a preferred embodiment, the $R^1$ is any one of the following structures:
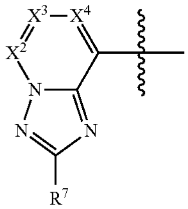
,
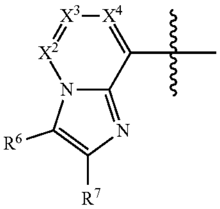
, -continued
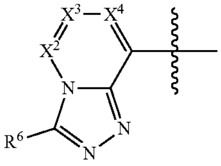, 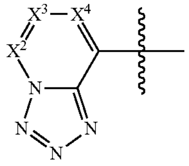,
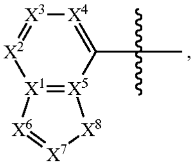, 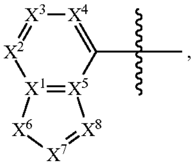,
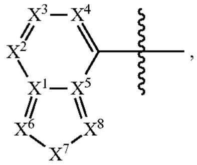, 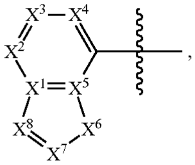,
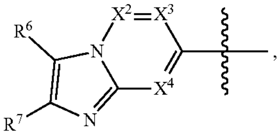, 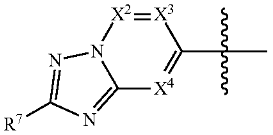,
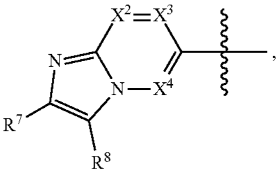, 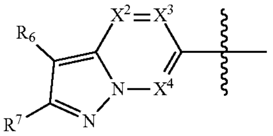,
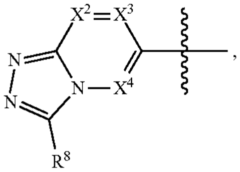, 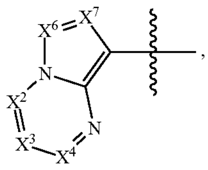,
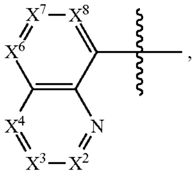, 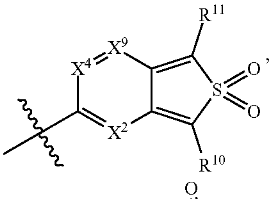,
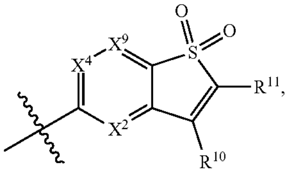, 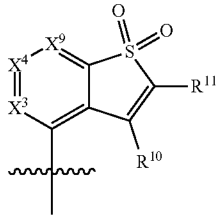,
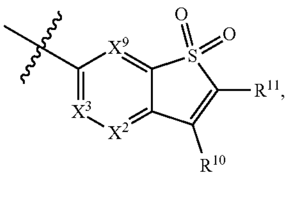 or 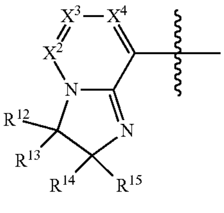,
wherein the definitions of each letter and group are as defined in the present disclosure.
In a preferred embodiment, the $R^1$ is any one of the following structures:
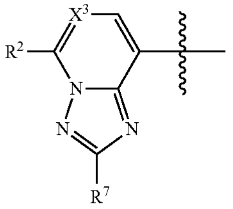, 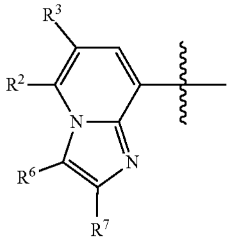,
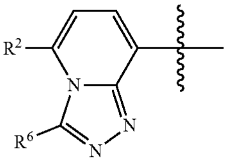, 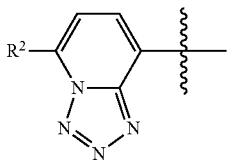,
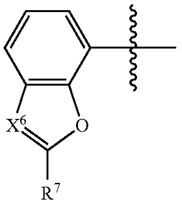, 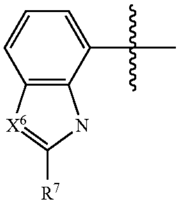,
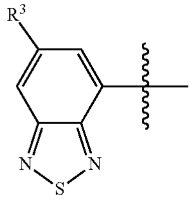, 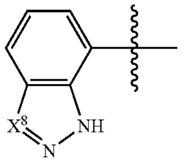,
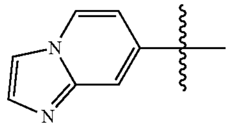, 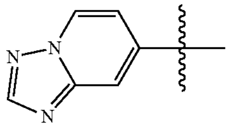,
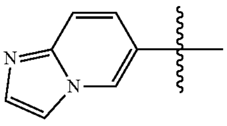, 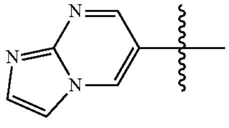,
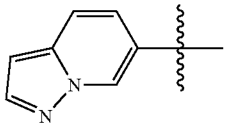, 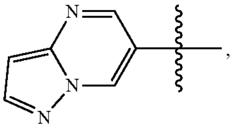,
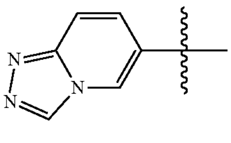, 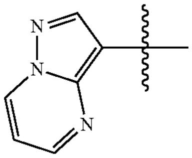,
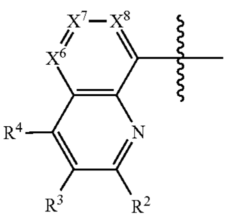, 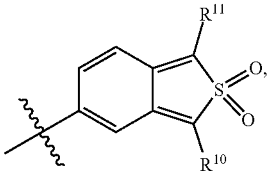

-continued

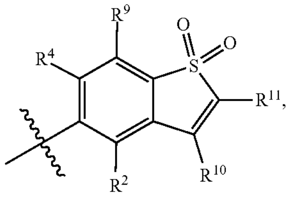

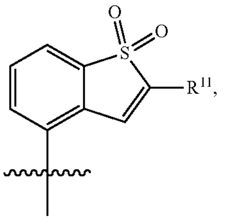

or

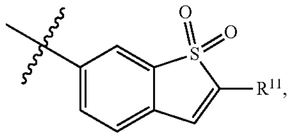

wherein the definitions of each letter and group are as defined in the present disclosure.

In another preferred example, the compound as shown in formula (I) is the compound as shown in formulae (Ia-1), (Ia-2), (Ia-3), (Ia-4), (Ia-5) or (Ia-6), (Ia-1)

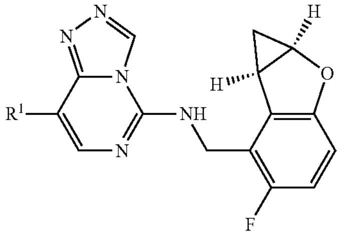

(Ia-2)

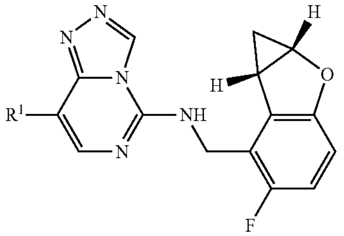

(Ia-3)

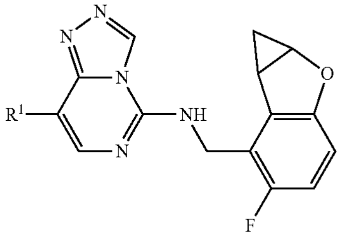

(Ia-4)

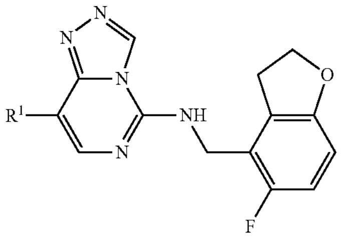

-continued (Ia-5)

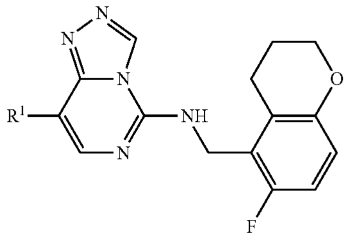

(Ia-6)

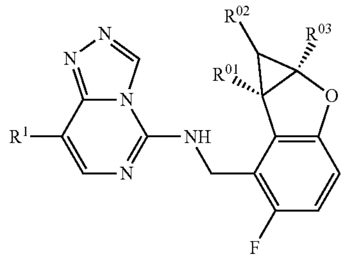

wherein the definition of $R^1$ is as described above.

In another preferred example, the compound as shown in formula (I) is the compound as shown in formulae (Ia-7), (Ia-8), (Ia-9), (Ia-10) or (Ia-11), (Ia-7)

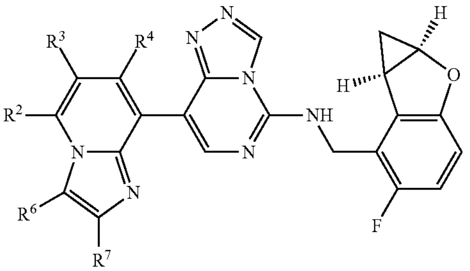

(Ia-8)

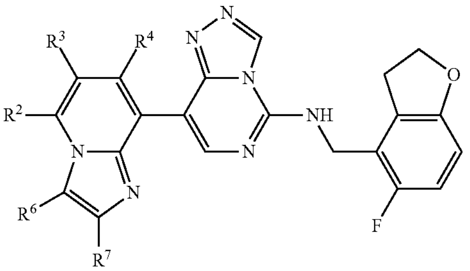

(Ia-9)

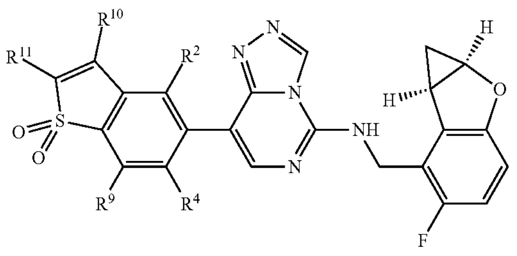

-continued (Ia-10)

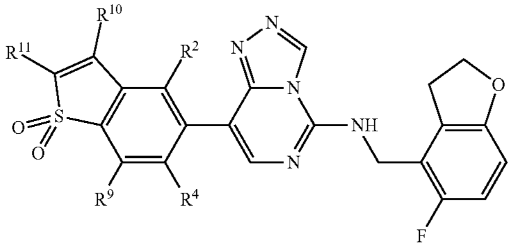

(Ia-11)

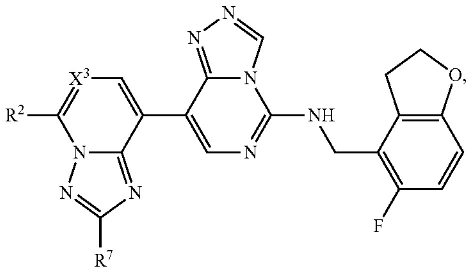

wherein the definitions of $X^3$, $R^2$, $R^3$, $R^4$, $R^6$, $R^7$, $R^9$, $R^{10}$ and $R^{11}$ are as described above.

In another preferred example, the compound as shown in formula (I) is the compound as shown in formulae (Tb) or (Ic), (Ib)

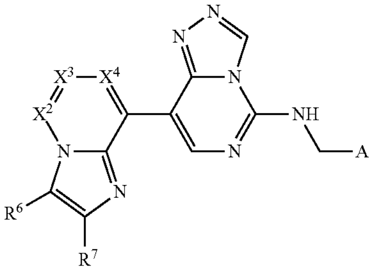

(Ic)

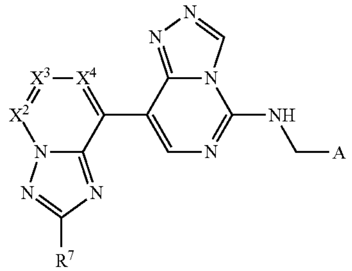

wherein the definitions of $X^2$, $X^3$, $X^4$, $R^6$, $R^7$, and A are as defined in the present disclosure.

In a further preferred example, the compound as shown in formula (I) is selected from the compounds as shown in Table 1 below:

TABLE 1

| Compound No. | Compound structure | Compound name |
|---|---|---|
| 1 | 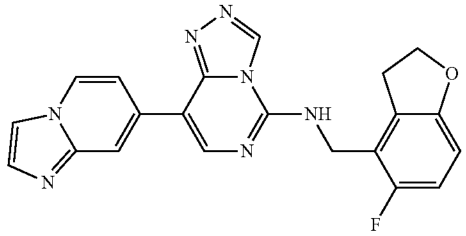 [SMILES: Fc1ccc2c(c1CNc1ncc(-c3ccn4ccnc4c3)c3nncn13)CCO2] | N-((5-fluoro-2,3-dihydrobenzofuran-4-yl)methyl)-8-(imidazo[1,2-a]pyridin-7-yl)-[1,2,4]triazolo[4,3-c]pyrimidin-5-amine |
| 2 | 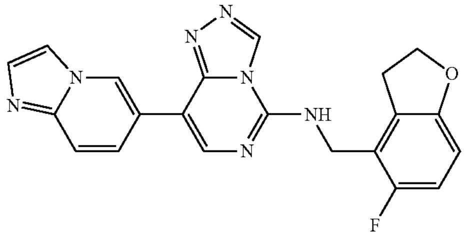 [SMILES: Fc1ccc2c(c1CNc1ncc(-c3ccc4nccn4c3)c3nncn13)CCO2] | N-((5-fluoro-2,3-dihydrobenzofuran-4-yl)methyl)-8-(imidazo[1,2-a]pyridin-6-yl)-[1,2,4]triazolo[4,3-c]pyrimidin-5-amine |
| 3 | 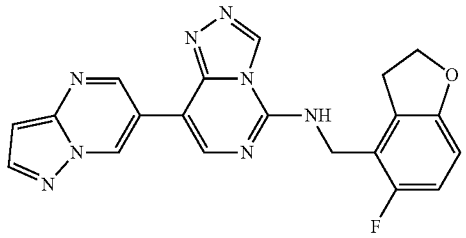 | N-((5-fluoro-2,3-dihydrobenzofuran-4-yl)methyl)-8-(pyrazolo[1,5-a]pyrimidin-6-yl)-[1,2,4]triazolo[4,3-c]pyrimidin-5-amine |

TABLE 1-continued

| Compound No. | Compound structure | Compound name |
|---|---|---|
| 4 | 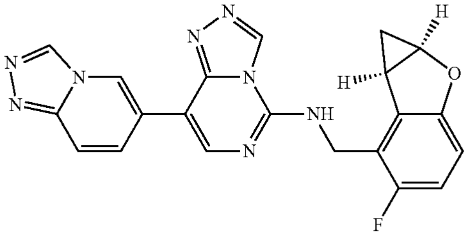 [SMILES: Fc1ccc2c(c1CNc1ncc(-c3ccc4nncn4c3)c3nncn13)[C@H]1C[C@H]1O2] | 8-([1,2,4]triazolo[4,3-a]pyridin-6-yl)-N-(((1aR,6bR)-5-fluoro-1a,6b-dihydro-1H-cyclopropa[b]benzofuran-6-yl)methyl)-[1,2,4]triazolo[4,3-c]pyrimidin-5-amine |
| 5 | 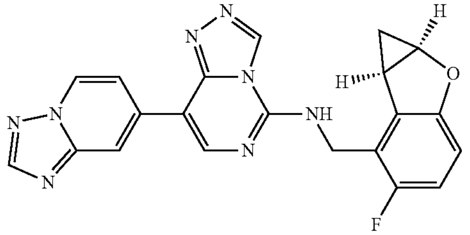 [SMILES: Fc1ccc2c(c1CNc1ncc(-c3ccn4ncnc4c3)c3nncn13)[C@H]1C[C@H]1O2] | 8-([1,2,4]triazolo[1,5-a]pyridin-7-yl)-N-(((1aR,6bR)-5-fluoro-1a,6b-dihydro-1H-cyclopropa[b]benzofuran-6-yl)methyl)-[1,2,4]triazolo[4,3-c]pyrimidin-5-amine |
| 6 | 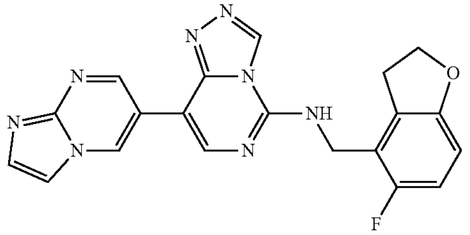 [SMILES: Fc1ccc2c(c1CNc1ncc(-c3cnc4nccn4c3)c3nncn13)CCO2] | N-((5-fluoro-2,3-dihydrobenzofuran-4-yl)methyl)-8-(imidazo[1,2-a]pyrimidin-6-yl)-[1,2,4]triazolo[4,3-c]pyrimidin-5-amine |
| 7 | 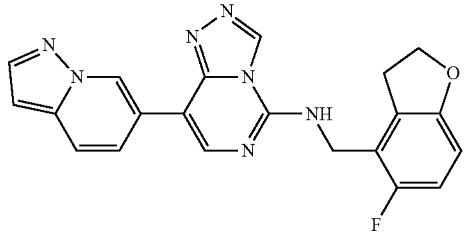 | N-((5-fluoro-2,3-dihydrobenzofuran-4-yl)methyl)-8-(pyrazolo[1,5-a]pyridin-6-yl)-[1,2,4]triazolo[4,3-c]pyrimidin-5-amine |
| 8 | 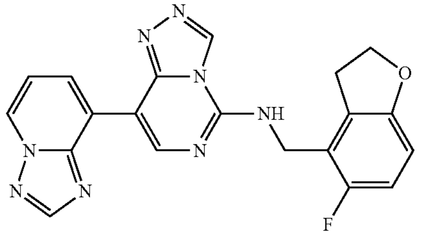 [SMILES: Fc1ccc2c(c1CNc1ncc(-c3cccn4ncnc34)c3nncn13)CCO2] | 8-([1,2,4]triazolo[1,5-a]pyridin-8-yl)-N-((5-fluoro-2,3-dihydrobenzofuran-4-yl)methyl)-[1,2,4]triazolo[4,3-c]pyrimidin-5-amine |
| 9 | 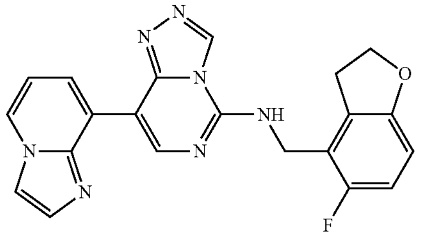 [SMILES: Fc1ccc2c(c1CNc1ncc(-c3cccn4ccnc34)c3nncn13)CCO2] | N-((5-fluoro-2,3-dihydrobenzofuran-4-yl)methyl)-8-(imidazo[1,2-a]pyridin-8-yl)-[1,2,4]triazolo[4,3-c]pyrimidin-5-amine |

TABLE 1-continued

| Compound No. | Compound structure | Compound name |
|---|---|---|
| 10 | 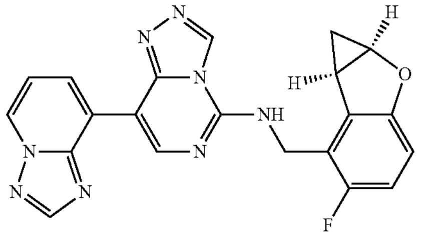 [SMILES: Fc1ccc2c(c1CNc1ncc(-c3cccn4ncnc34)c3nncn13)[C@H]1C[C@H]1O2] | 8-([1,2,4]triazolo[1,5-a]pyridin-8-yl)-N-(((1aR,6bR)-5-fluoro-1a,6b-dihydro-1H-cyclopropa[b]benzofuran-6-yl)methyl)-[1,2,4]triazolo[4,3-c]pyrimidin-5-amine |
| 11 | 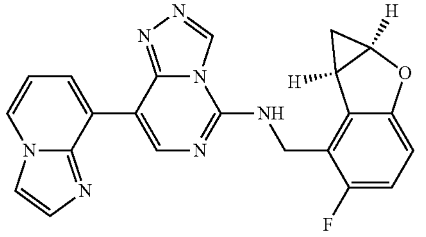 | N-(((1aR,6bR)-5-fluoro-1a,6b-dihydro-1H-cyclopropa[b]benzofuran-6-yl)methyl)-8-(imidazo[1,2-a]pyridin-8-yl)-[1,2,4]triazolo[4,3-c]pyrimidin-5-amine |
| 12 | 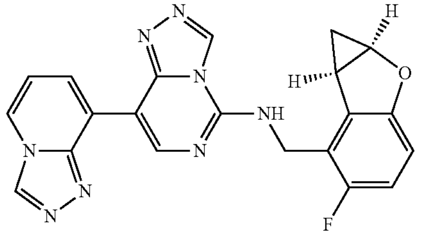 [SMILES: Fc1ccc2c(c1CNc1ncc(-c3cccn4cnnc34)c3nncn13)[C@H]1C[C@H]1O2] | 8-([1,2,4]triazolo[4,3-a]pyridin-8-yl)-N-(((1aR,6bR)-5-fluoro-1a,6b-dihydro-1H-cyclopropa[b]benzofuran-6-yl)methyl)-[1,2,4]triazolo[4,3-c]pyrimidin-5-amine |
| 13 | 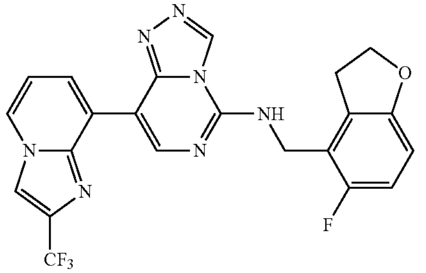 [SMILES: Fc1ccc2c(c1CNc1ncc(-c3cccn4cc(C(F)(F)F)nc34)c3nncn13)CCO2] | N-((5-fluoro-2,3-dihydrobenzofuran-4-yl)methyl)-8-(2-(trifluoromethyl)imidazo[1,2-a]pyridin-8-yl)-[1,2,4]triazolo[4,3-c]pyrimidin-5-amine |
| 14 | 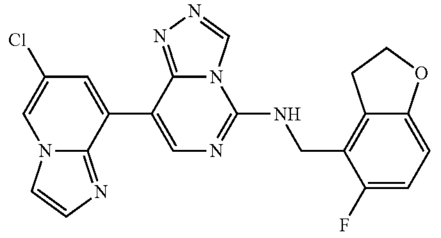 [SMILES: Fc1ccc2c(c1CNc1ncc(-c3cc(Cl)cn4ccnc34)c3nncn13)CCO2] | 8-(6-chloroimidazo[1,2-a]pyridin-8-yl)-N-((5-fluoro-2,3-dihydrobenzofuran-4-yl)methyl)-[1,2,4]triazolo[4,3-c]pyrimidin-5-amine |
| 15 | 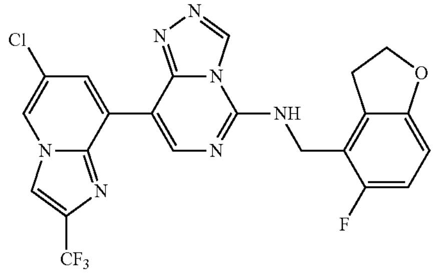 [SMILES: Fc1ccc2c(c1CNc1ncc(-c3cc(Cl)cn4cc(C(F)(F)F)nc34)c3nncn13)CCO2] | 8-(6-chloro-2-(trifluoromethyl)imidazo[1,2-a]pyridin-8-yl)-N-((5-fluoro-2,3-dihydrobenzofuran-4-yl)methyl)-[1,2,4]triazolo[4,3-c]pyrimidin-5-amine |

TABLE 1-continued

| Compound No. | Compound structure | Compound name |
|---|---|---|
| 16 | 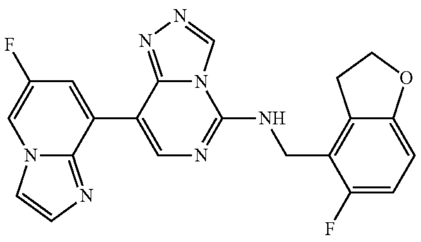 [SMILES: Fc1cc(-c2cnc(NCc3c(F)ccc4c3CCO4)n3cnnc23)c2nccn2c1] | N-((5-fluoro-2,3-dihydrobenzofuran-4-yl)methyl)-8-(6-fluoroimidazo[1,2-a]pyridin-8-yl)-[1,2,4]triazolo[4,3-c]pyrimidin-5-amine |
| 17 | 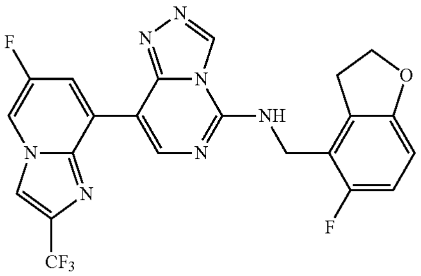 [SMILES: Fc1cc(-c2cnc(NCc3c(F)ccc4c3CCO4)n3cnnc23)c2nc(C(F)(F)F)cn2c1] | N-((5-fluoro-2,3-dihydrobenzofuran-4-yl)methyl)-8-(6-fluoro-2-(trifluoromethyl)imidazo[1,2-a]pyridin-8-yl)-[11,2,4]triazolo[4,3-c]pyrimidin-5-amine |
| 18 | 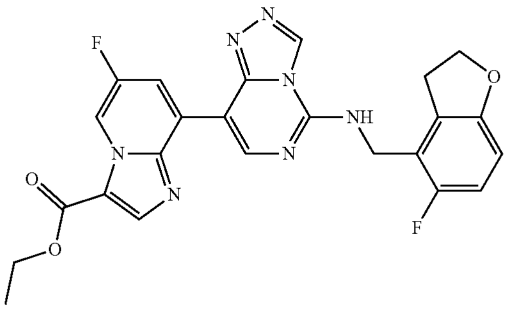 [SMILES: CCOC(=O)c1cnc2c(-c3cnc(NCc4c(F)ccc5c4CCO5)n4cnnc34)cc(F)cn12] | Ethyl 6-fluoro-8-(5-(((5-fluoro-2,3-dihydrobenzofuran-4-yl)methyl)amino)-[1,2,4]triazolo[4,3-c]pyrimidin-8-yl)imidazo[1,2-a]pyridine-3-carboxylate |
| 19 | 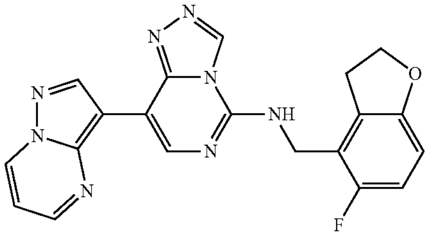 [SMILES: Fc1ccc2c(c1CNc1ncc(-c3cnn4cccnc34)c3nncn13)CCO2] | N-((5-fluoro-2,3-dihydrobenzofuran-4-yl)methyl)-8-(pyrazolo[1,5-a]pyrimidin-3-yl)-[1,2,4]triazolo[4,3-c]pyrimidin-5-amine |
| 20 | 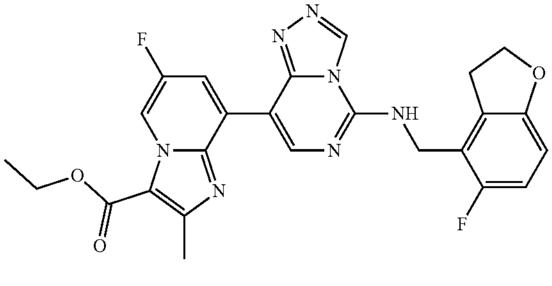 [SMILES: CCOC(=O)c1c(C)nc2c(-c3cnc(NCc4c(F)ccc5c4CCO5)n4cnnc34)cc(F)cn12] | Ethyl 6-fluoro-8-(5-(((5-fluoro-2,3-dihydrobenzofuran-4-yl)methyl)amino)-[1,2,4]triazolo[4,3-c]pyrimidin-8-yl)-2-methylimidazo[1,2-a]pyridine-3-carboxylate |

TABLE 1-continued

| Compound No. | Compound structure | Compound name |
|---|---|---|
| 21 | 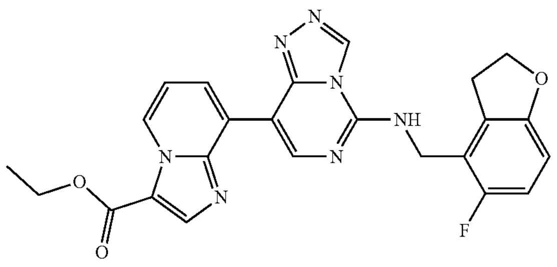 [SMILES: CCOC(=O)c1cnc2c(-c3cnc(NCc4c(F)ccc5c4CCO5)n4cnnc34)cccn12] | Ethyl 8-(5-(((5-fluoro-2,3-dihydrobenzofuran-4-yl)methyl)amino)-[1,2,4]triazolo[4,3-c]pyrimidin-8-yl)imidazo[1,2-a]pyridine-3-carboxylate |
| 22 | 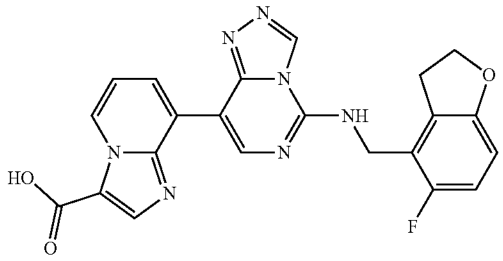 [SMILES: O=C(O)c1cnc2c(-c3cnc(NCc4c(F)ccc5c4CCO5)n4cnnc34)cccn12] | 8-(5-(((5-fluoro-2,3-dihydrobenzofuran-4-yl)methyl)amino)-[1,2,4]triazolo[4,3-c]pyrimidin-8-yl)imidazo[1,2-a]pyridine-3-carboxylic acid |
| 23 | 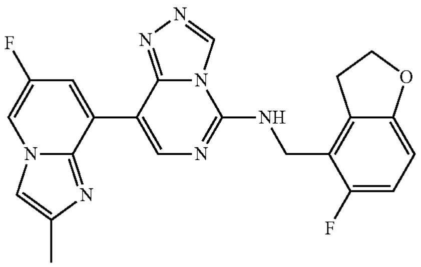 [SMILES: Cc1cn2cc(F)cc(-c3cnc(NCc4c(F)ccc5c4CCO5)n4cnnc34)c2n1] | N-((5-fluoro-2,3-dihydrobenzofuran-4-yl)methyl)-8-(6-fluoro-2-methylimidazo[1,2-a]pyridin-8-yl)-[1,2,4]triazolo[4,3-c]pyrimidin-5-amine |
| 24 | 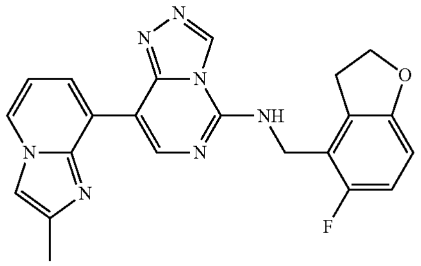 [SMILES: Cc1cn2cccc(-c3cnc(NCc4c(F)ccc5c4CCO5)n4cnnc34)c2n1] | N-((5-fluoro-2,3-dihydrobenzofuran-4-yl)methyl)-8-(2-methylimidazo[1,2-a]pyridin-8-yl)-[1,2,4]triazolo[4,3-c]pyrimidin-5-amine |
| 25 | 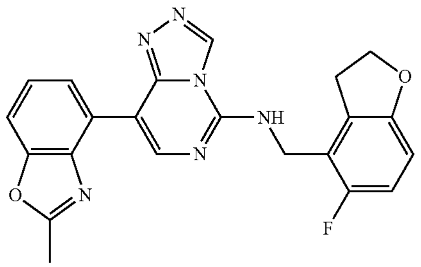 [SMILES: Cc1nc2c(-c3cnc(NCc4c(F)ccc5c4CCO5)n4cnnc34)cccc2o1] | N-((5-fluoro-2,3-dihydrobenzofuran-4-yl)methyl)-8-(2-methylbenzo[d]oxazol-4-yl)-[1,2,4]triazolo[4,3-c]pyrimidin-5-amine |

TABLE 1-continued

| Compound No. | Compound structure | Compound name |
| --- | --- | --- |
| 26 | 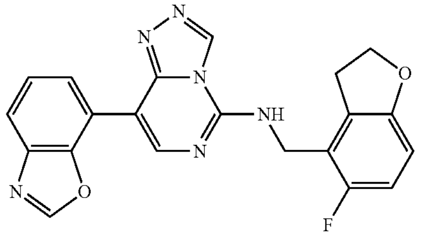 [SMILES: Fc1ccc2c(c1CNc1ncc(-c3cccc4ncoc34)c3nncn13)CCO2] | 8-(benzo[d]oxazol-7-yl)-N-((5-fluoro-2,3-dihydrobenzofuran-4-yl)methyl)-[1,2,4]triazolo[4,3-c]pyrimidin-5-amine |
| 27 | 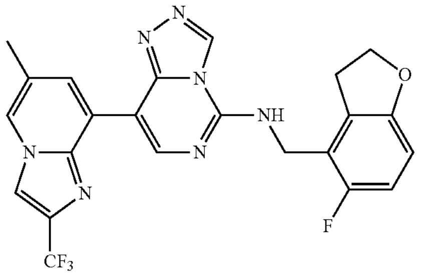 [SMILES: Cc1cc(-c2cnc(NCc3c(F)ccc4c3CCO4)n3cnnc23)c2nc(C(F)(F)F)cn2c1] | N-((5-fluoro-2,3-dihydrobenzofuran-4-yl)methyl)-8-(6-methyl-2-(trifluoromethyl)imidazo[1,2-a]pyridin-8-yl)-[1,2,4]triazolo[4,3-c]pyrimidin-5-amine |
| 28 | 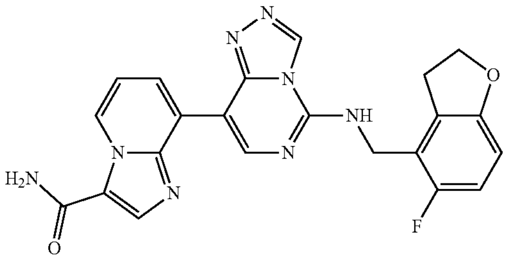 [SMILES: NC(=O)c1cnc2c(-c3cnc(NCc4c(F)ccc5c4CCO5)n4cnnc34)cccn12] | 8-(5-(((5-fluoro-2,3-dihydrobenzofuran-4-yl)methyl)amino)-[1,2,4]triazolo[4,3-c]pyrimidin-8-yl)imidazo[1,2-a]pyridine-3-carboxamide |
| 29 | 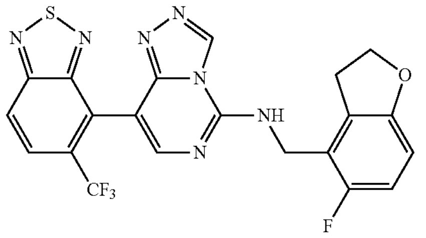 [SMILES: Fc1ccc2c(c1CNc1ncc(-c3c(C(F)(F)F)ccc4nsnc34)c3nncn13)CCO2] | N-((5-fluoro-2,3-dihydrobenzofuran-4-yl)methyl)-8-(5-(trifluoromethyl)benzo[c][1,2,5]thiadiazol-4-yl)-[1,2,4]triazolo[4,3-c]pyrimidin-5-amine |
| 30 | 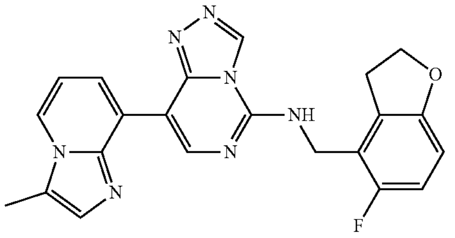 [SMILES: Cc1cnc2c(-c3cnc(NCc4c(F)ccc5c4CCO5)n4cnnc34)cccn12] | N-((5-fluoro-2,3-dihydrobenzofuran-4-yl)methyl)-8-(3-methylimidazo[1,2-a]pyridin-8-yl)-[1,2,4]triazolo[4,3-c]pyrimidin-5-amine |
| 31 | 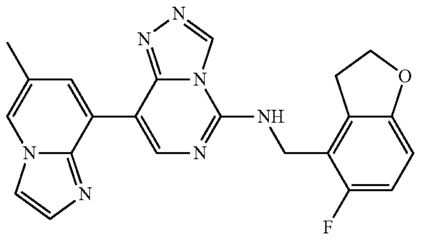 [SMILES: Cc1cc(-c2cnc(NCc3c(F)ccc4c3CCO4)n3cnnc23)c2nccn2c1] | N-((5-fluoro-2,3-dihydrobenzofuran-4-yl)methyl)-8-(6-methylimidazo[1,2-a]pyridin-8-yl)-[1,2,4]triazolo[4,3-c]pyrimidin-5-amine |

TABLE 1-continued

| Compound No. | Compound structure | Compound name |
|---|---|---|
| 32 | 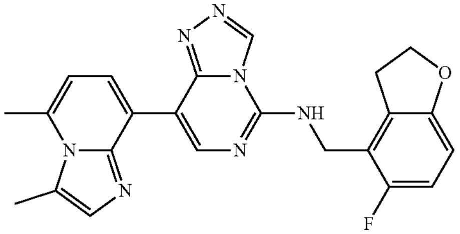 [SMILES: Cc1ccc(-c2cnc(NCc3c(F)ccc4c3CCO4)n3cnnc23)c2ncc(C)n12] | 8-(3,5-dimethylimidazo[1,2-a]pyridin-8-yl)-N-((5-fluoro-2,3-dihydrobenzofuran-4-yl)methyl)-[1,2,4]triazolo[4,3-c]pyrimidin-5-amine |
| 33 | 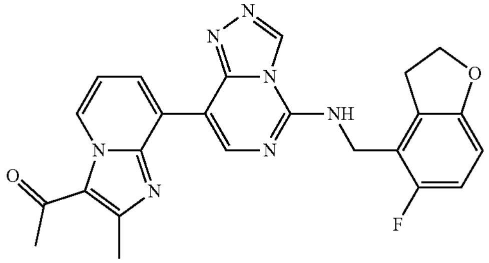 [SMILES: CC(=O)c1c(C)nc2c(-c3cnc(NCc4c(F)ccc5c4CCO5)n4cnnc34)cccn12] | 1-(8-(5-(((5-fluoro-2,3-dihydrobenzofuran-4-yl)methyl)amino)-[1,2,4]triazolo[4,3-c]pyrimidin-8-yl)-2-methylimidazo[1,2-a]pyridin-3-yl)ethan-1-one |
| 34 | 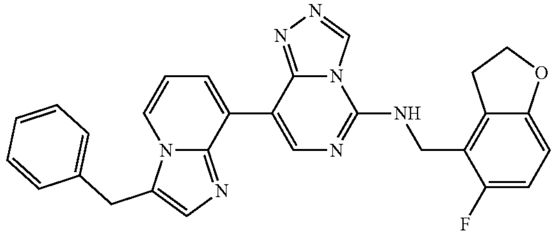 [SMILES: Fc1ccc2c(c1CNc1ncc(-c3cccn4c(Cc5ccccc5)cnc34)c3nncn13)CCO2] | 8-(3-phenylmethylimidazo[1,2-a]pyridin-8-yl)-N-((5-fluoro-2,3-dihydrobenzofuran-4-yl)methyl)-[1,2,4]triazolo[4,3-c]pyrimidin-5-amine |
| 35 | 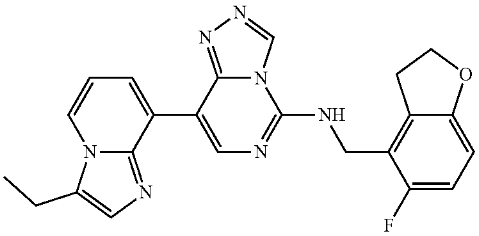 [SMILES: CCc1cnc2c(-c3cnc(NCc4c(F)ccc5c4CCO5)n4cnnc34)cccn12] | 8-(3-ethylimidazo[1,2-a]pyridin-8-yl)-N-((5-fluoro-2,3-dihydrobenzofuran-4-yl)methyl)-[1,2,4]triazolo[4,3-c]pyrimidin-5-amine |
| 36 | 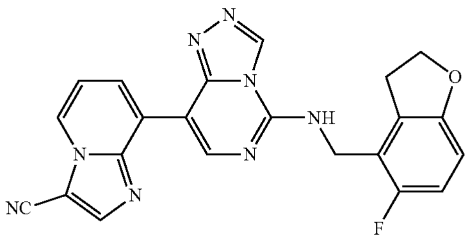 [SMILES: N#Cc1cnc2c(-c3cnc(NCc4c(F)ccc5c4CCO5)n4cnnc34)cccn12] | 8-(5-(((5-fluoro-2,3-dihydrobenzofuran-4-yl)methyl)amino)-[1,2,4]triazolo[4,3-c]pyrimidin-8-yl)imidazo[1,2-a]pyridine-3-carbonitrile |
| 37 | 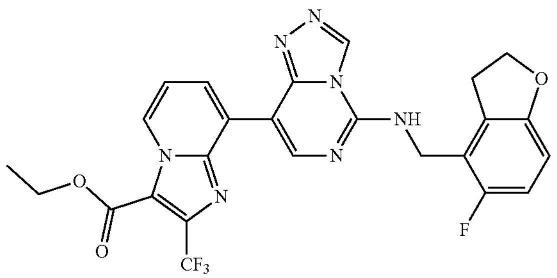 [SMILES: CCOC(=O)c1c(C(F)(F)F)nc2c(-c3cnc(NCc4c(F)ccc5c4CCO5)n4cnnc34)cccn12] | Ethyl 8-(5-(((5-fluoro-2,3-dihydrobenzofuran-4-yl)methyl)amino)-[1,2,4]triazolo[4,3-c]pyrimidin-8-yl)-2-(trifluoromethyl)imidazo[1,2-a]pyridine-3-carboxylate |

TABLE 1-continued

| Compound No. | Compound structure | Compound name |
| --- | --- | --- |
| 38 | 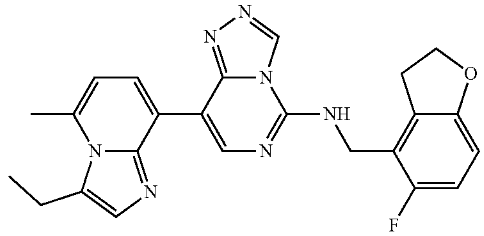 [SMILES: CCc1cnc2c(-c3cnc(NCc4c(F)ccc5c4CCO5)n4cnnc34)ccc(C)n12] | 8-(3-ethyl-5-methylimidazo[1,2-a]pyridin-8-yl)-N-((5-fluoro-2,3-dihydrobenzofuran-4-yl)methyl)-[1,2,4]triazolo[4,3-c]pyrimidin-5-amine |
| 39 | 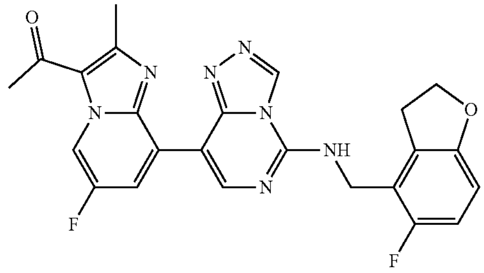 [SMILES: CC(=O)c1c(C)nc2c(-c3cnc(NCc4c(F)ccc5c4CCO5)n4cnnc34)cc(F)cn12] | 1-(6-fluoro-8-(5-(((5-fluoro-2,3-dihydrobenzofuran-4-yl)methyl)amino)-[1,2,4]triazolo[4,3-c]pyrimidin-8-yl)-2-methylimidazo[1,2-a]pyridin-3-yl)ethan-1-one |
| 40 | 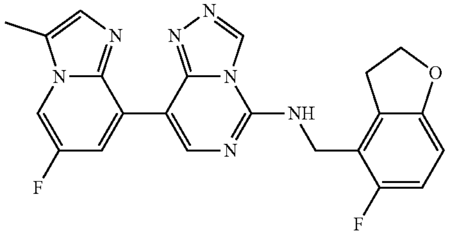 [SMILES: Cc1cnc2c(-c3cnc(NCc4c(F)ccc5c4CCO5)n4cnnc34)cc(F)cn12] | N-((5-fluoro-2,3-dihydrobenzofuran-4-yl)methyl)-8-(6-fluoro-3-methylimidazo[1,2-a]pyridin-8-yl)-[1,2,4]triazolo[4,3-c]pyrimidin-5-amine |
| 41 | 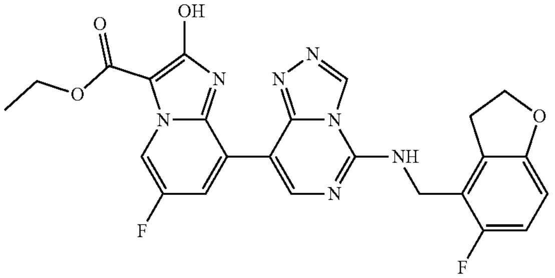 [SMILES: CCOC(=O)c1c(O)nc2c(-c3cnc(NCc4c(F)ccc5c4CCO5)n4cnnc34)cc(F)cn12] | Ethyl 6-fluoro-8-(5-(((5-fluoro-2,3-dihydrobenzofuran-4-yl)methyl)amino)-[1,2,4]triazolo[4,3-c]pyrimidin-8-yl)-2-hydroxyimidazo[1,2-a]pyridine-3-carboxylate |
| 42 | 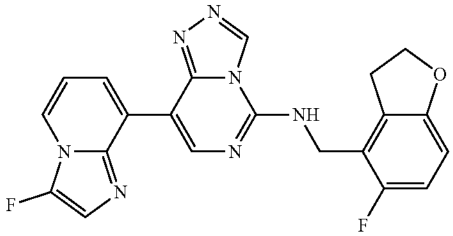 [SMILES: Fc1ccc2c(c1CNc1ncc(-c3cccn4c(F)cnc34)c3nncn13)CCO2] | N-((5-fluoro-2,3-dihydrobenzofuran-4-yl)methyl)-8-(3-fluoroimidazo[1,2-a]pyridin-8-yl-[1,2,4]triazolo[4,3-c]pyrimidin-5-amine |
| 43 | 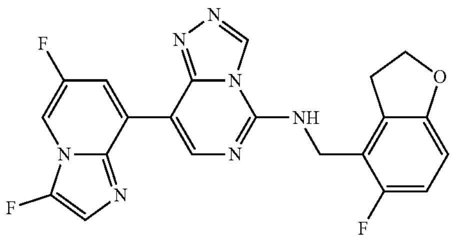 [SMILES: Fc1cc(-c2cnc(NCc3c(F)ccc4c3CCO4)n3cnnc23)c2ncc(F)n2c1] | 8-(3,6-difluoroimidazo[1,2-a]pyridin-8-yl)-N-((5-fluoro-2,3-dihydrobenzofuran-4-yl)methyl)-[1,2,4]triazolo[4,3-c]pyrimidin-5-amine |

TABLE 1-continued

| Compound No. | Compound structure | Compound name |
| --- | --- | --- |
| 44 | 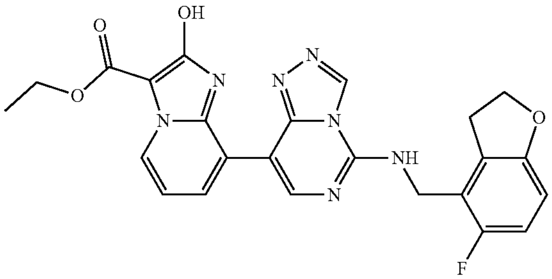 [SMILES: CCOC(=O)c1c(O)nc2c(-c3cnc(NCc4c(F)ccc5c4CCO5)n4cnnc34)cccn12] | Ethyl 8-(5-(((5-fluoro-2,3-dihydrobenzofuran-4-yl)methyl)amino)-[1,2,4]triazolo[4,3-c]pyrimidin-8-yl)-2-hydroxyimidazo[1,2-a]pyridine-3-carboxylate |
| 45 | 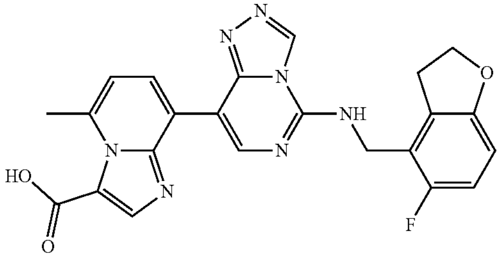 [SMILES: Cc1ccc(-c2cnc(NCc3c(F)ccc4c3CCO4)n3cnnc23)c2ncc(C(=O)O)n12] | 8-(5-(((5-fluoro-2,3-dihydrobenzofuran-4-yl)methyl)amino)-[1,2,4]triazolo[4,3-c]pyrimidin-8-yl)-5-methylimidazo[1,2-a]pyridine-3-carboxylic acid |
| 46 | 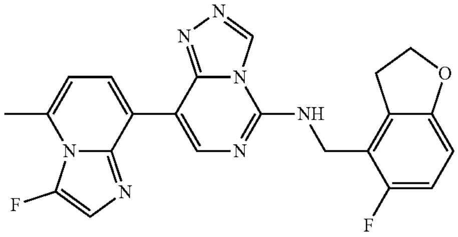 | N-((5-fluoro-2,3-dihydrobenzofuran-4-yl)methyl)-8-(3-fluoro-5-methylimidazo[1,2-a]pyridin-8-yl)-[1,2,4]triazolo[4,3-c]pyrimidin-5-amine |
| 47 | 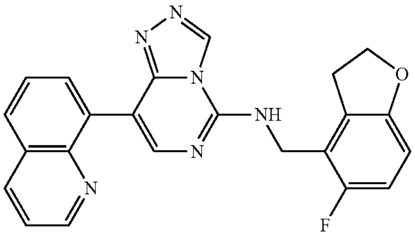 [SMILES: Fc1ccc2c(c1CNc1ncc(-c3cccc4cccnc34)c3nncn13)CCO2] | N-((5-fluoro-2,3-dihydrobenzofuran-4-yl)methyl)-8-(quinolin-8-yl)-[1,2,4]triazolo[4,3-c]pyrimidin-5-amine |
| 48 | 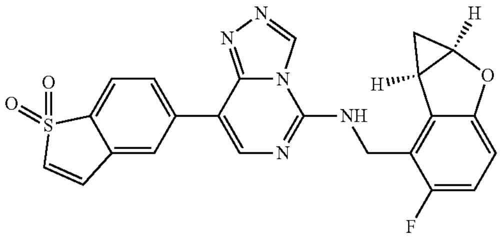 [SMILES: O=S1(=O)C=Cc2cc(-c3cnc(NCc4c(F)ccc5c4[C@H]4C[C@H]4O5)n4cnnc34)ccc21] | 5-(5-((((1aR,6bR)-5-fluoro-1a,6b-dihydro-1H-cyclopropa[b]benzofuran-6-yl)methyl)amino)-[1,2,4]triazolo[4,3-c]pyrimidin-8-yl)benzo[b]thiophene 1,1-dioxide |
| 49 | 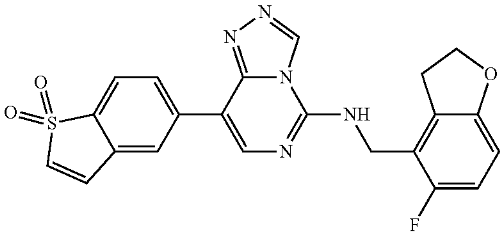 [SMILES: O=S1(=O)C=Cc2cc(-c3cnc(NCc4c(F)ccc5c4CCO5)n4cnnc34)ccc21] | 5-(5-(((5-fluoro-2,3-dihydrobenzofuran-4-yl)methyl)amino)-[1,2,4]triazolo[4,3-c]pyrimidin-8-yl)benzo[b]thiophene 1,1-dioxide |

TABLE 1-continued

| Compound No. | Compound structure | Compound name |
|---|---|---|
| 50 | 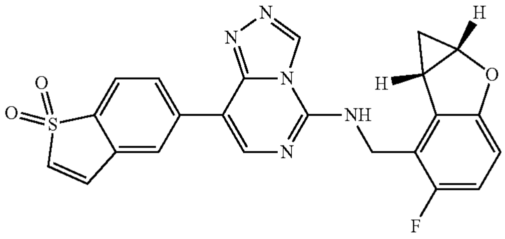 [SMILES: O=S1(=O)C=Cc2cc(-c3cnc(NCc4c(F)ccc5c4[C@@H]4C[C@@H]4O5)n4cnnc34)ccc21] | 5-(5-((((1aS,6bS)-5-fluoro-1a,6b-dihydro-1H-cyclopropa[b]benzofuran-6-yl)methyl)amino)-[1,2,4]triazolo[4,3-c]pyrimidin-8-yl)benzo[b]thiophene 1,1-dioxide |
| 51 | 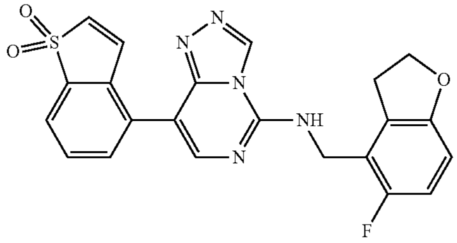 [SMILES: O=S1(=O)C=Cc2c(-c3cnc(NCc4c(F)ccc5c4CCO5)n4cnnc34)cccc21] | 4-(5-(((5-fluoro-2,3-dihydrobenzofuran-4-yl)methyl)amino)-[1,2,4]triazolo[4,3-c]pyrimidin-8-yl)benzo[b]thiophene 1,1-dioxide |
| 52 | 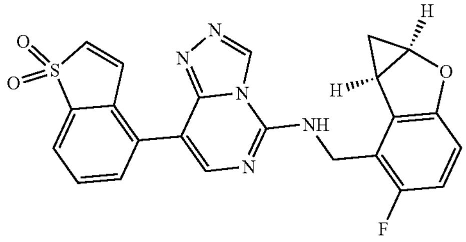 [SMILES: O=S1(=O)C=Cc2c(-c3cnc(NCc4c(F)ccc5c4[C@H]4C[C@H]4O5)n4cnnc34)cccc21] | 4-(5-((((1aR,6bR)-5-fluoro-1a,6b-dihydro-1H-cyclopropa[b]benzofuran-6-yl)methyl)amino)-[1,2,4]triazolo[4,3-c]pyrimidin-8-yl)benzo[b]thiophene 1,1-dioxide |
| 53 | 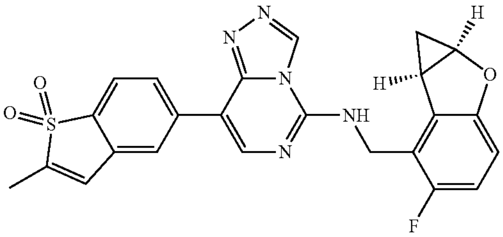 | 5-(5-((((1aR,6bR)-5-fluoro-1a,6b-dihydro-1H-cyclopropa[b]benzofuran-6-yl)methyl)amino)-[1,2,4]triazolo[4,3-c]pyrimidin-8-yl)-2-methylbenzo[b]thiophene 1,1-dioxide |
| 54 | 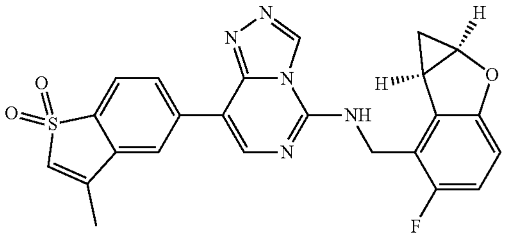 [SMILES: CC1=CS(=O)(=O)c2ccc(-c3cnc(NCc4c(F)ccc5c4[C@H]4C[C@H]4O5)n4cnnc34)cc21] | 5-(5-((((1aR,6bR)-5-fluoro-1a,6b-dihydro-1H-cyclopropa[b]benzofuran-6-yl)methyl)amino)-[1,2,4]triazolo[4,3-c]pyrimidin-8-yl)-3-methylbenzo[b]thiophene 1,1-dioxide |
| 55 | 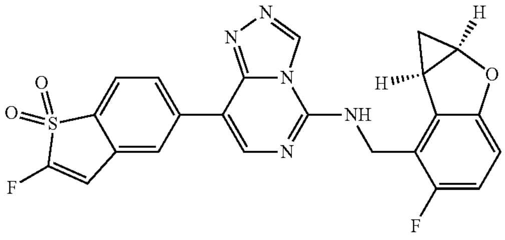 [SMILES: O=S1(=O)C(F)=Cc2cc(-c3cnc(NCc4c(F)ccc5c4[C@H]4C[C@H]4O5)n4cnnc34)ccc21] | 2-fluoro-5-(5-((((1aR,6bR)-5-fluoro-1a,6b-dihydro-1H-cyclopropa[b]benzofuran-6-yl)methyl)amino)-[1,2,4]triazolo[4,3-c]pyrimidin-8-yl)benzo[b]thiophene 1,1-dioxide |

TABLE 1-continued

| Compound No. | Compound structure | Compound name |
|---|---|---|
| 56 | 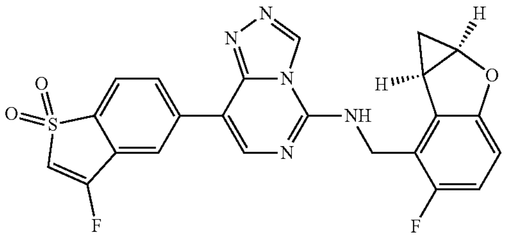 [SMILES: O=S1(=O)C=C(F)c2cc(-c3cnc(NCc4c(F)ccc5c4[C@H]4C[C@H]4O5)n4cnnc34)ccc21] | 3-fluoro-5-(5-((((1aR,6bR)-5-fluoro-1a,6b-dihydro-1H-cyclopropa[b]benzofuran-6-yl)methyl)amino)-[1,2,4]triazolo[4,3-c]pyrimidin-8-yl)benzo[b]thiophene 1,1-dioxide |
| 57 | 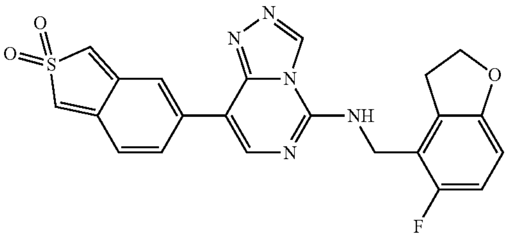 [SMILES: O=S1(=O)C=c2ccc(-c3cnc(NCc4c(F)ccc5c4CCO5)n4cnnc34)cc2=C1] | 5-(5-(((5-fluoro-2,3-dihydrobenzofuran-4-yl)methyl)amino)-[1,2,4]triazolo[4,3-c]pyrimidin-8-yl)benzo[c]thiophene 2,2-dioxide |
| 58 | 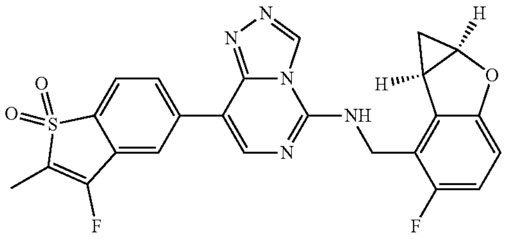 [SMILES: CC1=C(F)c2cc(-c3cnc(NCc4c(F)ccc5c4[C@H]4C[C@H]4O5)n4cnnc34)ccc2S1(=O)=O] | 3-fluoro-5-(5-((((1aR,6bR)-5-fluoro-1a,6b-dihydro-1H-cyclopropa[b]benzofuran-6-yl)methyl)amino)-[1,2,4]triazolo[4,3-c]pyrimidin-8-yl)-2-methylbenzo[b]thiophene 1,1-dioxide |
| 59 | 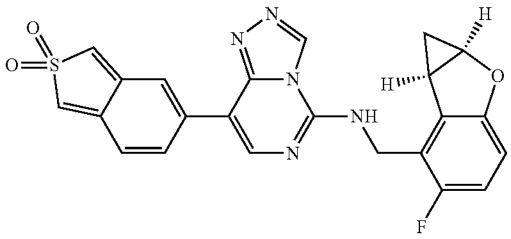 [SMILES: O=S1(=O)C=c2ccc(-c3cnc(NCc4c(F)ccc5c4[C@H]4C[C@H]4O5)n4cnnc34)cc2=C1] | 5-(5-((((1aR,6bR)-5-fluoro-1a,6b-dihydro-1H-cyclopropa[b]benzofuran-6-yl)methyl)amino)-[1,2,4]triazolo[4,3-c]pyrimidin-8-yl)benzo[c]thiophene 2,2-dioxide |
| 60 | 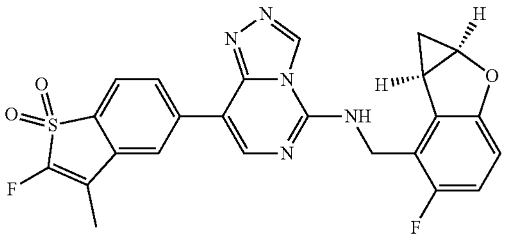 [SMILES: CC1=C(F)S(=O)(=O)c2ccc(-c3cnc(NCc4c(F)ccc5c4[C@H]4C[C@H]4O5)n4cnnc34)cc21] | 2-fluoro-5-(5-((((1aR,6bR)-5-fluoro-1a,6b-dihydro-1H-cyclopropa[b]benzofuran-6-yl)methyl)amino)-[1,2,4]triazolo[4,3-c]pyrimidin-8-yl)-3-methylbenzo[b]thiophene 1,1-dioxide |
| 61 | 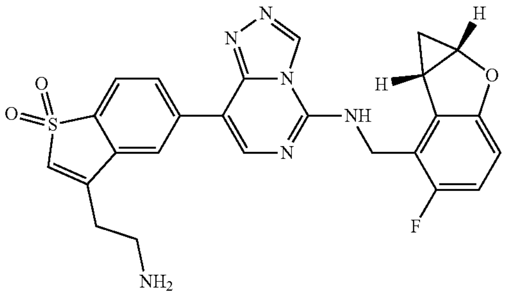 [SMILES: NCCC1=CS(=O)(=O)c2ccc(-c3cnc(NCc4c(F)ccc5c4[C@@H]4C[C@@H]4O5)n4cnnc34)cc21] | 3-(2-aminoethyl)-5-(5-((((1aS,6bS)-5-fluoro-1a,6b-dihydro-1H-cyclopropa[b]benzofuran-6-yl)methyl)amino)-[1,2,4]triazolo[4,3-c]pyrimidin-8-yl)benzo[b]thiophene 1,1-dioxide |

TABLE 1-continued

| Compound No. | Compound structure | Compound name |
|---|---|---|
| 62 | 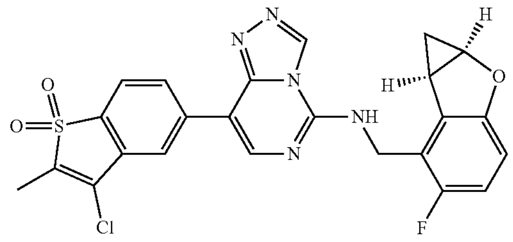 [SMILES: CC1=C(Cl)c2cc(-c3cnc(NCc4c(F)ccc5c4[C@H]4C[C@H]4O5)n4cnnc34)ccc2S1(=O)=O] | 3-chloro-5-(5-((((1aR,6bR)-5-fluoro-1a,6b-dihydro-1H-cyclopropa[b]benzofuran-6-yl)methyl)amino)-[1,2,4]triazolo[4,3-c]pyrimidin-8-yl)-2-methylbenzo[b]thiophene 1,1-dioxide |
| 63 | 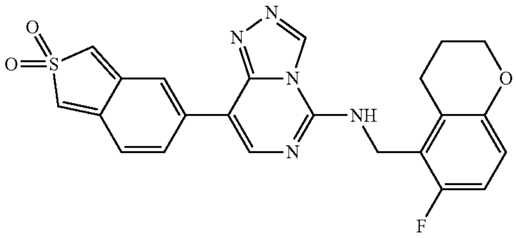 [SMILES: O=S1(=O)C=c2ccc(-c3cnc(NCc4c(F)ccc5c4CCCO5)n4cnnc34)cc2=C1] | 5-(5-(((6-fluorochroman-5-yl)methyl)amino)-[1,2,4]triazolo[4,3-c]pyrimidin-8-yl)benzo[c]thiophene 2,2-dioxide |
| 64 | 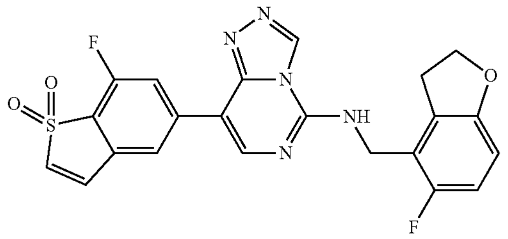 [SMILES: O=S1(=O)C=Cc2cc(-c3cnc(NCc4c(F)ccc5c4CCO5)n4cnnc34)cc(F)c21] | 7-fluoro-5-(5-(((5-fluoro-2,3-dihydrobenzofuran-4-yl)methyl)amino)-[1,2,4]triazolo[4,3-c]pyrimidin-8-yl)benzo[b]thiophene 1,1-dioxide |
| 65 | 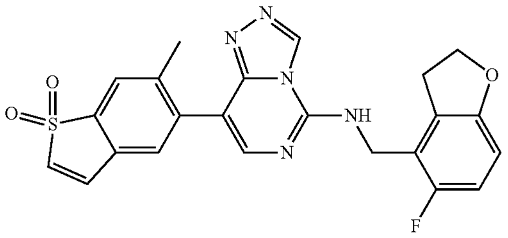 [SMILES: Cc1cc2c(cc1-c1cnc(NCc3c(F)ccc4c3CCO4)n3cnnc13)C=CS2(=O)=O] | 5-(5-(((5-fluoro-2,3-dihydrobenzofuran-4-yl)methyl)amino)-[1,2,4]triazolo[4,3-c]pyrimidin-8-yl)-6-methylbenzo[b]thiophene 1,1-dioxide |
| 66 | 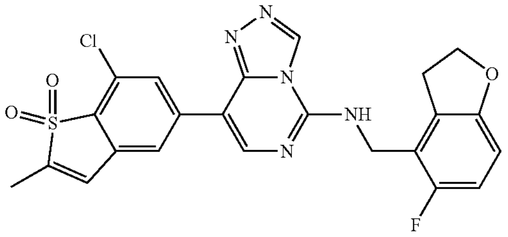 [SMILES: CC1=Cc2cc(-c3cnc(NCc4c(F)ccc5c4CCO5)n4cnnc34)cc(Cl)c2S1(=O)=O] | 7-chloro-5-(5-(((5-fluoro-2,3-dihydrobenzofuran-4-yl)methyl)amino)-[1,2,4]triazolo[4,3-c]pyrimidin-8-yl)-2-methylbenzo[b]thiophene 1,1-dioxide |
| 67 | 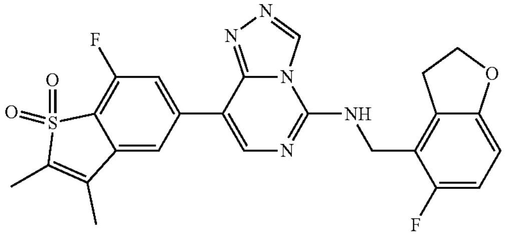 [SMILES: CC1=C(C)S(=O)(=O)c2c(F)cc(-c3cnc(NCc4c(F)ccc5c4CCO5)n4cnnc34)cc21] | 7-fluoro-5-(5-(((5-fluoro-2,3-dihydrobenzofuran-4-yl)methyl)amino)-[1,2,4]triazolo[4,3-c]pyrimidin-8-yl)-2,3-dimethylbenzo[b]thiophene 1,1-dioxide |

TABLE 1-continued

| Compound No. | Compound structure | Compound name |
|---|---|---|
| 68 | 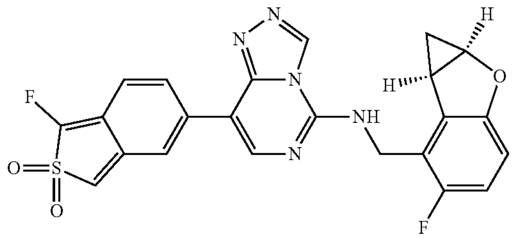 [SMILES: O=S1(=O)C=c2cc(-c3cnc(NCc4c(F)ccc5c4[C@H]4C[C@H]4O5)n4cnnc34)ccc2=C1F] | 1-fluoro-5-(5-((((1aR,6bR)-5-fluoro-1a,6b-dihydro-1H-cyclopropa[b]benzofuran-6-yl)methyl)amino)-[1,2,4]triazolo[4,3-c]pyrimidin-8-yl)benzo[c]thiophene 2,2-dioxide |
| 69 | 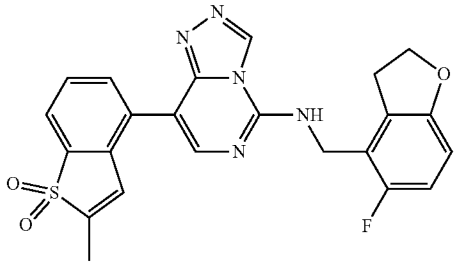 [SMILES: CC1=Cc2c(-c3cnc(NCc4c(F)ccc5c4CCO5)n4cnnc34)cccc2S1(=O)=O] | 4-(5-(((5-fluoro-2,3-dihydrobenzofuran-4-yl)methyl)amino)-[1,2,4]triazolo[4,3-c]pyrimidin-8-yl)-2-methylbenzo[b]thiophene 1,1-dioxide |
| 70 | 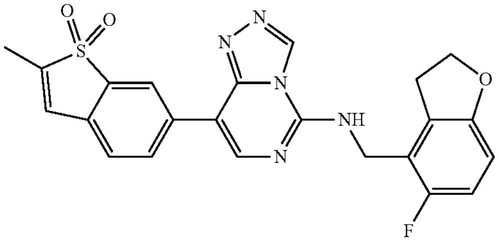 [SMILES: CC1=Cc2ccc(-c3cnc(NCc4c(F)ccc5c4CCO5)n4cnnc34)cc2S1(=O)=O] | 6-(5-(((5-fluoro-2,3-dihydrobenzofuran-4-yl)methyl)amino)-[1,2,4]triazolo[4,3-c]pyrimidin-8-yl)-2-methylbenzo[b]thiophene 1,1-dioxide |
| 71 | 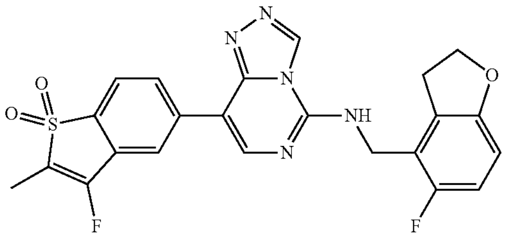 [SMILES: CC1=C(F)c2cc(-c3cnc(NCc4c(F)ccc5c4CCO5)n4cnnc34)ccc2S1(=O)=O] | 3-fluoro-5-(5-(((5-fluoro-2,3-dihydrobenzofuran-4-yl)methyl)amino)-[1,2,4]triazolo[4,3-c]pyrimidin-8-yl)-2-methylbenzo[b]thiophene 1,1-dioxide |
| 72 | 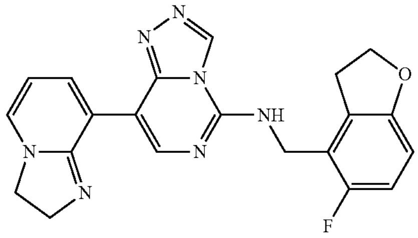 | 8-(2,3-dihydroimidazo[1,2-a]pyridin-8-yl)-N-((5-fluoro-2,3-dihydrobenzofuran-4-yl)methyl)-[1,2,4]triazolo[4,3-c]pyrimidin-5-amine |
| 73 | 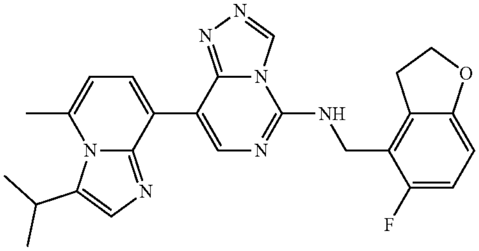 [SMILES: Cc1ccc(-c2cnc(NCc3c(F)ccc4c3CCO4)n3cnnc23)c2ncc(C(C)C)n12] | N-((5-fluoro-2,3-dihydrobenzofuran-4-yl)methyl)-8-(3-isopropyl-5-methylimidazo[1,2-a]pyridin-8-yl)-[1,2,4]triazolo[4,3-c]pyrimidin-5-amine |

TABLE 1-continued

| Compound No. | Compound structure | Compound name |
| --- | --- | --- |
| 74 | 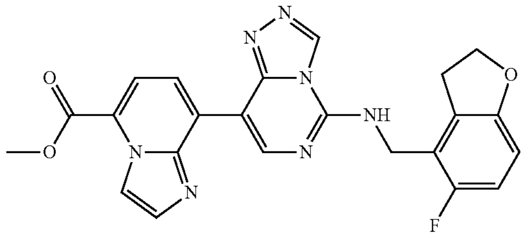 [SMILES: COC(=O)c1ccc(-c2cnc(NCc3c(F)ccc4c3CCO4)n3cnnc23)c2nccn12] | Methyl 8-(5-(((5-fluoro-2,3-dihydrobenzofuran-4-yl)methyl)amino)-[1,2,4]triazolo[4,3-c]pyrimidin-8-yl)imidazo[1,2-a]pyridine-5-carboxylate |
| 75 | 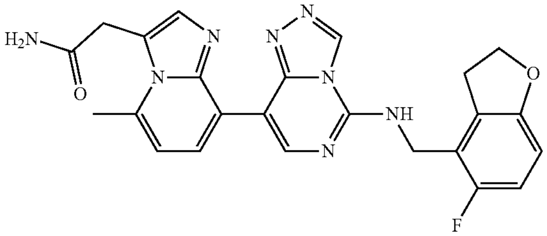 [SMILES: Cc1ccc(-c2cnc(NCc3c(F)ccc4c3CCO4)n3cnnc23)c2ncc(CC(N)=O)n12] | 2-(8-(5-(((5-fluoro-2,3-dihydrobenzofuran-4-yl)methyl)amino)-[1,2,4]triazolo[4,3-c]pyrimidin-8-yl)-5-methylimidazo[1,2-a]pyridin-3-yl)acetamide |
| 76 | 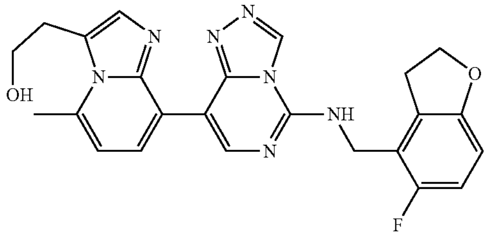 [SMILES: Cc1ccc(-c2cnc(NCc3c(F)ccc4c3CCO4)n3cnnc23)c2ncc(CCO)n12] | 2-(8-(5-(((5-fluoro-2,3-dihydrobenzofuran-4-yl)methyl)amino)-[1,2,4]triazolo[4,3-c]pyrimidin-8-yl)-5-methylimidazo[1,2-a]pyridin-3-yl)ethan-1-ol |
| 77 | 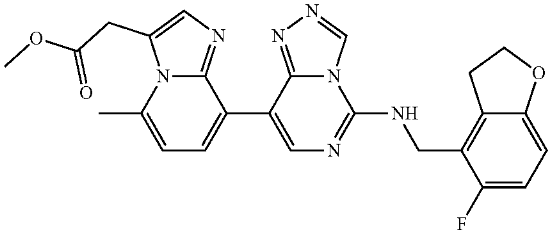 [SMILES: COC(=O)Cc1cnc2c(-c3cnc(NCc4c(F)ccc5c4CCO5)n4cnnc34)ccc(C)n12] | Methyl 2-(8-(5-(((5-fluoro-2,3-dihydrobenzofuran-4-yl)methyl)amino)-[1,2,4]triazolo[4,3-c]pyrimidin-8-yl)-5-methylimidazo[1,2-a]pyridin-3-yl)acetate |
| 78 | 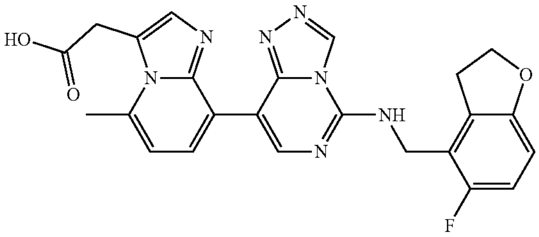 [SMILES: Cc1ccc(-c2cnc(NCc3c(F)ccc4c3CCO4)n3cnnc23)c2ncc(CC(=O)O)n12] | 2-(8-(5-(((5-fluoro-2,3-dihydrobenzofuran-4-yl)methyl)amino)-[1,2,4]triazolo[4,3-c]pyrimidin-8-yl)-5-methylimidazo[1,2-a]pyridin-3-yl)acetic acid |
| 79 | 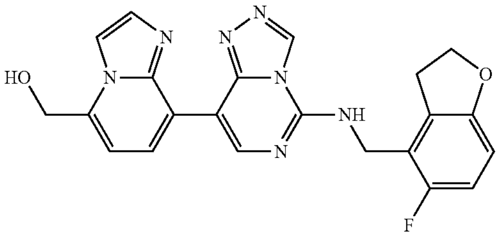 [SMILES: OCc1ccc(-c2cnc(NCc3c(F)ccc4c3CCO4)n3cnnc23)c2nccn12] | (8-(5-(((5-fluoro-2,3-dihydrobenzofuran-4-yl)methyl)amino)-[1,2,4]triazolo[4,3-c]pyrimidin-8-yl)imidazo[1,2-a]pyridin-5-yl)methanol |

TABLE 1-continued

| Compound No. | Compound structure | Compound name |
|---|---|---|
| 80 | 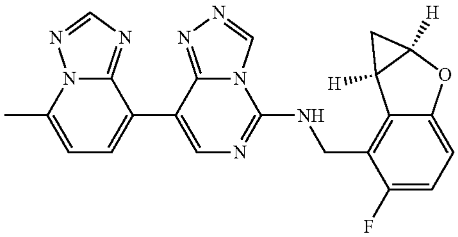 | N-(((1aR,6bR)-5-fluoro-1a,6b-dihydro-1H-cyclopropa[b]benzofuran-6-yl)methyl)-8-(5-methyl-[1,2,4]triazolo[1,5-a]pyridin-8-yl)-[1,2,4]triazolo[4,3-c]pyrimidin-5-amine |
| 81 | 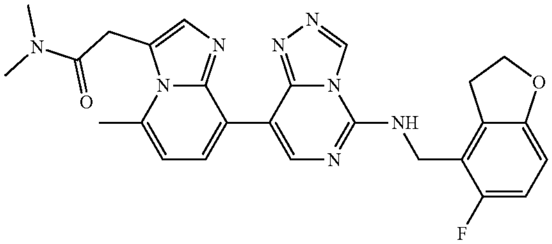 [SMILES: Cc1ccc(-c2cnc(NCc3c(F)ccc4c3CCO4)n3cnnc23)c2ncc(CC(=O)N(C)C)n12] | 2-(8-(5-(((5-fluoro-2,3-dihydrobenzofuran-4-yl)methyl)amino)-[1,2,4]triazolo[4,3-c]pyrimidin-8-yl)-5-methylimidazo[1,2-a]pyridin-3-yl)-N,N-dimethylacetamide |
| 82 | 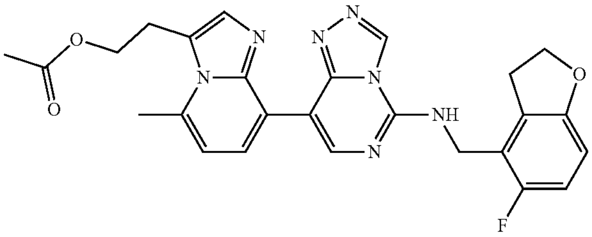 [SMILES: CC(=O)OCCc1cnc2c(-c3cnc(NCc4c(F)ccc5c4CCO5)n4cnnc34)ccc(C)n12] | 2-(8-(5-(((5-fluoro-2,3-dihydrobenzofuran-4-yl)methyl)amino)-[1,2,4]triazolo[4,3-c]pyrimidin-8-yl)-5-methylimidazo[1,2-a]pyridin-3-yl)ethyl acetate |
| 83 | 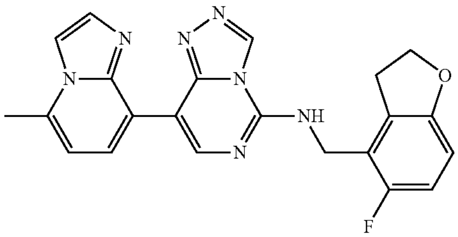 [SMILES: Cc1ccc(-c2cnc(NCc3c(F)ccc4c3CCO4)n3cnnc23)c2nccn12] | N-((5-fluoro-2,3-dihydrobenzofuran-4-yl)methyl)-8-(5-methylimidazo[1,2-a]pyridin-8-yl)-[1,2,4]triazolo[4,3-c]pyrimidin-5-amine |
| 84 | 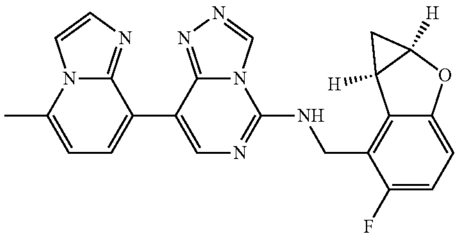 [SMILES: Cc1ccc(-c2cnc(NCc3c(F)ccc4c3[C@H]3C[C@H]3O4)n3cnnc23)c2nccn12] | N-(((1aR,6bR)-5-fluoro-1a,6b-dihydro-1H-cyclopropa[b]benzofuran-6-yl)methyl)-8-(5-methylimidazo[1,2-a]pyridin-8-yl)-[1,2,4]triazolo[4,3-c]pyrimidin-5-amine |
| 85 | 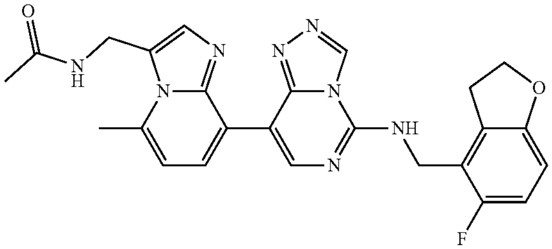 [SMILES: CC(=O)NCc1cnc2c(-c3cnc(NCc4c(F)ccc5c4CCO5)n4cnnc34)ccc(C)n12] | N-((8-(5-(((5-fluoro-2,3-dihydrobenzofuran-4-yl)methyl)amino)-[1,2,4]triazolo[4,3-c]pyrimidin-8-yl)-5-methylimidazo[1,2-a]pyridin-3-yl)methyl)acetamide |

TABLE 1-continued

| Compound No. | Compound structure | Compound name |
|---|---|---|
| 86 | 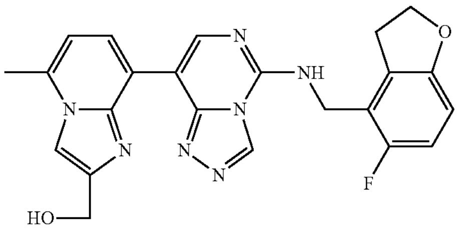 [SMILES: Cc1ccc(-c2cnc(NCc3c(F)ccc4c3CCO4)n3cnnc23)c2nc(CO)cn12] | (8-(5-(((5-fluoro-2,3-dihydrobenzofuran-4-yl)methyl)amino)-[1,2,4]triazolo[4,3-c]pyrimidin-8-yl)-5-methylimidazo[1,2-a]pyridin-2-yl)methanol |
| 87 | 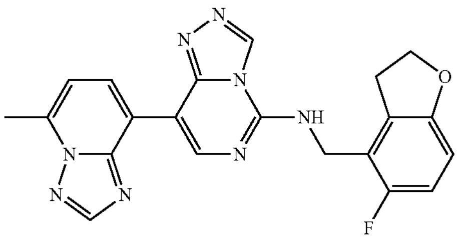 | N-((5-fluoro-2,3-dihydrobenzofuran-4-yl)methyl)-8-(5-methyl-[1,2,4]triazolo[1,5-a]pyridin-8-yl)-[1,2,4]triazolo[4,3-c]pyrimidin-5-amine |
| 88 | 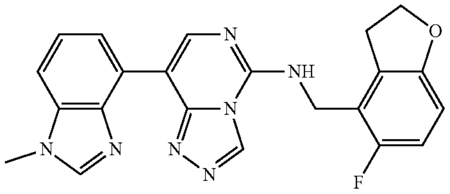 [SMILES: Cn1cnc2c(-c3cnc(NCc4c(F)ccc5c4CCO5)n4cnnc34)cccc21] | N-((5-fluoro-2,3-dihydrobenzofuran-4-yl)methyl)-8-(1-methyl-1H-benzo[d]imidazol-4-yl)-[1,2,4]triazolo[4,3-c]pyrimidin-5-amine |
| 89 | 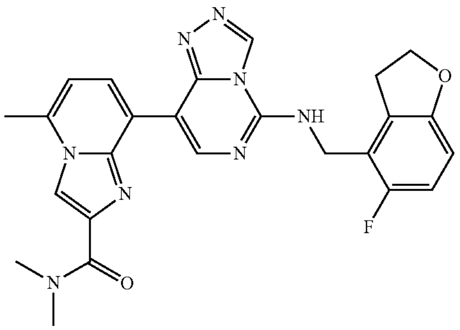 [SMILES: Cc1ccc(-c2cnc(NCc3c(F)ccc4c3CCO4)n3cnnc23)c2nc(C(=O)N(C)C)cn12] | 8-(5-(((5-fluoro-2,3-dihydrobenzofuran-4-yl)methyl)amino)-[1,2,4]triazolo[4,3-c]pyrimidin-8-yl)-N,N,5-trimethylimidazo[1,2-a]pyridine-2-carboxamide |
| 90 | 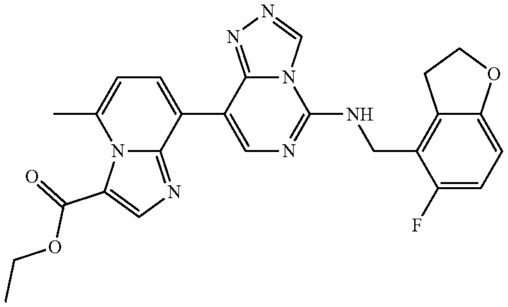 [SMILES: CCOC(=O)c1cnc2c(-c3cnc(NCc4c(F)ccc5c4CCO5)n4cnnc34)ccc(C)n12] | Ethyl 8-(5-(((5-fluoro-2,3-dihydrobenzofuran-4-yl)methyl)amino)-[1,2,4]triazolo[4,3-c]pyrimidin-8-yl)-5-methylimidazo[1,2-a]pyridine-3-carboxylate |

TABLE 1-continued

| Compound No. | Compound structure | Compound name |
|---|---|---|
| 91 | 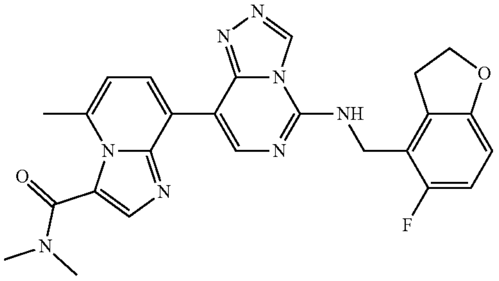 [SMILES: Cc1ccc(-c2cnc(NCc3c(F)ccc4c3CCO4)n3cnnc23)c2ncc(C(=O)N(C)C)n12] | 8-(5-(((5-fluoro-2,3-dihydrobenzofuran-4-yl)methyl)amino)-[1,2,4]triazolo[4,3-c]pyrimidin-8-yl)-N,N,5-trimethylimidazo[1,2-a]pyridine-3-carboxamide |
| 92 | 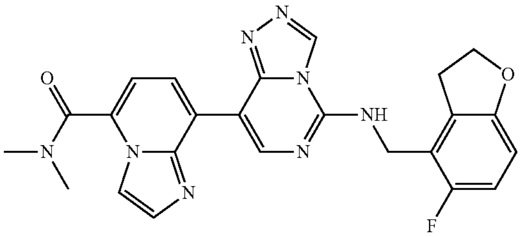 [SMILES: CN(C)C(=O)c1ccc(-c2cnc(NCc3c(F)ccc4c3CCO4)n3cnnc23)c2nccn12] | 8-(5-(((5-fluoro-2,3-dihydrobenzofuran-4-yl)methyl)amino)-[1,2,4]triazolo[4,3-c]pyrimidin-8-yl)-N,N-dimethylimidazo[1,2-a]pyridine-5-carboxamide |
| 93 | 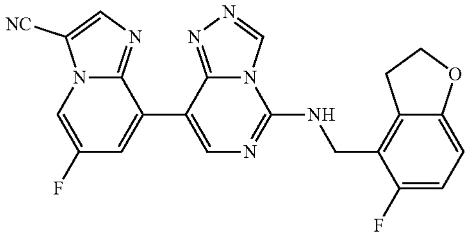 [SMILES: N#Cc1cnc2c(-c3cnc(NCc4c(F)ccc5c4CCO5)n4cnnc34)cc(F)cn12] | 6-fluoro-8-(5-(((5-fluoro-2,3-dihydrobenzofuran-4-yl)methyl)amino)-[1,2,4]triazolo[4,3-c]pyrimidin-8-yl)imidazo[1,2-a]pyridine-3-carbonitrile |
| 94 | 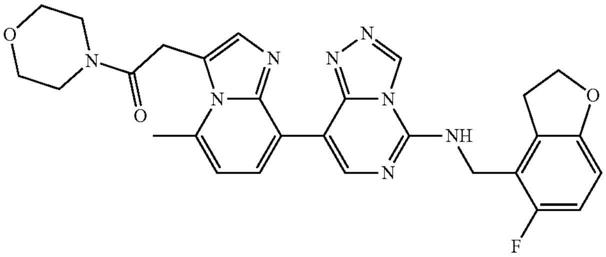 [SMILES: Cc1ccc(-c2cnc(NCc3c(F)ccc4c3CCO4)n3cnnc23)c2ncc(CC(=O)N3CCOCC3)n12] | 2-(8-(5-(((5-fluoro-2,3-dihydrobenzofuran-4-yl)methyl)amino)-[1,2,4]triazolo[4,3-c]pyrimidin-8-yl)-5-methylimidazo[1,2-a]pyridin-3-yl)-1-morpholinoethan-1-one |
| 95 | 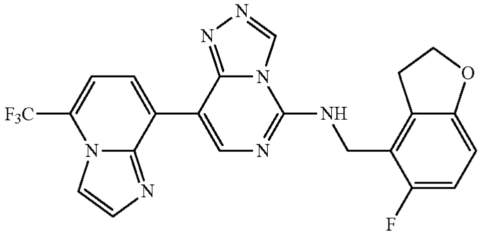 | N-((5-fluoro-2,3-dihydrobenzofuran-4-yl)methyl)-8-(5-(trifluoromethyl)imidazo[1,2-a]pyridin-8-yl)-[1,2,4]triazolo[4,3-c]pyrimidin-5-amine |

TABLE 1-continued

| Compound No. | Compound structure | Compound name |
|---|---|---|
| 96 | 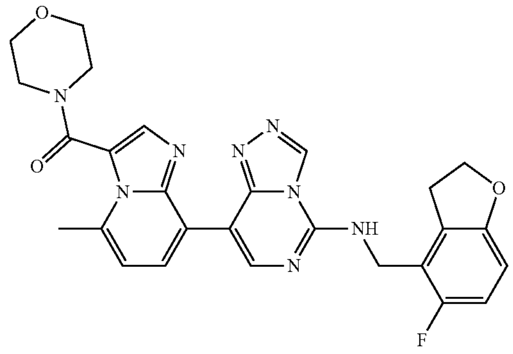 [SMILES: Cc1ccc(-c2cnc(NCc3c(F)ccc4c3CCO4)n3cnnc23)c2ncc(C(=O)N3CCOCC3)n12] | (8-(5-(((5-fluoro-2,3-dihydrobenzofuran-4-yl)methyl)amino)-[1,2,4]triazolo[4,3-c]pyrimidin-8-yl)-5-methylimidazo[1,2-a]pyridin-3-yl)(morpholino)methanone |
| 97 | 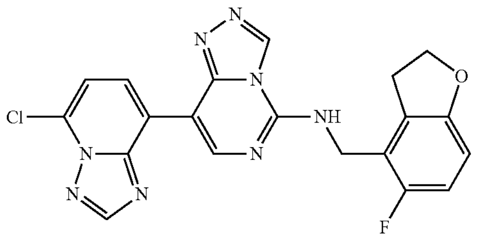 [SMILES: Fc1ccc2c(c1CNc1ncc(-c3ccc(Cl)n4ncnc34)c3nncn13)CCO2] | 8-(5-chloro-[1,2,4]triazolo[1,5-a]pyridin-8-yl)-N-((5-fluoro-2,3-dihydrobenzofuran-4-yl)methyl)-[1,2,4]triazolo[4,3-c]pyrimidin-5-amine |
| 98 | 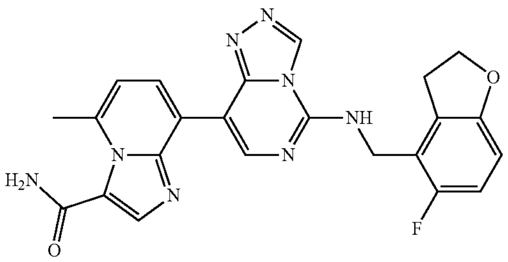 | 8-(5-(((5-fluoro-2,3-dihydrobenzofuran-4-yl)methyl)amino)-[1,2,4]triazolo[4,3-c]pyrimidin-8-yl)-5-methylimidazo[1,2-a]pyridine-3-carboxamide |
| 99 | 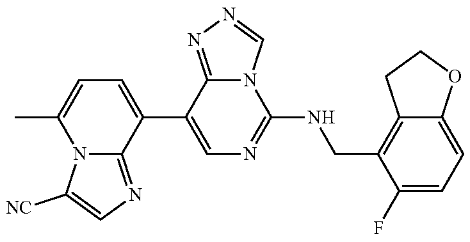 [SMILES: Cc1ccc(-c2cnc(NCc3c(F)ccc4c3CCO4)n3cnnc23)c2ncc(C#N)n12] | 8-(5-(((5-fluoro-2,3-dihydrobenzofuran-4-yl)methyl)amino)-[1,2,4]triazolo[4,3-c]pyrimidin-8-yl)-5-methylimidazo[1,2-a]pyridine-3-carbonitrile |
| 100 | 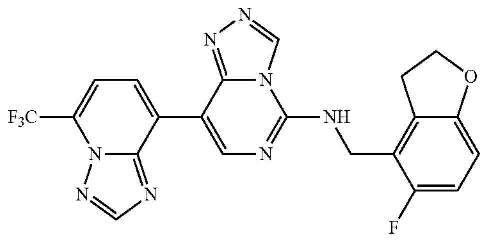 | N-((5-fluoro-2,3-dihydrobenzofuran-4-yl)methyl)-8-(5-(trifluoromethyl)-[1,2,4]triazolo[1,5-a]pyridin-8-yl)-[1,2,4]triazolo[4,3-c]pyrimidin-5-amine |

TABLE 1-continued

| Compound No. | Compound structure | Compound name |
|---|---|---|
| 101 | 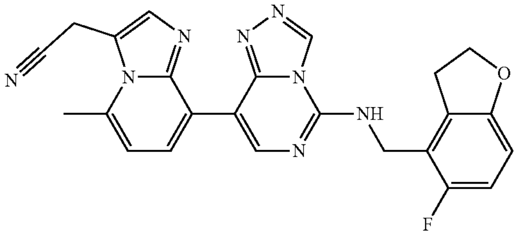 [SMILES: Cc1ccc(-c2cnc(NCc3c(F)ccc4c3CCO4)n3cnnc23)c2ncc(CC#N)n12] | 2-(8-(5-(((5-fluoro-2,3-dihydrobenzofuran-4-yl)methyl)amino)-[1,2,4]triazolo[4,3-c]pyrimidin-8-yl)-5-methylimidazo[1,2-a]pyridin-3-yl)acetonitrile |
| 102 | 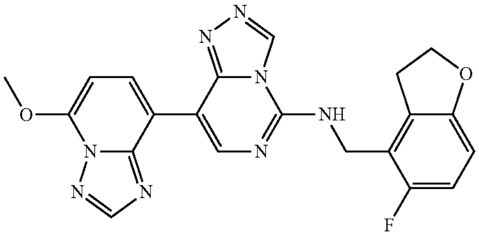 | N-((5-fluoro-2,3-dihydrobenzofuran-4-yl)methyl)-8-(5-methoxy-[1,2,4]triazolo[1,5-a]pyridin-8-yl)-[1,2,4]triazolo[4,3-c]pyrimidin-5-amine |
| 103 | 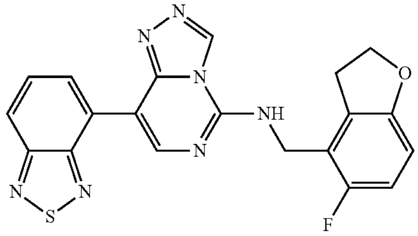 [SMILES: Fc1ccc2c(c1CNc1ncc(-c3cccc4nsnc34)c3nncn13)CCO2] | 8-(benzo[c][1,2,5]thiadiazol-4-yl)-N-((5-fluoro-2,3-dihydrobenzofuran-4-yl)methyl)-[1,2,4]triazolo[4,3-c]pyrimidin-5-amine |
| 104 | 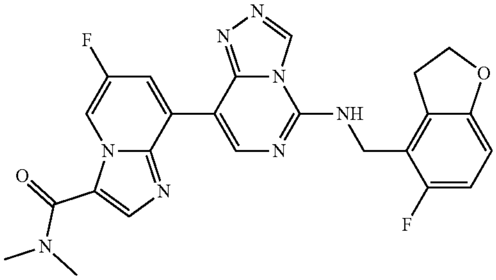 [SMILES: CN(C)C(=O)c1cnc2c(-c3cnc(NCc4c(F)ccc5c4CCO5)n4cnnc34)cc(F)cn12] | 6-fluoro-8-(5-(((5-fluoro-2,3-dihydrobenzofuran-4-yl)methyl)amino)-[1,2,4]triazolo[4,3-c]pyrimidin-8-yl)-N,N-dimethylimidazo[1,2-a]pyridine-3-carboxamide |
| 105 | 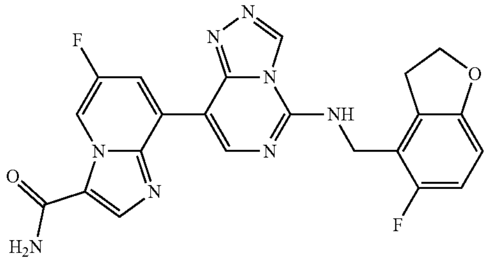 [SMILES: NC(=O)c1cnc2c(-c3cnc(NCc4c(F)ccc5c4CCO5)n4cnnc34)cc(F)cn12] | 6-fluoro-8-(5-(((5-fluoro-2,3-dihydrobenzofuran-4-yl)methyl)amino)-[1,2,4]triazolo[4,3-c]pyrimidin-8-yl)imidazo[1,2-a]pyridine-3-carboxamide |
| 106 | 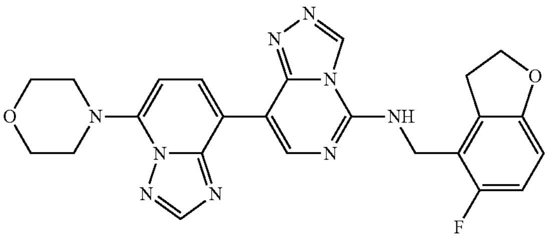 | N-((5-fluoro-2,3-dihydrobenzofuran-4-yl)methyl)-8-(5-morpholino-[1,2,4]triazolo[1,5-a]pyridin-8-yl)-[1,2,4]triazolo[4,3-c]pyrimidin-5-amine |

TABLE 1-continued

| Compound No. | Compound structure | Compound name |
|---|---|---|
| 107 | 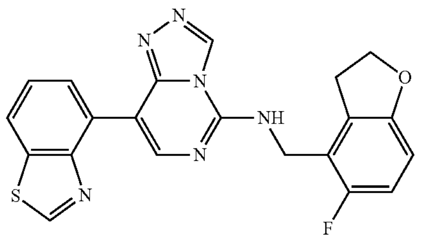 [SMILES: Fc1ccc2c(c1CNc1ncc(-c3cccc4scnc34)c3nncn13)CCO2] | 8-(benzo[d]thiazol-4-yl)-N-((5-fluoro-2,3-dihydrobenzofuran-4-yl)methyl)-[1,2,4]triazolo[4,3-c]pyrimidin-5-amine |
| 108 | 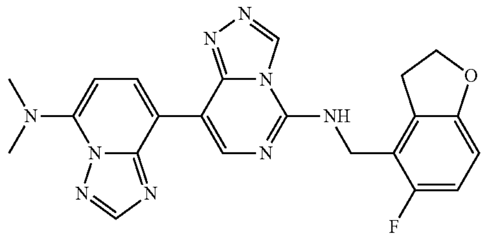 [SMILES: CN(C)c1ccc(-c2cnc(NCc3c(F)ccc4c3CCO4)n3cnnc23)c2ncnn12] | 8-(5-(dimethylamino)-[1,2,4]triazolo[1,5-a]pyridin-8-yl)-N-((5-fluoro-2,3-dihydrobenzofuran-4-yl)methyl)-[1,2,4]triazolo[4,3-c]pyrimidin-5-amine |
| 109 | 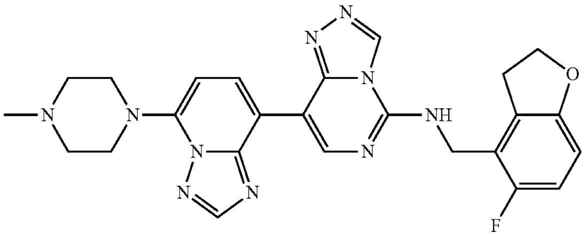 [SMILES: CN1CCN(c2ccc(-c3cnc(NCc4c(F)ccc5c4CCO5)n4cnnc34)c3ncnn23)CC1] | N-((5-fluoro-2,3-dihydrobenzofuran-4-yl)methyl)-8-(5-(4-methylpiperazin-1-yl)-[1,2,4]triazolo[1,5-a]pyridin-8-yl)-[1,2,4]triazolo[4,3-c]pyrimidin-5-amine |
| 110 | 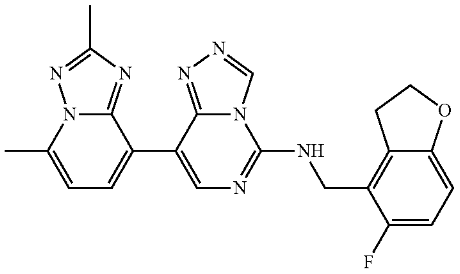 [SMILES: Cc1nc2c(-c3cnc(NCc4c(F)ccc5c4CCO5)n4cnnc34)ccc(C)n2n1] | 8-(2,5-dimethyl-[1,2,4]triazolo[1,5-a]pyridin-8-yl)-N-((5-fluoro-2,3-dihydrobenzofuran-4-yl)methyl)-[1,2,4]triazolo[4,3-c]pyrimidin-5-amine |
| 111 | 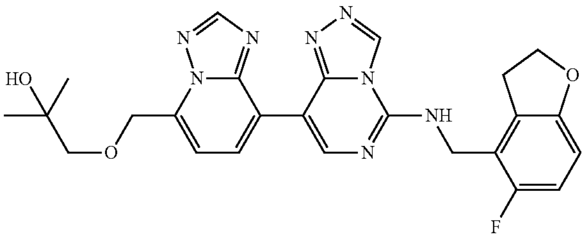 [SMILES: CC(C)(O)COCc1ccc(-c2cnc(NCc3c(F)ccc4c3CCO4)n3cnnc23)c2ncnn12] | 1-((8-(5-(((5-fluoro-2,3-dihydrobenzofuran-4-yl)methyl)amino)-[1,2,4]triazolo[4,3-c]pyrimidin-8-yl)-[1,2,4]triazolo[1,5-a]pyridin-5-yl)methoxy)-2-methylpropan-2-ol |
| 112 | 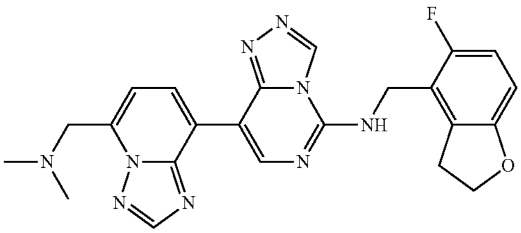 [SMILES: CN(C)Cc1ccc(-c2cnc(NCc3c(F)ccc4c3CCO4)n3cnnc23)c2ncnn12] | 8-(5-((dimethylamino)methyl)-[1,2,4]triazolo[1,5-a]pyridin-8-yl)-N-((5-fluoro-2,3-dihydrobenzofuran-4-yl)methyl)-[1,2,4]triazolo[4,3-c]pyrimidin-5-amine |

TABLE 1-continued

| Compound No. | Compound structure | Compound name |
| --- | --- | --- |
| 113 | 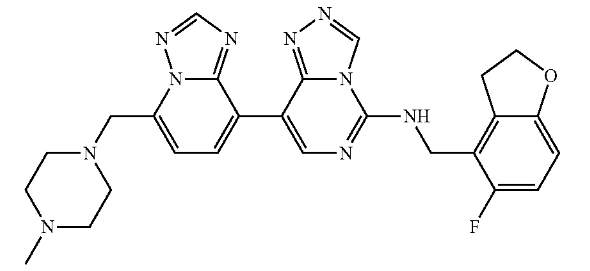 [SMILES: CN1CCN(Cc2ccc(-c3cnc(NCc4c(F)ccc5c4CCO5)n4cnnc34)c3ncnn23)CC1] | N-((5-fluoro-2,3-dihydrobenzofuran-4-yl)methyl)-8-(5-((4-methylpiperazin-1-yl)methyl)-[1,2,4]triazolo[1,5-a]pyridin-8-yl)-[1,2,4]triazolo[4,3-c]pyrimidin-5-amine |
| 114 | 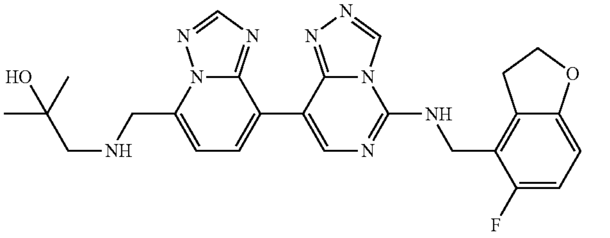 [SMILES: CC(C)(O)CNCc1ccc(-c2cnc(NCc3c(F)ccc4c3CCO4)n3cnnc23)c2ncnn12] | 1-(((8-(5-(((5-fluoro-2,3-dihydrobenzofuran-4-yl)methyl)amino)-[1,2,4]triazolo[4,3-c]pyrimidin-8-yl)-[1,2,4]triazolo[1,5-a]pyridin-5-yl)methyl)amino)-2-methylpropan-2-ol |
| 115 | 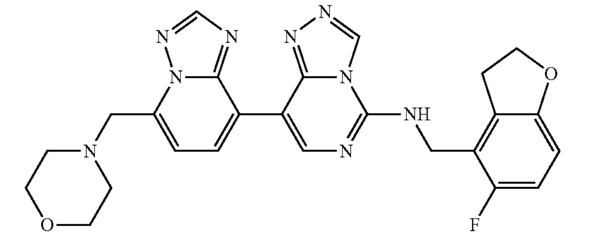 [SMILES: Fc1ccc2c(c1CNc1ncc(-c3ccc(CN4CCOCC4)n4ncnc34)c3nncn13)CCO2] | N-((5-fluoro-2,3-dihydrobenzofuran-4-yl)methyl)-8-(5-(morpholinomethyl)-[1,2,4]triazolo[1,5-a]pyridin-8-yl)-[1,2,4]triazolo[4,3-c]pyrimidin-5-amine |
| 116 | 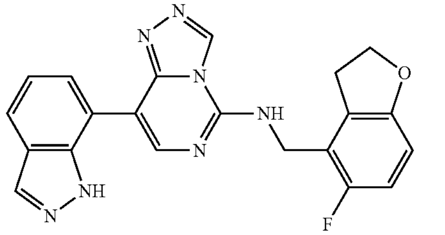 [SMILES: Fc1ccc2c(c1CNc1ncc(-c3cccc4cn[nH]c34)c3nncn13)CCO2] | N-((5-fluoro-2,3-dihydrobenzofuran-4-yl)methyl)-8-(1H-indazol-7-yl)-[1,2,4]triazolo[4,3-c]pyrimidin-5-amine |
| 117 | 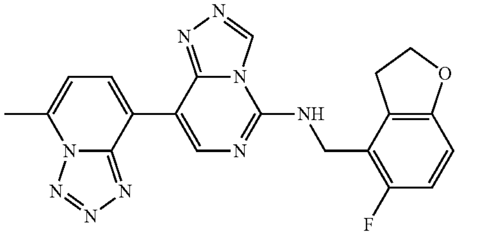 [SMILES: Cc1ccc(-c2cnc(NCc3c(F)ccc4c3CCO4)n3cnnc23)c2nnnn12] | N-((5-fluoro-2,3-dihydrobenzofuran-4-yl)methyl)-8-(5-methyltetrazolo[1,5-a]pyridin-8-yl)-[1,2,4]triazolo[4,3-c]pyrimidin-5-amine |
| 118 | 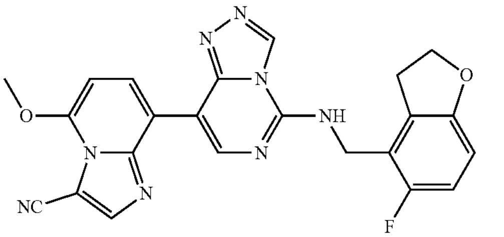 [SMILES: COc1ccc(-c2cnc(NCc3c(F)ccc4c3CCO4)n3cnnc23)c2ncc(C#N)n12] | 8-(5-(((5-fluoro-2,3-dihydrobenzofuran-4-yl)methyl)amino)-[1,2,4]triazolo[4,3-c]pyrimidin-8-yl)-5-methoxyimidazo[1,2-a]pyridine-3-carbonitrile |

TABLE 1-continued

| Compound No. | Compound structure | Compound name |
|---|---|---|
| 119 | 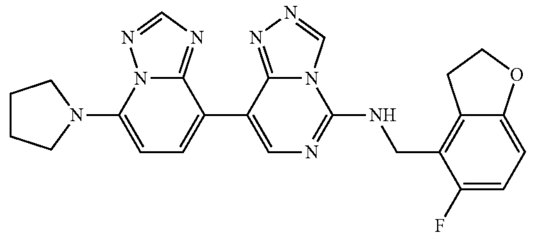 [SMILES: Fc1ccc2c(c1CNc1ncc(-c3ccc(N4CCCC4)n4ncnc34)c3nncn13)CCO2] | N-((5-fluoro-2,3-dihydrobenzofuran-4-yl)methyl)-8-(5-(pyrrolidin-1-yl)-[1,2,4]triazolo[1,5-a]pyridin-8-yl)-[1,2,4]triazolo[4,3-c]pyrimidin-5-amine |
| 120 | 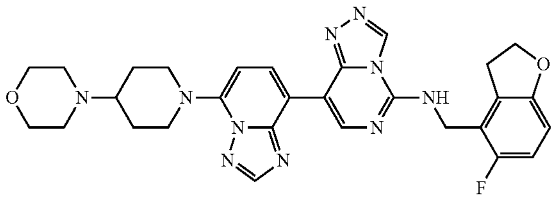 | N-((5-fluoro-2,3-dihydrobenzofuran-4-yl)methyl)-8-(5-(4-morpholinopiperidin-1-yl)-[1,2,4]triazolo[1,5-a]pyridin-8-yl)-[1,2,4]triazolo[4,3-c]pyrimidin-5-amine |
| 121 | 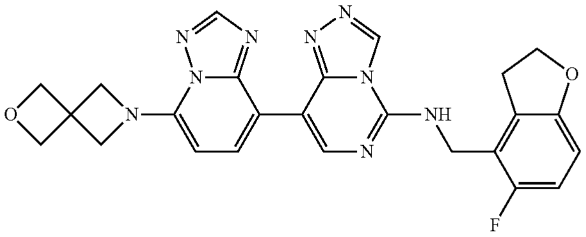 [SMILES: Fc1ccc2c(c1CNc1ncc(-c3ccc(N4CC5(COC5)C4)n4ncnc34)c3nncn13)CCO2] | 8-(5-(2-oxa-6-azaspiro[3.3]heptan-6-yl)-[1,2,4]triazolo[1,5-a]pyridin-8-yl)-N-((5-fluoro-2,3-dihydrobenzofuran-4-yl)methyl)-[1,2,4]triazolo[4,3-c]pyrimidin-5-amine |
| 122 | 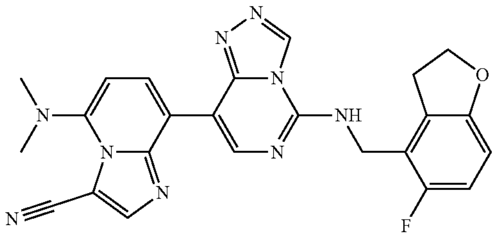 [SMILES: CN(C)c1ccc(-c2cnc(NCc3c(F)ccc4c3CCO4)n3cnnc23)c2ncc(C#N)n12] | 5-(dimethylamino)-8-(5-(((5-fluoro-2,3-dihydrobenzofuran-4-yl)methyl)amino)-[1,2,4]triazolo[4,3-c]pyrimidin-8-yl)imidazo[1,2-a]pyridine-3-carbonitrile |
| 123 | 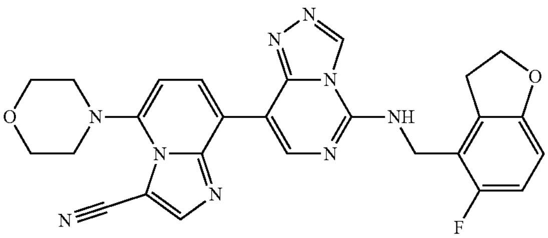 [SMILES: N#Cc1cnc2c(-c3cnc(NCc4c(F)ccc5c4CCO5)n4cnnc34)ccc(N3CCOCC3)n12] | 8-(5-(((5-fluoro-2,3-dihydrobenzofuran-4-yl)methyl)amino)-[1,2,4]triazolo[4,3-c]pyrimidin-8-yl)-5-morpholinoimidazo[1,2-a]pyridine-3-carbonitrile |
| 124 | 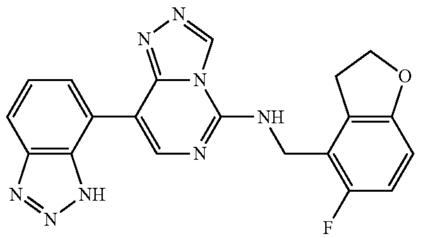 [SMILES: Fc1ccc2c(c1CNc1ncc(-c3cccc4nn[nH]c34)c3nncn13)CCO2] | 8-(1H-benzo[d][1,2,3]triazol-7-yl)-N-((5-fluoro-2,3-dihydrobenzofuran-4-yl)methyl)-[1,2,4]triazolo[4,3-c]pyrimidin-5-amine |

TABLE 1-continued

| Compound No. | Compound structure | Compound name |
|---|---|---|
| 125 | 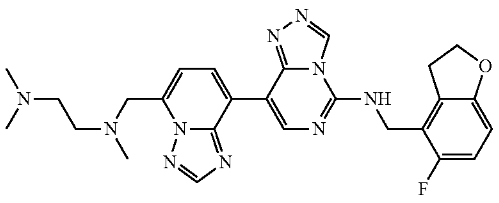 [SMILES: CN(C)CCN(C)Cc1ccc(-c2cnc(NCc3c(F)ccc4c3CCO4)n3cnnc23)c2ncnn12] | N1-((8-(5-(((5-fluoro-2,3-dihydrobenzofuran-4-yl)methyl)amino)-[1,2,4]triazolo[4,3-c]pyrimidin-8-yl)-[1,2,4]triazolo[1,5-a]pyridin-5-yl)methyl)-N1,N2,N2-trimethylethane-1,2-diamine |
| 126 | 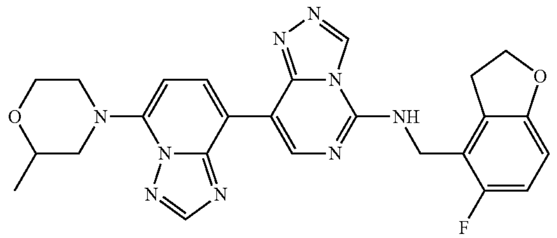 | N-((5-fluoro-2,3-dihydrobenzofuran-4-yl)methyl)-8-(5-(2-methylmorpholino)-[1,2,4]triazolo[1,5-a]pyridin-8-yl)-[1,2,4]triazolo[4,3-c]pyrimidin-5-amine |
| 127 | 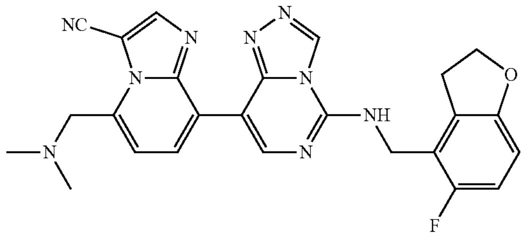 [SMILES: CN(C)Cc1ccc(-c2cnc(NCc3c(F)ccc4c3CCO4)n3cnnc23)c2ncc(C#N)n12] | 5-((dimethylamino)methyl)-8-(5-(((5-fluoro-2,3-dihydrobenzofuran-4-yl)methyl)amino)-[1,2,4]triazolo[4,3-c]pyrimidin-8-yl)imidazo[1,2-a]pyridine-3-carbonitrile |
| 128 | 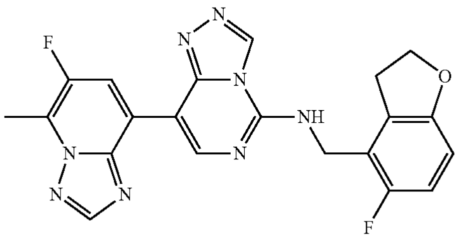 | N-((5-fluoro-2,3-dihydrobenzofuran-4-yl)methyl)-8-(6-fluoro-5-methyl-[1,2,4]triazolo[1,5-a]pyridin-8-yl)-[1,2,4]triazolo[4,3-c]pyrimidin-5-amine |
| 129 | 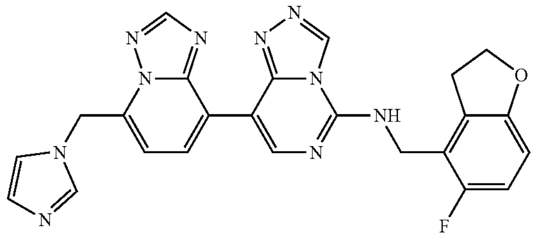 [SMILES: Fc1ccc2c(c1CNc1ncc(-c3ccc(Cn4ccnc4)n4ncnc34)c3nncn13)CCO2] | 8-(5-((1H-imidazol-1-yl)methyl)-[1,2,4]triazolo[1,5-a]pyridin-8-yl)-N-((5-fluoro-2,3-dihydrobenzofuran-4-yl)methyl)-[1,2,4]triazolo[4,3-c]pyrimidin-5-amine |
| 130 | 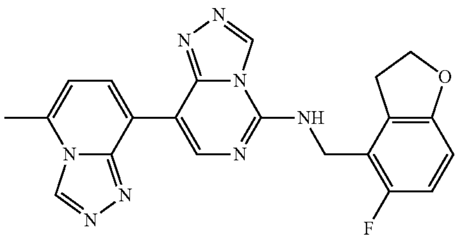 | N-((5-fluoro-2,3-dihydrobenzofuran-4-yl)methyl)-8-(5-methyl-[1,2,4]triazolo[4,3-a]pyridin-8-yl)-[1,2,4]triazolo[4,3-c]pyrimidin-5-amine |

TABLE 1-continued

| Compound No. | Compound structure | Compound name |
|---|---|---|
| 131 | 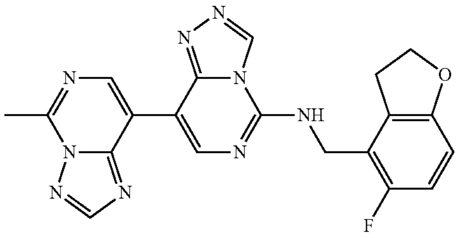 [SMILES: Cc1ncc(-c2cnc(NCc3c(F)ccc4c3CCO4)n3cnnc23)c2ncnn12] | N-((5-fluoro-2,3-dihydrobenzofuran-4-yl)methyl)-8-(5-methyl-[1,2,4]triazolo[1,5-c]pyrimidin-8-yl)-[1,2,4]triazolo[4,3-c]pyrimidin-5-amine |
| 132 | 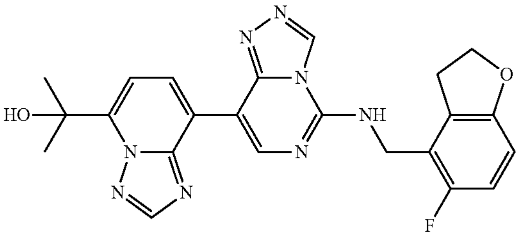 [SMILES: CC(C)(O)c1ccc(-c2cnc(NCc3c(F)ccc4c3CCO4)n3cnnc23)c2ncnn12] | 2-(8-(5-(((5-fluoro-2,3-dihydrobenzofuran-4-yl)methyl)amino)-[1,2,4]triazolo[4,3-c]pyrimidin-8-yl)-[1,2,4]triazolo[1,5-a]pyridin-5-yl)propan-2-ol |
| 133 | 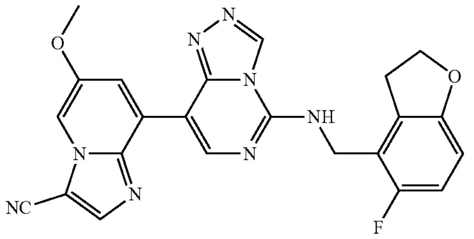 [SMILES: COc1cc(-c2cnc(NCc3c(F)ccc4c3CCO4)n3cnnc23)c2ncc(C#N)n2c1] | 8-(5-(((5-fluoro-2,3-dihydrobenzofuran-4-yl)methyl)amino)-[1,2,4]triazolo[4,3-c]pyrimidin-8-yl)-6-methoxyimidazo[1,2-a]pyridine-3-carbonitrile |
| 134 | 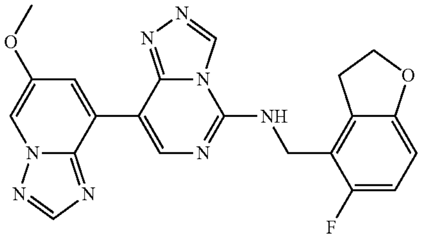 [SMILES: COc1cc(-c2cnc(NCc3c(F)ccc4c3CCO4)n3cnnc23)c2ncnn2c1] | N-((5-fluoro-2,3-dihydrobenzofuran-4-yl)methyl)-8-(6-methoxy-[1,2,4]triazolo[1,5-a]pyridin-8-yl)-[1,2,4]triazolo[4,3-c]pyrimidin-5-amine |
| 135 | 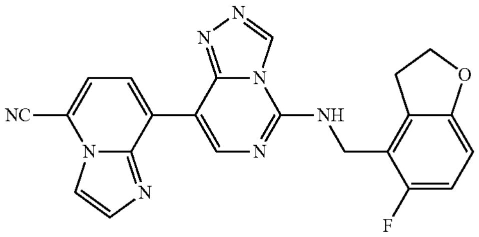 [SMILES: N#Cc1ccc(-c2cnc(NCc3c(F)ccc4c3CCO4)n3cnnc23)c2nccn12] | 8-(5-(((5-fluoro-2,3-dihydrobenzofuran-4-yl)methyl)amino)-[1,2,4]triazolo[4,3-c]pyrimidin-8-yl)imidazo[1,2-a]pyridine-5-carbonitrile |
| 136 | 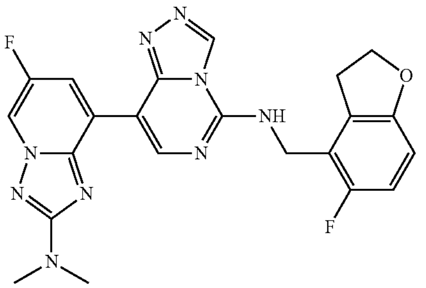 [SMILES: CN(C)c1nc2c(-c3cnc(NCc4c(F)ccc5c4CCO5)n4cnnc34)cc(F)cn2n1] | 8-(2-(dimethylamino)-6-fluoro-[1,2,4]triazolo[1,5-a]pyridin-8-yl)-N-((5-fluoro-2,3-dihydrobenzofuran-4-yl)methyl)-[1,2,4]triazolo[4,3-c]pyrimidin-5-amine |

TABLE 1-continued

| Compound No. | Compound structure | Compound name |
|---|---|---|
| 137 | 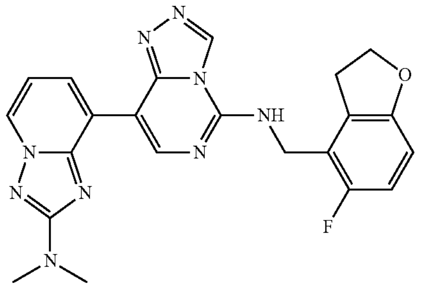 [SMILES: CN(C)c1nc2c(-c3cnc(NCc4c(F)ccc5c4CCO5)n4cnnc34)cccn2n1] | 8-(2-(dimethylamino)-[1,2,4]triazolo[1,5-a]pyridin-8-yl)-N-((5-fluoro-2,3-dihydrobenzofuran-4-yl)methyl)-[1,2,4]triazolo[4,3-c]pyrimidin-5-amine |
| 138 | 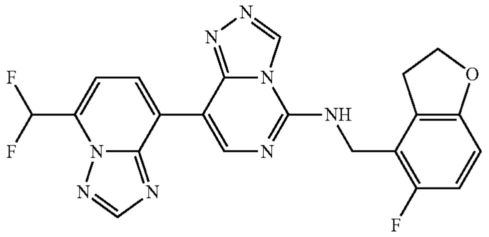 [SMILES: Fc1ccc2c(c1CNc1ncc(-c3ccc(C(F)F)n4ncnc34)c3nncn13)CCO2] | 8-(5-(difluoromethyl)-[1,2,4]triazolo[1,5-a]pyridin-8-yl)-N-((5-fluoro-2,3-dihydrobenzofuran-4-yl)methyl)-[1,2,4]triazolo[4,3-c]pyrimidin-5-amine |
| 139 | 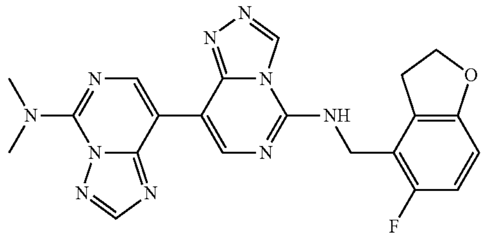 [SMILES: CN(C)c1ncc(-c2cnc(NCc3c(F)ccc4c3CCO4)n3cnnc23)c2ncnn12] | 8-(5-(dimethylamino)-[1,2,4]triazolo[1,5-c]pyrimidin-8-yl)-N-((5-fluoro-2,3-dihydrobenzofuran-4-yl)methyl)-[1,2,4]triazolo[4,3-c]pyrimidin-5-amine |
| 140 | 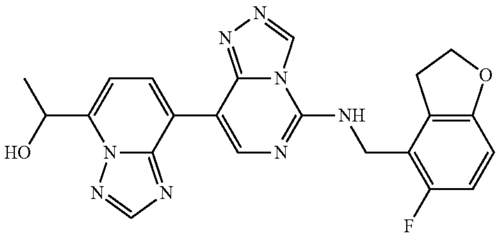 [SMILES: CC(O)c1ccc(-c2cnc(NCc3c(F)ccc4c3CCO4)n3cnnc23)c2ncnn12] | 1-(8-(5-(((5-fluoro-2,3-dihydrobenzofuran-4-yl)methyl)amino)-[1,2,4]triazolo[4,3-c]pyrimidin-8-yl)-[1,2,4]triazolo[1,5-a]pyridin-5-yl)ethan-1-ol |
| 141 | 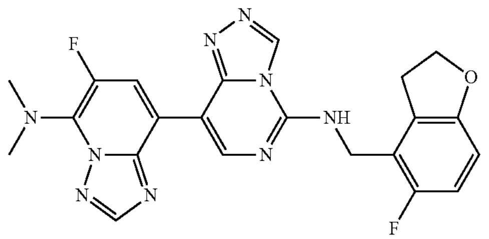 [SMILES: CN(C)c1c(F)cc(-c2cnc(NCc3c(F)ccc4c3CCO4)n3cnnc23)c2ncnn12] | 8-(5-(dimethylamino)-6-fluoro-[1,2,4]triazolo[1,5-a]pyridin-8-yl)-N-((5-fluoro-2,3-dihydrobenzofuran-4-yl)methyl)-[1,2,4]triazolo[4,3-c]pyrimidin-5-amine |
| 142 | 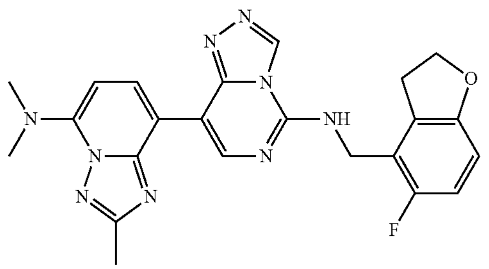 [SMILES: Cc1nc2c(-c3cnc(NCc4c(F)ccc5c4CCO5)n4cnnc34)ccc(N(C)C)n2n1] | 8-(5-(dimethylamino)-2-methyl-[1,2,4]triazolo[1,5-a]pyridin-8-yl)-N-((5-fluoro-2,3-dihydrobenzofuran-4-yl)methyl)-[1,2,4]triazolo[4,3-c]pyrimidin-5-amine |

TABLE 1-continued

| Compound No. | Compound structure | Compound name |
| --- | --- | --- |
| 143 | 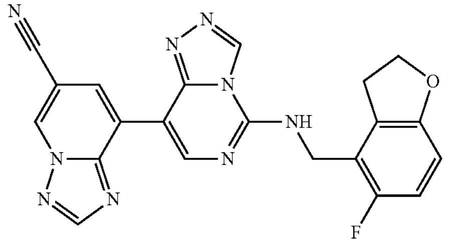 [SMILES: N#Cc1cc(-c2cnc(NCc3c(F)ccc4c3CCO4)n3cnnc23)c2ncnn2c1] | 8-(5-(((5-fluoro-2,3-dihydrobenzofuran-4-yl)methyl)amino)-[1,2,4]triazolo[4,3-c]pyrimidin-8-yl)-[1,2,4]triazolo[1,5-a]pyridine-6-carbonitrile |
| 144 | 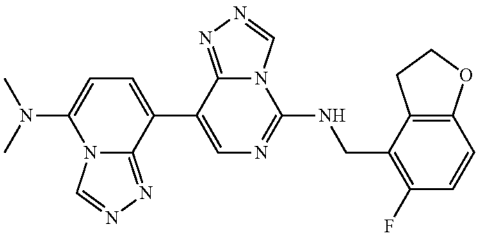 [SMILES: CN(C)c1ccc(-c2cnc(NCc3c(F)ccc4c3CCO4)n3cnnc23)c2nncn12] | 8-(5-(dimethylamino)-[1,2,4]triazolo[4,3-a]pyridin-8-yl)-N-((5-fluoro-2,3-dihydrobenzofuran-4-yl)methyl)-[1,2,4]triazolo[4,3-c]pyrimidin-5-amine |
| 145 | 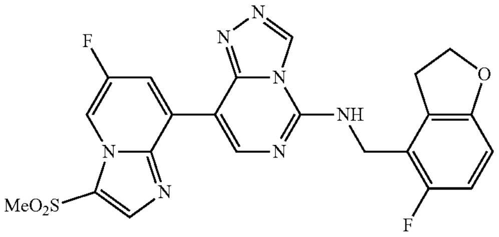 [SMILES: CS(=O)(=O)c1cnc2c(-c3cnc(NCc4c(F)ccc5c4CCO5)n4cnnc34)cc(F)cn12] | N-((5-fluoro-2,3-dihydrobenzofuran-4-yl)methyl)-8-(6-fluoro-3-(methylsulfonyl)imidazo[1,2-a]pyridin-8-yl)-[1,2,4]triazolo[4,3-c]pyrimidin-5-amine |
| 146 | 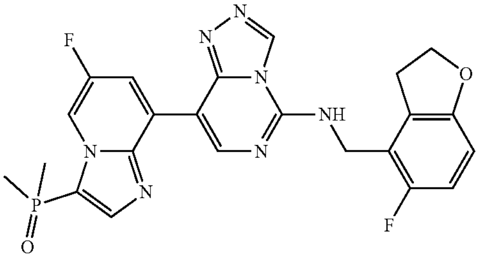 [SMILES: CP(C)(=O)c1cnc2c(-c3cnc(NCc4c(F)ccc5c4CCO5)n4cnnc34)cc(F)cn12] | (6-fluoro-8-(5-(((5-fluoro-2,3-dihydrobenzofuran-4-yl)methyl)amino)-[1,2,4]triazolo[4,3-c]pyrimidin-8-yl)imidazo[1,2-a]pyridin-3-yl)dimethylphosphine oxide |
| 147 | 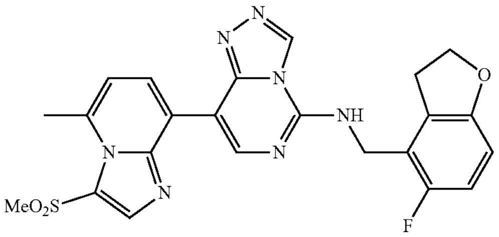 [SMILES: Cc1ccc(-c2cnc(NCc3c(F)ccc4c3CCO4)n3cnnc23)c2ncc(S(C)(=O)=O)n12] | N-((5-fluoro-2,3-dihydrobenzofuran-4-yl)methyl)-8-(5-methyl-3-(methylsulfonyl)imidazo[1,2-a]pyridin-8-yl)-[1,2,4]triazolo[4,3-c]pyrimidin-5-amine |
| 148 | 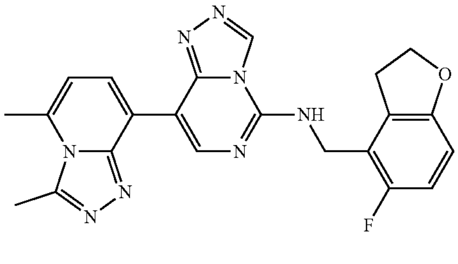 [SMILES: Cc1ccc(-c2cnc(NCc3c(F)ccc4c3CCO4)n3cnnc23)c2nnc(C)n12] | 8-(3,5-dimethyl-[1,2,4]triazolo[4,3-a]pyridin-8-yl)-N-(5-fluoro-2,3-dihydrobenzofuran-4-yl)methyl)-[1,2,4]triazole[4,3-c]pyrimidin-5-amine |

TABLE 1-continued

| Compound No. | Compound structure | Compound name |
| --- | --- | --- |
| 149 | 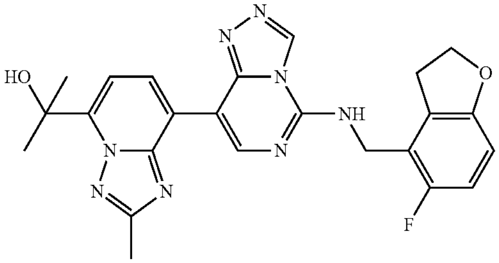 [SMILES: Cc1nc2c(-c3cnc(NCc4c(F)ccc5c4CCO5)n4cnnc34)ccc(C(C)(C)O)n2n1] | 2-(8-(5-(((5-fluoro-2,3-dihydrobenzofuran-4-yl)methyl)amino)-[1,2,4]triazolo[4,3-c]pyrimidin-8-yl)-2-methyl[1,2,4]triazolo[1,5-a]pyridin-5-yl)propan-2-ol |

The present disclosure also provides an isotopically-labeled compound of the compound as shown in formula (I), the pharmaceutically acceptable salt, hydrate, prodrug, and stereoisomer thereof or the solvate thereof. The isotope in the isotopically-labeled compound is selected from $^{2}H$, $^{3}H$, $^{11}C$, $^{13}C$, $^{14}C$, $^{15}N$, $^{18}F$, $^{31}P$, $^{32}P$, $^{35}S$, $^{36}Cl$ and $^{125}I$. Atoms that can be isotopically labeled in the compound of formula (I) include, but are not limited to hydrogen, carbon, nitrogen, oxygen, phosphorous, fluorine, chlorine, and iodine and they can be replaced by isotopes $^{2}H$, $^{3}H$, $^{11}C$, $^{13}C$, $^{14}C$, $^{15}N$, $^{18}F$, $^{31}P$, $^{32}P$ $^{35}S$, $^{36}Cl$, $^{125}I$, etc., respectively.

The present disclosure also provides a method for preparing the compound as shown in formula (I), which method comprises the step of:

subjecting halo intermediate compound $B_0$ to a coupling reaction so as to obtain the compound as shown in formula (I),

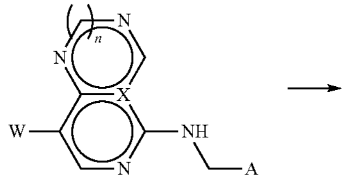

$B_0$

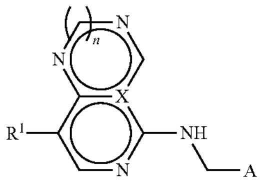

(I)

wherein W represents halogen, preferably Br; the definitions of A, $R^1$, X and n are as described above.

In the present disclosure, the halo intermediate $B_0$ and the intermediate $E_0$ are subjected to a coupling reaction so as to obtain the compound as shown in formula (I),

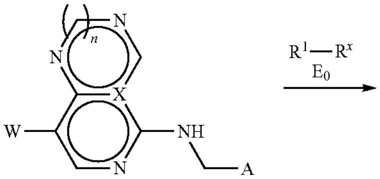

$B_0$

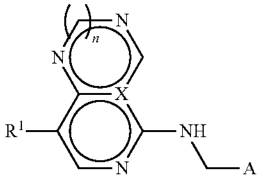

(I)

wherein W represents halogen, preferably Br; $R^x$ is —$B(OH)_2$ or

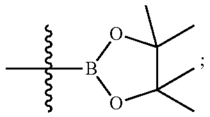 [SMILES: *B1OC(C)(C)C(C)(C)O1]

the definitions of A, $R^1$, X and n are as described above.

In a preferred example, the halo intermediate compound B is subjected to a coupling reaction so as to obtain the compound as shown in formula I-A according to the following reaction equation:

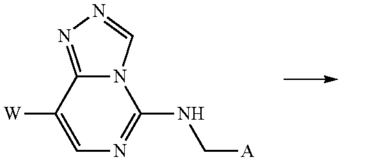

B

-continued

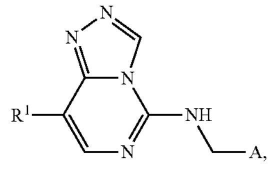

I-A wherein W represents halogen, preferably Br; the definitions of A and $R^1$ are as described above.

In a preferred example, the halo intermediate compound B and the intermediate $E_0$ are subjected to a coupling reaction as shown below so as to obtain the compound as shown in formula I-A

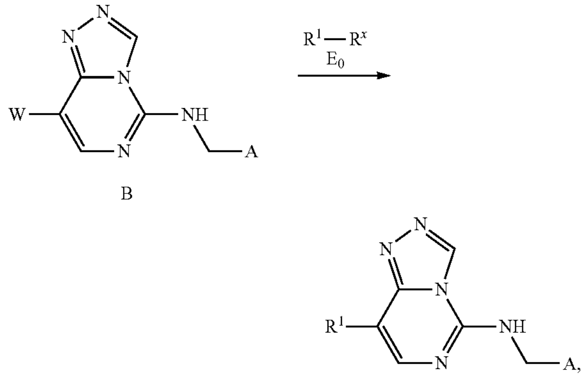

B

I-A wherein W represents halogen, preferably Br; $R^x$ is —$B(OH)_2$ or

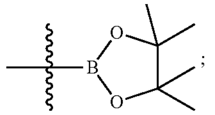 [SMILES: *B1OC(C)(C)C(C)(C)O1]

the definitions of A and $R^1$ are as described above.

The present disclosure also provides a method for preparing the compound as shown in formula (Ib), which method comprises the step of: subjecting intermediate B-1 to a ring closure reaction as shown below so as to obtain the compound as shown in formula (Ib),

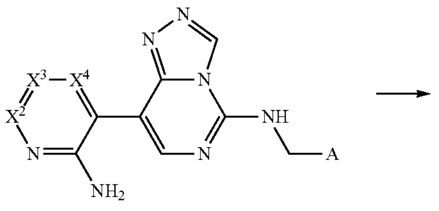

B-1

-continued

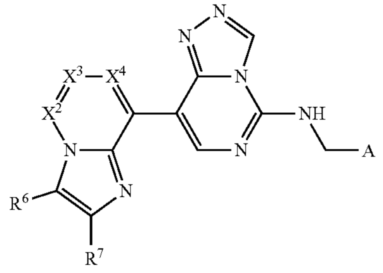

(Ib)

wherein the definitions of $X^2$, $X^3$, $X^4$, $R^6$, $R^7$, and A are as defined in the present disclosure.

The method for preparing the compound as shown in formula (Ib) may also further comprise the step of: subjecting the halo intermediate compound B to a coupling reaction so as to obtain the intermediate B-1:

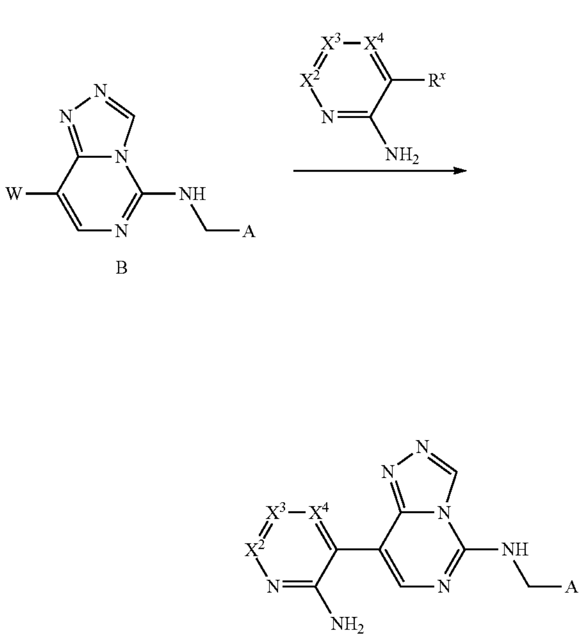

B

B-1 wherein W represents halogen, preferably Br; $R^x$ is —$B(OH)_2$ or

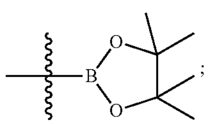 [SMILES: *B1OC(C)(C)C(C)(C)O1]

the definitions of A, $X^2$, $X^3$ and $X^4$ are as defined in the present disclosure.

The present disclosure also provides a method for preparing the compound as shown in formula (Ic), which method comprises the step of: subjecting halo intermediate compound B and intermediate $E_{01}$ to a coupling reaction as shown below so as to obtain the compound as shown in formula (Ic),

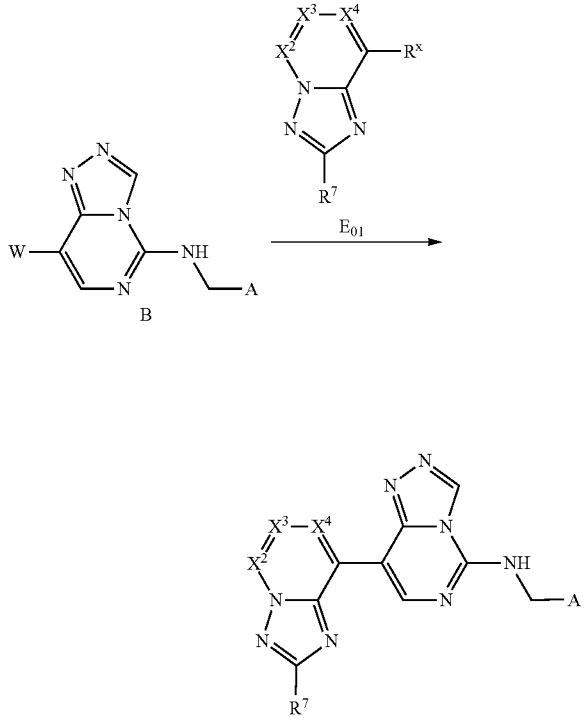
B
$E_{01}$
(Ic)

wherein W represents halogen, preferably Br; $R^x$ is $-B(OH)_2$ or

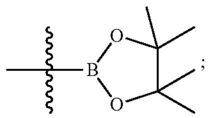 [SMILES: *B1OC(C)(C)C(C)(C)O1]

the definitions of A and $R^1$ are as described above.

The method for preparing the compound as shown in formula (Ic) may also further comprise the following steps for preparing the intermediate $E_{01}$,

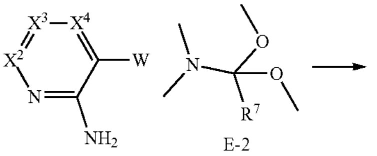
E-1 E-2

-continued

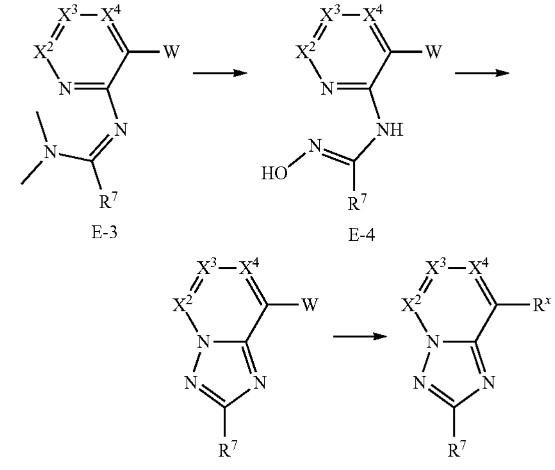
E-3 E-4 E-5 $E_{01}$ wherein W represents halogen, preferably Br; $R^x$ is $-B(OH)_2$ or

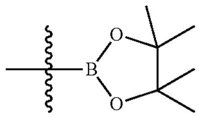

the definitions of $X^2$, $X^3$, $X^4$ and $R^7$ are as defined in the present disclosure.

The present disclosure also provides a method for preparing intermediate compounds C1-7, C1-a, or C1-b, which method comprises the steps of:

reacting compound C1-1 with 1,2-dihaloethane (such as 1,2-dibromoethane) so as to obtain compound C1-2, subjecting the C1-2 to an elimination reaction so as to obtain compound C1-3, subjecting the C1-3 and p-toluenesulfonyl hydrazide to condensation so as to obtain sulfonylhydrazone C1-4, subjecting the C1-4 to a furan-fused three-membered ring closure reaction so as to obtain compound C1-5, substituting the bromine atom in the C1-5 with cyano under catalytic conditions so as to obtain compound C1-6, reducing the cyano to an amine group and in-situ protecting the amine group with Boc-anhydride so as to obtain C1-7;

and/or, further, subjecting the C1-7 to separation by chiral SFC so as to obtain C1-7a and C1-7b, and removing the protecting groups of C1-7a and C1-7b so as to obtain C1-a and C1-b, respectively,

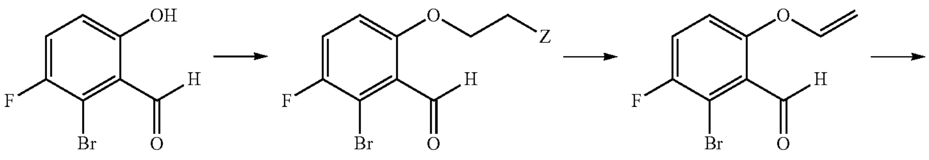
C1-1 C1-2 C1-3

-continued

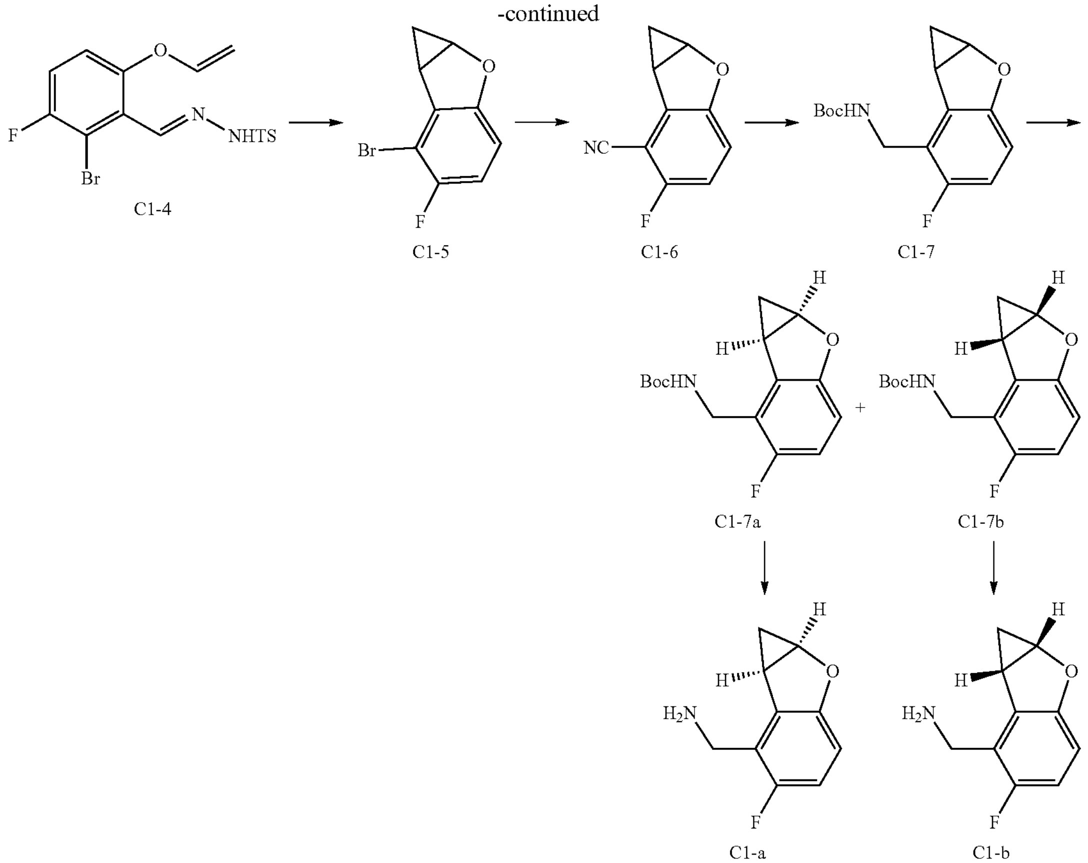

C1-4 C1-5 C1-6 C1-7 C1-7a C1-7b C1-a C1-b wherein Z is halogen (such as Cl, Br or I), preferably Br.

The present disclosure also provides a method for preparing intermediate compound B, which method comprises the steps of:

reacting compound D-1 with hydrazine hydrate so as to obtain compound D-2, subjecting the compound D-2 and trimethylorthoformate to ring closure under the action of a catalyst (such as trifluoroacetic acid) so as to obtain intermediate D, and reacting the D with the intermediate C so as to obtain intermediate B according to the following reaction equations:

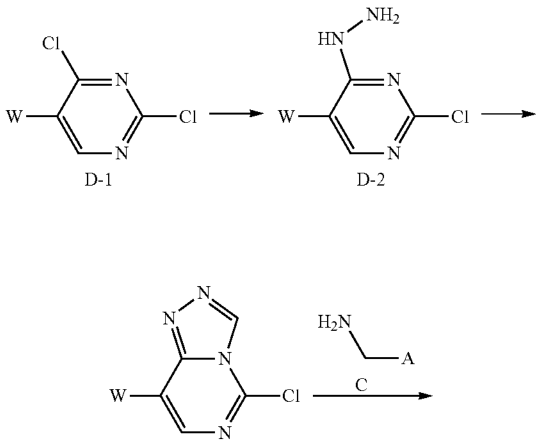

D-1 D-2 D

-continued

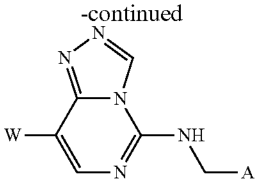

B wherein the definitions of W and A are as described above.

The present disclosure also provides intermediate compounds:

D-2

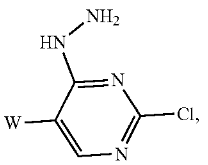

D

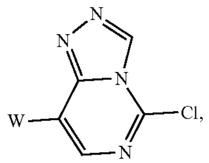

-continued

B

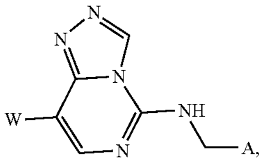

B1

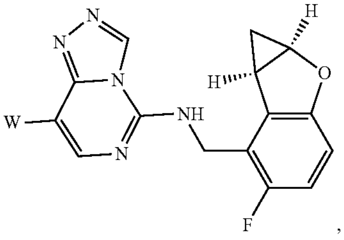
,

B2

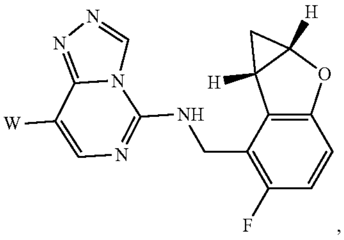
,

C1-a

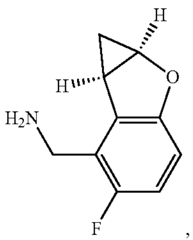
,

C1-b

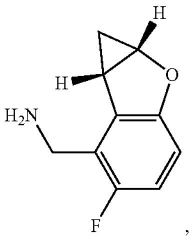
,

C1-7a

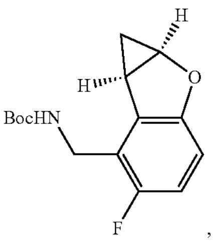
,

-continued

C1-7b

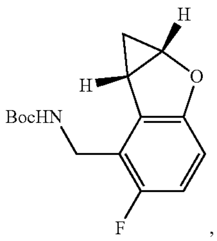
, and

C1-7

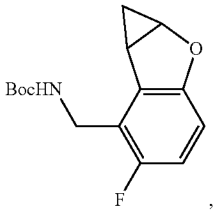
, wherein W represents halogen (such as Cl, Br or I).

The solvents involved in the present disclosure, e.g. can be selected from: methanol, ethanol, isopropanol, toluene, xylene, chlorobenzene, water, dichloromethane, chloroform, carbon tetrachloride, 1,2-dichloroethane, dioxane, DMF, acetonitrile, DMSO, NMP, THE or combinations thereof; for example, the solvents are selected from dichloromethane, chloroform, 1,2-dichloroethane, dioxane, DMF, acetonitrile, DMSO, NMP, THE or combinations thereof.

The bases involved in the present disclosure can include organic bases and inorganic bases.

The organic bases involved in the present disclosure e.g. can be selected from: TEA, DIPEA or combinations thereof.

The inorganic bases involved in the present disclosure e.g. can be selected from: sodium hydride, sodium methoxide, potassium carbonate, sodium carbonate, cesium carbonate, potassium tert-butoxide, sodium tert-butoxide, lithium tert-butoxide, LiHMIDS, LDA, butyl lithium, potassium hydroxide, potassium acetate, lithium aluminum hydride or combinations thereof, for example, the inorganic bases are selected from sodium hydride, potassium carbonate, sodium carbonate, cesium carbonate, potassium tert-butoxide, sodium tert-butoxide, LiHMDS, LDA, butyl lithium or combinations thereof.

The isotopically-labeled compound of the compound as shown in formula (I) as defined in the present disclosure can be prepared by a similar synthesis method as that of the unlabeled compound, except that the unlabeled starting raw materials and/or reagents are replaced by the isotopically-labeled starting raw materials and/or reagents.

The present disclosure also provides a pharmaceutical composition comprising the compound as shown in formula (I), the pharmaceutically acceptable salt, hydrate, prodrug, and stereoisomer thereof, the solvate thereof, or their isotopically-labeled compounds as described above, and a pharmaceutically acceptable excipient. The pharmaceutically acceptable excipient can be one or more of diluents, absorbents, wetting agents, binders, disintegrating agents, and lubricating agents.

The present disclosure also provides the use of the compound as shown in formula (I), the pharmaceutically acceptable salt, hydrate, prodrug, stereoisomer thereof, and solvate thereof, or their isotopically-labeled compounds as described above, or the pharmaceutical composition as described above in the preparation of a drug. The drug is preferably a drug for treating cancer.

The present disclosure also provides the use of the compound as shown in formula (I), the pharmaceutically acceptable salt, hydrate, prodrug, stereoisomer thereof, and solvate thereof, or their isotopically-labeled compounds as described above, or the pharmaceutical composition as described above in the preparation of a drug for treating cancer related to the mechanism of action of an EED protein and/or a PRC2 protein complex.

Preferably, the cancer includes but is not limited to lymphoma (such as diffuse large B-cell lymphoma, follicular lymphoma, non-Hodgkin's lymphoma), leukemia, multiple myeloma, mesothelioma, gastric cancer, malignant rhabdoid tumor, liver cancer, prostate cancer, breast cancer, cerebroma including neuroblastoma, glioma, glioblastoma and astrocytoma, cervical cancer, colon cancer, melanoma, endometrial carcinoma, esophageal carcinoma, head and neck cancer, lung cancer, nasopharyngeal carcinoma, ovarian cancer, pancreatic cancer, renal carcinoma, rectal cancer, thyroid cancer, parathyroid tumor, uterine cancer, and soft tissue sarcoma.

Preferably, the compound, the pharmaceutically acceptable salt, hydrate, prodrug, and stereoisomer thereof, solvate thereof, or their isotopically-labeled compounds can be used in combination with an additional drug; more preferably, the additional drug is selected from an anti-cancer drug, an immuno-oncology drug, an antiallergic drug, an antiemetic, an analgesic, or a cell protective drug.

The present disclosure also provides a pharmaceutical preparation comprising the compound as shown in formula (I), the pharmaceutically acceptable salt, hydrate, prodrug, and stereoisomer thereof, solvate thereof, or their isotopically-labeled compounds as described above, or the pharmaceutical composition as described above. The pharmaceutical preparation is preferably in the form of tablets, capsules (e.g., sustained-release or time-release capsules), pills, powders, granules (e.g., small granules), elixirs, tinctures, suspensions (e.g., nanosuspensions, microsuspensions) and spray-dried dispersions and other forms of suspensions, syrups, emulsions, solutions, etc. The mode of administration of the pharmaceutical preparation is preferably oral administration, sublingual administration, injection including subcutaneous injection, intravenous injection, intramuscular injection, intrasternal injection, infusion and the like, nasal administration (e.g., nasal inhalation), local topical (e.g., cream and ointment) administration, rectal administration (e.g., suppositories) and other manners. The compound disclosed in the present disclosure can be administered alone or in combination with an appropriate pharmaceutical carrier.

The present disclosure also provides the pharmaceutical preparation which can be formulated into an appropriate drug dosage to facilitate the control of the drug dosage. The dosage regimen of the compound disclosed in the present disclosure differs according to specific factors, e.g., the pharmacodynamics and the administration method, the subjects, and the subjects' sex, age, health status, weight, disease characteristics, other concurrent medication status, administration frequency, liver and kidney function, desired effect and the like. The compound disclosed in the present disclosure can be administered in a single daily dose or in multiple daily doses (e.g., two to four times per day).

The present disclosure also provides a method for treating cancer, which method comprises administering to a patient in need of the treatment a therapeutically effective amount of the compound as shown in formula (I), the pharmaceutically acceptable salt, hydrate, prodrug, and stereoisomer thereof, or solvate thereof, or their isotopically-labeled compounds as described above, or the pharmaceutical composition as described above. The cancer includes but is not limited to lymphoma (such as diffuse large B-cell lymphoma, follicular lymphoma, non-Hodgkin's lymphoma), leukemia, multiple myeloma, mesothelioma, gastric cancer, malignant rhabdoid tumor, liver cancer, prostate cancer, breast cancer, cerebroma including neuroblastoma, glioma, glioblastoma and astrocytoma, cervical cancer, colon cancer, melanoma, endometrial carcinoma, esophageal carcinoma, head and neck cancer, lung cancer, nasopharyngeal carcinoma, ovarian cancer, pancreatic cancer, renal carcinoma, rectal cancer, thyroid cancer, parathyroid tumor, uterine cancer, and soft tissue sarcoma.

The present disclosure also provides the compound as shown in formula (I), the pharmaceutically acceptable salt, hydrate, prodrug, and stereoisomer thereof, or solvate thereof, or the aforementioned isotopically-labeled compounds used in combination with with an additional drug, wherein the additional drug is selected from: an anti-cancer drug, an immuno-oncology drug, an antiallergic drug, an antiemetic, an analgesic, a cell protective drug, etc. and the combined use results in a better efficacy.

In the present disclosure, the cancer is preferably a cancer related to an EED protein and/or a PRC2 protein complex.

The present disclosure also provides a method for inhibiting the activity of an EED protein and/or a PRC2 protein complex, which method comprises administering to a subject a therapeutically effective amount of the compound as shown in formula (I), the pharmaceutically acceptable salt, hydrate, prodrug, and stereoisomer thereof, or solvate thereof, or their isotopically-labeled compounds as described above, or the pharmaceutical composition as described above.

The present disclosure also provides a method for blocking EED binding to H3K27 (such as H3K27me3), which method comprises administering to a subject a therapeutically effective amount of the compound as shown in formula (I), the pharmaceutically acceptable salt, hydrate, prodrug, and stereoisomer thereof, or solvate thereof, or their isotopically-labeled compounds as described above, or the pharmaceutical composition as described above.

It should be understood that, within the scope of the present disclosure, each of the above-mentioned technical features of the present disclosure and each of the technical features specifically described hereinafter (e.g., examples) may be combined with each other to constitute a new or preferred technical solution. Due to space limitations, it will not be repeated herein.

Description of Terminology

Unless otherwise defined, all technical and scientific terms used herein have the same meaning as commonly understood by those of ordinary skill in the art to which the present disclosure pertains.

As used herein, when referring to specifically recited numerical values, the term "about" means that the value can vary from the recited value by no more than 1%. For example, as used herein, the expression "about 100" includes all values between 99 and 101 (e.g., 99.1, 99.2, 99.3, 99.4, etc.).

As used herein, the terms "contain" or "include (comprise)" can be open, semi-closed, and closed. In other words, the term also includes "essentially consist of" or "consist of".

Definitions of Groups

Definitions of standard chemical terms can be found in references (including Carey and Sundberg "ADVANCED ORGANIC CHEMISTRY 4TH ED." Vols. A (2000) and B (2001), Plenum Press, New York). Unless otherwise specified, conventional methods within the technical scope of the art, e.g., mass spectrometry, NMR, IR, and UV/VIS spectroscopy, and pharmacological methods are used. Unless specific definitions are provided, the terms used in the description regarding analytical chemistry, organic synthetic chemistry, and drugs and medicinal chemistry are known in the art. Standard techniques can be used in chemical synthesis, chemical analysis, drug preparation, formulation and delivery, and treatment of patients. For example, the reaction and purification can be carried out according to the manufacturer's instructions for the kit, or in a manner known in the art or according to the description of the present disclosure. In general, the above-mentioned techniques and methods can be implemented according to conventional methods well known in the art according to the descriptions in a number of summary and more specific documents cited and discussed in this specification. In this specification, groups and substituents thereof can be selected by those skilled in the art to provide stable moieties and compounds.

When a substituent is described by a general chemical formula written from left to right, this substituent also includes chemically equivalent substituents obtained when the structural formula is written from right to left. For example, —$CH_2O$— is equivalent to $OCH_2$—.

The section headings used herein are for the purpose of organizing the article and should not be interpreted as the limitation on the subject. All documents or document parts cited in this application, including but not limited to patents, patent applications, articles, books, operation manuals and papers, are incorporated herein by reference in their entireties.

Some chemical groups defined herein are preceded by simplified symbols to indicate the total number of carbon atoms present in the group. For example, $C_{1-6}$ alkyl refers to an alkyl group having a total of 1 to 6 carbon atoms (such as 1, 2, 3, 4, 5, 6 carbon atoms) as defined below. The total number of carbon atoms in the simplified symbol does not include carbons that may be present in the substituents of the group.

In addition to the foregoing, when used in the specification and claims of this application, unless otherwise specifically noted, the following terms have the meanings as indicated below.

In the present application, the term "halogen" refers to fluorine, chlorine, bromine or iodine.

"Hydroxy" refers to the —OH group.

"Carbonyl" refers to the —C(=O)— group. When the R in the

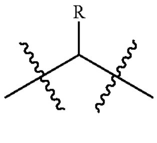

is carbonyl,

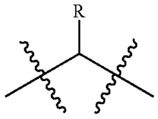

is

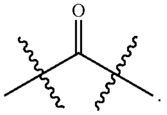 [SMILES: *C(*)=O]

"Cyano" refers to —CN.

"Amino" refers to —$NH_2$.

"Substituted amino" refers to an amino group substituted by one or two groups selected from alkyl, alkylcarbonyl, arylalkyl, heteroarylalkyl groups as defined below, e.g., monoalkylamino, dialkylamino, alkylacylamino, arylalkylamino, heteroarylalkylamino.

"Carboxyl" refers to —COOH.

In the present application, as a group or a part of other groups (e.g., used in a group, such as alkyl substituted by halogen), the term "alkyl" refers to a fully saturated linear or branched chain hydrocarbon group consisting of only carbon atoms and hydrogen atoms, has for example 1-12 (preferably 1-8, more preferably 1-6, more preferably 1-4) carbon atoms, and is connected to the rest of the molecule via a single bond, including but not limited to methyl, ethyl, n-propyl, isopropyl, n-butyl, isobutyl, sec-butyl, tert-butyl, n-pentyl, 2-methylbutyl, 2,2-dimethylpropyl, n-hexyl, heptyl, 2-methylhexyl, 3-methylhexyl, octyl, nonyl and decyl.

In the present application, as a group or a part of other groups, the term "haloalkyl" refers to an alkyl group (as defined in the present disclosure) where one or more hydrogen atoms are substituted by halogen (as defined in the present disclosure), wherein the number of the halogen can be one or more; and when the number of the halogen is more than one, the halogen can be the same or different. For example, fluoroalkyl refers to an alkyl group substituted with one or more fluoro. Examples of haloalkyl include, but are not limited to trifluoromethyl and difluoromethyl.

In the present application, preferably, in "heterocycloalkyl", the number of the carbon atom is 3, 4, 5, or 6, the heteroatom is selected from N, O and S, and the number of the heteroatom is 1, 2, 3 or 4; further preferably, the number of the carbon atom is 4 or 5, the heteroatom is selected from N and O, and the number of the heteroatom is 1 or 2; such as

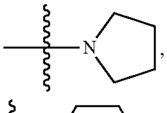

,

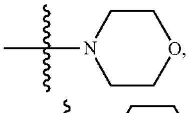

,

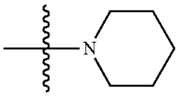

, or

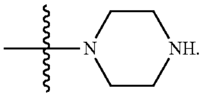

In the present application, preferably, in "heterospirocycloalkyl", the number of the carbon atom is 4, 5 or 6, the heteroatom is selected from N, O and S, the number of the heteroatom is 1, 2, 3 or 4; further preferably, the heteroatom is selected from N and O, and the number of the heteroatom is 1 or 2; such as

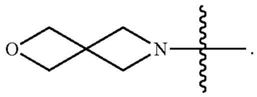 [SMILES: *N1CC2(COC2)C1]

In the present application, as a group or part of other groups, the term "cyclic hydrocarbon group" means a stable non-aromatic monocyclic or polycyclic hydrocarbon group consisting of only carbon atoms and hydrogen atoms, and can include fused ring system, bridged ring system or spiro ring system, has 3-15 carbon atoms, preferably 3-10 carbon atoms, more preferably 3-8 carbon atoms, and it is saturated or unsaturated and can be connected to the rest of the molecule via a single bond through any suitable carbon atom. Unless otherwise specifically noted in the specification, the carbon atom in the cyclic hydrocarbon group can be optionally oxidized. Examples of cyclic hydrocarbon include, but are not limited to, cyclopropyl, cyclobutyl, cyclopentyl, cyclopentenyl, cyclohexyl, cyclohexenyl, cyclohexadienyl, cycloheptyl, cyclooctyl, 1H-indenyl, 2,3-dihydroindenyl, 1,2,3,4-tetrahydro-naphthyl, 5,6,7,8-tetrahydro-naphthyl, 8,9-dihydro-7H-benzocyclohepten-6-yl, 6,7,8,9-tetrahydro-5H-benzocycloheptenyl, 5,6,7,8,9,10-hexahydro-benzocyclooctenyl, fluorenyl, bicyclo[2.2.1]heptyl, 7,7-dimethyl-bicyclo[2.2.1]heptyl, bicyclo[2.2.1]heptenyl, bicyclo[2.2.2]octyl, bicyclo[3.1.1]heptyl, bicyclo[3.2.1]octyl, bicyclo[2.2.2]octenyl, bicyclo[3.2.1]octenyl, adamantyl, octahydro-4,7-methylene-1H-indenyl, and octahydro-2,5-methylene-pentalenyl.

In the present application, as a group or part of other groups, the term "cycloalkyl" means a saturated cyclic hydrocarbon group.

In the present application, as a group or part of other groups, the term "cycloalkenyl" means a cyclic hydrocarbon group having at least one double bond (such as a carbon-carbon double bond). Cycloalkenyl can be connected to the rest of the molecule via the atom of the double bond therein.

In the present application, as a group or part of other groups, the term "heterocyclyl" means a stable 3- to 20-membered non-aromatic cyclic group consisting of 2 to 14 carbon atoms and 1 to 6 heteroatoms selected from nitrogen, phosphorus, oxygen and sulfur. Unless otherwise specifically noted in the specification, the heterocyclyl can be a monocyclic, bicyclic, tricyclic or polycyclic ring system, which can include a fused ring system, a bridged ring system or a spiro ring system. The nitrogen, carbon or sulfur atom in the heterocyclyl can be optionally oxidized, and the nitrogen atom can be optionally quaternized. The heterocyclyl can be partially or fully saturated. The heterocyclyl can be connected to the rest of the molecule via a single bond through a carbon atom or a heteroatom. In a heterocyclyl containing a fused ring, the one or more rings can be an aryl group or a heteroaryl group as defined below, provided that the site connected to the rest of the molecule is a non-aromatic ring atom. For the purposes of the present disclosure, the heterocyclyl is preferably a stable 4- to 11-membered non-aromatic monocyclic, bicyclic, bridged cyclic or spiro cyclic group containing 1 to 3 heteroatoms selected from nitrogen, oxygen and sulfur, more preferably a stable 4- to 8-membered non-aromatic monocyclic, bicyclic, bridged cyclic or spiro cyclic group containing 1 to 3 heteroatoms selected from nitrogen, oxygen and sulfur. Examples of heterocyclyl include, but are not limited to: pyrrolidinyl, morpholinyl, piperazinyl, homopiperazinyl, piperidinyl, thiomorpholinyl, 2,7-diazaspiro[3.5]nonan-7-yl, 2-oxa-6-azaspiro[3.3]heptane-6-yl, 2,5-diaza-bicyclo[2.2.1]heptane-2-yl, azetidinyl, pyranyl, tetrahydropyranyl, thiopyranyl, tetrahydrofuryl, oxazinyl, dioxolanyl, tetrahydroisoquinolinyl, decahydroisoquinolinyl, imidazolinyl, imidazolidinyl, quinolizinyl, thiazolidinyl, isothiazolidinyl, isoxazolidinyl, indolinyl, octahydroindolyl, octahydroisoindolyl, pyrrolidinyl, pyrazolidinyl, and phthalimido.

In the present application, as a group or part of other groups, the term "aryl" means a conjugated cyclic hydrocarbon group having 6 to 18 carbon atoms (preferably having 6 to 10 carbon atoms). For the purposes of the present disclosure, the aryl can be a monocyclic, bicyclic, tricyclic or polycyclic ring system, and can also be fused to a cycloalkyl or heterocyclyl group as defined above, provided that the aryl is connected to the rest of the molecule via a single bond through the atom on the aromatic ring. Examples of aryl include, but are not limited to, phenyl, naphthyl, anthracenyl, phenanthrenyl, fluorenyl, 2,3-dihydro-1H-isoindolyl, 2-benzoxazolinone, and 2H-1,4-benzoxazine-3(4H)-one-7-yl.

In the present application, the term "arylalkyl" refers to an alkyl group as defined above substituted by an aryl group as defined above.

In the present application, as a group or a part of other groups, the term "heteroaryl" means a 5- to 16-membered conjugated cyclic group having 1 to 15 carbon atoms (preferably having 1 to 10 carbon atoms) and 1 to 6 heteroatoms selected from nitrogen, oxygen and sulfur within the ring. Unless otherwise specifically noted in the specification, the heteroaryl can be a monocyclic, bicyclic, tricyclic or polycyclic ring system, and can also be fused to cycloalkyl or heterocyclyl as defined above, provided that the heteroaryl is connected to the rest of the molecule via a single bond through the atom on the aromatic ring. The nitrogen, carbon or sulfur atom of the heteroaryl can be optionally oxidized, and the nitrogen atom can be optionally quaternized. For the purposes of the present disclosure, the heteroaryl is preferably a stable 5- to 12-membered aromatic group containing 1 to 5 heteroatoms selected from nitrogen, oxygen, and sulfur, and more preferably a stable 5- to 10-membered aromatic group containing 1 to 4 heteroatoms from nitrogen, oxygen and sulfur or a 5- to 6-membered aromatic group containing 1 to 3 heteroatoms selected from nitrogen, oxygen and sulfur (for example, the heteroaryl is $C_1$-$C_5$ heteroaryl, wherein the heteroatom is selected from N, O and S, and the number of the heteroatom is 1, 2, 3, or 4). Examples of heteroaryl include, but are not limited to, thienyl, imidazolyl, pyrazolyl, thiazolyl, oxazolyl, oxadiazolyl, isoxazolyl, pyridyl, pyrimidinyl, pyrazinyl, pyridazinyl, benzimidazolyl, benzpyrazolyl, indolyl, furyl, pyrrolyl, triazolyl, tetrazolyl, triazinyl, indolizinyl, isoindolyl, indazolyl, isoindazolyl, purinyl, quinolinyl, isoquinolinyl, diazanaphthyl, naphthyridinyl, quinoxalinyl, pteridinyl, carbazolyl, carbolinyl, phenanthridinyl, phenanthrolinyl, acridinyl, phenazinyl, isothiazolyl, benzothiazolyl, benzothienyl, oxtriazolyl, cinnolinyl, quinazolinyl, phenylthio, indolizinyl, o-phenanthrolinyl, isoxazolyl, phenoxazinyl, phenothiazinyl, 4,5,6,7-tetrahydrobenzo[b]thienyl, naphthopyridyl, [1,2,4]triazolo[4,3-b]pyridazine, [1,2,4]triazolo[4,3-a]pyrazine, [1,2,4]triazolo[4,3-c]pyrimidine, [1,2,4]triazolo[4,3-a]pyridine, imidazo[1,2-a]pyridine, imidazo[1,2-b]pyridazine, and imidazo[1,2-a]pyrazine.

In the present application, "optionally" means that the subsequently described event or condition can or cannot occur, and the description includes both the occurrence and non-occurrence of the event or condition. For example, "optionally substituted aryl" means that the aryl is substituted or unsubstituted, and the description includes both substituted aryl and unsubstituted aryl. The "optionally" substituents described in the claims and the specification of the present disclosure are selected from alkyl, alkenyl, alkynyl, halogen, haloalkyl, haloalkenyl, haloalkynyl, cyano, nitro, an optionally substituted aryl group, an optionally substituted heteroaryl group, an optionally substituted cyclic hydrocarbon group, an optionally substituted heterocyclic hydrocarbon group.

In the present disclosure, the term "substitution" or "substituent" refers to one or more hydrogen atoms being replaced by a group indicated. When the number of the substituent is not indicated, the substituent can be one or more; when the substitution position is not indicated, the substitution can occur at any position, provided that the formation of a stable or chemically feasible chemical is allowed.

Where any variable (such as R) appears more than once in the composition or structure of a compound, its definition in each case is independent. Thus, for example, if a group is substituted with 0-2 R, the group can optionally be substituted with up to two R, and R in each case has independent options. For example, in

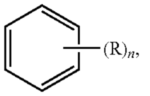

when n is 2, it means that the benzene ring is substituted with 2 R and each R has independent options, that is to say, the 2 R maybe the same or different. In addition, combinations of substituents and/or variants thereof are permissible only if such combinations result in stable compounds.

The terms "moiety", "structural moiety", "chemical moiety", "group" and "chemical group" as used herein refer to a particular fragment or functional group in a molecule. A chemical moiety is generally considered to be a chemical entity that is embedded or attached to a molecule.

When the compound of the present disclosure contains an olefinic double bond, the compounds of the present disclosure are intended to include E- and Z-geometric isomers unless otherwise stated.

"Tautomer" refers to an isomer formed by the transfer of a proton from one atom of a molecule to another atom of the same molecule. All tautomeric forms of the compounds of the present disclosure will also fall within the scope of the present disclosure.

The compounds or pharmaceutically acceptable salts thereof of the present disclosure may contain one or more chiral carbon atoms, thus resulting in enantiomers, diastereomers, and other stereoisomeric forms. Each chiral carbon atom can be defined as (R)- or (S)-based on stereochemistry. The present disclosure is intended to include all possible isomers, as well as racemate and optically pure forms thereof. Racemates, diastereomers or enantiomers may be used as raw materials or intermediates for the preparation of the compounds of the present disclosure. Optically active isomers can be prepared using chiral synthons or chiral reagents, or resolved using conventional techniques, such as by crystallization and chiral chromatography. The stereoisomer of the compound of the present disclosure can be (R)- or (S)-isomers.

Conventional techniques for the preparation/isolation of individual isomers include chiral synthesis from a suitable optically pure precursor, or resolution of the racemate (or racemic form of a salt or derivative) using, for example, chiral high performance liquid chromatography, for example, see Gerald Gubitz and Martin G. Schmid (Eds.), Chiral Separations, Methods and Protocols, Methods in Molecular Biology, Vol. 243, 2004; A. M. Stalcup, Chiral Separations, Annu. Rev. Anal. Chem. 3: 341-63, 2010; Fumiss et al. (eds.), Vogel's Encyclopedia of Practical Organic Chemistry 5.sup.TH ED., Longman Scientific and Technical Ltd., Essex, 1991, 809-816; Heller, Acc. Chem. Res. 1990, 23, 128.

In the present application, the term "pharmaceutically acceptable salt" includes pharmaceutically acceptable acid addition salts and pharmaceutically acceptable base addition salts.

"Pharmaceutically acceptable acid addition salt" refers to a salt formed with an inorganic acid or organic acid which retains the bioavailability of the free base without other side effects. Inorganic acid salts include, but are not limited to, hydrochlorides, hydrobromides, sulfates, nitrates, and phosphates; organic acid salts include, but are not limited to, formate, acetate, 2,2-dichloroacetate, trifluoroacetate, propionate, hexanoate, octoate, decanoate, undecylenate, glycolate, gluconate, lactate, sebacate, adipate, glutarate, malonates, oxalates, maleates, succinates, fumarates, tartrates, citrates, palmitates, stearates, oleates, cinnamate, laurate, malate, glutamate, pyroglutamate, aspartate, benzoate, methanesulfonate, besylate, p-toluenesulfonate, alginate, ascorbate, salicylate, 4-aminosalicylate, and naphthalene disulfonate. These salts can be prepared by methods known in the art.

"Pharmaceutically acceptable base addition salt" refers to a salt formed with an inorganic base or organic base capable of maintaining the bioavailability of the free acid without other side effects. Salts derived from inorganic bases include, but are not limited to, sodium salts, potassium salts, lithium salts, ammonium salts, calcium salts, magnesium salts, iron salts, zinc salts, copper salts, manganese salts, and aluminum salts. Preferred inorganic salts are ammonium, sodium, potassium, calcium and magnesium salts. Salts derived from organic bases include, but are not limited to, the following salts: primary amines, secondary amines and tertiary amines, substituted amines, including naturally substituted amines, cyclic amines, and basic ion exchange resins, for example, ammonia, isopropylamine, trimethylamine, diethylamine, triethylamine, tripropylamine, ethanolamine, diethanolamine, triethanolamine, dimethylethanolamine, 2-dimethylaminoethanol, 2-diethylaminoethanol, bicyclo hexylamine, lysine, arginine, histidine, caffeine, procaine, choline, betaine, ethylenediamine, glucosamine, methylglucosamine, theobromine, purine, piperazine, piperidine, N-ethylpiperidine, and polyamine resin. Preferred organic bases include isopropylamine, diethylamine, ethanolamine, trimethylamine, dicyclohexylamine, choline and caffeine. These salts can be prepared by methods known in the art.

In the present application, the "pharmaceutical composition" refers to a preparation of the compound of the present disclosure and a medium generally accepted in the art for delivering a bioactive compound to a mammal (such as a human being). The medium includes a pharmaceutically acceptable carrier. The purpose of the pharmaceutical composition is to promote the administration to the organism, facilitate the absorption of the active ingredients and then exert the biological activity.

The term “pharmaceutically acceptable” as used herein refers to a substance (such as a carrier or diluent) that does not affect the biological activity or properties of the compound of the present disclosure, and is relatively non-toxic, i.e., the substance can be administered to an individual without causing undesirable biological reaction or interacting with any of the components contained in the composition in an undesirable manner.

In the present application, the “pharmaceutically acceptable excipients” include, but are not limited to, any adjuvants, carriers, excipients, glidants, sweeteners, diluents, preservatives, dyes/colorants, flavoring agents, surfactants, wetting agents, dispersing agents, suspending agents, stabilizers, isotonic agents, solvents or emulsifiers approved and accepted by the relevant government authorities for use in humans or domestic animals.

The terms “preventive”, “preventing” and “prevent” as used herein include reducing the possibility of the occurrence or deterioration of a disease or condition in a patient.

The term “treatment” and other similar synonyms as used herein include the following meanings:

(i) preventing a disease or condition from occurring in a mammal, particularly when such a mammal is susceptible to the disease or condition, but has not been diagnosed as having the disease or condition;
(ii) inhibiting a disease or condition, i.e. curbing its development;
(iii) alleviating the disease or condition, i.e. causing the state of the disease or condition to subside; or
(iv) alleviating the symptoms caused by the disease or condition.

The term “effective amount”, “therapeutically effective amount” or “pharmaceutically effective amount” as used herein refers to a amount of at least one agent or compound, sufficient to alleviate one or more symptoms of the disease or condition being treated to some extent after administration. The result can be a reduction and/or alleviation of signs, symptoms or causes, or any other desired change in the biological system. For example, an “effective amount” for treatment is an amount of the composition comprising the compound disclosed herein that is required to provide a significant clinical condition relief. An effective amount suitable for any individual case can be determined using techniques such as a dose escalation trial.

As used herein, the terms “administration”, “administered”, “administering” and the like refers to a method capable of delivering a compound or composition to a desired site for biological action. These methods include, but are not limited to, oral route, duodenal route, parenteral injection (including intravenous, subcutaneous, intraperitoneal, intramuscular, intraarterial injection or infusion), topical administration and rectal administration. The techniques for the administration of the compounds and methods described herein are well known to those skilled in the art, for example, those discussed in Goodman and Gilman, The Pharmacological Basis of Therapeutics, current ed.; Pergamon; and Remington’s, Pharmaceutical Sciences (current edition), Mack Publishing Co., Easton, Pa. In a preferred embodiment, the compounds and compositions discussed herein are administered orally.

As used herein, the terms “pharmaceutical combination”, “drug combination”, “combined administration”, “administering other treatments”, “administering other therapeutic agents” and the like refer to a pharmaceutical treatment obtained by mixing or combining more than one active ingredients, including both fixed and unfixed combinations of active ingredients. The term “fixed combination” refers to the simultaneous administration of at least one compound described herein and at least one synergistic agent to a patient in the form of a single entity or a single dosage form. The term “unfixed combination” refers to the simultaneous administration, combined administration, or sequential administration at variable intervals of at least one of the compounds described herein and at least one synergistic preparation in the form of separate entities to a patient. These are also applied to a cocktail therapy, for example the administration of three or more active ingredients.

It will also be understood by those skilled in the art that, in the methods described below, functional groups of the intermediate compound may need to be protected by a suitable protecting group. Such functional groups include hydroxyl, amino, sulfhydryl and carboxylic acid. Suitable hydroxy protecting groups include trialkylsilyl or diarylalkylsilyl (e.g., tert-butyldimethylsilyl, tert-butyldiphenylsilyl or trimethylsilyl), tetrahydropyranyl, benzyl and the like. Suitable protecting groups for amino, guanyl and guanidyl include t-butoxycarbonyl, benzyloxycarbonyl and the like. Suitable sulfhydryl protecting groups include —C(O)—R" (wherein R" is alkyl, aryl or aralkyl), p-methoxybenzyl, trityl and the like. Suitable carboxy protecting groups include alkyl, aryl or aralkyl esters.

Protecting groups can be introduced and removed according to standard techniques known to those skilled in the art and as described herein. The use of protecting groups is described in detail in Greene, T. W. and P. G. M. Wuts, Protective Groups in Organic Synthesis, (1999), 4th Ed., Wiley. The protecting group can also be a polymeric resin.

On the basis of not departing from common knowledge in the art, the above-mentioned various preferred conditions can be combined in any manner, such that various preferred examples of the present disclosure are obtained.

Reagents and raw materials used in the present disclosure are all commercially available.

The positive effects of the present disclosure lie in:

in comparison to the compound, N-((5-fluoro-2,3-dihydrobenzofuran-4-yl)methyl)-8-(2-methylpyridin-3-yl)-[1,2,4]triazolo[4,3-c]pyrimidin-5-amine in US 20160176882 A1 and WO 2017219948 A1, the activity against cell proliferation of the compound of the present disclosure is increased by about 10-fold. When the compound disclosed in the present disclosure binds to an EED protein, the bicyclic structure outside the binding “pocket” enables the compound to have a better metabolic stability.

DETAILED DESCRIPTION OF THE PREFERRED EMBODIMENT

The starting materials used in the following examples can be purchased from chemical vendors e.g., Aldrich, TCI, Alfa Aesar, Bide, and Energy Chemical, or can be synthesized by known methods.

In the following examples, the ice bath refers to −5° C. to 0° C., the room temperature refers to 10° C. to 30° C., and the reflux temperature generally refers to the solvent reflux temperature under normal pressure. Overnight reaction refers to reaction for 8-15 hours. In the following examples, if the operating temperature is not specified, the operation is carried out at room temperature.

In the following examples, the isolation and purification of the intermediates and final products are performed by normal phase or reversed-phase column chromatography or other suitable methods. For the normal phase Flash column chromatography, ethyl acetate and n-hexane or methanol and dichloromethane, etc. are used as mobile phases. For the reversed-phase preparative high-performance liquid chromatography (HPLC), a C18 column is used and UV 214 nm and 254 nm are used for detection, wherein the mobile phases are A (water and 0.1% formic acid) and B (acetonitrile), or A (water and 0.1% ammonium bicarbonate) and B (acetonitrile).

In each example:

LCMS instrument: Pump Agilent 1260 UV detector: Agilent 1260 DAD

Mass Spectrometer API 3000

Chromatography column: Waters sunfire C18, 4.6x50 mm, 5 um

Mobile phase: A-$H_2O$ (0.1% HCOOH); B-acetonitrile

NMR instrument: Bruker Ascend 400M ($^1H$ NMR: 400 MHz; $^{13}C$ NMR: 100 MHz).

Example 1: 8-bromo-5-chloro-[1,2,4]triazolo[4,3-c]pyrimidine (D)

Step 1: 5-bromo-2-chloro-4-hydrazinopyrimidine (D-2)

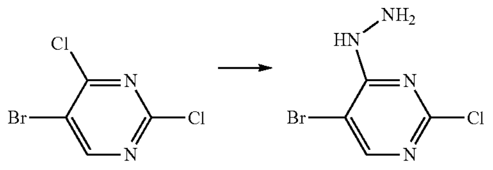

D-1 D-2

Into a 50 mL single-necked flask, D-1 (2 g, 8.78 mmol) and ethanol (20 mL) were added, and hydrazine hydrate (1.72 g, 53.65 mmol) was slowly added dropwise in an ice bath. The suspension was stirred at 60° C. for 3 hours. Upon completion of the reaction, the reaction mixture was cooled to room temperature to precipitate a light yellow solid. The solid was collected by filtration and the filter cake was washed with ethanol (5 mL) and dried to obtain a light yellow solid product D-2 (1.8 g, 92% yield).

$^1H$ NMR (DMSO-$d_6$, 400 MHz) δ 8.06 (s, 1H), 7.85 (s, 1H), 4.34 (s, 2H) ppm.

Step 2: 8-bromo-5-chloro-[1,2,4]triazolo[4,3-c]pyrimidine (D)

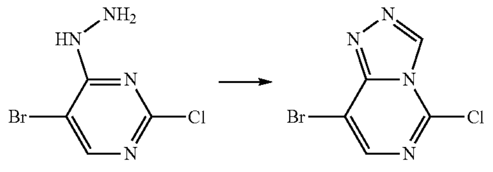

D-2 D

Into a 50 mL single-necked flask, D-2 (1.2 g, 5.37 mmol), trimethylorthoformate (12 mL), and trifluoroacetic acid (1 drop) were added and the mixture was warmed to 100° C. and reacted for 10 h. Upon completion of the reaction, the reaction mixture was cooled to room temperature and trimethylorthoformate was removed by rotary evaporation. The concentrate was purified by silica gel column chromatography (PE:EA=20:1) to obtain a yellow solid product D (960 mg, 77% yield).

$^1H$ NMR (400 MHz, $CDCl_3$) δ 9.03 (s, 1H), 8.05 (s, 1H) ppm; LCMS: m/z 232.9 $[M+H]^+$.

Example 2: ((1aR,6bR)-5-fluoro-1a,6b-dihydro-1H-cyclopropa[b]benzofuran-6-yl)methanamine (C1-a) and ((1aS,6bS)-5-fluoro-1a,6b-dihydro-1H-cyclopropa[b]benzofuran-6-yl)methanamine (C1-b)

Step 1: intermediate 2-bromo-6-(2-bromoethoxy)-3-fluorobenzaldehyde (C1-2)

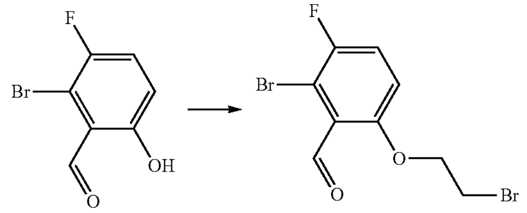

C1-1 C1-2

Into a 250 mL single-necked flask, C1-1 (19 g, 86.7 mmol) was added, and then anhydrous DMF (90 mL) was added and dissolved with stirring. Potassium carbonate (24 g, 173.5 mmol) and 1,2-dibromoethane (24 g, 130.1 mmol) were added sequentially and the mixture was warmed to 64° C. and stirred for 18 hours. Upon completion of the reaction, the reaction mixture was cooled to room temperature, diluted by adding ethyl acetate (400 mL) and stirred for 15 minutes. Insoluble salts were removed by filtration and the filter cake was washed once with ethyl acetate (100 mL). The filtrate was washed twice with saturated sodium chloride (100 mL). The organic phase was dried over anhydrous sodium sulfate, filtered and then concentrated under reduced pressure. The crude was rapidly purified by short silica gel column chromatography (petroleum ether:ethyl acetate=50:1) to obtain an intermediate C1-2 (25 g, 88% yield) as a yellow solid.

$^1H$ NMR (400 MHz, $CDCl_3$) δ 10.52-10.27 (m, 1H), 7.40-7.09 (m, 1H), 7.02-6.78 (m, 1H), 4.53-4.05 (m, 2H), 3.68 (t, J=6.0 Hz, 2H) ppm.

Step 2: intermediate 2-bromo-3-fluoro-6-(ethenyloxy)benzaldehyde (C1-3)

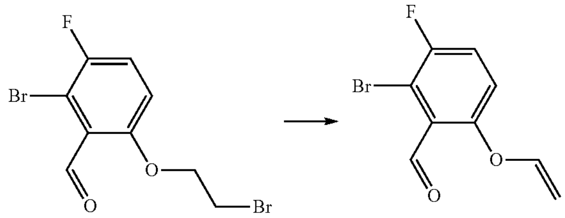

C1-2 C1-3

Into a 1 L single-necked flask, C1-2 (10 g, 30.7 mmol) was added, and then anhydrous tetrahydrofuran (400 mL) was added and dissolved with stirring. The reaction mixture was cooled to −20° C. and then sodium tert-butoxide (4.4 g, 46.0 mmol) was slowly added in batches. At the end of the addition, the mixture was warmed to room temperature and stirred overnight. Upon completion of the reaction, the reaction mixture was cooled to −10° C. The reaction was quenched by slowly adding water dropwise (60 mL). The reaction mixture was extracted with ethyl acetate (100 mL). The organic phase was dried over anhydrous sodium sulfate, filtered and concentrated under reduced pressure. The crude was purified by silica gel column chromatography (petroleum ether:ethyl acetate=80:1 to 30:1) to obtain C1-3 (5 g, 66% yield) as a light yellow solid.

$^1$H NMR (400 MHz, $CDCl_3$) δ 10.32 (d, J=9.8 Hz, 1H), 7.29 (dt, J=16.2, 8.3 Hz, 1H), 7.15-6.98 (m, 1H), 6.68-6.46 (m, 1H), 4.89-4.68 (m, 1H), 4.68-4.42 (m, 1H) ppm.

Step 3: intermediate (E)-N'-(2-bromo-3-fluoro-6-(ethenyloxy)benzylidene)-4-methylbenzenesulfonohydrazide (C1-4)

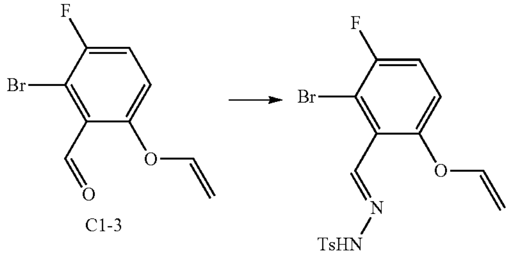

C1-3 C1-4

Into a 250 mL single-necked flask, C1-3 (5 g, 20.4 mmol) was added, and then anhydrous methanol (100 mL) was added and resolved with stirring. p-Toluenesulfonyl hydrazide (4.2 g, 22.4 mmol) was slowly added at room temperature. The mixture was stirred at room temperature for 18 hours. Upon completion of the reaction, a large amount of white solid was precipitated. The reaction mixture was cooled to 0° C. The solid product was collected by filtration. The mother liquor was concentrated and the solid crude was slurried with the mixed solvents of petroleum ether and ethyl acetate (20:1). The solid product was collected and dried under reduced pressure to obtain C1-4 (7.5 g, 89% yield) as a white solid.

$^1$H NMR (400 MHz, DMSO-$d_6$) δ 11.81 (s, 1H), 7.97 (s, 1H), 7.76 (d, J=7.6 Hz, 2H), 7.42 (t, J=9.0 Hz, 2H), 7.16 (dd, J=9.1, 4.3 Hz, 1H), 6.67 (dd, J=13.6, 6.2 Hz, 1H), 4.49 (dd, J=21.4, 9.8 Hz, 3H), 2.35 (s, 3H) ppm; LCMS: m/z 414.1 $[M+H]^+$.

Step 4: intermediate 6-bromo-5-fluoro-1a,6b-dihydro-1H-cyclopropa[b]benzofuran (C1-5)

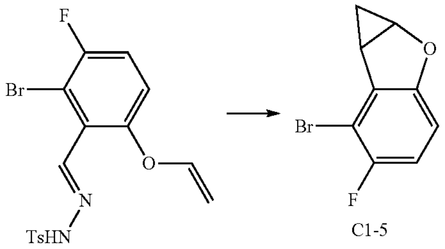

C1-4 C1-5

Into a 250 mL single-necked flask, C1-4 (3 g, 7.3 mmol) was added, and then toluene (100 mL) was added and dissolved with stirring. At room temperature, lithium tert-butoxide (639 mg, 7.9 mmol) and rhodium (II) octanoate dimer (56 mg, 72.6 μmol) were slowly added under nitrogen protection. The mixture was warmed to 100° C. and stirred for 3 hours. Upon completion of the reaction, the reaction mixture was cooled to room temperature and filtered. The filter cake was washed with ethyl acetate (50 mL) and the filtrate was concentrated under reduced pressure to obtain C1-5 (1.67 g, 100% yield) as a light yellow oil, which was directly used in the next reaction without further purification.

$^1$H NMR (400 MHz, $CDCl_3$) δ 7.03-6.81 (m, 2H), 4.97 (t, J=5.2 Hz, 1H), 2.84 (dt, J=9.0, 4.4 Hz, 1H), 1.26 (dt, J=8.0, 6.1 Hz, 1H), 0.55-0.37 (m, 1H) ppm.

Step 5: intermediate 5-fluoro-1a,6b-dihydro-1H-cyclopropa[b]benzofuran-6-carbonitrile (C1-6)

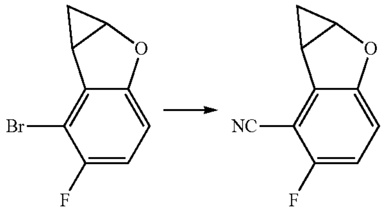

C1-5 C1-6

Into a 100 mL single-necked flask, C1-5 (1.9 g, 8.30 mmol), zinc cyanide (1.46 g, 12.4 mmol), palladium tetrakistriphenylphosphine (1.44 g, 1.24 mmol), and DMF (12 mL) were added. Under nitrogen protection, the mixture was warmed to 110° C. and stirred for 18 hours. Upon completion of the reaction, the reaction mixture was cooled to room temperature, diluted by adding ethyl acetate (20 mL) and filtered. The filtrate was washed twice with saturated brine (10 mL). The organic phase was dried over anhydrous sodium sulfate, filtered and concentrated under reduced pressure. The crude was purified by silica gel column chromatography (petroleum ether:ethyl acetate=100:1 to 20:1) to obtain C1-6 (1.35 g, 92% yield) as a white solid.

$^1$H NMR (400 MHz, $CDCl_3$) δ 7.03-6.84 (m, 2H), 4.97 (t, J=5.2 Hz, 1H), 2.84 (dt, J=9.0, 4.5 Hz, 1H), 1.33-1.20 (m, 1H), 0.52-0.40 (m, 1H) ppm.

Step 6: intermediate tert-butyl ((5-fluoro-1a,6b-dihydro-1H-cyclopropa[b]benzofuran-6-yl)methyl) carbamate (C1-7)

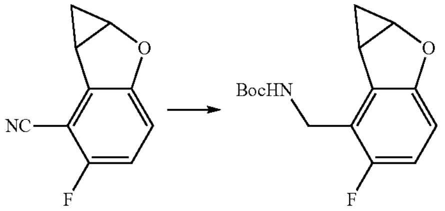

C1-6 C1-7

Into a 100 mL single-necked flask, C1-6 (1.2 g, 6.8 mmol) was added, and then methanol (30 mL) was added and dissolved. Di-tert-butyldicarbonate (2.2 g, 10.3 mmol) was added at room temperature. The reaction mixture was cooled to −5° C. Nickel chloride hexahydrate (1.95 g, 8.22 mmol) was added slowly and solid sodium borohydride (778 mg, 20.5 mmol) was added in batches. The mixture was warmed to room temperature naturally and stirred for 2 hours. Upon completion of the reaction, the mixture was filtered through celite. The filter cake was washed with methanol (10 mL) and the filtrate was cooled to 0° C. The reaction was quenched with water (5 mL). The resulting mixture was concentrated under reduced pressure. Ethyl acetate (80 mL) was added to the crude. The organic phase was washed with saturated brine (10 mL), then dried over anhydrous sodium sulfate, filtered and concentrated under reduced pressure. The resulting crude was separated and purified by silica gel column chromatography (petroleum ether:ethyl acetate=100:1 to 40:1) to obtain C1-7 (1.2 g, 63% yield) as a white solid.

$^1$H NMR (400 MHz, $CDCl_3$) δ 6.76 (t, J=9.3 Hz, 1H), 6.64 (dd, J=8.6, 3.7 Hz, 1H), 4.90 (s, 1H), 4.82 (t, J=5.3 Hz, 1H), 4.48 (d, J=6.1 Hz, 1H), 4.46-4.33 (m, 1H), 2.85 (d, J=3.8 Hz, 1H), 1.44 (s, 9H), 1.05 (dd, J=14.6, 6.0 Hz, 1H), 0.32 (s, 1H) ppm; LCMS: m/z 224.1 $[M-55]^+$.

Step 7: intermediate tert-butyl ((5-fluoro-1aR,6bR-dihydro-1H-cyclopropa[b]benzofuran-6-yl)methyl) carbamate (C1-7a) and ((5-fluoro-1aS,6bS-dihydro-1H-cyclopropa[b]benzofuran-6-yl)methyl)carbamate (C1-7b)

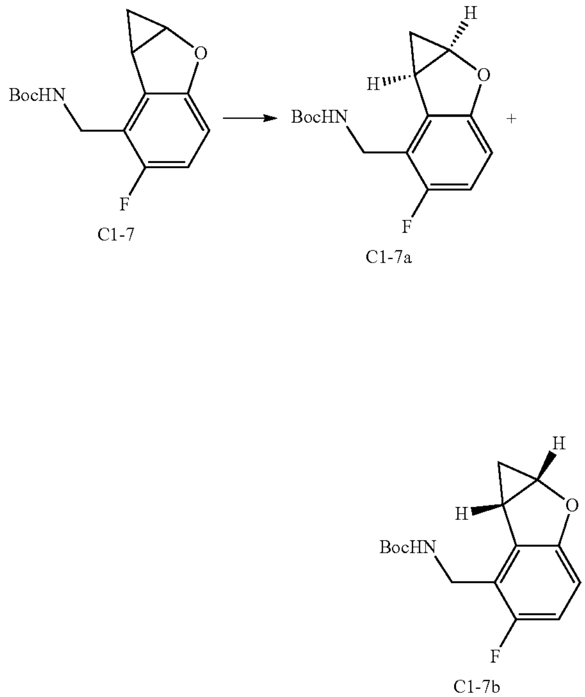

C1-7 C1-7a C1-7b

C1-7 (1.2 g, 4.3 mmol) was further purified by chiral SFC as follows: column: AD-H 20×250 mm, 10 μm (Daicel), flow rate: 80 g/min, mobile phase: 13% (0.2% ammonia in methanol/methanol), in $CO_2$, detection: 214 nM, so as to obtain C1-7a (0.52 g, 43.3% yield) with Rt: 0.99 min; and C1-7b (0.57 g, 47.5% yield) with Rt: 0.71 min.

C1-7a: $^1$H NMR (400 MHz, $CDCl_3$) δ 6.76 (t, J=9.3 Hz, 1H), 6.64 (dd, J=8.6, 3.9 Hz, 1H), 4.98-4.73 (m, 2H), 4.45 (ddd, J=41.3, 14.0, 5.7 Hz, 2H), 2.84 (s, 1H), 1.45 (d, J=7.7 Hz, 9H), 1.05 (dd, J=14.8, 6.0 Hz, 1H), 0.31 (d, J=4.6 Hz, 1H) ppm; LCMS: m/z 224.1 $[M-55]^+$.

C1-7b: $^1$H NMR (400 MHz, $CDCl_3$) δ 6.76 (t, J=9.3 Hz, 1H), 6.64 (dd, J=8.6, 3.9 Hz, 1H), 4.98-4.73 (m, 2H), 4.45 (ddd, J=41.3, 14.0, 5.7 Hz, 2H), 2.84 (s, 1H), 1.45 (d, J=7.7 Hz, 9H), 1.05 (dd, J=14.8, 6.0 Hz, 1H), 0.31 (d, J=4.6 Hz, 1H) ppm; LCMS: m/z 224.1 $[M-55]^+$.

Step 8: intermediate ((1aR,6bR)-5-fluoro-1a,6b-dihydro-1H-cyclopropa[b]benzofuran-6-yl)methanamine (C1-a)

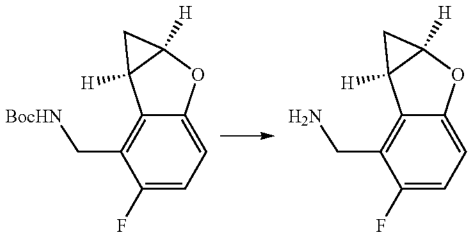

C1-7a C1-a

Into a 100 mL single-necked flask, compound C1-7a (1.2 g, 4.30 mmol) was added, and then dichloromethane (20 mL) was added and dissolved. Trifluoroacetic acid (4 mL, 52 mmol) was added at room temperature and stirred for 2 hours. Upon completion of the reaction, dichloromethane and trifluoroacetic acid were removed by concentration under reduced pressure to obtain the trifluoroacetate salt of C1-a (1.26 g, 100% yield) as a colorless solid. The product could be directly used in the next step.

$^1$H NMR (400 MHz, MeOD) δ 6.95 (t, J=9.5 Hz, 1H), 6.84 (dd, J=8.8, 4.0 Hz, 1H), 4.97 (t, J=5.4 Hz, 1H), 4.31 (q, J=13.7 Hz, 2H), 2.92-2.77 (m, 1H), 1.26-1.11 (m, 1H), 0.38-0.21 (m, 1H) ppm; LCMS: m/z 180.1 $[M+H]^+$.

Intermediate C1-7b was taken as the raw material to obtain the trifluoroacetate salt of C1-b using the method of step 8.

C1-b

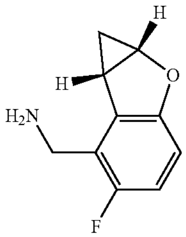

Example 3: intermediate 4-(aminomethyl)-5-fluoro-2,3-dihydrobenzofuran-3-ol (C2)

Step 1: intermediate 2-bromo-3,6-difluorobenzaldehyde (C2-2)

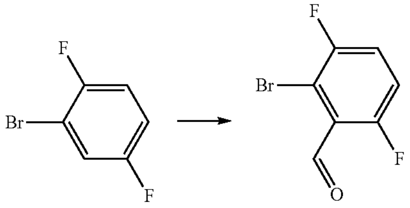

C2-1 C2-2

Into a dry 500 mL three-necked flask, C2-1 (22 g, 114 mmol) and dry THE (200 mL) were added and the mixture was cooled to −70° C. Lithium diisopropylamide (2 M, 68.4 mL) was slowly added dropwise into the reaction solution. The reaction solution was stirred at −70° C. for 45 minutes and then DMF (17.8 mL, 228 mmol) was added. The reaction solution was stirred at −70° C. for two hours and warmed to 0° C. Saturated ammonium chloride (200 mL) was added to the reaction solution. The reaction solution was extracted with EtOAc (200 mL×2). The combined organic phases were washed once with brine, dried over anhydrous sodium sulfate, filtered and concentrated under reduced pressure. The residue was purified on silica gel (petroleum ether:ethyl acetate=100:1) to obtain C2-2 (20 g, 79.4% yield) as a light yellow solid.

$^1$H NMR (400 MHz, $CDCl_3$) δ 10.34 (s, 1H), 7.34 (ddd, J=9.2, 7.4, 4.5 Hz, 1H), 7.16 (td, J=9.3, 4.0 Hz, 1H) ppm.

Step 2: intermediate 2-bromo-3-fluoro-6-methoxybenzaldehyde (C2-3)

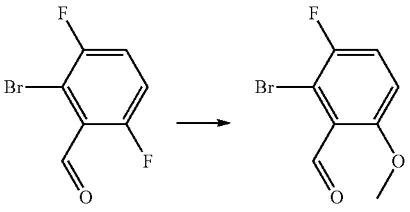

C2-2 C2-3

Into a 2 L three-necked flask, C2-2 (20 g, 90.5 mmol) was added and dissolved in anhydrous THE (1000 ml) and MeOH (200 ml) with stirring. Sodium methoxide (5.87 g, 108.6 mmol) was added and the reaction solution was stirred at 60° C. for 18 hours. Most of the solvent was removed by concentration under reduced pressure and 500 mL of water was added. The suspension was stirred for 30 minutes and filtered and the solid was collected. The solid was slurried with a mixed solution of petroleum ether and ethyl acetate (5:1) and filtered to obtain a solid, which was dried under reduced pressure to obtain C2-3 (18 g, 85% yield) as a yellow solid.

LC-MS: m/z 233.1 $[M+H]^+$.

Step 3: intermediate 2-bromo-3-fluoro-6-hydroxybenzaldehyde (C2-4)

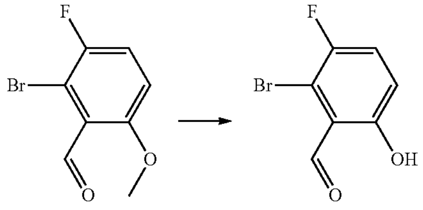

C2-3 C2-4

Into a 1 L single-necked flask, C2-3 (16.8 g, 72.1 mmol) and dichloromethane (300 mL) were added. At −78° C., boron tribromide (21.7 g, 86.5 mmol) was slowly added dropwise and the reaction solution was warmed to room temperature and stirred for 18 hours. The reaction solution was diluted with dichloromethane (300 mL) and saturated sodium hydrogen carbonate (300 mL) was slowly added. The organic phase was washed twice with brine, dried over anhydrous sodium sulfate, filtered and concentrated under reduced pressure. The residue was purified on silica gel (petroleum ether:ethyl acetate=50:1) to obtain C2-4 (10 g, 63.3% yield) as a light yellow solid.

$^1$H NMR (400 MHz, $CDCl_3$) δ 11.77 (s, 1H), 10.34 (s, 1H), 7.29 (dt, J=12.7, 6.3 Hz, 1H), 6.94 (dd, J=9.3, 4.1 Hz, 1H) ppm.

Step 4: intermediate 4-bromo-5-fluoro-2,3-dihydrobenzofuran-3-ol (C2-5)

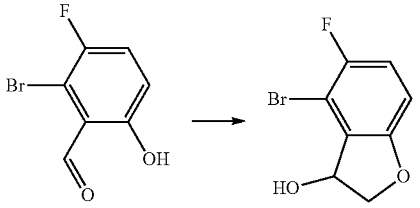

C2-4 C2-5

Into a dry 3-necked flask, trimethylsulfoxonium iodide (9.73 g, 44.2 mmol) and DMSO (50 ml) were added. In an ice-water bath, sodium tert-butoxide (4.25 g, 44.2 mmol) was added. The reaction solution was stirred at room temperature for 2 hours and C2-4 (8.8 g, 40.2 mmol) was added. The reaction solution was stirred at room temperature for 18 hours, and then ethyl acetate (250 ml) and water (250 ml) were added. The resulting mixture was extracted with ethyl acetate (250 ml×2). The organic phase was washed once with water and brine, respectively, dried over anhydrous sodium sulfate, filtered and concentrated under reduced pressure. The residue was purified on silica gel (petroleum ether:ethyl acetate=10:1) to obtain C2-5 (6.2 g, 66.2% yield) as a white solid.

$^1$H NMR (400 MHz, $CDCl_3$) δ 7.03 (t, J=8.7 Hz, 1H), 6.76 (dd, J=8.8, 3.5 Hz, 1H), 5.51-5.40 (m, 1H), 4.58 (ddd, J=13.4, 10.8, 4.6 Hz, 2H), 2.33 (d, J=4.9 Hz, 1H) ppm.

Step 5: intermediate 5-fluoro-3-hydroxy-2,3-dihydrobenzofuran-4-carbonitrile (C2-6)

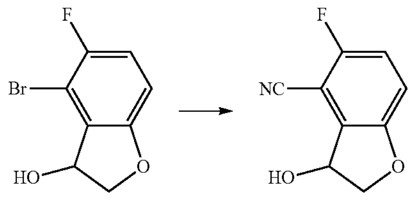

C2-5 C2-6

Into a dry single-necked flask, C2-5 (2.7 g, 11.6 mmol), zinc cyanide (2.04 g, 17.4 mmol), DMF (50 ml), and palladium tetrakistriphenylphosphine (1.34 g, 1.16 mmol) were added sequentially. The reaction solution was warmed to 120° C. under nitrogen protection and stirred for 18 hours. The reaction solution was cooled to room temperature and extracted with ethyl acetate (200 mL×3) and water (200 ml). The organic phase was washed once with water and brine, respectively, dried over anhydrous sodium sulfate, filtered and concentrated under reduced pressure. The residue was purified on silica gel (petroleum ether:ethyl acetate=5:1) to obtain C2-6 (1.6 g, 77% yield) as a white solid.

$^1$H NMR (400 MHz, $CDCl_3$) δ 7.20-6.99 (m, 2H), 5.63 (dd, J=6.9, 2.9 Hz, 1H), 4.69 (dd, J=10.8, 7.1 Hz, 1H), 4.55 (dd, J=10.8, 3.1 Hz, 1H), 2.74 (s, 1H) ppm.

Step 6: intermediate (5-fluoro-2,3-dihydrobenzofuran-4-yl)methanamine (C2)

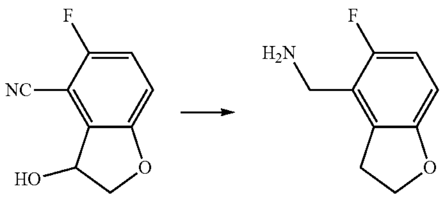

C2-6 C2

Into a 100 mL single-necked flask, C2-6 (1.55 g, 8.65 mmol), trifluoroacetic acid (1.09 g, 8.65 mmol), methanol (20 mL), and 10% palladium on carbon (2 g, containing 50% water) were added sequentially. The reaction mixture was bubbled with hydrogen gas for 5 minutes, ventilated with a hydrogen balloon three times and stirred at 60° C. under a hydrogen balloon for 48 hours. The mixture was filtered through celite and then washed with methanol (50 mL×2). The filtrate was concentrated under reduced pressure and dioxane (10 mL) and 10 M aqueous sodium hydroxide solution (1 mL) were added. The resulting mixture was extracted with dioxane (10 mL×2), and the organic phase was dried over anhydrous sodium sulfate, filtered and concentrated under reduced pressure to obtain a compound C2 (1.4 g, 90% purity, 87% yield), which was directly used in the next step.

$^1$H NMR (400 MHz, $CD_3OD$) δ 3.27 (t, 2H), 3.77 (s, 2H), 4.56 (t, 2H), 6.59 (dd 1H), 6.81 (dd, 1H) ppm; LC-MS: m/z 168.1 $[M+H]^+$.

Example 4: intermediate (6-fluorobenzodihydropyran-5-yl)methanamine (C3)

Step 1: intermediate 2-bromo-1-fluoro-4-(prop-2-yn-1-yloxy)benzene (C3-2)

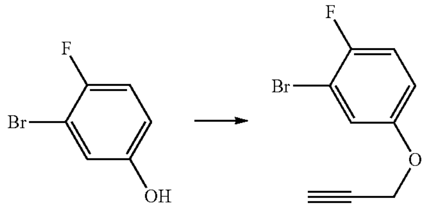

C3-1 C3-2

Into a dry 2 L single-necked flask, C3-1 (87 g, 455.5 mmol) and dry N,N-dimethylformamide (800 mL) were added at room temperature. Nitrogen gas was used to replace the air in the system three times. In an ice-water bath, 60% sodium hydride (20 g, 501 mmol) was added in batches over a period of 30 minutes. The reaction solution was stirred at room temperature for 15 minutes and then cooled with an ice-water bath. Then propargyl chloride (50.9 g, 683.3 mmol) was added. The reaction solution was stirred at room temperature for 18 hours. Upon completion of the reaction, water (1 L) was added and the resulting mixture was extracted with ethyl acetate (1 L) three times. The organic phase was washed once with saturated aqueous sodium chloride solution (500 mL), then dried over sodium sulfate, filtered and concentrated under reduced pressure to obtain a crude product. The crude product was purified by silica gel column chromatography (petroleum ether:ethyl acetate=20:1) to obtain a product C3-2 (80 g, 76.7% yield) as a yellow oily liquid.

$^1$H NMR (400 MHz, $CDCl_3$) δ 7.17 (dd, J=5.5, 3.0 Hz, 1H), 7.05 (dd, J=9.0, 8.1 Hz, 1H), 6.89 (ddd, J=9.1, 3.7, 3.2 Hz, 1H), 4.66 (d, J=2.4 Hz, 2H), 2.54 (t, J=2.4 Hz, 1H) ppm.

Step 2: intermediate 5-bromo-6-fluoro-2H-chromene (C3-3)

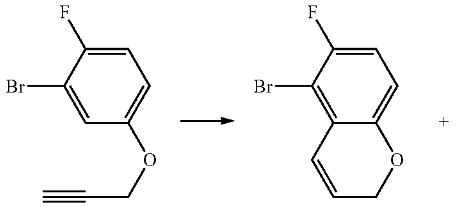

C3-2 C3-3

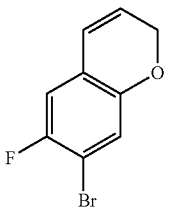

C3-3b

Into a dry 20 mL microwave tube, C3-2 (2 g, 8.7 mmol) and N,N-diethylaniline (15 mL) were added. The reaction solution was warmed to 250° C. in a microwave synthesizer and reacted for 2.5 hours. Upon completion of the reaction, the resulting mixture was diluted with ethyl acetate (100 mL) and washed with 2 N hydrochloric acid to remove N,N-diethylaniline. The organic phase was washed once with saturated aqueous sodium chloride solution (50 mL), then dried over sodium sulfate, filtered and concentrated under reduced pressure to obtain a crude product. The crude product was purified by silica gel column chromatography (petroleum ether:ethyl acetate=20:1) to obtain a brown oily mixture of C3-3 and C3-3b (1.88 g, 94% yield).

Step 3: intermediate 6-fluoro-2H-chromene-5-carbonitrile (C3-4)

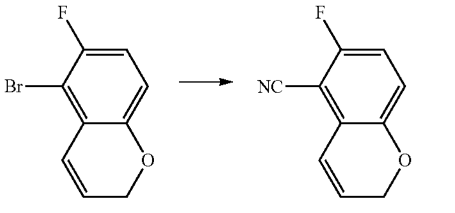

C3-3 C3-4

Into a dry 500 mL three-necked flask, the brown oily mixture of C3-3 and C3-3b (20.2 g, 88.2 mmol), zinc cyanide (13.5 g, 115 mmol), anhydrous N,N dimethylformamide (250 mL), and palladium tetrakistriphenylphosphine (10.2 g, 8.8 mmol) were added sequentially. The reaction solution was stirred at 110° C. under nitrogen protection for 18 hours. Upon completion of the reaction, the reaction mixture was cooled to room temperature. 1 L of water was added and the resulting mixture was extracted with ethyl acetate (500 mL) three times. The organic phase was washed once with saturated aqueous sodium chloride solution (500 mL), then dried over sodium sulfate, filtered and concentrated under reduced pressure to obtain a crude product. The crude product was purified by silica gel column chromatography (petroleum ether:ethyl acetate=50:1 to 10:1) to obtain a product C3-4 (8.12 g, 52.6% yield) as a white solid. The conversion product of C3-3b was separated and removed.

$^{1}$H NMR (400 MHz, $CDCl_3$) δ 7.02-6.85 (m, 2H), 6.70 (dt, J=10.0, 1.8 Hz, 1H), 6.07 (dt, J=10.0, 3.6 Hz, 1H), 4.88 (dd, J=3.6, 2.0 Hz, 2H) ppm; LC-MS: m/z 176.1 $[M+H]^+$.

Step 4: intermediate tert-butyl ((6-fluorobenzodihydropyran-5-yl)methyl)carbamate

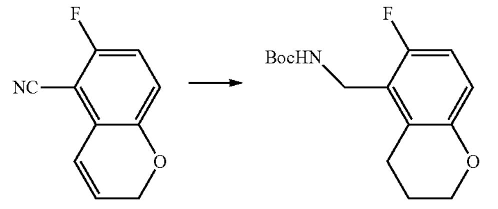

C3-4 C3-5

Into a 500 mL single-necked flask, C3-4 (4.6 g, 26.3 mmol), BOC-anhydride (7.45 g, 34.1 mmol), methanol (200 mL), and 10% palladium on carbon (1.6 g, 50%) were added sequentially. The reaction solution was first bubbled with hydrogen gas for 5 minutes. Then the flask was fitted with a hydrogen balloon and ventilated with same three times. The reaction solution was heated to 60° C. in hydrogen gas and stirred overnight. Upon completion of the reaction, the reaction solution was cooled to room temperature, filtered and concentrated under reduced pressure to obtain a relatively pure product C3-5 (7.4 g, 100%), which was directly used in the next step.

$^{1}$H NMR (400 MHz, $CDCl_3$) δ 6.81 (t, J=9.1 Hz, 1H), 6.70 (dd, J=9.0, 4.9 Hz, 1H), 4.75 (s, 1H), 4.32 (d, J=5.2 Hz, 2H), 4.18-4.05 (m, 2H), 3.49 (d, J=1.8 Hz, 2H), 2.86 (t, J=6.4 Hz, 2H), 2.10-1.91 (m, 2H), 1.45 (d, J=8.0 Hz, 9H) ppm; LC-MS: m/z 226.1 $[M-tBu+H]^+$.

Step 5: intermediate (6-fluorobenzodihydropyran-5-yl)methanamine (C3)

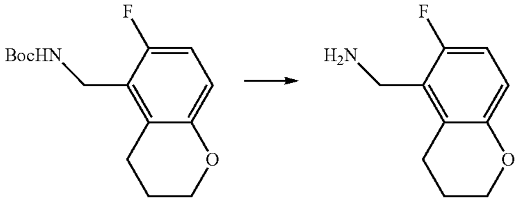

C3-5 C3

Into a 50 mL single-necked flask, C3-5 (1.0 g, 3.55 mmol) and 10 mL of HCl/dioxane solution (4 M) were added sequentially and the mixture was stirred at room temperature for 4 hours. Upon completion of the reaction, the mixture was concentrated under reduced pressure to obtain a compound C3 (612 mg, 95% yield) as a white solid.

$^{1}$H NMR (400 MHz, $CD_3OD$) δ 6.98 (t, J=9.2 Hz, 1H), 6.86 (dd, J=9.1, 5.1 Hz, 1H), 4.28-4.07 (m, 4H), 2.89 (t, J=6.4 Hz, 2H), 2.14-2.01 (m, 2H) ppm; LC-MS: m/z 182.1 $[M+H]^+$.

Example 5: 8-bromo-N-(((1aR,6bR)-5-fluoro-1a,6b-dihydro-1H-cyclopropa[b]benzofuran-6-yl)methyl)-[1,2,4]triazolo[4,3-c]pyrimidin-5-amine (B1)

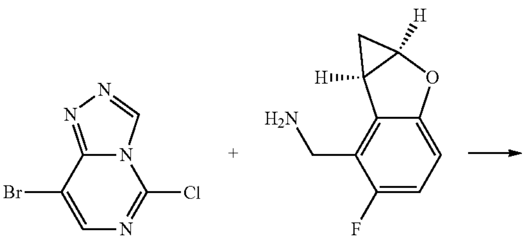

D C1-a

-continued

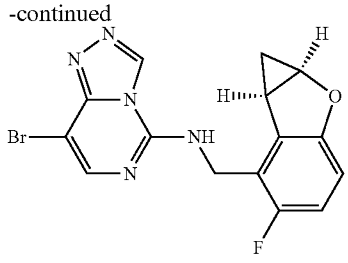

B1

Into a 100 mL single-necked flask, the trifluoroacetate salt of compound C1-a (1.0 g, 3.41 mmol), compound D (0.95 g, 4.09 mmol), triethylamine (0.69 g, 6.82 mmol), and acetonitrile (20 mL) were added sequentially. The mixture was stirred at room temperature for 3 hours. Upon completion of the reaction, the reaction mixture was diluted by adding and dissolving ethyl acetate (80 mL). The organic phase was washed with saturated brine (10 mL*2), dried over anhydrous sodium sulfate and concentrated under reduced pressure. The concentrate was purified by silica gel column chromatography (mobile phase: PE:EA=30:1 to PE:EA=10:1) to obtain a compound B1 (1.2 g, 94% yield). $^1$H NMR (400 MHz, DMSO-$d_6$) δ 9.50 (s, 1H), 8.87 (d, J=4.5 Hz, 1H), 7.85 (s, 1H), 6.94 (t, J=9.5 Hz, 1H), 6.77 (dd, J=8.7, 3.7 Hz, 1H), 4.92 (t, J=5.2 Hz, 1H), 4.79 (p, J=9.7 Hz, 1H), 2.88 (dt, J=8.7, 4.5 Hz, 1H), 0.97 (dd, J=14.4, 5.7 Hz, 1H), 0.10 (s, 1H) ppm; LCMS: m/z 376.0 $[M+H]^+$.

D was reacted with C1-b, C2 and C3, respectively using the method of example 5 to obtain intermediates B2, B3 and B4 as shown in Table 2.

TABLE 2

| Intermediates | Chinese name | Structural formula | Analysis data |
|---|---|---|---|
| B2 | 8-bromo-N-(((1aS,6bS)-5-fluoro-1a,6b-dihydro-1H-cyclopropa[b]benzofuran-6-yl)methyl)-[1,2,4]triazolo[4,3-c]pyrimidin-5-amine | 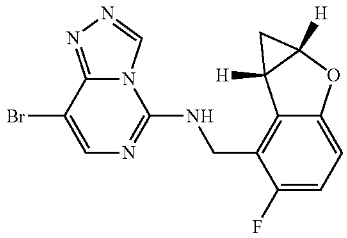 [SMILES: Fc1ccc2c(c1CNc1ncc(Br)c3nncn13)[C@@H]1C[C@@H]1O2] | LCMS: m/z 376.0 $[M + H]^+$ |
| B3 | 8-bromo-N-((5-fluoro-2,3-dihydrobenzofuran-4-yl)methyl)-[1,2,4]triazolo[4,3-c]pyrimidin-5-amine | 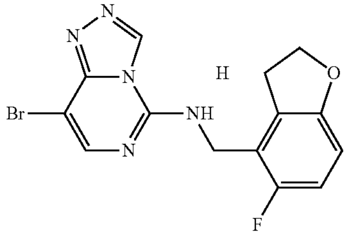 | LCMS: m/z 364.0 $[M + H]^+$ |
| B4 | 8-bromo-N-((6-fluorochroman-5-yl)methyl)-[1,2,4]triazolo[4,3-c]pyrimidin-5-amine | 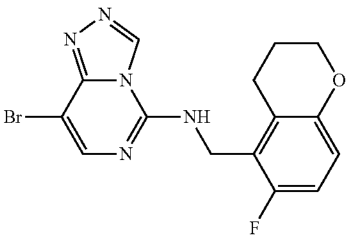 [SMILES: Fc1ccc2c(c1CNc1ncc(Br)c3nncn13)CCCO2] | $^1$HNMR (400 MHz, DMSO-$d_6$) δ 9.35 (s, 1H), 8.57 (s, 1H), 7.50 (s, 1H), 6.91 (t, J = 9.2 Hz, 1H), 6.71 (dd, J = 9.0, 4.8 Hz, 1H), 4.63 (d, J = 4.6 Hz, 2H), 4.10-3.97 (m, 2H), 2.85 (t, J = 6.4 Hz, 2H), 1.95-1.84 (m, 2H) ppm; LCMS: m/z 378.0 $[M + H]^+$ |

Example 6: 8-([1,2,4]triazolo[1,5-a]pyridin-8-yl)-N-((5-fluoro-2,3-dihydrobenzofuran-4-yl)methyl)-[1,2,4]triazolo[4,3-c]pyrimidin-5-amine Step 1: [1,2,4]triazolo[1,5-a]pyridin-8-ylboronic acid (E1)

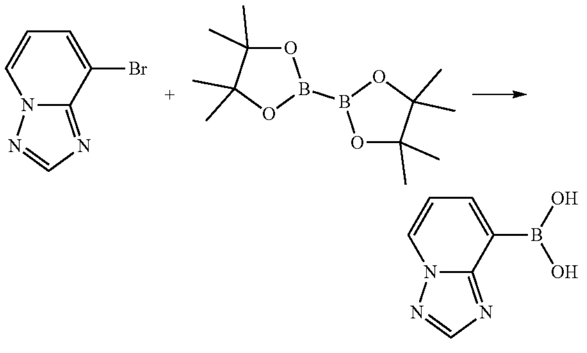

E1

Into a dry 30 mL sealed tube, 8-bromo-[1,2,4]triazolo[1,5-a]pyridine (200 mg, 1.01 mmol) and bis(pinacolato)diboron (513 mg, 2.02 mmol) were added sequentially. [1,1'-bis(diphenylphosphino)ferrocene]dichloropalladium(II) (35 mg, 0.05 mmol), and potassium acetate (198 mg, 2.02 mmol) dissolved in 10 ml of dry 1,4-dioxane were added. The reaction solution was bubbled with nitrogen gas for one minute and then warmed to 120 TC and stirred for 12 hours. The reaction solution was cooled to room temperature, and the raw materials were substantially converted to E1 (detected by LCMS). Then the reaction was not subjected to post-treatment, but was directly used in the next reaction by using a one-pot process.

LCMS: m/z 164.0 $[M+H]^+$

Step 2: 8-([1,2,4]triazolo[1,5-a]pyridin-8-yl)-N-((5-fluoro-2,3-dihydrobenzofuran-4-yl)methyl)-[1,2,4]triazolo[4,3-c]pyrimidin-5-amine

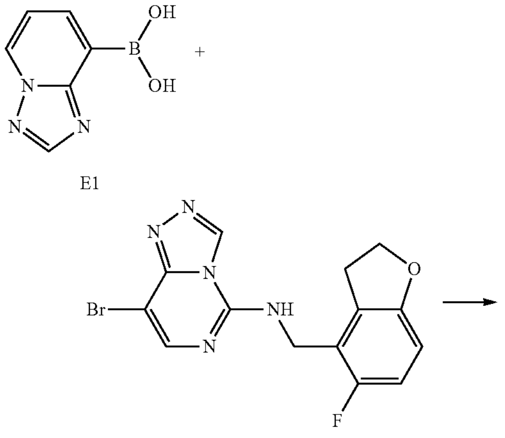

E1

B3

-continued

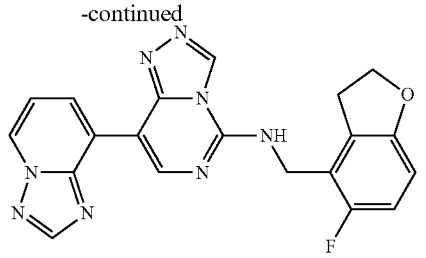

Into the above-mentioned reaction solution of intermediate E1, intermediate B3 (100 mg, 0.27 mmol), [1,1'-bis(diphenylphosphino)ferrocene]dichloropalladium(II) (21 mg, 0.03 mmol), potassium carbonate (76 mg, 0.54 mmol), and $H_2O$ (2 mL) were added sequentially. The resulting reaction solution was bubbled with nitrogen gas for one minute, warmed to 85° C. and stirred for 2 hours. The reaction solution was cooled to room temperature. The reaction system was slowly added dropwise into ice water (30 mL) and then extracted with ethyl acetate (30 mL×2). The organic phases were combined, dried over anhydrous sodium sulfate and filtered and the filtrate was concentrated under reduced pressure. The residue was purified by column chromatography with a developing agent system (ethyl acetate:methanol=10:1) to obtain a crude product, which was then subjected to high-performance liquid chromatography to obtain the product 8-([1,2,4]triazolo[1,5-a]pyridin-8-yl)-N-((5-fluoro-2,3-dihydrobenzofuran-4-yl)methyl)-[1,2,4]triazolo[4,3-c]pyrimidin-5-amine (39 mg, 35% yield) as a white solid.

$^1H$ NMR (400 MHz, DMSO-$d_6$) δ 9.56 (s, 1H), 9.51 (s, 1H), 9.19 (dd, J=7.6, 0.9 Hz, 1H), 8.98 (s, 1H), 8.93 (dd, J=6.7, 1.0 Hz, 1H), 8.63 (s, 1H), 7.43-7.38 (m, 1H), 7.01-6.95 (m, 1H), 6.73 (dd, J=8.6, 3.9 Hz, 1H), 4.79 (s, 2H), 4.56 (t, J=8.7 Hz, 2H), 3.33 (d, J=8.8 Hz, 2H) ppm; LCMS: m/z 403.1 $[M+H]^+$.

The following compound can be synthesized with 8-bromo-[1,2,4]triazolo[1,5-a]pyridine and intermediate B1 as the raw materials using the method of example 6:

Example 7: 8-([1,2,4]triazolo[1,5-a]pyridin-8-yl)-N-(((1aR,6bR)-5-fluoro-1a,6b-dihydro-1H-cyclopropa[b]benzofuran-6-yl)methyl)-[1,2,4]triazolo[4,3-c]pyrimidin-5-amine

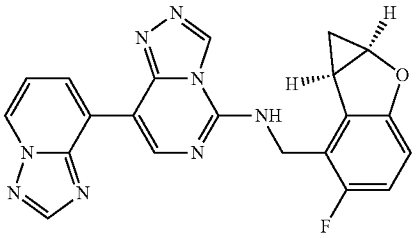 [SMILES: Fc1ccc2c(c1CNc1ncc(-c3cccn4ncnc34)c3nncn13)[C@H]1C[C@H]1O2]

$^1H$ NMR (400 MHz, DMSO-$d_6$) δ 9.44 (s, 1H), 9.37 (s, 1H), 9.05 (d, J=7.4 Hz, 1H), 8.78 (d, J=6.6 Hz, 1H), 8.48 (s, 1H), 7.26 (t, J=7.2 Hz, 1H), 6.85-6.79 (m, 1H), 6.65 (dd, J=8.6, 3.8 Hz, 1H), 4.82 (d, J=6.1 Hz, 1H), 4.79 (d, J=3.4 Hz, 2H), 3.04 (d, J=5.2 Hz, 1H), 2.83 (dd, J=9.2, 4.3 Hz, 1H), 1.10 (s, 1H), 0.92-0.82 (m, 1H) ppm; LCMS: m/z 414.8 $[M+H]^+$.

The following compound can be synthesized with 8-bromoimidazo[1,2-a]pyridine and intermediate B3 as the raw materials using the method of example 6:

Example 8: N-((5-fluoro-2,3-dihydrobenzofuran-4-yl)methyl)-8-(imidazo[1,2-a]pyridin-8-yl)-[1,2,4]triazolo[4,3-c]pyrimidin-5-amine

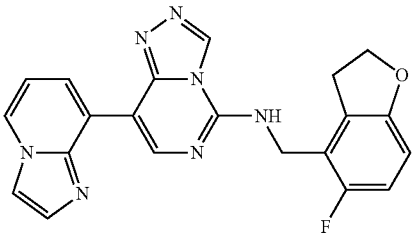

$^1$H NMR (400 MHz, DMSO-$d_6$) δ 9.67 (s, 1H), 9.56 (s, 1H), 8.90 (s, 1H), 8.80 (d, J=6.7 Hz, 1H), 8.55 (d, J=5.8 Hz, 1H), 8.05 (d, J=1.0 Hz, 1H), 7.66 (d, J=0.9 Hz, 1H), 7.08 (t, J=7.0 Hz, 1H), 7.02-6.93 (m, 1H), 6.72 (dd, J=8.7, 3.9 Hz, 1H), 4.78 (s, 2H), 4.55 (t, J=8.7 Hz, 2H) ppm; LCMS: m/z 401.7 $[M+H]^+$.

The following compound can be synthesized with 8-bromoimidazo[1,2-a]pyridine and intermediate B1 as the raw materials using the method of example 6:

Example 9: N-(((1aR,6bR)-5-fluoro-1a,6b-dihydro-1H-cyclopropa[b]benzofuran-6-yl)methyl)-8-(imidazo[1,2-a]pyridin-8-yl)-[1,2,4]triazolo[4,3-c]pyrimidin-5-amine

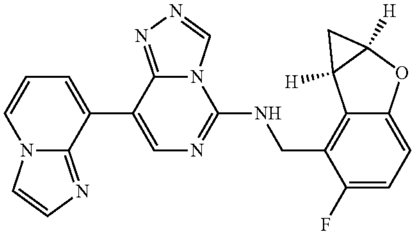 [SMILES: Fc1ccc2c(c1CNc1ncc(-c3cccn4ccnc34)c3nncn13)[C@H]1C[C@H]1O2]

$^1$H NMR (400 MHz, DMSO-$d_6$) δ 9.50 (s, 1H), 9.42 (s, 1H), 8.86 (s, 1H), 8.64 (dd, J=7.3, 1.0 Hz, 1H), 8.42 (dd, J=6.7, 1.1 Hz, 1H), 7.92 (d, J=1.2 Hz, 1H), 7.53 (d, J=1.2 Hz, 1H), 6.95 (t, J=7.0 Hz, 1H), 6.83 (dd, J=10.3, 8.8 Hz, 1H), 6.66 (dd, J=8.7, 3.9 Hz, 1H), 4.82 (dt, J=5.3, 2.7 Hz, 1H), 4.78 (s, 2H), 2.85 (dd, J=9.3, 4.5 Hz, 1H), 0.88 (dt, J=8.9, 6.0 Hz, 1H), 0.00 (ddd, J=6.0, 3.9, 1.9 Hz, 1H) ppm; LCMS: m/z 413.8 $[M+H]^+$.

The following compound can be synthesized with 8-bromo-[1,2,4]triazolo[4,3-a]pyridine and intermediate B1 as the raw materials using the method of example 6:

Example 10: 8-([1,2,4]triazolo[4,3-a]pyridin-8-yl)-N-(((1aR,6bR)-5-fluoro-1a,6b-dihydro-1H-cyclopropa[b]benzofuran-6-yl)methyl)-[1,2,4]triazolo[4,3-c]pyrimidin-5-amine

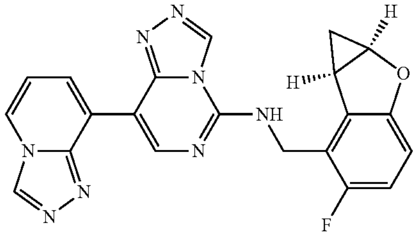

$^1$H NMR (400 MHz, DMSO-$d_6$) δ 9.42 (s, 1H), 9.32 (s, 1H), 9.00 (d, J=7.4 Hz, 1H), 8.68 (d, J=6.6 Hz, 1H), 8.35 (s, 1H), 7.25 (t, J=7.2 Hz, 1H), 6.85-6.79 (m, 1H), 6.63 (dd, J=8.6, 3.8 Hz, 1H), 4.82 (d, J=6.1 Hz, 1H), 4.79 (d, J=3.4 Hz, 2H), 3.04 (d, J=5.2 Hz, 1H), 2.83 (dd, J=9.2, 4.3 Hz, 1H), 1.10 (s, 1H), 0.23-0.18 (m, 1H) ppm; LCMS: m/z 414.8 $[M+H]^+$.

The following compound can be synthesized with 7-bromoimidazo[1,2-a]pyridine and intermediate B3 as the raw materials using the method of example 6:

Example 11: N-((5-fluoro-2,3-dihydrobenzofuran-4-yl)methyl)-8-(imidazo[1,2-a]pyridin-7-yl)-[1,2,4]triazolo[4,3-c]pyrimidin-5-amine

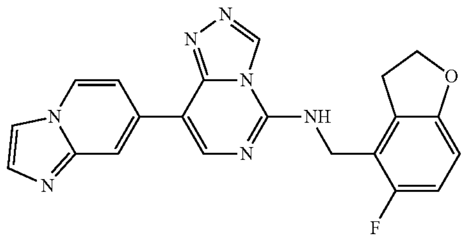 [SMILES: Fc1ccc2c(c1CNc1ncc(-c3ccn4ccnc4c3)c3nncn13)CCO2]

$^1$H NMR (400 MHz, DMSO-$d_6$) δ 9.52 (s, 1H), 8.84 (s, 1H), 8.69 (s, 1H), 8.59 (d, J=7.2 Hz, 1H), 8.32 (s, 1H), 7.95 (s, 1H), 7.66 (dd, J=7.3, 1.7 Hz, 1H), 7.60 (d, J=0.9 Hz, 1H), 7.02-6.89 (m, 1H), 6.72 (dd, J=8.6, 3.9 Hz, 1H), 4.75 (s, 2H), 4.55 (t, J=8.7 Hz, 2H), 3.31 (t, J=8.7 Hz, 2H) ppm; LCMS: m/z 401.8 $[M+H]^+$.

The following compound can be synthesized with 6-bromoimidazo[1,2-a]pyridine and intermediate B3 as the raw materials using the method of example 6:

Example 12: N-((5-fluoro-2,3-dihydrobenzofuran-4-yl)methyl)-8-(imidazo[1,2-a]pyridin-6-yl)-[1,2,4]triazolo[4,3-c]pyrimidin-5-amine

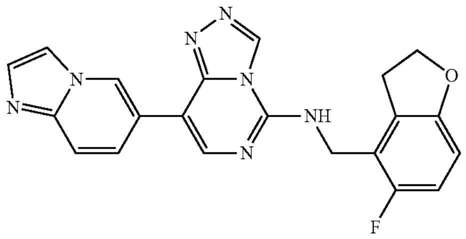 [SMILES: Fc1ccc2c(c1CNc1ncc(-c3ccc4nccn4c3)c3nncn13)CCO2]

$^1$H NMR (400 MHz, DMSO-$d_6$) δ 9.60 (s, 1H), 9.52 (s, 1H), 8.79 (s, 1H), 8.21 (s, 1H), 8.12 (s, 1H), 7.90 (dd, J=9.6, 1.7 Hz, 1H), 7.65 (d, J=9.5 Hz, 1H), 7.60 (s, 1H), 7.04-6.91 (m, 1H), 6.71 (dd, J=8.8, 3.8 Hz, 1H), 4.74 (s, 2H), 4.55 (t, J=8.7 Hz, 2H), 3.26 (t, J=8.7 Hz, 2H) ppm; LCMS: m/z 401.8 [M+H]$^+$.

The following compound can be synthesized with 6-bromopyrazolo[1,5-a]pyrimidine and intermediate B3 as the raw materials using the method of example 6:

Example 13: N-((5-fluoro-2,3-dihydrobenzofuran-4-yl)methyl)-8-(pyrazolo[1,5-a]pyrimidin-6-yl)-[1,2,4]triazolo[4,3-c]pyrimidin-5-amine

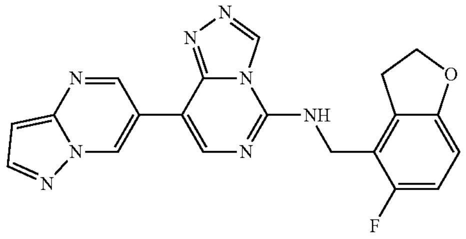 [SMILES: Fc1ccc2c(c1CNc1ncc(-c3cnc4ccnn4c3)c3nncn13)CCO2]

$^1$H NMR (400 MHz, DMSO-$d_6$) δ 9.94 (s, 1H), 9.55 (s, 1H), 9.29 (d, J=2.0 Hz, 1H), 8.91 (s, 1H), 8.40 (s, 1H), 8.27 (d, J=2.3 Hz, 1H), 7.02-6.92 (m, 1H), 6.80 (s, 1H), 6.72 (dd, J=8.7, 3.7 Hz, 1H), 4.76 (s, 2H), 4.56 (t, J=8.6 Hz, 2H), 2.06-1.90 (m, 2H) ppm; LCMS: m/z 402.8 [M+H]$^+$.

The following compound can be synthesized with 6-bromo-[1,2,4]triazolo[4,3-a]pyridine and intermediate B1 as the raw materials using the method of example 6:

Example 14: 8-([1,2,4]triazolo[4,3-a]pyridin-6-yl)-N-(((1aR,6bR)-5-fluoro-1a,6b-dihydro-1H-cyclopropa[b]benzofuran-6-yl)methyl)-[1,2,4]triazolo[4,3-c]pyrimidin-5-amine

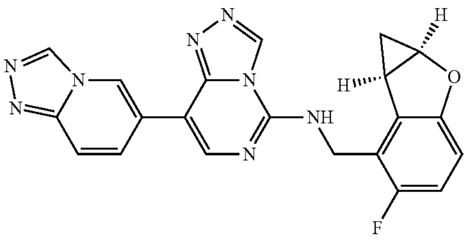 [SMILES: Fc1ccc2c(c1CNc1ncc(-c3ccc4nncn4c3)c3nncn13)[C@H]1C[C@H]1O2]

$^1$H NMR (400 MHz, DMSO-$d_6$) δ 9.71 (s, 1H), 9.57 (s, 1H), 9.46 (s, 1H), 8.99 (s, 1H), 8.30 (s, 1H), 8.07 (dd, J=9.8, 1.3 Hz, 1H), 7.87 (d, J=9.7 Hz, 1H), 6.98-6.92 (m, 1H), 6.78 (dd, J=8.7, 3.8 Hz, 1H), 4.93 (t, J=4.5 Hz, 1H), 4.88 (t, J=9.2 Hz, 2H), 2.96-2.90 (m, 1H), 1.23 (s, 1H), 1.02-0.97 (m, 1H) ppm; LCMS: m/z 415.1 [M+H]$^+$.

The following compound can be synthesized with 7-bromo-[1,2,4]triazolo[1,5-a]pyridine and intermediate B1 as the raw materials using the method of example 6:

Example 15: 8-([1,2,4]triazolo[1,5-a]pyridin-7-yl)-N-(((1aR,6bR)-5-fluoro-1a,6b-dihydro-1H-cyclopropa[b]benzofuran-6-yl)methyl)-[1,2,4]triazolo[4,3-c]pyrimidin-5-amine

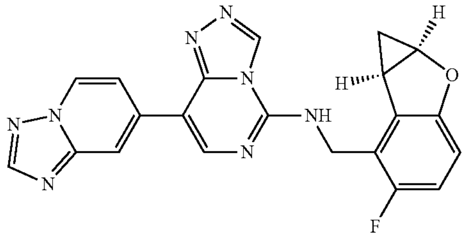 [SMILES: Fc1ccc2c(c1CNc1ncc(-c3ccn4ncnc4c3)c3nncn13)[C@H]1C[C@H]1O2]

$^1$H NMR (400 MHz, DMSO-$d_6$) δ 9.57 (s, 1H), 9.06 (s, 1H), 8.99 (d, J=7.3 Hz, 1H), 8.88 (s, 1H), 8.50 (s, 1H), 8.47 (s, 1H), 8.01 (dd, J=7.4, 1.7 Hz, 1H), 7.02-6.92 (m, 1H), 6.78 (dd, J=8.7, 3.9 Hz, 1H), 4.94 (dd, J=5.4, 1.7 Hz, 1H), 4.91 (d, J=4.2 Hz, 2H), 2.97-2.90 (m, 1H), 1.23 (s, 1H), 1.00 (dd, J=5.7, 3.1 Hz, 1H) ppm; LCMS: m/z 415.1 [M+H]$^+$.

The following compound can be synthesized with 6-bromoimidazo[1,2-a]pyrimidine and intermediate B3 as the raw materials using the method of example 6:

Example 16: N-((5-fluoro-2,3-dihydrobenzofuran-4-yl)methyl)-8-(imidazo[1,2-a]pyrimidin-6-yl)-[1,2,4]triazolo[4,3-c]pyrimidin-5-amine

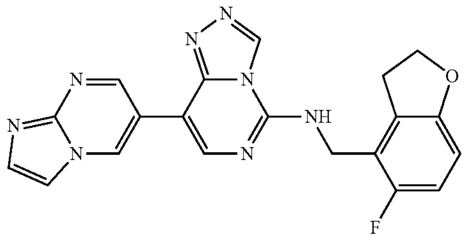

$^1$H NMR (400 MHz, DMSO-$d_6$) δ 9.88 (s, 1H), 9.52 (s, 1H), 9.20 (s, 1H), 8.89 (s, 1H), 8.33 (s, 1H), 8.11 (s, 1H), 7.75 (s, 1H), 6.96 (s, 1H), 6.72 (s, 1H), 4.65 (d, J=77.8 Hz, 4H), 3.57 (s, 2H) ppm; LCMS: m/z 402.8 [M+H]$^+$.

The following compound can be synthesized with 6-bromopyrazolo[1,5-a]pyridine and intermediate B3 as the raw materials using the method of example 6:

Example 17: N-((5-fluoro-2,3-dihydrobenzofuran-4-yl)methyl)-8-(pyrazolo[1,5-a]pyridin-6-yl)-[1,2,4]triazolo[4,3-c]pyrimidin-5-amine

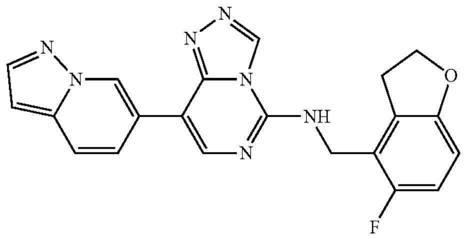 [SMILES: Fc1ccc2c(c1CNc1ncc(-c3ccc4ccnn4c3)c3nncn13)CCO2]

$^1$H NMR (400 MHz, DMSO-$d_6$) δ 9.78 (s, 1H), 9.54 (s, 1H), 8.82 (s, 1H), 8.29 (s, 1H), 8.04 (d, J=2.2 Hz, 1H), 7.92 (dd, J=9.5, 1.5 Hz, 1H), 7.79 (d, J=9.3 Hz, 1H), 7.01-6.92 (m, 1H), 6.72 (dd, J=8.7, 3.9 Hz, 1H), 6.65 (d, J=1.4 Hz, 1H), 4.75 (s, 2H), 4.56 (t, J=8.7 Hz, 2H), 3.31 (s, 2H) ppm; LCMS: m/z 401.8 $[M+H]^+$.

The following compound can be synthesized with 3-bromopyrazolo[1,5-a]pyrimidine and intermediate B3 as the raw materials using the method of example 6:

Example 18: N-((5-fluoro-2,3-dihydrobenzofuran-4-yl)methyl)-8-(pyrazolo[1,5-a]pyrimidin-3-yl)-[1,2,4]triazolo[4,3-c]pyrimidin-5-amine

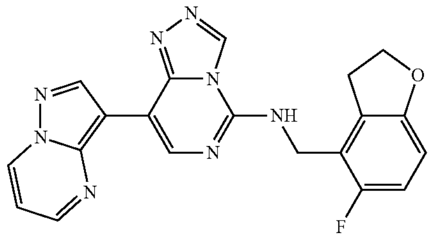 [SMILES: Fc1ccc2c(c1CNc1ncc(-c3cnn4cccnc34)c3nncn13)CCO2]

$^1$H NMR (400 MHz, DMSO-$d_6$) δ 9.51 (s, 1H), 9.25-9.19 (m, 2H), 8.80 (s, 1H), 8.71 (dd, J=4.0, 1.7 Hz, 1H), 8.64 (s, 1H), 7.17 (dd, J=7.0, 4.1 Hz, 1H), 7.00-6.93 (m, 1H), 6.72 (s, 1H), 4.74 (s, 2H), 4.55 (t, J=8.7 Hz, 2H), 3.31 (d, J=8.8 Hz, 2H) ppm; LCMS: m/z 402.8 $[M+H]^+$.

The following compound can be synthesized with 7-bromobenzo[d]oxazole and intermediate B3 as the raw materials using the method of example 6:

Example 19: 8-(benzo[d]oxazol-7-yl)-N-((5-fluoro-2,3-dihydrobenzofuran-4-yl)methyl)-[1,2,4]triazolo[4,3-c]pyrimidin-5-amine

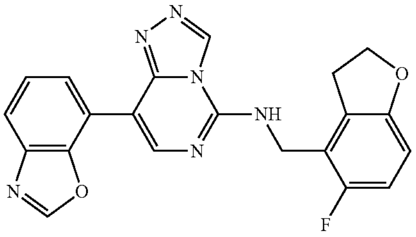 [SMILES: Fc1ccc2c(c1CNc1ncc(-c3cccc4ncoc34)c3nncn13)CCO2]

$^1$H NMR (400 MHz, DMSO-$d_6$) δ 9.53 (s, 1H), 8.86 (s, 1H), 8.83 (s, 1H), 8.49 (d, J=7.7 Hz, 1H), 8.41 (s, 1H), 7.79 (d, J=7.8 Hz, 1H), 7.54 (t, J=7.9 Hz, 1H), 7.01-6.93 (m, 1H), 6.72 (dd, J=8.6, 3.9 Hz, 1H), 4.77 (s, 2H), 4.56 (t, J=8.7 Hz, 2H), 3.32-3.30 (m, 2H) ppm; LCMS: m/z 402.8 $[M+H]^+$.

The following compound can be synthesized with 4-bromo-2-methylbenzo[d]oxazole and intermediate B3 as the raw materials using the method of example 6:

Example 20: N-((5-fluoro-2,3-dihydrobenzofuran-4-yl)methyl)-8-(2-methylbenzo[d]oxazol-4-yl)-[1,2,4]triazolo[4,3-c]pyrimidin-5-amine

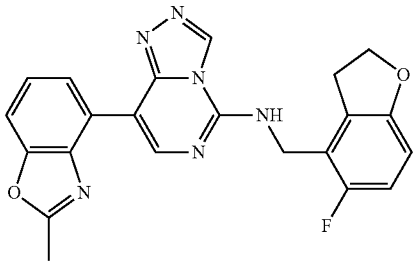 [SMILES: Cc1nc2c(-c3cnc(NCc4c(F)ccc5c4CCO5)n4cnnc34)cccc2o1]

$^1$H NMR (400 MHz, $CDCl_3$) δ 8.97 (s, 1H), 8.56 (s, 1H), 8.24 (d, J=7.4 Hz, 1H), 7.54-7.38 (m, 2H), 6.88-6.75 (m, 1H), 6.61 (dd, J=8.7, 3.9 Hz, 1H), 6.47 (s, 1H), 4.72 (d, J=5.3 Hz, 2H), 4.57 (t, J=8.7 Hz, 2H), 3.37 (t, J=8.7 Hz, 2H), 2.66 (s, 3H) ppm; LCMS: m/z 416.8 $[M+H]^+$.

Example 21: N-((5-fluoro-2,3-dihydrobenzofuran-4-yl)methyl)-8-(6-fluoroimidazo[1,2-a]pyridin-8-yl)-[1,2,4]triazolo[4,3-c]pyrimidin-5-amine Step 1: (2-amino-5-fluoropyridin-3-yl)boronic acid (E2)

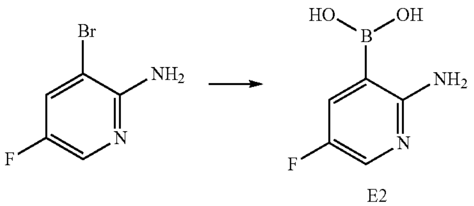 [SMILES: Nc1ncc(F)cc1Br ; Nc1ncc(F)cc1B(O)O]

E2

Into a 25 mL microwave tube, 3-bromo-5-fluoropyridin-2-amine (0.3 g, 1.57 mmol), bis(pinacolato)diboron (598 mg, 2.36 mmol), [1,1'-bis(diphenylphosphino)ferrocene]dichloropalladium(II) (115 mg, 0.157 mmol), bis(diphenylphosphino)ferrocene (87 mg, 0.157 mmol), potassium acetate (385 mg, 3.93 mmol), and 1,4-dioxane (10 mL) were added. Under nitrogen protection, the mixture was warmed to 110° C. in a microwave reactor and reacted for 4 hours. Upon completion of the reaction, the resulting reaction mixture was directly used in the next reaction without purification. LCMS: m/z 156.8 $[M+H]^+$.

Step 2: 8-(2-amino-5-fluoropyridin-3-yl)-N-((5-fluoro-2,3-dihydrobenzofuran-4-yl)methyl)-[1,2,4]triazolo[4,3-c]pyrimidin-5-amine (E2-2)

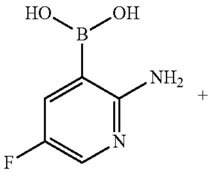

E2

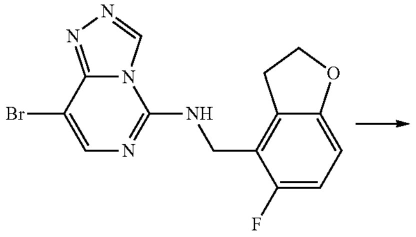

B3

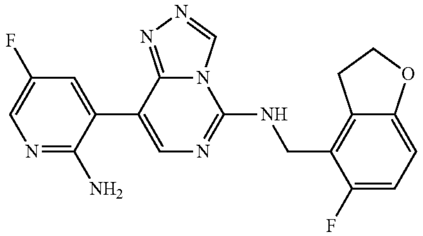

E2-2

Into the reaction solution obtained in the previous step, intermediate B3 (300 mg, 0.824 mmol), [1,1'-bis(diphenylphosphino)ferrocene]dichloropalladium(II) (121 mg, 0.165 mmol), potassium carbonate (342 mg, 2.47 mmol), and dioxane-$H_2O$ (12 mL, 4:1) were added. Under nitrogen protection, the mixture was warmed to 80° C. in a microwave reactor and reacted for 1 hour. Upon completion of the reaction, the mixture was then extracted with ethyl acetate (10 mL×3). The organic phases were combined, dried over anhydrous sodium sulfate and filtered and the filtrate was concentrated under reduced pressure. The residue was purified by Flash chromatography (methanol:ethyl acetate=1:20) to obtain E2-2 (300 mg, 87% yield) as a yellowish brown solid.

$^1H$ NMR (400 MHz, DMSO-$d_6$) δ 9.49 (s, 1H), 8.80 (s, 1H), 7.99 (d, J=2.9 Hz, 1H), 7.68 (s, 1H), 7.49 (d, J=9.0 Hz, 1H), 7.00-6.92 (m, 1H), 6.71 (dd, J=8.7, 3.8 Hz, 1H), 5.71 (s, 2H), 4.71 (s, 2H), 4.55 (s, 2H), 3.36 (s, 2H), LCMS: m/z 395.8 $[M+H]^+$.

Step 3: N-((5-fluoro-2,3-dihydrobenzofuran-4-yl)methyl)-8-(6-fluoroimidazo[1,2-a]pyridin-8-yl)-[1,2,4]triazolo[4,3-c]pyrimidin-5-amine

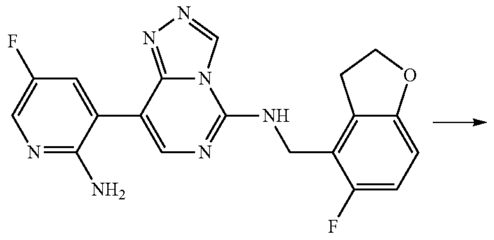

E2-2

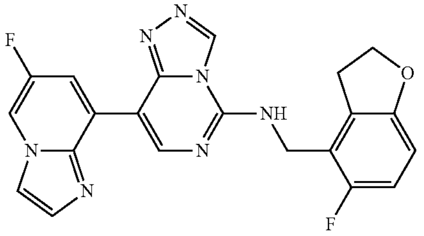

Into a 25 mL single-necked flask, E2-2 (80 mg, 0.2 mmol), 2-chloroacetaldehyde (159 mg, 2.0 mmol), potassium carbonate (28 mg, 0.2 mmol) and ethanol (5 mL) were added and the mixture was warmed to 90° C. and stirred for 5 hours. Upon completion of the reaction, the reaction mixture was extracted with ethyl acetate (30 mL×3). The organic phases were combined, dried over anhydrous sodium sulfate and then filtered and the filtrate was concentrated under reduced pressure. The residue was purified by Flash chromatography (methanol:ethyl acetate=1:50) to obtain N-((5-fluoro-2,3-dihydrobenzofuran-4-yl)methyl)-8-(6-fluoroimidazo[1,2-a]pyridin-8-yl)-[1,2,4]triazolo[4,3-c]pyrimidin-5-amine (8 mg, 9.4% yield) as a light yellow solid.

$^1H$ NMR (400 MHz, DMSO-$d_6$) δ 9.85 (s, 1H), 9.56 (s, 1H), 9.00 (s, 1H), 8.95 (dd, J=11.1, 2.3 Hz, 1H), 8.78-8.74 (m, 1H), 8.05 (s, 1H), 7.72 (s, 1H), 7.00-6.94 (m, 1H), 6.71 (dd, J=8.6, 3.8 Hz, 1H), 4.79 (s, 2H), 4.55 (t, J=8.7 Hz, 2H), 3.35 (s, 2H) ppm; LCMS: m/z 419.8$[M+H]^+$.

The following compound can be synthesized with 3-chloro-1,1,1-trifluoropropan-2-one and intermediate E2-2 as the raw materials using the method in step 3 of example 21:

Example 22: N-((5-fluoro-2,3-dihydrobenzofuran-4-yl)methyl)-8-(6-fluoroimidazo[1,2-a]pyridin-8-yl)-[1,2,4]triazolo[4,3-c]pyrimidin-5-amine

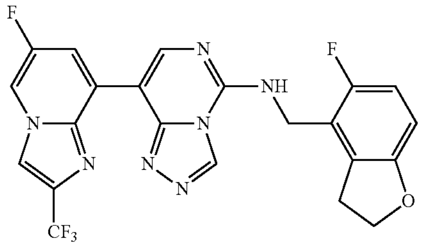 [SMILES: Fc1cc(-c2cnc(NCc3c(F)ccc4c3CCO4)n3cnnc23)c2nc(C(F)(F)F)cn2c1]

$^1H$ NMR (400 MHz, DMSO-$d_6$) δ 9.66 (s, 1H), 9.57 (s, 1H), 9.09 (dd, J=11.1, 2.3 Hz, 2H), 8.80 (d, J=3.0 Hz, 1H), 8.63 (s, 1H), 7.02-6.96 (m, 1H), 6.73 (dd, J=8.7, 3.8 Hz, 1H), 4.82 (s, 2H), 4.54 (s, 2H), 3.29 (d, J=8.8 Hz, 2H) ppm; LCMS: m/z 487.7 $[M+H]^+$.

The following compound can be synthesized with ethyl 2-chloro-3-oxopropanoate and intermediate E2-2 as the raw materials using the method in step 3 of example 21:

Example 23: Ethyl 6-fluoro-8-(5-(((5-fluoro-2,3-dihydrobenzofuran-4-yl)methyl)amino)-[1,2,4]triazolo[4,3-c]pyrimidin-8-yl)imidazo[1,2-a]pyridine-3-carboxylate

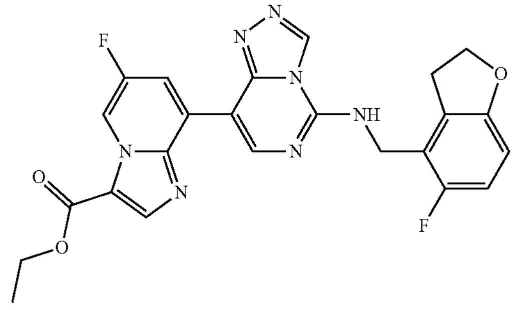 [SMILES: CCOC(=O)c1cnc2c(-c3cnc(NCc4c(F)ccc5c4CCO5)n4cnnc34)cc(F)cn12]

$^1H$ NMR (400 MHz, DMSO-$d_6$) δ 9.63 (s, 1H), 9.56 (s, 1H), 9.26-9.19 (m, 1H), 9.14-9.05 (m, 2H), 8.41 (s, 1H), 7.01-6.93 (m, 1H), 6.72 (dd, J=8.6, 3.8 Hz, 1H), 4.80 (d, J=5.0 Hz, 2H), 4.55 (t, J=8.7 Hz, 2H), 4.41 (q, J=7.1 Hz, 2H), 3.30 (s, 2H), 1.38 (t, J=7.1 Hz, 3H) ppm; LCMS: m/z 491.7 $[M+H]^+$.

The following compound can be synthesized with ethyl 2-chloroacetoacetate and intermediate E2-2 as the raw materials using the method in step 3 of example 21:

Example 24: Ethyl 6-fluoro-8-(5-(((5-fluoro-2,3-dihydrobenzofuran-4-yl)methyl)amino)-[1,2,4]triazolo[4,3-c]pyrimidin-8-yl)-2-methylimidazo[1,2-a]pyridine-3-carboxylate

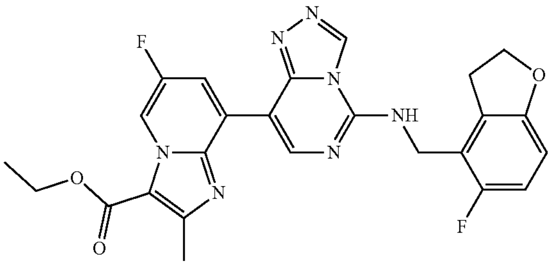 [SMILES: CCOC(=O)c1c(C)nc2c(-c3cnc(NCc4c(F)ccc5c4CCO5)n4cnnc34)cc(F)cn12]

$^1H$ NMR (400 MHz, DMSO-$d_6$) δ 9.64 (s, 1H), 9.58 (s, 1H), 9.22 (s, 1H), 9.08 (d, J=10.8 Hz, 2H), 7.03-6.94 (m, 1H), 6.72 (dd, J=8.7, 3.8 Hz, 1H), 4.80 (s, 2H), 4.55 (t, J=8.7 Hz, 2H), 4.40 (q, J=7.1 Hz, 2H), 3.27-3.29 (m, 2H), 2.68 (s, 3H), 1.39 (t, J=7.1 Hz, 3H) ppm; LCMS: m/z 505.8 $[M+H]^+$.

The following compound can be synthesized with 3-bromo-5-chloropyridin-2-amine, dichloroacetaldehyde and intermediate B3 as the raw materials using the method of example 21:

Example 25: 8-(6-chloroimidazo[1,2-a]pyridin-8-yl)-N-((5-fluoro-2,3-dihydrobenzofuran-4-yl)methyl)-[1,2,4]triazolo[4,3-c]pyrimidin-5-amine

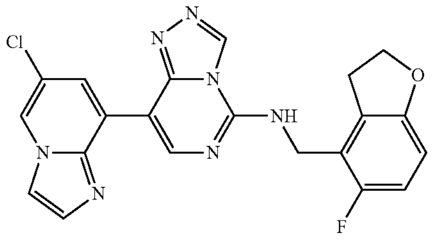 [SMILES: Fc1ccc2c(c1CNc1ncc(-c3cc(Cl)cn4ccnc34)c3nncn13)CCO2]

$^1H$ NMR (400 MHz, DMSO-$d_6$) δ 9.80 (s, 1H), 9.55 (s, 1H), 9.07-8.91 (m, 2H), 8.83 (d, J=1.8 Hz, 1H), 8.03 (s, 1H), 7.72 (s, 1H), 7.02-6.93 (m, 1H), 6.72 (dd, J=8.6, 3.8 Hz, 1H), 4.78 (s, 2H), 4.55 (t, J=8.7 Hz, 2H), 3.31 (s, 2H) ppm; LCMS: m/z 435.8 $[M+H]^+$.

The following compound can be synthesized with 3-bromo-5-fluoropyridin-2-amine, 3-chloro-1,1,1-trifluoropropan-2-one and intermediate B3 as the raw materials using the method of example 21:

Example 26: 8-(6-chloro-2-(trifluoromethyl)imidazo[1,2-a]pyridin-8-yl)-N-((5-fluoro-2,3-dihydrobenzofuran-4-yl)methyl)-[1,2,4]triazolo[4,3-c]pyrimidin-5-amine

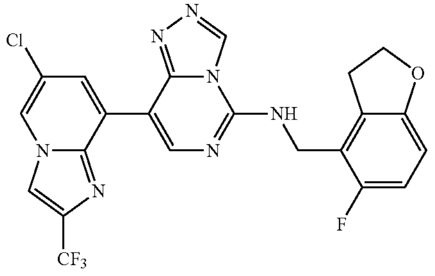 [SMILES: Fc1ccc2c(c1CNc1ncc(-c3cc(Cl)cn4cc(C(F)(F)F)nc34)c3nncn13)CCO2]

$^1H$ NMR (400 MHz, DMSO-$d_6$) δ 9.90 (s, 1H), 9.60 (s, 1H), 9.09 (d, J=2.0 Hz, 1H), 8.91 (s, 1H), 8.66 (s, 1H), 6.99-6.91 (m, 1H), 6.70 (dd, J=8.7, 3.8 Hz, 1H), 4.80 (s, 2H), 4.52 (t, J=8.7 Hz, 2H), 3.33 (s, 2H) ppm; LCMS: m/z 503.7 $[M+H]^+$.

The following compound can be synthesized with 3-bromo-5-fluoropyridin-2-amine, chloracetone and intermediate B3 as the raw materials using the method of example 21:

Example 27: N-((5-fluoro-2,3-dihydrobenzofuran-4-yl)methyl)-8-(6-fluoro-2-methylimidazo[1,2-a]pyridin-8-yl)-[1,2,4]triazolo[4,3-c]pyrimidin-5-amine

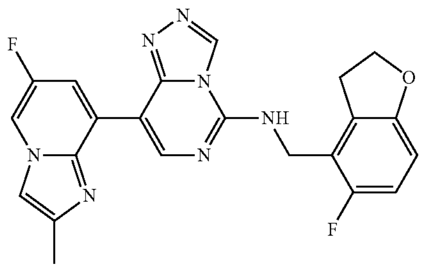 [SMILES: Cc1cn2cc(F)cc(-c3cnc(NCc4c(F)ccc5c4CCO5)n4cnnc34)c2n1]

$^1$H NMR (400 MHz, DMSO-$d_6$) δ 9.84 (s, 1H), 9.55 (s, 1H), 8.96 (s, 1H), 8.89 (dd, J=11.1, 2.3 Hz, 1H), 8.71-8.65 (m, 1H), 7.78 (s, 1H), 7.03-6.94 (m, 1H), 6.72 (dd, J=8.6, 3.8 Hz, 1H), 4.80 (s, 2H), 4.55 (t, J=8.7 Hz, 2H), 3.31 (t, J=8.9 Hz, 2H), 2.41 (s, 3H) ppm; LCMS: m/z 433.8 $[M+H]^+$.

The following compound can be synthesized with 3-bromo-5-methylpyridin-2-amine, 2-chloroacetaldehyde and intermediate B3 as the raw materials using the method of example 21:

Example 28: N-((5-fluoro-2,3-dihydrobenzofuran-4-yl)methyl)-8-(6-methylimidazo[1,2-a]pyridin-8-yl)-[1,2,4]triazolo[4,3-c]pyrimidin-5-amine

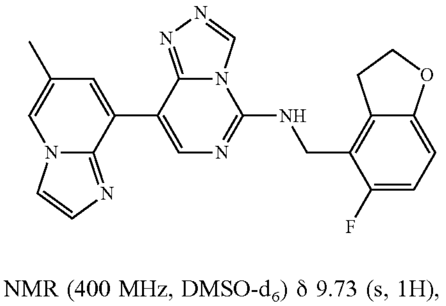

$^1$H NMR (400 MHz, DMSO-$d_6$) δ 9.73 (s, 1H), 9.62 (s, 1H), 8.96 (s, 1H), 8.75 (s, 1H), 8.41 (s, 1H), 8.01 (s, 1H), 7.66 (s, 1H), 7.07-7.00 (m, 1H), 6.78 (dd, J=8.7, 3.9 Hz, 1H), 4.84 (s, 2H), 4.62 (t, J=8.7 Hz, 2H), 3.38 (s, 2H), 2.44 (s, 3H) ppm; LCMS: m/z 415.8 $[M+H]^+$.

The following compound can be synthesized with 3-bromo-6-methylpyridin-2-amine, 2-chloropropanal and intermediate B3 as the raw materials using the method of example 21:

Example 29: 8-(3,5-dimethylimidazo[1,2-a]pyridin-8-yl)-N-((5-fluoro-2,3-dihydrobenzofuran-4-yl)methyl)-[1,2,4]triazolo[4,3-c]pyrimidin-5-amine

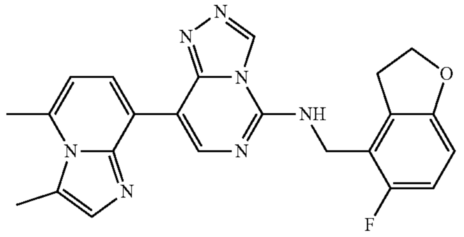

$^1$H NMR (400 MHz, DMSO-$d_6$) δ 9.51 (s, 1H), 9.45 (s, 1H), 8.78 (s, 1H), 8.49 (d, J=7.3 Hz, 1H), 7.34 (s, 1H), 7.00-6.93 (m, 1H), 6.79-6.70 (m, 2H), 4.76 (d, J=3.4 Hz, 2H), 4.55 (s, 2H), 3.31 (s, 2H), 2.93 (s, 3H), 2.82 (s, 3H) ppm; LCMS: m/z 430.0 $[M+H]^+$.

The following compound can be synthesized with 3-bromo-5-methylpyridin-2-amine, 3-chloro-1,1,1-trifluoropropan-2-one and intermediate B3 as the raw materials using the method of example 21:

Example 30: N-((5-fluoro-2,3-dihydrobenzofuran-4-yl)methyl)-8-(6-methyl-2-(trifluoromethyl)imidazo[1,2-a]pyridin-8-yl)-[1,2,4]triazolo[4,3-c]pyrimidin-5-amine

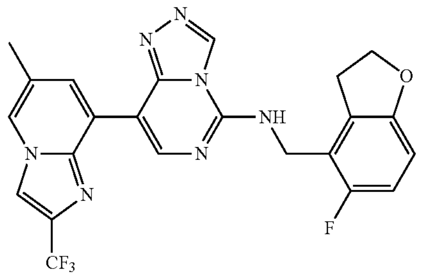 [SMILES: Cc1cc(-c2cnc(NCc3c(F)ccc4c3CCO4)n3cnnc23)c2nc(C(F)(F)F)cn2c1]

$^1$H NMR (400 MHz, DMSO-$d_6$) δ 9.60 (s, 1H), 9.47 (s, 1H), 8.99 (s, 1H), 8.82 (s, 1H), 8.56 (s, 1H), 8.39 (s, 1H), 7.02-6.93 (m, 1H), 6.72 (dd, J=8.7, 3.8 Hz, 1H), 4.80 (d, J=4.0 Hz, 2H), 4.54 (t, J=8.7 Hz, 2H), 3.30 (d, J=8.7 Hz, 2H), 2.41 (s, 3H) ppm; LCMS: m/z 483.7 $[M+H]^+$.

The following compound can be synthesized with 3-bromo-6-methylpyridin-2-amine, 2-chloropropanal and intermediate B3 as the raw materials using the method of example 21:

Example 31: 8-(3,5-dimethylimidazo[1,2-a]pyridin-8-yl)-N-((5-fluoro-2,3-dihydrobenzofuran-4-yl)methyl)-[1,2,4]triazolo[4,3-c]pyrimidin-5-amine

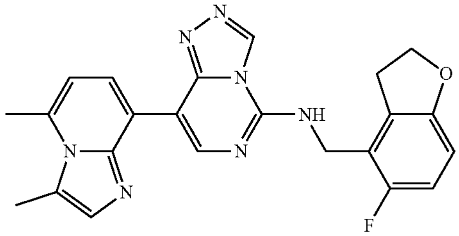

$^1$H NMR (400 MHz, DMSO-$d_6$) δ 9.51 (s, 1H), 9.45 (s, 1H), 8.78 (s, 1H), 8.49 (d, J=7.3 Hz, 1H), 7.34 (s, 1H), 7.00-6.93 (m, 1H), 6.79-6.70 (m, 2H), 4.76 (d, J=3.4 Hz, 2H), 4.55 (s, 2H), 3.31 (s, 2H), 2.93 (s, 3H), 2.82 (s, 3H) ppm; LCMS: m/z 430.0 [M+H]$^+$.

The following compound can be synthesized with 3-bromo-5-fluoropyridin-2-amine, 2-chloropropanal and intermediate B3 as the raw materials using the method of example 21:

Example 32: N-((5-fluoro-2,3-dihydrobenzofuran-4-yl)methyl)-8-(6-fluoro-3-methylimidazo[1,2-a]pyridin-8-yl)-[1,2,4]triazolo[4,3-c]pyrimidin-5-amine

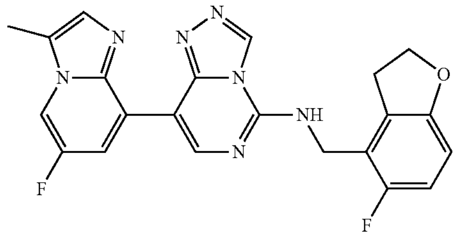 [SMILES: Cc1cnc2c(-c3cnc(NCc4c(F)ccc5c4CCO5)n4cnnc34)cc(F)cn12]

$^1$H NMR (400 MHz, DMSO-$d_6$) δ 9.84 (s, 1H), 9.59 (s, 1H), 8.93 (dd, J=11.1, 2.4 Hz, 1H), 8.50 (dd, J=4.0, 2.4 Hz, 1H), 7.52 (d, J=1.0 Hz, 1H), 6.96 (dd, J=10.3, 8.7 Hz, 1H), 6.71 (dd, J=8.6, 3.9 Hz, 1H), 4.78 (s, 2H), 4.55 (t, J=8.7 Hz, 2H), 3.34 (s, 6H), 3.32 (s, 4H) ppm; LCMS: m/z 434.1 [M+H]$^+$.

The following compound can be synthesized with 3-bromo-6-methylpyridin-2-amine, 2-chlorobutanal and intermediate B3 as the raw materials using the method of example 21:

Example 33: 8-(3-ethyl-5-methylimidazo[1,2-a]pyridin-8-yl)-N-((5-fluoro-2,3-dihydrobenzofuran-4-yl)methyl)-[1,2,4]triazolo[4,3-c]pyrimidin-5-amine

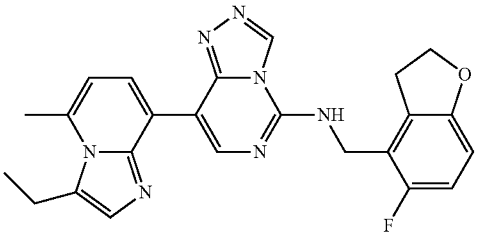 [SMILES: CCc1cnc2c(-c3cnc(NCc4c(F)ccc5c4CCO5)n4cnnc34)ccc(C)n12]

$^1$H NMR (400 MHz, DMSO-$d_6$) δ 9.52 (d, J=7.0 Hz, 1H), 9.45 (s, 1H), 8.77 (t, J=4.9 Hz, 1H), 8.48 (d, J=7.4 Hz, 1H), 7.38 (s, 1H), 7.01-6.92 (m, 1H), 6.78 (s, 1H), 6.71 (dd, J=8.7, 3.9 Hz, 1H), 4.76 (d, J=4.7 Hz, 2H), 4.55 (t, J=8.7 Hz, 2H), 3.34 (s, 2H), 3.30 (d, J=7.0 Hz, 2H), 2.92 (s, 3H), 1.35 (t, J=7.4 Hz, 3H) ppm; LCMS: m/z 444.0 [M+H]$^+$.

Example 34: N-((5-fluoro-2,3-dihydrobenzofuran-4-yl)methyl)-8-(2-(trifluoromethyl)imidazo[1,2-a]pyridin-8-yl)-[1,2,4]triazolo[4,3-c]pyrimidin-5-amine Step 1: imidazo[1,2-a]pyridin-8-ylboronic acid (E3-2)

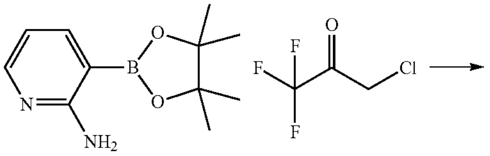

E3

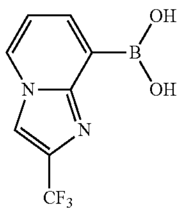

E3-2

Into a 25 mL microwave tube, E3 (100 mg, 0.45 mmol), 3-chloro-1,1,1-trifluoropropan-2-one (100 mg, 0.68 mmol), and 1,4-dioxane (4 mL) were added and the mixture was warmed to 90° C. and stirred for 2 hours. The reaction of the raw materials was completed (detected by LCMS). The reaction solution was cooled to room temperature and then directly used in the next step without any treatment.

LCMS: m/z 230.8 [M+H]$^+$.

Step 2: N-((5-fluoro-2,3-dihydrobenzofuran-4-yl)methyl)-8-(2-(trifluoromethyl)imidazo[1,2-a]pyridin-8-yl)-[1,2,4]triazolo[4,3-c]pyrimidin-5-amine

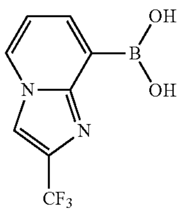

+

E3-2

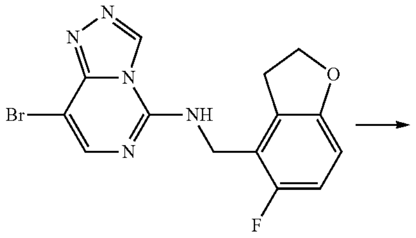

B3

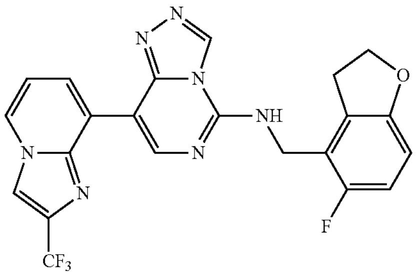

Into the reaction solution obtained in previous step, intermediate B3 (60 mg, 0.165 mmol), [1,1'-bis(diphenylphosphino)ferrocene]dichloropalladium(II) (12 mg, 0.0165 mmol), potassium carbonate (45 mg, 0.33 mmol) and $H_2O$ (1 mL) were added. Under nitrogen protection, the mixture was warmed to 80° C. in a microwave reactor and reacted for 1 hour. Upon completion of the reaction, the reaction solution was extracted with ethyl acetate (10 mL×3). The organic phases were combined, dried over anhydrous sodium sulfate and filtered and the filtrate was concentrated under reduced pressure. The residue was purified by Flash chromatography (100% ethyl acetate) to obtain N-((5-fluoro-2,3-dihydrobenzofuran-4-yl)methyl)-8-(2-(trifluoromethyl)imidazo[1,2-a]pyridin-8-yl)-[1,2,4]triazolo[4,3-c]pyrimidin-5-amine (55 mg, 71% yield) as a brown solid.

$^1$H NMR (400 MHz, MeOD) δ 9.31 (s, 1H), 9.12 (s, 1H), 8.43 (d, J=7.2 Hz, 1H), 8.26 (d, J=6.6 Hz, 1H), 8.09 (s, 1H), 7.12 (t, J=7.0 Hz, 1H), 6.85 (t, J=9.3 Hz, 1H), 6.67 (dd, J=8.6, 3.9 Hz, 1H), 4.63 (t, J=8.7 Hz, 2H), 4.12 (s, 2H), 3.42 (t, J=8.7 Hz, 2H) ppm; LCMS: m/z 469.8 $[M+H]^+$.

Example 35: intermediate 8-(2-aminopyridin-3-yl)-N-((5-fluoro-2,3-dihydrobenzofuran-4-yl)methyl)-[1,2,4]triazolo[4,3-c]pyrimidin-5-amine (E3-3)

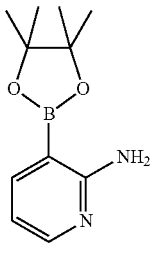

+

E3

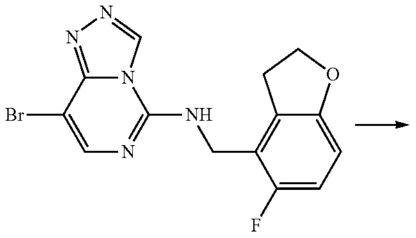

B3

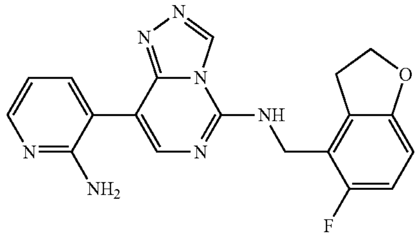

E3-3

Into a 25 mL microwave tube, 3-(4,4,5,5-tetramethyl-1,3,2-dioxaborolan-2-yl)pyridin-2-amine (220 mg, 1 mmol), intermediate B3 (300 mg, 0.824 mmol), [1,1'-bis(diphenylphosphino)ferrocene]dichloropalladium(II) (100 mg, 0.136 mmol), potassium carbonate (342 mg, 2.47 mmol) and dioxane —$H_2O$ (12 mL, V/V=4:1) were added. Under nitrogen protection, the mixture was warmed to 80° C. in a microwave reactor and reacted for 1 hour. Upon completion of the reaction, the mixture was then extracted with ethyl acetate (10 mL×3). The organic phases were combined, dried over anhydrous sodium sulfate and filtered and the filtrate was concentrated under reduced pressure. The residue was purified by Flash chromatography (methanol:ethyl acetate=1:20) to obtain E3-3 (262 mg, 84% yield) as a yellowish brown solid.

$^1$H NMR (400 MHz, DMSO-$d_6$) δ 9.44 (s, 1H), 8.65 (d, J=4.7 Hz, 1H), 8.00 (dd, J=4.9, 1.6 Hz, 1H), 7.60 (s, 1H), 7.49-7.40 (m, 1H), 7.01-6.91 (m, 1H), 6.72 (dd, J=8.7, 3.8 Hz, 1H), 6.64 (dd, J=7.3, 4.9 Hz, 1H), 5.71 (s, 2H), 4.71 (d, J=4.8 Hz, 2H), 4.56 (t, J=8.7 Hz, 2H), 3.32-3.26 (m, 2H) ppm; LCMS: m/z 377.8 $[M+H]^+$.

The following compound can be synthesized with intermediate E3-3 and chloracetone as the raw materials using the method in step 3 of example 21:

Example 36: N-((5-fluoro-2,3-dihydrobenzofuran-4-yl)methyl)-8-(2-methylimidazo[1,2-a]pyridin-8-yl)-[1,2,4]triazolo[4,3-c]pyrimidin-5-amine

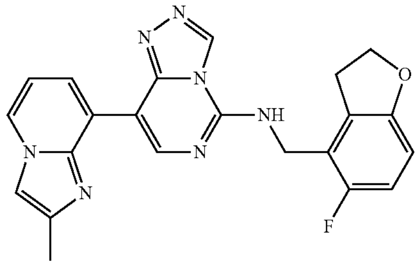 [SMILES: Cc1cn2cccc(-c3cnc(NCc4c(F)ccc5c4CCO5)n4cnnc34)c2n1]

$^1$H NMR (400 MHz, DMSO-$d_6$) δ 9.65 (s, 1H), 9.55 (s, 1H), 8.85 (t, J=5.2 Hz, 1H), 8.73 (d, J=6.8 Hz, 1H), 8.44 (d, J=5.8 Hz, 1H), 7.77 (s, 1H), 7.03-6.93 (m, 2H), 6.72 (dd, J=8.7, 3.9 Hz, 1H), 4.79 (d, J=4.9 Hz, 2H), 4.55 (t, J=8.7 Hz, 2H), 3.30 (d, J=8.8 Hz, 2H), 2.40 (s, 3H) ppm; LCMS: m/z 415.8 [M+H]$^+$.

The following compound can be synthesized with intermediate E3-3 and 2-chloropropanal as the raw materials using the method in step 3 of example 21:

Example 37: N-((5-fluoro-2,3-dihydrobenzofuran-4-yl)methyl)-8-(3-methylimidazo[1,2-a]pyridin-8-yl)-[1,2,4]triazolo[4,3-c]pyrimidin-5-amine

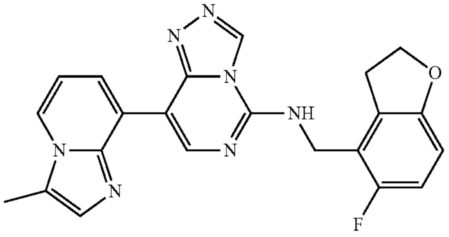 [SMILES: Cc1cnc2c(-c3cnc(NCc4c(F)ccc5c4CCO5)n4cnnc34)cccn12]

$^1$H NMR (400 MHz, DMSO-$d_6$) δ 9.65 (s, 1H), 9.56 (s, 1H), 8.89 (s, 1H), 8.79 (d, J=7.2 Hz, 1H), 8.25 (d, J=6.7 Hz, 1H), 7.45 (s, 1H), 7.13 (t, J=7.0 Hz, 1H), 7.01-6.93 (m, 1H), 6.72 (dd, J=8.6, 3.9 Hz, 1H), 4.78 (s, 2H), 4.56 (t, J=8.7 Hz, 2H), 3.33 (d, J=8.7 Hz, 2H), 2.51 (s, 3H) ppm; LCMS: m/z 415.8 [M+H]$^+$.

The following compound can be synthesized with intermediate E3-3 and ethyl 2-chloro-3-oxopropanoate as the raw materials using the method in step 3 of example 21:

Example 38: Ethyl 8-(5-(((5-fluoro-2,3-dihydrobenzofuran-4-yl)methyl)amino)-[1,2,4]triazolo[4,3-c]pyrimidin-8-yl)imidazo[1,2-a]pyridine-3-carboxylate

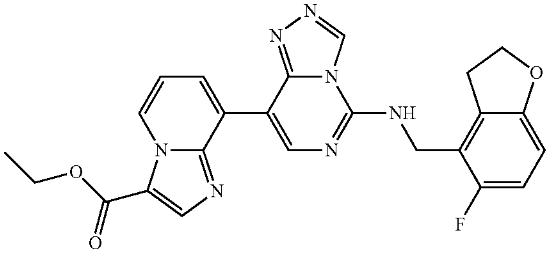 [SMILES: CCOC(=O)c1cnc2c(-c3cnc(NCc4c(F)ccc5c4CCO5)n4cnnc34)cccn12]

$^1$H NMR (400 MHz, $CDCl_3$) δ 9.34 (d, J=6.6 Hz, 1H), 8.56 (s, 1H), 8.26 (d, J=7.1 Hz, 1H), 8.16 (s, 1H), 7.62 (s, 1H), 7.20 (t, J=7.1 Hz, 1H), 6.73 (t, J=9.4 Hz, 1H), 6.59 (dd, J=8.6, 3.9 Hz, 1H), 4.66 (d, J=4.6 Hz, 2H), 4.53 (t, J=8.7 Hz, 2H), 4.46 (q, J=7.1 Hz, 2H), 3.35 (t, J=8.7 Hz, 2H), 1.46 (t, J=7.1 Hz, 3H) ppm; LCMS: m/z 473.8 [M+H]$^+$.

The following compound can be synthesized with intermediate E3-3 and 2-chlorobutanal as the raw materials using the method in step 3 of example 21:

Example 39: 8-(3-ethylimidazo[1,2-a]pyridin-8-yl)-N-((5-fluoro-2,3-dihydrobenzofuran-4-yl)methyl)-[1,2,4]triazolo[4,3-c]pyrimidin-5-amine

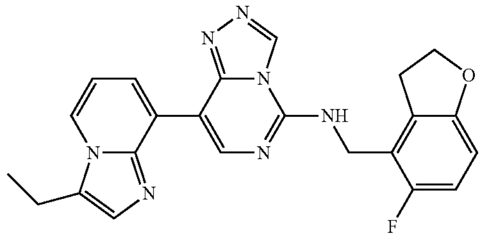 [SMILES: CCc1cnc2c(-c3cnc(NCc4c(F)ccc5c4CCO5)n4cnnc34)cccn12]

$^1$H NMR (400 MHz, DMSO-$d_6$) δ 9.72 (s, 1H), 9.35 (t, J=5.2 Hz, 1H), 8.83 (d, J=6.8 Hz, 1H), 8.22 (d, J=7.3 Hz, 1H), 8.12 (s, 1H), 8.05 (s, 1H), 7.63 (t, J=7.1 Hz, 1H), 6.97 (dd, J=10.3, 8.7 Hz, 1H), 6.72 (dd, J=8.7, 3.9 Hz, 1H), 4.77 (d, J=5.0 Hz, 2H), 4.56 (t, J=8.7 Hz, 2H), 3.10-2.98 (m, 2H), 1.39 (t, J=7.4 Hz, 3H) ppm; LCMS: m/z 430.0 [M+H]$^+$.

The following compound can be synthesized with intermediate E3-3 and 2-chloro-3-phenylpropanal as the raw materials using the method in step 3 of example 21:

Example 40: 8-(3-phenylmethylimidazo[1,2-a]pyridin-8-yl)-N-((5-fluoro-2,3-dihydrobenzofuran-4-yl)methyl)-[1,2,4]triazolo[4,3-c]pyrimidin-5-amine

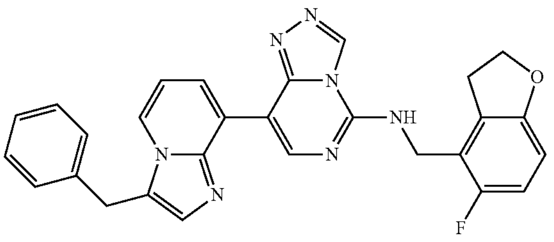 [SMILES: Fc1ccc2c(c1CNc1ncc(-c3cccn4c(Cc5ccccc5)cnc34)c3nncn13)CCO2]

$^1$H NMR (400 MHz, DMSO-$d_6$) δ 9.63 (s, 1H), 9.52 (s, 1H), 8.84 (t, J=5.1 Hz, 1H), 8.75 (dd, J=7.4, 1.2 Hz, 1H), 8.20 (dd, J=6.8, 1.2 Hz, 1H), 7.50 (s, 1H), 7.39-7.16 (m, 5H), 7.07 (t, J=7.0 Hz, 1H), 7.01-6.92 (m, 1H), 6.72 (dd, J=8.7, 3.9 Hz, 1H), 4.78 (d, J=5.1 Hz, 2H), 4.55 (t, J=8.7 Hz, 2H), 4.36 (s, 2H), 3.33 (s, 2H) ppm; LCMS: m/z 492.0 [M+H]$^+$.

Example 41: Ethyl 8-(5-(((5-fluoro-2,3-dihydrobenzofuran-4-yl)methyl)amino)-[1,2,4]triazolo[4,3-c]pyrimidin-8-yl)-2-(trifluoromethyl)imidazo[1,2-a]pyridine-3-carboxylate

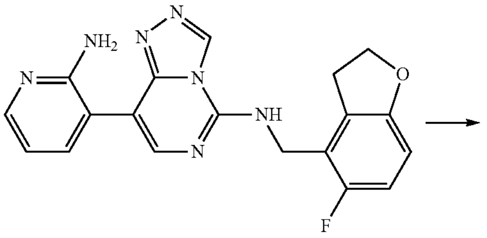

E3-3

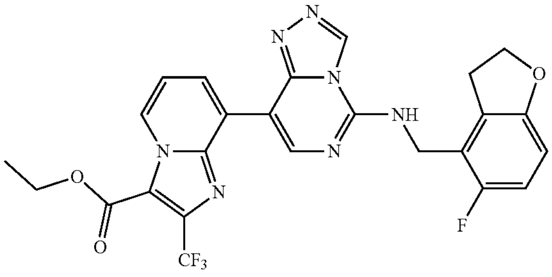

Into a 25 mL sealed tube, intermediate E3-3 (60 mg, 0.16 mmol), ethyl 2-bromo-4,4,4-trifluoro-3-oxobutanoate (315 mg, 1.59 mmol), and anhydrous ethanol (6 mL) were added in one portion. The reaction system was warmed to 90° C. and stirred for 16 hours. Upon completion of the reaction, ethanol was removed by concentration under reduced pressure. The crude was purified by silica gel column chromatography to obtain methyl 8-(5-(((5-fluoro-2,3-dihydrobenzofuran-4-yl)methyl)amino)-)[1,2,4]triazolo[4,3-c]pyrimidin-8-yl)-2-)trifluoromethyl)imidazo[1,2-a]pyridine-3-carboxylate (15 mg, 17% yield).

$^1$H NMR (400 MHz, DMSO-$d_6$) δ 9.55 (s, 1H), 9.28 (d, J=6.1 Hz, 2H), 9.02 (d, J=7.2 Hz, 1H), 7.56 (t, J=7.2 Hz, 1H), 6.97 (d, J=9.8 Hz, 1H), 6.73 (dd, J=8.6, 3.9 Hz, 1H), 4.80 (d, J=4.8 Hz, 2H), 4.55 (t, J=8.7 Hz, 2H), 4.45 (q, J=7.1 Hz, 2H), 3.34 (s, 2H), 3.30 (s, 3H), 3.17 (d, J=5.3 Hz, 1H), 1.37 (t, J=7.1 Hz, 3H), 1.23 (s, 2H) ppm; LCMS: m/z 541.9 $[M+H]^+$.

Example 42: 8-(5-(((5-fluoro-2,3-dihydrobenzofuran-4-yl)methyl)amino)-[1,2,4]triazolo[4,3-c]pyrimidin-8-yl)imidazo[1,2-a]pyridine-3-carboxylic acid

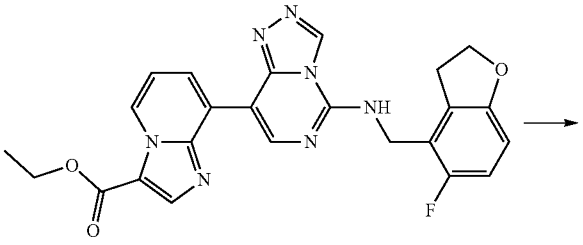

-continued

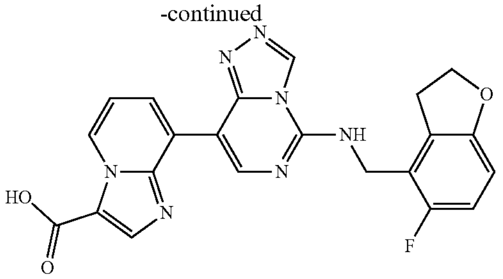

Into a 25 mL single-necked flask, ethyl 8-(5-(((5-fluoro-2,3-dihydrobenzofuran-4-yl)methyl)amino)-[1,2,4]triazolo[4,3-c]pyrimidin-8-yl)imidazo[1,2-a]pyridine-3-carboxylate (47 mg, 0.1 mmol), methanol (10 mL) and water (5 mL) were added, and then potassium hydroxide (56 mg, 1.0 mmol) was added with stirring. The reaction was stirred overnight. The raw materials were fully reacted (monitored by a TLC plate). Then 2 N hydrochloric acid was added to adjust the PH value to 6. The solution was spin-dried and then purified by Flash chromatography (eluents:dichloromethane:methanol=3:1) to obtain a white solid, 8-(5-(((5-fluoro-2,3-dihydrobenzofuran-4-yl)methyl)amino)-[1,2,4]triazolo[4,3-c]pyrimidin-8-yl)imidazo[1,2-a]pyridine-3-carboxylic acid (35 mg, 79% yield).

$^1$H NMR (400 MHz, DMSO-$d_6$) δ 9.64 (s, 1H), 9.47 (d, J=7.8 Hz, 1H), 9.36 (s, 1H), 8.78 (d, J=7.3 Hz, 1H), 8.20 (s, 1H), 7.21 (t, J=7.1 Hz, 1H), 6.92-6.83 (m, 1H), 6.66 (dd, J=8.6, 3.8 Hz, 1H), 4.79 (s, 2H), 4.58 (t, J=8.7 Hz, 2H), 3.39 (t, J=8.7 Hz, 2H) ppm; LCMS: m/z 446.4 $[M+H]^+$.

Example 43: N-((5-fluoro-2,3-dihydrobenzofuran-4-yl)methyl)-8-(3-fluoroimidazo[1,2-a]pyridin-8-yl-[1,2,4]triazolo[4,3-c]pyrimidin-5-amine

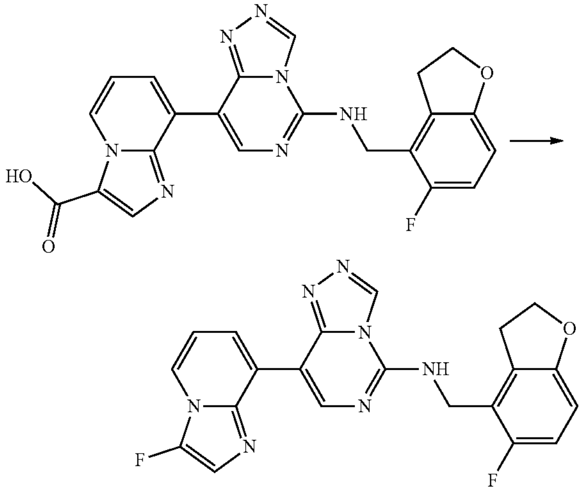

Into a 25 ml single-necked flask, compound 8-(5-(((5-fluoro-2,3-dihydrobenzofuran-4-yl)methyl)amino-[1,2,4]triazolo[4,3-c]pyrimidin-8-yl)imidazo[1,2-a]pyridine-3-carboxylic acid (55 mg, 0.123 mmol), potassium fluoride (36.5 mg, 0.628 mmol), 1-(chloromethyl)-4-fluoro-1,4-diazabicyclo[2.2.2]octane-1,4-2 tetrafluoroborate (111 mg, 0.314 mmol), dichloroethane (3 mL), and water (1 mL) were added sequentially. Under nitrogen protection, the mixture was refluxed at 70° C. for 16 hours. The reaction was completed (as detected) and then the resulting mixture was cooled to room temperature. The reaction was quenched by adding ice water (3 ml). The reaction mixture was extracted with ethyl acetate (3*5 ml) three times. The extraction liquid was extracted twice with saturated brine and purified water, respectively. The organic phase was dried over anhydrous sodium sulfate and the organic solvent was removed under reduced pressure. The crude product was subjected to purification by reverse phase column chromatography (0.05% aqueous formic acid solution:acetonitrile=2:3, volume ratio) to obtain an off-white solid compound, N-((5-fluoro-2,3-dihydrobenzofuran-4-yl)methyl)-8-(3-fluoroimidazo[1,2-a]pyridin-8-yl-[1,2,4]triazolo[4,3-c]pyrimidin-5-amine (5 mg, 9.7% yield).

$^1$H NMR (400 MHz, DMSO-$d_6$) δ 9.64-9.62 (m, 1H), 9.57 (s, 1H), 9.13 (s, 1H), 8.80 (dd, J=7.3, 1.1 Hz, 1H), 8.28 (dd, J=6.8, 1.1 Hz, 1H), 7.45 (d, J=7.2 Hz, 1H), 7.19 (t, J=7.0 Hz, 1H), 6.96 (dd, J=10.3, 8.7 Hz, 1H), 6.71 (dd, J=8.6, 3.9 Hz, 1H), 4.77 (s, 2H), 4.55 (t, J=8.7 Hz, 2H), 3.32 (d, J=8 Hz, 2H) ppm; LCMS: m/z 419.9 $[M+H]^+$.

According to the method of example 42, the following compound can be obtained by hydrolyzing the raw material, ethyl 8-(5-(((5-fluoro-2,3-dihydrobenzofuran-4-yl)methyl)amino)-[1,2,4]triazolo[4,3-c]pyrimidin-8-yl)-5-methylimidazo[1,2-a]pyridine-3-carboxylate:

Example 44: 8-(5-(((5-fluoro-2,3-dihydrobenzofuran-4-yl)methyl)amino)-[1,2,4]triazolo[4,3-c]pyrimidin-8-yl)-5-methylimidazo[1,2-a]pyridine-3-carboxylic acid

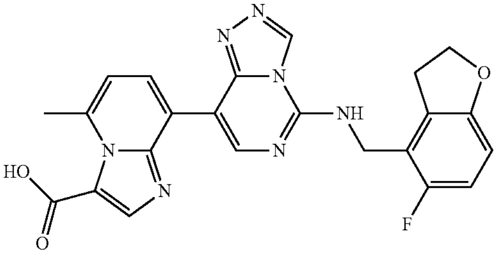 [SMILES: Cc1ccc(-c2cnc(NCc3c(F)ccc4c3CCO4)n3cnnc23)c2ncc(C(=O)O)n12]

$^1$H NMR (400 MHz, DMSO-$d_6$) δ 9.61 (s, 1H), 9.32 (s, 1H), 8.74 (d, J=7.3 Hz, 1H), 8.10 (s, 1H), 7.21 (t, J=7.1 Hz, 1H), 6.90-6.81 (m, 1H), 6.62 (dd, J=8.6, 3.8 Hz, 1H), 4.75 (s, 2H), 4.52 (t, J=8.7 Hz, 2H), 3.35 (t, J=8.7 Hz, 2H), 2.79 (d, J=6.8 Hz, 3H) ppm; LCMS: m/z 460.0 $[M+H]^+$.

According to the method of example 43, the following compound can be obtained using intermediate 8-5-(((5-fluoro-2,3-dihydrobenzofuran-4-yl)methyl)amino)-[1,2,4]triazolo[4,3-c]pyrimidin-8-yl)-5-methylimidazo[1,2-a]pyridine-3-carboxylic acid as the raw material:

Example 45: N-((5-fluoro-2,3-dihydrobenzofuran-4-yl)methyl)-8-(3-fluoro-5-methylimidazo[1,2-a]pyridin-8-yl)-[1,2,4]triazolo[4,3-c]pyrimidin-5-amine

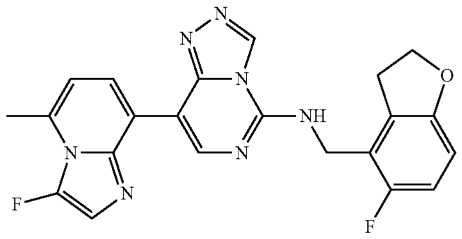 [SMILES: Cc1ccc(-c2cnc(NCc3c(F)ccc4c3CCO4)n3cnnc23)c2ncc(F)n12]

$^1$H NMR (400 MHz, DMSO-$d_6$) δ 9.59 (s, 1H), 9.44 (s, 1H), 9.02 (s, 1H), 8.60 (d, J=7.4 Hz, 1H), 7.42 (d, J=7.0 Hz, 1H), 6.96 (dd, J=10.3, 8.7 Hz, 1H), 6.89 (d, J=7.5 Hz, 1H), 6.71 (dd, J=8.6, 3.9 Hz, 1H), 4.76 (s, 2H), 4.55 (t, J=8.7 Hz, 2H), 3.32 (d, J=8.8 Hz, 2H), 2.77 (d, J=6.8 Hz, 3H) ppm; LCMS: m/z 434.0 $[M+H]^+$.

According to the method of example 43, the following compound can be obtained using intermediate 6-fluoro-8-(5-(((5-fluoro-2,3-dihydrobenzofuran-4-yl)methyl)amino)-[1,2,4]triazolo[4,3-c]pyrimidine-8-imidazo[1,2-a]pyridine-3-carboxylic acid as the raw material:

Example 46: 8-(3,6-difluoroimidazo[1,2-a]pyridin-8-yl)-N-((5-fluoro-2,3-dihydrobenzofuran-4-yl)methyl)-[1,2,4]triazolo[4,3-c]pyrimidin-5-amine

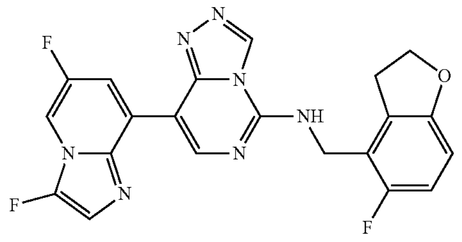 [SMILES: Fc1cc(-c2cnc(NCc3c(F)ccc4c3CCO4)n3cnnc23)c2ncc(F)n2c1]

$^1$H NMR (400 MHz, DMSO-$d_6$) δ 9.75 (s, 1H), 9.56 (s, 1H), 9.05 (s, 1H), 8.93 (dd, J=11.3, 2.4 Hz, 1H), 8.58 (t, J=2.9 Hz, 1H), 7.53 (d, J=7.2 Hz, 1H), 7.07-6.88 (m, 1H), 6.72 (dd, J=8.7, 3.9 Hz, 1H), 4.79 (s, 2H), 4.55 (t, J=8.7 Hz, 2H), 3.30 (s, 1H) ppm; LCMS: m/z 438.0 $[M+H]^+$.

Example 47: Ethyl 8-(5-(((5-fluoro-2,3-dihydrobenzofuran-4-yl)methyl)amino)-[1,2,4]triazolo[4,3-c]pyrimidin-8-yl)-2-hydroxyimidazo[1,2-a]pyridine-3-carboxylate

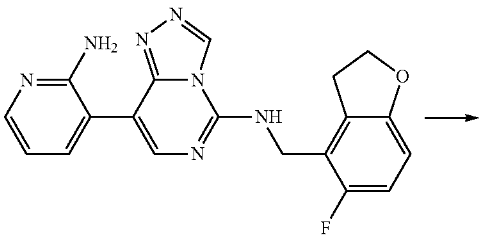

E3-3

-continued

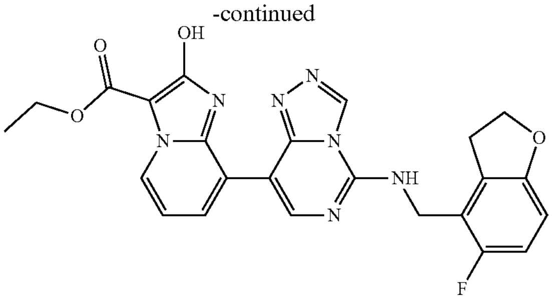

Into a 25 mL sealed tube, E3-3 (150 mg, 0.40 mmol), diethyl 2-bromopropanedioate (475 mg, 1.99 mmol), and anhydrous ethanol (6 mL) were added in one portion. The reaction system was warmed to 90° C. and stirred for 16 hours. Upon completion of the reaction, ethanol was removed by concentration under reduced pressure. The crude was purified by HPLC to obtain methyl 8-(5-(((5-fluoro-2,3-dihydrobenzofuran-4-yl)methyl)amino)-[1,2,4]triazolo[4,3-c]pyrimidin-8-yl)-2-hydroxyimidazo[1,2-a]pyridine-3-carboxylate (8 mg, 4% yield).

$^1$H NMR (400 MHz, MeOD-$d_4$) δ 9.59 (d, J=6.3 Hz, 1H), 9.38 (s, 1H), 8.03 (s, 1H), 7.87 (d, J=7.6 Hz, 1H), 7.44-7.36 (m, 1H), 6.93-6.85 (m, 1H), 6.67 (dd, J=8.6, 3.9 Hz, 1H), 4.87 (s, 2H), 4.61 (t, J=8.7 Hz, 2H), 4.40 (q, J=7.1 Hz, 2H), 3.44 (t, J=8.7 Hz, 2H), 1.41 (t, J=7.1 Hz, 3H) ppm; LCMS: m/z 490.0 $[M+H]^+$.

According to the method of example 47, the following compound can be obtained using intermediate E2-2 and diethyl 2-bromopropanedioate as the raw materials:

Example 48: Ethyl 6-fluoro-8-(5-(((5-fluoro-2,3-dihydrobenzofuran-4-yl)methyl)amino)-[1,2,4]triazolo[4,3-c]pyrimidin-8-yl)-2-hydroxyimidazo[1,2-a]pyridine-3-carboxylate

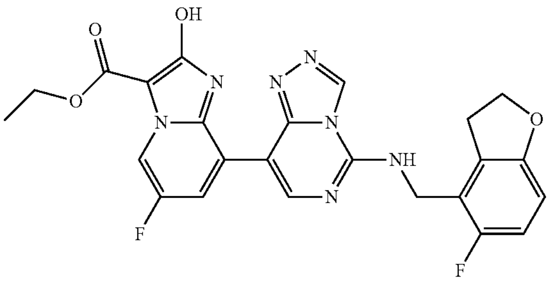 [SMILES: CCOC(=O)c1c(O)nc2c(-c3cnc(NCc4c(F)ccc5c4CCO5)n4cnnc34)cc(F)cn12]

$^1$H NMR (400 MHz, DMSO-$d_6$) δ 9.60 (t, J=12.0 Hz, 1H), 8.96 (d, J=11.4 Hz, OH), 8.67 (s, OH), 6.96 (t, J=9.5 Hz, 1H), 6.70 (s, 1H), 6.06 (s, 5H), 4.77 (s, 1H), 4.53 (d, J=8.7 Hz, 1H), 4.47-4.27 (m, 1H), 3.30 (s, 3H) ppm; LCMS: m/z 508.0 $[M+H]^+$.

Example 49: 8-(5-(((5-fluoro-2,3-dihydrobenzofuran-4-yl)methyl)amino)-[1,2,4]triazolo[4,3-c]pyrimidin-8-yl)imidazo[1,2-a]pyridine-3-carbonitrile

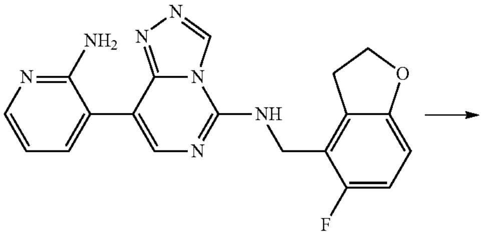

E3-3

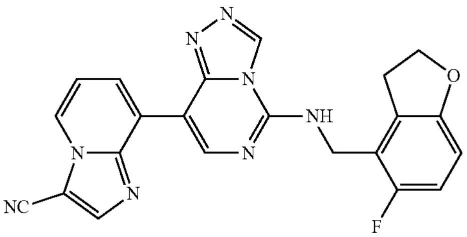

Methoxyacrylonitrile (110 mg, 1.32 mmol) was dissolved in the mixed solvents of dioxane (6 mL) and water (2 mL). At 0° C., N-bromosuccinimide (235 mg, 1.32 mmol) was added with stirring. The reaction solution was stirred for another 30 minutes at 0° C. and then E3-3 (100 mg, 0.26 mmol) was added. The mixture was stirred at room temperature for 2 hours and then heated to 90° C. and the stirring was continued for 16 hours at this temperature. The reaction was completed and the solvents were removed by concentration under reduced pressure. The residue was purified by Flash column chromatography (dichloromethane:methanol=9:1, volume ratio) to obtain a compound 8-(5-(((5-fluoro-2,3-dihydrobenzofuran-4-yl)methyl)amino)-[1,2,4]triazolo[4,3-c]pyrimidin-8-yl)imidazo[1,2-a]pyridine-3-carbonitrile (12 mg, 11% yield).

$^1$H NMR (400 MHz, DMSO-$d_6$) δ 9.55 (s, 1H), 9.41 (s, 1H), 9.03-8.99 (m, 1H), 8.97 (t, J=5.2 Hz, 1H), 8.64 (dd, J=6.6, 1.0 Hz, 1H), 8.54 (s, 1H), 7.47-7.41 (m, 1H), 7.00-6.93 (m, 1H), 6.72 (dd, J=8.7, 3.9 Hz, 1H), 4.78 (d, J=5.0 Hz, 2H), 4.55 (t, J=8.7 Hz, 2H), 3.31 (s, 2H) ppm; LCMS: m/z 427.0 $[M+H]^+$.

Example 50: N-((5-fluoro-2,3-dihydrobenzofuran-4-yl)methyl)-8-(5-(trifluoromethyl)benzo[c][1,2,5]thiadiazol-4-yl)-[1,2,4]triazolo[4,3-c]pyrimidin-5-amine Step 1: Intermediate E4-2 can be synthesized with 3-bromo-4-(trifluoromethyl)benzene-1,2-diamine and intermediate B3 as the raw materials using the method of example 21

E4-2

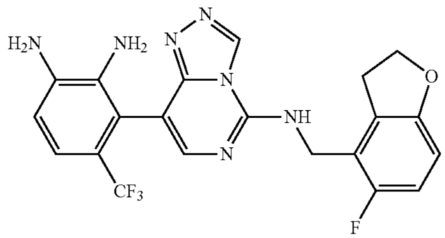

$^{1}$H NMR (400 MHz, DMSO-$d_6$) δ 9.43 (d, J=16.9 Hz, 1H), 8.60 (dd, J=9.1, 4.5 Hz, 1H), 7.56 (s, 1H), 7.50 (d, J=5.6 Hz, 1H), 6.98 (d, J=8.9 Hz, 1H), 6.73 (d, J=4.4 Hz, 1H), 5.03 (s, 1H), 4.87 (s, 1H), 4.70 (dd, J=11.4, 4.8 Hz, 2H), 4.55 (q, J=8.9 Hz, 2H), 3.29 (dd, J=18.8, 10.2 Hz, 2H) ppm; LCMS: m/z 459.7 $[M+H]^+$.

Step 2: N-((5-fluoro-2,3-dihydrobenzofuran-4-yl)methyl)-8-(5-(trifluoromethyl)benzo[c][1,2,5]thiadiazol-4-yl)-[1,2,4]triazolo[4,3-c]pyrimidin-5-amine

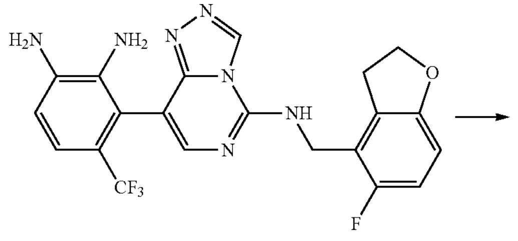

E4-2

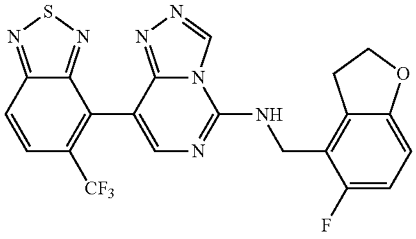

Into a 25 mL single-necked flask, compound E4-2 (20 mg, 0.043 mmol), thionyl chloride (13.78 mg, 0.14 mmol), triethylamine (24.26 mg, 0.188 mmol), and dichloromethane (3 mL) were added sequentially and the mixture was reacted at 0° C. for 2 h. The reaction was completed and the reaction solution was concentrated under reduced pressure. The residue was purified by silica gel column chromatography (mobile phase:ethyl acetate:methanol=15:1) to obtain a compound N-((5-fluoro-2,3-dihydrobenzofuran-4-yl)methyl)-8-(5-(trifluoromethyl)benzo[c][1,2,5]thiadiazol-4-yl)-[1,2,4]triazolo[4,3-c]pyrimidin-5-amine (6 mg, 28.2% yield).

$^{1}$H NMR (400 MHz, DMSO-$d_6$) δ 9.56 (s, 1H), 9.26 (d, J=1.7 Hz, 1H), 9.20 (s, 1H), 9.07 (s, 1H), 8.56 (d, J=3.7 Hz, 1H), 6.98 (t, J=9.5 Hz, 1H), 6.73 (dd, J=8.6, 3.8 Hz, 1H), 4.81 (s, 2H), 4.56 (t, J=8.7 Hz, 2H), 2.10-1.91 (m, 2H) ppm; LCMS: m/z 487.4 $[M+H]^+$.

Example 51: 1-(8-(5-(((5-fluoro-2,3-dihydrobenzofuran-4-yl)methyl)amino)-[1,2,4]triazolo[4,3-c]pyrimidin-8-yl)-2-methylimidazo[1,2-a]pyridin-3-yl)ethan-1-one

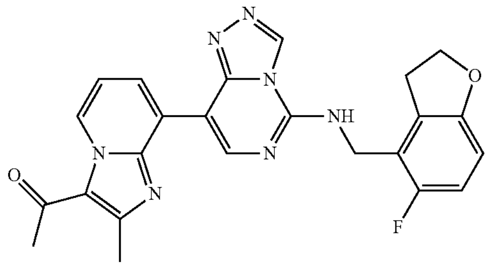 [SMILES: CC(=O)c1c(C)nc2c(-c3cnc(NCc4c(F)ccc5c4CCO5)n4cnnc34)cccn12]

Into a 25 mL sealed tube, intermediate E3-3 (50 mg, 0.13 mmol), 3-chloropentane-2,4-dione (89 mg, 0.66 mmol), and anhydrous ethanol (6 mL) were added in one portion. The reaction system was warmed to 90° C. and stirred for 4 hours. Upon completion of the reaction, the resulting mixture was concentrated under reduced pressure to obtain a residue, which was purified by Flash silica gel column chromatography (eluents:methanol:ethyl acetate=1:20) to obtain a compound 1-(8-(5-(((5-fluoro-2,3-dihydrobenzofuran-4-yl)methyl)amino)-[1,2,4]triazolo[4,3-c]pyrimidin-8-yl)-2-methylimidazo[1,2-a]pyridin-3-yl)ethan-1-one (4.8 mg, 8% yield).

$^{1}$H NMR (400 MHz, $CDCl_3$) δ 9.19 (s, 1H), 8.53 (s, 1H), 8.27 (s, 1H), 7.94 (s, 1H), 7.46 (s, 1H), 6.99 (s, 1H), 6.74 (d, J=8.0 Hz, 1H), 6.58 (s, 1H), 4.87 (d, J=6.3 Hz, 1H), 4.71 (s, 2H), 4.53 (d, J=7.7 Hz, 2H), 3.33 (d, J=7.0 Hz, 2H), 1.97 (d, J=6.7 Hz, 2H) ppm; LCMS: m/z 431.9 $[M+H]^+$.

According to the method of example 51, the following compound can be obtained using intermediate E2-2 as the raw material:

Example 52: 1-(6-fluoro-8-(5-(((5-fluoro-2,3-dihydrobenzofuran-4-yl)methyl)amino)-[1,2,4]triazolo[4,3-c]pyrimidin-8-yl)-2-methylimidazo[1,2-a]pyridin-3-yl)ethan-1-one

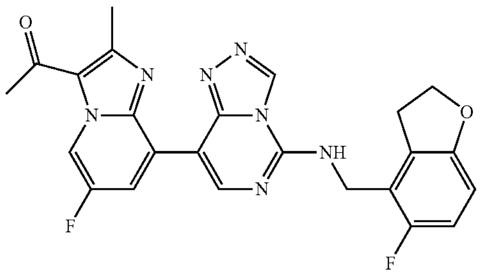 [SMILES: CC(=O)c1c(C)nc2c(-c3cnc(NCc4c(F)ccc5c4CCO5)n4cnnc34)cc(F)cn12]

$^{1}$H NMR (400 MHz, DMSO-$d_6$) δ 9.65 (dd, J=4.7, 2.6 Hz, 1H), 9.63 (s, 1H), 9.56 (s, 1H), 9.11 (dd, J=10.6, 2.5 Hz, 1H), 9.04 (s, 1H), 6.98 (t, J=9.4 Hz, 1H), 6.73 (dd, J=8.6, 3.9 Hz, 1H), 4.81 (d, J=4.7 Hz, 2H), 4.55 (t, J=8.7 Hz, 2H), 3.31 (s, OH), 2.81 (s, 3H), 2.65 (s, 3H) ppm; LCMS: m/z 476.1 $[M+H]^+$.

Example 53: 8-(2,3-dihydroimidazo[1,2-a]pyridin-8-yl)-N-((5-fluoro-2,3-dihydrobenzofuran-4-yl)methyl)-[1,2,4]triazolo[4,3-c]pyrimidin-5-amine Step 1: 2-((3-bromopyridin-2-yl)amino)ethan-1-ol E4-3

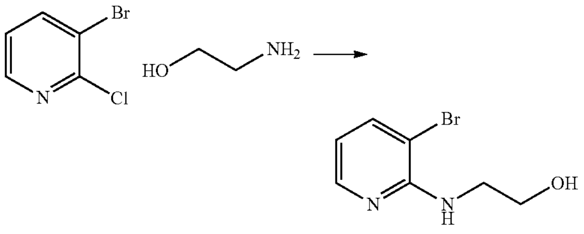

E4-3

3-bromo-2-chloropyridine (3.00 g, 15.6 mmol) and 2-aminoethan-1-ol (3.81 g, 62.4 mmol) were dissolved in pyridine (6 mL). The mixture was stirred at 180° C. for 90 minutes. Upon completion of the reaction, the mixture was cooled to room temperature and saturated sodium hydrogen carbonate solution was added into the reaction solution. The resulting mixture was then extracted with dichloromethane. The organic phases were mixed, dried, concentrated and purified by silica gel column chromatography to obtain intermediate E4-3 (3.18 g, 94% yield).

$^1$H NMR (400 MHz, DMSO-$d_6$) δ 8.03 (dd, J=4.8, 1.6 Hz, 1H), 7.73 (dq, J=7.7, 1.6 Hz, 1H), 6.57-6.45 (m, 1H), 6.12 (t, J=5.6 Hz, 1H), 4.80 (t, J=5.1 Hz, 1H), 3.57 (q, J=5.6, 4.5 Hz, 2H), 3.50-3.38 (m, 2H) ppm. LCMS: m/z 218.0 $[M+H]^+$.

Step 2: (2-((2-hydroxyethyl)amino)pyridin-3-yl)boronic acid E4-4

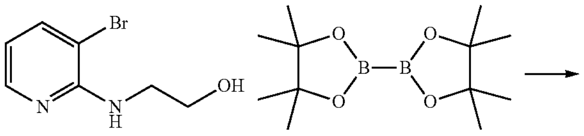

E4-3

E4-4

In a 25 mL single-necked flask, E4-3 (300 mg, 1.38 mmol), bis(pinacolato)diboron (306 mg, 1.21 mmol), potassium acetate (118 mg, 1.21 mmol), [1,1'-bis(diphenylphosphino)ferrocene]dichloropalladium(II) (35 mg, 0.05 mmol), and 1,4-dioxane (6 mL) were added sequentially. The reaction system was warmed to 90° C. and reacted under nitrogen atmosphere for 16 hours. The raw materials were substantially converted to E4-4 (monitored by TLC) and then the reaction solution was directly used in the next step without any treatment.

Step 3: 2-((3-(5-(((5-fluoro-2,3-dihydrobenzofuran-4-yl)methyl)amino)-[1,2,4]triazolo[4,3-c]pyrimidin-8-yl)pyridin-2-yl)amino)ethan-1-ol E4-5

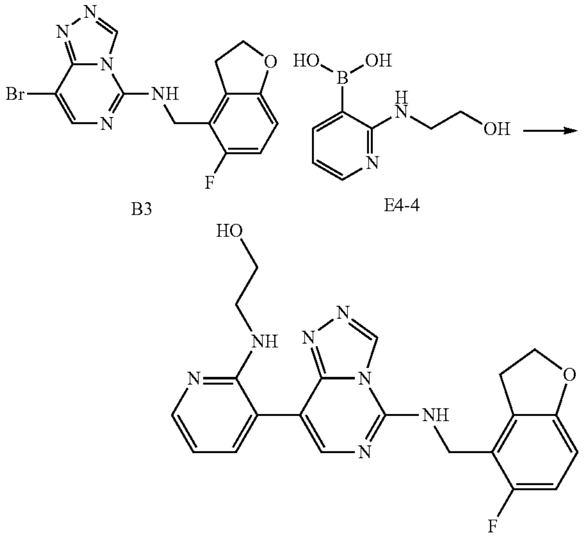

B3

E4-4

E4-5

To the reaction solution obtained in the previous step, B3 (302 mg, 0.83 mmol), potassium carbonate (573 mg, 4.15 mmol), [1,1'-bis(diphenylphosphino)ferrocene]dichloropalladium(II) (100 mg, 0.14 mmol) and water (3 mL) were added. The reaction system was warmed to 80° C. under nitrogen atmosphere and reacted for 5 hours. The reaction was completed (monitored by LCMS). The resulting mixture was cooled to room temperature and diluted and dissolved in ethyl acetate (30 mL). The organic phase was washed with water (5 mL*2), dried over anhydrous sodium sulfate and concentrated under reduced pressure. The crude was purified by Flash silica gel column chromatography (mobile phase:ethyl acetate:methanol=10:1, volume ratio) to obtain a compound E4-5 (130 mg, 22% yield).

LCMS: m/z 422.0 $[M+H]^+$.

Step 4: 8-(2,3-dihydroimidazo[1,2-a]pyridin-8-yl)-N-((5-fluoro-2,3-dihydrobenzofuran-4-yl)methyl)-[1,2,4]triazolo[4,3-c]pyrimidin-5-amine

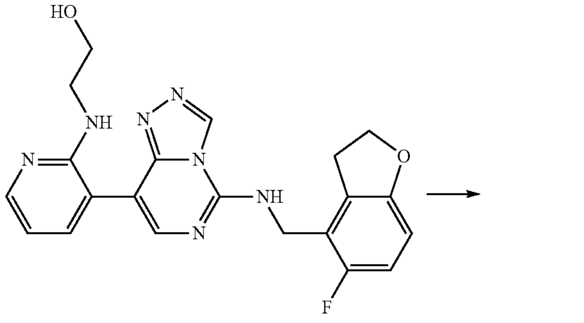

E4-5

-continued

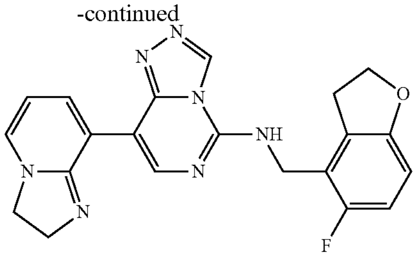

To a 25 mL eggplant-shaped flask, E4-5 (80 mg, 0.19 mmol) and xylene (5 mL) were added. In a stirring state, thionyl chloride (1.5 mL) was added dropwise and the reaction solution was stirred at 100° C. for 16 hours. The reaction was completed and the reaction solution was filtered to obtain a solid. The solid was dissolved in dichloromethane and then washed with saturated aqueous sodium hydrogen carbonate solution. The organic phase was concentrated. The crude was purified by HPLC to obtain 8-(2,3-dihydroimidazo[1,2-a]pyridin-8-yl)-N-((5-fluoro-2,3-dihydrobenzofuran-4-yl)methyl)-[1,2,4]triazolo[4,3-c]pyrimidin-5-amine (4 mg, 5% yield).

$^1$H NMR (400 MHz, $CDCl_3$) δ 8.99 (s, 1H), 7.98 (s, 1H), 7.52 (d, J=6.8 Hz, 1H), 7.14 (d, J=6.3 Hz, 1H), 6.78-6.71 (m, 1H), 6.60 (dd, J=8.6, 3.8 Hz, 1H), 6.00 (t, J=6.7 Hz, 1H), 4.61-4.50 (m, 4H), 4.15 (t, J=10.3 Hz, 2H), 3.78 (t, J=10.4 Hz, 2H), 3.36 (t, J=8.7 Hz, 2H) ppm; LCMS: m/z 404.0 $[M+H]^+$.

Example 54: N-((5-fluoro-2,3-dihydrobenzofuran-4-yl)methyl)-8-(quinolin-8-yl)-[1,2,4]triazolo[4,3-c]pyrimidin-5-amine

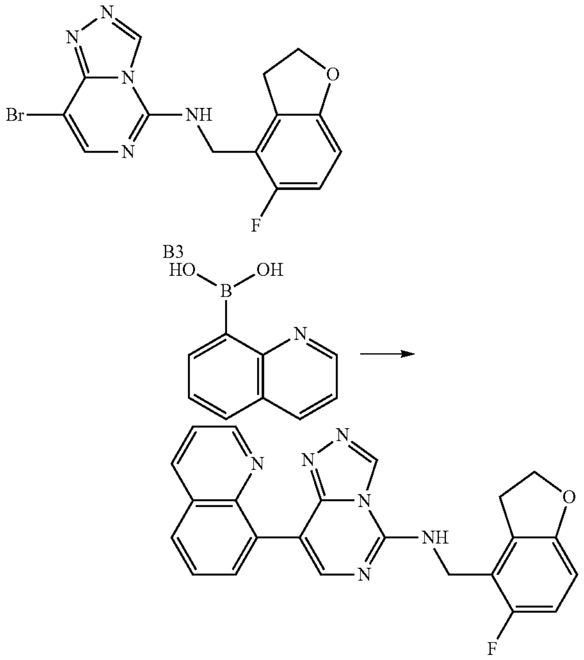

Into a 10 mL sealed tube, B3 (50 mg, 0.14 mmol), quinolin-8-ylboronic acid (24 mg, 0.20 mmol), [1,1'-bis(diphenylphosphino)ferrocene]dichloropalladium(II) (10.1 mg, 0.014 mmol), potassium carbonate (58.5 mg, 0.423 mmol), anhydrous dioxane (2 mL) and water (0.5 mL) were added sequentially. The tube was sealed under nitrogen protection and the mixture was stirred in 80° C. oil bath for 2 hours. Upon completion of the reaction, the reaction solution was filtered and then spin-dried. The product in the residue was dissolved in 3 ml DMF and was then purified by prep-HPLC (0.05% aqueous trifluoroacetic acid solution: acetonitrile=3:7) to obtain a product N-((5-fluoro-1,3-dihydroisobenzofuran-4-yl)methyl)-8-(quinolin-8-yl)-[1,2,4]triazolo[4,3-c]pyrimidin-5-amine (21 mg, 37.5% yield).

$^1$H NMR (400 MHz, DMSO-$d_6$) δ 9.50 (s, 1H), 8.84 (dd, J=4.1, 1.8 Hz, 1H), 8.79 (s, 1H), 8.45 (dd, J=8.3, 1.8 Hz, 1H), 8.11 (dd, J=7.2, 1.5 Hz, 1H), 8.04 (dd, J=8.3, 1.5 Hz, 1H), 7.97 (s, 1H), 7.72 (dd, J=8.2, 7.2 Hz, 1H), 7.58 (dd, J=8.3, 4.1 Hz, 1H), 7.02-6.92 (m, 1H), 6.73 (dd, J=8.6, 3.9 Hz, 1H), 4.76 (d, J=4.7 Hz, 2H), 4.57 (t, J=8.7 Hz, 2H), 3.39 (s, 5H) ppm; LCMS: m/z 413.0 $[M+H]^+$.

Example 55: 5-(5-((((1aR,6bR)-5-fluoro-1a,6b-dihydro-1H-cyclopropa[b]benzofuran-6-yl)methyl)amino)-[1,2,4]triazolo[4,3-c]pyrimidin-8-yl)benzo[b]thiophene 1,1-dioxide Step 1: 5-bromobenzo[b]thiophene 1,1-dioxide (E5-2)

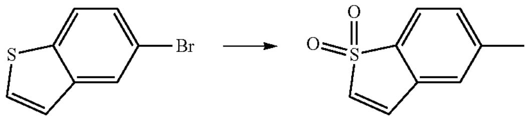

E5-1 E5-2

Into a 500 mL round-bottom flask, E5-1 (10 g, 46.9 mmol), dichloromethane (120 mL) and formic acid (85% aqueous solution, 10 mL) were added. Hydrogen peroxide (35% aqueous solution, 16.7 mL, 141 mmol) was then slowly added at room temperature. The reaction solution was stirred at room temperature overnight. Upon completion of the reaction, 200 mL of saturated brine was added and the resulting mixture was extracted with dichloromethane (200 mL*3). The organic layers were combined, then dried over anhydrous sodium sulfate, filtered and spin-dried to obtain a residue, which was purified by Flash chromatography (petroleum ether:ethyl acetate=10:1) to obtain a white solid E5-2 (9.9 g, 86% yield).

$^1$H NMR (400 MHz, $CDCl_3$) δ 7.68 (d, J=8.0 Hz, 1H), 7.59 (d, J=8.0 Hz, 1H), 7.53 (s, 1H), 7.18 (d, J=6.9 Hz, 1H), 6.77 (d, J=6.9 Hz, 1H) ppm; LCMS: m/z 244.9 $[M+H]^+$.

Step 2: (1,1-dihydroxybenzo[b]thiophen-5-yl)boronic acid (E5-3)

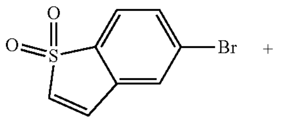

E5-2

-continued

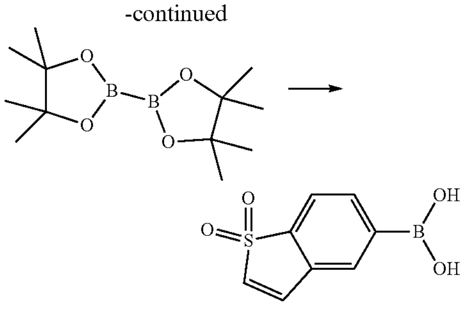

E5-3

Into a dry 30 mL sealed tube, E5-2 (130 mg, 0.53 mmol) and bis(pinacolato)diboron (188 mg, 0.74 mmol) were added sequentially. [1,1'-bis(diphenylphosphino)ferrocene] dichloropalladium(II) (23 mg, 0.032 mmol), and potassium acetate (156 mg, 1.59 mmol) dissolved in 5 ml of dry 1,4-dioxane were added. The reaction mixture was bubbled with nitrogen gas for one minute and then the reaction system was warmed to 90° C. and stirred for 12 hours. The reaction solution was cooled to room temperature, and the raw materials were substantially converted to E5-3 (detected by LCMS). Then the reaction was not subjected to post-treatment, but was directly used in the next reaction by using a one-pot process.

LCMS: m/z 210.7 $[M+H]^+$.

Step 3: 5-(5-((((1aR,6bR)-5-fluoro-1a,6b-dihydro-1H-cyclopropa[b]benzofuran-6-yl)methyl)amino)-[1,2,4]triazolo[4,3-c]pyrimidin-8-yl)benzo[b]thiophene 1,1-dioxide

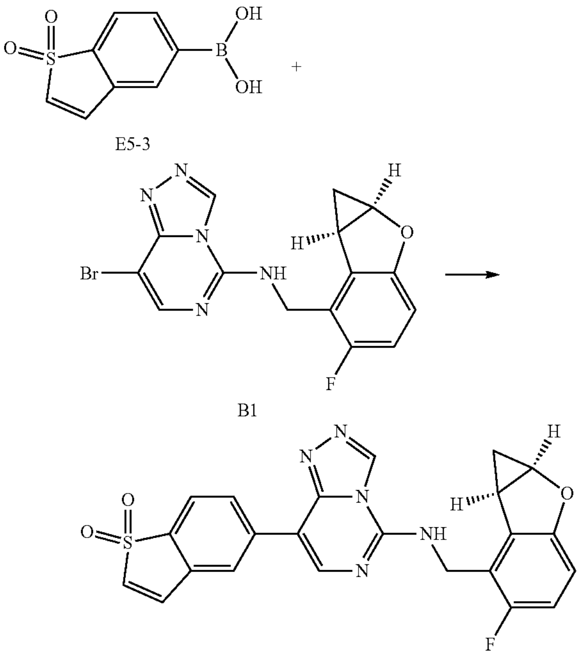

E5-3

B1

Into the above-mentioned reaction solution of E5-3, intermediate B1 (100 mg, 0.26 mmol), [1,1'-bis(diphenylphosphino)ferrocene]dichloropalladium(II) (21 mg, 0.03 mmol), potassium carbonate (76 mg, 0.54 mmol), and $H_2O$ (2 mL) were added sequentially. The resulting reaction solution was bubbled with nitrogen gas for one minute, then warmed to 85° C. and stirred for 2 hours. The reaction solution was cooled to room temperature. The reaction system was slowly added dropwise into ice water (30 mL) and then extracted with ethyl acetate (30 mL×2). The organic phases were combined, dried over anhydrous sodium sulfate and filtered and the filtrate was concentrated under reduced pressure. The residue was purified by Flash chromatography (neat ethyl acetate) to obtain a product 5-(5-((((1aR,6bR)-5-fluoro-1a,6b-dihydro-1H-cyclopropa[b]benzofuran-6-yl)methyl)amino)-[1,2,4]triazolo[4,3-c]pyrimidin-8-yl)benzo[b]thiophene 1,1-dioxide (64 mg, 52% yield) as a white solid.

$^1H$ NMR (400 MHz, DMSO-$d_6$) δ 9.43 (s, 1H), 8.36-8.23 (m, 2H), 8.11 (s, 1H), 7.80 (d, J=7.9 Hz, 1H), 7.58 (d, J=6.8 Hz, 1H), 7.29 (d, J=6.6 Hz, 1H), 6.82 (t, J=9.4 Hz, 1H), 6.65 (d, J=6.3 Hz, 1H), 4.86-4.62 (m, 3H), 2.86-2.75 (m, 1H), 0.93-0.81 (m, 1H), 0.05-0.04 (m, 1H) ppm; LCMS: m/z 461.7 $[M+H]^+$.

The following compound can be synthesized with intermediate B3 and 5-bromobenzo[b]thiophene as the raw materials using the method of example 55:

Example 56: 5-(5-(((5-fluoro-2,3-dihydrobenzofuran-4-yl)methyl)amino)-[1,2,4]triazolo[4,3-c]pyrimidin-8-yl)benzo[b]thiophene 1,1-dioxide

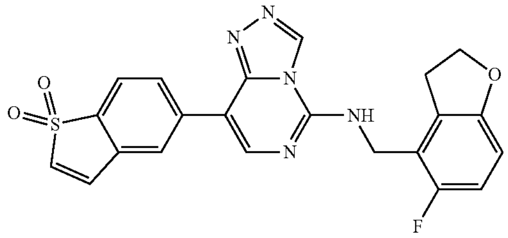 [SMILES: O=S1(=O)C=Cc2cc(-c3cnc(NCc4c(F)ccc5c4CCO5)n4cnnc34)ccc21]

$^1H$ NMR (400 MHz, DMSO-$d_6$) δ 9.63 (s, 1H), 9.11 (s, 1H), 8.47-8.36 (m, 2H), 8.25 (s, 1H), 7.93 (d, J=8.0 Hz, 1H), 7.72 (d, J=6.9 Hz, 1H), 7.42 (d, J=6.9 Hz, 1H), 7.00-6.92 (m, 1H), 6.71 (dd, J=8.6, 3.8 Hz, 1H), 4.75 (s, 2H), 4.55 (t, J=8.7 Hz, 2H), 3.33-3.29 (m, 2H) ppm; LCMS: m/z 449.8 $[M+H]^+$.

The following compound can be synthesized with intermediate B2 and 5-bromobenzo[b]thiophene as the raw materials using the method of example 55:

Example 57: 5-(5-((((1aS,6bS)-5-fluoro-1a,6b-dihydro-1H-cyclopropa[b]benzofuran-6-yl)methyl)amino)-[1,2,4]triazolo[4,3-c]pyrimidin-8-yl)benzo[b]thiophene 1,1-dioxide

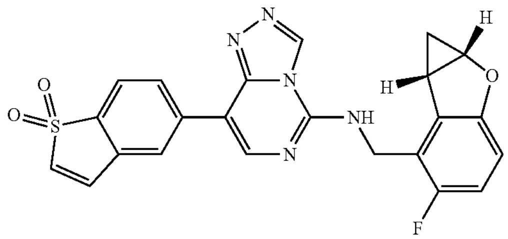 [SMILES: O=S1(=O)C=Cc2cc(-c3cnc(NCc4c(F)ccc5c4[C@@H]4C[C@@H]4O5)n4cnnc34)ccc21]

$^1$H NMR (400 MHz, DMSO-$d_6$) δ 9.43 (s, 1H), 8.36-8.23 (m, 2H), 8.11 (s, 1H), 7.80 (d, J=7.9 Hz, 1H), 7.58 (d, J=6.8 Hz, 1H), 7.29 (d, J=6.6 Hz, 1H), 6.82 (t, J=9.4 Hz, 1H), 6.65 (d, J=6.3 Hz, 1H), 4.86-4.62 (m, 3H), 2.86-2.75 (m, 1H), 0.93-0.81 (m, 1H), 0.05-0.04 (m, 1H) ppm; LCMS: m/z 461.7 $[M+H]^+$.

The following compound can be synthesized with intermediate B3 and 4-bromobenzo[b]thiophene as the raw materials using the method of example 55:

Example 58: 4-(5-(((5-fluoro-2,3-dihydrobenzofuran-4-yl)methyl)amino)-[1,2,4]triazolo[4,3-c]pyrimidin-8-yl)benzo[b]thiophene 1,1-dioxide

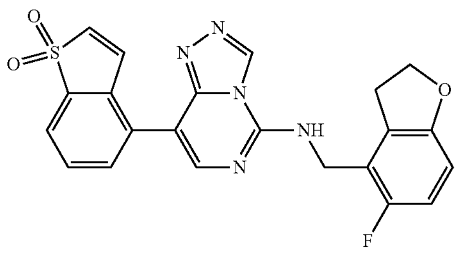 [SMILES: O=S1(=O)C=Cc2c(-c3cnc(NCc4c(F)ccc5c4CCO5)n4cnnc34)cccc21]

$^1$H NMR (400 MHz, DMSO-$d_6$) δ 9.49 (s, 1H), 8.87 (s, 1H), 7.96-7.66 (m, 4H), 7.44 (d, J=7.1 Hz, 1H), 7.34 (d, J=7.1 Hz, 1H), 6.97 (t, J=9.4 Hz, 1H), 6.73 (dd, J=8.6, 3.9 Hz, 1H), 4.74 (d, J=4.5 Hz, 2H), 4.57 (t, J=8.7 Hz, 2H) ppm; LCMS: m/z 449.8 $[M+H]^+$.

The following compound can be synthesized with intermediate B1 and 4-bromobenzo[b]thiophene as the raw materials using the method of example 55:

Example 59: 4-(5-((((1aR,6bR)-5-fluoro-1a,6b-dihydro-1H-cyclopropa[b]benzofuran-6-yl)methyl)amino)-[1,2,4]triazolo[4,3-c]pyrimidin-8-yl)benzo[b]thiophene 1,1-dioxide

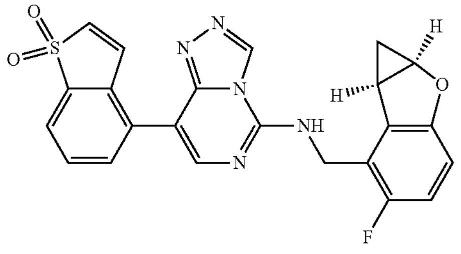 [SMILES: O=S1(=O)C=Cc2c(-c3cnc(NCc4c(F)ccc5c4[C@H]4C[C@H]4O5)n4cnnc34)cccc21]

$^1$H NMR (400 MHz, DMSO-$d_6$) δ 9.34 (s, 1H), 8.82 (s, 1H), 7.76-7.51 (m, 4H), 7.26 (d, J=7.1 Hz, 1H), 7.17 (d, J=7.1 Hz, 1H), 6.85-6.74 (m, 1H), 6.62 (dd, J=8.7, 3.9 Hz, 1H), 4.84-4.67 (m, 3H), 0.96-0.80 (m, 1H), 0.00 (s, 1H) ppm; LCMS: m/z 461.7 $[M+H]^+$.

The following compound can be synthesized with intermediate B3 and 5-bromo-6-methylbenzo[b]thiophene as the raw materials using the method of example 55:

Example 60: 5-(5-(((5-fluoro-2,3-dihydrobenzofuran-4-yl)methyl)amino)-[1,2,4]triazolo[4,3-c]pyrimidin-8-yl)-6-methylbenzo[b]thiophene 1,1-dioxide

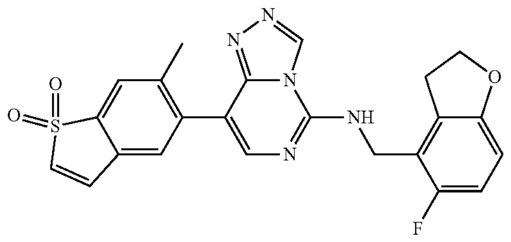 [SMILES: Cc1cc2c(cc1-c1cnc(NCc3c(F)ccc4c3CCO4)n3cnnc13)C=CS2(=O)=O]

$^1$H NMR (400 MHz, DMSO-$d_6$) δ 9.48 (s, 1H), 8.78 (s, 1H), 7.85 (s, 1H), 7.69 (s, 1H), 7.62 (d, J=6.9 Hz, 1H), 7.58 (s, 1H), 7.34 (d, J=6.8 Hz, 1H), 6.97 (t, J=9.4 Hz, 1H), 6.72 (dd, J=8.6, 3.9 Hz, 1H), 4.73 (d, J=4.0 Hz, 2H), 4.56 (t, J=8.7 Hz, 2H), 3.35 (s, 2H), 2.31 (s, 3H) ppm; LCMS: m/z 463.7 $[M+H]^+$.

The following compound can be synthesized with intermediate B3 and 5-bromo-7-fluorobenzo[b]thiophene as the raw materials using the method of example 55:

Example 61: 7-fluoro-5-(5-(((5-fluoro-2,3-dihydrobenzofuran-4-yl)methyl)amino)-[1,2,4]triazolo[4,3-c]pyrimidin-8-yl)benzo[b]thiophene 1,1-dioxide

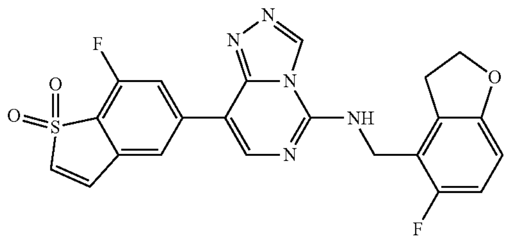 [SMILES: O=S1(=O)C=Cc2cc(-c3cnc(NCc4c(F)ccc5c4CCO5)n4cnnc34)cc(F)c21]

$^1$H NMR (400 MHz, DMSO-$d_6$) δ 9.54 (s, 1H), 9.07 (s, 1H), 8.44-8.31 (m, 3H), 7.75 (dd, J=6.8, 2.4 Hz, 1H), 7.50 (d, J=6.7 Hz, 1H), 7.02-6.89 (m, 1H), 6.72 (dd, J=8.7, 3.9 Hz, 1H), 4.76 (s, 2H), 4.55 (t, J=8.7 Hz, 2H), 3.55 (s, 2H) ppm; LCMS: m/z 467.7 $[M+H]^+$.

The following compound can be synthesized with intermediate B2 and 2-(5-bromobenzo[b]thiophen-3-yl)ethylamine hydrochloride as the raw materials using the method of example 55:

Example 62: 3-(2-aminoethyl)-5-(5-((((1aS,6bS)-5-fluoro-1a,6b-dihydro-1H-cyclopropa[b]benzofuran-6-yl)methyl)amino)-[1,2,4]triazolo[4,3-c]pyrimidin-8-yl)benzo[b]thiophene 1,1-dioxide

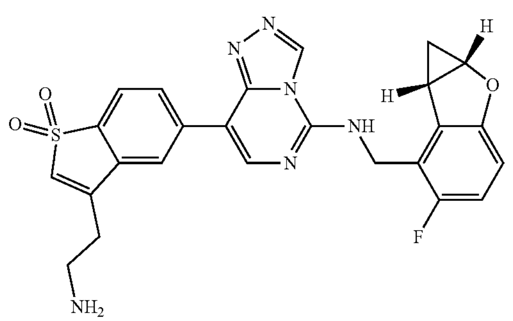 [SMILES: NCCC1=CS(=O)(=O)c2ccc(-c3cnc(NCc4c(F)ccc5c4[C@@H]4C[C@@H]4O5)n4cnnc34)cc21]

$^1$H NMR (400 MHz, DMSO-$d_6$) δ 9.67 (s, 1H), 9.29 (t, J=5.2 Hz, 1H), 8.56-8.40 (m, 2H), 8.35 (s, 1H), 8.10 (s, 3H), 7.96 (d, J=8.0 Hz, 1H), 7.32 (s, 1H), 6.94 (dd, J=10.3, 8.7 Hz, 1H), 6.77 (dd, J=8.7, 3.8 Hz, 1H), 5.01-4.82 (m, 3H), 3.22 (q, J=6.8 Hz, 2H), 3.08 (t, J=7.4 Hz, 2H), 2.98 (dt, J=9.1, 4.5 Hz, 1H), 0.95 (dt, J=9.1, 5.8 Hz, 1H), 0.09 (ddd, J=6.1, 4.0, 1.9 Hz, 1H) ppm; LCMS: m/z 504.7 $[M+H]^+$.

The following compound can be synthesized with intermediate B3 and 5-bromobenzo[c]thiophene as the raw materials using the method of example 55:

Example 63: 5-(5-(((5-fluoro-2,3-dihydrobenzofuran-4-yl)methyl)amino)-[1,2,4]triazolo[4,3-c]pyrimidin-8-yl)benzo[c]thiophene 2,2-dioxide

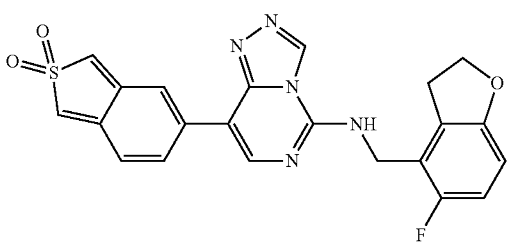 [SMILES: O=S1(=O)C=c2ccc(-c3cnc(NCc4c(F)ccc5c4CCO5)n4cnnc34)cc2=C1]

$^1$H NMR (400 MHz, $CDCl_3$) δ 8.89 (s, 1H), 8.28 (s, 1H), 8.08 (d, J=6.8 Hz, 1H), 8.01 (s, 1H), 7.78 (d, J=7.9 Hz, 1H), 7.31 (d, J=6.9 Hz, 1H), 6.90-6.82 (m, 1H), 6.75 (d, J=6.9 Hz, 1H), 6.68 (dd, J=8.6, 4.0 Hz, 1H), 6.17 (s, 1H), 4.84 (d, J=5.4 Hz, 2H), 4.64 (t, J=8.7 Hz, 2H), 3.42 (t, J=8.7 Hz, 2H) ppm; LCMS: m/z 449.7 $[M+H]^+$ The following compound can be synthesized with intermediate B1 and 5-bromobenzo[c]thiophene as the raw materials using the method of example 55:

Example 64: 5-(5-((((1aR,6bR)-5-fluoro-1a,6b-dihydro-1H-cyclopropa[b]benzofuran-6-yl)methyl)amino)-[1,2,4]triazolo[4,3-c]pyrimidin-8-yl)benzo[c]thiophene 2,2-dioxide

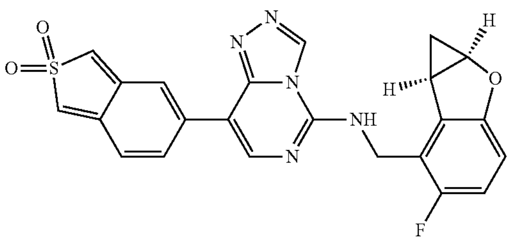 [SMILES: O=S1(=O)C=c2ccc(-c3cnc(NCc4c(F)ccc5c4[C@H]4C[C@H]4O5)n4cnnc34)cc2=C1]

$^1$H NMR (DMSO-$d_6$) δ 9.55 (s, 1H), 9.06 (s, 1H), 8.45-8.36 (m, 2H), 8.25 (s, 1H), 7.93 (d, J=8.1 Hz, 1H), 7.71 (d, J=6.9 Hz, 1H), 7.41 (d, J=6.8 Hz, 1H), 6.98-6.90 (m, 1H), 6.78 (dd, J=8.7, 3.9 Hz, 1H), 4.93 (dd, J=12.5, 8.8 Hz, 2H), 2.98-2.89 (m, 1H), 2.03-1.93 (m, 1H), 0.99 (dt, J=9.0, 5.9 Hz, 1H), 0.13 (s, 1H).

The following compound can be synthesized with intermediate B4 and 5-bromobenzo[c]thiophene as the raw materials using the method of example 55:

Example 65: 5-(5-(((6-fluorochroman-5-yl)methyl)amino)-[1,2,4]triazolo[4,3-c]pyrimidin-8-yl)benzo[c]thiophene 2,2-dioxide

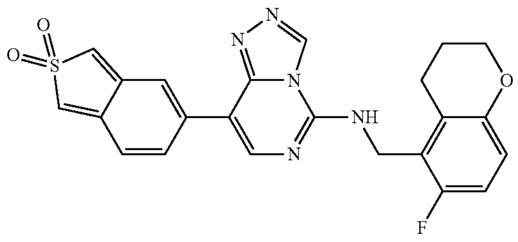 [SMILES: O=S1(=O)C=c2ccc(-c3cnc(NCc4c(F)ccc5c4CCCO5)n4cnnc34)cc2=C1]

$^1$H NMR (400 MHz, MeOD) δ 8.50 (s, 1H), 7.38 (d, J=9.7 Hz, 1H), 7.34-7.26 (m, 1H), 7.22 (d, J=6.1 Hz, 1H), 7.00 (t, J=7.1 Hz, 1H), 6.58 (dd, J=6.9, 2.9 Hz, 1H), 6.06 (t, J=8.1 Hz, 1H), 6.03-5.90 (m, 2H), 4.51 (d, J=5.5 Hz, 1H), 4.04-3.91 (m, 2H), 3.38-3.28 (m, 2H), 2.17-2.04 (m, 2H), 1.27-1.14 (m, 2H) ppm; LCMS: m/z 463.7 $[M+H]^+$.

Example 66: 6-(5-(((5-fluoro-2,3-dihydrobenzofuran-4-yl)methyl)amino)-[1,2,4]triazolo[4,3-c]pyrimidin-8-yl)-2-methylbenzo[b]thiophene 1,1-dioxide Step 1: 6-bromo-2-methylbenzo[b]thiophene E6-2

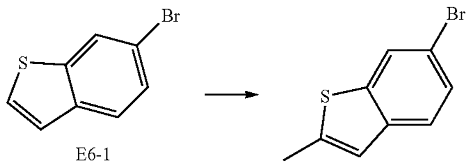

E6-1

E6-2

Into a 25 mL three-necked flask, E6-1 (1 g, 4.69 mmol) and anhydrous tetrahydrofuran (10 mL) were added under nitrogen protection and the mixture was cooled to −70° C. Lithium diisopropylamide (2 M in THF, 3.52 mL, 7.04 mmol) was slowly added. The reaction continued for another 40 minutes at −70° C. Methyl iodide (1.33 g, 9.39 mmol) was slowly added and then the reaction solution was warmed to room temperature and reacted for 2 hours. Upon completion of the reaction, the reaction was quenched by adding ice water (5 mL). HCl (1 N) was used to adjust the pH to neutral. The resulting mixture was diluted with ethyl acetate (10 mL). The organic phase was washed with saturated sodium chloride solution (5 mL), then dried over anhydrous sodium sulfate and concentrated under reduced pressure to obtain a crude E6-2 (960 mg) as light yellow solid, which was directly used in the next step.

Step 2: 6-bromo-2-methylbenzo[b]thiophene 1,1-dioxide (E6-3)

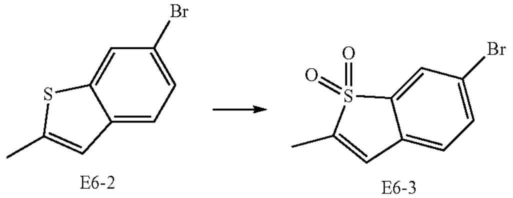

E6-2 E6-3

Into a 25 mL single-necked flask, intermediate E6-2 (960 mg, 4.23 mmol) was added. Acetic acid (10 mL) was added and dissolved with stirring. Then hydrogen peroxide (30% aqueous solution, 4.8 g, 42.27 mmol) was added. The mixture was warmed to 100° C. and reacted for 3 h. Upon completion of the reaction, The resulting mixture was cooled to room temperature. Ice water (8 mL) was added and the mixture was stirred for 5-10 minutes and then extracted twice with ethyl acetate (8 mL). The organic phase was washed once with water (5 mL) and saturated brine (5 mL), respectively. The organic phase was dried over anhydrous sodium sulfate and concentrated under reduced pressure. The residue was subjected to column chromatography (mobile phase:petroleum ether to 10% petroleum ether/ethyl acetate) to obtain E6-3 (800 mg, 66% yield) as a white solid.

$^1$H NMR (400 MHz, $CDCl_3$) δ 7.83 (s, 1H), 7.65 (dd, J=8.0, 1.7 Hz, 1H), 7.16 (d, J=8.0 Hz, 1H), 6.75 (s, 1H), 2.21 (d, J=1.7 Hz, 3H) ppm; LCMS: m/z 278.7 [M+H]$^+$.

Step 3: The following compound can be synthesized with intermediates B3 and E6-3 as the raw materials using the method of example 55:

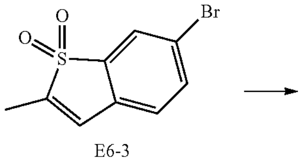

E6-3

-continued

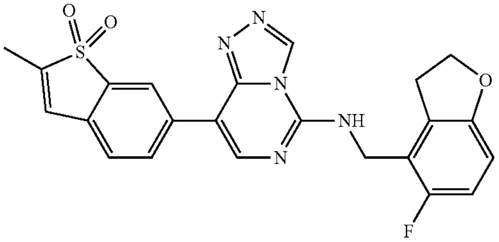

$^1$H NMR (400 MHz, DMSO-$d_6$) δ 9.52 (s, 1H), 8.91 (s, 1H), 8.72 (s, 1H), 8.50 (dd, J=8.0, 1.4 Hz, 1H), 8.32 (s, 1H), 7.63 (d, J=8.0 Hz, 1H), 7.28 (s, 1H), 7.01-6.92 (m, 1H), 6.71 (dd, J=8.6, 3.9 Hz, 1H), 4.74 (s, 2H), 4.56 (t, J=8.7 Hz, 2H), 3.32 (s, 2H), 2.24-2.09 (m, 3H) ppm; LCMS: m/z 463.7 [M+H]$^+$.

The following compound can be synthesized with intermediate B1 and 5-bromo-benzothiophene as the raw materials using the method of example 66:

Example 67: 5-(5-((((1aR,6bR)-5-fluoro-1a,6b-dihydro-1H-cyclopropa[b]benzofuran-6-yl)methyl) amino)-[1,2,4]triazolo[4,3-c]pyrimidin-8-yl)-2-methylbenzo[b]thiophene 1,1-dioxide

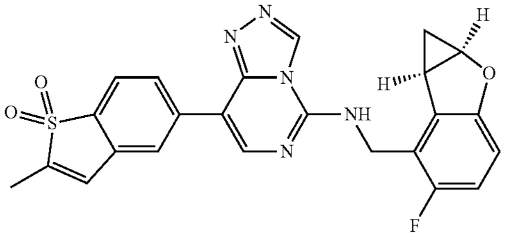 [SMILES: CC1=Cc2cc(-c3cnc(NCc4c(F)ccc5c4[C@H]4C[C@H]4O5)n4cnnc34)ccc2S1(=O)=O]

$^1$H NMR (400 MHz, DMSO-$d_6$) δ 9.53 (s, 1H), 9.06 (s, 1H), 8.34 (d, J=6.6 Hz, 2H), 8.24 (s, 1H), 7.94 (d, J=8.5 Hz, 1H), 7.31 (s, 1H), 7.07-6.89 (m, 1H), 6.78 (dd, J=8.7, 3.9 Hz, 1H), 4.93 (td, J=5.3, 1.8 Hz, 1H), 4.89 (d, J=3.2 Hz, 2H), 3.00-2.87 (m, 1H), 2.16 (d, J=1.5 Hz, 3H), 0.99 (dt, J=8.9, 6.0 Hz, 1H), 0.13 (ddd, J=5.9, 3.9, 1.9 Hz, 1H) ppm; LCMS: m/z 475.7 [M+H]$^+$ The following compound can be synthesized with intermediate B3 and 4-bromo-benzothiophene as the raw materials using the method of example 66:

Example 68: 4-(5-(((5-fluoro-2,3-dihydrobenzofuran-4-yl)methyl)amino)-[1,2,4]triazolo[4,3-c]pyrimidin-8-yl)-2-methylbenzo[b]thiophene 1,1-dioxide

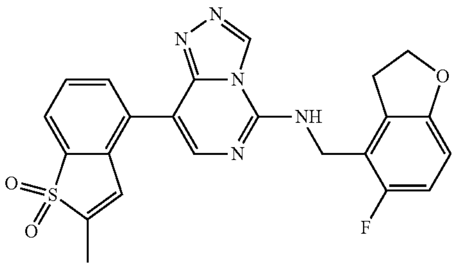 [SMILES: CC1=Cc2c(-c3cnc(NCc4c(F)ccc5c4CCO5)n4cnnc34)cccc2S1(=O)=O]

$^1$H NMR (400 MHz, DMSO-$d_6$) δ 9.52 (s, 1H), 8.91 (s, 1H), 8.72 (s, 1H), 8.50 (dd, J=8.0, 1.4 Hz, 1H), 8.32 (s, 1H), 7.63 (d, J=8.0 Hz, 1H), 7.28 (s, 1H), 7.00-6.90 (m, 1H), 6.71 (dd, J=8.6, 3.9 Hz, 1H), 4.74 (s, 2H), 4.56 (t, J=8.7 Hz, 2H), 3.32 (s, 2H), 2.27-2.08 (m, 3H) ppm; LCMS: m/z 463.7 $[M+H]^+$.

The following compound can be synthesized with intermediate B3 and 5-bromo-7-chlorobenzothiophene as the raw materials using the method of example 66:

Example 69: 7-chloro-5-(5-(((5-fluoro-2,3-dihydrobenzofuran-4-yl)methyl)amino)-[1,2,4]triazolo[4,3-c]pyrimidin-8-yl)-2-methylbenzo[b]thiophene 1,1-dioxide

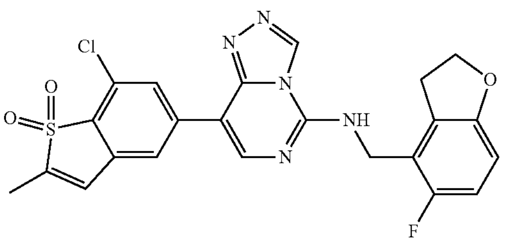 [SMILES: CC1=Cc2cc(-c3cnc(NCc4c(F)ccc5c4CCO5)n4cnnc34)cc(Cl)c2S1(=O)=O]

$^1$H NMR (400 MHz, $CDCl_3$) δ 9.58 (s, 1H), 8.81 (s, 1H), 8.12 (s, 1H), 8.03 (d, J=11.7 Hz, 2H), 6.91-6.75 (m, 2H), 6.71 (d, J=4.7 Hz, 1H), 4.93 (s, 2H), 4.85 (s, 1H), 2.93 (s, 1H), 2.59 (s, 1H), 2.25 (s, 3H), 1.04 (s, 1H).

The following compound can be synthesized with intermediate B3 and 5-bromo-7-fluorobenzothiophene as the raw materials using the method of example 66:

Example 70: 7-fluoro-5-(5-(((5-fluoro-2,3-dihydrobenzofuran-4-yl)methyl)amino)-[1,2,4]triazolo[4,3-c]pyrimidin-8-yl)-2,3-dimethylbenzo[b]thiophene 1,1-dioxide

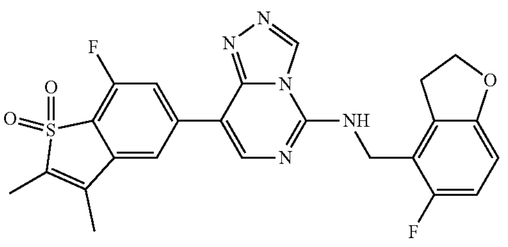

$^1$H NMR (400 MHz, DMSO-$d_6$) δ 9.57 (s, 1H), 9.00 (t, J=4.9 Hz, 1H), 7.72 (s, 1H), 7.45 (s, 1H), 7.28 (s, 1H), 7.03-6.90 (m, 1H), 6.72 (dd, J=8.6, 3.9 Hz, 1H), 4.74 (d, J=4.8 Hz, 2H), 4.55 (t, J=8.7 Hz, 2H), 3.33 (d, J=8.9 Hz, 2H), 2.17 (dd, J=7.2, 1.6 Hz, 6H) ppm; LCMS: m/z 495.7 $[M+H]^+$.

Example 71: 5-(5-((((1aR,6bR)-5-fluoro-1a,6b-dihydro-1H-cyclopropa[b]benzofuran-6-yl)methyl)amino)-[1,2,4]triazolo[4,3-c]pyrimidin-8-yl)-3-methylbenzo[b]thiophene 1,1-dioxide Step 1: 1-((4-bromophenyl)thio)propan-2-one (E7-2)

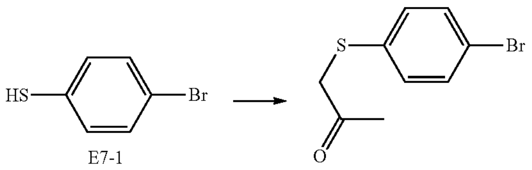

E7-1 E7-2

Into a 50 mL single-necked flask, compound E7-1 (800 mg, 4.23 mmol), bromoacetone (638 mg, 4.65 mmol), potassium carbonate (1.75 g, 12.7 mmol), and acetonitrile (15 mL) were added sequentially. The reaction mixture was warmed to 75° C., stirred for 3 hours and then cooled to room temperature. Water (30 mL) was added and the resulting mixture was extracted with ethyl acetate (50 mL*2). The organic phase was dried over anhydrous sodium sulfate and concentrated under reduced pressure. The crude was purified by silica gel column chromatography (ethyl acetate:methanol=5:1) to obtain the compound E7-2 (960 mg, 92% yield).

$^1$H NMR (400 MHz, DMSO-$d_6$) δ 7.55-7.45 (m, 2H), 7.32-7.20 (m, 2H), 4.05 (s, 2H), 2.21 (s, 3H). ppm; LCMS: m/z 244.8 $[M+H]^+$.

Step 2: 5-bromo-3-methylbenzo[b]thiophene (E7-3)

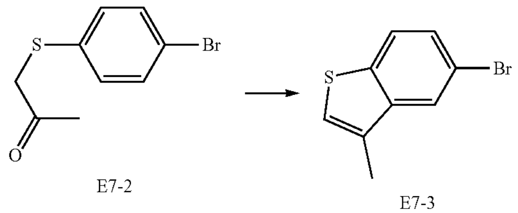

E7-2 E7-3

Into a 50 mL eggplant-shaped flask, E7-2 (260 mg, 1.06 mmol), chlorobenzene (20 mL), and polyphosphoric acid (5 mL) were added sequentially. The reaction system was warmed to 135° C. and stirred for 20 hours. The reaction was completed (monitored by TLC) and the reaction solution was poured into ice water (30 mL). Then the resulting mixture was extracted with dichloromethane (40 mL*3). The organic phases were combined and concentrated under reduced pressure. The crude was purified by silica gel column chromatography (eluents:ethyl acetate:methanol=5:1) to obtain the compound E7-3 (200 mg, 83% yield).

$^1$H NMR (400 MHz, $CDCl_3$) δ 7.77 (d, J=1.6 Hz, 1H), 7.61 (d, J=8.5 Hz, 1H), 7.36 (s, 1H), 7.02 (s, 1H), 2.33 (d, J=1.0 Hz, 3H) ppm.

Step 3: 5-bromo-3-methylbenzo[b]thiophene 1,1-dioxide (E7-4)

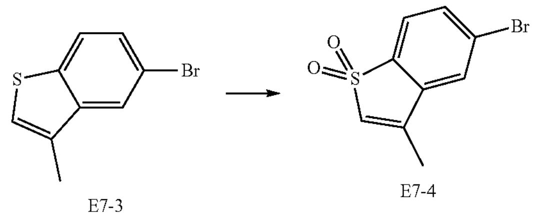

E7-3 E7-4

Into a 50 mL single-necked flask, compound E7-3 (200 mg, 0.88 mmol), dichloromethane (4 mL), formic acid (1 mL, 85% aqueous solution), and hydrogen peroxide (0.5 mL, 35% aqueous solution) were added sequentially. The reaction system was stirred at room temperature overnight. Upon completion of the reaction, water (10 mL) was added into the reaction solution. The resulting mixture was extracted with dichloromethane (20 mL*2). The organic phase was dried over anhydrous sodium sulfate and concentrated under reduced pressure to obtain the compound E7-4 (210 mg, 92% yield).

$^1$H NMR (400 MHz, DMSO-$d_6$) δ 7.89 (s, 1H), 7.87-7.76 (m, 2H), 7.21-7.16 (m, 1H), 2.37-2.19 (m, 3H) ppm; LCMS: m/z 260.7 $[M+H]^+$.

Step 4: The following compound can be synthesized with intermediates B1 and E7-4 as the raw materials using the method of example 55:

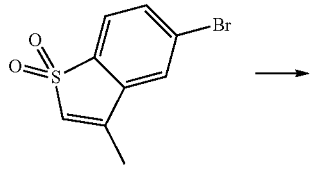

E7-4

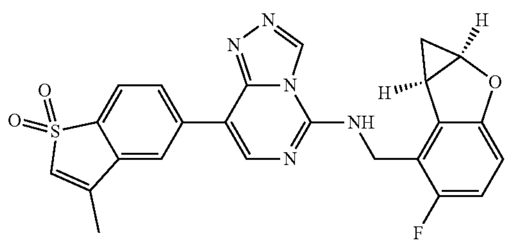

$^1$H NMR (400 MHz, DMSO-$d_6$) δ 9.43 (s, 1H), 8.96 (s, 1H), 8.41 (d, J=8.4 Hz, 1H), 8.23 (s, 2H), 7.80 (d, J=8.0 Hz, 1H), 7.03 (d, J=1.3 Hz, 1H), 6.86-6.80 (m, 1H), 6.66 (dd, J=8.7, 3.9 Hz, 1H), 4.85-4.74 (m, 3H), 2.85-2.79 (m, 1H), 2.23 (s, 3H), 0.89-0.83 (m, 1H), −0.00 (s, 1H) ppm; LCMS: m/z 475.7 $[M+H]^+$.

Example 72: 2-fluoro-5-(5-((((1aR,6bR)-5-fluoro-1a,6b-dihydro-1H-cyclopropa[b]benzofuran-6-yl)methyl)amino)-[1,2,4]triazolo[4,3-c]pyrimidin-8-yl)benzo[b]thiophene 1,1-dioxide Step 1: 5-bromo-2-fluorobenzo[b]thiophene (E8-2)

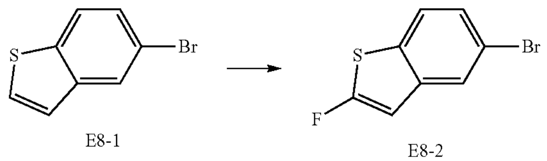 [SMILES: Brc1ccc2sccc2c1 ; Fc1cc2cc(Br)ccc2s1]

E8-1 E8-2

Into a 25 mL three-necked flask, E8-1 (500 mg, 2.35 mmol) and anhydrous tetrahydrofuran (10 mL) were added under nitrogen protection and the mixture was cooled to −70° C. Lithium diisopropylamide (2M in THF, 1.5 mL, 3 mmol) was slowly added. The reaction continued for another 40 minutes at −70° C. N-fluorodibenzenesulfonimide (2.2 g, 2.35 mmol) was slowly added and the resulting mixture was warmed to room temperature and reacted overnight. Upon completion of the reaction, the reaction was quenched by adding ice water (30 mL). The mixture was then extracted with ethyl acetate (20 mL×2). The organic phase was washed with saturated sodium chloride solution (5 mL), dried over anhydrous sodium sulfate and concentrated under reduced pressure. The residue was purified by Flash chromatography (eluents: 100% petroleum ether) to obtain a light yellow solid E8-2 (170 mg, 31% yield).

$^1$H NMR (400 MHz, $CDCl_3$) δ 7.69 (d, J=1.8 Hz, 1H), 7.44 (d, J=8.6 Hz, 1H), 7.33 (dd, J=8.6, 1.9 Hz, 1H), 6.58 (d, J=2.3 Hz, 1H).

The following compound can be synthesized with intermediates B1 and E8-2 as the raw materials using the method of example 55:

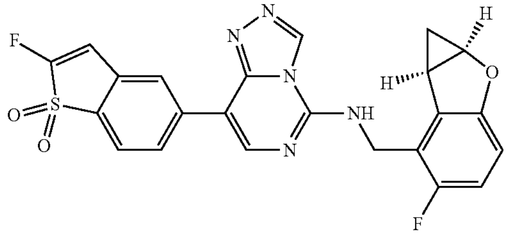 [SMILES: O=S1(=O)C(F)=Cc2cc(-c3cnc(NCc4c(F)ccc5c4[C@H]4C[C@H]4O5)n4cnnc34)ccc21]

$^1$H NMR (400 MHz, $CDCl_3$) δ 9.27 (s, 1H), 8.19 (s, 1H), 8.00 (dd, J=8.1, 1.4 Hz, 1H), 7.94 (s, 1H), 7.80 (s, 1H), 7.64 (d, J=8.0 Hz, 1H), 6.74 (d, J=10.0 Hz, 1H), 6.65 (d, J=4.0 Hz, 1H), 6.59 (d, J=2.0 Hz, 1H), 4.92-4.84 (m, 2H), 4.81-4.77 (m, 1H), 2.87 (dd, J=9.2, 4.7 Hz, 1H), 1.01-0.99 (m, 1H), 0.32-0.26 (m, 1H) ppm; LCMS: m/z 479.7 $[M+H]^+$.

Example 73: 2-fluoro-5-(5-((((1aR,6bR)-5-fluoro-1a,6b-dihydro-1H-cyclopropa[b]benzofuran-6-yl)methyl)amino)-[1,2,4]triazolo[4,3-c]pyrimidin-8-yl)-3-methylbenzo[b]thiophene 1,1-dioxide The following compound can be synthesized with intermediates B1 and E7-3 as the raw materials using the method of example 72:

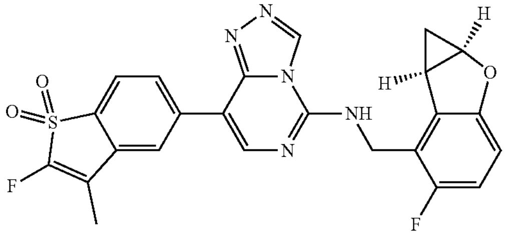 [SMILES: CC1=C(F)S(=O)(=O)c2ccc(-c3cnc(NCc4c(F)ccc5c4[C@H]4C[C@H]4O5)n4cnnc34)cc21]

$^1$H NMR (400 MHz, $CDCl_3$) δ 8.88 (s, 1H), 8.21 (s, 1H), 8.11-8.03 (m, 1H), 8.02 (s, 1H), 7.69 (d, J=8.0 Hz, 1H), 6.87-6.77 (m, 1H), 6.71 (dd, J=8.7, 4.0 Hz, 1H), 6.18 (s, 1H), 5.00 (ddd, J=51.2, 14.3, 5.5 Hz, 2H), 4.88 (td, J=5.4, 1.9 Hz, 1H), 3.04-2.86 (m, 1H), 2.21 (d, J=3.2 Hz, 3H), 1.16-1.06 (m, 1H), 0.41-0.30 (m, 1H) ppm; LCMS: m/z 493.7 $[M+H]^+$.

The following compound can be synthesized with intermediate B1 and 5-bromo-3-fluorobenzo[b]thiophene as the raw materials using the method of example 55:

Example 74: 3-fluoro-5-(5-((((1aR,6bR)-5-fluoro-1a,6b-dihydro-1H-cyclopropa[b]benzofuran-6-yl)methyl)amino)-[1,2,4]triazolo[4,3-c]pyrimidin-8-yl)benzo[b]thiophene 1,1-dioxide

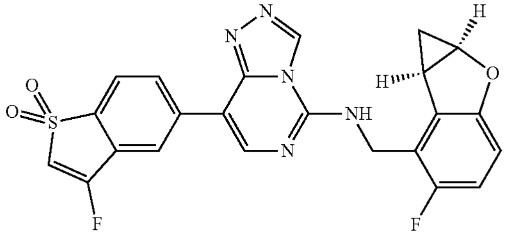

$^1$H NMR (400 MHz, DMSO-$d_6$) δ 9.51 (s, 1H), 9.13 (s, 1H), 8.56-8.38 (m, 2H), 8.26 (s, 1H), 7.97 (dd, J=8.2, 2.4 Hz, 1H), 7.43 (d, J=3.1 Hz, 1H), 6.91-6.77 (m, 1H), 6.66 (dd, J=8.7, 3.9 Hz, 1H), 4.85-4.80 (m, 1H), 4.78 (d, J=4.6 Hz, 2H), 2.94-2.79 (m, 1H), 0.92-0.80 (m, 1H), 0.00 (t, J=4.1 Hz, 1H) ppm; LCMS: m/z 479.6 $[M+H]^+$.

The following compound can be synthesized with intermediate B1 and 5-bromo-3-fluorobenzo[b]thiophene as the raw materials using the method of example 66:

Example 75: 3-fluoro-5-(5-((((1aR,6bR)-5-fluoro-1a,6b-dihydro-1H-cyclopropa[b]benzofuran-6-yl)methyl)amino)-[1,2,4]triazolo[4,3-c]pyrimidin-8-yl)-2-methylbenzo[b]thiophene 1,1-dioxide

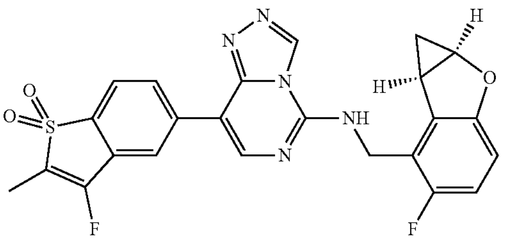 [SMILES: CC1=C(F)c2cc(-c3cnc(NCc4c(F)ccc5c4[C@H]4C[C@H]4O5)n4cnnc34)ccc2S1(=O)=O]

$^1$H NMR (400 MHz, $CDCl_3$) δ 9.09 (s, 1H), 8.26-8.19 (m, 1H), 8.16 (s, 1H), 8.02 (s, 1H), 7.79 (dd, J=8.0, 2.3 Hz, 1H), 6.91 (s, 1H), 6.76 (d, J=8.8 Hz, 1H), 6.69-6.57 (m, 1H), 4.97 (ddd, J=42.7, 14.3, 5.3 Hz, 2H), 4.84 (td, J=5.4, 1.8 Hz, 1H), 3.03-2.85 (m, 1H), 2.15 (s, 3H), 1.08 (dt, J=8.8, 6.2 Hz, 1H), 0.33 (ddd, J=6.1, 4.0, 1.9 Hz, 1H) ppm; LCMS: m/z 493.7 $[M+H]^+$.

The following compound can be synthesized with intermediate B1 and 5-bromo-7-chlorobenzothiophene as the raw materials using the method of example 66:

Example 76: 3-chloro-5-(5-((((1aR,6bR)-5-fluoro-1a,6b-dihydro-1H-cyclopropa[b]benzofuran-6-yl)methyl)amino)-[1,2,4]triazolo[4,3-c]pyrimidin-8-yl)-2-methylbenzo[b]thiophene 1,1-dioxide

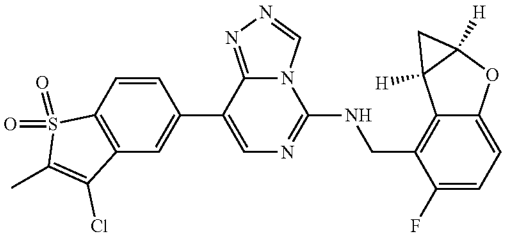 [SMILES: CC1=C(Cl)c2cc(-c3cnc(NCc4c(F)ccc5c4[C@H]4C[C@H]4O5)n4cnnc34)ccc2S1(=O)=O]

$^1$H NMR (400 MHz, $CDCl_3$) δ 8.96 (s, 1H), 8.34-8.19 (m, 2H), 8.05 (s, 1H), 7.82 (d, J=7.9 Hz, 1H), 6.89-6.75 (m, 1H), 6.70 (dd, J=8.7, 4.0 Hz, 1H), 6.45 (s, 1H), 5.12-4.91 (m, 2H), 4.91-4.82 (m, 1H), 3.02-2.89 (m, 1H), 2.26 (s, 3H), 1.15-1.08 (m, 1H), 0.45-0.28 (m, 1H) ppm; LCMS: m/z 509.6 $[M+H]^+$.

Example 77: Methyl 8-(5-(((5-fluoro-2,3-dihydrobenzofuran-4-yl)methyl)amino)-[1,2,4]triazolo[4,3-c]pyrimidin-8-yl)imidazo[1,2-a]pyridine-5-carboxylate Step 1: intermediate (2-amino-6-(methyloxycarbonyl)pyridin-3-yl)boronic acid E9-2

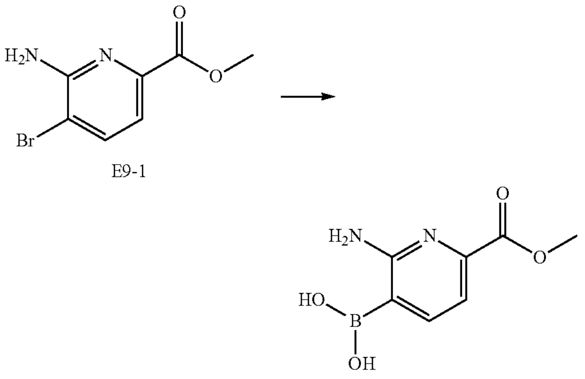

E9-1

E9-2

Into a 25 mL single-necked flask, compound E9-1 (200 mg, 0.87 mmol), bis(pinacolato)diboron (439 mg, 1.73 mmol), potassium acetate (212 mg, 2.16 mmol), [1,1'-bis(diphenylphosphino)ferrocene]dichloropalladium(II) (63 mg, 0.09 mmol) and 1,4-dioxane (10 mL) were added sequentially. The reaction system was warmed to 90° C. and reacted under nitrogen atmosphere for 16 hours. The reaction was completed (monitored by LCMS) and the reaction solution was directly used in the next step.

LCMS: m/z 196.9 [M+H]$^+$.

Step 2: intermediate methyl 6-amino-5-(5-((((5-fluoro-2,3-dihydrobenzofuran-4-yl)methyl)amino)amino]-[1,2,4]triazole[4,3-c]pyrimidine-8-pyridylpicolinic acid E9-3

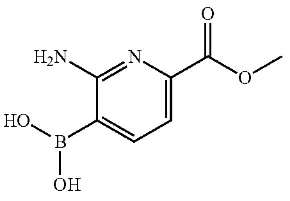

E9-2

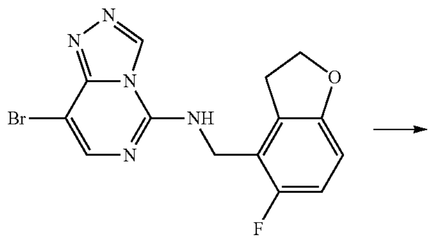

B3

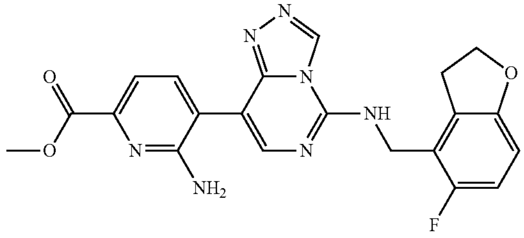

E9-3

To the reaction solution obtained in the previous step, intermediate B3 (315 mg, 0.87 mmol), potassium carbonate (359 mg, 2.60 mmol), [1,1'-bis(diphenylphosphino)ferrocene]dichloropalladium(II) (63 mg, 0.09 mmol) and water (3 mL) were added. The reaction system was warmed to 80° C. and reacted under nitrogen atmosphere for 5 h. The reaction was completed (as detected) and the reaction system was cooled to room temperature and diluted and dissolved in ethyl acetate (30 mL). The organic phase was washed with water (5 mL*2), then dried over anhydrous sodium sulfate and concentrated under reduced pressure. The crude was purified by silica gel column chromatography (mobile phase:ethyl acetate:methanol=10:1) to obtain the compound E9-3 (260 mg, 69% yield).

LCMS: m/z 436.1 [M+H]$^+$.

Step 3: Methyl 8-(5-(((5-fluoro-2,3-dihydrobenzofuran-4-yl)methyl)amino)-[1,2,4]triazolo[4,3-c]pyrimidin-8-yl) imidazo[1,2-a]pyridine-5-carboxylate can be synthesized with intermediate E9-2 and 2-chloroacetaldehyde as the raw materials using the method in step 3 of example 21:

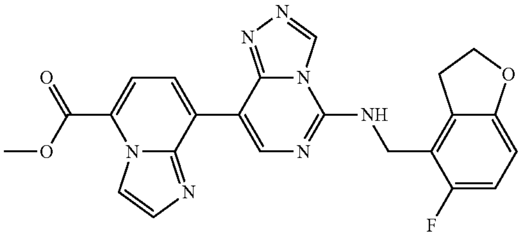 [SMILES: COC(=O)c1ccc(-c2cnc(NCc3c(F)ccc4c3CCO4)n3cnnc23)c2nccn12]

$^1$H NMR (400 MHz, DMSO-$d_6$) δ 9.79 (s, 1H), 9.55 (s, 1H), 9.05 (s, 1H), 8.93 (d, J=7.9 Hz, 1H), 8.90 (d, J=1.3 Hz, 1H), 8.01 (d, J=7.9 Hz, 1H), 7.86 (d, J=1.3 Hz, 1H), 6.98-6.94 (m, 1H), 6.72 (dd, J=8.6, 3.8 Hz, 1H), 4.80 (s, 2H), 4.56 (t, J=8.6 Hz, 2H), 3.99 (s, 3H), 3.33 (s, 2H) ppm; LCMS: m/z 459.9 [M+H]$^+$.

Example 78: (8-(5-(((5-fluoro-2,3-dihydrobenzofuran-4-yl)methyl)amino)-[1,2,4]triazolo[4,3-c]pyrimidin-8-yl)imidazo[1,2-a]pyridin-5-yl)methanol Step 1: intermediate (6-amino-5-(5-((((5-fluoro-2,3-dihydrobenzofuran-4-yl)methyl]amino)amino]-[1,2,4]triazolo[4,3-c]pyrimidin-8-yl)pyridin-2-yl)methanol E9-4

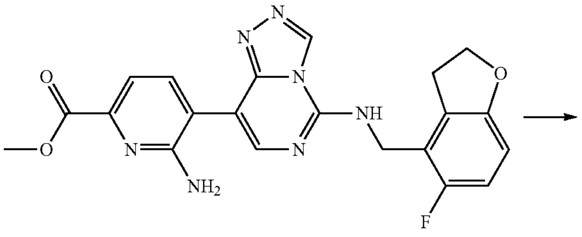

E9-3

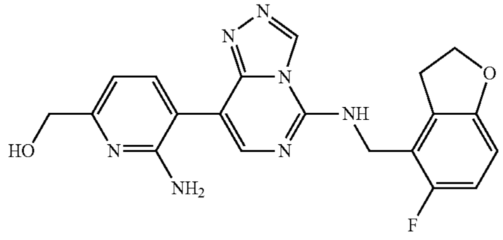

E9-4

E9-3 (50 mg, 0.11 mmol) was dissolved in tetrahydrofuran (10 mL) and lithium aluminium hydride (22 mg, 0.57 mmol) was added at 0° C. The reaction solution was stirred at room temperature for 16 h. The reaction was completed and quenched by adding water (10 mL). The resulting mixture was extracted with ethyl acetate (30 mL×2) and the organic phase was dried and concentrated to obtain the target compound E9-4 (35 mg, 76% yield).

LCMS: m/z 408.1 [M+H]$^+$.

Step 2: (8-(5-(((5-fluoro-2,3-dihydrobenzofuran-4-yl) methyl)amino)-[1,2,4]triazolo[4,3-c]pyrimidin-8-yl)imidazo[1,2-a]pyridin-5-yl)methanol can be synthesized with intermediate E9-4 and 2-chloroacetaldehyde as the raw materials using the method in step 3 of example 21:

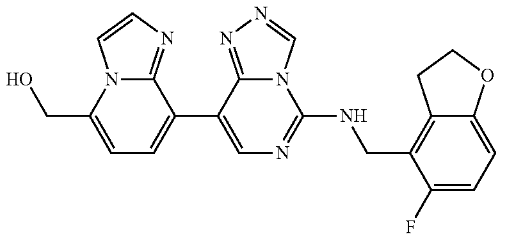 [SMILES: OCc1ccc(-c2cnc(NCc3c(F)ccc4c3CCO4)n3cnnc23)c2nccn12]

$^1$H NMR (400 MHz, DMSO-$d_6$) δ 9.62 (d, J=1.1 Hz, 2H), 8.98 (s, 1H), 8.79 (d, J=7.4 Hz, 1H), 7.99 (d, J=1.3 Hz, 1H), 7.72 (d, J=1.3 Hz, 1H), 7.10 (d, J=7.5 Hz, 1H), 7.01-6.93 (m, 1H), 6.71 (dd, J=8.7, 3.9 Hz, 1H), 5.78 (t, J=5.7 Hz, 1H), 4.82 (d, J=5.7 Hz, 2H), 4.77 (s, 2H), 4.55 (t, J=8.7 Hz, 2H), 3.28 (s, 2H) ppm; LCMS: m/z 432.0 $[M+H]^+$.

Intermediate E10-1 can be synthesized with 3-bromo-6-methylpyridin-2-amine and intermediate B3 as the raw materials using the methods in steps 1 and 2 of example 21:

E10-1

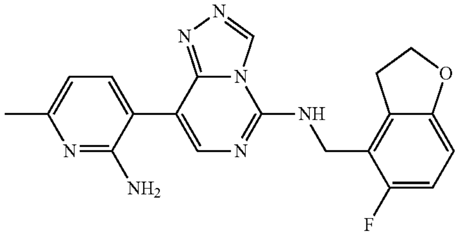

$^1$H NMR (400 MHz, MeOD) δ 9.28 (s, 1H), 7.73 (s, 1H), 7.50 (d, J=7.5 Hz, 1H), 7.39 (d, J=2.5 Hz, 1H), 6.85 (t, J=9.3 Hz, 1H), 6.71-6.62 (m, 2H), 4.77 (s, 2H), 4.63 (t, J=8.7 Hz, 2H), 4.00 (s, 2H), 3.38 (d, J=8.2 Hz, 2H), 2.43 (s, 3H) ppm; LCMS: m/z 392.1 $[M+H]^+$.

The following compound can be synthesized with intermediate E10-1 and 2-chloro-3-methylbutanal as the raw materials using the method in step 3 of example 21:

Example 79: N-((5-fluoro-2,3-dihydrobenzofuran-4-yl)methyl)-8-(3-isopropyl-5-methylimidazo[1,2-a]pyridin-8-yl)-[1,2,4]triazolo[4,3-c]pyrimidin-5-amine

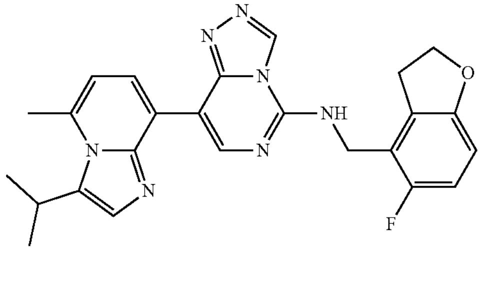 [SMILES: Cc1ccc(-c2cnc(NCc3c(F)ccc4c3CCO4)n3cnnc23)c2ncc(C(C)C)n12]

$^1$H NMR (400 MHz, DMSO-$d_6$) δ 9.85 (s, 1H), 9.56 (s, 1H), 9.00 (s, 1H), 8.95 (dd, J=11.1, 2.3 Hz, 1H), 8.78-8.74 (m, 1H), 8.05 (s, 1H), 7.72 (s, 1H), 7.00-6.94 (m, 1H), 6.71 (dd, J=8.6, 3.8 Hz, 1H), 4.79 (s, 2H), 4.55 (t, J=8.7 Hz, 2H), 3.35 (s, 2H) ppm; LCMS: m/z 420.0 $[M+H]^+$.

Example 80: Methyl 2-(8-(5-(((5-fluoro-2,3-dihydrobenzofuran-4-yl)methyl)amino)-[1,2,4]triazolo[4,3-c]pyrimidin-8-yl)-5-methylimidazo[1,2-a]pyridin-3-yl)acetate Step 1: methyl 3-chloro-4-carbonylbutyrate E11-2

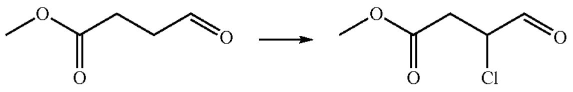

E11-1 E11-2

Into a dry 100 mL single-necked flask, E11-1 (290 mg, 2.5 mmol) and chloroform (9 mL) were added sequentially. In an ice bath, L-proline (57.57 mL, 0.5 mmol) and N-chlorosuccinimide (400 mg, 3 mmol) were added with stirring. The reaction temperature was raised to room temperature and the reaction solution was stirred and reacted at room temperature for 3 hours to obtain a chloroform solution of the crude E11-2. The reaction solution was directly used in the next step without any treatment.

Step 2: Compound E11-3 as below can be synthesized with E11-2 and intermediate E10-1 as the raw materials using the method of example 21:

E11-3

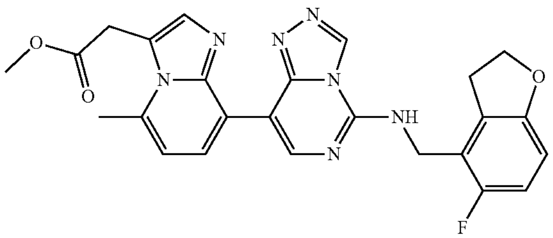

$^1$H NMR (400 MHz, DMSO-$d_6$) δ 9.51 (s, 1H), 9.40 (s, 1H), 8.79 (t, J=4.9 Hz, 1H), 8.52 (d, J=7.4 Hz, 1H), 7.52 (s, 1H), 7.01-6.91 (m, 1H), 6.84 (d, J=7.8 Hz, 1H), 6.71 (dd, J=8.7, 3.9 Hz, 1H), 4.77 (d, J=4.6 Hz, 2H), 4.55 (t, J=8.7 Hz, 2H), 4.42 (s, 2H), 3.69 (s, 3H), 3.31 (s, 2H), 2.78 (s, 3H) ppm; LCMS: m/z 488.0 $[M+H]^+$.

Example 81: 2-(8-(5-(((5-Fluoro-2,3-dihydrobenzofuran-4-yl)methyl)amino)-[1,2,4]triazolo[4,3-c]pyrimidin-8-yl)-5-methylimidazo[1,2-a]pyridin-3-yl)ethan-1-ol E11-4

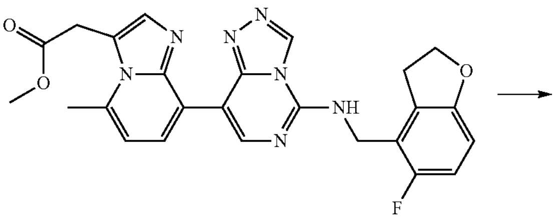

E11-3

-continued

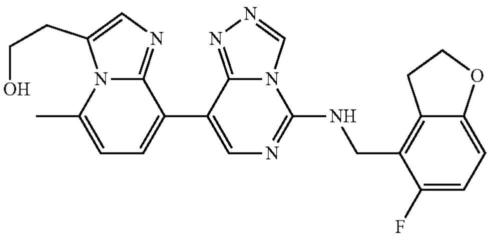

E11-4

Into a dry 25 mL single-necked flask, E11-3 (30 mg, 0.06 mmol) and tetrahydrofuran (5 mL) were added sequentially. In an ice bath, lithium aluminium hydride (11.39 mg, 0.3 mmol) was added with stirring. The reaction temperature was raised to room temperature and the reaction solution was stirred and reacted at room temperature for 1 hour. Upon completion of the reaction, the reaction solution was cooled to 0° C. and the reaction was quenched with water. The resulting mixture was extracted with dichloromethane (20 mL×3). The organic phases were combined, then dried over anhydrous sodium sulfate and filtered. The filtrate was concentrated under reduced pressure and finally purified by preparative high-performance liquid chromatography to obtain the compound E11-4 (15 mg, 54.4%).

$^1$H NMR (400 MHz, DMSO-d$_6$) δ 9.50 (s, 1H), 9.42 (s, 1H), 8.76 (t, J=5.0 Hz, 1H), 8.47 (d, J=7.4 Hz, 1H), 7.43 (s, 1H), 6.95 (d, J=9.7 Hz, 1H), 6.79 (d, J=7.6 Hz, 1H), 6.71 (dd, J=8.6, 3.9 Hz, 1H), 4.88 (t, J=5.2 Hz, 1H), 4.76 (d, J=4.9 Hz, 2H), 4.55 (t, J=8.7 Hz, 2H), 3.79-3.75 (m, 2H), 3.41 (d, J=6.8 Hz, 2H), 3.31 (s, 2H), 2.91 (s, 3H) ppm; LCMS: m/z 460.0 [M+H]$^+$.

Example 82: 2-(8-(5-(((5-fluoro-2,3-dihydrobenzofuran-4-yl)methyl)amino)-[1,2,4]triazolo[4,3-c]pyrimidin-8-yl)-5-methylimidazo[1,2-a]pyridin-3-yl)ethyl acetate

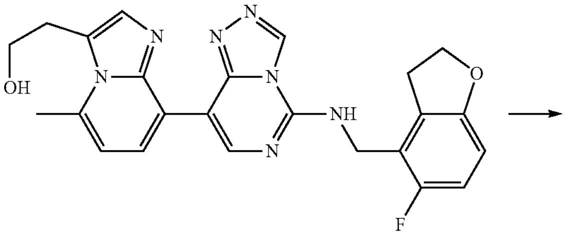

E11-4

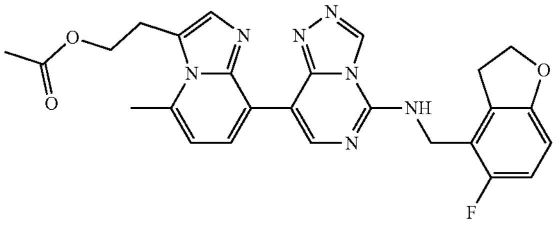

E11-4 (20 mg) was dissolved in pyridine (1 mL). 4-dimethylaminopyridine (2 mg) and acetic anhydride (10 mg) were added and the mixture was stirred at room temperature overnight. Dichloromethane (10 mL) and water (10 mL) were added into the reaction solution and the resulting mixture was extracted with dichloromethane (10 mL*3). The organic layer was dried over sodium sulfate and then spin-dried. The yellow solid obtained was washed with ethyl acetate (2 mL) under stirring to obtain a white solid, 2-(8-(5-(((5-fluoro-2,3-dihydrobenzofuran-4-yl)methyl)amino)-[1,2,4]triazolo[4,3-c]pyrimidin-8-yl)-5-methylimidazo[1,2-a]pyridin-3-yl)ethyl acetate (13 mg, 59.5% yield).

$^1$H NMR (400 MHz, DMSO-d$_6$) δ 9.51 (s, 1H), 9.41 (s, 1H), 8.78 (s, 1H), 8.50 (d, J=7.3 Hz, 1H), 7.44 (s, 1H), 6.96 (t, J=9.4 Hz, 1H), 6.82 (d, J=7.5 Hz, 1H), 6.71 (dd, J=8.6, 3.8 Hz, 1H), 4.76 (d, J=3.6 Hz, 2H), 4.55 (t, J=8.7 Hz, 2H), 4.39 (t, J=6.7 Hz, 2H), 3.61 (t, J=6.7 Hz, 2H), 3.32-3.28 (m, 2H), 2.91 (s, 3H), 2.03 (s, 3H) ppm; LCMS: m/z 502.0 [M+H]$^+$.

Example 83: 2-(8-(5-(((5-fluoro-2,3-dihydrobenzofuran-4-yl)methyl)amino)-[1,2,4]triazolo[4,3-c]pyrimidin-8-yl)-5-methylimidazo[1,2-a]pyridin-3-yl)acetamide

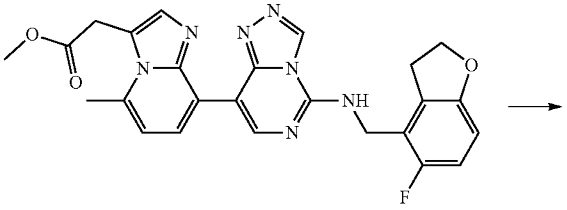

E11-3

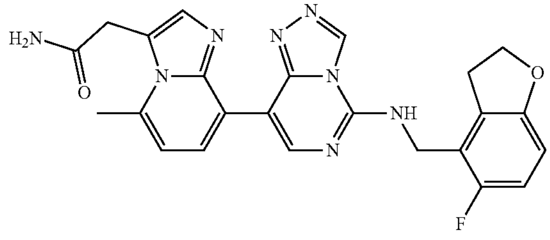

Into a 20 mL sealed tube, E11-3 (40 mg, 0.082 mmol) and a saturated solution of ammonia methanol (8 mL) were added. The mixture was stirred at 85° C. for 16 hours. Upon completion of the reaction, the reaction solution was cooled down and a white solid was precipitated out. The resulting reaction solution was filtered and washed with ethyl acetate to obtain the target compound 2-(8-(5-((((5-fluoro-2,3-dihydrobenzofuran-4-yl)methyl)amino)amino]-[1,2,4]triazolo[4,3-c]pyrimidin-8-yl)-5-methylimidazo[1,2-a]pyridin-3-yl)acetamide (26 mg, 67% yield).

$^1$H NMR (400 MHz, DMSO-d$_6$) δ 9.51 (d, J=1.4 Hz, 1H), 9.41 (d, J=13.3 Hz, 1H), 8.50 (d, J=7.4 Hz, 1H), 7.52 (s, 1H), 7.46 (s, 1H), 7.10 (s, 2H), 7.01-6.91 (m, 1H), 6.80 (d, J=7.3 Hz, 1H), 6.71 (dd, J=8.6, 3.9 Hz, 1H), 4.77 (d, J=3.9 Hz, 2H), 4.55 (t, J=8.7 Hz, 2H), 4.07 (s, 2H), 3.32 (d, J=8.8 Hz, 2H), 2.85 (s, 3H). ppm; LCMS: m/z 473.1 [M+H]$^+$.

Example 84: 2-(8-(5-(((5-fluoro-2,3-dihydrobenzofuran-4-yl)methyl)amino)-[1,2,4]triazolo[4,3-c]pyrimidin-8-yl)-5-methylimidazo[1,2-a]pyridin-3-yl)-N,N-dimethylacetamide Step 1: 2-(8-(5-(((5-fluoro-2,3-dihydrobenzofuran-4-yl)methyl)amino)-[1,2,4]triazolo[4,3-c]pyrimidin-8-yl)-5-methylimidazo[1,2-a]pyridin-3-yl)acetic acid E11-5

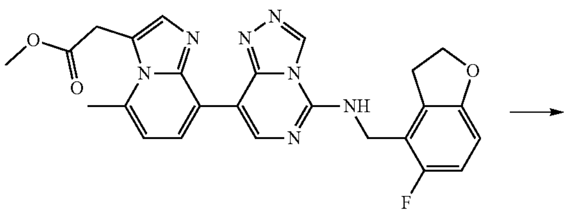

E11-3

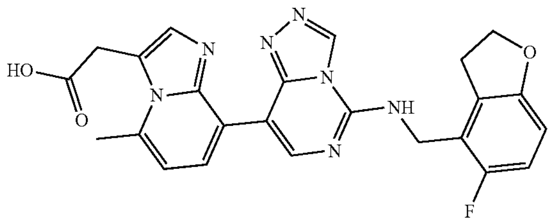

E11-5

Into a 25 mL single-necked flask, E11-3 (30 mg, 0.06 mmol) and methanol (3 mL) were added sequentially. A solution of sodium hydroxide (24 mg, 0.6 mmol) in water (1 mL) was added. The mixture was stirred and reacted at room temperature for 1 hour. Upon completion of the reaction, the PH was adjusted with 1M HCl to 7 and a white solid was precipitated out. The white solid was washed with water and methanol and then dried under vacuum to obtain a crude E11-5 (12 mg, 42.2%).

$^1$H NMR (400 MHz, DMSO-$d_6$) δ 9.51 (s, 1H), 9.43 (s, 1H), 8.79 (s, 1H), 8.49 (d, J=7.4 Hz, 1H), 7.42 (s, 1H), 7.01-6.92 (m, 1H), 6.78 (d, J=7.5 Hz, 1H), 6.71 (dd, J=8.6, 3.9 Hz, 1H), 4.76 (s, 2H), 4.55 (t, J=8.7 Hz, 2H), 4.10 (s, 2H), 3.27-3.14 (m, 2H), 2.86 (s, 3H) ppm; LCMS: m/z 474.1 $[M+H]^+$.

Step 2: 2-(8-(5-(((5-fluoro-2,3-dihydrobenzofuran-4-yl)methyl)amino)-[1,2,4]triazolo[4,3-c]pyrimidin-8-yl)-5-methylimidazo[1,2-a]pyridin-3-yl)-N,N-dimethylacetamide

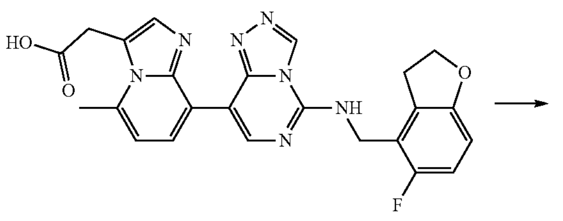

E11-5

-continued

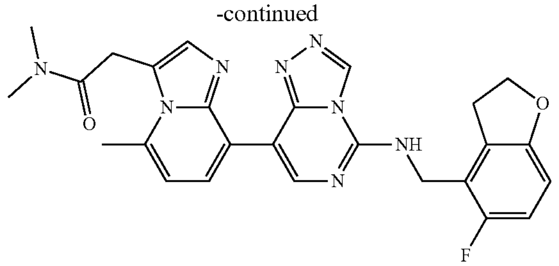

Into a dry 25 mL single-necked flask, E11-5 (20 mg, 0.04 mmol) and dimethylformamide (2 mL) were added sequentially. Then dimethylamine hydrochloride (2.16 mg, 0.05 mmol), 2-(7-azabenzotriazol)-N,N,N',N'-tetramethyluoniumhexafluorophosphate (20 mg, 0.05 mmol) and triethylamine (12.14 mg, 0.12 mmol) were added sequentially. The mixture was stirred and reacted at room temperature for 1 hour. Upon completion of the reaction, water (10 mL) was slowly added dropwise and a white solid was precipitated out. The white solid was washed with water and methanol to obtain a pure product 2-(8-(5-(((5-fluoro-2,3-dihydrobenzofuran-4-yl)methyl)amino)-[1,2,4]triazolo[4,3-c]pyrimidin-8-yl)-5-methylimidazo[1,2-a]pyridin-3-yl)-N,N-dimethylacetamide (5 mg, 25.7% yield).

$^1$H NMR (400 MHz, DMSO-$d_6$) δ 9.48 (s, 1H), 9.44 (s, 1H), 8.77 (s, 1H), 8.50 (d, J=7.4 Hz, 1H), 7.38 (s, 1H), 6.96 (t, J=9.4 Hz, 1H), 6.77 (d, J=7.6 Hz, 1H), 6.71 (dd, J=8.6, 3.7 Hz, 1H), 4.76 (s, 2H), 4.55 (t, J=8.7 Hz, 2H), 4.36 (s, 2H), 3.31-3.25 (m, 2H), 3.13 (s, 3H), 2.88 (d, J=9.9 Hz, 3H), 2.75 (s, 3H) ppm; LCMS: m/z 501.1 $[M+H]^+$.

The following compound can be synthesized with 8-bromo-5-methyl[1,2,4]-triazolo[1,5-a]pyridine and intermediate B1 as the raw materials using the method of example 6:

Example 85: N-(((1aR,6bR)-5-fluoro-1a,6b-dihydro-1H-cyclopropa[b]benzofuran-6-yl)methyl)-8-(5-methyl-[1,2,4]triazolo[1,5-a]pyridin-8-yl)-[1,2,4]triazolo[4,3-c]pyrimidin-5-amine

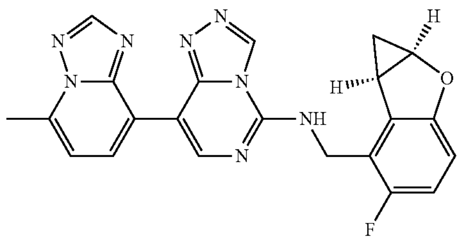

$^1$H NMR (400 MHz, DMSO-$d_6$) δ 9.57 (s, 1H), 9.45 (s, 1H), 9.11 (d, J=7.7 Hz, 1H), 9.04 (s, 1H), 8.63 (s, 1H), 7.29 (dd, J=7.7, 1.1 Hz, 1H), 6.96 (dd, J=10.3, 8.7 Hz, 1H), 6.78 (dd, J=8.7, 3.9 Hz, 1H), 5.00-4.85 (m, 3H), 2.97 (dt, J=9.1, 4.5 Hz, 1H), 2.79 (s, 3H), 1.02 (dt, J=9.0, 5.9 Hz, 1H), 0.14 (ddd, J=6.1, 4.0, 1.9 Hz, 1H) ppm; LCMS: m/z 429.0 $[M+H]^+$.

The following compound can be synthesized with 8-bromo-5-methyl[1,2,4]-triazolo[1,5-a]pyridine and intermediate B3 as the raw materials using the method of example 6:

Example 86: N-((5-fluoro-2,3-dihydrobenzofuran-4-yl)methyl)-8-(5-methyl-[1,2,4]triazolo[1,5-a]pyridin-8-yl)-[1,2,4]triazolo[4,3-c]pyrimidin-5-amine

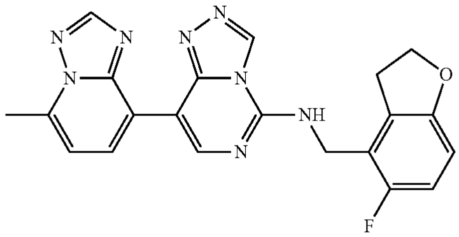 [SMILES: Cc1ccc(-c2cnc(NCc3c(F)ccc4c3CCO4)n3cnnc23)c2ncnn12]

$^1H$ NMR (400 MHz, DMSO-$d_6$) δ 9.54 (s, 1H), 9.45 (s, 1H), 9.11 (d, J=7.7 Hz, 1H), 8.90 (t, J=5.0 Hz, 1H), 8.64 (d, J=9.7 Hz, 1H), 7.28 (d, J=7.8 Hz, 1H), 7.02-6.92 (m, 1H), 6.72 (dd, J=8.6, 3.9 Hz, 1H), 4.78 (d, J=4.9 Hz, 2H), 4.56 (t, J=8.7 Hz, 2H), 3.35 (s, 2H), 2.79 (s, 3H) ppm; LCMS: m/z 417.0 $[M+H]^+$.

The following compound can be synthesized with 8-bromo-5-methylimidazo[1,2-a]pyridine and intermediate B1 as the raw materials using the method of example 6:

Example 87: N-(((1aR,6bR)-5-fluoro-1a,6b-dihydro-1H-cyclopropa[b]benzofuran-6-yl)methyl)-8-(5-methylimidazo[1,2-a]pyridin-8-yl)-[1,2,4]triazolo[4,3-c]pyrimidin-5-amine

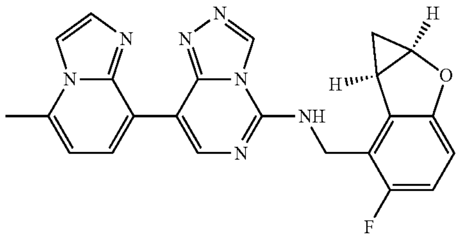

$^1H$ NMR (400 MHz, $CDCl_3$) δ 8.99 (d, J=7.0 Hz, 1H), 8.87 (d, J=6.1 Hz, 1H), 8.58 (d, J=7.5 Hz, 1H), 8.31 (d, J=3.7 Hz, 1H), 7.52 (t, J=5.2 Hz, 1H), 7.01 (d, J=7.5 Hz, 1H), 6.73 (dd, J=10.0, 8.8 Hz, 1H), 6.64 (dd, J=8.7, 4.0 Hz, 1H), 4.95 (dd, J=14.2, 5.5 Hz, 1H), 4.89-4.74 (m, 2H), 3.08-2.96 (m, 1H), 2.83 (s, 3H), 1.08-1.00 (m, 1H), 0.28 (ddd, J=6.2, 4.0, 1.9 Hz, 1H) ppm; LCMS: m/z 428.1 $[M+H]^+$.

The following compound can be synthesized with 2-chloroacetaldehyde and intermediate E10-1 as the raw materials using the method in step 3 of example 21:

Example 88: N-((5-fluoro-2,3-dihydrobenzofuran-4-yl)methyl)-8-(5-methylimidazo[1,2-a]pyridin-8-yl)-[1,2,4]triazolo[4,3-c]pyrimidin-5-amine

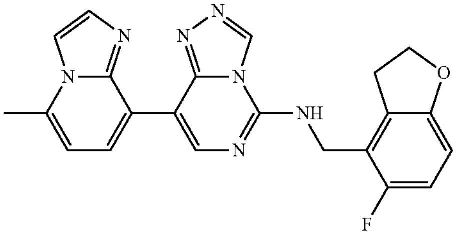 [SMILES: Cc1ccc(-c2cnc(NCc3c(F)ccc4c3CCO4)n3cnnc23)c2nccn12]

$^1H$ NMR (400 MHz, DMSO-$d_6$) δ 9.61 (s, 1H), 9.52 (s, 1H), 8.81 (s, 1H), 8.75 (d, J=7.4 Hz, 1H), 7.93 (s, 1H), 7.73 (s, 1H), 6.97 (dd, J=13.0, 5.9 Hz, 2H), 6.71 (dd, J=8.7, 3.9 Hz, 1H), 4.77 (s, 2H), 4.55 (t, J=8.7 Hz, 2H), 2.67 (s, 3H), 2.33 (s, 2H) ppm; LCMS: m/z 416.0 $[M+H]^+$.

The following compound can be synthesized with 3-acetamidopropanal and intermediate E10-1 as the raw materials using the method in step 3 of example 21:

Example 89: N-((8-(5-(((5-fluoro-2,3-dihydrobenzofuran-4-yl)methyl)amino)-[1,2,4]triazolo[4,3-c]pyrimidin-8-yl)-5-methylimidazo[1,2-a]pyridin-3-yl)methyl)acetamide

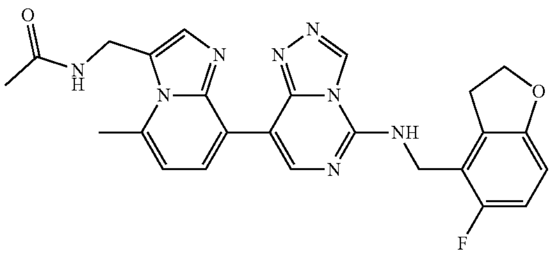 [SMILES: CC(=O)NCc1cnc2c(-c3cnc(NCc4c(F)ccc5c4CCO5)n4cnnc34)ccc(C)n12]

$^1H$ NMR (400 MHz, $CDCl_3$) δ 9.51 (s, 1H), 9.40 (s, 1H), 8.78 (s, 1H), 8.55 (d, J=7.4 Hz, 1H), 8.38 (s, 1H), 7.57 (s, 1H), 7.00-6.94 (m, 1H), 6.87 (d, J=7.7 Hz, 1H), 6.71 (dd, J=8.6, 3.9 Hz, 1H), 4.86-4.71 (m, 4H), 4.55 (t, J=8.7 Hz, 2H), 3.31 (s, 2H), 2.86 (s, 3H), 1.86 (s, 3H) ppm; LCMS: m/z 487.0 $[M+H]^+$.

Compound methyl 8-(5-(((5-fluoro-2,3-dihydrobenzofuran-4-yl)methyl)amino)-[1,2,4]triazolo[4,3-c]pyrimidin-8-yl)-5-methylimidazo[1,2-a]pyridine-2-carboxylate E12-1 can be synthesized with 3-acetamidopropanal and intermediate E10-1 as the raw materials using the method in step 3 of example 21:

E12-1

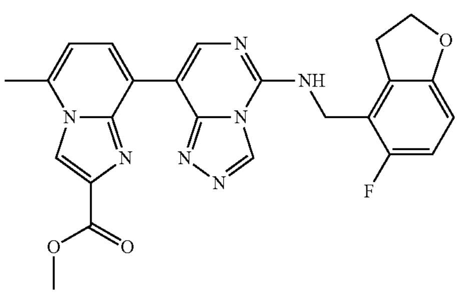

$^1$H NMR (400 MHz, MeOD) δ 9.74 (s, 1H), 8.51 (s, 1H), 8.26 (s, 1H), 8.05 (d, J=7.4 Hz, 1H), 7.35 (d, J=7.2 Hz, 1H), 6.83 (t, J=9.4 Hz, 1H), 6.66 (dd, J=8.6, 3.8 Hz, 1H), 4.65 (d, J=8.7 Hz, 2H), 4.16 (s, 3H), 3.46 (t, J=8.7 Hz, 2H), 2.89 (s, 3H) ppm; LCMS: m/z 428.1 [M+H]$^+$.

The following compound can be obtained by reducing the raw material E12-1 with lithium aluminium hydride using the method of example 81:

Example 90: (8-(5-(((5-fluoro-2,3-dihydrobenzofuran-4-yl)methyl)amino)-[1,2,4]triazolo[4,3-c]pyrimidin-8-yl)-5-methylimidazo[1,2-a]pyridin-2-yl)methanol

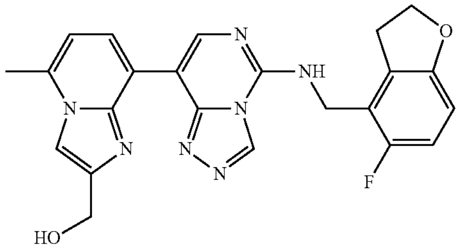 [SMILES: Cc1ccc(-c2cnc(NCc3c(F)ccc4c3CCO4)n3cnnc23)c2nc(CO)cn12]

$^1$H NMR (400 MHz, DMSO-$d_6$) δ 9.60 (s, 1H), 9.53 (s, 1H), 8.81 (s, 1H), 8.73 (d, J=7.4 Hz, 1H), 7.75 (s, 1H), 6.96 (dd, J=20.7, 8.6 Hz, 2H), 6.72 (dd, J=8.7, 3.9 Hz, 1H), 5.27 (t, J=5.6 Hz, 1H), 4.78 (s, 2H), 4.69 (d, J=5.7 Hz, 2H), 4.55 (t, J=8.7 Hz, 2H), 3.29 (s, 2H), 2.64 (s, 3H) ppm; LCMS: m/z 446.0 [M+H]$^+$.

Example 91: 8-(5-(((5-fluoro-2,3-dihydrobenzofuran-4-yl)methyl)amino)-[1,2,4]triazolo[4,3-c]pyrimidin-8-yl)-N,N,5-trimethylimidazo[1,2-a]pyridine-2-carboxamide

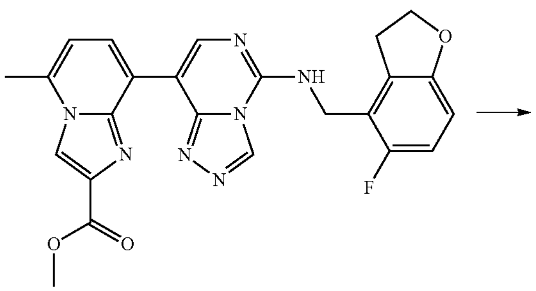

E12-1

-continued

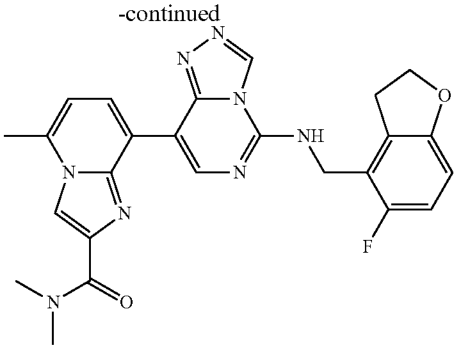

Into a dry 25 mL three-necked flask, dry tetrahydrofuran (2 mL) and a solution of dimethylamine in tetrahydrofuran (0.1 mL, 0.2 mmol) were added and in an ice-water bath, a solution of trimethylaluminum in toluene (0.07 mL, 0.14 mmol) was added. The mixture was stirred in an ice-water bath for 10 minutes and then E12-1 (47 mg, 0.1 mmol, dissolved in 2 mL of tetrahydrofuran) was added. The reaction solution was refluxed for 2 hours and cooled to room temperature. Ice water (5 mL) was slowly added and the resulting mixture was extracted with dichloromethane (10 mL*3). The organic layer was washed with brine (10 mL), then dried over anhydrous sodium sulfate and spin-dried to obtain a yellow solid. The yellow solid was washed with ethyl acetate to obtain a white pure product, 8-(5-(((5-fluoro-2,3-dihydrobenzofuran-4-yl)methyl)amino)-[1,2,4]triazolo[4,3-c]pyrimidin-8-yl)-N,N,5-trimethylimidazo[1,2-a]pyridine-2-carboxamide (33 mg, 0.068 mmol, 68% yield).

$^1$H NMR (400 MHz, $CDCl_3$) δ 9.22 (s, 1H), 9.07 (s, 1H), 8.27 (s, 1H), 7.86 (d, J=7.2 Hz, 1H), 7.57 (s, 2H), 6.89 (d, J=7.3 Hz, 1H), 6.77-6.66 (m, 1H), 6.62 (dd, J=8.7, 3.9 Hz, 1H), 4.83 (d, J=14.2 Hz, 1H), 4.74 (dd, J=11.1, 5.7 Hz, 2H), 3.11-3.02 (m, 1H), 2.69 (s, 3H), 1.00 (dt, J=8.9, 6.1 Hz, 1H), 0.24-0.15 (m, 1H) ppm; LCMS: m/z 487.1 [M+H]$^+$.

The following compound can be synthesized with ethyl 2-chloro-3-oxopropanoate and intermediate E10-1 as the raw materials using the method in step 3 of example 21:

Example 92: Ethyl 8-(5-(((5-fluoro-2,3-dihydrobenzofuran-4-yl)methyl)amino)-[1,2,4]triazolo[4,3-c]pyrimidin-8-yl)-5-methylimidazo[1,2-a]pyridine-3-carboxylate

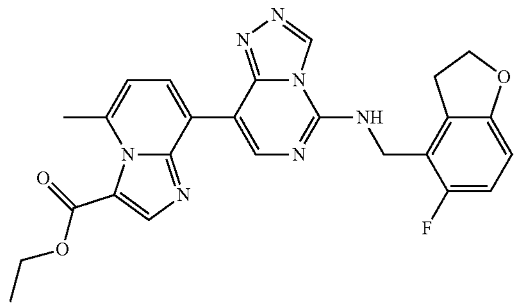 [SMILES: CCOC(=O)c1cnc2c(-c3cnc(NCc4c(F)ccc5c4CCO5)n4cnnc34)ccc(C)n12]

$^1$H NMR (400 MHz, DMSO-$d_6$) δ 9.53 (s, 1H), 9.21 (s, 1H), 8.87 (t, J=5.1 Hz, 1H), 8.76 (d, J=7.6 Hz, 1H), 8.32 (s, 1H), 7.21 (d, J=7.7 Hz, 1H), 7.03-6.92 (m, 1H), 6.72 (dd, J=8.6, 3.9 Hz, 1H), 4.77 (d, J=5.0 Hz, 2H), 4.55 (t, J=8.7 Hz,

2H), 4.35 (q, J=7.1 Hz, 2H), 3.17 (d, J=5.3 Hz, 2H), 2.77 (s, 3H), 1.36 (t, J=7.1 Hz, 3H) ppm; LCMS: m/z 488.1 $[M+H]^+$.

The following compound can be synthesized with a solution of dimethylamine in tetrahydrofuran, and ethyl 8-(5-(((5-fluoro-2,3-dihydrobenzofuran-4-yl)methyl) amino)-[1,2,4]triazolo[4,3-c]pyrimidin-8-yl)-5-methylimidazo[1,2-a]pyridine-3-carboxylate (example 92) as the raw materials using the method of example 92:

Example 93: 8-(5-(((5-fluoro-2,3-dihydrobenzofuran-4-yl)methyl)amino)-[1,2,4]triazolo[4,3-c]pyrimidin-8-yl)-N,N,5-trimethylimidazo[1,2-a]pyridine-3-carboxamide

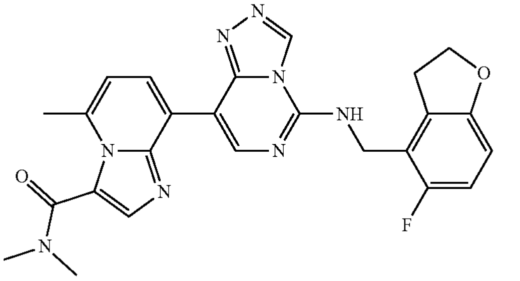 [SMILES: Cc1ccc(-c2cnc(NCc3c(F)ccc4c3CCO4)n3cnnc23)c2ncc(C(=O)N(C)C)n12]

$^1$H NMR (400 MHz, $CDCl_3$) δ 8.96 (s, 1H), 8.92 (s, 1H), 8.41 (s, 1H), 7.93 (d, J=7.3 Hz, 1H), 7.64 (s, 1H), 6.76 (d, J=7.5 Hz, 1H), 6.64 (t, J=9.3 Hz, 1H), 6.52 (dd, J=8.6, 3.9 Hz, 1H), 4.60 (d, J=4.7 Hz, 2H), 4.54 (t, J=8.7 Hz, 2H), 3.37 (t, J=8.6 Hz, 2H), 3.24 (d, J=18.8 Hz, 6H), 2.58 (s, 3H) ppm; LCMS: m/z 487.1 $[M+H]^+$.

The following compound can be synthesized with 4-bromo-1-methyl-1H-benzo[d]imidazole and intermediate B3 as the raw materials using the method of example 6:

Example 94: N-((5-fluoro-2,3-dihydrobenzofuran-4-yl)methyl)-8-(1-methyl-1H-benzo[d]imidazol-4-yl)-[1,2,4]triazolo[4,3-c]pyrimidin-5-amine

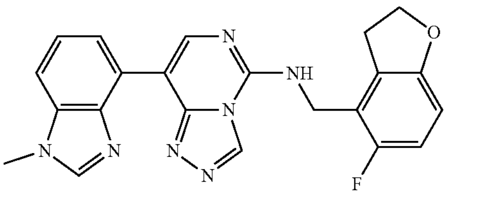 [SMILES: Cn1cnc2c(-c3cnc(NCc4c(F)ccc5c4CCO5)n4cnnc34)cccc21]

$^1$H NMR (400 MHz, DMSO-$d_6$) δ 9.62 (s, 1H), 9.27 (s, 1H), 8.58 (d, J=7.5 Hz, 1H), 8.30 (s, 1H), 7.57 (d, J=8.0 Hz, 1H), 7.42 (t, J=7.8 Hz, 1H), 7.03-6.92 (m, 1H), 6.73 (dd, J=8.6, 3.8 Hz, 1H), 4.79 (s, 2H), 4.57 (t, J=8.7 Hz, 2H), 3.92 (s, 3H), 3.35 (d, J=8.7 Hz, 2H) ppm; LCMS: m/z 416.0 $[M+H]^+$.

Example 95: 8-(5-(((5-fluoro-2,3-dihydrobenzofuran-4-yl)methyl)amino)-[1,2,4]triazolo[4,3-c]pyrimidin-8-yl)-N,N-dimethylimidazo[1,2-a]pyridine-5-carboxamide Step 1: 6-amino-5-bromo-N,N-dimethyl methylpicolinamide E13-1

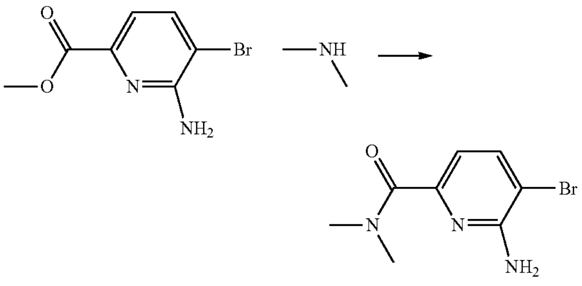

E13-1

Into a 25 mL round-bottom flask, methyl 6-amino-5-bromopyridine-2-carboxylate (100 mg, 0.43 mmol) and dichloromethane (5 mL) were added. After the mixture was dissolved with stirring, magnesium dichloride (49 mg, 0.52 mmol) was added in an ice-water bath. The resulting suspension was stirred for another 5 minutes in an ice-water bath and then a solution of dimethylamine in dichloromethane (2 M, 0.35 mL) was added. After the resulting mixture was stirred at normal temperature for 6 hours, almost all the raw materials were converted into the desired product (monitored by LCMS). The reaction solution was spin-dried to obtain a white solid, which was washed with water to remove the inorganic substances. A white solid was obtained by filtration and the white solid was dried under high vacuum to obtain E13-1 (88 mg, 83.8% yield).

$^1$H NMR (400 MHz, $CDCl_3$) δ 7.73 (d, J=7.9 Hz, 1H), 6.80 (d, J=7.9 Hz, 1H), 5.02 (s, 2H), 3.09 (s, 3H), 3.04 (s, 3H) ppm; LCMS: m/z 244.0 $[M+1]^+$.

Step 2: The following compound can be synthesized with E13-1 and intermediate B3 as the raw materials using the method of example 21:

8-(5-(((5-fluoro-2,3-dihydrobenzofuran-4-yl)methyl) amino)-[1,2,4]triazolo[4,3-c]pyrimidin-8-yl)-N,N-dimethylimidazo[1,2-a]pyridine-5-carboxamide

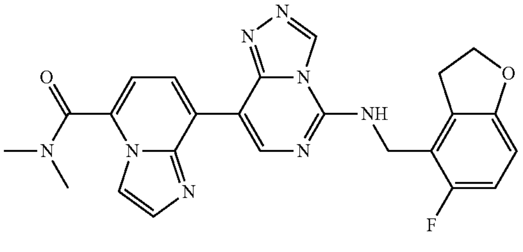 [SMILES: CN(C)C(=O)c1ccc(-c2cnc(NCc3c(F)ccc4c3CCO4)n3cnnc23)c2nccn12]

$^1$H NMR (400 MHz, $CDCl_3$) δ 9.14 (s, 1H), 8.86 (s, 1H), 8.58 (s, 1H), 8.00 (d, J=7.3 Hz, 1H), 7.80 (s, 1H), 7.50 (s, 1H), 7.00 (d, J=7.3 Hz, 1H), 6.73 (t, J=9.3 Hz, 1H), 6.60 (dd, J=8.6, 3.7 Hz, 1H), 4.70 (s, 2H), 4.56 (t, J=8.6 Hz, 2H), 3.39 (t, J=8.6 Hz, 2H), 3.19 (d, J=35.5 Hz, 6H) ppm; LCMS: m/z 473.1 $[M+H]^+$.

Example 96: 6-fluoro-8-(5-(((5-fluoro-2,3-dihydrobenzofuran-4-yl)methyl)amino)-[1,2,4]triazolo[4,3-c]pyrimidin-8-yl)imidazo[1,2-a]pyridine-3-carbonitrile Step 1: (Z)-2-bromo-3-methoxyacrylonitrile E14-1

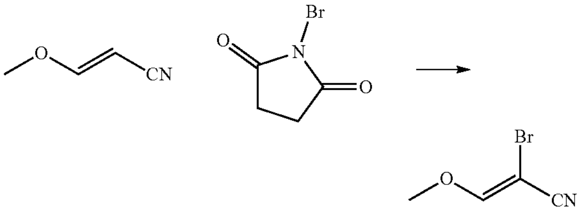

E14-1

Into a 25 mL round-bottom flask, 3-methoxyacrylonitrile (2.0 g, 24.4 mmol), 1,4 dioxane (30 mL) and water (10 mL) were added. In an ice-water bath, N-bromosuccinimide (980 mg, 24.4 mmol) was added in batches over 15 minutes. The reaction solution was stirred in the ice-water bath for half an hour and then the ice-water bath war removed. Stirring of the reaction system was continued at normal temperature overnight to obtain a liquid of E14-1 in dioxane, which was directly used in the next step without any treatment.

Step 2: 6-fluoro-8-(5-(((5-fluoro-2,3-dihydrobenzofuran-4-yl)methyl)amino)-[1,2,4]triazolo[4,3-c]pyrimidin-8-yl)imidazo[1,2-a]pyridine-3-carbonitrile

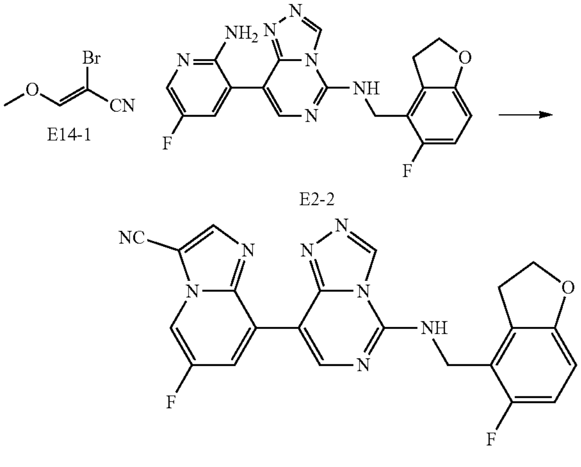

E14-1

E2-2

Into the reaction solution obtained in the previous step, 8-(2-amino-5-fluoropyridin-3-yl)-N-((5-fluoro-2,3-dihydrobenzofuran-4-yl)methyl)-[1,2,4]triazolo[4,3-c]pyrimidin-5-amine E2-2 (780 mg, 2.0 mmol) was added and the reaction solution was refluxed for 10 hours. Then the resulting mixture was allowed to cool down and stand for 5 hours. A brown solid was precipitated out. The mixture was filtered to obtain the brown solid, which was washed with a small amount of cold methanol under stirring. The resulting mixture was filtered to obtain a yellow solid. The yellow solid was dried under vacuum to obtain 6-fluoro-8-(5-(((5-fluoro-2,3-dihydrobenzofuran-4-yl)methyl)amino)-[1,2,4]triazolo[4,3-c]pyrimidin-8-yl)imidazo[1,2-a]pyridine-3-carbonitrile (490 mg, 55% yield).

$^1$H NMR (400 MHz, DMSO-$d_6$) δ 9.64 (s, 1H), 9.57 (s, 1H), 9.17 (dd, J=11.0, 2.2 Hz, 1H), 9.10 (t, J=4.9 Hz, 1H), 8.96-8.83 (m, 1H), 8.53 (s, 1H), 6.99-6.86 (m, 1H), 6.70 (dd, J=8.6, 3.8 Hz, 1H), 4.80 (d, J=4.8 Hz, 2H), 4.56 (t, J=8.7 Hz, 2H), 3.35 (d, J=9.0 Hz, 2H) ppm; LCMS: m/z 445.1 $[M+H]^+$.

The following compound can be synthesized with methyl 2-(8-(5-(((5-fluoro-2,3-dihydrobenzofuran-4-yl)methyl)amino)-[1,2,4]triazolo[4,3-c]pyrimidin-8-yl)-5-methylimidazo[1,2-a]pyridin-3-yl)acetate E11-3 and morpholine as the raw materials using the method in step 2 of example 84:

Example 97: 2-(8-(5-(((5-fluoro-2,3-dihydrobenzofuran-4-yl)methyl)amino)-[1,2,4]triazolo[4,3-c]pyrimidin-8-yl)-5-methylimidazo[1,2-a]pyridin-3-yl)-1-morpholinoethan-1-one

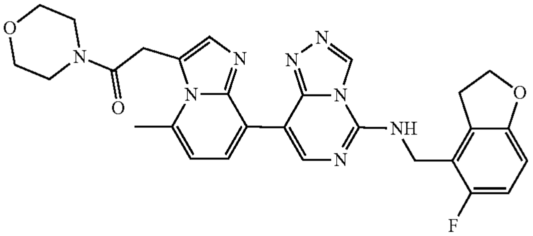 [SMILES: Cc1ccc(-c2cnc(NCc3c(F)ccc4c3CCO4)n3cnnc23)c2ncc(CC(=O)N3CCOCC3)n12]

$^1$H NMR (400 MHz, DMSO-$d_6$) δ 9.51 (s, 1H), 9.43 (s, 1H), 8.77 (t, J=5.0 Hz, 1H), 8.51 (d, J=7.4 Hz, 1H), 7.40 (s, 1H), 7.01-6.93 (m, 1H), 6.78 (d, J=7.6 Hz, 1H), 6.71 (dd, J=8.6, 3.9 Hz, 1H), 4.77 (d, J=5.0 Hz, 2H), 4.55 (t, J=8.7 Hz, 2H), 4.40 (s, 2H), 3.65 (s, 2H), 3.60 (dd, J=9.5, 5.2 Hz, 4H), 3.50 (d, J=4.8 Hz, 2H), 3.31 (s, 2H), 2.75 (d, J=14.2 Hz, 3H) ppm; LCMS: m/z 544.0 $[M+H]^+$.

The following compound can be synthesized with 3-bromo-6-(trifluoromethyl)pyridin-2-amine and intermediate B3 as the raw materials using the method of example 21:

Example 98: N-((5-fluoro-2,3-dihydrobenzofuran-4-yl)methyl)-8-(5-(trifluoromethyl)imidazo[1,2-a]pyridin-8-yl)-[1,2,4]triazolo[4,3-c]pyrimidin-5-amine

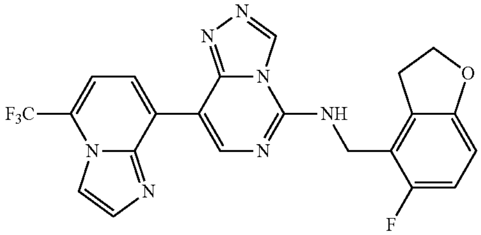

$^1$H NMR (400 MHz, DMSO-$d_6$) δ 9.74 (s, 1H), 9.56 (s, 1H), 9.06 (s, 1H), 8.95 (d, J=7.8 Hz, 1H), 8.14 (s, 1H), 7.90 (d, J=1.3 Hz, 1H), 7.78 (d, J=7.9 Hz, 1H), 6.98 (s, 1H), 6.74 (d, J=3.9 Hz, 1H), 4.80 (s, 2H), 4.56 (t, J=8.8 Hz, 2H), 3.37 (s, 2H) ppm; LCMS: m/z 470.1 $[M+H]^+$.

The following compound can be synthesized with morpholine and 8-(5-(((5-fluoro-2,3-dihydrobenzofuran-4-yl)methyl)amino)-[1,2,4]triazolo[4,3-c]pyrimidin-8-yl)-5-methylimidazo[1,2-a]pyridine-3-carboxylic acid (example 44) as the raw materials using the method in step 2 of example 84:

Example 99: (8-(5-(((5-fluoro-2,3-dihydrobenzofuran-4-yl)methyl)amino)-[1,2,4]triazolo[4,3-c]pyrimidin-8-yl)-5-methylimidazo[1,2-a]pyridin-3-yl)(morpholino)methanone

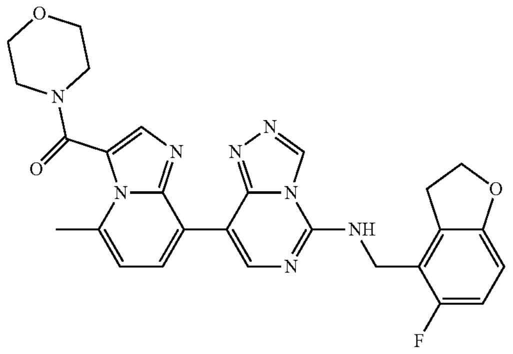 [SMILES: Cc1ccc(-c2cnc(NCc3c(F)ccc4c3CCO4)n3cnnc23)c2ncc(C(=O)N3CCOCC3)n12]

$^1$H NMR (400 MHz, $CDCl_3$) δ 9.25 (s, 1H), 8.62 (s, 1H), 8.23 (s, 1H), 7.71 (s, 1H), 7.55-7.41 (m, 1H), 6.89-6.67 (m, 2H), 6.60 (dd, J=8.5, 3.7 Hz, 1H), 4.71 (s, 2H), 4.59 (t, J=8.7 Hz, 2H), 3.78 (d, J=31.2 Hz, 8H), 3.40 (t, J=7.8 Hz, 2H), 2.62 (s, 3H) ppm; LCMS: m/z 529.2 $[M+H]^+$.

The following compound can be synthesized with 8-bromo-5-chloro-[1,2,4]triazolo[1,5-a]pyridine and intermediate B3 as the raw materials using the method of example 6:

Example 100: 8-(5-chloro-[1,2,4]triazolo[1,5-a]pyridin-8-yl)-N-((5-fluoro-2,3-dihydrobenzofuran-4-yl)methyl)-[1,2,4]triazolo[4,3-c]pyrimidin-5-amine

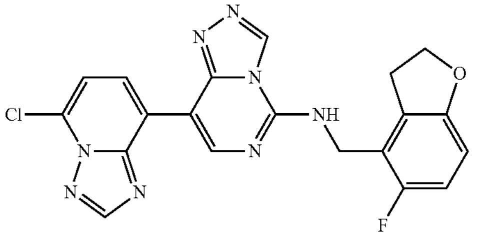 [SMILES: Fc1ccc2c(c1CNc1ncc(-c3ccc(Cl)n4ncnc34)c3nncn13)CCO2]

$^1$H NMR (400 MHz, MeOD) δ 9.40-9.30 (m, 1H), 9.25-9.19 (m, 1H), 8.88 (dd, J=9.3, 7.4 Hz, 1H), 8.53-8.47 (m, 1H), 7.38 (d, J=8.0 Hz, 2H), 6.84 (dd, J=17.3, 7.3 Hz, 1H), 6.70-6.64 (m, 1H), 4.82 (d, J=18.0 Hz, 1H), 4.63 (dd, J=20.5, 11.7 Hz, 1H), 3.45 (d, J=17.4 Hz, 2H) ppm; LCMS: m/z 437.0 $[M+H]^+$.

The following compound can be synthesized by subjecting the raw materials, ammonia chloride and 8-(5-(((5-fluoro-2,3-dihydrobenzofuran-4-yl)methyl)amino)-[1,2,4]triazolo[4,3-c]pyrimidin-8-yl)-5-methylimidazo[1,2-a]pyridine-3-carboxylic acid (example 44) to condensation using the method in step 2 of example 84:

Example 101: 8-(5-(((5-fluoro-2,3-dihydrobenzofuran-4-yl)methyl)amino)-[1,2,4]triazolo[4,3-c]pyrimidin-8-yl)-5-methylimidazo[1,2-a]pyridine-3-carboxamide

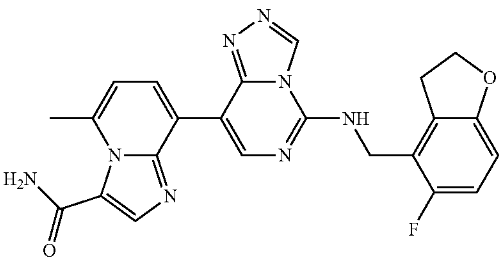 [SMILES: Cc1ccc(-c2cnc(NCc3c(F)ccc4c3CCO4)n3cnnc23)c2ncc(C(N)=O)n12]

$^1$H NMR (400 MHz, DMSO-$d_6$) δ 9.53 (s, 1H), 9.33 (s, 1H), 8.83 (d, J=4.9 Hz, 1H), 8.71 (d, J=7.5 Hz, 1H), 8.19 (s, 1H), 8.00 (s, 1H), 7.59 (s, 1H), 7.07 (d, J=8.2 Hz, 1H), 7.01-6.92 (m, 1H), 6.72 (dd, J=8.6, 3.9 Hz, 1H), 4.77 (d, J=5.0 Hz, 2H), 4.56 (t, J=8.7 Hz, 2H), 3.35 (s, 2H), 2.69 (d, J=14.5 Hz, 3H) ppm; LCMS: m/z 459.1 $[M+H]^+$.

Example 102: 8-(5-(((5-fluoro-2,3-dihydrobenzofuran-4-yl)methyl)amino)-[1,2,4]triazolo[4,3-c]pyrimidin-8-yl)-5-methylimidazo[1,2-a]pyridine-3-carbonitrile

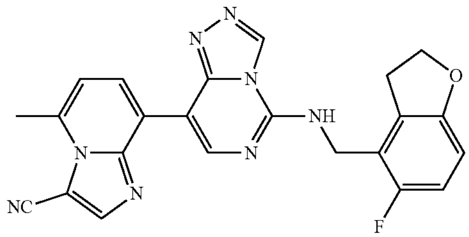 [SMILES: Cc1ccc(-c2cnc(NCc3c(F)ccc4c3CCO4)n3cnnc23)c2ncc(C#N)n12]

Into a 25 mL round-bottom flask, 8-(5-(((5-fluoro-2,3-dihydrobenzofuran-4-yl)methyl)amino)-[1,2,4]triazolo[4,3-c]pyrimidin-8-yl)-5-methylimidazo[1,2-a]pyridine-3-carboxamide (example 101) (30 mg, 0.07 mmol) and anhydrous tetrahydrofuran (2 ml) were added and in an ice-water bath, trifluoroacetic anhydride (29 mg, 0.14 mmol) and triethylamine (14 mg, 0.14 mmol) were added. The reaction system was stirred at normal temperature overnight. The reaction solution was spin-dried to obtain a yellow solid. The yellow solid was washed with methanol and the resulting mixture was filtered to obtain a white solid. The white solid was dried under vacuum to obtain pure 8-(5-(((5-fluoro-2,3-dihydrobenzofuran-4-yl)methyl)amino)-[1,2,4]triazolo[4,3-c]pyrimidin-8-yl)-5-methylimidazo[1,2-a]pyridine-3-carbonitrile (24 mg, 80%).

$^1$H NMR (400 MHz, DMSO-$d_6$) δ 9.53 (s, 1H), 9.23 (s, 1H), 8.91 (t, J=4.9 Hz, 1H), 8.81 (d, J=7.6 Hz, 1H), 8.56 (s, 1H), 7.21 (d, J=7.7 Hz, 1H), 7.00-6.92 (m, 1H), 6.72 (dd, J=8.6, 3.8 Hz, 1H), 4.77 (d, J=4.9 Hz, 2H), 4.55 (t, J=8.7 Hz, 2H), 3.35 (s, 2H), 2.99 (s, 3H) ppm; LCMS: m/z 441.1 $[M+H]^+$.

Example 103: N-((5-fluoro-2,3-dihydrobenzofuran-4-yl)methyl)-8-(5-(trifluoromethyl)-[1,2,4]triazolo[1,5-a]pyridin-8-yl)-[1,2,4]triazolo[4,3-c]pyrimidin-5-amine Step 1: N-(3-bromo-6-(trifluoromethyl)pyridin-2-yl)-N'-hydroxycarboximide E15-1

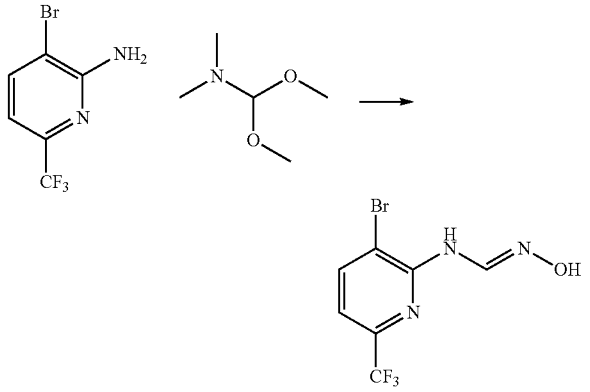

E15-1

To a mixture solution of 3-bromo-6-(trifluoromethyl)pyridin-2-amine (400 mg, 1.46 mmol) in isopropanol (10 mL), N,N-dimethylformamide dimethylacetal (300 mg, 2.49 mmol) was added and under nitrogen, the mixture was stirred at 80° C. for 3 hours. All the raw materials were converted into intermediates (shown by LCMS). The reaction system was cooled to 50° C. Then hydroxylamine hydrochloride (173 mg, 2.49 mmol) was added and the resulting mixture was stirred at the temperature for 5 hours. The mixture was cooled to room temperature and subjected to rotary evaporation to remove the solvent. Water was added and then the resulting mixture was extracted with ethyl acetate (30 mL×3). The combined organic layer was concentrated and purified to obtain a yellow oil E15-1 (450 mg, 97% yield).

LCMS: m/z 284.1 $[M+H]^+$.

Step 2: 8-bromo-5-(trifluoromethyl)-[1,2,4]triazolo[1,5-a]pyridine E15-2

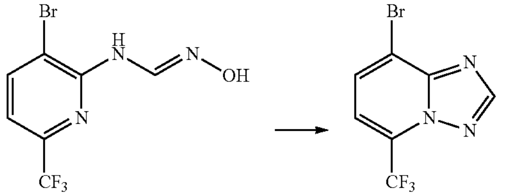

E15-1 E15-2

To a solution of E15-1 (450 mg, 1.59 mmol) in tetrahydrofuran, trifluoroacetic anhydride (0.66 g, 3.18 mmol) was added. The mixture was stirred at 100° C. for 16 hours. The reaction was completed (shown by LCMS). The reaction mixture was concentrated and purified to obtain a colorless oil E15-2 (400 mg, 95% yield).

LCMS: m/z 266.1 $[M+H]^+$.

Step 3: N-((5-fluoro-2,3-dihydrobenzofuran-4-yl)methyl)-8-(5-(trifluoromethyl)-[1,2,4]triazolo[1,5-a]pyridin-8-yl)-[1,2,4]triazolo[4,3-c]pyrimidin-5-amine was obtained with E15-2 and intermediate B3 as the raw materials using the method of example 6

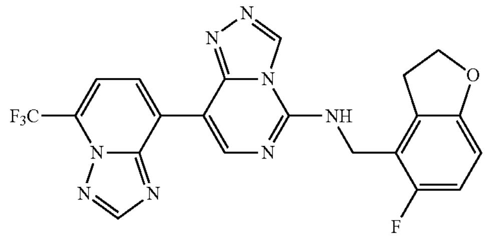

$^1H$ NMR (400 MHz, DMSO-$d_6$) δ 9.66 (d, J=2.6 Hz, 1H), 9.58 (s, 1H), 9.36 (d, J=7.9 Hz, 1H), 9.18 (t, J=4.9 Hz, 1H), 8.82 (d, J=2.4 Hz, 1H), 8.03 (d, J=8.0 Hz, 1H), 6.97 (t, J=9.4 Hz, 1H), 6.72 (dd, J=8.6, 3.8 Hz, 1H), 4.81 (d, J=4.8 Hz, 2H), 4.56 (t, J=8.7 Hz, 2H), 3.32 (s, 2H) ppm; LCMS: m/z 471.1 $[M+H]^+$.

Example 104: 2-(8-(5-(((5-fluoro-2,3-dihydrobenzofuran-4-yl)methyl)amino)-[1,2,4]triazolo[4,3-c]pyrimidin-8-yl)-5-methylimidazo[1,2-a]pyridin-3-yl)acetonitrile Step 1: 2-(8-(5-(((5-Fluoro-2,3-dihydrobenzofuran-4-yl)methyl)amino)-[1,2,4]triazolo[4,3-c]pyrimidin-8-yl)-5-methylimidazo[1,2-a]pyridin-3-yl)acetamide E16-1

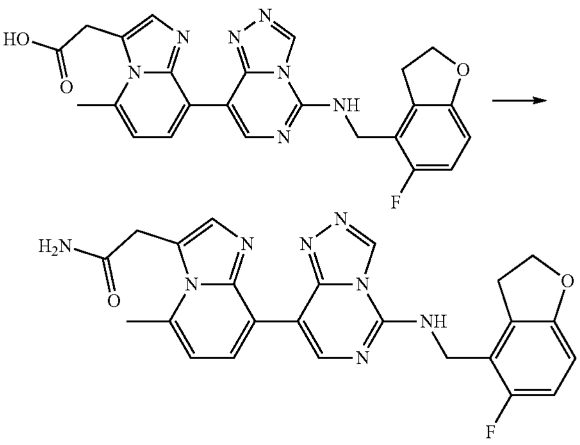

E16-1

Into a 25 mL round-bottom flask, 2-(8-(5-(((5-fluoro-2,3-dihydrobenzofuran-4-yl)methyl)amino)amino]-[1,2,4]triazolo[4,3-c]pyrimidin-8-yl)-5-methylimidazo[1,2-a]pyridin-3-yl)acetic acid (example 84) (100 mg, 0.21 mmol) and dimethylformamide (2 mL) were added. At room temperature, ammonium hydrogen carbonate (83 mg, 1.05 mmol) and O-(7-azabenzotriazol-1-yl)-N,N,N',N'-tetramethyluracilhexafluorophosphate (103 mg, 0.27 mmol) were added, respectively. The reaction mixture was stirred at normal temperature overnight to obtain a yellow turbid liquid. The reaction solution was quenched with water (10 ml) and extracted with ethyl acetate (10 ml*3). The organic phases were combined, washed with saturated brine (10 ml), dried over anhydrous sodium sulfate and concentrated. The crude product was purified by Flash column chromatography (ethyl acetate:dichloromethane:methanol=(1:1:1) as the mobile phase) and eluted to obtain the target product E16-1 (90 mg, 90.7% yield) which was pure.

Step 2: 2-(8-(5-(((5-fluoro-2,3-dihydrobenzofuran-4-yl)methyl)amino)-[1,2,4]triazolo[4,3-c]pyrimidin-8-yl)-5-methylimidazo[1,2-a]pyridin-3-yl)acetonitrile

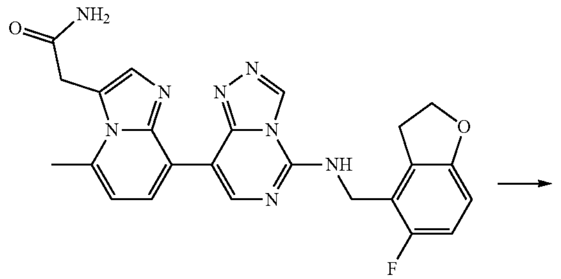

E16-1

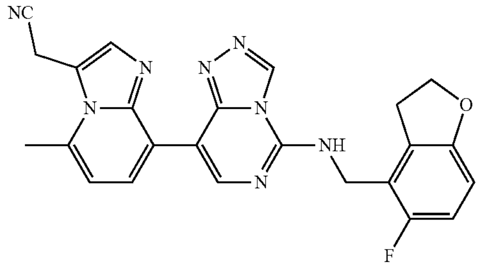

Into a 25 mL round-bottom flask, E16-1 (90 mg, 0.19 mmol) and anhydrous tetrahydrofuran (2 ml) were added and in an ice-water bath, trifluoroacetic anhydride (80 mg, 0.38 mmol) and triethylamine (29 mg, 0.29 mmol) were added. The reaction system was stirred at normal temperature overnight. The reaction solution was spin-dried to obtain a yellow solid. The yellow solid was washed with methanol and the resulting mixture was filtered to obtain a white solid. The white solid was dried under vacuum to obtain pure 2-(8-(5-(((5-fluoro-2,3-dihydrobenzofuran-4-yl)methyl)amino)-[1,2,4]triazolo[4,3-c]pyrimidin-8-yl)-5-methylimidazo[1,2-a]pyridin-3-yl)acetonitrile (30 mg, 35%).

$^1$H NMR (400 MHz, DMSO-d$_6$) δ 9.53 (d, J=6.4 Hz, 1H), 9.36 (d, J=1.8 Hz, 1H), 8.86 (d, J=16.3 Hz, 1H), 8.56 (d, J=7.4 Hz, 1H), 7.62 (s, 1H), 6.96 (t, J=9.5 Hz, 1H), 6.90 (d, J=7.6 Hz, 1H), 6.71 (dd, J=8.7, 3.8 Hz, 1H), 4.81 (s, 2H), 4.77 (d, J=5.1 Hz, 2H), 4.55 (t, J=8.7 Hz, 2H), 3.32 (d, J=8.9 Hz, 2H), 2.96 (s, 3H) ppm; LCMS: m/z 455.1 [M+H]$^+$ Example 105: N-((5-fluoro-2,3-dihydrobenzofuran-4-yl)methyl)-8-(5-methoxy-triazolo[1,5-a]pyridin-8-yl)-[1,2,4]triazolo[4,3-c]pyrimidin-5-amine Step 1: 8-bromo-5-methoxy-[1,2,4]triazolo[1,5-a]pyridine E17-1

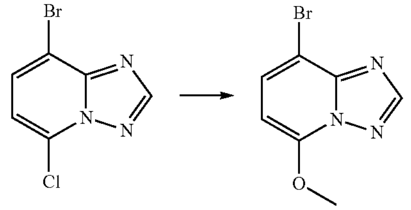

E17-1

Into a 25 mL round-bottom flask, 8-bromo-5-chloro-[1,2,4]triazolo[1,5-a]pyridine (150 mg, 0.65 mmol) and anhydrous methanol (5 ml) were added and then sodium methoxide (175.58 mg, 3.25 mmol) was added. The reaction system was stirred at 80° C. for 3 hours. The reaction solution was spin-dried and then purified by Flash silica gel column chromatography (eluents:petroleum ether:ethyl acetate=5:1) to obtain a pure E17-1 (0.11 g, 74.2%). LCMS: m/z 227.9, 229.9 [M+H]$^+$.

Step 2: N-((5-fluoro-2,3-dihydrobenzofuran-4-yl)methyl)-8-(5-methoxy-[1,2,4]triazolo[1,5-a]pyridin-8-yl)-[1,2,4]triazolo[4,3-c]pyrimidin-5-amine can be obtained with 8-bromo-5-methoxy-[1,2,4]triazolo[1,5-a]pyridine (E17-1) and intermediate B3 as the raw materials using the method of example 6.

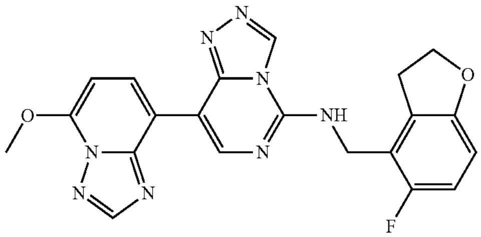 [SMILES: COc1ccc(-c2cnc(NCc3c(F)ccc4c3CCO4)n3cnnc23)c2ncnn12]

$^1$H NMR (400 MHz, DMSO-d$_6$) δ 9.54 (s, 1H), 9.33 (s, 1H), 9.17 (d, J=8.4 Hz, 1H), 8.83 (s, 1H), 8.59 (s, 1H), 6.99-6.93 (m, 1H), 6.91 (d, J=8.5 Hz, 1H), 6.72 (dd, J=8.6, 3.9 Hz, 1H), 4.77 (s, 2H), 4.55 (s, 2H), 4.20 (s, 3H), 3.30 (t, J=6.4 Hz, 2H) ppm; LCMS: m/z 433.1 [M+H]$^+$.

The following compound can be synthesized with 4-bromobenzo[c][1,2,5]thiadiazole and intermediate B3 as the raw materials using the method of example 6:

Example 106: 8-(benzo[c][1,2,5]thiadiazol-4-yl)-N-((5-fluoro-2,3-dihydrobenzofuran-4-yl)methyl)-[1,2,4]triazolo[4,3-c]pyrimidin-5-amine

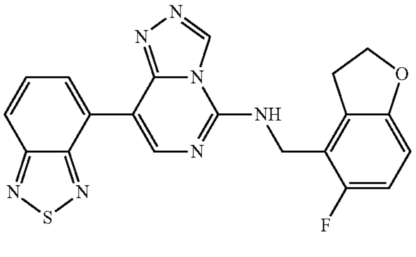 [SMILES: Fc1ccc2c(c1CNc1ncc(-c3cccc4nsnc34)c3nncn13)CCO2]

$^1H$ NMR (400 MHz, DMSO-$d_6$) δ 9.55 (d, J=3.1 Hz, 1H), 8.95 (s, 1H), 8.92 (t, J=5.1 Hz, 1H), 8.83 (dd, J=7.1, 0.9 Hz, 1H), 8.08 (dd, J=8.7, 1.0 Hz, 1H), 7.88 (dd, J=8.7, 7.2 Hz, 1H), 7.00-6.94 (m, 1H), 6.73 (dd, J=8.6, 3.9 Hz, 1H), 4.79 (d, J=5.0 Hz, 2H), 4.56 (t, J=8.7 Hz, 2H), 3.32 (s, 2H) ppm; LCMS: m/z 420.0 $[M+H]^+$.

The following compound can be obtained by subjecting the raw material ethyl 6-fluoro-8-(5-(((5-fluoro-2,3-dihydrobenzofuran-4-yl)methyl)amino)-[1,2,4]triazolo[4,3-c]pyrimidin-8-yl)imidazo[1,2-a]pyridine-3-carboxylate (example 23) to hydrolysis, and then to condensation with dimethylamine hydrochloride using the method of example 84:

Example 107: 6-fluoro-8-(5-(((5-fluoro-2,3-dihydrobenzofuran-4-yl)methyl)amino)-triazolo[4,3-c]pyrimidin-8-yl)-N,N-dimethylimidazo[1,2-a]pyridine-3-carboxamide

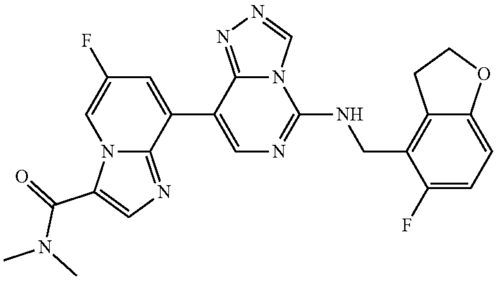 [SMILES: CN(C)C(=O)c1cnc2c(-c3cnc(NCc4c(F)ccc5c4CCO5)n4cnnc34)cc(F)cn12]

$^1H$ NMR (400 MHz, DMSO-$d_6$) δ 9.71 (s, 1H), 9.56 (s, 1H), 9.14-8.95 (m, 3H), 8.21 (s, 1H), 7.01-6.94 (m, 1H), 6.72 (dd, J=8.6, 3.9 Hz, 1H), 4.79 (d, J=4.9 Hz, 2H), 4.56 (t, J=8.7 Hz, 2H), 3.34 (s, 2H), 3.20 (s, 6H) ppm; LCMS: m/z 491.0 $[M+H]^+$.

The following compound can be obtained by subjecting the raw material ethyl 6-fluoro-8-(5-(((5-fluoro-2,3-dihydrobenzofuran-4-yl)methyl)amino)-[1,2,4]triazolo[4,3-c]pyrimidin-8-yl)imidazo[1,2-a]pyridine-3-carboxylate (example 23) to hydrolysis, and then to condensation with ammonium chloride using the method of example 84:

Example 108: 6-fluoro-8-(5-(((5-fluoro-2,3-dihydrobenzofuran-4-yl)methyl)amino)-triazolo[4,3-c]pyrimidin-8-yl)imidazo[1,2-a]pyridine-3-carboxamide

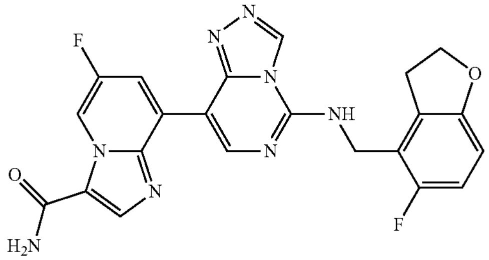 [SMILES: NC(=O)c1cnc2c(-c3cnc(NCc4c(F)ccc5c4CCO5)n4cnnc34)cc(F)cn12]

$^1H$ NMR (400 MHz, DMSO-$d_6$) δ 9.66 (d, J=6.7 Hz, 1H), 9.59-9.48 (m, 2H), 9.04 (dd, J=10.6, 2.6 Hz, 2H), 8.47 (d, J=4.3 Hz, 1H), 8.14 (s, 1H), 7.55 (s, 1H), 7.02-6.94 (m, 1H), 6.72 (dd, J=8.6, 3.9 Hz, 1H), 4.80 (d, J=4.9 Hz, 2H), 4.56 (t, J=8.8 Hz, 2H), 3.32 (d, J=9.0 Hz, 2H) ppm; LCMS: m/z 463.0 $[M+H]^+$.

Example 109: 8-(5-(dimethylamino)-[1,2,4]triazolo[1,5-a]pyridin-8-yl)-N-((5-fluoro-2,3-dihydrobenzofuran-4-yl)methyl)-[1,2,4]triazolo[4,3-c]pyrimidin-5-amine Step 1: 8-iodo-N,N-dimethyl-[1,2,4]triazolo[1,5-a]pyridin-5-amine E18-1

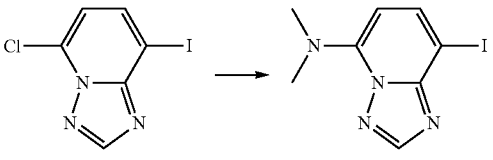

E18-1

To a solution of dimethylamine in tetrahydrofuran (4 mL, 2 M/L), 5-chloro-8-iodo-triazolo[1,5-a]pyridine (200 mg, 0.72 mmol) was added. The mixture was stirred at 90° C. for 16 h. The reaction was completed (shown by LCMS). The reaction mixture was concentrated and purified (petroleum ether:ethyl acetate=1:1) to obtain E18-1 (190 mg, 90%).

LCMS: m/z 288.9 $[M+H]^+$.

Step 2: The following compound can be synthesized with E18-1 and intermediate B3 as the raw materials using the method of example 6:

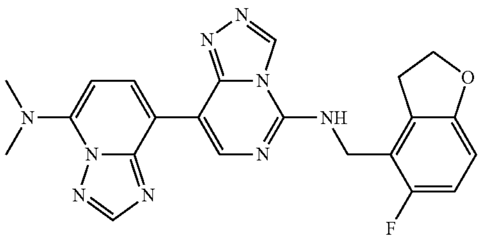

$^1$H NMR (400 MHz, $CDCl_3$) δ 9.34 (s, 1H), 8.63 (s, 1H), 8.31 (d, J=8.4 Hz, 2H), 6.85-6.72 (m, 1H), 6.61 (dd, J=8.6, 3.9 Hz, 1H), 6.48 (d, J=8.1 Hz, 1H), 4.77 (s, 2H), 4.57 (t, J=8.7 Hz, 2H), 3.41 (t, J=8.7 Hz, 2H), 3.24 (s, 6H) ppm; LCMS: m/z 446.1 $[M+H]^+$.

The following compound can be synthesized with 4-bromobenzothiazole and intermediate B3 as the raw materials using the method of example 6:

Example 110: 8-(benzo[d]thiazol-4-yl)-N-((5-fluoro-2,3-dihydrobenzofuran-4-yl)methyl)-[1,2,4]triazolo[4,3-c]pyrimidin-5-amine

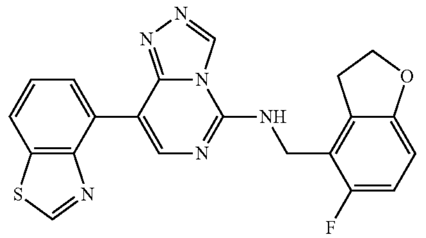 [SMILES: Fc1ccc2c(c1CNc1ncc(-c3cccc4scnc34)c3nncn13)CCO2]

$^1$H NMR (400 MHz, DMSO-$d_6$) δ 9.51 (s, 1H), 9.43 (s, 1H), 8.78 (t, J=4.9 Hz, 1H), 8.49 (s, 1H), 8.32 (d, J=6.8 Hz, 1H), 8.18 (d, J=8.0 Hz, 1H), 7.61 (t, J=7.8 Hz, 1H), 7.04-6.93 (m, 1H), 6.72 (dd, J=8.6, 3.9 Hz, 1H), 4.77 (d, J=4.8 Hz, 2H), 4.56 (t, J=8.7 Hz, 2H), 3.34 (s, 2H) ppm; LCMS: m/z 419.1 $[M+H]^+$.

The following compound can be synthesized with 5-chloro-8-iodo-[1,2,4]triazolo[1,5-a]pyridine, morpholine and intermediate B3 as the raw materials using the method of example 109:

Example 111: N-((5-fluoro-2,3-dihydrobenzofuran-4-yl)methyl)-8-(5-morpholino-triazolo[1,5-a]pyridin-8-yl)-[1,2,4]triazolo[4,3-c]pyrimidin-5-amine

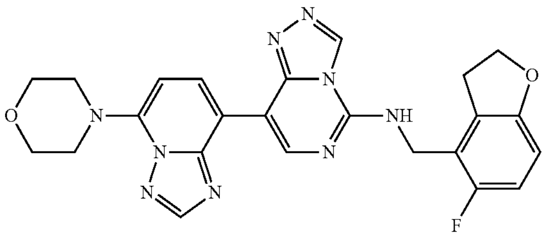 [SMILES: Fc1ccc2c(c1CNc1ncc(-c3ccc(N4CCOCC4)n4ncnc34)c3nncn13)CCO2]

$^1$H NMR (400 MHz, DMSO-$d_6$) δ 9.53 (s, 1H), 9.32 (s, 1H), 9.10 (d, J=8.3 Hz, 1H), 8.81 (s, 1H), 8.59 (s, 1H), 6.99-6.94 (m, 1H), 6.81 (d, J=8.3 Hz, 1H), 6.72 (dd, J=8.7, 3.9 Hz, 1H), 4.77 (s, 2H), 4.55 (t, J=8.7 Hz, 2H), 3.92-3.81 (m, 4H), 3.56-3.46 (m, 4H), 3.35 (s, 2H) ppm; LCMS: m/z 488.1 $[M+H]^+$.

The following compound can be synthesized with 8-bromo-5-chloro-[1,2,4]triazolo[1,5-a]pyridine, N-methylpiperazine and intermediate B3 as the raw materials using the method of example 109:

Example 112: N-((5-fluoro-2,3-dihydrobenzofuran-4-yl)methyl)-8-(5-(4-methylpiperazin-1-yl)-[1,2,4]triazolo[1,5-a]pyridin-8-yl)-[1,2,4]triazolo[4,3-c]pyrimidin-5-amine

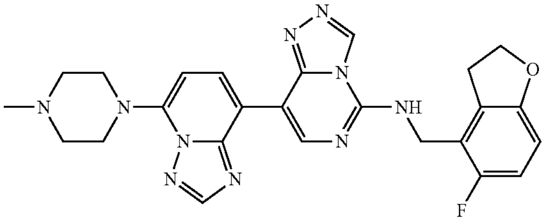 [SMILES: CN1CCN(c2ccc(-c3cnc(NCc4c(F)ccc5c4CCO5)n4cnnc34)c3ncnn23)CC1]

$^1$H NMR (400 MHz, DMSO-$d_6$) δ 9.52 (s, 1H), 9.31 (s, 1H), 9.08 (d, J=8.3 Hz, 1H), 8.80 (d, J=4.7 Hz, 1H), 8.58 (s, 1H), 6.99-6.92 (m, 1H), 6.78 (d, J=8.3 Hz, 1H), 6.71 (dd, J=8.7, 3.9 Hz, 1H), 4.77 (d, J=4.3 Hz, 2H), 4.55 (t, J=8.7 Hz, 2H), 3.51 (s, 4H), 3.34 (d, J=7.4 Hz, 2H), 2.58 (s, 4H), 2.28 (s, 3H) ppm; LCMS: m/z 501.2 $[M+H]^+$.

Example 113: 8-(2,5-dimethyl-[1,2,4]triazolo[1,5-a]pyridin-8-yl)-N-((5-fluoro-2,3-dihydrobenzofuran-4-yl)methyl)-[1,2,4]triazolo[4,3-c]pyrimidin-5-amine Step 1: (E)-N-(3-bromo-6-methylpyridin-2-yl)-N'-hydroxyacetamidine E19-1

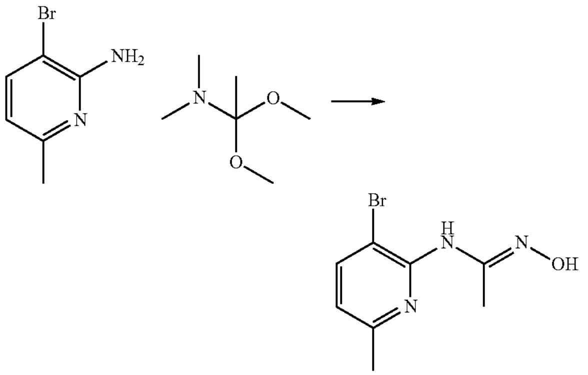

E19-1

To a mixture solution of 3-bromo-6-methylpyridin-2-amine (5.0 g, 26.7 mmol) in isopropanol (60 mL), 1,1-dimethoxy-N,N-dimethylethane-1-amine (5.3 g, 40.1 mmol) was added and the mixture was stirred under nitrogen at 80° C. for 3 hours. The reaction system was cooled to 50° C. Then hydroxylamine hydrochloride (3.7 g, 53.5 mmol) was added and the resulting mixture was stirred at this temperature for 5 hours. The reaction was substantially completed (shown by LCMS). The solvent was evaporated and water was added. Then the resulting mixture was extracted with ethyl acetate (50 mL substantially). The combined organic layer was concentrated and purified by Flash column chromatography (petroleum ether:ethyl acetate=5:1) to obtain E19-1 (5.3 g, 88%).

LCMS: m/z 244.1 $[M+H]^+$.

Step 2: 8-bromo-2,5-dimethyl-[1,2,4]triazolo[1,5-a] pyridine E19-2

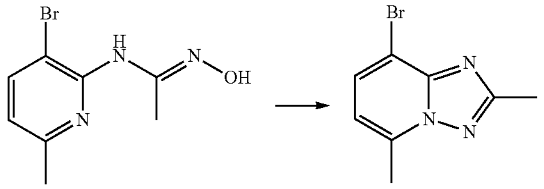

E19-1 E19-2

To a solution of E19-1 (5.3 g, 21.7 mmol) in tetrahydrofuran, trifluoroacetic anhydride (6.84 g, 32.6 mmol) was added. The mixture was stirred at 100° C. for 16 hours. The reaction was completed (shown by LCMS). The resulting mixture was concentrated by Flash column chromatography (petroleum ether:ethyl acetate=2:1) to obtain E19-2 (2.9 g, 59%).

$^1$H NMR (400 MHz, DMSO-$d_6$) δ 7.88 (d, J=7.7 Hz, 1H), 7.07-6.88 (m, 1H), 2.66 (s, 3H), 2.52 (s, 3H) ppm; LCMS: m/z 226.0 $[M+H]^+$.

Step 3: 8-(2,5-dimethyl-[1,2,4]triazolo[1,5-a]pyridin-8-yl)-N-((5-fluoro-2,3-dihydrobenzofuran-4-yl)methyl)-[1,2,4]triazolo[4,3-c]pyrimidin-5-amine can be obtained with E19-2 and intermediate B3 as the raw materials using the method of example 6:

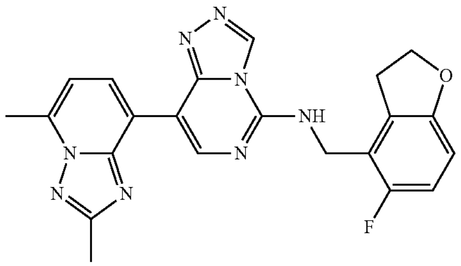 [SMILES: Cc1nc2c(-c3cnc(NCc4c(F)ccc5c4CCO5)n4cnnc34)ccc(C)n2n1]

$^1$H NMR (400 MHz, DMSO-$d_6$) δ 9.53 (s, 1H), 9.44 (s, 1H), 9.05 (d, J=7.7 Hz, 1H), 8.88 (t, J=5.1 Hz, 1H), 7.19 (d, J=8.4 Hz, 1H), 7.03-6.92 (m, 1H), 6.72 (dd, J=8.7, 3.9 Hz, 1H), 4.79 (d, J=4.9 Hz, 2H), 4.55 (t, J=8.7 Hz, 2H), 3.30 (d, J=8.8 Hz, 2H), 2.74 (s, 3H), 2.58 (s, 3H) ppm; LCMS: m/z 431.1 $[M+H]^+$.

Example 114: 1-((8-(5-(((5-fluoro-2,3-dihydrobenzofuran-4-yl)methyl)amino)-triazolo[4,3-c]pyrimidin-8-yl)-[1,2,4]triazolo[1,5-a]pyridin-5-yl) methoxy)-2-methylpropan-2-ol Step 1: 8-bromo-5-(bromomethyl)-[1,2,4]triazolo[1,5-a]pyridine E20-1

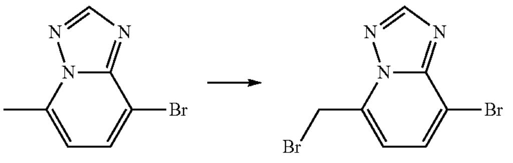

E20-1

Into a 100 mL round-bottom flask, 8-bromo-5-methyl-[1,2,4]triazolo[1,5-a]pyridine (2 g, 9.43 mmol) and carbon tetrachloride (20 ml) were added and in an ice-water bath bromosuccinimide (2 g, 11.3 mmol) and azobisisobutyronitrile (310 mg, 0.2 mmol) were added. Upon completion of the addition, the reaction system was raised from normal temperature to 80° C. and then reacted for 16 hours while the temperature was kept at 80° C. The reaction solution was washed with an aqueous solution of sodium sulfite and then spin-dried to obtain a reddish-brown solid. The solid was then purified by Flash column chromatography (eluents: petroleum ether:ethyl acetate=3:1) to obtain a reddish-brown solid. The reddish-brown solid was dried under vacuum to obtain pure E20-1 (1.7 g, 62% yield).

$^1$H NMR (400 MHz, $CDCl_3$) δ 8.48 (s, 1H), 7.77 (d, J=7.7 Hz, 1H), 7.07 (d, J=7.7 Hz, 1H), 4.90 (s, 2H) ppm; LCMS: m/z 291.9 $[M+H]^+$.

Step 2: 1-((8-bromo-[1,2,4]triazolo[1,5-a]pyridin-5-yl) methoxy)-2-methylpropan-2-ol E20-2

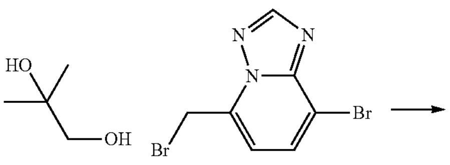

E20-1

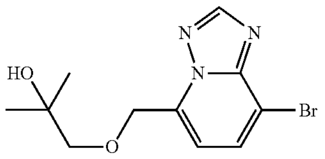

E20-2

Into a 50 mL round-bottom flask, 2-methylpropane-1,2-diol (60 mg, 0.67 mmol) and anhydrous tetrahydrofuran (4 ml) were added and after the mixture was stirred in an ice-water bath for 5 minutes, potassium tert-butoxide (90 mg, 0.80 mmol) was added. The reaction solution was stirred in the ice-water bath for another 30 minutes and then warmed to room temperature and stirred for another 2 hours. E20-1 (97 mg, 0.34 mmol) was added and the stirring of the resulting mixture was continued overnight. 10 mL of water was added and the resulting mixture was extracted with ethyl acetate (10 ml*3). The organic phases were combined, washed with saturated brine (10 ml), dried over anhydrous sodium sulfate and concentrated. The crude product was purified by Flash column chromatography (eluents:petroleum ether:ethyl acetate=2:1) to obtain pure E20-2 (40 mg, 20% yield).

$^1$H NMR (400 MHz, $CDCl_3$) δ 8.42 (s, 1H), 7.80 (d, J=7.7 Hz, 1H), 7.05 (d, J=7.7 Hz, 1H), 5.04 (s, 2H), 3.55 (s, 2H), 1.72 (s, 1H), 1.27 (s, 6H) ppm; LCMS: m/z 300.0, 302.0 $[M+H]^+$.

Step 3: The following compound can be obtained with E20-2 and intermediate B3 as the raw materials using the method of example 6:

1720

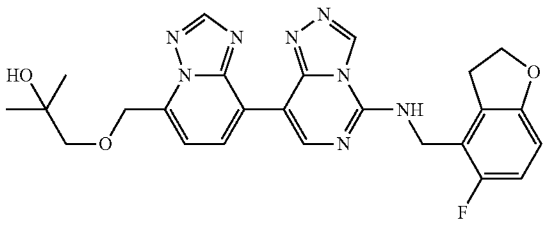

$^1$H NMR (400 MHz, MeOD) δ 9.35 (d, J=2.7 Hz, 1H), 9.08 (d, J=3.4 Hz, 1H), 8.78 (d, J=7.6 Hz, 1H), 8.44 (s, 1H), 7.44 (s, 1H), 7.40 (d, J=7.8 Hz, 1H), 6.89-6.81 (m, 1H), 6.67 (dd, J=8.6, 3.9 Hz, 1H), 5.35 (t, J=4.6 Hz, 1H), 5.13 (s, 2H), 4.84 (s, 2H), 4.64 (t, J=8.7 Hz, 2H), 3.93 (s, 2H), 3.22 (s, 2H), 1.28 (s, 6H) ppm; LCMS: m/z 460.2 $[M+H]^+$.

Example 115: 8-(5-((dimethylamino)methyl)-[1,2,4]triazolo[1,5-a]pyridin-8-yl)-N-((5-fluoro-2,3-dihydrobenzofuran-4-yl)methyl)-[1,2,4]triazolo[4,3-c]pyrimidin-5-amine Step 1: 1-(8-bromo-[1,2,4]triazolo[1,5-a]pyridin-5-yl)-N, N-dimethylmethanamine E20-3

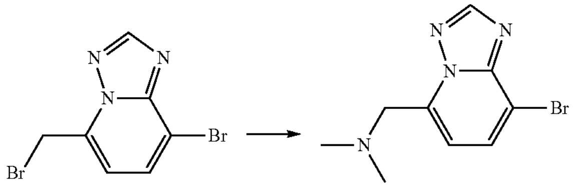

E20-1 E20-3

Into a 100 mL round-bottom flask, E20-1 (1 g, 3.44 mmol) and tetrahydrofuran (15 ml) were added and in an ice-water bath, a solution of 1 M dimethylamine in tetrahydrofuran (17 ml, 17.2 mmol) and potassium carbonate (0.59 g, 1.43 mmol) were added. Upon completion of the addition, the reaction system was raised from normal temperature to 80° C. and then reacted for 3 hours while the temperature was kept at 80° C. Upon completion of the reaction, the reaction solution was spin-dried to obtain a yellowish brown solid, which was eluted and purified by Flash column chromatography (petroleum ether:ethyl acetate=5:1) to obtain a yellow solid, E20-3 (0.6 g, 68.3% yield).

$^1$H NMR (400 MHz, DMSO-$d_6$) δ 8.74-8.38 (m, 1H), 8.14-7.85 (m, 1H), 7.31-6.90 (m, 1H), 4.03-3.78 (m, 2H), 2.38-2.20 (m, 6H) ppm; LCMS: m/z 255.0, 257.0 $[M+H]^+$.

Step 2: 8-(5-((dimethylamino)methyl)-[1,2,4]triazolo[1,5-a]pyridin-8-yl)-N-((5-fluoro-2,3-dihydrobenzofuran-4-yl)methyl)-[1,2,4]triazolo[4,3-c]pyrimidin-5-amine can be obtained with E20-3 and intermediate B3 as the raw materials using the method of example 6:

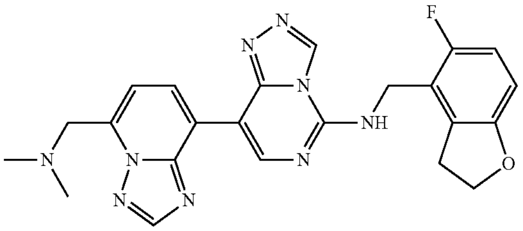 [SMILES: CN(C)Cc1ccc(-c2cnc(NCc3c(F)ccc4c3CCO4)n3cnnc23)c2ncnn12]

$^1$H NMR (400 MHz, DMSO-$d_6$) δ 9.55 (s, 1H), 9.46 (s, 1H), 9.18 (d, J=7.7 Hz, 1H), 8.93 (s, 1H), 8.63 (s, 1H), 7.38 (d, J=7.7 Hz, 1H), 6.97 (dd, J=10.3, 8.7 Hz, 1H), 6.72 (dd, J=8.6, 3.9 Hz, 1H), 4.78 (d, J=4.9 Hz, 2H), 4.56 (t, J=8.7 Hz, 2H), 4.01 (s, 2H), 3.36 (t, 2H), 2.35 (s, 6H) ppm; LCMS: m/z 460.2 $[M+H]^+$.

The following compound can be obtained with E20-1, N-methylmorpholine and intermediate B3 as the raw materials using the method of example 115:

Example 116: N-((5-fluoro-2,3-dihydrobenzofuran-4-yl)methyl)-8-(5-((4-methylpiperazin-1-yl)methyl)-[1,2,4]triazolo[1,5-a]pyridin-8-yl)-[1,2,4]triazolo[4,3-c]pyrimidin-5-amine

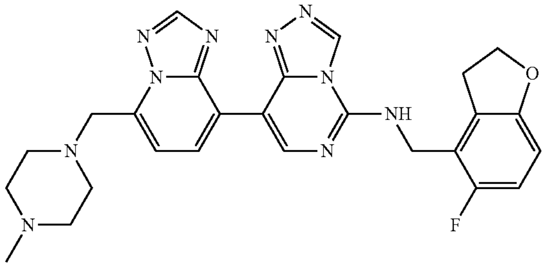 [SMILES: CN1CCN(Cc2ccc(-c3cnc(NCc4c(F)ccc5c4CCO5)n4cnnc34)c3ncnn23)CC1]

$^1$H NMR (400 MHz, DMSO-$d_6$) δ 9.55 (s, 1H), 9.45 (s, 1H), 9.16 (d, J=7.7 Hz, 1H), 8.93 (s, 1H), 8.63 (s, 1H), 7.38 (d, J=7.8 Hz, 1H), 7.02-6.92 (m, 1H), 6.72 (dd, J=8.7, 3.9 Hz, 1H), 4.78 (d, J=4.7 Hz, 2H), 4.56 (t, J=8.7 Hz, 2H), 4.07 (s, 2H), 3.30 (s, 2H), 2.61 (s, 4H), 2.40 (s, 4H), 2.19 (s, 3H) ppm; LCMS: m/z 515.2 $[M+H]^+$.

The following compound can be obtained with E20-1, 1-amino-2-methyl-2-propanol and intermediate B3 as the raw materials using the method of example 115:

Example 117: 1-(((8-(5-(((5-fluoro-2,3-dihydrobenzofuran-4-yl)methyl)amino)-triazolo[4,3-c]pyrimidin-8-yl)-[1,2,4]triazolo[1,5-a]pyridin-5-yl)methyl)amino)-2-methylpropan-2-ol

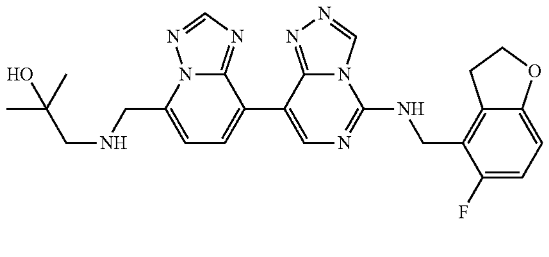 [SMILES: CC(C)(O)CNCc1ccc(-c2cnc(NCc3c(F)ccc4c3CCO4)n3cnnc23)c2ncnn12]

$^1$H NMR (400 MHz, DMSO-$d_6$) δ 9.55 (s, 1H), 9.45 (s, 1H), 9.16 (d, J=7.7 Hz, 1H), 8.92 (s, 1H), 8.65 (s, 1H), 7.42 (d, J=7.7 Hz, 1H), 6.96 (d, J=10.1 Hz, 1H), 6.72 (dd, J=8.6, 4.0 Hz, 1H), 4.79 (d, J=4.9 Hz, 2H), 4.56 (s, 2H), 4.28 (s, 3H), 3.37 (s, 1H), 3.30 (s, 2H), 2.07 (s, 2H), 1.12 (s, 6H) ppm; LCMS: m/z 504.1 [M+H]$^+$.

The following compound can be obtained with E20-1, morpholine and intermediate B3 as the raw materials using the method of example 115:

Example 118: N-((5-fluoro-2,3-dihydrobenzofuran-4-yl)methyl)-8-(5-(morpholinomethyl)-[1,2,4]triazolo[1,5-a]pyridin-8-yl)-[1,2,4]triazolo[4,3-c]pyrimidin-5-amine

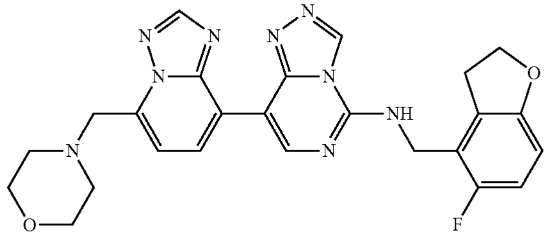 [SMILES: Fc1ccc2c(c1CNc1ncc(-c3ccc(CN4CCOCC4)n4ncnc34)c3nncn13)CCO2]

$^1$H NMR (400 MHz, DMSO-$d_6$) δ 9.55 (s, 1H), 9.45 (s, 1H), 9.17 (d, J=7.7 Hz, 1H), 8.94 (s, 1H), 8.64 (s, 1H), 7.42 (d, J=7.8 Hz, 1H), 6.97 (t, J=9.4 Hz, 1H), 6.72 (dd, J=8.4, 3.6 Hz, 1H), 4.79 (s, 2H), 4.56 (t, J=8.7 Hz, 2H), 4.08 (s, 2H), 3.65 (s, 4H), 3.33 (s, 2H), 2.60 (s, 4H) ppm; LCMS: m/z 502.1 [M+H]$^+$.

The following compound can be obtained with 7-boronic acid pinacol ester-2H-indazole and intermediate B3 as the raw materials using the method in step 2 of example 6:

Example 119: N-((5-fluoro-2,3-dihydrobenzofuran-4-yl)methyl)-8-(1H-indazol-7-yl)-[1,2,4]triazolo[4,3-c]pyrimidin-5-amine

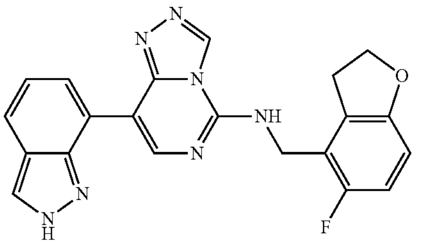 [SMILES: Fc1ccc2c(c1CNc1ncc(-c3cccc4c[nH]nc34)c3nncn13)CCO2]

$^1$H NMR (400 MHz, DMSO-$d_6$) δ 12.86 (s, 1H) 9.52 (s, 1H) 8.78 (t, J=5.0 Hz, 1H) 8.15 (d, J=1.3 Hz, 1H) 7.94 (s, 1H) 7.81 (d, J=8.0 Hz, 1H) 7.69 (d, J=7.1 Hz 1H) 7.22 (t, J=7.6 Hz, 1H) 7.04-6.90 (m, 1H) 6.72 (dd, J=8.6, 3.9 Hz, 1H) 4.76 (d, J=4.8 Hz, 2H) 4.57 (t, J=8.8 Hz, 2H) 3.38 (m, 2H) ppm; LCMS: m/z 402.1 [M+H]$^+$.

Example 120: N-((5-fluoro-2,3-dihydrobenzofuran-4-yl)methyl)-8-(5-methyltetrazolo[1,5-a]pyridin-8-yl)-[1,2,4]triazolo[4,3-c]pyrimidin-5-amine Step 1: 8-bromo-5-methyltetrazolo[1,5-a]pyridine E21-1

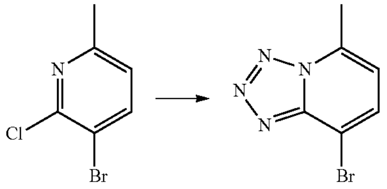

E21-1

A mixture of 3-bromo-2-chloro-6-methylpyridine (1.00 g, 4.84 mmol), trimethylsilyl azide (1.12 g, 9.69 mmol), and tetrabutylammonium fluoride trihydrate (3.06 g, 9.69 mmol) was stirred at 85° C. for 16 hours. Upon completion of the reaction, the mixture was cooled to room temperature. The mixture was diluted by adding dichloromethane (50 mL) and then the resulting mixture was washed with water (10 mL*4) and saturated brine (10 mL*2), respectively. The organic phases were mixed, dried, concentrated and purified by silica gel column chromatography to obtain E21-1 (0.50 g, 48% yield).

$^1$H NMR (400 MHz, $CDCl_3$) δ 7.80 (d, J=7.6 Hz, 1H), 6.91 (dd, J=7.6, 0.8 Hz, 1H), 2.92 (d, J=0.8 Hz, 3H) ppm; LCMS: m/z 214.9 [M+H]$^+$.

Step 2: The following compound can be obtained with E21-1 and intermediate B3 as the raw materials using the method of example 6:

N-((5-fluoro-2,3-dihydrobenzofuran-4-yl)methyl)-8-(5-methyltetrazolo[1,5-a]pyridin-8-yl)-[1,2,4]triazolo[4,3-c]pyrimidin-5-amine

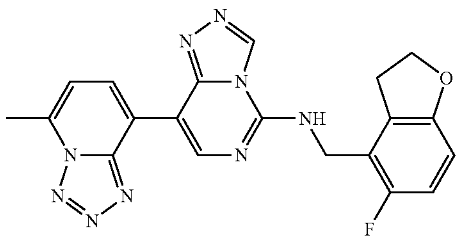 [SMILES: Cc1ccc(-c2cnc(NCc3c(F)ccc4c3CCO4)n3cnnc23)c2nnnn12]

$^1$H NMR (400 MHz, DMSO-$d_6$) δ 9.58 (s, 1H), 9.40 (s, 1H), 9.29 (d, J=7.5 Hz, 1H), 9.06 (br s, 1H), 7.52-7.48 (m, 1H), 7.01-6.95 (m, 1H), 6.73 (dd, J=3.9, 8.7 Hz, 1H), 4.81 (br s, 2H), 4.57 (t, J=8.8 Hz, 2H), 3.32-3.32 (m, 2H), 2.93 (s, 3H) ppm; LCMS: m/z 418.1 [M+H]$^+$.

Example 121: 8-(5-(((5-fluoro-2,3-dihydrobenzofuran-4-yl)methyl)amino)-triazolo[4,3-c]pyrimidin-8-yl)-5-methoxyimidazo[1,2-a]pyridine-3-carbonitrile Step 1: 5-chloro-8-iodoimidazo[1,2-a]pyridine-3-carbonitrile E22-1

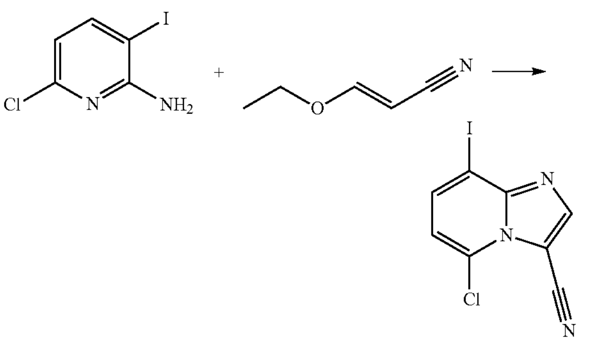

E22-1

Into a 50 mL round-bottom flask, 3-ethoxyacrylonitrile (1.14 g, 11.79 mmol), dioxane (12 ml) and water (4 ml) were added. In an ice bath, N-bromosuccinimide (2.1 g, 11.79 mmol) was added in batches and the mixture was stirred for 30 minutes. Subsequently, the mixture was stirred at room temperature for another 2 hours and then 5-chloro-8-iodo-imidazo[1,2-a]pyridine-3-carbonitrile (1 g, 3.93 mmol) was added to the reaction solution. Upon completion of the reaction (as detected by LCMS), water (10 mL) was added and the resulting mixture was extracted with ethyl acetate (10 mL*3). The organic layers were collected, dried over anhydrous sodium sulfate and spin-dried. The crude was purified by Flash column chromatography (eluents:petroleum ether:ethyl acetate=10:1) to obtain a yellow solid E22-1 (800 mg, 67% yield).

LCMS: m/z 303.9 $[M+H]^+$.

Step 2: 5-hydroxy-8-iodoimidazo[1,2-a]pyridine-3-carbonitrile E22-2

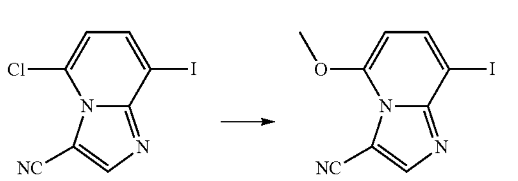

E22-1 E22-2

Into a 25 mL round-bottom flask, E22-1 (500 mg, 1.65 mmol) and methanol (5 ml) were added and in an ice bath, a sodium methoxide solution (0.5 ml) was added. The reaction was warmed to 80° C. and the mixture was reacted for 1 hour while the temperature was kept at 80° C. Upon completion of the reaction (as detected by LCMS), water (10 ml) was added and the resulting mixture was extracted with ethyl acetate (20 ml*3). The organic phases were combined, dried over anhydrous sodium sulfate and spin-dried. The crude obtained was purified by Flash column chromatography (eluents:petroleum ether:ethyl acetate=1:1) to obtain a white solid, E22-2 (300 mg, 60% yield).

LCMS: m/z 299.9 $[M+H]^+$.

Step 3: The following compound can be obtained with E22-2 and intermediate B3 as the raw materials using the method of example 6:

8-(5-(((5-fluoro-2,3-dihydrobenzofuran-4-yl)methyl)amino)-[1,2,4]triazolo[4,3-c]pyrimidin-8-yl)-5-methoxyimidazo[1,2-a]pyridine-3-carbonitrile

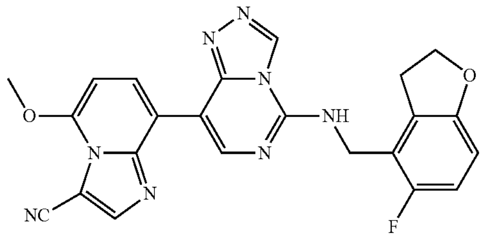 [SMILES: COc1ccc(-c2cnc(NCc3c(F)ccc4c3CCO4)n3cnnc23)c2ncc(C#N)n12]

$^1$H NMR (400 MHz, DMSO-$d_6$) δ 9.52 (s, 1H), 9.18 (s, 1H), 8.96 (d, J=8.3 Hz, 1H), 8.83 (s, 1H), 8.51 (s, 1H), 6.96 (s, 1H), 6.90 (d, J=8.4 Hz, 1H), 6.71 (dd, J=8.6, 3.8 Hz, 1H), 4.76 (s, 2H), 4.55 (t, J=8.7 Hz, 2H), 4.21 (s, 3H), 3.27-3.23 (m, 2H) ppm; LCMS: m/z 457.1 $[M+H]^+$.

The following compound can be synthesized with 8-iodo-5-chloro-[1,2,4]triazolo[1,5-a]pyridine, tetrahydropyrrole and intermediate B3 as the raw materials using the method of example 109:

Example 122: N-((5-fluoro-2,3-dihydrobenzofuran-4-yl)methyl)-8-(5-(pyrrolidin-1-yl)-[1,2,4]triazolo[1,5-a]pyridin-8-yl)-[1,2,4]triazolo[4,3-c]pyrimidin-5-amine

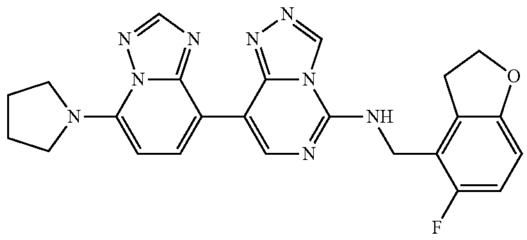 [SMILES: Fc1ccc2c(c1CNc1ncc(-c3ccc(N4CCCC4)n4ncnc34)c3nncn13)CCO2]

$^1$H NMR (400 MHz, DMSO-$d_6$) δ 9.51 (s, 1H), 9.24 (s, 1H), 9.02 (d, J=8.4 Hz, 1H), 8.68 (s, 1H), 8.46 (s, 1H), 7.00-6.91 (m, 1H), 6.71 (dd, J=8.6, 3.8 Hz, 1H), 6.41 (d, J=8.5 Hz, 1H), 4.75 (s, 2H), 4.55 (t, J=8.7 Hz, 2H), 3.82 (s, 4H), 3.31 (s, 2H), 2.00 (s, 4H) ppm; LCMS: m/z 472.1 $[M+H]^+$.

The following compound can be synthesized with 8-iodo-5-chloro-[1,2,4]triazolo[1,5-a]pyridine, 4-(piperidin-4-yl)morpholine and intermediate B3 as the raw materials using the method of example 109:

Example 123: N-((5-fluoro-2,3-dihydrobenzofuran-4-yl)methyl)-8-(5-(4-morpholinopiperidin-1-yl)-[1,2,4]triazolo[1,5-a]pyridin-8-yl)-[1,2,4]triazolo[4,3-c]pyrimidin-5-amine

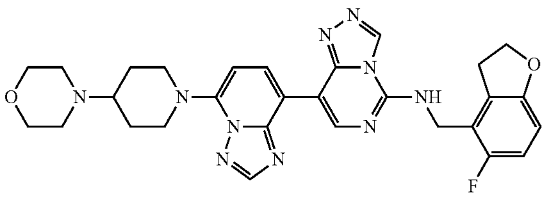 [SMILES: Fc1ccc2c(c1CNc1ncc(-c3ccc(N4CCC(N5CCOCC5)CC4)n4ncnc34)c3nncn13)CCO2]

$^1$H NMR (400 MHz, DMSO-$d_6$) δ 9.52 (s, 1H), 9.31 (s, 1H), 9.07 (d, J=8.3 Hz, 1H), 8.78 (s, 1H), 8.58 (s, 1H), 7.01-6.92 (m, 1H), 6.78 (d, J=8.3 Hz, 1H), 6.71 (dd, J=8.7, 3.9 Hz, 1H), 4.76 (s, 2H), 4.55 (t, J=8.7 Hz, 2H), 4.12 (d, J=11.9 Hz, 2H), 3.72-3.50 (m, 4H), 3.32-3.28 (m, 2H), 2.91 (t, J=11.1 Hz, 2H), 2.58-2.51 (m, 4H), 2.43 (d, J=9.8 Hz, 1H), 1.96 (d, J=12.3 Hz, 2H), 1.66 (dd, J=20.5, 11.4 Hz, 2H) ppm; LCMS: m/z 571.2 $[M+H]^+$.

The following compound can be synthesized with 8-iodo-5-chloro-[1,2,4]triazolo[1,5-a]pyridine, 2-oxa-6-azaspiro[3.3]heptane and intermediate B3 as the raw materials using the method of example 109:

Example 124: 8-(5-(2-oxa-6-azaspiro[3.3]heptan-6-yl)-[1,2,4]triazolo[1,5-a]pyridin-8-yl)-N-((5-fluoro-2,3-dihydrobenzofuran-4-yl)methyl)-[1,2,4]triazolo[4,3-c]pyrimidin-5-amine

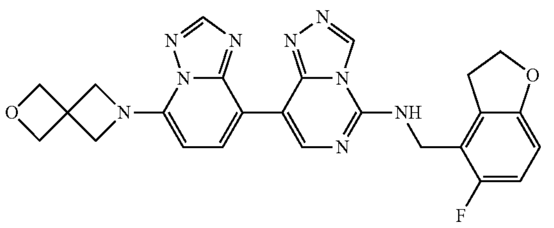 [SMILES: Fc1ccc2c(c1CNc1ncc(-c3ccc(N4CC5(COC5)C4)n4ncnc34)c3nncn13)CCO2]

$^1$H NMR (400 MHz, DMSO-$d_6$) δ 9.51 (s, 1H), 9.25 (s, 1H), 9.05 (d, J=8.3 Hz, 1H), 8.70 (s, 1H), 8.50 (s, 1H), 7.02-6.91 (m, 1H), 6.71 (dd, J=8.6, 3.9 Hz, 1H), 6.26 (d, J=8.4 Hz, 1H), 4.76 (d, J=11.0 Hz, 6H), 4.62-4.44 (m, 6H), 3.31 (d, J=8.8 Hz, 2H) ppm; LCMS: m/z 500.2 $[M+H]^+$.

Example 125: 5-(dimethylamino)-8-(5-(((5-fluoro-2,3-dihydrobenzofuran-4-yl)methyl)amino)-[1,2,4]triazolo[4,3-c]pyrimidin-8-yl)imidazo[1,2-a]pyridine-3-carbonitrile Step 1: 5-(dimethylamino)-8-iodoimidazo[1,2-a]pyridine-3-carbonitrile E22-3

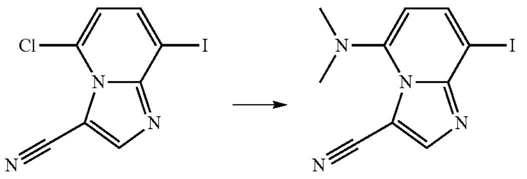

E22-1 E22-3

Into a 25 mL round-bottom flask, E22-1 (100 mg, 0.329 mmol) and N,N-dimethylformamide (3 ml) were added. In an ice bath, solid dimethylamine hydrochloride (80 mg, 0.99 mmol) and potassium carbonate (140 mg, 0.99 mmol) were added. The reaction system was warmed to 110° C. and stirred overnight while the temperature was kept at 110° C. Upon completion of the reaction (as detected by LCMS), water (5 mL) was added and the resulting mixture was extracted with ethyl acetate (10 mL*3). The organic layers were collected, dried over anhydrous sodium sulfate and spin-dried. The crude was purified by Flash column chromatography (eluents:petroleum ether:ethyl acetate=12:1) to obtain a white solid E22-3 (80 mg, 77.6% yield).

LCMS: m/z 313.0 $[M+H]^+$.

Step 2: The following compound can be obtained with E22-3 and intermediate B3 as the raw materials using the method of example 6:

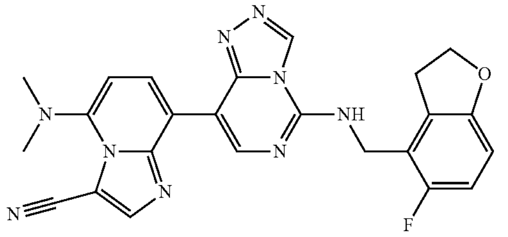 [SMILES: CN(C)c1ccc(-c2cnc(NCc3c(F)ccc4c3CCO4)n3cnnc23)c2ncc(C#N)n12]

$^1$H NMR (400 MHz, DMSO-$d_6$) δ 9.52 (s, 1H), 9.19 (s, 1H), 8.87 (d, J=8.0 Hz, 1H), 8.86 (s, 1H), 8.53 (s, 1H), 7.06 (d, J=8.1 Hz, 1H), 7.02-6.92 (m, 1H), 6.72 (dd, J=8.6, 3.9 Hz, 1H), 4.77 (d, J=4.3 Hz, 2H), 4.55 (t, J=8.7 Hz, 2H), 3.31 (s, 2H), 2.86 (s, 6H) ppm; LCMS: m/z 470.1 $[M+H]^+$.

The following compound can be obtained with E22-1, morpholine and intermediate B3 as the raw materials using the method of example 125:

Example 126: 8-(5-(((5-fluoro-2,3-dihydrobenzofuran-4-yl)methyl)amino)-triazolo[4,3-c]pyrimidin-8-yl)-5-morpholinoimidazo[1,2-a]pyridine-3-carbonitrile

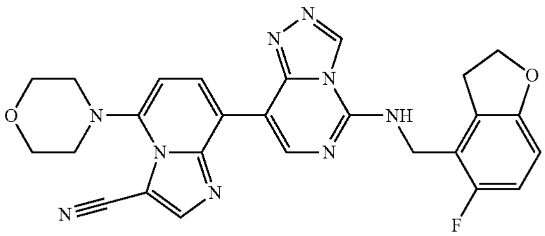 [SMILES: N#Cc1cnc2c(-c3cnc(NCc4c(F)ccc5c4CCO5)n4cnnc34)ccc(N3CCOCC3)n12]

$^1$H NMR (400 MHz, DMSO-$d_6$) δ 9.52 (s, 1H), 9.19 (s, 1H), 8.88 (d, J=8.0 Hz, 2H), 8.54 (s, 1H), 7.14 (d, J=8.1 Hz, 1H), 7.01-6.93 (m, 1H), 6.72 (dd, J=8.7, 3.9 Hz, 1H), 4.76 (s, 2H), 4.56 (t, J=8.7 Hz, 2H), 3.93 (d, J=12.5 Hz, 4H), 3.33 (s, 2H), 3.28 (s, 2H), 3.04 (dd, J=16.6, 5.9 Hz, 2H) ppm; LCMS: m/z 512.2 [M+H]$^+$.

The following compound can be synthesized with 4-bromo-2H-benzo[d][1,2,3]triazole and intermediate B3 as the raw materials using the method of example 6:

Example 127: 8-(1H-benzo[d][1,2,3]triazol-7-yl)-N-((5-fluoro-2,3-dihydrobenzofuran-4-yl)methyl)-[1,2,4]triazolo[4,3-c]pyrimidin-5-amine

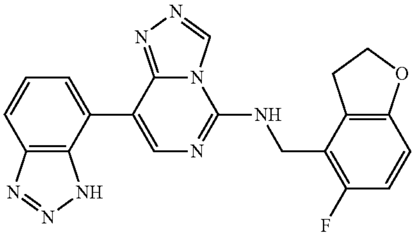

$^1$H NMR (400 MHz, DMSO-$d_6$) δ 9.67 (s, 1H) 9.11 (br s, 1H) 8.99 (br s, 1H) 8.47 (d, J=7.1 Hz, 1H) 7.84 (d, J=8.3 Hz, 1H) 7.55-7.65 (m, 1H) 6.95-7.00 (m, 1H) 6.71 (dd, J=8.6, 3.9 Hz, 1H) 4.79 (br s, 2H) 4.55 (t, J=8.7 Hz, 2H) 3.36 (t, J=8.7 Hz, 2H) ppm; LCMS: m/z 403.1 [M+H]$^+$.

The following compound can be obtained with E20-1, N1,N1,N2-trimethylethane-1,2-diamine and intermediate B3 as the raw materials using the method of example 115:

Example 128: N1-((8-(5-(((5-fluoro-2,3-dihydrobenzofuran-4-yl)methyl)amino)-triazolo[4,3-c]pyrimidin-8-yl)-[1,2,4]triazolo[1,5-a]pyridin-5-yl)methyl)-N1,N2,N2-trimethylethane-1,2-diamine

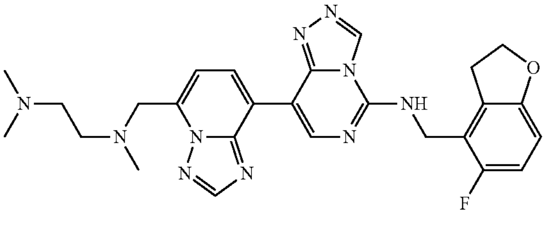 [SMILES: CN(C)CCN(C)Cc1ccc(-c2cnc(NCc3c(F)ccc4c3CCO4)n3cnnc23)c2ncnn12]

$^1$H NMR (400 MHz, DMSO-$d_6$) δ 9.54 (s, 1H), 9.43 (s, 1H), 9.14 (d, J=7.7 Hz, 1H), 8.94 (s, 1H), 8.62 (s, 1H), 7.40 (d, J=7.7 Hz, 1H), 6.97 (t, J=9.5 Hz, 1H), 6.72 (dd, J=8.5, 3.7 Hz, 1H), 4.78 (s, 2H), 4.56 (s, 2H), 4.11 (s, 2H), 3.35 (d, J=8.6 Hz, 2H), 2.64 (d, J=7.0 Hz, 2H), 2.46 (d, J=6.9 Hz, 2H), 2.36 (s, 3H), 2.15 (s, 6H) ppm; LCMS: m/z 517.2 [M+H]$^+$.

The following compound can be synthesized with 8-bromo-5-chloro-[1,2,4]triazolo[1,5-a]pyridine, 2-methylmorpholine and intermediate B3 as the raw materials using the method of example 109:

Example 129: N-((5-fluoro-2,3-dihydrobenzofuran-4-yl)methyl)-8-(5-(2-methylmorpholino)-[1,2,4]triazolo[1,5-a]pyridin-8-yl)-[1,2,4]triazolo[4,3-c]pyrimidin-5-amine

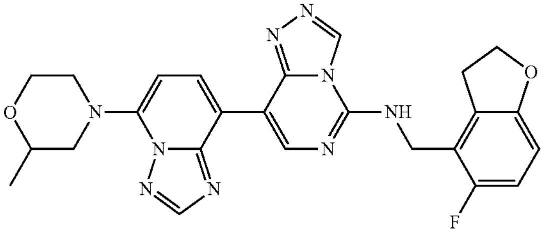

$^1$H NMR (400 MHz, DMSO-$d_6$) δ 9.53 (s, 1H), 9.32 (s, 1H), 9.09 (d, J=8.2 Hz, 1H), 8.81 (s, 1H), 8.60 (s, 1H), 6.97 (s, 1H), 6.80 (d, J=8.3 Hz, 1H), 6.76-6.67 (m, 1H), 4.77 (d, J=4.0 Hz, 2H), 4.55 (t, J=8.7 Hz, 2H), 3.99 (d, J=11.3 Hz, 3H), 3.82 (dd, J=19.0, 9.7 Hz, 2H), 3.31 (s, 2H), 2.96 (dd, J=11.6, 8.7 Hz, 1H), 2.70 (d, J=10.6 Hz, 1H), 1.19 (d, J=6.2 Hz, 3H) ppm; LCMS: m/z 502.2 [M+H]$^+$.

Example 130: 5-((dimethylamino)methyl)-8-(5-(((5-fluoro-2,3-dihydrobenzofuran-4-yl)methyl)amino)-[1,2,4]triazolo[4,3-c]pyrimidin-8-yl)imidazo[1,2-a]pyridine-3-carbonitrile Step 1: 8-bromo-5-methylimidazo[1,2-a]pyridine-3-carbonitrile E23-1

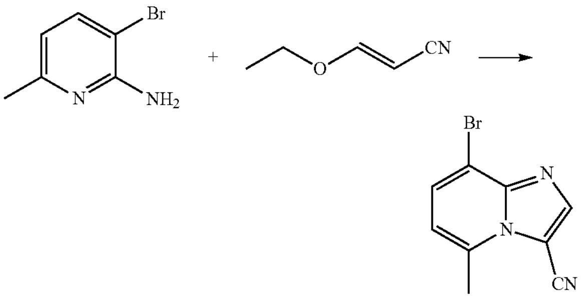

E23-1

At 02, to a solution of 3-ethoxyprop-2-enenitrile (2.6 g, 25.7 mmol) in 1,4dioxane (30 mL) and water (10 mL), N-bromosuccinimide (3.81 g, 16.1 mmol) was added. The mixture was stirred at 0 for 2 hours. Then compound 3-bromo-6-methylpyridin-2-amine (1 g, 5.35 mmol) was added into the mixture. The reaction system was warmed to room temperature and stirred for 2 h. Subsequently, the reaction system was stirred at 90° C. for 16 hours. The reaction was completed (detected by LCMS). Water (30 mL) was added into the reaction system and the reaction mixture was extracted with ethyl acetate (30 mL*3). The organic layers were combined and concentrated. The crude product was purified by Flash column chromatography (eluents: petroleum ether:ethyl acetate=1:1) to obtain E23-1 (600 mg, 47% yield).

LCMS: m/z 236.1 $[M+H]^+$.

Step 2: 8-bromo-5-(bromomethyl)imidazo[1,2-a]pyridine-3-carbonitrile E23-2

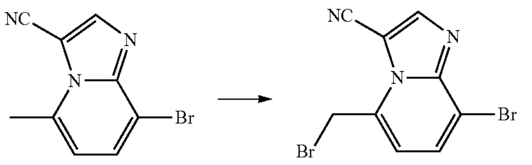

E23-1 E23-2

To a solution of compound E23-1 (450 mg, 1.91 mmol) in carbon tetrachloride (10 mL), N-bromosuccinimide (407 mg, 2.29 mmol) and azobisisobutyronitrile (47 mg, 0.29 mmol) were added and the mixture was stirred under nitrogen at 80° C. for 16 h. The reaction was successfully carried out (as shown by LCMS). The mixture was concentrated and purified by Flash column chromatography (petroleum ether: ethyl acetate=2:1) to obtain E23-2 (350 mg, 58% yield).

$^1$H NMR (400 MHz, DMSO-$d_6$) δ 8.66 (s, 1H), 8.00 (d, J=7.7 Hz, 1H), 7.39 (d, J=7.7 Hz, 1H), 5.28 (s, 2H). LCMS: m/z 313.9 $[M+H]^+$.

Step 3: 8-bromo-5-((dimethylamino)methyl)imidazo[1,2-a]pyridine-3-carbonitrile E23-3

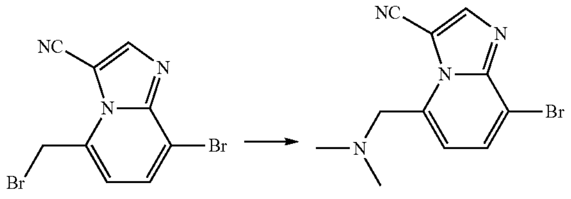

E23-2 E23-3

Into a 25 mL reaction vial, E23-2 (100 mg, 0.32 mmol) and a solution of dimethylamine in tetrahydrofuran (2 M, 10 ml) were added. The reaction system was stirred at 70° C. for 15 hours. The reaction solution was spin-dried and then extracted with ethyl acetate and water. The organic layer was spin-dried and then purified by Flash column chromatography (petroleum ether:ethyl acetate=2:1) to obtain E23-3 (70 mg, 78.4% yield).

LCMS: m/z 279.0, 281.0 $[M+H]^+$.

Step 4: The following compound can be obtained with E23-3 and intermediate B3 as the raw materials using the method of example 6:

N-((5-fluoro-2,3-dihydrobenzofuran-4-yl)methyl)-8-(5-(2-methylmorpholino)-[1,2,4]triazolo[1,5-a]pyridin-8-yl)-[1,2,4]triazolo[4,3-c]pyrimidin-5-amine

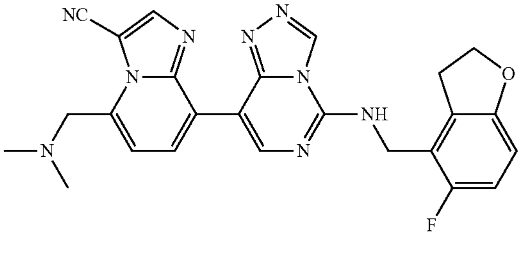 [SMILES: CN(C)Cc1ccc(-c2cnc(NCc3c(F)ccc4c3CCO4)n3cnnc23)c2ncc(C#N)n12]

$^1$H NMR (400 MHz, DMSO-$d_6$) δ 9.47 (s, 1H), 9.19 (s, 1H), 8.89 (s, 1H), 8.76 (d, J=7.6 Hz, 1H), 8.47 (s, 1H), 7.25 (d, J=7.7 Hz, 1H), 6.93-6.87 (m, 1H), 6.65 (dd, J=8.6, 3.8 Hz, 1H), 4.71 (s, 2H), 4.50 (d, J=8.7 Hz, 2H), 3.86 (s, 2H), 3.24 (s, 2H), 2.14 (s, 6H) ppm; LCMS: m/z 484.1 $[M+H]^+$.

Example 131: N-((5-fluoro-2,3-dihydrobenzofuran-4-yl)methyl)-8-(6-fluoro-5-methyl-[1,2,4]triazolo[1,5-a]pyridin-8-yl)-[1,2,4]triazolo[4,3-c]pyrimidin-5-amine Step 1: 3-bromo-5-fluoro-6-methylpyridin-2-amine E24-1

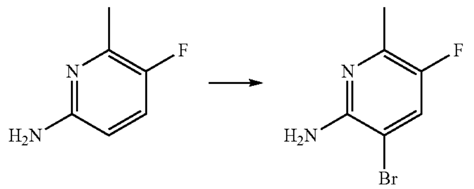

E24-1

At 0° C., to a solution of 5-fluoro-6-methylpyridin-2-amine (4.50 g, 35.7 mmol) in acetonitrile (50 mL), N-bromosuccinimide (7.62 g, 42.8 mmol) was added in batches. The mixture was slowly warmed to room temperature and stirred and reacted at room temperature for 12 hours. Upon completion of the reaction, the mixture was diluted by adding ethyl acetate (100 mL) and then washed with a saturated aqueous sodium carbonate solution (50 mL*3) and saturated brine (80 mL), respectively. The organic phase was dried and concentrated to obtain a crude E24-1 (7.40 g, 60% yield), which was directly used in the next step.

$^1$H NMR (400 MHz, $CDCl_3$) δ 7.38 (d, J=8.0 Hz, 1H), 4.76 (br s, 2H), 2.31 (d, J=2.8 Hz, 3H) ppm; LCMS: m/z 204.9 $[M+H]^+$.

Step 2: (E)-N'-(3-bromo-5-fluoro-6-methylpyridin-2-yl)-N,N-dimethylformamidine E24-2

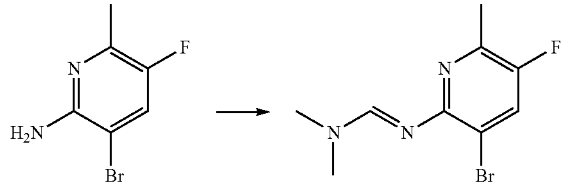

E24-1 E24-2

Into a 250 mL single-necked flask, E24-1 (3.00 g, 14.6 mmol), N,N-dimethylformamide dimethylacetal (3.49 g, 29.3 mmol), and toluene (100 mL) were added sequentially. The reaction system was warmed to 110° C. and reacted for 12 hours. No raw material was left (as detected by LCMS) and the reaction solution was concentrated to obtain a crude E24-2 (3.80 g), which was directly used in the next step.

LCMS: m/z 261.9 $[M+H]^+$.

Step 3: (E)-N-(3-bromo-5-fluoro-6-methylpyridin-2-yl)-N'-hydroxyformamidine E24-3

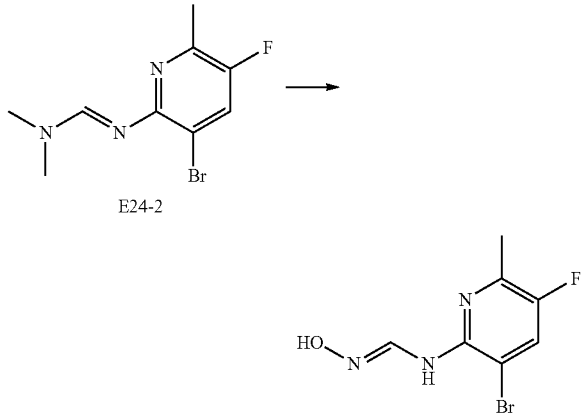

E24-2 E24-3

Into a 250 mL single-necked flask, E24-2 (3.80 g, 14.6 mmol), hydroxylamine hydrochloride (2.03 g, 29.2 mmol), sodium acetate (2.40 g, 29.2 mmol) and ethanol (60 mL) were added sequentially. The reaction system was warmed to 55° C. under nitrogen atmosphere and reacted for 12 hours. The reaction was completed (monitored by LCMS). The reaction system was cooled to room temperature. Ethanol was removed from the reaction mixture by concentration under reduced pressure so as to obtain a crude, (E)-N-(3-bromo-5-fluoro-6-methylpyridin-2-yl)-N'-hydroxyformamidine. The crude was slurried with water (50 mL) and the solid was collected and dried to obtain a brown solid product E24-3 (3.08 g, 85.0% yield).

$^1$H NMR (400 MHz, $CDCl_3$) δ 8.26 (br s, 1H), 8.08 (s, 2H), 7.50 (d, J=7.6 Hz, 1H), 2.39 (d, J=2.8 Hz, 3H) ppm; LCMS: m/z 247.9 $[M+H]^+$.

Step 4: 8-bromo-6-fluoro-5-methyl-[1,2,4]triazolo[1,5-a]pyridine E24-4

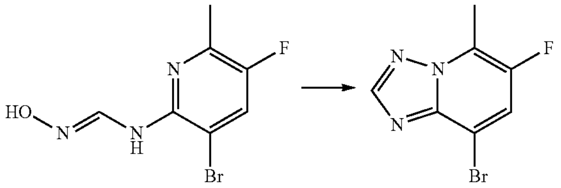

E24-3 E24-4

At 0° C., to a solution of E24-3 (3.08 g, 12.4 mmol) in tetrahydrofuran (30 mL), trifluoroacetic anhydride (7.82 g, 37.3 mmol) was added dropwise. The mixture was slowly warmed to room temperature and then stirred and reacted at room temperature for 12 hours. Upon completion of the reaction, the reaction was quenched by adding saturated aqueous sodium hydrogen carbonate solution (50 mL) to the mixture at 0° C. The mixture was diluted by adding water (50 mL) and then extracted with dichloromethane (100 mL*3). The combined organic phase was washed with saturated brine (30 mL*2), dried and concentrated. The concentrate was purified by silica gel column chromatography (petroleum ether:ethyl acetate=10:1) to obtain a yellow solid product E24-4 (2.10 g, 73.5% yield).

$^1$H NMR (400 MHz, $CDCl_3$) δ 8.41 (s, 1H), 7.74 (d, J=8.0 Hz, 1H), 2.74 (d, J=2.8 Hz, 3H) ppm; LCMS: m/z 229.8 $[M+H]^+$.

Step 5: The following compound can be obtained with E24-4 and intermediate B3 as the raw materials using the method of example 6:

N-((5-fluoro-2,3-dihydrobenzofuran-4-yl)methyl)-8-(6-fluoro-5-methyl-[1,2,4]triazolo[1,5-a]pyridin-8-yl)-[1,2,4]triazolo[4,3-c]pyrimidin-5-amine

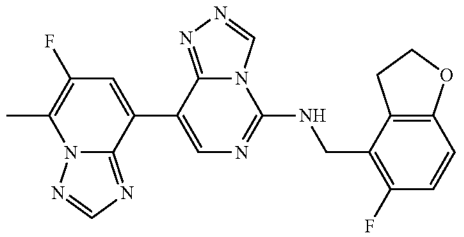 [SMILES: Cc1c(F)cc(-c2cnc(NCc3c(F)ccc4c3CCO4)n3cnnc23)c2ncnn12]

$^1$H NMR (400 MHz, DMSO-$d_6$) δ 9.62 (s, 1H), 9.57 (s, 1H), 9.32 (d, J=11.5 Hz, 1H), 9.09-9.04 (m, 1H), 8.70 (s, 1H), 6.98 (t, J=9.5 Hz, 1H), 6.73 (dd, J=3.9, 8.6 Hz, 1H), 4.80 (d, J=3.4 Hz, 2H), 4.56 (t, J=8.7 Hz, 2H), 3.64-3.58 (m, 1H), 3.32-3.30 (m, 2H), 2.76 (d, J=2.5 Hz, 3H) ppm; LCMS: m/z 435.1 $[M+H]^+$.

The following compound can be obtained with E20-1, imidazole and intermediate B3 as the raw materials using the method of example 115:

Example 132: 8-(5-((1H-imidazol-1-yl)methyl)-[1,2,4]triazolo[1,5-a]pyridin-8-yl)-N-((5-fluoro-2,3-dihydrobenzofuran-4-yl)methyl)-[1,2,4]triazolo[4,3-c]pyrimidin-5-amine

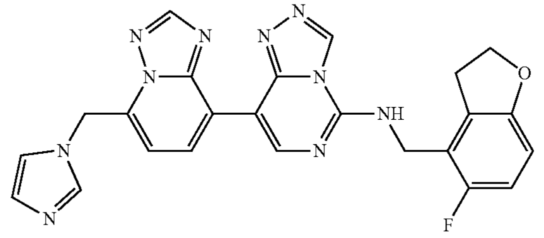 [SMILES: Fc1ccc2c(c1CNc1ncc(-c3ccc(Cn4ccnc4)n4ncnc34)c3nncn13)CCO2]

$^{1}H$ NMR (400 MHz, DMSO-$d_6$) δ 9.54-9.51 (m, 1H), 9.44 (s, 1H), 9.12 (d, J=7.8 Hz, 1H), 8.72 (s, 1H), 7.90 (s, 1H), 7.35 (s, 1H), 7.07 (d, J=7.9 Hz, 1H), 6.96 (s, 1H), 6.72 (s, 1H), 5.81 (s, 2H), 4.78 (s, 2H), 4.55 (s, 2H), 3.17-3.15 (m, 2H) ppm; LCMS: m/z 483.1 $[M+H]^+$.

Example 133: N-((5-fluoro-2,3-dihydrobenzofuran-4-yl)methyl)-8-(5-methyl-triazolo[4,3-a]pyridin-8-yl)-[1,2,4]triazolo[4,3-c]pyrimidin-5-amine Step 1: 3-bromo-2-hydrazino-6-methylpyridine E25-1

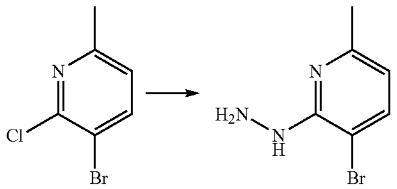

E25-1

3-bromo-2-chloro-6-methylpyridine (4.50 g, 21.80 mmol) was dissolved in N-methylpyrrolidone (12 mL). At 25° C., hydrazine hydrate (4.32 mL, 87.18 mmol) was added into the mixture. In a hydrothermal synthesis reactor, the reaction mixture was reacted at 110° C. for 16 hours. After completion of the reaction, water (100 mL) was added into the reaction solution and then the resulting mixture was extracted with ethyl acetate. The organic phases were mixed, dried and concentrated to obtain a crude E25-1 (3.50 g, 79.5% yield) and the crude was directly used in the next step.

$^{1}H$ NMR (400 MHz, DMSO-$d_6$) δ 7.59 (d, J=7.8 Hz, 1H) 7.24 (s, 1H) 6.43 (d, J=7.6 Hz, 1H) 4.21 (s, 2H) 2.32 (s, 3H) ppm; LCMS: m/z 203.9 $[M+H]^+$.

Step 2: 8-bromo-5-methyl-[1,2,4]triazole[4,3-a]pyridine E25-2

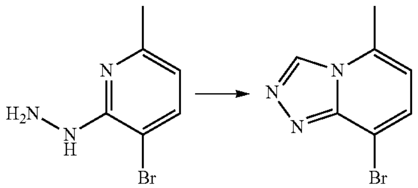

E25-1 E25-2

Into a 100 mL single-necked flask, E25-1 (3.5 g, 17.0 mmol), trimethylorthoformate (33.0 g, 311 mmol) and trifluoroacetic acid (39.5 mg, 0.35 mmol) were added sequentially. The reaction solution was warmed to 100° C. and reacted under nitrogen atmosphere for 10 hours. No raw material was left (as detected by TLC) and after the reaction solution was spin-dried, the crude was slurried with methyl tert-butyl ether (20 mL) and then filtered. The resulting solid was dried under vacuum to obtain E25-2 (3 g, 81.6% yield).

$^{1}H$ NMR (400 MHz, $CDCl_3$) δ 8.84 (s, 1H) 7.48 (d, J=7.1 Hz, 1H) 6.57 (dd, J=7.2, 0.8 Hz, 1H) 2.66 (d, J=0.6 Hz, 3H) ppm; LCMS: m/z 211.8 $[M+H]^+$.

Step 3: The following compound can be obtained with E25-2 and intermediate B3 as the raw materials using the method of example 6:

N-((5-fluoro-2,3-dihydrobenzofuran-4-yl)methyl)-8-(5-methyl-[1,2,4]triazolo[4,3-a]pyridin-8-yl)-[1,2,4]triazolo[4,3-c]pyrimidin-5-amine

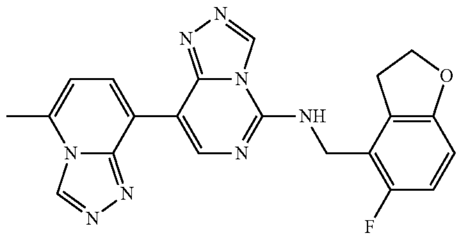 [SMILES: Cc1ccc(-c2cnc(NCc3c(F)ccc4c3CCO4)n3cnnc23)c2nncn12]

$^{1}H$ NMR (400 MHz, DMSO-$d_6$) δ 9.63 (s, 1H), 9.55 (s, 1H), 9.39 (s, 1H), 8.96 (d, J=7.3 Hz, 1H), 8.92 (s, 1H), 7.02 (d, J=7.3 Hz, 1H), 6.97 (t, J=9.4 Hz, 1H), 6.72 (dd, J=3.8, 8.8 Hz, 1H), 4.79 (br d, J=4.4 Hz, 2H), 4.56 (t, J=8.8 Hz, 2H), 3.37-3.40 (m, 2H), 2.72 (s, 3H) ppm; LCMS: m/z 417.0 $[M+H]^+$.

Example 134: N-((5-fluoro-2,3-dihydrobenzofuran-4-yl)methyl)-8-(5-methyl-triazolo[1,5-c]pyrimidin-8-yl)-[1,2,4]triazolo[4,3-c]pyrimidin-5-amine Step 1: 5-bromo-4-amino-2-methylpyrimidine E26-1

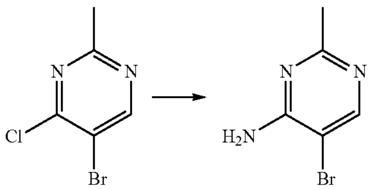

E26-1

5-bromo-4-chloro-2-methylpyrimidine (1.9 g, 9.16 mmol) and ammonia water (7.28 g, 58.16 mmol, 28% purity) were dissolved in N-methylpyrrolidone (12 mL). In a hydrothermal synthesis reactor, the mixture was reacted at 110° C. for 4 hours. After completion of the reaction, water (20 mL) was added into the reaction solution and then the resulting mixture was extracted with ethyl acetate. The organic phases were mixed, dried and concentrated. The crude was separated by column chromatography (mobile phase:petroleum ether/ethyl acetate=1:1) to obtain E26-1 (800 mg, 46.4% yield).

$^1$H NMR (400 MHz, $CDCl_3$) δ 8.27 (s, 1H) 5.56 (br s, 2H) 2.47 (s, 3H) ppm; LCMS: m/z 187.8 $[M+H]^+$.

Step 2: (E)-N'-(5-bromo-2-methylpyrimidin-4-yl)-N,N-dimethylformamidine E26-2

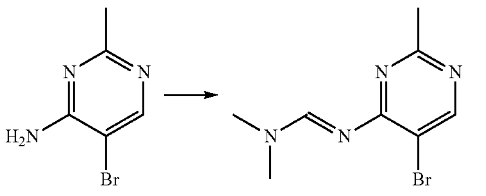

E26-1 E26-2

E26-1 (0.5 g, 2.66 mmol) and 1,1-dimethoxy-N,N-dimethylmethanamine (633 mg, 5.32 mmol) were dissolved in toluene (10 mL). The reaction solution was reacted at 100° C. under nitrogen atmosphere for 10 hours. The reaction was completed (monitored by LCMS). The reaction solution was concentrated to dryness to obtain E26-2 (0.65 g, 100% yield).

$^1$H NMR (400 MHz, $CDCl_3$) δ 8.61 (s, 1H) 8.45 (s, 1H) 3.20 (s, 3H), 3.18 (s, 3H), 2.53 (s, 3H) ppm; LCMS: m/z 243.1 $[M+H]^+$.

Step 3: (E)-N-(5-bromo-2-methylpyrimidin-4-yl)-N'-hydroxyformamidine E26-3

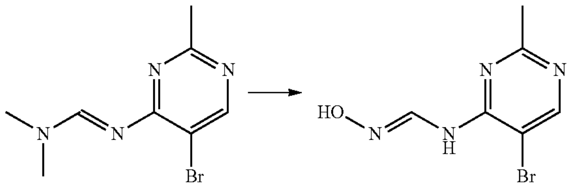

E26-2 E26-3

E26-2 (0.646 g, 2.66 mmol), hydroxylamine hydrochloride (369 mg, 5.31 mmol) and anhydrous sodium acetate (479 mg, 5.85 mmol) were dissolved in anhydrous ethanol (10 mL). The reaction solution was reacted at 50° C. under nitrogen atmosphere for 4 hours. The reaction was completed (detected by TLC). The reaction solution was filtered and the filter cake was rinsed with water and dried to obtain E26-3 (400 mg, 65.1% yield).

$^1$H NMR (400 MHz, DMSO-$d_6$) δ 11.08 (br s, 1H) 8.59 (s, 1H) 8.24 (br s, 1H) 7.96 (s, 1H) 2.47 (s, 3H) ppm; LCMS: m/z 231.0 $[M+H]^+$.

Step 4: 8-bromo-5-methyl-[1,2,4]triazole[1,5-c]pyrimidine E26-4

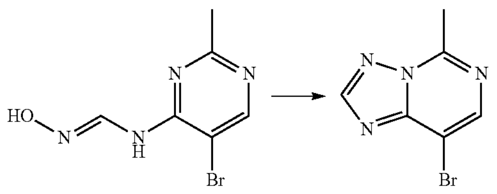

E26-3 E26-4

At 0° C., to a solution of E26-3 (750 mg, 3.25 mmol) in anhydrous tetrahydrofuran (25 mL), trifluoroacetic anhydride (2.05 g, 9.74 mmol) was added dropwise. The reaction mixture was warmed to 25° C. naturally and reacted for 12 hours. The reaction was completed (detected by TLC). After the reaction solution was spin-dried, saturated sodium hydrogen carbonate solution (20 mL) was added and the mixture was extracted with dichloromethane/methanol (100 mL, V/V=10:1). After the organic phase was dried and concentrated, the resulting crude was separated by Flash silica gel column chromatography to obtain E26-4 (320 mg, 46.2% yield).

$^1$H NMR (400 MHz, DMSO-$d_6$) δ 8.72 (s, 1H) 8.47 (s, 1H) 2.86 (s, 3H) ppm; LCMS: m/z 212.8 $[M+H]^+$.

Step 5: The following compound can be obtained with E26-4 and intermediate B3 as the raw materials using the method of example 6:

N-((5-fluoro-2,3-dihydrobenzofuran-4-yl)methyl)-8-(5-methyl-[1,2,4]triazolo[1,5-c]pyrimidin-8-yl)-[1,2,4]triazolo[4,3-c]pyrimidin-5-amine

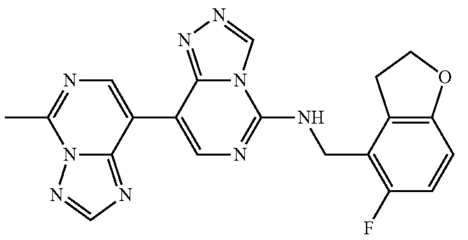 [SMILES: Cc1ncc(-c2cnc(NCc3c(F)ccc4c3CCO4)n3cnnc23)c2ncnn12]

$^1$H NMR (400 MHz, DMSO-$d_6$) δ 9.68 (s, 1H), 9.55 (s, 1H), 9.38 (s, 1H), 9.02 (br t, J=5.1 Hz, 1H), 8.78 (s, 1H), 7.00-6.93 (m, 1H), 6.72 (dd, J=3.9, 8.6 Hz, 1H), 4.78 (d, J=4.9 Hz, 2H), 4.55 (t, J=8.8 Hz, 2H), 3.32-3.30 (m, 2H), 2.96 (s, 3H) ppm; LCMS: m/z 418.0 $[M+H]^+$.

Example 135: 2-(8-(5-(((5-fluoro-2,3-dihydrobenzofuran-4-yl)methyl)amino)-triazolo[4,3-c]pyrimidin-8-yl)-[1,2,4]triazolo[1,5-a]pyridin-5-yl)propan-2-ol Step 1: (E)-5-bromo-6-(((dimethylamino)methylene)amino)-pyridine-2-carboxylic acid methyl ester E27-1

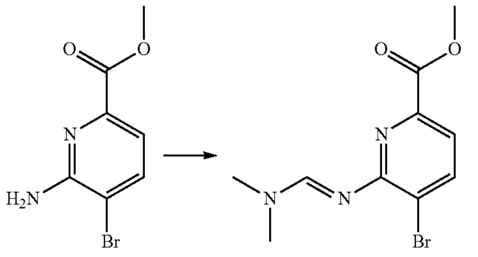

E27-1

(E)-5-bromo-6-(((dimethylamino)methylene)amino)-pyridine-2-carboxylic acid methyl ester (5.0 g, 21.6 mmol) and 1,1-dimethoxy-N,N-dimethyl methanamine (5.16 g, 43.3 mmol) were dissolved in toluene (100 mL). The reaction solution was warmed to 110° C. and reacted for 4 hours. No raw material was left (as detected by TLC) and the reaction solution was concentrated to obtain a crude E27-1 (6.00 g).

LCMS: m/z 285.7 $[M+H]^+$.

Step 2: (E)-5-bromo-6-(((hydroxyamino)methylene) amino)-pyridine-2-carboxylic acid methyl ester E27-2

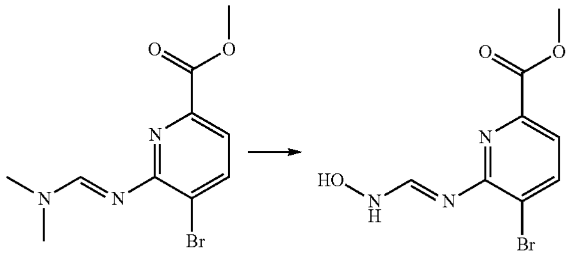

E27-1 E27-2

Into a reaction vial, E27-1 (6.0 g, 20.97 mmol), hydroxylamine hydrochloride (2.91 g, 41.94 mmol), sodium acetate (3.44 g, 41.9 mmol) and ethanol (60 mL) were added sequentially. The reaction solution was warmed to 50° C. under nitrogen atmosphere and reacted for 4 hours. The reaction was completed (monitored by LCMS) and the reaction mixture was cooled to room temperature and filtered to obtain E27-2 (5.9 g, 85.0% yield).

$^1$H NMR (400 MHz, $CDCl_3$) δ 8.41-8.29 (m, 1H), 8.26-8.19 (m, 1H), 7.93 (d, J=7.9 Hz, 1H), 7.57 (d, J=7.9 Hz, 1H), 3.97 (s, 3H) ppm; LCMS: m/z 273.7$[M+H]^+$.

Step 3: 8-bromo-[1,2,4]triazolo[1,5-a]pyridine-5-carboxylic acid methyl ester E27-3

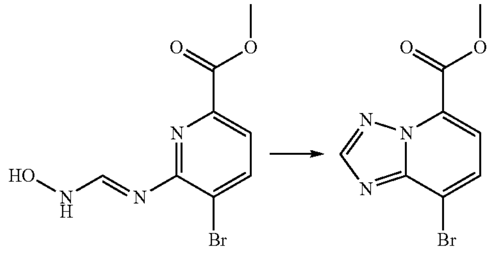

E27-2 E27-3

At room temperature, to a solution of E27-2 (10 g, 36.49 mmol) in tetrahydrofuran (100 mL), trifluoroacetic anhydride (23.0 g, 109 mmol) was added dropwise. Then the reaction system was slowly warmed to 75° C. and then stirred and reacted for 3 hours. Upon completion of the reaction, at 0° C., aqueous saturated sodium hydrogen carbonate solution (100 mL) was added to the mixture to quench the reaction. The mixture was extracted with ethyl acetate (100 mL*3). The combined organic phase was dried and concentrated. The concentrate was purified by silica gel column chromatography (petroleum ether:ethyl acetate=5:1 to 4:1) to obtain a white solid, E27-3 (5.00 g, 53.5% yield).

$^1$H NMR (400 MHz, $CDCl_3$) δ 8.52 (s, 1H), 7.85 (d, J=7.8 Hz, 1H), 7.68 (d, J=7.9 Hz, 1H), 4.08 (s, 3H) ppm; LCMS: m/z 256.0$[M+H]^+$.

Step 4: 2-(8-bromo-[1,2,4]triazolo[1,5-a]pyridin-5-yl)propan-2-ol E27-4

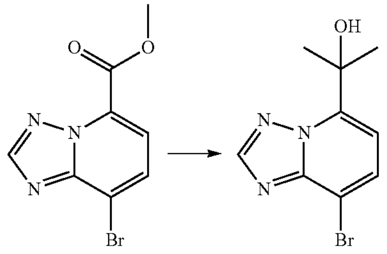

E27-3 E27-4

At −30° C., to a solution of E27-3 (500 mg, 1.95 mmol) in tetrahydrofuran (10 mL), methylmagnesium bromide (3 M, 2.60 mL) was added dropwise and at this temperature, the mixture was stirred for three hours. Upon completion of the reaction, the reaction was quenched by adding water (10 mL) to the reaction solution. The resulting mixture was extracted with ethyl acetate (10 mL*3). The combined organic phase was dried, concentrated and then purified by Flash silica gel column chromatography to obtain E27-4 (400 mg, 80.0% yield).

$^1$H NMR (400 MHz, DMSO-$d_6$) δ 8.61 (s, 1H), 8.05 (d, J=8.0 Hz, 1H), 7.28 (d, J=8.0 Hz, 1H), 5.91 (s, 1H), 1.72 (s, 6H) ppm; LCMS: m/z 255.9 [M+H]$^+$.

Step 5: The following compound can be obtained with E27-4 and intermediate B3 as the raw materials using the method of example 6:

2-(8-(5-(((5-fluoro-2,3-dihydrobenzofuran-4-yl)methyl)amino)-[1,2,4]triazolo[4,3-c]pyrimidin-8-yl)-[1,2,4]triazolo[1,5-a]pyridin-5-yl)propan-2-ol

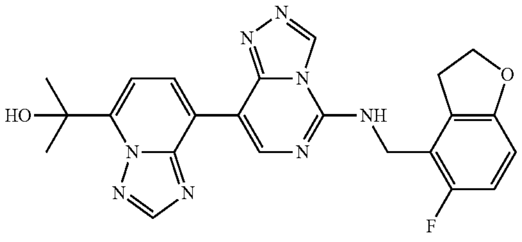 [SMILES: CC(C)(O)c1ccc(-c2cnc(NCc3c(F)ccc4c3CCO4)n3cnnc23)c2ncnn12]

$^1$H NMR (400 MHz, DMSO-$d_6$) δ 9.55 (s, 1H), 9.39 (s, 1H), 9.12 (d, J=7.9 Hz, 1H), 8.96-8.90 (m, 1H), 8.66 (s, 1H), 7.52 (d, J=8.0 Hz, 1H), 6.99-6.94 (m, 1H), 6.73-6.70 (m, 1H), 5.87 (s, 1H), 4.78 (d J=4.4 Hz, 2H), 4.58-4.53 (m, 2H), 3.40-3.35 (m, 2H) 1.78 (s, 6H) ppm; LCMS: m/z 461.2 [M+H]$^+$.

The following compound can be obtained with 3-bromo-5-methoxypyridin-2-amine and intermediate B3 as the raw materials using the method of example 96:

Example 136: 8-(5-(((5-fluoro-2,3-dihydrobenzofuran-4-yl)methyl)amino)-triazolo[4,3-c]pyrimidin-8-yl)-6-methoxyimidazo[1,2-a]pyridine-3-carbonitrile

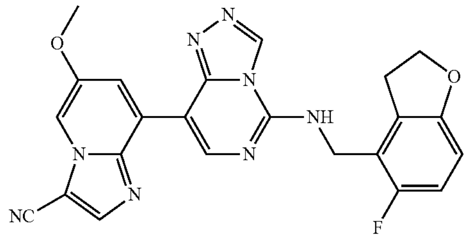 [SMILES: COc1cc(-c2cnc(NCc3c(F)ccc4c3CCO4)n3cnnc23)c2ncc(C#N)n2c1]

$^1$H NMR (400 MHz, DMSO-$d_6$) δ 9.77 (s, 1H), 9.50 (s, 1H), 9.40 (s, 1H), 8.88 (d, J=2.3 Hz, 1H), 8.46 (s, 1H), 8.13 (d, J=2.2 Hz, 1H), 7.00-6.91 (m, 1H), 6.70 (dd, J=8.7, 3.9 Hz, 1H), 4.77 (d, J=5.0 Hz, 2H), 4.54 (t, J=8.7 Hz, 2H), 3.97 (s, 3H), 3.17 (d, J=5.3 Hz, 2H) ppm; LCMS: m/z 456.0 [M+H]$^+$.

The following compound can be synthesized with 3-bromo-5-methoxypyridin-2-amine and intermediate B3 as the raw materials using the method of example 103:

Example 137: N-((5-fluoro-2,3-dihydrobenzofuran-4-yl)methyl)-8-(6-methoxy-triazolo[1,5-a]pyridin-8-yl)-[1,2,4]triazolo[4,3-c]pyrimidin-5-amine

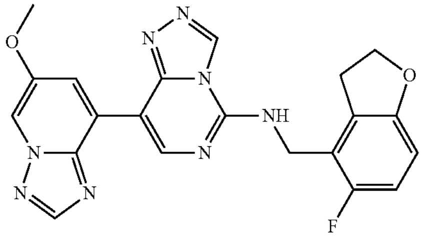 [SMILES: COc1cc(-c2cnc(NCc3c(F)ccc4c3CCO4)n3cnnc23)c2ncnn2c1]

$^1$H NMR (400 MHz, DMSO-$d_6$) δ 9.59 (s, 1H), 9.55 (s, 1H), 9.05 (d, J=2.3 Hz, 1H), 9.01 (s, 1H), 8.65 (d, J=2.3 Hz, 1H), 8.53 (s, 1H), 7.00-6.94 (m, 1H), 6.72 (dd, J=8.7, 3.9 Hz, 1H), 4.79 (s, 2H), 4.55 (t, J=8.7 Hz, 2H), 3.93 (s, 3H), 3.31 (s, 2H) ppm; LCMS: m/z 433.1 [M+H]$^+$.

Example 138: 8-(5-(((5-fluoro-2,3-dihydrobenzofuran-4-yl)methyl)amino)-triazolo[4,3-c]pyrimidin-8-yl)imidazo[1,2-a]pyridine-5-carbonitrile Step 1: 6-amino-5-bromo-pyridine-2-carboxamide E28-1

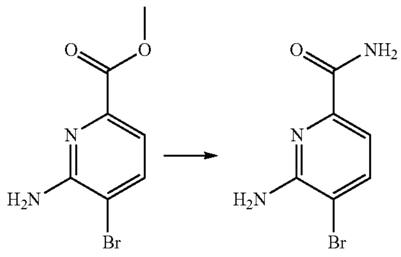

E28-1

Into a hydrothermal synthesis reactor, methyl-6-bromo-5-pyridine-2-carboxylate (5.00 g, 21.6 mmol), ammonia water (18.20 g, 145.41 mmol) and N-methylpyrrolidone (20 mL) were added sequentially and the mixture was stirred at 110° C. for 3 hours. Upon completion of the reaction (as monitored by LCMS), 100 mL of saturated brine was added to the mixture. Then the resulting mixture was filtered and the filter cake was washed with 100 mL of water to obtain a white solid, which was dried under vacuum to obtain pure E28-1 (3.00 g, 64.2% yield).

$^1$H NMR (400 MHz, $CDCl_3$) δ 7.80 (d, J=8.0 Hz, 1H), 7.57 (br s, 1H), 7.44 (d, J=8.0 Hz, 1H), 5.64 (br s, 1H), 4.99 (br s, 2H) ppm; LCMS: m/z 215.9 $[M+H]^+$.

Step 2: 6-amino-5-bromo-pyridine-2-carbonitrile E28-2

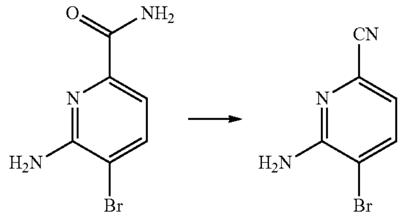

E28-1 E28-2

Under nitrogen atmosphere and at 0° C., to a solution of E28-1 (2.00 g, 9.26 mmol) and pyridine (3.66 g, 46.3 mmol) in dichloromethane (20 mL), trifluoromethanesulfonic anhydride (7.84 g, 27.77 mmol) was added dropwise. The reaction solution was warmed to 25° C. and stirred for 12 hours. The reaction was completed (monitored by LCMS) and in an ice bath, 100 mL of saturated sodium hydrogen carbonate was added to quench the reaction. Subsequently, the mixture was extracted with dichloromethane (50 mL*3) and the combined organic phase was washed with saturated brine (50 mL), dried and concentrated. The concentrate was purified by silica gel column chromatography (petroleum ether:ethyl acetate=1:0) to obtain a yellow solid E28-2 (1.00 g, 54.5% yield).

$^1$H NMR (400 MHz, $CDCl_3$) δ 7.75 (d, J=8.0 Hz, 1H), 6.92 (d, J=8.0 Hz, 1H), 5.27 (br s, 2H) ppm; LCMS: m/z 294.0 $[M+H]^+$.

Step 3: 8-bromo-imidazo[1,2-a]pyridine-5-carbonitrile E28-3

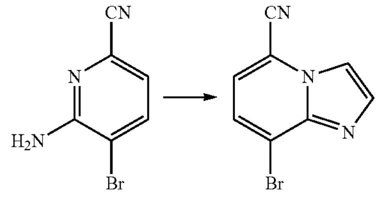

E28-2 E28-3

E28-2 (1.00 g, 5.05 mmol), 2-chloroacetaldehyde (5.44 g, 69.3 mmol) and sodium hydrogen carbonate (458 mg, 5.45 mmol) were dissolved in tert-amyl alcohol (20 mL). The reaction system was warmed to 140° C. under nitrogen atmosphere and reacted under microwave for 2 hours. The reaction was completed (monitored by LCMS). The reaction mixture was diluted with dichloromethane (100 mL). The resulting mixture was washed with saturated brine (100 mL*3), dried and concentrated. The concentrate was purified by silica gel column chromatography (petroleum ether: ethyl acetate=10:1 to 3:1) to obtain a yellow solid E28-3 (400 mg, 35.7% yield).

$^1$H NMR (400 MHz, $CDCl_3$) δ 8.04 (d, J=1.1 Hz, 1H), 7.92 (d, J=1.1 Hz, 1H), 7.55 (d, J=7.6 Hz, 1H), 7.28 (d, J=7.6 Hz, 1H) ppm; LCMS: m/z 222.0 $[M+H]^+$.

Step 4: The following compound can be obtained with E28-3 and intermediate B3 as the raw materials using the method of example 6:

8-(5-(((5-fluoro-2,3-dihydrobenzofuran-4-yl)methyl)amino)-[1,2,4]triazolo[4,3-c]pyrimidin-8-yl)imidazo[1,2-a]pyridine-5-carbonitrile

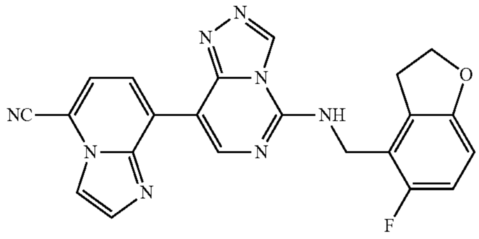 [SMILES: N#Cc1ccc(-c2cnc(NCc3c(F)ccc4c3CCO4)n3cnnc23)c2nccn12]

$^1$H NMR (400 MHz, DMSO-$d_6$) δ 9.88 (s, 1H), 9.42 (br s, 1H), 9.13 (br s, 1H), 8.96 (d, J=7.9 Hz, 1H), 8.20 (s, 1H), 7.94 (d, J=8.0 Hz, 1H), 7.88 (d, J=1.0 Hz, 1H), 6.95 (t, J=9.5 Hz, 1H), 6.70 (dd, J=3.9, 8.6 Hz, 1H), 4.79 (s, 2H), 4.54 (t, J=8.8 Hz, 2H), 3.32-3.31 (m, 2H) ppm; LCMS: m/z 427.3 $[M+H]^+$.

Example 139: 8-(2-(dimethylamino)-6-fluoro-[1,2,4]triazolo[1,5-a]pyridin-8-yl)-N-((5-fluoro-2,3-dihydrobenzofuran-4-yl)methyl)-[1,2,4]triazolo[4,3-c]pyrimidin-5-amine Step 1: Ethyl N-[(3-bromo-5fluoro-2pyridyl)aminothioacyl]amino carboxylate E29-1

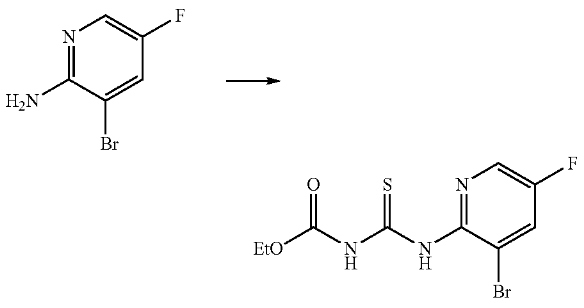

E29-1

3-bromo-5-fluoropyridin-2-amine (2.30 g, 12.0 mmol) and ethoxycarbonyl isothiocyanate (1.66 g, 12.6 mmol) were dissolved in 1,4-dioxane (25 mL). After the reaction system was vacuumed and replaced with nitrogen 3 times, the reaction mixture was stirred and reacted at 20° C. for 4 hours. Upon completion of the reaction (as monitored by TLC), the reaction solution was concentrated to obtain a crude E29-1 (4.0 g, 11.9 mmol, 98.7% yield).

LCMS: m/z 321.9/323.9 $[M+H]^+$.

Step 2: 8-bromo-6-fluoro-[1,2,4]triazolo[1,5-a]pyridin-2-amine E29-2

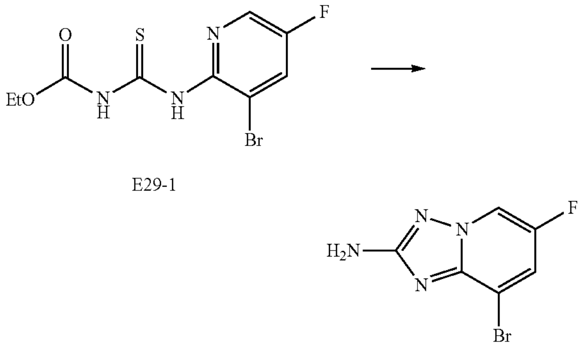

E29-1

E29-2

E29-1(4.0 g, 11.9 mmol), hydroxylamine hydrochloride (4.31 g, 62.1 mmol) and N,N-diisopropylethylamine (4.81 g, 37.2 mmol) were dissolved in methanol (30 mL) and ethanol (30 mL). After the reaction system was vacuumed and replaced with nitrogen 3 times, the reaction mixture was reacted at 70° C. for 12 hours. The reaction was completed (monitored by LCMS). The reaction solution was diluted by adding water (50 mL) and a white solid was precipitated out. The solid was collected by filtration and then dried under vacuum to obtain E29-2 (1.50 g, 6.49 mmol, 52.3% yield).

$^1H$ NMR (400 MHz, DMSO-$d_6$) δ 8.98 (dd, J=2.3, 4.1 Hz, 1H), 8.00 (dd, J=2.3, 8.5 Hz, 1H), 6.30 (s, 2H) ppm; LCMS: m/z 231.7/233.7 $[M+H]^+$.

Step 3: 8-bromo-6-fluoro-N,N-dimethyl-[1,2,4]triazolo[1,5-a]pyridin-2-amine E29-3

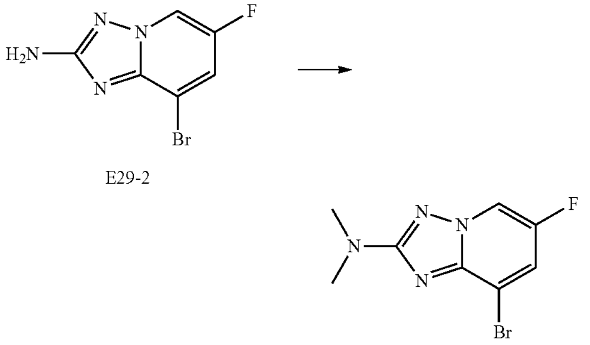

E29-2

E29-3

At 0° C., to a solution of E29-2 (1.50 g, 6.49 mmol) in N,N-dimethylformamide (20 mL), sodium hydride (779 mg, 19.5 mmol, 60% content) was added. The reaction solution was reacted at 20° C. for 0.5 hours. Methyl iodide (3.69 g, 26.0 mmol) was added into the reaction solution and the reaction was continued at 20° C. for 4 hours. Upon completion of the reaction (as monitored by TLC), saturated ammonium chloride solution was added to quench the reaction and then the reaction mixture was extracted with dichloromethane. The organic phase was dried, concentrated and purified by silica gel column chromatography to obtain E29-3 (720 mg, 2.78 mmol, 42.8% yield).

$^1H$ NMR (400 MHz, DMSO-$d_6$) δ 9.09 (dd, J=2.4, 4.0 Hz, 1H), 8.06 (dd, J=2.4, 8.4 Hz, 1H), 3.04 (s, 6H) ppm; LCMS: m/z 258.7/260.7 $[M+H]^+$ Step 4: The following compound can be obtained with E29-3 and intermediate B3 as the raw materials using the method of example 6:

8-(2-(dimethylamino)-6-fluoro-[1,2,4]triazolo[1,5-a]pyridin-8-yl)-N-((5-fluoro-2,3-dihydrobenzofuran-4-yl)methyl)-[1,2,4]triazolo[4,3-c]pyrimidin-5-amine

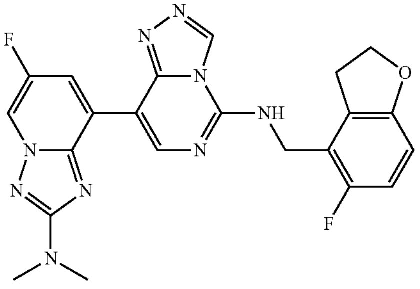 [SMILES: CN(C)c1nc2c(-c3cnc(NCc4c(F)ccc5c4CCO5)n4cnnc34)cc(F)cn2n1]

$^1H$ NMR (400 MHz, DMSO-$d_6$) δ 9.62 (s, 1H), 9.55 (s, 1H), 9.18 (dd, J=2.3, 11.3 Hz, 1H), 8.98-8.90 (m, 2H), 6.98 (t, J=9.5 Hz, 1H), 6.73 (dd, J=3.9, 8.6 Hz, 1H), 4.80 (d, J=4.8 Hz, 2H), 4.55 (t, J=8.7 Hz, 2H), 3.31-3.28 (m, 2H), 3.10 (s, 6H) ppm; LCMS: m/z 464.3 $[M+H]^+$.

Example 140: 8-(2-(dimethylamino)-[1,2,4]triazolo[1,5-a]pyridin-8-yl)-N-((5-fluoro-2,3-dihydrobenzofuran-4-yl)methyl)-[1,2,4]triazolo[4,3-c]pyrimidin-5-amine Step 1: Intermediate E30-1 can be obtained with 8-bromo-[1,2,4]triazolo[1,5-a]pyridin-2-amine as the raw material using the method in step 3 of example 139.

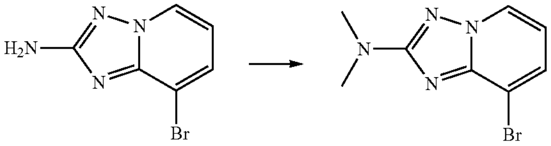

E30-1

LCMS: m/z 243.0, 229.0 $[M+H]^+$.

Step 2: The following compound can be obtained with E30-1 and intermediate B3 as the raw materials using the method of example 6:

8-(2-(dimethylamino)-[1,2,4]triazolo[1,5-a]pyridin-8-yl)-N-((5-fluoro-2,3-dihydrobenzofuran-4-yl)methyl)-[1,2,4]triazolo[4,3-c]pyrimidin-5-amine

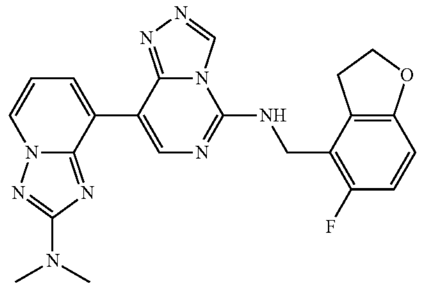 [SMILES: CN(C)c1nc2c(-c3cnc(NCc4c(F)ccc5c4CCO5)n4cnnc34)cccn2n1]

$^1$H NMR (400 MHz, DMSO-$d_6$) δ 9.53 (s, 1H), 9.50 (s, 1H), 9.07 (dd, J=7.7, 1.2 Hz, 1H), 8.82 (s, 1H), 8.61 (dd, J=6.6, 1.2 Hz, 1H), 7.10 (dd, J=7.7, 6.6 Hz, 1H), 6.98 (dd, J=10.3, 8.7 Hz, 1H), 6.73 (dd, J=8.7, 3.9 Hz, 1H), 4.79 (s, 2H), 4.55 (t, J=8.7 Hz, 2H), 3.30 (d, J=8.8 Hz, 2H), 3.10 (s, 6H) ppm; LCMS: m/z 446.1 $[M+H]^+$.

Example 141: 8-(5-(difluoromethyl)-[1,2,4]triazolo[1,5-a]pyridin-8-yl)-N-((5-fluoro-2,3-dihydrobenzofuran-4-yl)methyl)-[1,2,4]triazolo[4,3-c]pyrimidin-5-amine Step 1: 8-bromo-[1,2,4]triazolo[1,5-a]pyridine-5-methanol E31-1

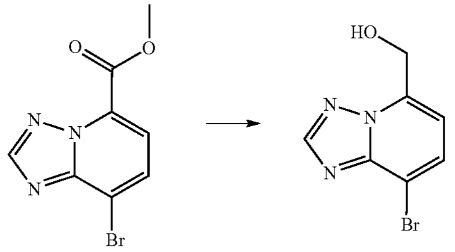

E27-3 E31-1

At 0° C., to a solution of E27-3 (3.5 g, 13.6 mmol) in tetrahydrofuran (30 mL), lithium borohydride (893 mg, 41.0 mmol) and calcium chloride (4.55 g, 14.0 mmol) were slowly added and the mixture was stirred at this temperature for 2 hours. Upon completion of the reaction, the reaction solution was added dropwise into ice water to quench the reaction. The resulting reaction mixture was extracted with ethyl acetate (100 mL*3). The organic phase was dried over anhydrous sodium sulfate and the concentrate obtained was purified by silica gel column chromatography to obtain a white solid E31-1 (1.3 g, 5.70 mmol, 41.7% yield).

$^1$H NMR (400 MHz, DMSO-$d_6$) δ 8.59 (s, 1H), 8.05 (d, J=7.8 Hz, 1H), 7.16 (d, J=7.8 Hz, 1H), 5.93 (br t, J=5.6 Hz, 1H), 4.90 (br d, J=5.0 Hz, 2H) ppm; LCMS: m/z 228.1 $[M+H]^+$.

Step 2: 8-bromo-[1,2,4]triazolo[1,5-a]pyridine-5-carbaldehyde E31-2

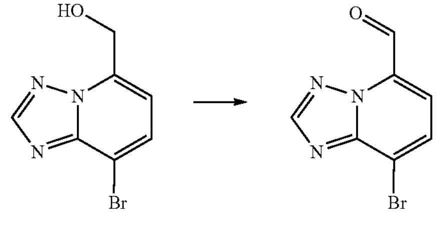

E31-1 E31-2

At 0° C., to a solution of E31-1 (400 mg, 1.75 mmol) in dichloromethane (16 mL) and N,N-dimethylformamide (8 mL), Dess-Martin periodinane (1.12 g, 2.63 mmol) was slowly added and the mixture was stirred at 25° C. for 2 hours. Upon completion of the reaction, the reaction solution was added dropwise into saturated aqueous sodium hydrogen carbonate solution to quench the reaction. The resulting reaction mixture was extracted with dichloromethane (60 mL*3). The combined organic phase was dried over anhydrous sodium sulfate and concentrated to obtain a white solid E31-2 (300 mg, crude).

$^1$H NMR (400 MHz, DMSO-$d_6$) δ 10.51 (s, 1H), 8.75 (s, 1H), 8.18 (d, J=7.8 Hz, 1H), 7.67 (d, J=7.8 Hz, 1H) ppm.

Step 3: 8-bromo-5-(difluoromethyl)-[1,2,4]triazolo[1,5-a]pyridine E31-3

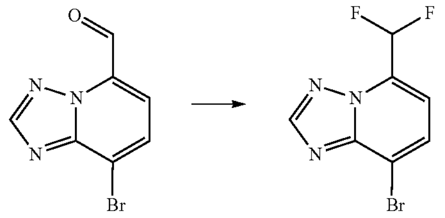

E31-2 E31-3

At 0° C., to a solution of E31-2 (280 mg, 1.24 mmol) in dichloromethane (40 mL), diethylaminosulfur trifluoride (399 mg, 2.48 mmol) was slowly added and the mixture was stirred at 25° C. for 12 hours. Upon completion of the reaction, the reaction solution was added dropwise into saturated aqueous sodium hydrogen carbonate solution to quench the reaction. The resulting reaction mixture was extracted with dichloromethane (20 mL*3). The combined organic phase was dried and concentrated. The concentrate was purified by silica gel column chromatography to obtain a white solid E31-3 (270 mg, 1.09 mmol, 87.8% yield).

$^1$H NMR (400 MHz, DMSO-$d_6$) δ 8.73 (s, 1H), 8.16 (d, J=7.8 Hz, 1H), 7.57 (t, J=52.4 Hz), 7.50 (d, J=7.8 Hz, 1H); LCMS: m/z 249.7 $[M+H]^+$.

Step 4: The following two compounds can be obtained with E31-3 and intermediate B3 as the raw materials using the method of example 6:

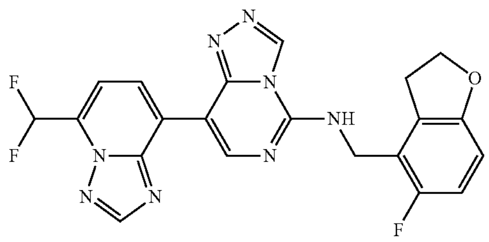 [SMILES: Fc1ccc2c(c1CNc1ncc(-c3ccc(C(F)F)n4ncnc34)c3nncn13)CCO2]

$^1$H NMR (400 MHz, DMSO-$d_6$) δ 9.60 (s, 1H), 9.57 (s, 1H), 9.33 (br d, J=7.6 Hz, 1H), 9.09 (br s, 1H), 8.77 (s, 1H), 7.78 (br s, 1H), 7.65 (t, J=52.8 Hz, 1H), 6.98 (br t, J=9.5 Hz, 1H), 6.73 (br dd, J=3.4, 8.5 Hz, 1H), 4.81 (br d, J=3.4 Hz, 2H), 4.56 (t, J=8.5 Hz, 2H), 3.31-3.23 (m, 2H) ppm; LCMS: m/z 453.3 $[M+H]^+$.

Example 142: 8-(5-(dimethylamino)-[1,2,4]triazolo[1,5-c]pyrimidin-8-yl)-N-((5-fluoro-2,3-dihydrobenzofuran-4-yl)methyl)-[1,2,4]triazolo[4,3-c]pyrimidin-5-amine Step 1: 5-bromo-N2,N2-dimethylpyrimidine-2,4-diamine E32-1

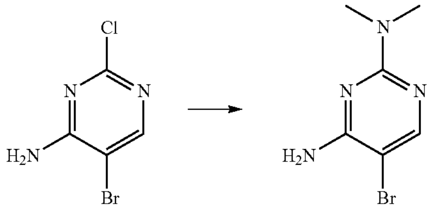

E32-1

In a hydrothermal synthesis reactor, 5-bromo-2chloropyrimidin-4-amine (3.0 g, 14.4 mmol) was added into aqueous dimethylamine solution (70 mL, 40%) and the reaction solution was reacted at 100° C. for 12 hours. It was found by LCMS monitoring that the reaction was completed. The reaction solution was extracted with ethyl acetate (100 mL*3). The organic phase was then washed with brine, subsequently dried over anhydrous sodium sulfate and concentrated to obtain E32-1 (3.33 g, crude), which was directly used in the next step.

$^1$H NMR (400 MHz, DMSO-$d_6$) δ 7.96 (s, 1H), 6.70 (br s, 2H), 3.07 (s, 6H) ppm; LCMS: m/z 217.1 $[M+H]^+$.

Step 2: (E)-N'-(5-bromo-2-(dimethylamino)pyrimidin-4-yl)-N,N-dimethylformamidine E32-2

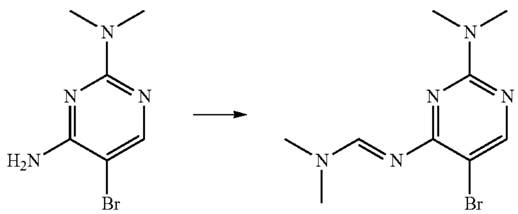

E32-1 E32-2

E32-1 (2.5 g, 11.5 mmol) was dissolved in toluene (30 mL) and N,N-dimethylformamide dimethyl acetal (2.74 g, 23.0 mmol) was added into the solution. The mixture was stirred at 110° C. for 8 hours and it was found by LCMS monitoring that the reaction was completed. Water was added to the reaction solution to quench the reaction. The resulting reaction mixture was extracted with ethyl acetate. The organic phase was washed with saturated brine, then dried and concentrated to obtain E32-2 (3.0 g, crude), which was directly used in the next step.

$^1$H NMR (400 MHz, $CDCl_3$) δ 8.58 (s, 1H), 8.18 (s, 1H), 3.18 (s, 3H), 3.15 (s, 3H), 3.13 (s, 6H) ppm; LCMS: m/z 272.2 $[M+H]^+$.

Step 3: (E)-N-(5-bromo-2-(dimethylamino)pyrimidin-4-yl)-N'-hydroxyformamidine E32-3

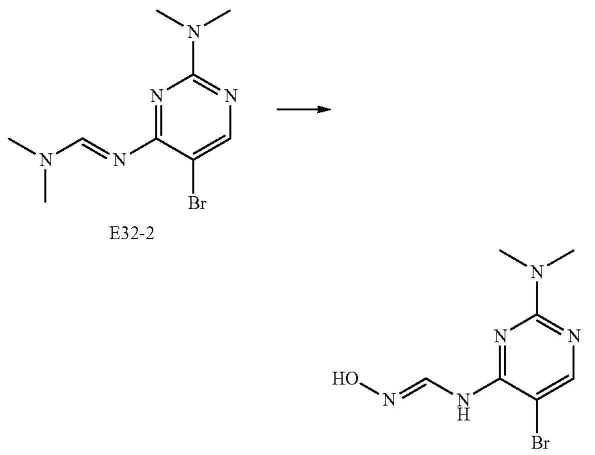

E32-2

E32-3

E32-2 (3 g, 11.0 mmol) was dissolved in ethanol (40 mL). Hydroxylamine hydrochloride (1.53 g, 22.0 mmol) and sodium acetate (1.81 g, 22.0 mmol) were added into the reaction solution. The well-mixed reaction solution was reacted at 60° C. for 4 hours. It was found by LCMS detection that the reaction was completed. The reaction solution was concentrated. The residue was slurried by adding water, and the resulting slurry was filtered and the solid was collected and dried to obtain E32-3 (2.8 g, 94.5% yield).

$^1$H NMR (400 MHz, DMSO-$d_6$) δ 10.92 (s, 1H), 8.21 (s, 1H), 8.09-8.02 (m, 1H), 8.01-7.94 (m, 1H), 3.08 (s, 6H) ppm; LCMS: m/z 262.1 [M+H]$^+$.

Step 4: 8-bromo-N,N-dimethyl-[1,2,4]triazolo[1,5-c]pyrimidin-5-amine E32-4

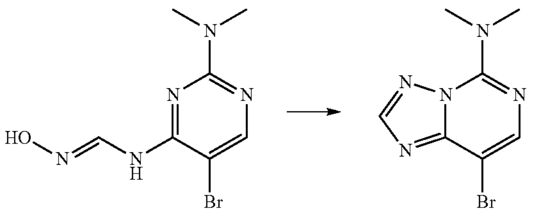

E32-3 E32-4

E32-3 (2.8 g, 10.8 mmol) was dissolved in tetrahydrofuran (30 mL). At 0° C., trifluoroacetic anhydride (11.3 g, 53.8 mmol) was added dropwise into the reaction solution. After the dropwise addition was complete, the resulting mixture was reacted at 25° C. for 14 hours. It was found by LCMS monitoring that the reaction was completed. After ice water was added into the reaction solution to quench the reaction, the resulting mixture was extracted with ethyl acetate (150 mL*3). The organic phase was sequentially washed with saturated sodium hydrogen carbonate solution and saturated brine, then dried and concentrated. The crude was separated by Flash silica gel column chromatography to obtain E32-4 (2.0 g, 76.7% yield).

$^1$H NMR (400 MHz, $CDCl_3$) δ 8.25 (s, 1H), 7.99 (s, 1H), 3.49 (s, 6H) ppm; LCMS: m/z 244.1 [M+H]$^+$.

Step 5: 8-(5-(dimethylamino)-[1,2,4]triazolo[1,5-c]pyrimidin-8-yl)-N-((5-fluoro-2,3,-dihydrobenzofuran-4-yl)methyl)-[1,2,4]triazolo[4,3-c]pyrimidin-5-amine

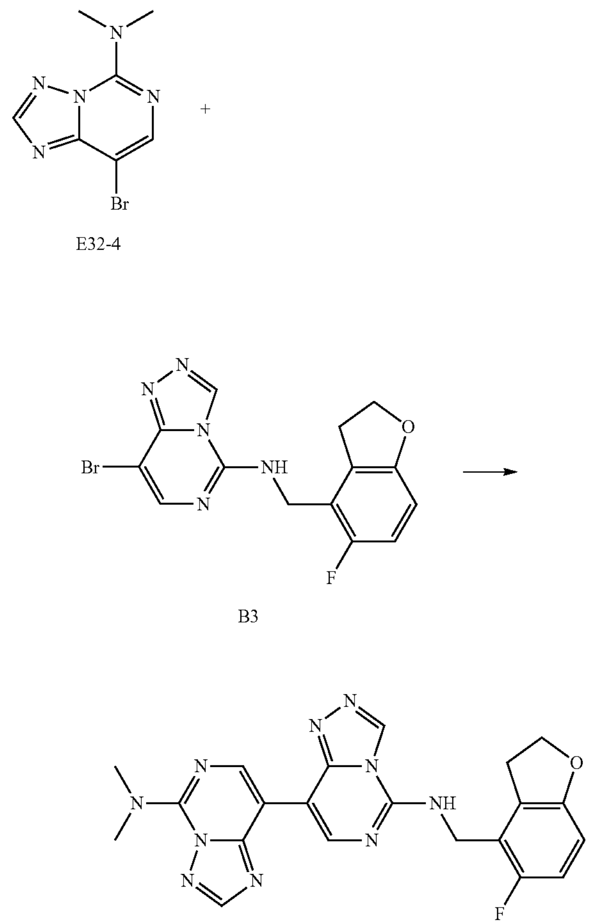

E32-4

B3

E32-4 (600 mg, 1.65 mmol), 8-bromo-N-((5-fluoro-2,3-dihydrobenzofuran-4-yl)methyl)-[1,2,4]triazolo[4,3-c]pyrimidin-5-amine B3 (800 mg, 3.30 mmol), hexabutylditin (1.49 g, 2.57 mmol) and tris(dibenzylideneacetone)dipalladium (473 mg, 517 umol) were dissolved in dioxane (4 mL) and N,N-dimethylformamide (4 mL). The reaction system was warmed to 100° C. under nitrogen atmosphere and stirred for 12 hours. A product was produced as detected by LCMS. The reaction solution was filtered and concentrated. The crude was separated through Flash silica gel column chromatography to obtain a crude product, which was separated by HPLC and basified to obtain 8-(5-(dimethylamino)-[1,2,4]triazolo[1,5-c]pyrimidin-8-yl)-N-((5-fluoro-2,3-dihydrobenzofuran-4-yl)methyl)-[1,2,4]triazolo[4,3-c]pyrimidin-5-amine (20 mg, 3.12% yield).

$^1$H NMR (400 MHz, DMSO-$d_6$) δ 9.46 (br s, 1H), 9.35 (s, 1H), 9.07 (s, 1H), 8.59 (s, 1H), 6.93 (t, J=9.2 Hz, 1H), 6.68 (dd, J=4.0, 8.8 Hz, 1H), 4.73 (s, 2H), 4.53 (t, J=8.8 Hz, 2H), 3.44 (s, 6H), 3.32-3.28 (m, 2H) ppm; LCMS: m/z 447.3 [M+H]$^+$.

Example 143: 1-(8-(5-(((5-fluoro-2,3-dihydrobenzofuran-4-yl)methyl)amino)-triazolo[4,3-c]pyrimidin-8-yl)-[1,2,4]triazolo[1,5-a]pyridin-5-yl)ethan-1-ol

Step 1: 1-(8-bromo-[1,2,4]triazolo[1,5-a]pyridin-5-yl)ethanol E31-7

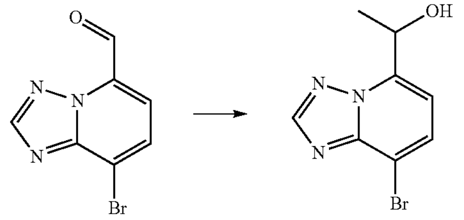

E31-2 E31-7

At −30° C., to a solution of E31-2 (300 mg, 1.33 mmol) in tetrahydrofuran (10 mL), a solution of methylmagnesium bromide (3 M, 1.33 mL) was added dropwise and the mixture was stirred at this temperature for 2 hours. Upon completion of the reaction, saturated aqueous ammonium chloride solution was used to quench the reaction. The resulting mixture was extracted with ethyl acetate (50 mL*3). The combined organic phase was dried, concentrated and then purified by Flash silica gel column chromatography to obtain E31-7 (270 mg, 84.0% yield).

$^1$H NMR (400 MHz, $CDCl_3$) δ 8.43 (s, 1H), 7.80 (d, J=8.0 Hz, 1H), 6.97 (d, J=7.8 Hz, 1H), 5.40-5.37 (m, 1H), 4.01 (d, J=5.4 Hz, 1H), 1.74 (d, J=6.5 Hz, 3H) ppm; LCMS: 242.1 m/z $[M+H]^+$.

Step 2: The following compound can be obtained with E31-7 and intermediate B3 as the raw materials using the method of example 6:

1-(8-(5-(((5-fluoro-2,3-dihydrobenzofuran-4-yl)methyl)amino)-[1,2,4]triazolo[4,3-c]pyrimidin-8-yl)-[1,2,4]triazolo[1,5-a]pyridin-5-yl)ethan-1-ol

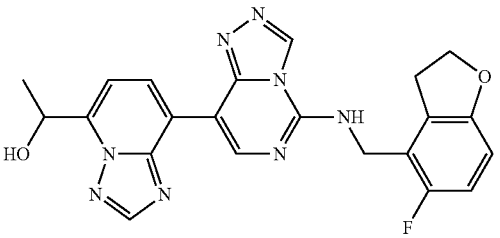 [SMILES: CC(O)c1ccc(-c2cnc(NCc3c(F)ccc4c3CCO4)n3cnnc23)c2ncnn12]

$^1$H NMR (400 MHz, DMSO-$d_6$) δ 9.55 (s, 1H), 9.43 (s, 1H), 9.19-9.17 (d, J=8.0 Hz, 1H), 8.93 (s, 1H), 8.64 (s, 1H), 7.44-7.42 (d, J=8.0 Hz, 1H), 6.99-6.94 (m, 1H), 6.73-6.70 (m, 1H), 5.90-5.89 (d, J=4.0 Hz, 1H), 5.43-5.40 (m, 1H), 4.78 (s, 2H), 4.55 (t, J=8.8 Hz, 2H), 3.34-3.27 (m, 2H), 1.56-1.54 (d, J=8.0 Hz, 3H) ppm; LCMS: 447.3 m/z $[M+H]^+$.

Example 144: 8-(5-(dimethylamino)-6-fluoro-[1,2,4]triazolo[1,5-a]pyridin-8-yl)-N-((5-fluoro-2,3-dihydrobenzofuran-4-yl)methyl)-[1,2,4]triazolo[4,3-c]pyrimidin-5-amine

Step 1: tert-butyl (6-chloro-5-fluoropyridin-2-yl)-carbamate E33-1

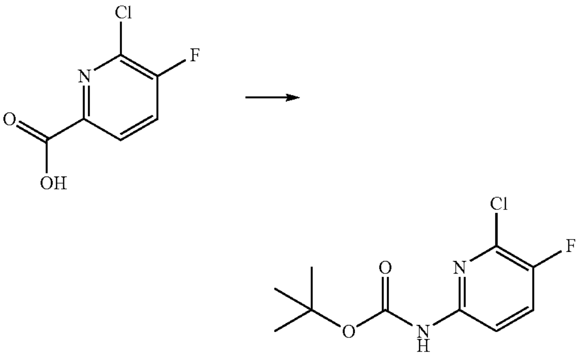

E33-1

6-chloro-5-fluoropyridine-2-carboxylic acid (9.5 g, 54.1 mmol), tert-butanol (44.2 g, 596 mmol), 4 A molecular sieves (5 g), diphenyl phosphorazidate (19.4 g, 70.4 mmol) and N,N-diisopropylethylamine (21.0 g, 162 mmol) were dissolved in toluene (150 mL). The mixture was stirred at 85° C. for 2 hours. The reaction was completed (detected by LCMS). Upon completion of the reaction, the reaction solution was cooled to room temperature and subjected to rotary evaporation under reduced pressure to obtain a solid. Then the solid was extracted with ethyl acetate (250 mL*3). The organic phases were mixed, dried, concentrated and purified by silica gel column chromatography to obtain E33-1 (6.0 g, 45% yield).

$^1$H NMR (400 MHz, DMSO-$d_6$) δ 10.20 (s, 1H), 7.91-7.85 (m, 1H), 7.82-7.77 (m, 1H), 1.46 (s, 9H) ppm; LCMS: m/z 190.8 $[M-55]^+$.

Step 2: 6-chloro-5-fluoropyridin-2-amine E33-2

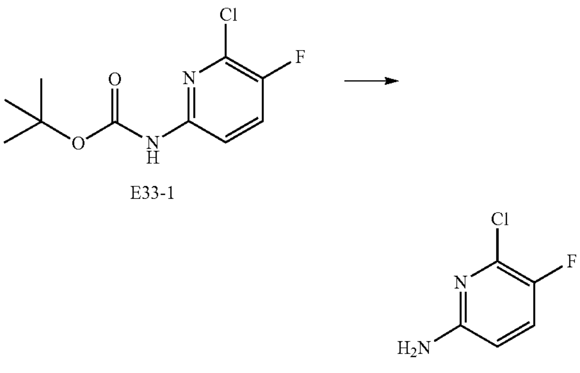

E33-1

E33-2

E33-1 (6 g, 24.3 mmol) was dissolved in hydrochloric acid/ethyl acetate (35 mL). At 25° C., the mixture was reacted for 12 hours. The reaction was completed (detected by LCMS). The reaction mixture was diluted by adding water and filtered. The resulting solid was slurried and then dried to obtain E33-2 (3.5 g, 98% yield).

$^1$H NMR (400 MHz, DMSO-$d_6$) δ 7.49 (t, J=8.6 Hz, 1H), 6.42 (dd, J=2.7, 8.8 Hz, 1H) ppm; LCMS: m/z 147.2 $[M+H]^+$.

Step 3: 3-bromo-6-chloro-5-fluoropyridin-2-amine E33-3

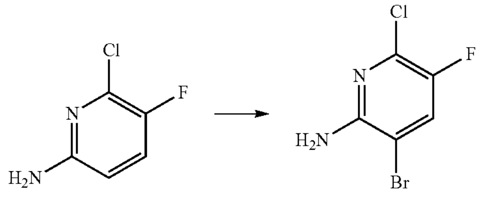

E33-2 E33-3

E33-2 (3.50 g, 24.0 mmol), N-bromosuccinimide (4.70 g, 26.3 mmol), and potassium carbonate (3.63 g, 26.3 mmol) were dissolved in dichloromethane (20 ml) and N,N-dimethylformamide (2 ml). At 25° C., the mixture was reacted for 30 minutes. No raw material was left (as detected by TLC). Sodium sulfite solution was added to quench the reaction and then the resulting mixture was extracted with ethyl acetate. The organic phases were mixed, dried and concentrated to obtain a crude E33-3 (5.3 g, 98% yield).

$^1$H NMR (400 MHz, DMSO-$d_6$) δ 8.05 (d, J=7.6 Hz, 1H), 6.59 (s, 2H) ppm; LCMS: m/z 227.0 $[M+H]^+$.

Step 4: (E)-N'-(3-bromo-6-chloro-5-fluoropyridin-2-yl)-N,N-dimethylformamidine E33-4

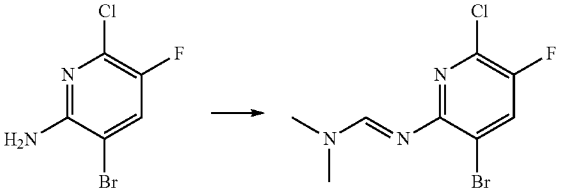

E33-3 E33-4

E33-3 (5.30 g, 24 mmol) and N,N-dimethylformamide dimethylacetal (14.0 g, 118 mmol) were dissolved in toluene (45 ml). The reaction mixture was warmed to 100° C. and reacted for 5 hours. The reaction was completed (monitored by LCMS) and the reaction mixture was cooled to room temperature and concentrated under reduced pressure to obtain a crude E33-4 (5.80 g, crude).

$^1$H NMR (400 MHz, DMSO-$d_6$) δ 8.31 (s, 1H), 8.19 (d, J=7.8 Hz, 1H), 3.14 (s, 3H), 3.04 (s, 3H) ppm; LCMS: m/z 282.0 $[M+H]^+$.

Step 5: (E)-N-(3-bromo-6-chloro-5-fluoropyridin-2-yl)-N'-hydroxyformamidine E33-5

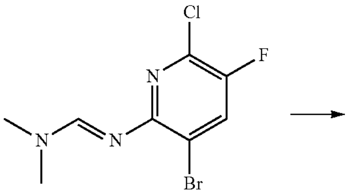

E33-4

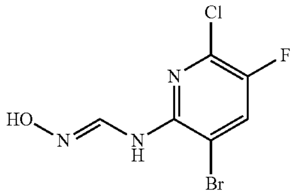

E33-5

E33-4 (5.80 g, crude), hydroxylamine hydrochloride (2.90 g, 41.4 mmol) and sodium acetate (3.70 g, 45.5 mmol) were dissolved in ethyl acetate (50 ml) and the mixture was warmed to 50° C. and reacted for 1 hour. The reaction was completed (monitored by LCMS). The mixture was cooled to room temperature. Water was added. The resulting mixture was filtered and a solid was collected, namely, E33-5 (7.88 g, crude) was obtained.

$^1$H NMR (400 MHz, DMSO-$d_6$) δ 10.85 (br s, 1H), 8.42 (d, J=7.6 Hz, 1H), 8.30-7.83 (m, 1H), 7.75 (s, 1H) ppm; LCMS: m/z 270.0 $[M+H]^+$.

Step 6: 8-bromo-5-chloro-6-fluoro-[1,2,4]triazolo[1,5-a]pyridine E33-6

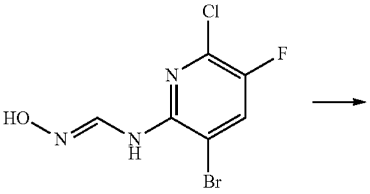

E33-5

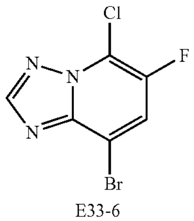

E33-6

E33-5 (7.0, crude) was dissolved in polyphosphoric acid (70 ml). The temperature was raised to 80° C. and the reaction lasted for 2 hours. The reaction was completed (monitored by LCMS) and the reaction mixture was cooled to room temperature. Saturated sodium hydrogen carbonate solution was added to quench the reaction. The resulting mixture was extracted with ethyl acetate and the organic phase was dried and concentrated to obtain E33-6 (3.80 g, 58% yield).

$^1H$ NMR (400 MHz, DMSO-$d_6$) δ 8.71 (s, 1H), 8.52 (d, J=8.6 Hz, 1H) ppm; LCMS: m/z 251.8 [M+H]$^+$.

Step 7: 8-bromo-6-fluoro-N,N-dimethyl-[1,2,4]triazolo[1,5-a]pyridin-5-amine E33-7

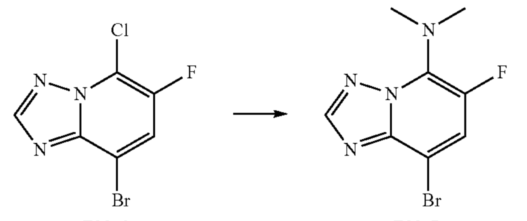

E33-6 E33-7

E33-6 (500 mg, 2.0 mmol), dimethylamine hydrochloride (814 mg, 10 mmol), and N,N-diisopropylethylamine (3.60 g, 28 mmol) were dissolved in N,N-dimethylformamide (3 ml). The mixture was warmed to 100° C. and reacted for 6 hours. The reaction was completed (monitored by LCMS) and the mixture was diluted by adding water and then extracted with ethyl acetate. The organic phase was washed, dried and concentrated. The resulting crude was purified by Flash silica gel column chromatography to obtain E33-7 (420 mg, 81.2% yield).

$^1H$ NMR (400 MHz, DMSO-$d_6$) δ 8.53 (s, 1H), 8.18 (d, J=11.5 Hz, 1H), 3.09 (d, J=3.0 Hz, 6H) ppm; LCMS: m/z 258.9 [M+H]$^+$.

Step 8: The following compound can be obtained with E33-7 and intermediate B3 as the raw materials using the method of example 6:

8-(5-(dimethylamino)-6-fluoro-[1,2,4]triazolo[1,5-a]pyridin-8-yl)-N-((5-fluoro-2,3-dihydrobenzofuran-4-yl)methyl)-[1,2,4]triazolo[4,3-c]pyrimidin-5-amine

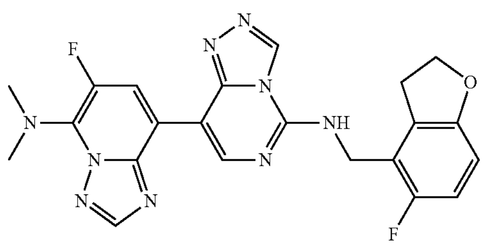 [SMILES: CN(C)c1c(F)cc(-c2cnc(NCc3c(F)ccc4c3CCO4)n3cnnc23)c2ncnn12]

$^1H$ NMR (400 MHz, DMSO-$d_6$) δ 9.54 (s, 1H), 9.49 (s, 1H), 9.25 (d, J=14.4 Hz, 1H), 8.95-8.90 (m, 1H), 8.62 (s, 1H), 6.97 (t, J=9.5 Hz, 1H), 6.72 (dd, J=4.1, 8.7 Hz, 1H), 4.77 (br d, J=4.0 Hz, 2H), 4.55 (t, J=8.7 Hz, 2H), 3.27 (br d, J=5.1 Hz, 2H), 3.15 (d, J=2.8 Hz, 6H) ppm; LCMS m/z 464.1 [M+H]$^+$.

Example 145: 8-(5-(dimethylamino)-2-methyl-[1,2,4]triazolo[1,5-a]pyridin-8-yl)-N-((5-fluoro-2,3-dihydrobenzofuran-4-yl)methyl)-[1,2,4]triazolo[4,3-c]pyrimidin-5-amine Step 1: (E)-N'-(3-bromo-6-chloropyridin-2-yl)-N,N-dimethylacetamidine E34-1

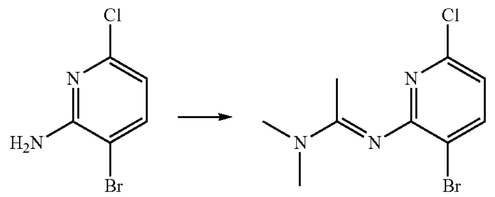

E34-1

2-amine-3-bromo-6-chloropyridine (2.30 g, 11.1 mmol) was added into toluene (25 mL) and the reaction solution was reacted at 100° C. for 12 hours. It was found by LCMS monitoring that the reaction was completed. The reaction solution was directly concentrated to obtain E34-1 (3.00 g, crude).

LCMS: m/z 277.7 [M+H]$^+$.

Step 2: (E)-N'-(3-bromo-6-chloropyridine-2-yl)-N-hydroxyacetamidine E34-2

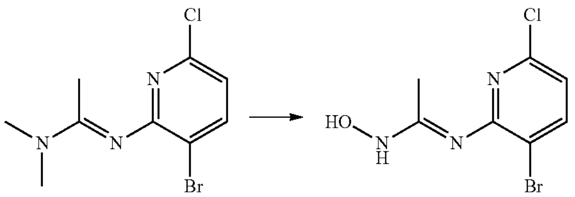

E34-1 E34-2

E34-1 (3.00 g, 10.8 mmol) was dissolved in ethanol (40 mL). Hydroxylamine hydrochloride (1.51 g, 21.7 mmol) and sodium acetate (1.78 g, 21.7 mmol) were then added into the solution. The mixture was stirred at 60° C. for 5 hours and it was found by LCMS monitoring that the reaction was completed. The reaction solution was dried and concentrated to obtain a crude. The crude was slurried with water (20 mL) at 25° C. for 2 hours. The mixture was filtered and the solid was collected and dried to obtain a product E34-2 (2.60 g, 87.1% yield).

$^1H$ NMR (400 MHz, DMSO-$d_6$) δ 10.58 (s, 1H), 8.50 (s, 1H), 8.05 (d, J=8.0 Hz, 1H), 6.97 (d, J=8.0 Hz, 1H), 2.29 (s, 3H) ppm; LCMS: m/z 265.9 [M+H]$^+$.

Step 3: 8-bromo-5-chloro-2-methyl-[,2,4]triazolo[1,5-a]pyridine E34-3

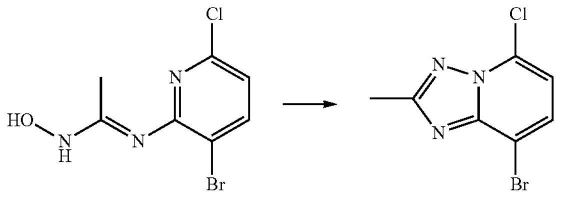

E34-2 E34-3

E34-2 (2.25 g, 8.51 mmol) was added into polyphosphoric acid (40 g). The well-mixed reaction solution was reacted at 95° C. for 4 hours. It was found by LCMS detection that the reaction was completed. The reaction solution was poured into a mixture of ice and water (200 mL). Sodium carbonate was directly added into the mixture until the pH of the mixture reached 7. The resulting mixture was extracted with ethyl acetate. The organic phase was washed with brine, then dried over anhydrous sodium sulfate and finally concentrated to obtain E34-3 (2.00 g, crude), which was directly used in the next step.

$^1$H NMR (400 MHz, $CDCl_3$) δ 7.69 (d, J=8.0 Hz, 1H), 6.98 (d, J=8.0 Hz, 1H), 2.69 (S, 3H) ppm; LCMS: m/z 248.1 $[M+H]^+$.

Step 4: 8-bromo-5-dimethylamino-2-methyl-[1,2,4]triazolo[1,5-a]pyridine E34-4

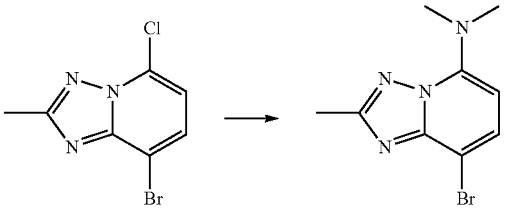

E34-3 E34-4

E34-3 (2.15 g, 8.72 mmol) was dissolved in N,N-diisopropylethylamine (20 mL) and then dimethylamine hydrochloride was added. The reaction solution was reacted at 80° C. for 5 hours. It was found by LCMS monitoring that the reaction was completed. Saturated brine was added to the reaction solution to quench the reaction and then the resulting mixture was extracted with ethyl acetate. The organic phase was washed again with saturated brine, then dried and concentrated. The crude was separated by Flash silica gel column chromatography to obtain E34-4 (2.00 g, 76.7% yield).

$^1$H NMR (400 MHz, $CDCl_3$) δ 7.61 (d, J=8.0 Hz, 1H), 6.17 (d, J=8.0 Hz, 1H), 3.12 (s, 6H), 2.65 (s, 3H) ppm; LCMS: m/z 257.2 $[M+H]^+$.

Step 5: The following compound can be obtained with E34-4 and intermediate B3 as the raw materials using the method of example 6:

8-(5-(dimethylamino)-2-methyl-[1,2,4]triazolo[1,5-a]pyridin-8-yl)-N-((5-fluoro-2,3-dihydrobenzofuran-4-yl)methyl)-[1,2,4]triazolo[4,3-c]pyrimidin-5-amine

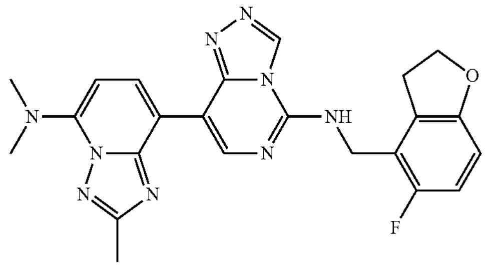 [SMILES: Cc1nc2c(-c3cnc(NCc4c(F)ccc5c4CCO5)n4cnnc34)ccc(N(C)C)n2n1]

$^1$H NMR (400 MHz, DMSO-$d_6$) δ 9.50 (s, 1H), 9.28 (s, 1H), 9.00 (d, J=8.4 Hz, 1H), 8.74 (d, J=1.2 Hz, 1H), 6.96 (t, J=9.6 Hz, 1H), 6.71 (dd, J=3.9, 8.8 Hz, 1H), 6.61 (d, J=8.4 Hz, 1H), 4.76 (s, 2H), 4.54 (t, J=8.8 Hz, 2H), 3.31-3.27 (m, 2H), 3.13 (s, 6H), 2.55 (s, 3H) ppm; LCMS: m/z 460.3 $[M+H]^+$.

Example 146: 8-(5-(((5-fluoro-2,3-dihydrobenzofuran-4-yl)methyl)amino)-triazolo[4,3-c]pyrimidin-8-yl)-[1,2,4]triazolo[1,5-a]pyridine-6-carbonitrile Step 1: Methyl 6-amino-5-bromonicotinate E35-1

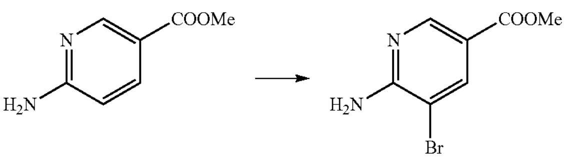

E35-1

Methyl 6-aminonicotinate (4.0 g, 26.3 mmol) and N-bromosuccinimide (5.15 g, 28.9 mmol) were dissolved in dichloromethane (100 mL). At 20° C., under nitrogen atmosphere, the mixture was reacted for 1 hour. The reaction was completed (monitored by LCMS) and the reaction solution was sequentially washed with sodium sulfite solution, sodium carbonate solution and water. The organic phase was dried and concentrated to obtain E35-1 (6.1 g, crude).

LCMS: m/z 231.0 $[M+H]^+$.

Step 2: (E) 5-bromo-6-(((dimethylamino)methylene) amino)nicotinic acid methyl ester E35-2

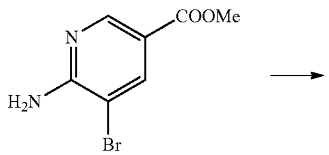

E35-1

-continued

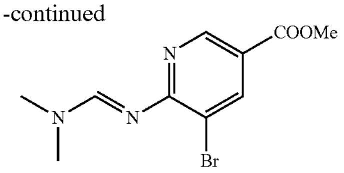

E35-2

E35-1 (6.1 g, 26.4 mmol) and N, N-dimethylformamide dimethylacetal (6.3 g, 53 mmol) were dissolved in toluene (50 ml). The mixture was warmed to 100° C. and reacted under nitrogen atmosphere for 12 hours. The reaction was completed (monitored by LCMS) and the reaction solution was concentrated under reduced pressure to obtain E35-2 (7.6 g, crude).

LCMS: m/z 285.7/287.7 [M+H]$^+$.

Step 3: (E) 5-bromo-6-(N'-hydroxyformamidinyl)nicotinic acid methyl ester E35-3

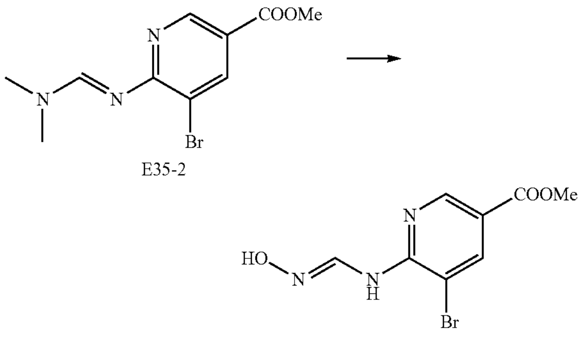

E35-2

E35-3

E35-2 (5.0 g, 17.5 mmol), sodium acetate (3.2 g, 39 mmol) and hydroxylamine hydrochloride (2.4 g, 25 mmol) were dissolved in ethanol (50 mL). The mixture was warmed to 50° C. and reacted for 4 hours. The reaction was completed (monitored by LCMS) and water was added. The resulting mixture was filtered and a solid was collected, namely, E35-3 (4.0 g, 84% yield) was obtained.

$^1$H NMR (400 MHz, DMSO-$d_6$) δ 11.01 (s, 1H), 8.71 (d, J=1.9 Hz, 1H), 8.45 (d, J=9.4 Hz, 1H), 8.38 (d, J=1.9 Hz, 1H), 8.00 (s, 1H), 3.84 (s, 3H) ppm; LCMS: m/z 276.0 [M+H]$^+$.

Step 4: 8-bromo-[1,2,4]triazolo[1,5,a]pyridine-6-carboxylic acid methyl ester E35-4

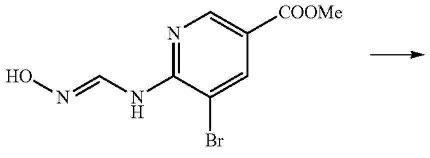

E35-3

-continued

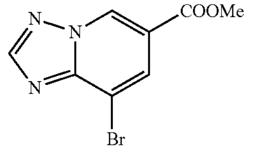

E35-4

E35-3 (4.0 g, 15 mmol) was dissolved in polyphosphoric acid (20 mL). The temperature was raised to 100° C. and the reaction lasted 2 hours. The reaction was completed (monitored by LCMS) and the reaction mixture was cooled to room temperature. Saturated sodium hydrogen carbonate solution was added to quench the reaction. The resulting mixture was extracted with ethyl acetate and the organic phase was dried and concentrated to obtain E35-4 (2.8 g, 75% yield).

$^1$H NMR (400 MHz, DMSO-$d_6$) δ 9.53 (d, J=1.4 Hz, 1H), 8.74 (s, 1H), 8.29 (d, J=1.3 Hz, 1H), 3.92 (s, 3H) ppm; LCMS: m/z 257.7 [M+H]$^+$.

Step 5: 8-bromo-[1,2,4]triazolo[1,5-a]pyridine-6-carboxamide E35-5

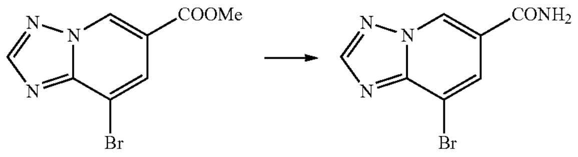

E35-4 E35-5

E35-4 (2.4 g, 9.4 mmol) and ammonia water (15 g, 103 mmol) were dissolved in ethanol (5 mL). The reaction system was warmed to 80° C. and the reaction mixture was reacted under nitrogen atmosphere for 2 hours. No raw material was left (as monitored by TLC) and the mixture was cooled to room temperature. Water was added and the resulting mixture was extracted with ethyl acetate. The organic phases were mixed, dried, concentrated and purified by Flash silica gel column chromatography to obtain E35-5 (830 mg, 37% yield).

$^1$H NMR (400 MHz, DMSO-$d_6$) δ 9.46 (d, J=1.3 Hz, 1H), 8.68 (s, 1H), 8.35 (d, J=1.3 Hz, 1H), 8.25 (br s, 1H), 7.79 (br s, 1H).

Step 6: 8-(4,4,5,5-tetramethyl-1,3,2-dioxaborolan-2-yl)-[1,2,4]triazolo[1,5-a]pyridine-6-carboxamide E35-6

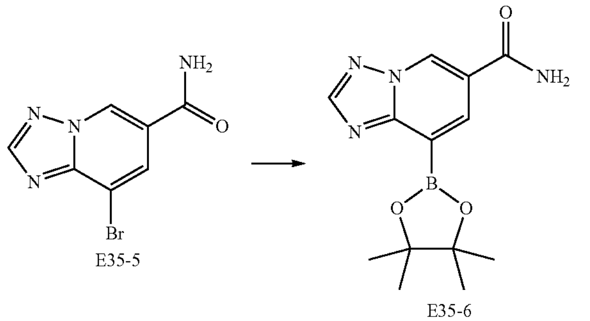 [SMILES: NC(=O)c1cc(Br)c2ncnn2c1 ; CC1(C)OB(c2cc(C(N)=O)cn3ncnc23)OC1(C)C]

E35-5

E35-6

E35-5 (400 mg, 1.7 mmol), bis(pinacolato)diboron (506 mg, 2.0 mmol), potassium acetate (489 mg, 5.0 mmol), and a complex of [1,1'-bis(diphenylphosphino)ferrocene]dichloropalladium(II) with dichloromethane (271 mg, 0.33 mmol) were dissolved in 1,4-dioxane (10 mL). The temperature was raised to 120° C. and the mixture was reacted under nitrogen atmosphere for 5 hours. No raw material was left (as detected by TLC) and the resulting reaction solution contained E35-6 and was directly used in the next step without any treatment.

Step 7: 8-(5-(((5-fluoro-2,3-dihydrobenzofuran-4-yl)methyl)amino)-[1,2,4]triazolo[4,3-c]pyridin-8-yl)-[1,2,4]triazolo[1,5-a]pyridine-6-carboxamide E35-7

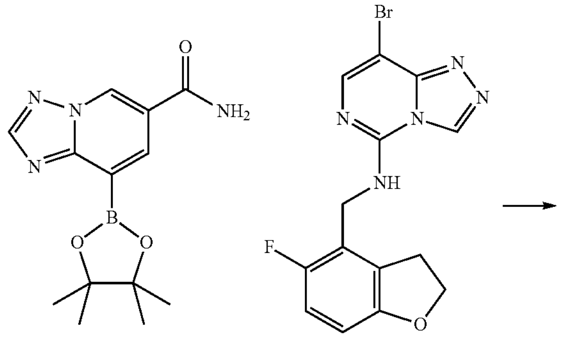

E35-6 B3

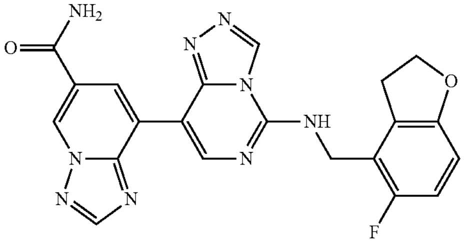

E35-7

To the reaction solution obtained in the previous step, B3 (302 mg, 0.83 mmol), sodium carbonate (528 mg, 4.98 mmol), [1,1'-bis(diphenylphosphino)ferrocene]dichloropalladium(II) (136 mg, 0.17 mmol) and water (2 mL) were added. The reaction system was warmed to 100° C. under nitrogen atmosphere and reacted for 2 hours. The reaction was completed (monitored by LCMS). The resulting mixture was cooled to room temperature and diluted and dissolved in ethyl acetate. The organic phase was washed with water, dried over anhydrous sodium sulfate and concentrated under reduced pressure. The crude was purified by Flash silica gel column chromatography and then purified by HPLC to obtain E35-7 (34 mg, 4.6% yield).

LCMS: m/z 446.1 $[M+H]^+$.

Step 8: 8-(5-(((5-fluoro-2,3-dihydrobenzofuran-4-yl)methyl)amino)-[1,2,4]triazolo[4,3-c]pyridin-8-yl)-[1,2,4]triazolo[1,5-a]pyridine-6-cyan

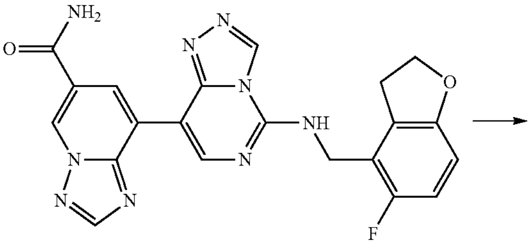

E35-7

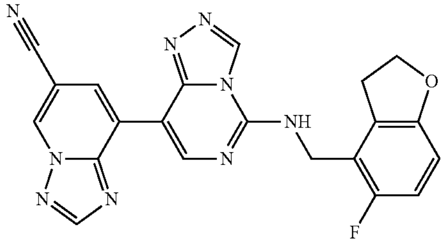

1880

At 0° C., to a solution of E35-7 (34 mg, 0.76 mmol) and triethylamine (31 mg, 0.31 mmol) in tetrahydrofuran (1.5), trifluoroacetic anhydride (48.1 mg, 0.23 mmol) was added. The mixture was reacted at 25° C. for 12 hours. The reaction was completed (monitored by LCMS) and saturated sodium hydrogen carbonate solution and water were added into the reaction solution. The resulting mixture was extracted with ethyl acetate. The organic phases were mixed, dried and concentrated. The resulting crude was purified by Flash silica gel column chromatography and then purified by HPLC to obtain the final compound 8-(5-(((5-fluoro-2,3-dihydrobenzofuran-4-yl)methyl)amino)-[1,2,4]triazolo[4,3-c]pyridin-8-yl)-[1,2,4]triazolo[1,5-a]pyridine-6-cyan (7.5 mg, 23% yield).

$^1H$ NMR (400 MHz, DMSO-$d_6$) δ 9.81 (s, 1H), 9.59 (s, 1H), 9.57 (br s, 1H), 9.40 (s, 1H), 9.14 (br d, J=1.1 Hz, 1H), 8.86 (s, 1H), 6.97 (t, J=9.6 Hz, 1H), 6.72 (dd, J=3.9, 8.6 Hz, 1H), 4.80 (s, 2H), 4.55 (t, J=8.7 Hz, 2H), 3.25-3.22 (m, 2H) ppm; LCMS: m/z 428.0 $[M+H]^+$.

Example 147: N-((5-fluoro-2,3-dihydrobenzofuran-4-yl)methyl)-8-(6-fluoro-3-(methylsulfonyl)imidazo[1,2-a]pyridin-8-yl)-[1,2,4]triazolo[4,3-c]pyrimidin-5-amine

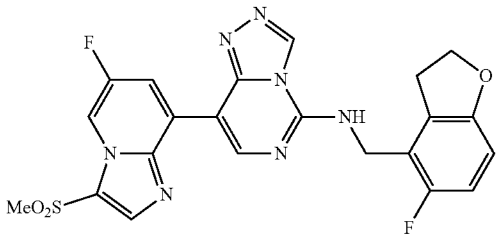 [SMILES: CS(=O)(=O)c1cnc2c(-c3cnc(NCc4c(F)ccc5c4CCO5)n4cnnc34)cc(F)cn12]

Step 1: N-((5-fluoro-2,3-dihydrobenzofuran-4-yl)methyl)-8-(6-fluoro-3-iodoimidazo[1,2-a]pyridin-8-yl)-[1,2,4]triazolo[4,3-c]pyrimidin-5-amine E36-1

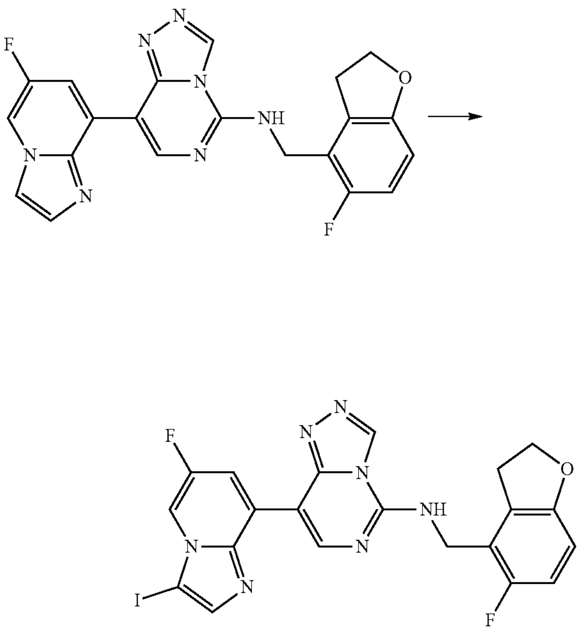

E36-1

Into a 25 mL round-bottom flask, N-((5-fluoro-2,3-dihydrobenzofuran-4-yl)methyl)-8-(6-fluoroimidazo[1,2-a]pyridin-8-yl)-[1,2,4]triazolo[4,3-c]pyrimidin-5-amine (example 21) (600 mg, 1.43 mmol), anhydrous dichloromethane (10 ml) and glacial acetic acid (2 ml) were added and in an ice bath, iodosuccinimide (353.9 mg, 1.57 mmol) was added. The mixture was then stirred at room temperature for 1 hour. The reaction solution was poured into water. The resulting mixture was extracted with dichloromethane (50 mL*3), washed with brine and dried over anhydrous sodium sulfate, and then passed through a silica gel column (eluents:dichloromethane:methanol=20:1) and dried under vacuum to obtain pure E36-1 (0.39 g, 50.0% yield).

LCMS: m/z 546.1 $[M+H]^+$.

Step 2: N-((5-fluoro-2,3-dihydrobenzofuran-4-yl)methyl)-8-(6-fluoro-3-(methylsulfonyl)imidazo[1,2-a]pyridin-8-yl)-[1,2,4]triazolo[4,3-c]pyrimidin-5-amine

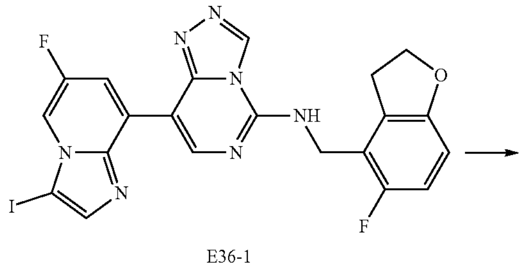

E36-1

-continued

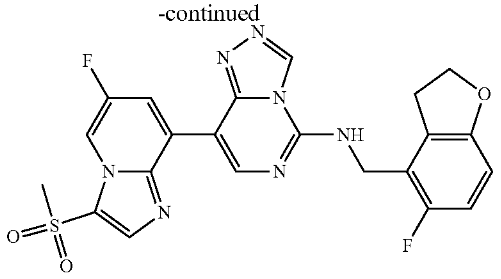

Into a sealed tube, E36-1 (100 mg, 0.18 mmol) and anhydrous dimethylsulfoxide (3 ml) were added and sodium methanesulfinate (55.13 mg, 0.54 mmol) and cuprous iodide (102.84 mg, 0.54 mmol) were added sequentially. The mixture was purged with nitrogen for five minutes, sealed and then reacted in a microwave reactor at 120° C. for 20 minutes and then reacted under microwave at 100° C. for another 3 hours. After the reaction mixture was cooled, dichloromethane (50 mL) was added and the resulting mixture was washed with water (30 mL) and saturated brine (30 mL). The organic layer was spin-dried and then subjected to preparative liquid chromatography to obtain N-((5-fluoro-2,3-dihydrobenzofuran-4-yl)methyl)-8-(6-fluoro-3-(methylsulfonyl)imidazo[1,2-a]pyridin-8-yl)-[1,2,4]triazolo[4,3-c]pyrimidin-5-amine (17 mg, 19.0% yield).

$^1$H NMR (400 MHz, DMSO-$d_6$) δ 9.70 (s, 1H), 9.26-9.21 (m, 1H), 8.97 (dd, J=10.7, 2.4 Hz, 1H), 8.86-8.83 (m, 1H), 8.72 (s, 1H), 8.33 (s, 1H), 6.90 (d, J=10.2 Hz, 1H), 6.69-6.65 (m, 1H), 4.81 (s, 2H), 4.52 (t, J=8.8 Hz, 2H), 3.50 (s, 3H), 3.31-3.29 (m, 2H) ppm; LCMS: m/z 498.1 $[M+H]^+$.

Example 148: (6-fluoro-8-(5-(((5-fluoro-2,3-dihydrobenzofuran-4-yl)methyl)amino)-triazolo[4,3-c]pyrimidin-8-yl)imidazo[1,2-a]pyridin-3-yl)dimethylphosphine oxide

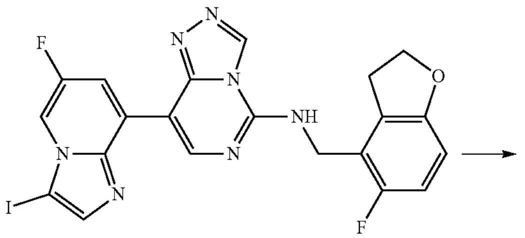

E36-1

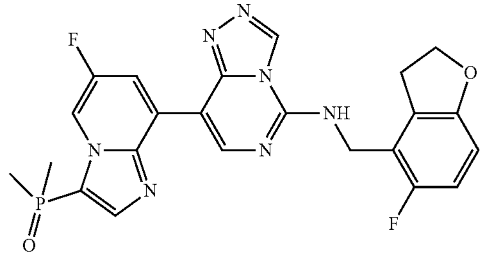

Into a sealed tube, E36-1 (100 mg, 0.18 mmol) and anhydrous 1,4-dioxane (4 ml) were added. Dimethylphosphine oxide (42.15 mg, 0.54 mmol), tris(dibenzylideneacetone)dipalladium (16.48 mg, 0.02 mmol), 4,5-bis(diphenylphosphino)-9,9-dimethylxanthene (10.42 mg, 0.02 mmol), and triethylamine (0.05 mL) were added sequentially. The mixture was purged with nitrogen for five minutes, sealed and then stirred at 100° C. for 15 hours. After the reaction mixture was cooled, dichloromethane (50 mL) was added and the resulting mixture was washed with water (30 mL) and saturated brine (30 mL). The organic layer was spin-dried and then purified by Flash column chromatography (eluents:dichloromethane:methanol=4:1) to obtain (6-fluoro-8-(5-(((5-fluoro-2,3-dihydrobenzofuran-4-yl)methyl)amino)-[1,2,4]triazolo[4,3-c]pyrimidin-8-yl)imidazo[1,2-a]pyridin-3-yl)dimethylphosphine oxide (55 mg, 61.68% yield).

$^1$H NMR (400 MHz, DMSO-$d_6$) δ 9.70 (s, 1H), 9.55 (s, 1H), 9.12-8.97 (m, 3H), 8.12 (s, 1H), 7.02-6.92 (m, 1H), 6.73 (s, 1H), 4.79 (s, 2H), 4.55 (t, J=8.7 Hz, 2H), 3.32 (d, J=8.9 Hz, 2H), 1.92 (s, 3H), 1.89 (s, 3H) ppm; LCMS: m/z 496.1 $[M+H]^+$.

The following compound can be obtained with N-((5-fluoro-2,3-dihydrobenzofuran-4-yl)methyl)-8-(5-methylimidazo[1,2-a]pyridin-8-yl)-[1,2,4]triazolo[4,3-c]pyrimidin-5-amine (example 88) as the raw material using the method of example 148:

Example 149: N-((5-fluoro-2,3-dihydrobenzofuran-4-yl)methyl)-8-(5-methyl-3-(methylsulfonyl)imidazo[1,2-a]pyridin-8-yl)-[1,2,4]triazolo[4,3-c]pyrimidin-5-amine

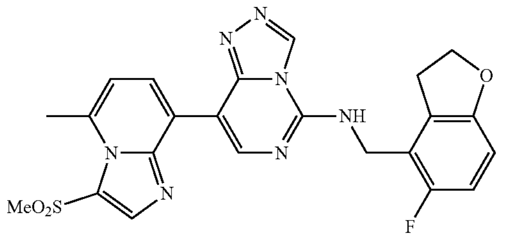 [SMILES: Cc1ccc(-c2cnc(NCc3c(F)ccc4c3CCO4)n3cnnc23)c2ncc(S(C)(=O)=O)n12]

$^1$H NMR (400 MHz, DMSO-$d_6$) δ 9.21 (s, 1H), 9.00 (t, J=5.7 Hz, 1H), 8.64 (s, 1H), 8.53 (d, J=7.6 Hz, 1H), 8.33 (s, 1H), 7.24 (d, J=7.9 Hz, 1H), 6.95-6.87 (m, 1H), 6.66 (dd, J=8.6, 3.8 Hz, 1H), 4.79 (d, J=5.6 Hz, 2H), 4.52 (t, J=8.7 Hz, 2H), 3.65 (s, 3H), 3.30 (d, J=8.7 Hz, 2H), 3.07 (s, 3H) ppm; LCMS: m/z 494.1 $[M+H]^+$.

Example 150: 8-(5-(dimethylamino)-[1,2,4]triazolo[4,3-a]pyridin-8-yl)-N-((5-fluoro-2,3-dihydrobenzofuran-4-yl)methyl)-[1,2,4]triazolo[4,3-c]pyrimidin-5-amine Step 1: 3-bromo-6-chloro-2-hydrazinopyridine E37-1

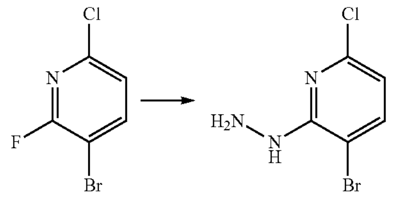

E37-1

A solution of 3-bromo-6-chloro-2-fluoro-pyridine (1.00 g, 4.75 mmol) and hydrazine hydrate (4.10 mL) in N,N-dimethylformamide was stirred and reacted at 80° C. for 2 hours. Upon completion of the reaction (as monitored by LCMS), the mixture was concentrated to obtain a crude. Then the crude was slurried with water at 25° C. for 30 minutes, then filtered and dried under vacuum to obtain a brown solid E37-1 (1.00 g, 94.6% yield).

$^1$H NMR (400 MHz, $CDCl_3$) δ 7.55 (d, J=8.0 Hz, 1H), 6.58 (d, J=7.6 Hz, 1H), 6.32 (br s, 1H), 3.95 (br d, J=2.8 Hz, 2H) ppm; LCMS: m/z 224.0 $[M+H]^+$.

Step 2: 8-bromo-5-chloro-[1,2,4]triazolo[4,3-a]pyridine E37-2

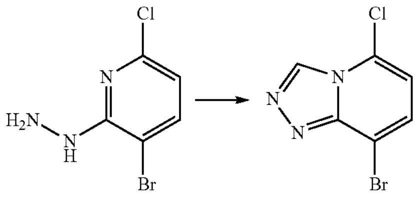

E37-1 E37-2

A mixture of E37-1 (1.00 g, 4.49 mmol), trimethylorthoformate (9.68 g, 91.2 mmol) and trifluoroacetic acid (20 mg, 0.175 mmol) was reacted under nitrogen atmosphere at 100° C. for 12 hours. No raw material was left (as monitored by LCMS). The reaction solution was concentrated to obtain a crude and then the crude was slurried with methyl tert-butyl ether to obtain E37-2 (960 mg, 91.9% yield).

$^1$H NMR (400 MHz, $CDCl_3$) δ 9.03 (s, 1H), 7.53 (d, J=7.6 Hz, 1H), 6.84 (d, J=7.6 Hz, 1H) ppm; LCMS: m/z 234.0 $[M+H]^+$.

Step 3: 8-bromo-N,N-methyl-[1,2,4]triazolo[4,3-a]pyridin-5-amine E37-3

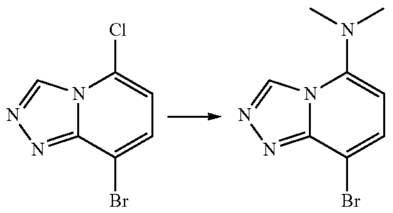

E37-2 E37-3

E37-2 (960 mg, 4.13 mmol) and 40% aqueous dimethylamine solution (30 mL) were mixed and reacted at 100° C. for 12 hours. The reaction was completed (monitored by LCMS and TLC) and the mixture was cooled to room temperature and extracted with ethyl acetate. The combined organic phase was washed with saturated brine, dried and concentrated to obtain a crude. Then the crude was slurried with ethyl acetate and a solid was collected, i.e., an off-white solid E37-3 (620 mg, 62.3% yield) was obtained.

$^1$H NMR (400 MHz, $CDCl_3$) δ 8.89 (s, 1H), 7.46 (d, J=7.6 Hz, 1H), 6.12 (d, J=7.6 Hz, 1H), 2.92 (s, 6H) ppm; LCMS: m/z 241.1 $[M+H]^+$.

Step 4: The following compound can be obtained with E37-3 and intermediate B3 as the raw materials using the method of example 6:

8-(5-(dimethylamino)-[1,2,4]triazolo[4,3-a]pyridin-8-yl)-N-((5-fluoro-2,3-dihydrobenzofuran-4-yl)methyl)-[1,2,4]triazolo[4,3-c]pyrimidin-5-amine

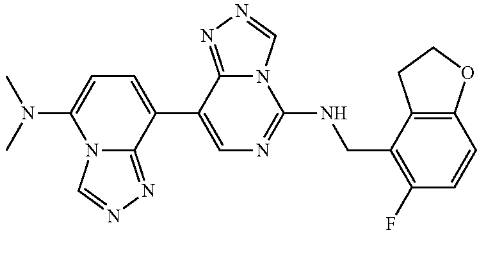 [SMILES: CN(C)c1ccc(-c2cnc(NCc3c(F)ccc4c3CCO4)n3cnnc23)c2nncn12]

$^1$H NMR (400 MHz, DMSO-$d_6$) δ 9.52 (d, J=8.0 Hz, 2H), 9.35 (s, 1H), 8.96 (d, J=8.0 Hz, 1H), 8.83 (br s, 1H), 7.01-6.92 (m, 1H), 6.71 (dd, J=8.4, 3.6 Hz, 1H), 6.60 (d, J=8.0 Hz, 1H), 4.77 (br d, J=3.6 Hz, 2H), 4.56 (t, J=8.8 Hz, 2H), 3.33-3.32 (m, 2H), 2.93 (s, 6H) ppm; LCMS: m/z 446.3 $[M+H]^+$.

Example 151: 8-(3,5-dimethyl-[1,2,4]triazolo[4,3-a]pyridin-8-yl)-N-(5-fluoro-2,3-dihydrobenzofuran-4-yl)methyl)-[1,2,4]triazole[4,3-c]pyrimidin-5-amine Step 1: 8-bromo-3,5-dimethyl-[1,2,4]triazolo[4,3-a]pyridine E38-1

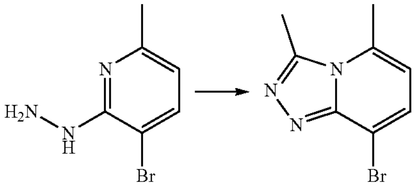

E25-1 E38-1

E25-1 (700 mg, 3.46 mmoL), trifluoroacetic acid (7.9 mg, 0.07 mmoL) and triethyl orthoacetate (10.1 g, 63.4 mmoL) were mixed. The mixture was warmed to 100° C. and reacted under nitrogen atmosphere for 10 hours. The reaction was completed (monitored by LCMS) and the reaction solution was cooled to room temperature, concentrated and slurried with methyl tert-butyl ether to obtain 8-bromo-3,5-dimethyl-[1,2,4]triazolo[4,3-a]pyridine E38-1 (600 mg, 76.6% yield).

$^1$H NMR (400 MHz, DMSO-$d_6$) δ 7.52 (d, J=7.1 Hz, 1H), 6.58 (dd, J=1.0, 7.3 Hz, 1H), 2.94 (s, 3H), 2.80 (s, 3H) ppm; LCMS: m/z 228.0 $[M+H]^+$.

Step 2: The following compound can be obtained with E38-1 and intermediate B3 as the raw materials using the method of example 6:

8-(3,5-dimethyl-[1,2,4]triazolo[4,3-a]pyridin-8-yl)-N-(5-fluoro-2,3-dihydrobenzofuran-4-yl)methyl)-[1,2,4]triazole[4,3-c]pyrimidin-5-amine

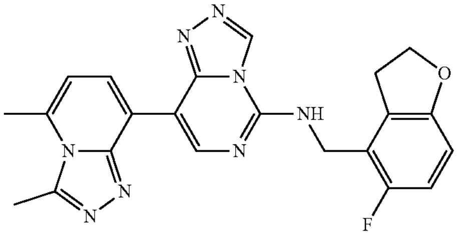 [SMILES: Cc1ccc(-c2cnc(NCc3c(F)ccc4c3CCO4)n3cnnc23)c2nnc(C)n12]

$^1$H NMR (400 MHz, DMSO-$d_6$) δ 9.55 (s, 1H), 9.43 (s, 1H), 9.18 (d, J=7.9 Hz, 1H), 8.94 (br s, 1H), 8.65 (s, 1H), 7.44 (d, J=7.9 Hz, 1H), 6.97 (t, J=9.6 Hz, 1H), 6.72 (dd, J=3.8, 8.6 Hz, 1H), 5.90 (d, J=4.9 Hz, 1H), 5.47-5.38 (m, 1H), 4.78 (br s, 2H), 4.55 (t, J=8.8 Hz, 2H), 3.31-3.30 (m, 2H), 1.55 (d, J=6.4 Hz, 3H) ppm; LCMS: m/z 431.3 $[M+H]^+$.

Pharmacology and Application

Although EED, as one of the main components of the PRC2 protein complex, does not have an enzymatically catalytic activity, it plays an important role in the integral function of PRC2. The effect of EED on PRC2 is specifically embodied in two aspects: 1) EED directly binds to the trimethylated H3K27Me3, which enables the location of the PCR2 complex to the chromatin that needs to be modified; and 2) EED has strong allosteric potentiation effects on the enzymatically catalytic function of EZH2. Therefore, the development of target compounds for the allosteric protein EED provides a new strategy for inhibiting the enzymatic activity of EZH2. Moreover, such inhibitors have better or complementary advantages relative to catalytic site inhibitors of EZH2 enzymes, for example, when patients develop resistance to EZH2 enzyme inhibitors, EED inhibitors can also play a role in inhibiting the activity of EZH2 enzymes. The present disclosure discloses that the compounds can be used as EED target inhibitors and have therapeutic effects on diseases related to the mechanism of action of EED and/or PRC2.

The biological functions of the compounds disclosed in the present disclosure have been demonstrated in tests at biochemical and cellular levels. For example, in biochemical tests, the compounds disclosed in the present disclosure can strongly compete for binding with the H3K27Me3 polypeptide that binds to the EED protein ($IC_{50}$ can reach <0.2 nM). At the cellular level, the compounds disclosed in the present disclosure can not only inhibit the methylation level of histone H3K27 but also further inhibit the proliferation of cancer cells through this effect ($IC_{50}$ can reach <1 nM). In comparison to the compound, N-((5-fluoro-2,3-dihydrobenzofuran-4-yl)methyl)-8-(2-methylpyridin-3-yl)-[1,2,4]triazolo[4,3-c]pyrimidin-5-amine in US 20160176882 A1 and WO 2017219948 A1, the activity against cell proliferation of the compound of the present disclosure is increased by about 10-fold. When the compound disclosed in the present disclosure binds to an EED protein, the bicyclic structure outside the binding "pocket" enables the compound to have a better metabolic stability.

Example 152: Evaluation of Effects of Compounds in Blocking the Binding of EED to H3K27Me3 with AlphaScreen (a-Screening) Method Firstly, compound solutions of different concentration gradients were prepared. Compound powder was dissolved in DMSO to prepare a mother liquor. 1.5 μl of the mother liquor of the compound was taken and added into 198.5 μl of a reaction buffer (25 mM HEPES (pH 8.0), 50 mM NaCl, 0.015% Tween 20, 0.5% BSA). The mixture was mixed uniformly. Then a 3-fold series dilution was carried out with the above-mentioned buffer containing 0.75% DMSO. 9 different test concentrations were provided for one same compound. 5 μL of compounds of different concentration gradients were taken and added into the ProxiPlate-384 Plus, White detection plate (PerkinElmer, 6008280) and two replicates in parallel were provided for each concentration gradient.

Secondly, a reaction for blocking the binding was carried out. The above-mentioned buffer was used to dilute His6-tagged full-length EED protein (441 amino acids) to 60 nM and biotinylated polypeptide fragment H3K27me3 (amino acids at positions 19-33) (Biotinylated-H3K27me3) to 75 nM. 5 μl of the polypeptide fragment at the concentration of 75 nM and 5 1 of the protein at the concentration of 60 nM were transferred to the detection wells containing the compound, respectively. The detection plate was sealed with the film and incubation was carried out at room temperature for 30 minutes.

Finally, the detection was carried out with the AlphaScreen method. Prior use, nickel chelate receptor beads and streptavidin donor beads (at the ratio of 1:1, Perkin Elmer, product number 6760619M) were mixed with the above-mentioned reaction buffer. Then 5 μl of the above-mentioned pre-mixed detection solution was added to each of the detection wells. The donor beads and receptor beads were both at a final concentration of 5 μg/mL. The detection plate was covered and sealed with tinfoil and placed in the dark at room temperature for 1 hour. The signal was read using the AlphaScreen detector on the Spectra max i3. AlphaScreen signals were standardlized based on the readings obtained from positive controls (maximum signal controls) and negative controls (minimum signal controls) to give the inhibition rates for compounds at different concentrations, and afterwards non-linear regression analysis was carried out using GraphPad Prism 5, inhibition curves were made based on the Dose-Response equation of Y=Bottom+(Top−Bottom)/(1+10^((Log IC50−X)*HillSlope)) and the $IC_{50}$ values of each compound were obtained.

To rule out the false positive results produced due to the interference with the AlphaScreen detection system by the compound, the compound was diluted using the same method, biotinylated polypeptide Biotinylated-$(His)_6$ was used to replace the EED and polypeptide H3K27me3 in the detection system, and after incubation was carried out for the same period of time, the signal values were read on the Spectra max i3. The data was processed using the same method.

Table 3 below shows the $IC_{50}$ values of part of the compounds of the present disclosure.

TABLE 3

| Compound name | $IC_{50}$ (μM), AlphaScreen |
|---|---|
| N-((5-fluoro-2,3-dihydrobenzofuran-4-yl)methyl)-8-(imidazo[1,2-a]pyridin-7-yl)-[1,2,4]triazolo[4,3-c]pyrimidin-5-amine | 0.0150 |
| N-((5-fluoro-2,3-dihydrobenzofuran-4-yl)methyl)-8-(imidazo[1,2-a]pyridin-6-yl)-[1,2,4]triazolo[4,3-c]pyrimidin-5-amine | 0.0424 |
| N-((5-fluoro-2,3-dihydrobenzofuran-4-yl)methyl)-8-(pyrazolo[1,5-a]pyrimidin-6-yl)-[1,2,4]triazolo[4,3-c]pyrimidin-5-amine | 0.0057 |
| 8-([1,2,4]triazolo[4,3-a]pyridin-6-yl)-N-(((1aR,6bR)-5-fluoro-1a,6b-dihydro-1H-cyclopropa[b]benzofuran-6-yl)methyl)-[1,2,4]triazolo[4,3-c]pyrimidin-5-amine | 0.0042 |
| 8-([1,2,4]triazolo[1,5-a]pyridin-7-yl)-N-(((1aR,6bR)-5-fluoro-1a,6b-dihydro-1H-cyclopropa[b]benzofuran-6-yl)methyl)-[1,2,4]triazolo[4,3-c]pyrimidin-5-amine | 0.0045 |
| N-((5-fluoro-2,3-dihydrobenzofuran-4-yl)methyl)-8-(imidazo[1,2-a]pyrimidin-6-yl)-[1,2,4]triazolo[4,3-c]pyrimidin-5-amine | 0.0049 |
| N-((5-fluoro-2,3-dihydrobenzofuran-4-yl)methyl)-8-(pyrazolo[1,5-a]pyridin-6-yl)-[1,2,4]triazolo[4,3-c]pyrimidin-5-amine | 0.0043 |
| 8-([1,2,4]triazolo[1,5-a]pyridin-8-yl)-N-((5-fluoro-2,3-dihydrobenzofuran-4-yl)methyl)-[1,2,4]triazolo[4,3-c]pyrimidin-5-amine | 0.0047 |
| N-((5-fluoro-2,3-dihydrobenzofuran-4-yl)methyl)-8-(imidazo[1,2-a]pyridin-8-yl)-[1,2,4]triazolo[4,3-c]pyrimidin-5-amine | 0.0044 |
| 8-([1,2,4]triazolo[1,5-a]pyridin-8-yl)-N-(((1aR,6bR)-5-fluoro-1a,6b-dihydro-1H-cyclopropa[b]benzofuran-6-yl)methyl)-[1,2,4]triazolo[4,3-c]pyrimidin-5-amine | 0.0040 |
| N-(((1aR,6bR)-5-fluoro-1a,6b-dihydro-1H-cyclopropa[b]benzofuran-6-yl)methyl)-8-(imidazo[1,2-a]pyridin-8-yl)-[1,2,4]triazolo[4,3-c]pyrimidin-5-amine | 0.0035 |
| 8-([1,2,4]triazolo[4,3-a]pyridin-8-yl)-N-(((1aR,6bR)-5-fluoro-1a,6b-dihydro-1H-cyclopropa[b]benzofuran-6-yl)methyl)-[1,2,4]triazolo[4,3-c]pyrimidin-5-amine | 0.0095 |
| N-((5-fluoro-2,3-dihydrobenzofuran-4-yl)methyl)-8-(2-(trifluoromethyl)imidazo[1,2-a]pyridin-8-yl)-[1,2,4]triazolo[4,3-c]pyrimidin-5-amine | 0.0035 |
| 8-(6-chloroimidazo[1,2-a]pyridin-8-yl)-N-((5-fluoro-2,3-dihydrobenzofuran-4-yl)methyl)-[1,2,4]triazolo[4,3-c]pyrimidin-5-amine | 0.0044 |
| 8-(6-chloro-2-(trifluoromethyl)imidazo[1,2-a]pyridin-8-yl)-N-((5-fluoro-2,3-dihydrobenzofuran-4-yl)methyl)-[1-1,2,4]triazolo[4,3-c]pyrimidin-5-amine | 0.0096 |
| N-((5-fluoro-2,3-dihydrobenzofuran-4-yl)methyl)-8-(6-fluoroimidazo[1,2-a]pyridin-8-yl)-[1,2,4]triazolo[4,3-c]pyrimidin-5-amine | 0.0049 |

TABLE 3-continued

| Compound name | $IC_{50}$ (μM), AlphaScreen |
|---|---|
| N-((5-fluoro-2,3-dihydrobenzofuran-4-yl)methyl)-8-(6-fluoro-2-(trifluoromethyl)imidazo[1,2-a]pyridin-8-yl)-[11,2,4]triazolo[4,3-c]pyrimidin-5-amine | 0.0023 |
| Ethyl 6-fluoro-8-(5-(((5-fluoro-2,3-dihydrobenzofuran-4-yl)methyl)amino)-[1,2,4]triazolo[4,3-c]pyrimidin-8-yl)imidazo[1,2-a]pyridine-3-carboxylate | 0.0221 |
| N-((5-fluoro-2,3-dihydrobenzofuran-4-yl)methyl)-8-(pyrazolo[1,5-a]pyrimidin-3-yl)-[1,2,4]triazolo[4,3-c]pyrimidin-5-amine | 0.0021 |
| Ethyl 6-fluoro-8-(5-(((5-fluoro-2,3-dihydrobenzofuran-4-yl)methyl)amino)-[1,2,4]triazolo[4,3-c]pyrimidin-8-yl)-2-methylimidazo[1,2-a]pyridine-3-carboxylate | 0.0452 |
| Ethyl 8-(5-(((5-fluoro-2,3-dihydrobenzofuran-4-yl)methyl)amino)-[1,2,4]triazolo[4,3-c]pyrimidin-8-yl)imidazo[1,2-a]pyridine-3-carboxylate | 0.0023 |
| 8-(5-(((5-fluoro-2,3-dihydrobenzofuran-4-yl)methyl)amino)-[1,2,4]triazolo[4,3-c]pyrimidin-8-yl)imidazo[1,2-a]pyridine-3-carboxylic acid | 0.0051 |
| N-((5-fluoro-2,3-dihydrobenzofuran-4-yl)methyl)-8-(6-fluoro-2-methylimidazo[1,2-a]pyridin-8-yl)-[1,2,4]triazolo[4,3-c]pyrimidin-5-amine | 0.0030 |
| N-((5-fluoro-2,3-dihydrobenzofuran-4-yl)methyl)-8-(2-methylimidazo[1,2-a]pyridin-8-yl)-[1,2,4]triazolo[4,3-c]pyrimidin-5-amine | 0.0141 |
| N-((5-fluoro-2,3-dihydrobenzofuran-4-yl)methyl)-8-(2-methylbenzo[d]oxazol-4-yl)-[1,2,4]triazolo[4,3-c]pyrimidin-5-amine | 0.0092 |
| 8-(benzo[d]oxazol-7-yl)-N-((5-fluoro-2,3-dihydrobenzofuran-4-yl)methyl)-[1,2,4]triazolo[4,3-c]pyrimidin-5-amine | 0.0049 |
| N-((5-fluoro-2,3-dihydrobenzofuran-4-yl)methyl)-8-(6-methyl-2-(trifluoromethyl)imidazo[1,2-a]pyridin-8-yl)-[1,2,4]triazolo[4,3-c]pyrimidin-5-amine | 0.0157 |
| 8-(5-(((5-fluoro-2,3-dihydrobenzofuran-4-yl)methyl)amino)-[1,2,4]triazolo[4,3-c]pyrimidin-8-yl)imidazo[1,2-a]pyridine-3-carboxamide | 0.0035 |
| N-((5-fluoro-2,3-dihydrobenzofuran-4-yl)methyl)-8-(5-(trifluoromethyl)benzo[c][1,2,5]thiadiazol-4-yl)-[1,2,4]triazolo[4,3-c]pyrimidin-5-amine | 0.0464 |
| N-((5-fluoro-2,3-dihydrobenzofuran-4-yl)methyl)-8-(3-methylimidazo[1,2-a]pyridin-8-yl)-[1,2,4]triazolo[4,3-c]pyrimidin-5-amine | 0.0046 |
| N-((5-fluoro-2,3-dihydrobenzofuran-4-yl)methyl)-8-(6-methylimidazo[1,2-a]pyridin-8-yl)-[1,2,4]triazolo[4,3-c]pyrimidin-5-amine | 0.0243 |
| 8-(3,5-dimethylimidazo[1,2-a]pyridin-8-yl)-N-((5-fluoro-2,3-dihydrobenzofuran-4-yl)methyl)-[1,2,4]triazolo[4,3-c]pyrimidin-5-amine | 0.0051 |
| 1-(8-(5-(((5-fluoro-2,3-dihydrobenzofuran-4-yl)methyl)amino)-[1,2,4]triazolo[4,3-c]pyrimidin-8-yl)-2-methylimidazo[1,2-a]pyridin-3-yl)ethan-1-one | 0.0048 |
| 8-(3-phenylmethylimidazo[1,2-a]pyridin-8-yl)-N-((5-fluoro-2,3-dihydrobenzofuran-4-yl)methyl)-[1,2,4]triazolo[4,3-c]pyrimidin-5-amine | 0.0012 |
| 8-(3-ethylimidazo[1,2-a]pyridin-8-yl)-N-((5-fluoro-2,3-dihydrobenzofuran-4-yl)methyl)-[1,2,4]triazolo[4,3-c]pyrimidin-5-amine | 0.0025 |
| 8-(5-(((5-fluoro-2,3-dihydrobenzofuran-4-yl)methyl)amino)-[1,2,4]triazolo[4,3-c]pyrimidin-8-yl)imidazo[1,2-a]pyridine-3-carbonitrile | 0.0047 |
| Ethyl 8-(5-(((5-fluoro-2,3-dihydrobenzofuran-4-yl)methyl)amino)-[1,2,4]triazolo[4,3-c]pyrimidin-8-yl)-2-(trifluoromethyl)imidazo[1,2-a]pyridine-3-carboxylate | 0.0290 |
| 8-(3-ethyl-5-methylimidazo[1,2-a]pyridin-8-yl)-N-((5-fluoro-2,3-dihydrobenzofuran-4-yl)methyl)-[1,2,4]triazolo[4,3-c]pyrimidin-5-amine | 0.0030 |
| 1-(6-fluoro-8-(5-(((5-fluoro-2,3-dihydrobenzofuran-4-yl)methyl)amino)-[1,2,4]triazolo[4,3-c]pyrimidin-8-yl)-2-methylimidazo[1,2-a]pyridin-3-yl)ethan-1-one | 0.0160 |
| N-((5-fluoro-2,3-dihydrobenzofuran-4-yl)methyl)-8-(6-fluoro-3-methylimidazo[1,2-a]pyridin-8-yl)-[1,2,4]triazolo[4,3-c]pyrimidin-5-amine | 0.0074 |
| Ethyl 6-fluoro-8-(5-(((5-fluoro-2,3-dihydrobenzofuran-4-yl)methyl)amino)-[1,2,4]triazolo[4,3-c]pyrimidin-8-yl)-2-hydroxyimidazo[1,2-a]pyridine-3-carboxylate | 0.0912 |
| N-((5-fluoro-2,3-dihydrobenzofuran-4-yl)methyl)-8-(3-fluoroimidazo[1,2-a]pyridin-8-yl-[1,2,4]triazolo[4,3-c]pyrimidin-5-amine | 0.0092 |
| 8-(3,6-difluoroimidazo[1,2-a]pyridin-8-yl)-N-((5-fluoro-2,3-dihydrobenzofuran-4-yl)methyl)-[1,2,4]triazolo[4,3-c]pyrimidin-5-amine | 0.0052 |
| Ethyl 8-(5-(((5-fluoro-2,3-dihydrobenzofuran-4-yl)methyl)amino)-[1,2,4]triazolo[4,3-c]pyrimidin-8-yl)-2-hydroxyimidazo[1,2-a]pyridine-3-carboxylate | 0.0221 |
| 8-(5-(((5-fluoro-2,3-dihydrobenzofuran-4-yl)methyl)amino)-[1,2,4]triazolo[4,3-c]pyrimidin-8-yl)-5-methylimidazo[1,2-a]pyridine-3-carboxylic acid | 0.0054 |
| N-((5-fluoro-2,3-dihydrobenzofuran-4-yl)methyl)-8-(3-fluoro-5-methylimidazo[1,2-a]pyridin-8-yl)-[1,2,4]triazolo[4,3-c]pyrimidin-5-amine | 0.0058 |
| N-((5-fluoro-2,3-dihydrobenzofuran-4-yl)methyl)-8-(quinolin-8-yl)-[1,2,4]triazolo[4,3-c]pyrimidin-5-amine | 0.0051 |
| 5-(5-((((1aR,6bR)-5-fluoro-1a,6b-dihydro-1H-cyclopropa[b]benzofuran-6-yl)methyl)amino)-[1,2,4]triazolo[4,3-c]pyrimidin-8-yl)benzo[b]thiophene 1,1-dioxide | 0.0038 |

TABLE 3-continued

| Compound name | $IC_{50}$ (μM), AlphaScreen |
|---|---|
| 5-(5-(((5-fluoro-2,3-dihydrobenzofuran-4-yl)methyl)amino)-[1,2,4]triazolo[4,3-c]pyrimidin-8-yl)benzo[b]thiophene 1,1-dioxide | 0.0049 |
| 5-(5-((((1aS,6bS)-5-fluoro-1a,6b-dihydro-1H-cyclopropa[b]benzofuran-6-yl)methyl)amino)-[1,2,4]triazolo[4,3-c]pyrimidin-8-yl)benzo[b]thiophene 1,1-dioxide | 0.0150 |
| 4-(5-(((5-fluoro-2,3-dihydrobenzofuran-4-yl)methyl)amino)-[1,2,4]triazolo[4,3-c]pyrimidin-8-yl)benzo[b]thiophene 1,1-dioxide | 0.0100 |
| 4-(5-((((1aR,6bR)-5-fluoro-1a,6b-dihydro-1H-cyclopropa[b]benzofuran-6-yl)methyl)amino)-[1,2,4]triazolo[4,3-c]pyrimidin-8-yl)benzo[b]thiophene 1,1-dioxide | 0.0044 |
| 5-(5-((((1aR,6bR)-5-fluoro-1a,6b-dihydro-1H-cyclopropa[b]benzofuran-6-yl)methyl)amino)-[1,2,4]triazolo[4,3-c]pyrimidin-8-yl)-2-methylbenzo[b]thiophene 1,1-dioxide | 0.0049 |
| 5-(5-((((1aR,6bR)-5-fluoro-1a,6b-dihydro-1H-cyclopropa[b]benzofuran-6-yl)methyl)amino)-[1,2,4]triazolo[4,3-c]pyrimidin-8-yl)-3-methylbenzo[b]thiophene 1,1-dioxide | 0.0049 |
| 2-fluoro-5-(5-((((1aR,6bR)-5-fluoro-1a,6b-dihydro-1H-cyclopropa[b]benzofuran-6-yl)methyl)amino)-[1,2,4]triazolo[4,3-c]pyrimidin-8-yl)benzo[b]thiophene 1,1-dioxide | 0.5660 |
| 3-fluoro-5-(5-((((1aR,6bR)-5-fluoro-1a,6b-dihydro-1H-cyclopropa[b]benzofuran-6-yl)methyl)amino)-[1,2,4]triazolo[4,3-c]pyrimidin-8-yl)benzo[b]thiophene 1,1-dioxide | 0.1230 |
| 5-(5-(((5-fluoro-2,3-dihydrobenzofuran-4-yl)methyl)amino)-[1,2,4]triazolo[4,3-c]pyrimidin-8-yl)benzo[c]thiophene 2,2-dioxide | 0.0049 |
| 3-fluoro-5-(5-((((1aR,6bR)-5-fluoro-1a,6b-dihydro-1H-cyclopropa[b]benzofuran-6-yl)methyl)amino)-[1,2,4]triazolo[4,3-c]pyrimidin-8-yl)-2-methylbenzo[b]thiophene 1,1-dioxide | 0.0042 |
| 5-(5-((((1aR,6bR)-5-fluoro-1a,6b-dihydro-1H-cyclopropa[b]benzofuran-6-yl)methyl)amino)-[1,2,4]triazolo[4,3-c]pyrimidin-8-yl)benzo[c]thiophene 2,2-dioxide | 0.0063 |
| 2-fluoro-5-(5-((((1aR,6bR)-5-fluoro-1a,6b-dihydro-1H-cyclopropa[b]benzofuran-6-yl)methyl)amino)-[1,2,4]triazolo[4,3-c]pyrimidin-8-yl)-3-methylbenzo[b]thiophene 1,1-dioxide | 0.0041 |
| 3-(2-aminoethyl)-5-(5-((((1aS,6bS)-5-fluoro-1a,6b-dihydro-1H-cyclopropa[b]benzofuran-6-yl)methyl)amino)-[1,2,4]triazolo[4,3-c]pyrimidin-8-yl)benzo[b]thiophene 1,1-dioxide | 0.0054 |
| 3-chloro-5-(5-((((1aR,6bR)-5-fluoro-1a,6b-dihydro-1H-cyclopropa[b]benzofuran-6-yl)methyl)amino)-[1,2,4]triazolo[4,3-c]pyrimidin-8-yl)-2-methylbenzo[b]thiophene 1,1-dioxide | 0.0110 |
| 5-(5-(((6-fluorochroman-5-yl)methyl)amino)-[1,2,4]triazolo[4,3-c]pyrimidin-8-yl)benzo[c]thiophene 2,2-dioxide | 0.0064 |
| 7-fluoro-5-(5-(((5-fluoro-2,3-dihydrobenzofuran-4-yl)methyl)amino)-[1,2,4]triazolo[4,3-c]pyrimidin-8-yl)benzo[b]thiophene 1,1-dioxide | 0.0045 |
| 5-(5-(((5-fluoro-2,3-dihydrobenzofuran-4-yl)methyl)amino)-[1,2,4]triazolo[4,3-c]pyrimidin-8-yl)-6-methylbenzo[b]thiophene 1,1-dioxide | 0.0041 |
| 7-chloro-5-(5-(((5-fluoro-2,3-dihydrobenzofuran-4-yl)methyl)amino)-[1,2,4]triazolo[4,3-c]pyrimidin-8-yl)-2-methylbenzo[b]thiophene 1,1-dioxide | 0.0039 |
| 7-fluoro-5-(5-(((5-fluoro-2,3-dihydrobenzofuran-4-yl)methyl)amino)-[1,2,4]triazolo[4,3-c]pyrimidin-8-yl)-2,3-dimethylbenzo[b]thiophene 1,1-dioxide | 0.0020 |
| 1-fluoro-5-(5-((((1aR,6bR)-5-fluoro-1a,6b-dihydro-1H-cyclopropa[b]benzofuran-6-yl)methyl)amino)-[1,2,4]triazolo[4,3-c]pyrimidin-8-yl)benzo[c]thiophene 2,2-dioxide | 0.1862 |
| 4-(5-(((5-fluoro-2,3-dihydrobenzofuran-4-yl)methyl)amino)-[1,2,4]triazolo[4,3-c]pyrimidin-8-yl)-2-methylbenzo[b]thiophene 1,1-dioxide | 0.0122 |
| 6-(5-(((5-fluoro-2,3-dihydrobenzofuran-4-yl)methyl)amino)-[1,2,4]triazolo[4,3-c]pyrimidin-8-yl)-2-methylbenzo[b]thiophene 1,1-dioxide | 0.0027 |
| 3-fluoro-5-(5-(((5-fluoro-2,3-dihydrobenzofuran-4-yl)methyl)amino)-[1,2,4]triazolo[4,3-c]pyrimidin-8-yl)-2-methylbenzo[b]thiophene 1,1-dioxide | 0.0026 |
| 8-(2,3-dihydroimidazo[1,2-a]pyridin-8-yl)-N-((5-fluoro-2,3-dihydrobenzofuran-4-yl)methyl)-[1,2,4]triazolo[4,3-c]pyrimidin-5-amine | 0.0052 |
| N-((5-fluoro-2,3-dihydrobenzofuran-4-yl)methyl)-8-(3-isopropyl-5-methylimidazo[1,2-a]pyridin-8-yl)-[1,2,4]triazolo[4,3-c]pyrimidin-5-amine | 0.0028 |
| Methyl 8-(5-(((5-fluoro-2,3-dihydrobenzofuran-4-yl)methyl)amino)-[1,2,4]triazolo[4,3-c]pyrimidin-8-yl)imidazo[1,2-a]pyridine-5-carboxylate | 0.0080 |
| 2-(8-(5-(((5-fluoro-2,3-dihydrobenzofuran-4-yl)methyl)amino)-[1,2,4]triazolo[4,3-c]pyrimidin-8-yl)-5-methylimidazo[1,2-a]pyridin-3-yl)acetamide | 0.0118 |
| 2-(8-(5-(((5-fluoro-2,3-dihydrobenzofuran-4-yl)methyl)amino)-[1,2,4]triazolo[4,3-c]pyrimidin-8-yl)-5-methylimidazo[1,2-a]pyridin-3-yl)ethan-1-ol | 0.0099 |

TABLE 3-continued

| Compound name | $IC_{50}$ (μM), AlphaScreen |
|---|---|
| Methyl 2-(8-(5-(((5-fluoro-2,3-dihydrobenzofuran-4-yl)methyl)amino)-[1,2,4]triazolo[4,3-c]pyrimidin-8-yl)-5-methylimidazo[1,2-a]pyridin-3-yl)acetate | 0.0062 |
| 2-(8-(5-(((5-fluoro-2,3-dihydrobenzofuran-4-yl)methyl)amino)-[1,2,4]triazolo[4,3-c]pyrimidin-8-yl)-5-methylimidazo[1,2-a]pyridin-3-yl)acetic acid | 0.0054 |
| (8-(5-(((5-fluoro-2,3-dihydrobenzofuran-4-yl)methyl)amino)-[1,2,4]triazolo[4,3-c]pyrimidin-8-yl)imidazo[1,2-a]pyridin-5-yl)methanol | 0.0210 |
| N-(((1aR,6bR)-5-fluoro-1a,6b-dihydro-1H-cyclopropa[b]benzofuran-6-yl)methyl)-8-(5-methyl-[1,2,4]triazolo[1,5-a]pyridin-8-yl)-[1,2,4]triazolo[4,3-c]pyrimidin-5-amine | 0.0035 |
| 2-(8-(5-(((5-fluoro-2,3-dihydrobenzofuran-4-yl)methyl)amino)-[1,2,4]triazolo[4,3-c]pyrimidin-8-yl)-5-methylimidazo[1,2-a]pyridin-3-yl)-N,N-dimethylacetamide | 0.0114 |
| 2-(8-(5-(((5-fluoro-2,3-dihydrobenzofuran-4-yl)methyl)amino)-[1,2,4]triazolo[4,3-c]pyrimidin-8-yl)-5-methylimidazo[1,2-a]pyridin-3-yl)ethyl acetate | 0.0062 |
| N-((5-fluoro-2,3-dihydrobenzofuran-4-yl)methyl)-8-(5-methylimidazo[1,2-a]pyridin-8-yl)-[1,2,4]triazolo[4,3-c]pyrimidin-5-amine | 0.0058 |
| (8-(5-(((5-fluoro-2,3-dihydrobenzofuran-4-yl)methyl)amino)-[1,2,4]triazolo[4,3-c]pyrimidin-8-yl)-5-methylimidazo[1,2-a]pyridin-2-yl)methanol | 0.0083 |
| N-((5-fluoro-2,3-dihydrobenzofuran-4-yl)methyl)-8-(5-methyl-[1,2,4]triazolo[1,5-a]pyridin-8-yl)-[1,2,4]triazolo[4,3-c]pyrimidin-5-amine | 0.0089 |
| N-((5-fluoro-2,3-dihydrobenzofuran-4-yl)methyl)-8-(1-methyl-1H-benzo[d]imidazol-4-yl)-[1,2,4]triazolo[4,3-c]pyrimidin-5-amine | 0.0086 |

Example 153: ELISA (H3K27 Trimethylation) Analysis 3-fold series dilution with DMSO was carried out on the representative compounds of the present disclosure; and 10 concentration gradients were detected for each compound, with the highest detection concentration of 10 μM. The compounds were diluted 200-fold into the G401 cells cultured in a 96-well plate (DMSO at a final concentration of 0.5%). After the cells, administered with the compound, were cultured for 72 hours, the trimethylation level of the histone H3K27 was detected using the ELISA method.

Extraction of the histone: in a 96-well plate, the compound-treated cells were washed three times with 1×PBS (10×PBS buffer (80 g NaCl (Sigma, product number S3014), 2 g KCl (Sigma, product number 60128), 14.4 g $Na_2HPO_4$ (Sigma, product number S5136), and 2.4 g $KH_2PO_4$ (Sigma, product number P9791) in 1 L of water, adjusting the pH to 7.4)). 100 μL of 0.4 N HCl was added into each well. The plate was placed at 4° C. and gently agitated for 2 hours to lyse the cells. The cell lysate was then neutralized with 80 μL of neutralization buffer (0.5 M disodium hydrogen phosphate, pH 12.5, 2.5 mM DTT; 1% cocktail (Sigma, product number P8340)) (the cell lysate and the neutralization buffer were thoroughly mixed to uniformity).

ELISA detection method: the cell lysate was transferred in parallel to two 384-well detection plates (PerkinElmer, OptiPlate-384HB, product number 6007290), wherein one of the plates was used to detect the H3K27 trimethylation level and the other plate was used to determine the level of H3. PBS was used to adjust the final volume to 50 μL/well. The plates were coated at 4° C. overnight. On the following day, the solution inside the wells was discarded and the plates were washed 5 times with TBST buffer (1×TBS (10×TBS: 24.2 g Tris (Sigma, product number T6066), 80 g NaCl (Sigma, product number S3014) in 1 L of water, adjusting the pH with HCl to 7.6), 0.1% Tween-20) and dried on an absorbent paper by inversion. 70 μL of blocking buffer (TBST, 5% BSA) was added into the coated reaction wells and the plates were incubated at room temperature for 1 hour. The blocking buffer was discarded and primary antibodies were added (30 μL/well). The desired primary antibodies were all diluted with a blocking buffer and the dilution factor was as follows: anti-H3K27me3 antibody (Cell Signaling Technology, product number 9733), 1:2000 dilution; anti-H3 antibody (Cell Signaling Technology, product number 4499), 1:10000 dilution. After the primary antibodies were added, the plates were placed at room temperature and incubated for 1 hour. After the plates were washed with TBST 5 times, the plates were dried by inversion. A secondary antibody (30 μL/well) was added to each of the reaction wells and the plates were incubated at room temperature for 1 hour. The secondary antibody (anti-rabbit antibody (Jackson ImmunoResearch, product number 111-035-003)) was diluted 2000-fold with a blocking buffer before use. After 1 hour, the plates were washed with TBST and dried by inversion. 30 μL of ECL substrate (Pierce, product number 34080) was added into each well and centrifuged at 2000 rpm for 30 seconds. The signal of each sample was detected using SpectraMax (Molecular Devices). Data processing: H3K27 methylation readings were first standardlized using H3 signals and 0.5% DMSO-treated samples was used as the control to calculate the inhibition percentage of the compounds. Data were fit to obtain Dose-Response curves using the GraphPad prism 5 program and the $IC_{50}$ values of the test compounds were obtained.

Table 4 below shows the $IC_{50}$ values of part of the compounds of the present disclosure.

TABLE 4

| Compound name | $IC_{50}$ (μM), ELISA, G401 |
|---|---|
| N-((5-fluoro-2,3-dihydrobenzofuran-4-yl)methyl)-8-(imidazo[1,2-a]pyridin-7-yl)-[1,2,4]triazolo[4,3-c]pyrimidin-5-amine | 0.0056 |
| N-((5-fluoro-2,3-dihydrobenzofuran-4-yl)methyl)-8-(imidazo[1,2-a]pyridin-6-yl)-[1,2,4]triazolo[4,3-c]pyrimidin-5-amine | 0.0580 |
| N-((5-fluoro-2,3-dihydrobenzofuran-4-yl)methyl)-8-(pyrazolo[1,5-a]pyrimidin-6-yl)-[1,2,4]triazolo[4,3-c]pyrimidin-5-amine | 0.0180 |
| 8-([1,2,4]triazolo[4,3-a]pyridin-6-yl)-N-(((1aR,6bR)-5-fluoro-1a,6b-dihydro-1H-cyclopropa[b]benzofuran-6-yl)methyl)-[1,2,4]triazolo[4,3-c]pyrimidin-5-amine | 0.0064 |
| 8-([1,2,4]triazolo[1,5-a]pyridin-7-yl)-N-(((1aR,6bR)-5-fluoro-1a,6b-dihydro-1H-cyclopropa[b]benzofuran-6-yl)methyl)-[1,2,4]triazolo[4,3-c]pyrimidin-5-amine | 0.0073 |
| N-((5-fluoro-2,3-dihydrobenzofuran-4-yl)methyl)-8-(imidazo[1,2-a]pyrimidin-6-yl)-[1,2,4]triazolo[4,3-c]pyrimidin-5-amine | 0.0129 |
| N-((5-fluoro-2,3-dihydrobenzofuran-4-yl)methyl)-8-(pyrazolo[1,5-a]pyridin-6-yl)-[1,2,4]triazolo[4,3-c]pyrimidin-5-amine | 0.0061 |
| 8-([1,2,4]triazolo[1,5-a]pyridin-8-yl)-N-((5-fluoro-2,3-dihydrobenzofuran-4-yl)methyl)-[1,2,4]triazolo[4,3-c]pyrimidin-5-amine | 0.0009 |
| N-((5-fluoro-2,3-dihydrobenzofuran-4-yl)methyl)-8-(imidazo[1,2-a]pyridin-8-yl)-[1,2,4]triazolo[4,3-c]pyrimidin-5-amine | 0.0008 |
| 8-([1,2,4]triazolo[1,5-a]pyridin-8-yl)-N-(((1aR,6bR)-5-fluoro-1a,6b-dihydro-1H-cyclopropa[b]benzofuran-6-yl)methyl)-[1,2,4]triazolo[4,3-c]pyrimidin-5-amine | 0.0007 |
| N-(((1aR,6bR)-5-fluoro-1a,6b-dihydro-1H-cyclopropa[b]benzofuran-6-yl)methyl)-8-(imidazo[1,2-a]pyridin-8-yl)-[1,2,4]triazolo[4,3-c]pyrimidin-5-amine | 0.0010 |
| 8-([1,2,4]triazolo[4,3-a]pyridin-8-yl)-N-(((1aR,6bR)-5-fluoro-1a,6b-dihydro-1H-cyclopropa[b]benzofuran-6-yl)methyl)-[1,2,4]triazolo[4,3-c]pyrimidin-5-amine | 0.0074 |
| N-((5-fluoro-2,3-dihydrobenzofuran-4-yl)methyl)-8-(2-(trifluoromethyl)imidazo[1,2-a]pyridin-8-yl)-[1,2,4]triazolo[4,3-c]pyrimidin-5-amine | 0.0024 |
| 8-(6-chloroimidazo[1,2-a]pyridin-8-yl)-N-((5-fluoro-2,3-dihydrobenzofuran-4-yl)methyl)-[1,2,4]triazolo[4,3-c]pyrimidin-5-amine | 0.0085 |
| 8-(6-chloro-2-(trifluoromethyl)imidazo[1,2-a]pyridin-8-yl)-N-((5-fluoro-2,3-dihydrobenzofuran-4-yl)methyl)-[1-1,2,4]triazolo[4,3-c]pyrimidin-5-amine | 0.0890 |
| N-((5-fluoro-2,3-dihydrobenzofuran-4-yl)methyl)-8-(6-fluoroimidazo[1,2-a]pyridin-8-yl)-[1,2,4]triazolo[4,3-c]pyrimidin-5-amine | 0.0029 |
| N-((5-fluoro-2,3-dihydrobenzofuran-4-yl)methyl)-8-(6-fluoro-2-(trifluoromethyl)imidazo[1,2-a]pyridin-8-yl)-[11,2,4]triazolo[4,3-c]pyrimidin-5-amine | 0.0171 |
| Ethyl 6-fluoro-8-(5-(((5-fluoro-2,3-dihydrobenzofuran-4-yl)methyl)amino)-[1,2,4]triazolo[4,3-c]pyrimidin-8-yl)imidazo[1,2-a]pyridine-3-carboxylate | 0.0470 |
| N-((5-fluoro-2,3-dihydrobenzofuran-4-yl)methyl)-8-(pyrazolo[1,5-a]pyrimidin-3-yl)-[1,2,4]triazolo[4,3-c]pyrimidin-5-amine | 0.0104 |
| Ethyl 6-fluoro-8-(5-(((5-fluoro-2,3-dihydrobenzofuran-4-yl)methyl)amino)-[1,2,4]triazolo[4,3-c]pyrimidin-8-yl)-2-methylimidazo[1,2-a]pyridine-3-carboxylate | 0.0870 |
| Ethyl 8-(5-(((5-fluoro-2,3-dihydrobenzofuran-4-yl)methyl)amino)-[1,2,4]triazolo[4,3-c]pyrimidin-8-yl)imidazo[1,2-a]pyridine-3-carboxylate | 0.0060 |
| 8-(5-(((5-fluoro-2,3-dihydrobenzofuran-4-yl)methyl)amino)-[1,2,4]triazolo[4,3-c]pyrimidin-8-yl)imidazo[1,2-a]pyridine-3-carboxylic acid | 0.3290 |
| N-((5-fluoro-2,3-dihydrobenzofuran-4-yl)methyl)-8-(6-fluoro-2-methylimidazo[1,2-a]pyridin-8-yl)-[1,2,4]triazolo[4,3-c]pyrimidin-5-amine | 0.0035 |
| N-((5-fluoro-2,3-dihydrobenzofuran-4-yl)methyl)-8-(2-methylimidazo[1,2-a]pyridin-8-yl)-[1,2,4]triazolo[4,3-c]pyrimidin-5-amine | 0.0030 |
| N-((5-fluoro-2,3-dihydrobenzofuran-4-yl)methyl)-8-(2-methylbenzo[d]oxazol-4-yl)-[1,2,4]triazolo[4,3-c]pyrimidin-5-amine | 0.0078 |
| 8-(benzo[d]oxazol-7-yl)-N-((5-fluoro-2,3-dihydrobenzofuran-4-yl)methyl)-[1,2,4]triazolo[4,3-c]pyrimidin-5-amine | 0.0130 |
| N-((5-fluoro-2,3-dihydrobenzofuran-4-yl)methyl)-8-(6-methyl-2-(trifluoromethyl)imidazo[1,2-a]pyridin-8-yl)-[1,2,4]triazolo[4,3-c]pyrimidin-5-amine | 0.0410 |
| 8-(5-(((5-fluoro-2,3-dihydrobenzofuran-4-yl)methyl)amino)-[1,2,4]triazolo[4,3-c]pyrimidin-8-yl)imidazo[1,2-a]pyridine-3-carboxamide | 0.0041 |
| N-((5-fluoro-2,3-dihydrobenzofuran-4-yl)methyl)-8-(5-(trifluoromethyl)benzo[c][1,2,5]thiadiazol-4-yl)-[1,2,4]triazolo[4,3-c]pyrimidin-5-amine | 0.1700 |
| N-((5-fluoro-2,3-dihydrobenzofuran-4-yl)methyl)-8-(3-methylimidazo[1,2-a]pyridin-8-yl)-[1,2,4]triazolo[4,3-c]pyrimidin-5-amine | 0.0016 |
| N-((5-fluoro-2,3-dihydrobenzofuran-4-yl)methyl)-8-(6-methylimidazo[1,2-a]pyridin-8-yl)-[1,2,4]triazolo[4,3-c]pyrimidin-5-amine | 0.0140 |
| 8-(3,5-dimethylimidazo[1,2-a]pyridin-8-yl)-N-((5-fluoro-2,3-dihydrobenzofuran-4-yl)methyl)-[1,2,4]triazolo[4,3-c]pyrimidin-5-amine | 0.0027 |

TABLE 4-continued

| Compound name | $IC_{50}$ (μM), ELISA, G401 |
|---|---|
| 1-(8-(5-(((5-fluoro-2,3-dihydrobenzofuran-4-yl)methyl)amino)-[1,2,4]triazolo[4,3-c]pyrimidin-8-yl)-2-methylimidazo[1,2-a]pyridin-3-yl)ethan-1-one | 0.0025 |
| 8-(3-phenylmethylimidazo[1,2-a]pyridin-8-yl)-N-((5-fluoro-2,3-dihydrobenzofuran-4-yl)methyl)-[1,2,4]triazolo[4,3-c]pyrimidin-5-amine | 0.0045 |
| 8-(3-ethylimidazo[1,2-a]pyridin-8-yl)-N-((5-fluoro-2,3-dihydrobenzofuran-4-yl)methyl)-[1,2,4]triazolo[4,3-c]pyrimidin-5-amine | 0.0009 |
| 8-(5-(((5-fluoro-2,3-dihydrobenzofuran-4-yl)methyl)amino)-[1,2,4]triazolo[4,3-c]pyrimidin-8-yl)imidazo[1,2-a]pyridine-3-carbonitrile | 0.0032 |
| Ethyl 8-(5-(((5-fluoro-2,3-dihydrobenzofuran-4-yl)methyl)amino)-[1,2,4]triazolo[4,3-c]pyrimidin-8-yl)-2-(trifluoromethyl)imidazo[1,2-a]pyridine-3-carboxylate | 0.2020 |
| 8-(3-ethyl-5-methylimidazo[1,2-a]pyridin-8-yl)-N-((5-fluoro-2,3-dihydrobenzofuran-4-yl)methyl)-[1,2,4]triazolo[4,3-c]pyrimidin-5-amine | 0.0025 |
| 1-(6-fluoro-8-(5-(((5-fluoro-2,3-dihydrobenzofuran-4-yl)methyl)amino)-[1,2,4]triazolo[4,3-c]pyrimidin-8-yl)-2-methylimidazo[1,2-a]pyridin-3-yl)ethan-1-one | 0.0015 |
| N-((5-fluoro-2,3-dihydrobenzofuran-4-yl)methyl)-8-(6-fluoro-3-methylimidazo[1,2-a]pyridin-8-yl)-[1,2,4]triazolo[4,3-c]pyrimidin-5-amine | 0.0057 |
| Ethyl 6-fluoro-8-(5-(((5-fluoro-2,3-dihydrobenzofuran-4-yl)methyl)amino)-[1,2,4]triazolo[4,3-c]pyrimidin-8-yl)-2-hydroxyimidazo[1,2-a]pyridine-3-carboxylate | 0.0910 |
| N-((5-fluoro-2,3-dihydrobenzofuran-4-yl)methyl)-8-(3-fluoroimidazo[1,2-a]pyridin-8-yl-[1,2,4]triazolo[4,3-c]pyrimidin-5-amine | 0.0035 |
| 8-(3,6-difluoroimidazo[1,2-a]pyridin-8-yl)-N-((5-fluoro-2,3-dihydrobenzofuran-4-yl)methyl)-[1,2,4]triazolo[4,3-c]pyrimidin-5-amine | 0.0077 |
| Ethyl 8-(5-(((5-fluoro-2,3-dihydrobenzofuran-4-yl)methyl)amino)-[1,2,4]triazolo[4,3-c]pyrimidin-8-yl)-2-hydroxyimidazo[1,2-a]pyridine-3-carboxylate | 0.0680 |
| 8-(5-(((5-fluoro-2,3-dihydrobenzofuran-4-yl)methyl)amino)-[1,2,4]triazolo[4,3-c]pyrimidin-8-yl)-5-methylimidazo[1,2-a]pyridine-3-carboxylic acid | 0.0040 |
| N-((5-fluoro-2,3-dihydrobenzofuran-4-yl)methyl)-8-(3-fluoro-5-methylimidazo[1,2-a]pyridin-8-yl)-[1,2,4]triazolo[4,3-c]pyrimidin-5-amine | 0.0061 |
| N-((5-fluoro-2,3-dihydrobenzofuran-4-yl)methyl)-8-(quinolin-8-yl)-[1,2,4]triazolo[4,3-c]pyrimidin-5-amine | 0.0029 |
| 5-(5-((((1aR,6bR)-5-fluoro-1a,6b-dihydro-1H-cyclopropa[b]benzofuran-6-yl)methyl)amino)-[1,2,4]triazolo[4,3-c]pyrimidin-8-yl)benzo[b]thiophene 1,1-dioxide | 0.0008 |
| 5-(5-(((5-fluoro-2,3-dihydrobenzofuran-4-yl)methyl)amino)-[1,2,4]triazolo[4,3-c]pyrimidin-8-yl)benzo[b]thiophene 1,1-dioxide | 0.0021 |
| 5-(5-((((1aS,6bS)-5-fluoro-1a,6b-dihydro-1H-cyclopropa[b]benzofuran-6-yl)methyl)amino)-[1,2,4]triazolo[4,3-c]pyrimidin-8-yl)benzo[b]thiophene 1,1-dioxide | 0.0160 |
| 4-(5-(((5-fluoro-2,3-dihydrobenzofuran-4-yl)methyl)amino)-[1,2,4]triazolo[4,3-c]pyrimidin-8-yl)benzo[b]thiophene 1,1-dioxide | 0.0210 |
| 4-(5-((((1aR,6bR)-5-fluoro-1a,6b-dihydro-1H-cyclopropa[b]benzofuran-6-yl)methyl)amino)-[1,2,4]triazolo[4,3-c]pyrimidin-8-yl)benzo[b]thiophene 1,1-dioxide | 0.0092 |
| 5-(5-((((1aR,6bR)-5-fluoro-1a,6b-dihydro-1H-cyclopropa[b]benzofuran-6-yl)methyl)amino)-[1,2,4]triazolo[4,3-c]pyrimidin-8-yl)-2-methylbenzo[b]thiophene 1,1-dioxide | 0.0041 |
| 5-(5-((((1aR,6bR)-5-fluoro-1a,6b-dihydro-1H-cyclopropa[b]benzofuran-6-yl)methyl)amino)-[1,2,4]triazolo[4,3-c]pyrimidin-8-yl)-3-methylbenzo[b]thiophene 1,1-dioxide | 0.0136 |
| 2-fluoro-5-(5-((((1aR,6bR)-5-fluoro-1a,6b-dihydro-1H-cyclopropa[b]benzofuran-6-yl)methyl)amino)-[1,2,4]triazolo[4,3-c]pyrimidin-8-yl)benzo[b]thiophene 1,1-dioxide | 0.1600 |
| 3-fluoro-5-(5-((((1aR,6bR)-5-fluoro-1a,6b-dihydro-1H-cyclopropa[b]benzofuran-6-yl)methyl)amino)-[1,2,4]triazolo[4,3-c]pyrimidin-8-yl)benzo[b]thiophene 1,1-dioxide | 0.0780 |
| 5-(5-(((5-fluoro-2,3-dihydrobenzofuran-4-yl)methyl)amino)-[1,2,4]triazolo[4,3-c]pyrimidin-8-yl)benzo[c]thiophene 2,2-dioxide | 0.0003 |
| 3-fluoro-5-(5-((((1aR,6bR)-5-fluoro-1a,6b-dihydro-1H-cyclopropa[b]benzofuran-6-yl)methyl)amino)-[1,2,4]triazolo[4,3-c]pyrimidin-8-yl)-2-methylbenzo[b]thiophene 1,1-dioxide | 0.0058 |
| 5-(5-((((1aR,6bR)-5-fluoro-1a,6b-dihydro-1H-cyclopropa[b]benzofuran-6-yl)methyl)amino)-[1,2,4]triazolo[4,3-c]pyrimidin-8-yl)benzo[c]thiophene 2,2-dioxide | 0.0006 |
| 2-fluoro-5-(5-((((1aR,6bR)-5-fluoro-1a,6b-dihydro-1H-cyclopropa[b]benzofuran-6-yl)methyl)amino)-[1,2,4]triazolo[4,3-c]pyrimidin-8-yl)-3-methylbenzo[b]thiophene 1,1-dioxide | 0.0220 |
| 3-(2-aminoethyl)-5-(5-((((1aS,6bS)-5-fluoro-1a,6b-dihydro-1H-cyclopropa[b]benzofuran-6-yl)methyl)amino)-[1,2,4]triazolo[4,3-c]pyrimidin-8-yl)benzo[b]thiophene 1,1-dioxide | 0.0750 |

TABLE 4-continued

| Compound name | $IC_{50}$ (μM), ELISA, G401 |
|---|---|
| 3-chloro-5-(5-((((1aR,6bR)-5-fluoro-1a,6b-dihydro-1H-cyclopropa[b]benzofuran-6-yl)methyl)amino)-[1,2,4]triazolo[4,3-c]pyrimidin-8-yl)-2-methylbenzo[b]thiophene 1,1-dioxide | 0.127 |
| 5-(5-(((6-fluorochroman-5-yl)methyl)amino)-[1,2,4]triazolo[4,3-c]pyrimidin-8-yl)benzo[c]thiophene 2,2-dioxide | 0.0020 |
| 7-fluoro-5-(5-(((5-fluoro-2,3-dihydrobenzofuran-4-yl)methyl)amino)-[1,2,4]triazolo[4,3-c]pyrimidin-8-yl)benzo[b]thiophene 1,1-dioxide | 0.0028 |
| 5-(5-(((5-fluoro-2,3-dihydrobenzofuran-4-yl)methyl)amino)-[1,2,4]triazolo[4,3-c]pyrimidin-8-yl)-6-methylbenzo[b]thiophene 1,1-dioxide | 0.0009 |
| 7-chloro-5-(5-(((5-fluoro-2,3-dihydrobenzofuran-4-yl)methyl)amino)-[1,2,4]triazolo[4,3-c]pyrimidin-8-yl)-2-methylbenzo[b]thiophene 1,1-dioxide | 0.0260 |
| 7-fluoro-5-(5-(((5-fluoro-2,3-dihydrobenzofuran-4-yl)methyl)amino)-[1,2,4]triazolo[4,3-c]pyrimidin-8-yl)-2,3-dimethylbenzo[b]thiophene 1,1-dioxide | 0.0140 |
| 1-fluoro-5-(5-((((1aR,6bR)-5-fluoro-1a,6b-dihydro-1H-cyclopropa[b]benzofuran-6-yl)methyl)amino)-[1,2,4]triazolo[4,3-c]pyrimidin-8-yl)benzo[c]thiophene 2,2-dioxide | 0.0750 |
| 4-(5-(((5-fluoro-2,3-dihydrobenzofuran-4-yl)methyl)amino)-[1,2,4]triazolo[4,3-c]pyrimidin-8-yl)-2-methylbenzo[b]thiophene 1,1-dioxide | 0.0036 |
| 6-(5-(((5-fluoro-2,3-dihydrobenzofuran-4-yl)methyl)amino)-[1,2,4]triazolo[4,3-c]pyrimidin-8-yl)-2-methylbenzo[b]thiophene 1,1-dioxide | 0.0079 |
| 3-fluoro-5-(5-(((5-fluoro-2,3-dihydrobenzofuran-4-yl)methyl)amino)-[1,2,4]triazolo[4,3-c]pyrimidin-8-yl)-2-methylbenzo[b]thiophene 1,1-dioxide | 0.0073 |
| N-((5-fluoro-2,3-dihydrobenzofuran-4-yl)methyl)-8-(3-isopropyl-5-methylimidazo[1,2-a]pyridin-8-yl)-[1,2,4]triazolo[4,3-c]pyrimidin-5-amine | 0.0007 |
| Methyl 8-(5-(((5-fluoro-2,3-dihydrobenzofuran-4-yl)methyl)amino)-[1,2,4]triazolo[4,3-c]pyrimidin-8-yl)imidazo[1,2-a]pyridine-5-carboxylate | 0.0035 |
| 2-(8-(5-(((5-fluoro-2,3-dihydrobenzofuran-4-yl)methyl)amino)-[1,2,4]triazolo[4,3-c]pyrimidin-8-yl)-5-methylimidazo[1,2-a]pyridin-3-yl)acetamide | 0.0030 |
| 2-(8-(5-(((5-fluoro-2,3-dihydrobenzofuran-4-yl)methyl)amino)-[1,2,4]triazolo[4,3-c]pyrimidin-8-yl)-5-methylimidazo[1,2-a]pyridin-3-yl)ethan-1-ol | 0.0016 |
| Methyl 2-(8-(5-(((5-fluoro-2,3-dihydrobenzofuran-4-yl)methyl)amino)-[1,2,4]triazolo[4,3-c]pyrimidin-8-yl)-5-methylimidazo[1,2-a]pyridin-3-yl)acetate | 0.0038 |
| 2-(8-(5-(((5-fluoro-2,3-dihydrobenzofuran-4-yl)methyl)amino)-[1,2,4]triazolo[4,3-c]pyrimidin-8-yl)-5-methylimidazo[1,2-a]pyridin-3-yl)acetic acid | 0.0040 |
| (8-(5-(((5-fluoro-2,3-dihydrobenzofuran-4-yl)methyl)amino)-[1,2,4]triazolo[4,3-c]pyrimidin-8-yl)imidazo[1,2-a]pyridin-5-yl)methanol | 0.0052 |
| N-(((1aR,6bR)-5-fluoro-1a,6b-dihydro-1H-cyclopropa[b]benzofuran-6-yl)methyl)-8-(5-methyl-[1,2,4]triazolo[1,5-a]pyridin-8-yl)-[1,2,4]triazolo[4,3-c]pyrimidin-5-amine | 0.0024 |
| 2-(8-(5-(((5-fluoro-2,3-dihydrobenzofuran-4-yl)methyl)amino)-[1,2,4]triazolo[4,3-c]pyrimidin-8-yl)-5-methylimidazo[1,2-a]pyridin-3-yl)-N,N-dimethylacetamide | 0.0016 |
| 2-(8-(5-(((5-fluoro-2,3-dihydrobenzofuran-4-yl)methyl)amino)-[1,2,4]triazolo[4,3-c]pyrimidin-8-yl)-5-methylimidazo[1,2-a]pyridin-3-yl)ethyl acetate | 0.0010 |
| N-((5-fluoro-2,3-dihydrobenzofuran-4-yl)methyl)-8-(5-methylimidazo[1,2-a]pyridin-8-yl)-[1,2,4]triazolo[4,3-c]pyrimidin-5-amine | 0.0013 |
| N-(((1aR,6bR)-5-fluoro-1a,6b-dihydro-1H-cyclopropa[b]benzofuran-6-yl)methyl)-8-(5-methylimidazo[1,2-a]pyridin-8-yl)-[1,2,4]triazolo[4,3-c]pyrimidin-5-amine | 0.0012 |
| N-((8-(5-(((5-fluoro-2,3-dihydrobenzofuran-4-yl)methyl)amino)-[1,2,4]triazolo[4,3-c]pyrimidin-8-yl)-5-methylimidazo[1,2-a]pyridin-3-yl)methyl)acetamide | 0.0024 |
| (8-(5-(((5-fluoro-2,3-dihydrobenzofuran-4-yl)methyl)amino)-[1,2,4]triazolo[4,3-c]pyrimidin-8-yl)-5-methylimidazo[1,2-a]pyridin-2-yl)methanol | 0.0014 |
| N-((5-fluoro-2,3-dihydrobenzofuran-4-yl)methyl)-8-(5-methyl-[1,2,4]triazolo[1,5-a]pyridin-8-yl)-[1,2,4]triazolo[4,3-c]pyrimidin-5-amine | 0.0017 |
| N-((5-fluoro-2,3-dihydrobenzofuran-4-yl)methyl)-8-(1-methyl-1H-benzo[d]imidazol-4-yl)-[1,2,4]triazolo[4,3-c]pyrimidin-5-amine | 0.0013 |
| 8-(5-(((5-fluoro-2,3-dihydrobenzofuran-4-yl)methyl)amino)-[1,2,4]triazolo[4,3-c]pyrimidin-8-yl)-N,N,5-trimethylimidazo[1,2-a]pyridine-2-carboxamide | 0.0023 |
| 8-(5-(((5-fluoro-2,3-dihydrobenzofuran-4-yl)methyl)amino)-[1,2,4]triazolo[4,3-c]pyrimidin-8-yl)-N,N,5-trimethylimidazo[1,2-a]pyridine-3-carboxamide | 0.0014 |

TABLE 4-continued

| Compound name | $IC_{50}$ (μM), ELISA, G401 |
|---|---|
| 8-(5-(((5-fluoro-2,3-dihydrobenzofuran-4-yl)methyl)amino)-[1,2,4]triazolo[4,3-c]pyrimidin-8-yl)-N,N-dimethylimidazo[1,2-a]pyridine-5-carboxamide | 0.0007 |
| 6-fluoro-8-(5-(((5-fluoro-2,3-dihydrobenzofuran-4-yl)methyl)amino)-[1,2,4]triazolo[4,3-c]pyrimidin-8-yl)imidazo[1,2-a]pyridine-3-carbonitrile | 0.0089 |
| 2-(8-(5-(((5-fluoro-2,3-dihydrobenzofuran-4-yl)methyl)amino)-[1,2,4]triazolo[4,3-c]pyrimidin-8-yl)-5-methylimidazo[1,2-a]pyridin-3-yl)-1-morpholinoethan-1-one | 0.0143 |
| N-((5-fluoro-2,3-dihydrobenzofuran-4-yl)methyl)-8-(5-(trifluoromethyl)imidazo[1,2-a]pyridin-8-yl)-[1,2,4]triazolo[4,3-c]pyrimidin-5-amine | 0.0106 |
| (8-(5-(((5-fluoro-2,3-dihydrobenzofuran-4-yl)methyl)amino)-[1,2,4]triazolo[4,3-c]pyrimidin-8-yl)-5-methylimidazo[1,2-a]pyridin-3-yl)(morpholino)methanone | 0.0024 |
| 8-(5-chloro-[1,2,4]triazolo[1,5-a]pyridin-8-yl)-N-((5-fluoro-2,3-dihydrobenzofuran-4-yl)methyl)-[1,2,4]triazolo[4,3-c]pyrimidin-5-amine | 0.0330 |
| 8-(5-(((5-fluoro-2,3-dihydrobenzofuran-4-yl)methyl)amino)-[1,2,4]triazolo[4,3-c]pyrimidin-8-yl)-5-methylimidazo[1,2-a]pyridine-3-carboxamide | 0.0035 |
| 8-(5-(((5-fluoro-2,3-dihydrobenzofuran-4-yl)methyl)amino)-[1,2,4]triazolo[4,3-c]pyrimidin-8-yl)-5-methylimidazo[1,2-a]pyridine-3-carbonitrile | 0.0052 |
| N-((5-fluoro-2,3-dihydrobenzofuran-4-yl)methyl)-8-(5-(trifluoromethyl)-[1,2,4]triazolo[1,5-a]pyridin-8-yl)-[1,2,4]triazolo[4,3-c]pyrimidin-5-amine | 0.0069 |
| 2-(8-(5-(((5-fluoro-2,3-dihydrobenzofuran-4-yl)methyl)amino)-[1,2,4]triazolo[4,3-c]pyrimidin-8-yl)-5-methylimidazo[1,2-a]pyridin-3-yl)acetonitrile | 0.0070 |
| N-((5-fluoro-2,3-dihydrobenzofuran-4-yl)methyl)-8-(5-methoxy-[1,2,4]triazolo[1,5-a]pyridin-8-yl)-[1,2,4]triazolo[4,3-c]pyrimidin-5-amine | 0.0032 |
| 8-(benzo[c][1,2,5]thiadiazol-4-yl)-N-((5-fluoro-2,3-dihydrobenzofuran-4-yl)methyl)-[1,2,4]triazolo[4,3-c]pyrimidin-5-amine | 0.0023 |
| 6-fluoro-8-(5-(((5-fluoro-2,3-dihydrobenzofuran-4-yl)methyl)amino)-[1,2,4]triazolo[4,3-c]pyrimidin-8-yl)-N,N-dimethylimidazo[1,2-a]pyridine-3-carboxamide | 0.0047 |
| 6-fluoro-8-(5-(((5-fluoro-2,3-dihydrobenzofuran-4-yl)methyl)amino)-[1,2,4]triazolo[4,3-c]pyrimidin-8-yl)imidazo[1,2-a]pyridine-3-carboxamide | 0.0134 |
| N-((5-fluoro-2,3-dihydrobenzofuran-4-yl)methyl)-8-(5-morpholino-[1,2,4]triazolo[1,5-a]pyridin-8-yl)-[1,2,4]triazolo[4,3-c]pyrimidin-5-amine | 0.0011 |
| 8-(benzo[d]thiazol-4-yl)-N-((5-fluoro-2,3-dihydrobenzofuran-4-yl)methyl)-[1,2,4]triazolo[4,3-c]pyrimidin-5-amine | 0.0047 |
| 8-(5-(dimethylamino)-[1,2,4]triazolo[1,5-a]pyridin-8-yl)-N-((5-fluoro-2,3-dihydrobenzofuran-4-yl)methyl)-[1,2,4]triazolo[4,3-c]pyrimidin-5-amine | 0.0010 |
| N-((5-fluoro-2,3-dihydrobenzofuran-4-yl)methyl)-8-(5-(4-methylpiperazin-1-yl)-[1,2,4]triazolo[1,5-a]pyridin-8-yl)-[1,2,4]triazolo[4,3-c]pyrimidin-5-amine | 0.0041 |
| 8-(2,5-dimethyl-[1,2,4]triazolo[1,5-a]pyridin-8-yl)-N-((5-fluoro-2,3-dihydrobenzofuran-4-yl)methyl)-[1,2,4]triazolo[4,3-c]pyrimidin-5-amine | 0.0013 |
| 1-((8-(5-(((5-fluoro-2,3-dihydrobenzofuran-4-yl)methyl)amino)-[1,2,4]triazolo[4,3-c]pyrimidin-8-yl)-[1,2,4]triazolo[1,5-a]pyridin-5-yl)methoxy)-2-methylpropan-2-ol | 0.0064 |
| 8-(5-((dimethylamino)methyl)-[1,2,4]triazolo[1,5-a]pyridin-8-yl)-N-((5-fluoro-2,3-dihydrobenzofuran-4-yl)methyl)-[1,2,4]triazolo[4,3-c]pyrimidin-5-amine | 0.0006 |
| N-((5-fluoro-2,3-dihydrobenzofuran-4-yl)methyl)-8-(5-((4-methylpiperazin-1-yl)methyl)-[1,2,4]triazolo[1,5-a]pyridin-8-yl)-[1,2,4]triazolo[4,3-c]pyrimidin-5-amine | 0.0011 |
| 1-(((8-(5-(((5-fluoro-2,3-dihydrobenzofuran-4-yl)methyl)amino)-[1,2,4]triazolo[4,3-c]pyrimidin-8-yl)-[1,2,4]triazolo[1,5-a]pyridin-5-yl)methyl)amino)-2-methylpropan-2-ol | 0.0022 |
| N-((5-fluoro-2,3-dihydrobenzofuran-4-yl)methyl)-8-(5-(morpholinomethyl)-[1,2,4]triazolo[1,5-a]pyridin-8-yl)-[1,2,4]triazolo[4,3-c]pyrimidin-5-amine | 0.0011 |
| N-((5-fluoro-2,3-dihydrobenzofuran-4-yl)methyl)-8-(1H-indazol-7-yl)-[1,2,4]triazolo[4,3-c]pyrimidin-5-amine | 0.0016 |
| N-((5-fluoro-2,3-dihydrobenzofuran-4-yl)methyl)-8-(5-methyltetrazolo[1,5-a]pyridin-8-yl)-[1,2,4]triazolo[4,3-c]pyrimidin-5-amine | 0.0024 |
| 8-(5-(((5-fluoro-2,3-dihydrobenzofuran-4-yl)methyl)amino)-[1,2,4]triazolo[4,3-c]pyrimidin-8-yl)-5-methoxyimidazo[1,2-a]pyridine-3-carbonitrile | 0.0039 |
| N-((5-fluoro-2,3-dihydrobenzofuran-4-yl)methyl)-8-(5-(pyrrolidin-1-yl)-[1,2,4]triazolo[1,5-a]pyridin-8-yl)-[1,2,4]triazolo[4,3-c]pyrimidin-5-amine | 0.0027 |
| N-((5-fluoro-2,3-dihydrobenzofuran-4-yl)methyl)-8-(5-(4-morpholinopiperidin-1-yl)-[1,2,4]triazolo[1,5-a]pyridin-8-yl)-[1,2,4]triazolo[4,3-c]pyrimidin-5-amine | 0.0011 |

TABLE 4-continued

| Compound name | $IC_{50}$ (μM), ELISA, G401 |
|---|---|
| 8-(5-(2-oxa-6-azaspiro[3.3]heptan-6-yl)-[1,2,4]triazolo[1,5-a]pyridin-8-yl)-N-((5-fluoro-2,3-dihydrobenzofuran-4-yl)methyl)-[1,2,4]triazolo[4,3-c]pyrimidin-5-amine | 0.0017 |
| 5-(dimethylamino)-8-(5-(((5-fluoro-2,3-dihydrobenzofuran-4-yl)methyl)amino)-[1,2,4]triazolo[4,3-c]pyrimidin-8-yl)imidazo[1,2-a]pyridine-3-carbonitrile | 0.0009 |
| 8-(5-(((5-fluoro-2,3-dihydrobenzofuran-4-yl)methyl)amino)-[1,2,4]triazolo[4,3-c]pyrimidin-8-yl)-5-morpholinoimidazo[1,2-a]pyridine-3-carbonitrile | 0.0013 |
| 8-(1H-benzo[d][1,2,3]triazol-7-yl)-N-((5-fluoro-2,3-dihydrobenzofuran-4-yl)methyl)-[1,2,4]triazolo[4,3-c]pyrimidin-5-amine | 0.0007 |
| N1-((8-(5-(((5-fluoro-2,3-dihydrobenzofuran-4-yl)methyl)amino)-[1,2,4]triazolo[4,3-c]pyrimidin-8-yl)-[1,2,4]triazolo[1,5-a]pyridin-5-yl)methyl)-N1,N2,N2-trimethylethane-1,2-diamine | 0.0112 |
| N-((5-fluoro-2,3-dihydrobenzofuran-4-yl)methyl)-8-(5-(2-methylmorpholino)-[1,2,4]triazolo[1,5-a]pyridin-8-yl)-[1,2,4]triazolo[4,3-c]pyrimidin-5-amine | 0.0008 |
| 5-((dimethylamino)methyl)-8-(5-(((5-fluoro-2,3-dihydrobenzofuran-4-yl)methyl)amino)-[1,2,4]triazolo[4,3-c]pyrimidin-8-yl)imidazo[1,2-a]pyridine-3-carbonitrile | 0.0007 |
| N-((5-fluoro-2,3-dihydrobenzofuran-4-yl)methyl)-8-(6-fluoro-5-methyl-[1,2,4]triazolo[1,5-a]pyridin-8-yl)-[1,2,4]triazolo[4,3-c]pyrimidin-5-amine | 0.0036 |
| 8-(5-((1H-imidazol-1-yl)methyl)-[1,2,4]triazolo[1,5-a]pyridin-8-yl)-N-((5-fluoro-2,3-dihydrobenzofuran-4-yl)methyl)-[1,2,4]triazolo[4,3-c]pyrimidin-5-amine | 0.0006 |
| N-((5-fluoro-2,3-dihydrobenzofuran-4-yl)methyl)-8-(5-methyl-[1,2,4]triazolo[4,3-a]pyridin-8-yl)-[1,2,4]triazolo[4,3-c]pyrimidin-5-amine | 0.0002 |
| N-((5-fluoro-2,3-dihydrobenzofuran-4-yl)methyl)-8-(5-methyl-[1,2,4]triazolo[1,5-c]pyrimidin-8-yl)-[1,2,4]triazolo[4,3-c]pyrimidin-5-amine | 0.0045 |
| 2-(8-(5-(((5-fluoro-2,3-dihydrobenzofuran-4-yl)methyl)amino)-[1,2,4]triazolo[4,3-c]pyrimidin-8-yl)-[1,2,4]triazolo[1,5-a]pyridin-5-yl)propan-2-ol | 0.0004 |
| 8-(5-(((5-fluoro-2,3-dihydrobenzofuran-4-yl)methyl)amino)-[1,2,4]triazolo[4,3-c]pyrimidin-8-yl)-6-methoxyimidazo[1,2-a]pyridine-3-carbonitrile | 0.0042 |
| N-((5-fluoro-2,3-dihydrobenzofuran-4-yl)methyl)-8-(6-methoxy-[1,2,4]triazolo[1,5-a]pyridin-8-yl)-[1,2,4]triazolo[4,3-c]pyrimidin-5-amine | 0.0012 |
| 8-(5-(((5-fluoro-2,3-dihydrobenzofuran-4-yl)methyl)amino)-[1,2,4]triazolo[4,3-c]pyrimidin-8-yl)imidazo[1,2-a]pyridine-5-carbonitrile | 0.0048 |
| 8-(2-(dimethylamino)-6-fluoro-[1,2,4]triazolo[1,5-a]pyridin-8-yl)-N-((5-fluoro-2,3-dihydrobenzofuran-4-yl)methyl)-[1,2,4]triazolo[4,3-c]pyrimidin-5-amine | 0.0018 |
| 8-(2-(dimethylamino)-[1,2,4]triazolo[1,5-a]pyridin-8-yl)-N-((5-fluoro-2,3-dihydrobenzofuran-4-yl)methyl)-[1,2,4]triazolo[4,3-c]pyrimidin-5-amine | 0.0084 |
| 8-(5-(difluoromethyl)-[1,2,4]triazolo[1,5-a]pyridin-8-yl)-N-((5-fluoro-2,3-dihydrobenzofuran-4-yl)methyl)-[1,2,4]triazolo[4,3-c]pyrimidin-5-amine | 0.0055 |
| 8-(5-(dimethylamino)-[1,2,4]triazolo[1,5-c]pyrimidin-8-yl)-N-((5-fluoro-2,3-dihydrobenzofuran-4-yl)methyl)-[1,2,4]triazolo[4,3-c]pyrimidin-5-amine | 0.0018 |
| 8-(5-(dimethylamino)-6-fluoro-[1,2,4]triazolo[1,5-a]pyridin-8-yl)-N-((5-fluoro-2,3-dihydrobenzofuran-4-yl)methyl)-[1,2,4]triazolo[4,3-c]pyrimidin-5-amine | 0.0028 |
| 8-(5-(dimethylamino)-2-methyl-[1,2,4]triazolo[1,5-a]pyridin-8-yl)-N-((5-fluoro-2,3-dihydrobenzofuran-4-yl)methyl)-[1,2,4]triazolo[4,3-c]pyrimidin-5-amine | 0.0006 |
| 8-(5-(((5-fluoro-2,3-dihydrobenzofuran-4-yl)methyl)amino)-[1,2,4]triazolo[4,3-c]pyrimidin-8-yl)-[1,2,4]triazolo[1,5-a]pyridine-6-carbonitrile | 0.0143 |
| 8-(5-(dimethylamino)-[1,2,4]triazolo[4,3-a]pyridin-8-yl)-N-((5-fluoro-2,3-dihydrobenzofuran-4-yl)methyl)-[1,2,4]triazolo[4,3-c]pyrimidin-5-amine | 0.0078 |
| (6-fluoro-8-(5-(((5-fluoro-2,3-dihydrobenzofuran-4-yl)methyl)amino)-[1,2,4]triazolo[4,3-c]pyrimidin-8-yl)imidazo[1,2-a]pyridin-3-yl)dimethylphosphine oxide | 0.0023 |
| N-((5-fluoro-2,3-dihydrobenzofuran-4-yl)methyl)-8-(5-methyl-3-(methylsulfonyl)imidazo[1,2-a]pyridin-8-yl)-[1,2,4]triazolo[4,3-c]pyrimidin-5-amine | 0.0880 |
| 8-(3,5-dimethyl-[1,2,4]triazolo[4,3-a]pyridin-8-yl)-N-(5-fluoro-2,3-dihydrobenzofuran-4-yl)methyl)-[1,2,4]triazole[4,3-c]pyrimidin-5-amine | 0.0008 |

Example 154: Cell Proliferation Analysis

Human B-cell non-Hodgkin lymphoma cells, KARPAS-422 S, were cultured in a culture flask using standard cell culture conditions. The medium contained 15% fetal bovine serum (FBS, Invitrogen, product number 10099-141) and 1% penicillin/streptomycin solution (P/S) RPMI-1640 (Invitrogen, product number 11875), and the culture flask was placed and cultured in a sterile incubator at the temperature of 37° C. and 500 $CO_2$ with a relative humidity of 9500 To detect the effect of PRC2 inhibitors on cell proliferation, cells in exponential growth phase were taken and seeded into a 96-well plate (Corning, product number 3904) at a density of $1\times10^4$ cells/well, and 100 μL of the medium was added into each well. Subsequently, the compounds at different concentrations disclosed in the present disclosure were added into the wells where cells had already been seeded (9 concentration gradients were provided for each compound, with the highest detection concentration at 10 μM, 3-fold gradient dilution) and two replicates in parallel were provided for each treatment concentration. DMSO was at a final concentration of 0.5%. Afterwards, viable cell numbers were determined using Vi-CELL (Beckman Coulter) every 3-4 days. Cells counted were seeded into a new 96-well plate at the same density ($1\times10^4$ cells/well) each time. The wells were supplemented with a fresh medium to 100 μL and at the same time, compounds at different concentrations were added. The cells were cultured to day 13. 100 μL of CellTiter-Glo (CellTiter-GloCellTiter-GloCellTiter-GloCTG) (Promega, product number G7573) was added into each well. The plate was placed in the dark at room temperature for 10-20 minutes and the luminescence signal was read using SpectraMax i3x (Molecular Devices). Data were fit to obtain Dose-Response curves using GraphPad prism 5 and hence the $IC_{50}$ values of the test compounds were obtained.

Table 5 below shows the $IC_{50}$ values of part of the compounds of the present disclosure.

TABLE 5

| Compound name | $IC_{50}$ (μM), Karpas-422, 13 days |
|---|---|
| N-((5-fluoro-2,3-dihydrobenzofuran-4-yl)methyl)-8-(imidazo[1,2-a]pyridin-7-yl)-[1,2,4]triazolo[4,3-c]pyrimidin-5-amine | 0.0165 |
| N-((5-fluoro-2,3-dihydrobenzofuran-4-yl)methyl)-8-(imidazo[1,2-a]pyridin-6-yl)-[1,2,4]triazolo[4,3-c]pyrimidin-5-amine | 0.0941 |
| N-((5-fluoro-2,3-dihydrobenzofuran-4-yl)methyl)-8-(pyrazolo[1,5-a]pyrimidin-6-yl)-[1,2,4]triazolo[4,3-c]pyrimidin-5-amine | 0.0183 |
| 8-([1,2,4]triazolo[4,3-a]pyridin-6-yl)-N-(((1aR,6bR)-5-fluoro-1a,6b-dihydro-1H-cyclopropa[b]benzofuran-6-yl)methyl)-[1,2,4]triazolo[4,3-c]pyrimidin-5-amine | 0.0431 |
| 8-([1,2,4]triazolo[1,5-a]pyridin-7-yl)-N-(((1aR,6bR)-5-fluoro-1a,6b-dihydro-1H-cyclopropa[b]benzofuran-6-yl)methyl)-[1,2,4]triazolo[4,3-c]pyrimidin-5-amine | 0.0077 |
| N-((5-fluoro-2,3-dihydrobenzofuran-4-yl)methyl)-8-(pyrazolo[1,5-a]pyridin-6-yl)-[1,2,4]triazolo[4,3-c]pyrimidin-5-amine | 0.0154 |
| 8-([1,2,4]triazolo[1,5-a]pyridin-8-yl)-N-((5-fluoro-2,3-dihydrobenzofuran-4-yl)methyl)-[1,2,4]triazolo[4,3-c]pyrimidin-5-amine | 0.0014 |
| N-((5-fluoro-2,3-dihydrobenzofuran-4-yl)methyl)-8-(imidazo[1,2-a]pyridin-8-yl)-[1,2,4]triazolo[4,3-c]pyrimidin-5-amine | 0.0015 |
| 8-([1,2,4]triazolo[1,5-a]pyridin-8-yl)-N-(((1aR,6bR)-5-fluoro-1a,6b-dihydro-1H-cyclopropa[b]benzofuran-6-yl)methyl)-[1,2,4]triazolo[4,3-c]pyrimidin-5-amine | 0.0019 |
| N-(((1aR,6bR)-5-fluoro-1a,6b-dihydro-1H-cyclopropa[b]benzofuran-6-yl)methyl)-8-(imidazo[1,2-a]pyridin-8-yl)-[1,2,4]triazolo[4,3-c]pyrimidin-5-amine | 0.0006 |
| 8-([1,2,4]triazolo[4,3-a]pyridin-8-yl)-N-(((1aR,6bR)-5-fluoro-1a,6b-dihydro-1H-cyclopropa[b]benzofuran-6-yl)methyl)-[1,2,4]triazolo[4,3-c]pyrimidin-5-amine | 0.0048 |
| N-((5-fluoro-2,3-dihydrobenzofuran-4-yl)methyl)-8-(2-(trifluoromethyl)imidazo[1,2-a]pyridin-8-yl)-[1,2,4]triazolo[4,3-c]pyrimidin-5-amine | 0.0017 |
| 8-(6-chloroimidazo[1,2-a]pyridin-8-yl)-N-((5-fluoro-2,3-dihydrobenzofuran-4-yl)methyl)-[1,2,4]triazolo[4,3-c]pyrimidin-5-amine | 0.0420 |
| N-((5-fluoro-2,3-dihydrobenzofuran-4-yl)methyl)-8-(6-fluoroimidazo[1,2-a]pyridin-8-yl)-[1,2,4]triazolo[4,3-c]pyrimidin-5-amine | 0.0020 |
| N-((5-fluoro-2,3-dihydrobenzofuran-4-yl)methyl)-8-(6-fluoro-2-(trifluoromethyl)imidazo[1,2-a]pyridin-8-yl)-[11,2,4]triazolo[4,3-c]pyrimidin-5-amine | 0.0095 |
| N-((5-fluoro-2,3-dihydrobenzofuran-4-yl)methyl)-8-(pyrazolo[1,5-a]pyrimidin-3-yl)-[1,2,4]triazolo[4,3-c]pyrimidin-5-amine | 0.0097 |
| Ethyl 8-(5-(((5-fluoro-2,3-dihydrobenzofuran-4-yl)methyl)amino)-[1,2,4]triazolo[4,3-c]pyrimidin-8-yl)imidazo[1,2-a]pyridine-3-carboxylate | 0.0040 |
| N-((5-fluoro-2,3-dihydrobenzofuran-4-yl)methyl)-8-(6-fluoro-2-methylimidazo[1,2-a]pyridin-8-yl)-[1,2,4]triazolo[4,3-c]pyrimidin-5-amine | 0.0013 |
| N-((5-fluoro-2,3-dihydrobenzofuran-4-yl)methyl)-8-(2-methylimidazo[1,2-a]pyridin-8-yl)-[1,2,4]triazolo[4,3-c]pyrimidin-5-amine | 0.0024 |
| N-((5-fluoro-2,3-dihydrobenzofuran-4-yl)methyl)-8-(2-methylbenzo[d]oxazol-4-yl)-[1,2,4]triazolo[4,3-c]pyrimidin-5-amine | 0.0042 |
| 8-(benzo[d]oxazol-7-yl)-N-((5-fluoro-2,3-dihydrobenzofuran-4-yl)methyl)-[1,2,4]triazolo[4,3-c]pyrimidin-5-amine | 0.0136 |
| 8-(5-(((5-fluoro-2,3-dihydrobenzofuran-4-yl)methyl)amino)-[1,2,4]triazolo[4,3-c]pyrimidin-8-yl)imidazo[1,2-a]pyridine-3-carboxamide | 0.0037 |
| N-((5-fluoro-2,3-dihydrobenzofuran-4-yl)methyl)-8-(3-methylimidazo[1,2-a]pyridin-8-yl)-[1,2,4]triazolo[4,3-c]pyrimidin-5-amine | 0.0014 |
| N-((5-fluoro-2,3-dihydrobenzofuran-4-yl)methyl)-8-(6-methylimidazo[1,2-a]pyridin-8-yl)-[1,2,4]triazolo[4,3-c]pyrimidin-5-amine | 0.0116 |
| 8-(3,5-dimethylimidazo[1,2-a]pyridin-8-yl)-N-((5-fluoro-2,3-dihydrobenzofuran-4-yl)methyl)-[1,2,4]triazolo[4,3-c]pyrimidin-5-amine | 0.0019 |
| 1-(8-(5-(((5-fluoro-2,3-dihydrobenzofuran-4-yl)methyl)amino)-[1,2,4]triazolo[4,3-c]pyrimidin-8-yl)-2-methylimidazo[1,2-a]pyridin-3-yl)ethan-1-one | 0.0016 |

TABLE 5-continued

| Compound name | $IC_{50}$ (μM), Karpas-422, 13 days |
|---|---|
| 8-(3-phenylmethylimidazo[1,2-a]pyridin-8-yl)-N-((5-fluoro-2,3-dihydrobenzofuran-4-yl)methyl)-[1,2,4]triazolo[4,3-c]pyrimidin-5-amine | 0.0036 |
| 8-(3-ethylimidazo[1,2-a]pyridin-8-yl)-N-((5-fluoro-2,3-dihydrobenzofuran-4-yl)methyl)-[1,2,4]triazolo[4,3-c]pyrimidin-5-amine | 0.0009 |
| 8-(5-(((5-fluoro-2,3-dihydrobenzofuran-4-yl)methyl)amino)-[1,2,4]triazolo[4,3-c]pyrimidin-8-yl)imidazo[1,2-a]pyridine-3-carbonitrile | 0.0035 |
| 8-(3-ethyl-5-methylimidazo[1,2-a]pyridin-8-yl)-N-((5-fluoro-2,3-dihydrobenzofuran-4-yl)methyl)-[1,2,4]triazolo[4,3-c]pyrimidin-5-amine | 0.0022 |
| 1-(6-fluoro-8-(5-(((5-fluoro-2,3-dihydrobenzofuran-4-yl)methyl)amino)-[1,2,4]triazolo[4,3-c]pyrimidin-8-yl)-2-methylimidazo[1,2-a]pyridin-3-yl)ethan-1-one | 0.0011 |
| N-((5-fluoro-2,3-dihydrobenzofuran-4-yl)methyl)-8-(6-fluoro-3-methylimidazo[1,2-a]pyridin-8-yl)-[1,2,4]triazolo[4,3-c]pyrimidin-5-amine | 0.0040 |
| 8-(3,6-difluoroimidazo[1,2-a]pyridin-8-yl)-N-((5-fluoro-2,3-dihydrobenzofuran-4-yl)methyl)-[1,2,4]triazolo[4,3-c]pyrimidin-5-amine | 0.0075 |
| 5-(5-((((1aR,6bR)-5-fluoro-1a,6b-dihydro-1H-cyclopropa[b]benzofuran-6-yl)methyl)amino)-[1,2,4]triazolo[4,3-c]pyrimidin-8-yl)benzo[b]thiophene 1,1-dioxide | 0.0007 |
| 5-(5-(((5-fluoro-2,3-dihydrobenzofuran-4-yl)methyl)amino)-[1,2,4]triazolo[4,3-c]pyrimidin-8-yl)benzo[b]thiophene 1,1-dioxide | 0.0007 |
| 5-(5-((((1aS,6bS)-5-fluoro-1a,6b-dihydro-1H-cyclopropa[b]benzofuran-6-yl)methyl)amino)-[1,2,4]triazolo[4,3-c]pyrimidin-8-yl)benzo[b]thiophene 1,1-dioxide | 0.0038 |
| 4-(5-(((5-fluoro-2,3-dihydrobenzofuran-4-yl)methyl)amino)-[1,2,4]triazolo[4,3-c]pyrimidin-8-yl)benzo[b]thiophene 1,1-dioxide | 0.0130 |
| 4-(5-((((1aR,6bR)-5-fluoro-1a,6b-dihydro-1H-cyclopropa[b]benzofuran-6-yl)methyl)amino)-[1,2,4]triazolo[4,3-c]pyrimidin-8-yl)benzo[b]thiophene 1,1-dioxide | 0.0115 |
| 5-(5-((((1aR,6bR)-5-fluoro-1a,6b-dihydro-1H-cyclopropa[b]benzofuran-6-yl)methyl)amino)-[1,2,4]triazolo[4,3-c]pyrimidin-8-yl)-2-methylbenzo[b]thiophene 1,1-dioxide | 0.0125 |
| 5-(5-((((1aR,6bR)-5-fluoro-1a,6b-dihydro-1H-cyclopropa[b]benzofuran-6-yl)methyl)amino)-[1,2,4]triazolo[4,3-c]pyrimidin-8-yl)-3-methylbenzo[b]thiophene 1,1-dioxide | 0.0243 |
| 2-fluoro-5-(5-((((1aR,6bR)-5-fluoro-1a,6b-dihydro-1H-cyclopropa[b]benzofuran-6-yl)methyl)amino)-[1,2,4]triazolo[4,3-c]pyrimidin-8-yl)benzo[b]thiophene 1,1-dioxide | 0.0790 |
| 3-fluoro-5-(5-((((1aR,6bR)-5-fluoro-1a,6b-dihydro-1H-cyclopropa[b]benzofuran-6-yl)methyl)amino)-[1,2,4]triazolo[4,3-c]pyrimidin-8-yl)benzo[b]thiophene 1,1-dioxide | 0.0970 |
| 5-(5-(((5-fluoro-2,3-dihydrobenzofuran-4-yl)methyl)amino)-[1,2,4]triazolo[4,3-c]pyrimidin-8-yl)benzo[c]thiophene 2,2-dioxide | 0.0004 |
| 3-fluoro-5-(5-((((1aR,6bR)-5-fluoro-1a,6b-dihydro-1H-cyclopropa[b]benzofuran-6-yl)methyl)amino)-[1,2,4]triazolo[4,3-c]pyrimidin-8-yl)-2-methylbenzo[b]thiophene 1,1-dioxide | 0.0055 |
| 5-(5-((((1aR,6bR)-5-fluoro-1a,6b-dihydro-1H-cyclopropa[b]benzofuran-6-yl)methyl)amino)-[1,2,4]triazolo[4,3-c]pyrimidin-8-yl)benzo[c]thiophene 2,2-dioxide | 0.0008 |
| 2-fluoro-5-(5-((((1aR,6bR)-5-fluoro-1a,6b-dihydro-1H-cyclopropa[b]benzofuran-6-yl)methyl)amino)-[1,2,4]triazolo[4,3-c]pyrimidin-8-yl)-3-methylbenzo[b]thiophene 1,1-dioxide | 0.0320 |
| 3-(2-aminoethyl)-5-(5-((((1aS,6bS)-5-fluoro-1a,6b-dihydro-1H-cyclopropa[b]benzofuran-6-yl)methyl)amino)-[1,2,4]triazolo[4,3-c]pyrimidin-8-yl)benzo[b]thiophene 1,1-dioxide | 0.0330 |
| 5-(5-(((6-fluorochroman-5-yl)methyl)amino)-[1,2,4]triazolo[4,3-c]pyrimidin-8-yl)benzo[c]thiophene 2,2-dioxide | 0.0016 |
| 7-fluoro-5-(5-(((5-fluoro-2,3-dihydrobenzofuran-4-yl)methyl)amino)-[1,2,4]triazolo[4,3-c]pyrimidin-8-yl)benzo[b]thiophene 1,1-dioxide | 0.0005 |
| 5-(5-(((5-fluoro-2,3-dihydrobenzofuran-4-yl)methyl)amino)-[1,2,4]triazolo[4,3-c]pyrimidin-8-yl)-6-methylbenzo[b]thiophene 1,1-dioxide | 0.0005 |
| 7-fluoro-5-(5-(((5-fluoro-2,3-dihydrobenzofuran-4-yl)methyl)amino)-[1,2,4]triazolo[4,3-c]pyrimidin-8-yl)-2,3-dimethylbenzo[b]thiophene 1,1-dioxide | 0.0087 |
| 4-(5-(((5-fluoro-2,3-dihydrobenzofuran-4-yl)methyl)amino)-[1,2,4]triazolo[4,3-c]pyrimidin-8-yl)-2-methylbenzo[b]thiophene 1,1-dioxide | 0.0042 |
| 6-(5-(((5-fluoro-2,3-dihydrobenzofuran-4-yl)methyl)amino)-[1,2,4]triazolo[4,3-c]pyrimidin-8-yl)-2-methylbenzo[b]thiophene 1,1-dioxide | 0.0088 |
| 3-fluoro-5-(5-(((5-fluoro-2,3-dihydrobenzofuran-4-yl)methyl)amino)-[1,2,4]triazolo[4,3-c]pyrimidin-8-yl)-2-methylbenzo[b]thiophene 1,1-dioxide | 0.0049 |
| N-((5-fluoro-2,3-dihydrobenzofuran-4-yl)methyl)-8-(3-isopropyl-5-methylimidazo[1,2-a]pyridin-8-yl)-[1,2,4]triazolo[4,3-c]pyrimidin-5-amine | 0.0010 |
| Methyl 8-(5-(((5-fluoro-2,3-dihydrobenzofuran-4-yl)methyl)amino)-[1,2,4]triazolo[4,3-c]pyrimidin-8-yl)imidazo[1,2-a]pyridine-5-carboxylate | 0.0051 |
| 2-(8-(5-(((5-fluoro-2,3-dihydrobenzofuran-4-yl)methyl)amino)-[1,2,4]triazolo[4,3-c]pyrimidin-8-yl)-5-methylimidazo[1,2-a]pyridin-3-yl)acetamide | 0.0032 |
| 2-(8-(5-(((5-fluoro-2,3-dihydrobenzofuran-4-yl)methyl)amino)-[1,2,4]triazolo[4,3-c]pyrimidin-8-yl)-5-methylimidazo[1,2-a]pyridin-3-yl)ethan-1-ol | 0.0024 |
| Methyl 2-(8-(5-(((5-fluoro-2,3-dihydrobenzofuran-4-yl)methyl)amino)-[1,2,4]triazolo[4,3-c]pyrimidin-8-yl)-5-methylimidazo[1,2-a]pyridin-3-yl)acetate | 0.0010 |
| 2-(8-(5-(((5-fluoro-2,3-dihydrobenzofuran-4-yl)methyl)amino)-[1,2,4]triazolo[4,3-c]pyrimidin-8-yl)-5-methylimidazo[1,2-a]pyridin-3-yl)acetic acid | 0.0047 |
| (8-(5-(((5-fluoro-2,3-dihydrobenzofuran-4-yl)methyl)amino)-[1,2,4]triazolo[4,3-c]pyrimidin-8-yl)imidazo[1,2-a]pyridin-5-yl)methanol | 0.0086 |
| N-(((1aR,6bR)-5-fluoro-1a,6b-dihydro-1H-cyclopropa[b]benzofuran-6-yl)methyl)-8-(5-methyl-[1,2,4]triazolo[1,5-a]pyridin-8-yl)-[1,2,4]triazolo[4,3-c]pyrimidin-5-amine | 0.0044 |

TABLE 5-continued

| Compound name | $IC_{50}$ (μM), Karpas-422, 13 days |
|---|---|
| 2-(8-(5-(((5-fluoro-2,3-dihydrobenzofuran-4-yl)methyl)amino)-[1,2,4]triazolo[4,3-c]pyrimidin-8-yl)-5-methylimidazo[1,2-a]pyridin-3-yl)-N,N-dimethylacetamide | 0.0061 |
| 2-(8-(5-(((5-fluoro-2,3-dihydrobenzofuran-4-yl)methyl)amino)-[1,2,4]triazolo[4,3-c]pyrimidin-8-yl)-5-methylimidazo[1,2-a]pyridin-3-yl)ethyl acetate | 0.0017 |
| N-((5-fluoro-2,3-dihydrobenzofuran-4-yl)methyl)-8-(5-methylimidazo[1,2-a]pyridin-8-yl)-[1,2,4]triazolo[4,3-c]pyrimidin-5-amine | 0.0013 |
| N-(((1aR,6bR)-5-fluoro-1a,6b-dihydro-1H-cyclopropa[b]benzofuran-6-yl)methyl)-8-(5-methylimidazo[1,2-a]pyridin-8-yl)-[1,2,4]triazolo[4,3-c]pyrimidin-5-amine | 0.0009 |
| N-((8-(5-(((5-fluoro-2,3-dihydrobenzofuran-4-yl)methyl)amino)-[1,2,4]triazolo[4,3-c]pyrimidin-8-yl)-5-methylimidazo[1,2-a]pyridin-3-yl)methyl)acetamide | 0.0032 |
| (8-(5-(((5-fluoro-2,3-dihydrobenzofuran-4-yl)methyl)amino)-[1,2,4]triazolo[4,3-c]pyrimidin-8-yl)-5-methylimidazo[1,2-a]pyridin-2-yl)methanol | 0.0033 |
| N-((5-fluoro-2,3-dihydrobenzofuran-4-yl)methyl)-8-(5-methyl-[1,2,4]triazolo[1,5-a]pyridin-8-yl)-[1,2,4]triazolo[4,3-c]pyrimidin-5-amine | 0.0018 |
| N-((5-fluoro-2,3-dihydrobenzofuran-4-yl)methyl)-8-(1-methyl-1H-benzo[d]imidazol-4-yl)-[1,2,4]triazolo[4,3-c]pyrimidin-5-amine | 0.0016 |
| 8-(5-(((5-fluoro-2,3-dihydrobenzofuran-4-yl)methyl)amino)-[1,2,4]triazolo[4,3-c]pyrimidin-8-yl)-N,N,5-trimethylimidazo[1,2-a]pyridine-2-carboxamide | 0.0028 |
| Ethyl 8-(5-(((5-fluoro-2,3-dihydrobenzofuran-4-yl)methyl)amino)-[1,2,4]triazolo[4,3-c]pyrimidin-8-yl)-5-methylimidazo[1,2-a]pyridine-3-carboxylate | 0.0047 |
| 8-(5-(((5-fluoro-2,3-dihydrobenzofuran-4-yl)methyl)amino)-[1,2,4]triazolo[4,3-c]pyrimidin-8-yl)-N,N,5-trimethylimidazo[1,2-a]pyridine-3-carboxamide | 0.0012 |
| 8-(5-(((5-fluoro-2,3-dihydrobenzofuran-4-yl)methyl)amino)-[1,2,4]triazolo[4,3-c]pyrimidin-8-yl)-N,N-dimethylimidazo[1,2-a]pyridine-5-carboxamide | 0.0013 |
| 6-fluoro-8-(5-(((5-fluoro-2,3-dihydrobenzofuran-4-yl)methyl)amino)-[1,2,4]triazolo[4,3-c]pyrimidin-8-yl)imidazo[1,2-a]pyridine-3-carbonitrile | 0.0083 |
| 2-(8-(5-(((5-fluoro-2,3-dihydrobenzofuran-4-yl)methyl)amino)-[1,2,4]triazolo[4,3-c]pyrimidin-8-yl)-5-methylimidazo[1,2-a]pyridin-3-yl)-1-morpholinoethan-1-one | 0.0057 |
| N-((5-fluoro-2,3-dihydrobenzofuran-4-yl)methyl)-8-(5-(trifluoromethyl)imidazo[1,2-a]pyridin-8-yl)-[1,2,4]triazolo[4,3-c]pyrimidin-5-amine | 0.0070 |
| (8-(5-(((5-fluoro-2,3-dihydrobenzofuran-4-yl)methyl)amino)-[1,2,4]triazolo[4,3-c]pyrimidin-8-yl)-5-methylimidazo[1,2-a]pyridin-3-yl)(morpholino)methanone | 0.0011 |
| 8-(5-chloro-[1,2,4]triazolo[1,5-a]pyridin-8-yl)-N-((5-fluoro-2,3-dihydrobenzofuran-4-yl)methyl)-[1,2,4]triazolo[4,3-c]pyrimidin-5-amine | 0.0180 |
| 8-(5-(((5-fluoro-2,3-dihydrobenzofuran-4-yl)methyl)amino)-[1,2,4]triazolo[4,3-c]pyrimidin-8-yl)-5-methylimidazo[1,2-a]pyridine-3-carboxamide | 0.0022 |
| 8-(5-(((5-fluoro-2,3-dihydrobenzofuran-4-yl)methyl)amino)-[1,2,4]triazolo[4,3-c]pyrimidin-8-yl)-5-methylimidazo[1,2-a]pyridine-3-carbonitrile | 0.0030 |
| N-((5-fluoro-2,3-dihydrobenzofuran-4-yl)methyl)-8-(5-(trifluoromethyl)-[1,2,4]triazolo[1,5-a]pyridin-8-yl)-[1,2,4]triazolo[4,3-c]pyrimidin-5-amine | 0.0360 |
| 2-(8-(5-(((5-fluoro-2,3-dihydrobenzofuran-4-yl)methyl)amino)-[1,2,4]triazolo[4,3-c]pyrimidin-8-yl)-5-methylimidazo[1,2-a]pyridin-3-yl)acetonitrile | 0.0014 |
| N-((5-fluoro-2,3-dihydrobenzofuran-4-yl)methyl)-8-(5-methoxy-[1,2,4]triazolo[1,5-a]pyridin-8-yl)-[1,2,4]triazolo[4,3-c]pyrimidin-5-amine | 0.0011 |
| 8-(benzo[c][1,2,5]thiadiazol-4-yl)-N-((5-fluoro-2,3-dihydrobenzofuran-4-yl)methyl)-[1,2,4]triazolo[4,3-c]pyrimidin-5-amine | 0.0140 |
| 6-fluoro-8-(5-(((5-fluoro-2,3-dihydrobenzofuran-4-yl)methyl)amino)-[1,2,4]triazolo[4,3-c]pyrimidin-8-yl)-N,N-dimethylimidazo[1,2-a]pyridine-3-carboxamide | 0.0024 |
| 6-fluoro-8-(5-(((5-fluoro-2,3-dihydrobenzofuran-4-yl)methyl)amino)-[1,2,4]triazolo[4,3-c]pyrimidin-8-yl)imidazo[1,2-a]pyridine-3-carboxamide | 0.0046 |
| N-((5-fluoro-2,3-dihydrobenzofuran-4-yl)methyl)-8-(5-morpholino-[1,2,4]triazolo[1,5-a]pyridin-8-yl)-[1,2,4]triazolo[4,3-c]pyrimidin-5-amine | 0.0007 |
| 8-(benzo[d]thiazol-4-yl)-N-((5-fluoro-2,3-dihydrobenzofuran-4-yl)methyl)-[1,2,4]triazolo[4,3-c]pyrimidin-5-amine | 0.0036 |
| 8-(5-(dimethylamino)-[1,2,4]triazolo[1,5-a]pyridin-8-yl)-N-((5-fluoro-2,3-dihydrobenzofuran-4-yl)methyl)-[1,2,4]triazolo[4,3-c]pyrimidin-5-amine | 0.0014 |
| N-((5-fluoro-2,3-dihydrobenzofuran-4-yl)methyl)-8-(5-(4-methylpiperazin-1-yl)-[1,2,4]triazolo[1,5-a]pyridin-8-yl)-[1,2,4]triazolo[4,3-c]pyrimidin-5-amine | 0.0007 |
| 8-(2,5-dimethyl-[1,2,4]triazolo[1,5-a]pyridin-8-yl)-N-((5-fluoro-2,3-dihydrobenzofuran-4-yl)methyl)-[1,2,4]triazolo[4,3-c]pyrimidin-5-amine | 0.0013 |
| 1-((8-(5-(((5-fluoro-2,3-dihydrobenzofuran-4-yl)methyl)amino)-[1,2,4]triazolo[4,3-c]pyrimidin-8-yl)-[1,2,4]triazolo[1,5-a]pyridin-5-yl)methoxy)-2-methylpropan-2-ol | 0.0012 |
| 8-(5-((dimethylamino)methyl)-[1,2,4]triazolo[1,5-a]pyridin-8-yl)-N-((5-fluoro-2,3-dihydrobenzofuran-4-yl)methyl)-[1,2,4]triazolo[4,3-c]pyrimidin-5-amine | 0.0005 |
| N-((5-fluoro-2,3-dihydrobenzofuran-4-yl)methyl)-8-(5-((4-methylpiperazin-1-yl)methyl)-[1,2,4]triazolo[1,5-a]pyridin-8-yl)-[1,2,4]triazolo[4,3-c]pyrimidin-5-amine | 0.0007 |
| 1-(((8-(5-(((5-fluoro-2,3-dihydrobenzofuran-4-yl)methyl)amino)-[1,2,4]triazolo[4,3-c]pyrimidin-8-yl)-[1,2,4]triazolo[1,5-a]pyridin-5-yl)methyl)amino)-2-methylpropan-2-ol | 0.0021 |
| N-((5-fluoro-2,3-dihydrobenzofuran-4-yl)methyl)-8-(5-(morpholinomethyl)-[1,2,4]triazolo[1,5-a]pyridin-8-yl)-[1,2,4]triazolo[4,3-c]pyrimidin-5-amine | 0.0011 |
| N-((5-fluoro-2,3-dihydrobenzofuran-4-yl)methyl)-8-(1H-indazol-7-yl)-[1,2,4]triazolo[4,3-c]pyrimidin-5-amine | 0.0023 |
| N-((5-fluoro-2,3-dihydrobenzofuran-4-yl)methyl)-8-(5-methyltetrazolo[1,5-a]pyridin-8-yl)-[1,2,4]triazolo[4,3-c]pyrimidin-5-amine | 0.0025 |
| 8-(5-(((5-fluoro-2,3-dihydrobenzofuran-4-yl)methyl)amino)-[1,2,4]triazolo[4,3-c]pyrimidin-8-yl)-5-methoxyimidazo[1,2-a]pyridine-3-carbonitrile | 0.0062 |

TABLE 5-continued

| Compound name | $IC_{50}$ (μM), Karpas-422, 13 days |
|---|---|
| N-((5-fluoro-2,3-dihydrobenzofuran-4-yl)methyl)-8-(5-(pyrrolidin-1-yl)-[1,2,4]triazolo[1,5-a]pyridin-8-yl)-[1,2,4]triazolo[4,3-c]pyrimidin-5-amine | 0.0032 |
| N-((5-fluoro-2,3-dihydrobenzofuran-4-yl)methyl)-8-(5-(4-morpholinopiperidin-1-yl)-[1,2,4]triazolo[1,5-a]pyridin-8-yl)-[1,2,4]triazolo[4,3-c]pyrimidin-5-amine | 0.0008 |
| 8-(5-(2-oxa-6-azaspiro[3.3]heptan-6-yl)-[1,2,4]triazolo[1,5-a]pyridin-8-yl)-N-((5-fluoro-2,3-dihydrobenzofuran-4-yl)methyl)-[1,2,4]triazolo[4,3-c]pyrimidin-5-amine | 0.0018 |
| 5-(dimethylamino)-8-(5-(((5-fluoro-2,3-dihydrobenzofuran-4-yl)methyl)amino)-[1,2,4]triazolo[4,3-c]pyrimidin-8-yl)imidazo[1,2-a]pyridine-3-carbonitrile | 0.0009 |
| 8-(5-(((5-fluoro-2,3-dihydrobenzofuran-4-yl)methyl)amino)-[1,2,4]triazolo[4,3-c]pyrimidin-8-yl)-5-morpholinoimidazo[1,2-a]pyridine-3-carbonitrile | 0.0013 |
| 8-(1H-benzo[d][1,2,3]triazol-7-yl)-N-((5-fluoro-2,3-dihydrobenzofuran-4-yl)methyl)-[1,2,4]triazolo[4,3-c]pyrimidin-5-amine | 0.0012 |
| N1-((8-(5-(((5-fluoro-2,3-dihydrobenzofuran-4-yl)methyl)amino)-[1,2,4]triazolo[4,3-c]pyrimidin-8-yl)-[1,2,4]triazolo[1,5-a]pyridin-5-yl)methyl)-N1,N2,N2-trimethylethane-1,2-diamine | 0.0035 |
| N-((5-fluoro-2,3-dihydrobenzofuran-4-yl)methyl)-8-(5-(2-methylmorpholino)-[1,2,4]triazolo[1,5-a]pyridin-8-yl)-[1,2,4]triazolo[4,3-c]pyrimidin-5-amine | 0.0005 |
| 5-((dimethylamino)methyl)-8-(5-(((5-fluoro-2,3-dihydrobenzofuran-4-yl)methyl)amino)-[1,2,4]triazolo[4,3-c]pyrimidin-8-yl)imidazo[1,2-a]pyridine-3-carbonitrile | 0.0005 |
| N-((5-fluoro-2,3-dihydrobenzofuran-4-yl)methyl)-8-(6-fluoro-5-methyl-[1,2,4]triazolo[1,5-a]pyridin-8-yl)-[1,2,4]triazolo[4,3-c]pyrimidin-5-amine | 0.0047 |
| 8-(5-((1H-imidazol-1-yl)methyl)-[1,2,4]triazolo[1,5-a]pyridin-8-yl)-N-((5-fluoro-2,3-dihydrobenzofuran-4-yl)methyl)-[1,2,4]triazolo[4,3-c]pyrimidin-5-amine | 0.0009 |
| N-((5-fluoro-2,3-dihydrobenzofuran-4-yl)methyl)-8-(5-methyl-[1,2,4]triazolo[4,3-a]pyridin-8-yl)-[1,2,4]triazolo[4,3-c]pyrimidin-5-amine | 0.0002 |
| N-((5-fluoro-2,3-dihydrobenzofuran-4-yl)methyl)-8-(5-methyl-[1,2,4]triazolo[1,5-c]pyrimidin-8-yl)-[1,2,4]triazolo[4,3-c]pyrimidin-5-amine | 0.0025 |
| 2-(8-(5-(((5-fluoro-2,3-dihydrobenzofuran-4-yl)methyl)amino)-[1,2,4]triazolo[4,3-c]pyrimidin-8-yl)-[1,2,4]triazolo[1,5-a]pyridin-5-yl)propan-2-ol | 0.0002 |
| 8-(5-(((5-fluoro-2,3-dihydrobenzofuran-4-yl)methyl)amino)-[1,2,4]triazolo[4,3-c]pyrimidin-8-yl)-6-methoxyimidazo[1,2-a]pyridine-3-carbonitrile | 0.0045 |
| N-((5-fluoro-2,3-dihydrobenzofuran-4-yl)methyl)-8-(6-methoxy-[1,2,4]triazolo[1,5-a]pyridin-8-yl)-[1,2,4]triazolo[4,3-c]pyrimidin-5-amine | 0.0017 |
| 8-(5-(((5-fluoro-2,3-dihydrobenzofuran-4-yl)methyl)amino)-[1,2,4]triazolo[4,3-c]pyrimidin-8-yl)imidazo[1,2-a]pyridine-5-carbonitrile | 0.0036 |
| 8-(2-(dimethylamino)-6-fluoro-[1,2,4]triazolo[1,5-a]pyridin-8-yl)-N-((5-fluoro-2,3-dihydrobenzofuran-4-yl)methyl)-[1,2,4]triazolo[4,3-c]pyrimidin-5-amine | 0.0244 |
| 8-(2-(dimethylamino)-[1,2,4]triazolo[1,5-a]pyridin-8-yl)-N-((5-fluoro-2,3-dihydrobenzofuran-4-yl)methyl)-[1,2,4]triazolo[4,3-c]pyrimidin-5-amine | 0.0054 |

The compounds disclosed in the present disclosure can be used to treat cancer related to the mechanism of action of an EED protein and/or a PRC2 protein complex, including but not limited to lymphoma (such as diffuse large B-cell lymphoma, follicular lymphoma, non-Hodgkin's lymphoma), leukemia, multiple myeloma, mesothelioma, gastric cancer, malignant rhabdoid tumor, liver cancer, prostate cancer, breast cancer, cerebroma including neuroblastoma, glioma, glioblastoma and astrocytoma, cervical cancer, colon cancer, melanoma, endometrial carcinoma, esophageal carcinoma, head and neck cancer, lung cancer, nasopharyngeal carcinoma, ovarian cancer, pancreatic cancer, renal carcinoma, rectal cancer, thyroid cancer, parathyroid tumor, uterine cancer, and soft tissue sarcoma.

Although the specific embodiments of the present disclosure have been described above, it will be understood by those of skill in the art that these are merely illustrative, and that various alterations or modifications can be made to these embodiments without departing from the principle and essence of the present disclosure. Therefore, the scope of protection of the present disclosure is defined by the appended claims.

What is claimed is:

1. A compound as shown in formula (I), a pharmaceutically acceptable salt, hydrate, stereoisomer, or solvate thereof:

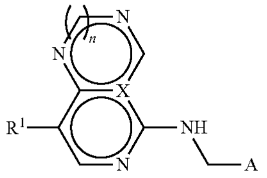

(I)

wherein

A is

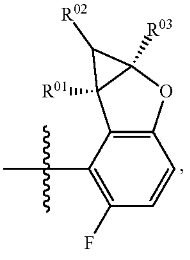

,

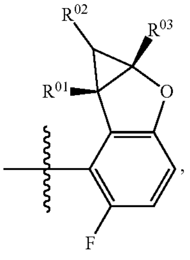

,

-continued

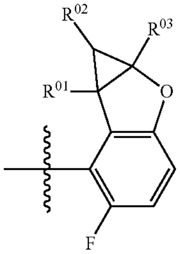, or 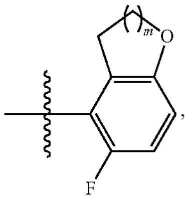, $R^{01}$, $R^{02}$ and $R^{03}$ are each independently hydrogen or halogen;

n is 0;

m is 1 or 2;

X is N;

$R^1$ is any one of the following structures:

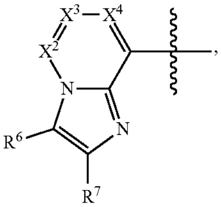, 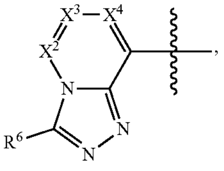, 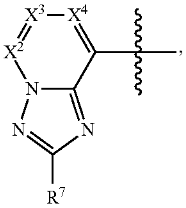, 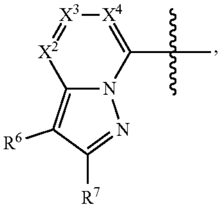, 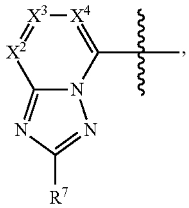, 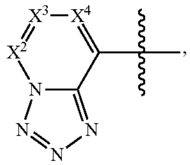, 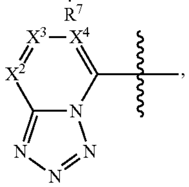, 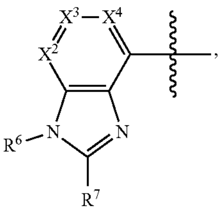, 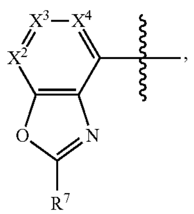, 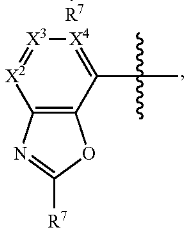, 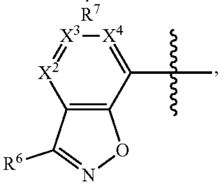, 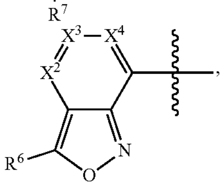, -continued

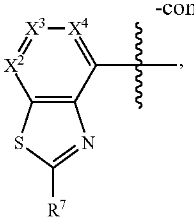, 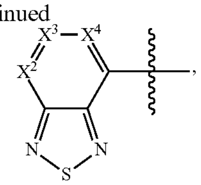, 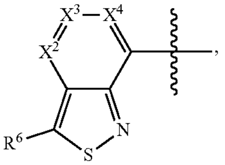, 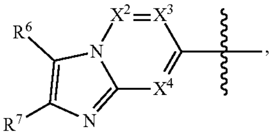, 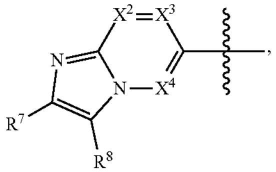, 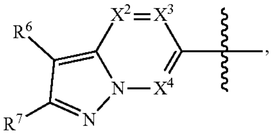, 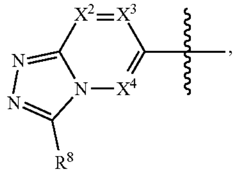, 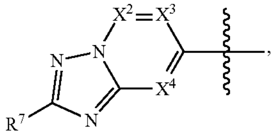, 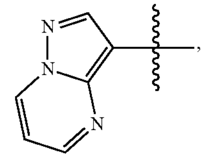, 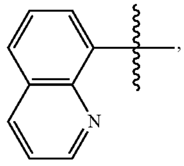, 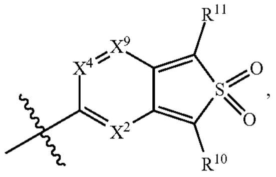, 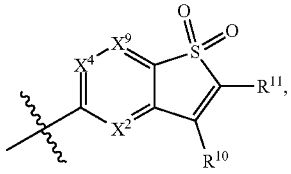, 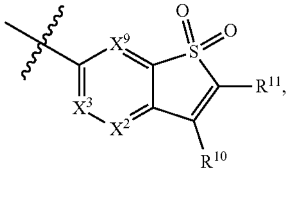, 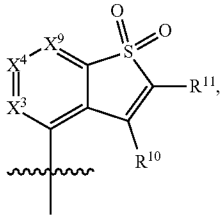, 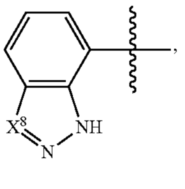, or 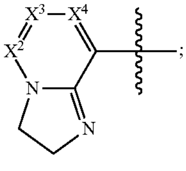;

$X^1$ is independently C or N;

$X^2$ is independently N or $CR^2$;

$X^3$ is independently N or $CR^3$;

$X^4$ is independently N or $CR^4$;

$X^8$ is independently $CR^8$ or N;

$X^9$ is independently N or $CR^9$;

$R^2$ is H, halogen, —CN, —$NR^aR^b$, $C_{1-4}$ alkyl, $C_{1-4}$ alkyl substituted with 1, 2 or 3 $R^5$ groups, $C_{1-4}$ haloalkyl, $C_{1-4}$ alkoxy, $C_{3-6}$ heterocycloalkyl, $C_{3-6}$ heterocycloalkyl substituted with 1, 2 or 3 $R^5$ groups, $C_{3-6}$ heterospirocycloalkyl, —$CO_2R^{16}$, —C(═O) $NR^{16}R^{17}$, or —$NR^aR^b$; each $R^{16}$ and $R^{17}$ are independently H or $C_{1-4}$ alkyl; $R^a$ and $R^b$ are independently H or $C_{1-4}$ alkyl; each $R^5$ is independently —OH, $C_{1-4}$ alkyl, $C_{1-4}$ alkoxy, $C_{1-4}$ alkoxy substituted with 1, 2 or 3 hydroxyl groups, —$NR^{a1}R^{b1}$, $C_{3-6}$ heterocycloalkyl, $C_{3-6}$ heterocycloalkyl substituted with 1, 2 or 3 $C_{1-4}$ alkyl groups, $C_{36}$ heterocycloalkyl substituted with 1, 2 or 3 $C_{3-6}$ heterocycloalkyl groups, or $C_{1-15}$ heteroaryl; $R^{a1}$ and $R^{b1}$ are independently H, $C_{1-4}$ alkyl, $C_{1-4}$ alkyl substituted with 1, 2 or 3 —$NR^{a2}R^{b2}$ groups, or $C_{1-4}$ alkyl substituted with 1, 2 or 3 hydroxyl groups; $R^{a2}$ and $R^{b2}$ are independently H or $C_{1-4}$ alkyl; the heteroatom in the $C_{3-6}$ heterocycloalkyl is selected from N, O and S, and the number of the heteroatom is 1, 2, 3 or 4; the heteroatom in the $C_{3-6}$ heterospirocycloalkyl is selected from N, O and S, and the number of the heteroatom is 1, 2, 3 or 4; the heteroatom in the $C_{1-15}$ heteroaryl is selected from N, O and S, and the number of the heteroatom is 1, 2, 3, 4, 5 or 6;

$R^3$ is H, halogen, —CN, $C_{1-4}$ alkyl, $C_{1-4}$ alkoxy, $C_{1-4}$ haloalkyl, or —C(=O) $NR^{16}R^{17}$;

$R^4$ is H, halogen, or $C_{1-4}$ alkyl;

$R^6$ is H, halogen, —CN, $C_{1-4}$ alkyl, $C_{1-4}$ alkyl substituted with 1, 2 or 3 $R^5$ groups, —$CO_2R^{16}$, —C(=O)$NR^{16}R^{17}$, —(C=O)$R^{16}$, $SO_2R^{16}$, or —$POR^{16}R^{17}$; each $R^{16}$ and each $R^{17}$ are independently H, $C_{1-4}$ alkyl, or $C_{3-6}$ heterocycloalkyl; each $R^5$ is independently —OH, —CN, —$NR^{a1}R^{b1}$, $C_{6-18}$ aryl, —C(=O)$NR^{16a}R^{17a}$, —$CO_2R^{16a}$, —O(C=O)$R^{16a}$, —NH(C=O)$R^{16a}$, or —(C=O)$R^{16a}$; $R^{a1}$ and $R^{b1}$ are independently H or $C_{1-4}$ alkyl; each $R^{16a}$ and $R^{17a}$ are independently H, $C_{1-4}$ alkyl or $C_{3-6}$ heterocycloalkyl;

$R^7$ is H, —OH, —$NR^aR^b$, $C_{1-4}$ alkyl, $C_{1-4}$ alkyl substituted with 1, 2 or 3 hydroxyl groups, $C_{1-4}$ haloalkyl, —$CO_2R^{16}$, or —C(=O)$NR^{16}R^{17}$; $R^a$ and $R^b$ are independently H or $C_{1-4}$ alkyl; $R^{16}$ and $R^{17}$ are independently H, $C_{1-4}$ alkyl or $C_{1-4}$ haloalkyl;

$R^8$ is H or $C_{1-4}$ alkyl;

$R^9$ is H, halogen, or $C_{1-4}$ alkyl;

$R^{10}$ is H, halogen, $C_{1-4}$ alkyl, or $C_{1-4}$ alkyl substituted with 1, 2 or 3 $R^5$ groups; each $R^5$ is independently —$NR^{a1}R^{b1}$; $R^{a1}$ and $R^{b1}$ are independently H or $C_{1-4}$ alkyl;

$R^{11}$ is H, halogen, or $C_{1-4}$ alkyl;

$R^{12}$, $R^{13}$, $R^{14}$, and $R^{15}$ are H.

2. The compound as shown in formula (I), the pharmaceutically acceptable salt, hydrate, stereoisomer, or solvate thereof according to claim 1, wherein A is

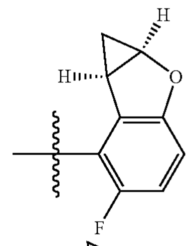
,
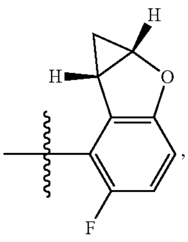
,
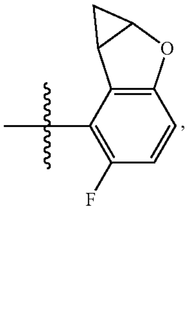
, or
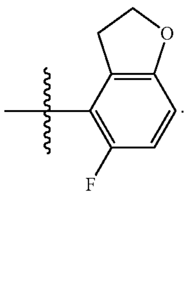
.

3. The compound as shown in formula (I), the pharmaceutically acceptable salt, hydrate, stereoisomer, or solvate thereof according to claim 1, wherein $R^1$ is any one of the following structures:

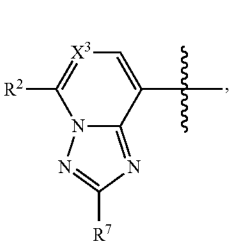
,
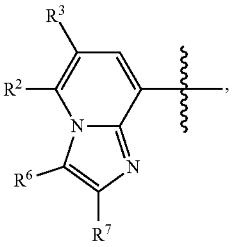
,
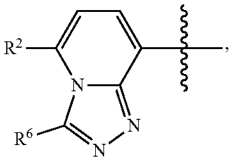
,
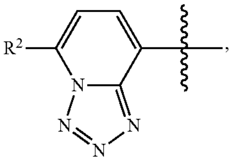
,
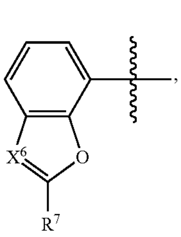
,
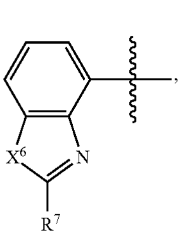
,
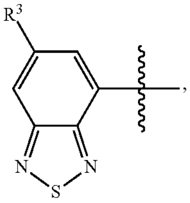
,
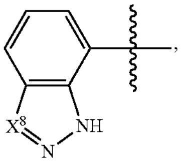
,
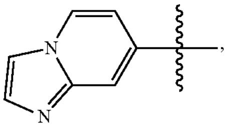
,
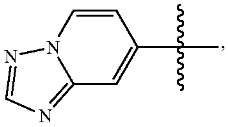
,
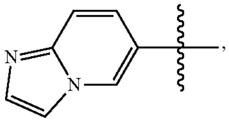
,
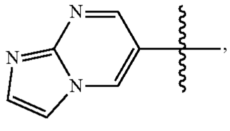
,
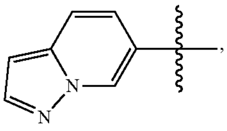
,
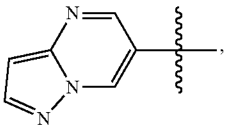
,
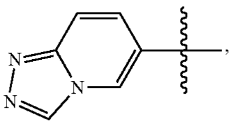
,
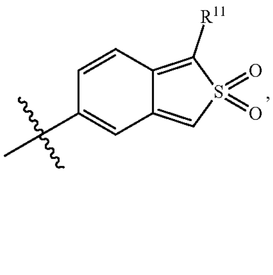
,
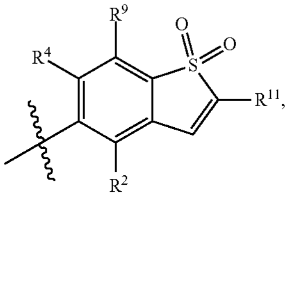
, -continued

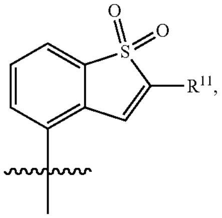

or

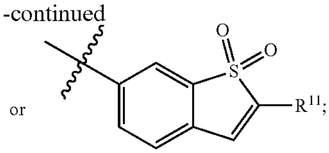

in the moiety

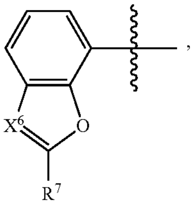

$X^6$ is N; $R^7$ is H, $C_{1-4}$ alkyl, $C_{1-4}$ haloalkyl, or —$NR^aR^b$; $R^a$ and $R^b$ are independently H or $C_{1-4}$ alkyl;

in the moiety

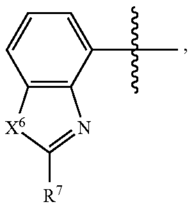

$X^6$ is $NR^6$, O or S; $R^6$ is $C_{1-4}$ alkyl; $R^7$ is H, $C_{1-4}$ alkyl, $C_{1-4}$ haloalkyl, or —$NR^aR^b$; $R^a$ and $R^b$ are independently H or $C_{1-4}$ alkyl;

in the moiety

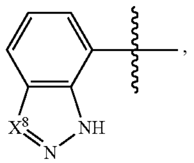

$X^8$ is $CR^8$ or N; $R^8$ is H or $C_{1-4}$ alkyl.

4. The compound as shown in formula (I), the pharmaceutically acceptable salt, hydrate, stereoisomer, or solvate thereof according to claim 3, wherein in the moiety

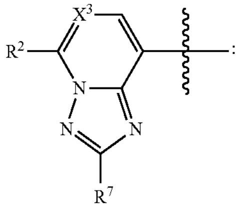

(i) $R^2$ is H, $C_{1-4}$ alkyl, $C_{1-4}$ alkyl substituted with 1, 2 or 3 $R^{5-2-1}$ groups, $C_{1-4}$ haloalkyl, $C_{1-4}$ alkoxy, $C_{3-6}$ heterocycloalkyl, $C_{3-6}$ heterocycloalkyl substituted with 1, 2 or 3 $C_{1-4}$ alkyl groups, $C_{3-6}$ heterospirocycloalkyl, or —$NR^aR^b$; $R^a$ and $R^b$ are independently H or $C_{1-4}$ alkyl;

each $R^{5-2-1}$ is independently —OH, $C_{1-4}$ alkyl, $C_{1-4}$ alkoxy, $C_{1-4}$ alkoxy substituted with 1, 2 or 3 hydroxyl groups, —$NR^{a1}R^{b1}$, $C_{3-6}$ heterocycloalkyl, or $C_{3-6}$ heterocycloalkyl substituted with 1, 2 or 3 $R^{5-2-2}$ groups; $R^{a1}$ and $R^{b1}$ are independently H, $C_{1-4}$ alkyl, $C_{1-4}$ alkyl substituted with 1, 2 or 3 —$NR^{a2}R^{b2}$ groups, or $C_{1-4}$ alkyl substituted with 1, 2 or 3 hydroxyl groups; $R^{5-2-2}$ is $C_{1-4}$ alkyl or $C_{3-6}$ heterocycloalkyl; $R^{a2}$ and $R^{b2}$ are independently H or $C_{1-4}$ alkyl;

wherein the heteroatom in the $C_{3-6}$ heterocycloalkyl is selected from N, O and S, and the number of the heteroatom is 1, 2, 3 or 4; the heteroatom in the $C_{3-6}$ heterospirocycloalkyl is selected from N, O and S, and the number of the heteroatom is 1, 2, 3 or 4;

or, (ii) when $X^3$ is $CR^3$, then $R^3$ is H, halogen, $C_{1-4}$ alkoxy, or —CN;

or, (iii) $R^7$ is H, $C_{1-4}$ alkyl, or —$NR^aR^b$; $R^a$ and $R^b$ are independently H or $C_{1-4}$ alkyl.

5. The compound as shown in formula (I), the pharmaceutically acceptable salt, hydrate, stereoisomer, or solvate thereof according to claim 4, wherein in the moiety

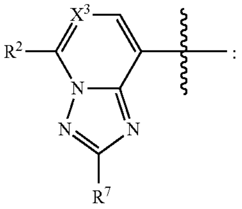

(i) $R^2$ is H, —$CH_3$, —$CF_3$, —$OCH_3$,

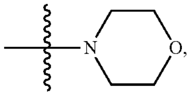

—$N(CH_3)_2$,

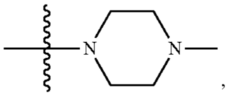 [SMILES: *N1CCN(C)CC1]

—$CH_2OCH_2C(CH_3)_2OH$, —$CH_2N(CH_3)_2$,

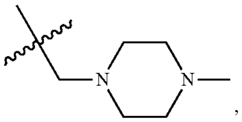 [SMILES: *CN1CCN(C)CC1]

—$CH_2NHCH_2C(CH_3)_2OH$,

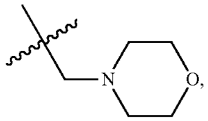, 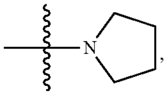,

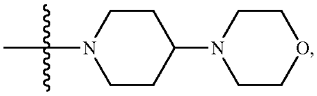, 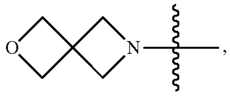,

—$CH_2N(CH_3)\ CH_2CH_2N(CH_3)_2$,

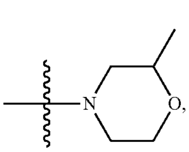, 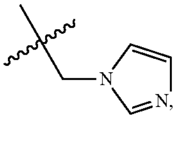

—$C(CH_3)_2OH$, or —$CHF_2$;

or, (ii) when $X^3$ is $CR^3$, then $R^3$ is H, —$OCH_3$, —F, or —CN;

or, (iii) $R^7$ is H, —$NH(CH_3)$, —$N(CH_3)_2$, or —$CH_3$.

6. The compound as shown in formula (I), the pharmaceutically acceptable salt, hydrate, stereoisomer, or solvate thereof according to claim 3, wherein in the moiety

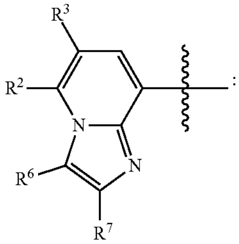:

(i) $R^2$ is H, —CN, $C_{1-4}$ alkyl, $C_{1-4}$ alkyl substituted with 1, 2 or 3 $R^{5-2-3}$ groups, $C_{1-4}$ haloalkyl, $C_{1-4}$ alkoxy, —$CO_2R^{16}$, —C(═O) $NR^{16}R^{17}$, or —$NR^aR^b$, wherein each $R^{16}$ and $R^{17}$ are independently H or $C_{1-4}$ alkyl; each $R^{5-2-3}$ is independently —OH or —$NR^{a1}R^{b1}$; $R^{a1}$ and $R^{b1}$ are independently H or $C_{1-4}$ alkyl;

or, (ii) $R^3$ is H, halogen, $C_{1-4}$ alkyl, $C_{1-4}$ alkoxy, or —C(═O) $NR^{16}R^{17}$; $R^{16}$ and $R^{17}$ are independently H or $C_{1-4}$ alkyl;

or, (iii) $R^6$ is H, halogen, —CN, $C_{1-4}$ alkyl, $C_{1-4}$ alkyl substituted with 1, 2 or 3 $R^5$-6-1 groups, —$CO_2R^{16}$, —C(═O) $NR^{16}R^{17}$, —(C═O) $R^{16-1}$, —$SO_2R^{16}$, or —$POR^{16}R^{17}$; each $R^{16}$ and each $R^{17}$ are independently H or $C_{1-4}$ alkyl; $R^{16}$-1 is H, $C_{1-4}$ alkyl or $C_{3-6}$ heterocycloalkyl;

each $R^{5-6-1}$ is independently $C_{6-18}$ aryl, —C(═O) $NR^{16a}R^{17a}$, —OH, —CN, —$CO_2R^{16a}$, —O(C═O) $R^{16a}$, —NH(C═O) $R^{16a}$, —(C═O) $R^{16a1}$, or —$NR^{a1}R^{b1}$; $R^{a1}$ and $R^{b1}$ are independently H or $C_{1-4}$ alkyl; each $R^{16a}$ and each $R^{17a}$ are independently H or $C_{1-4}$ alkyl; $R^{16a1}$ is $C_3$-$C_6$ heterocycloalkyl; for $R^{16-1}$ and $R^{16a1}$, the heteroatom in the $C_{3-6}$ heterocycloalkyl is selected from N, O and S, and the number of the heteroatom is 1, 2, 3 or 4;

or, (iv) $R^7$ is H, $C_{1-4}$ alkyl, $C_{1-4}$ alkyl substituted with 1, 2 or 3 hydroxyl groups, $C_{1-4}$ haloalkyl, —OH, —$CO_2R^{16}$, or —C(═O) $NR^{16}R^{17}$; $R^{16}$ and $R^{17}$ are independently H or $C_{1-4}$ alkyl.

7. The compound as shown in formula (I), the pharmaceutically acceptable salt, hydrate, stereoisomer, or solvate thereof according to claim 6, wherein in the moiety

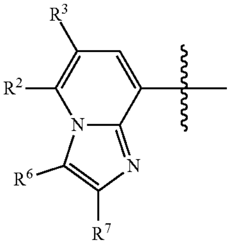:

(i) $R^2$ is H, —$CH_3$, —$CO_2CH_3$, —$CH_2OH$, —$CON(CH_3)_2$, —$CF_3$, —$CH_2N(CH_3)_2$, —$OCH_3$, —$N(CH_3)_2$,

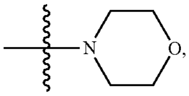, or —CN;

or, (ii) $R^3$ is H, —F, —Cl, —$CH_3$, —$OCH_3$, —$CONH_2$, —$CONHCH_3$, or —$CON(CH_3)_2$;

or, (iii) $R^6$ is H, —$COOCH_2CH_3$, —COOH, —$CONH_2$, —$CH_3$, —$COCH_3$,

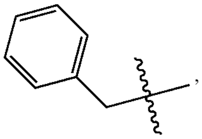 [SMILES: *Cc1ccccc1],

—$CH_2CH_3$, —F, —CN, —$CH(CH_3)_2$, —$CH_2CONH_2$, —$CH_2CH_2OH$, —$CH_2OH$, —$CH_2NH_2$, —$CH_2COOCH_3$, —$CH_2COOH$, —$CH_2CON(CH_3)_2$, —$CH_2CH_2OCOCH_3$, —$CH_2NHCOCH_3$, —$CON(CH_3)_2$, —CN,

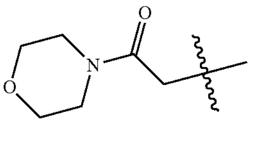, 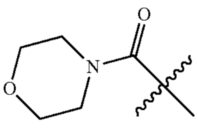,

—$CONH_2$, —$CH_2CN$, —$SO_2Me$, or —$PO(CH_3)_2$;

or, (iv) $R^7$ is H, —$CF_3$, —$CH_3$, —OH, —$CH_2OH$, —$COOCH_2CH_3$, —COOH, —$CONH_2$, or —$CON(CH_3)_2$.

8. The compound as shown in formula (I), the pharmaceutically acceptable salt, hydrate, stereoisomer, or solvate thereof according to claim 3, wherein in the moiety

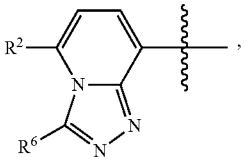

$R^2$ is H, halogen, $C_{1-4}$ alkyl, or $—NR^aR^b$; $R^a$ and $R^b$ are independently H or $C_{1-4}$ alkyl; $R^6$ is H or $C_{1-4}$ alkyl;

or, in the moiety

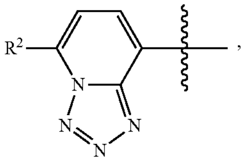

$R^2$ is $C_{1-4}$ alkyl;

or, in the moiety

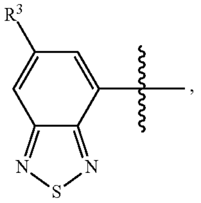

$R^3$ is H or $C_{1-4}$ haloalkyl;

or, in the moiety

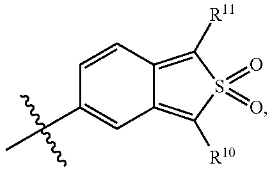

$R^{10}$ and $R^{11}$ are independently H or halogen;

or, in the moiety

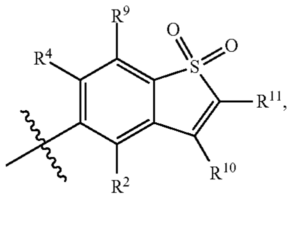

$R^2$ is H or halogen; $R^4$ is H, halogen or $C_{1-4}$ alkyl; $R^9$ is H, halogen or $C_{1-4}$ alkyl; $R^{10}$ is H, $C_{1-4}$ alkyl, $C_{1-4}$ alkyl substituted with 1, 2 or 3 amino groups, or halogen; $R^{11}$ is H, $C_{1-4}$ alkyl, or halogen;

or, in the moieties

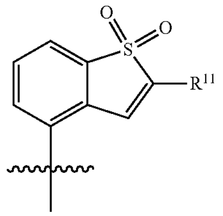

and

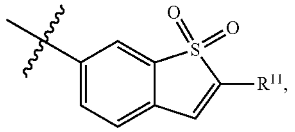

$R^{11}$ is independently H or $C_{1-4}$ alkyl.

9. The compound as shown in formula (I), the pharmaceutically acceptable salt, hydrate, stereoisomer, or solvate thereof according to claim 8, wherein in the moiety

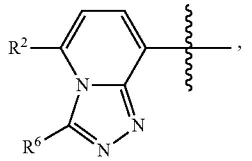

$R^2$ is H, —Cl, $—CH_3$, or $—N(CH_3)_2$; $R^6$ is H or $—CH_3$;

or, in the moiety

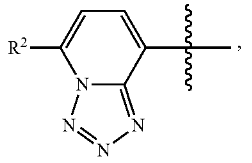

$R^2$ is-$CH_3$;

or, in the moiety

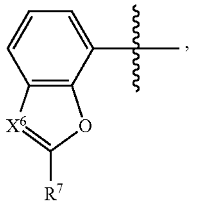

$X^6$ is N; $R^7$ is H, $—CH_3$, $—NH_2$, or $—CF_3$;

or, in the moiety

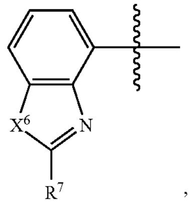

$X^6$ is —$NCH_3$, O or S; $R^7$ is H, —$CH_3$, —$NH_2$, or —$CF_3$; or, in the moiety

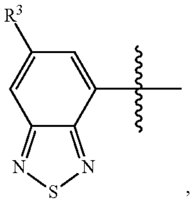
, $R^3$ is H or —$CF_3$;
or, in the moiety

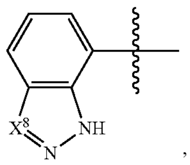
, $X^8$ is CH or N;
or, in the moiety

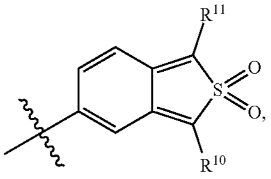

$R^{10}$ and $R^{11}$ are independently H or —F;
or, in the moiety

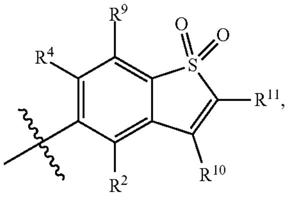

$R^2$ is H or —F; $R^4$ is H, —F or —$CH_3$; $R^9$ is H, F, —Cl, or —$CH_3$; $R^{10}$ is H, —$CH_3$, —$CH_2CH_2NH_2$, —F, or —Cl; $R^{11}$ is H, —$CH_3$, or —F;
or, in the moieties

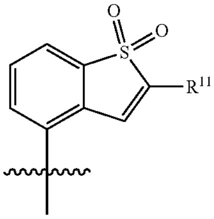
and
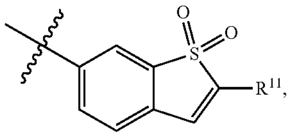

$R^{11}$ is independently H or —$CH_3$.

10. The compound as shown in formula (I), the pharmaceutically acceptable salt, hydrate, stereoisomer, or solvate thereof according to claim 1, wherein $R^1$ is

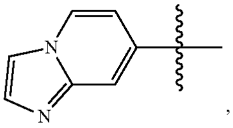
,
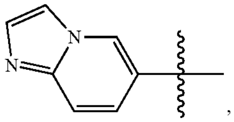
,
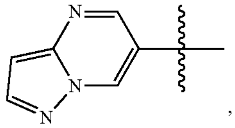
,
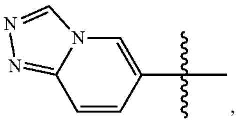
,
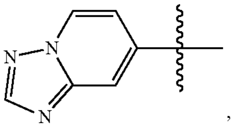
,
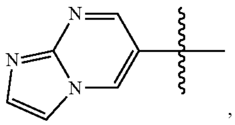
,
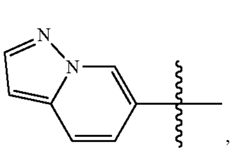
,
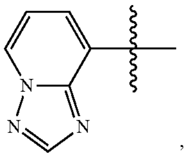
,
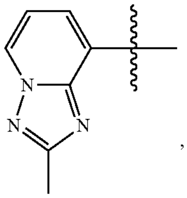
,
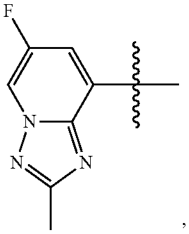
,
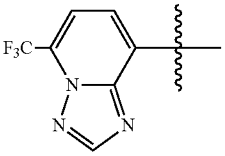
,
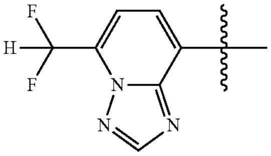
,
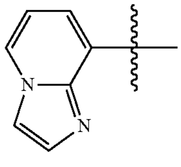
,
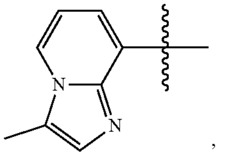
,
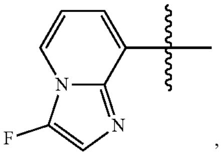
,
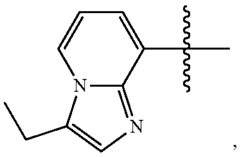
,
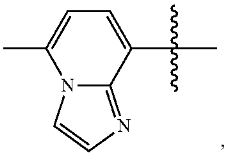
,
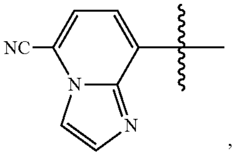
, -continued
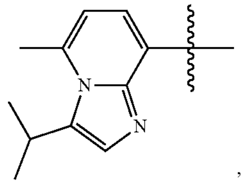,
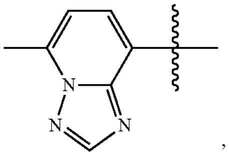,
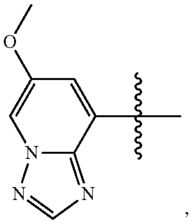,
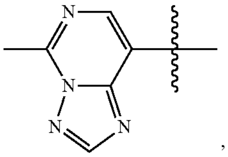,
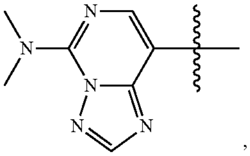,
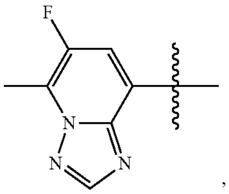,
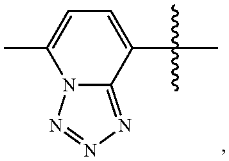,
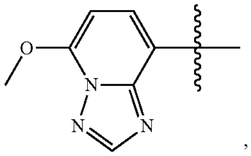,
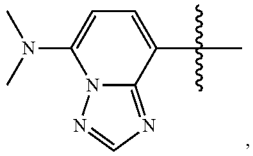,
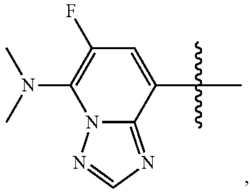,
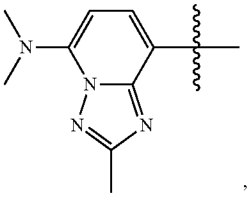,
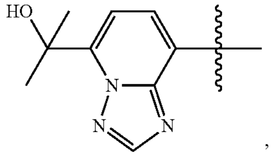,
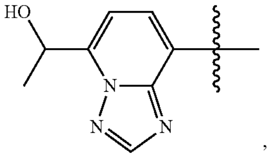,
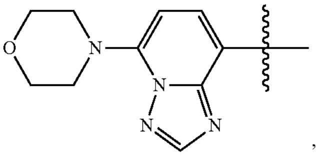,
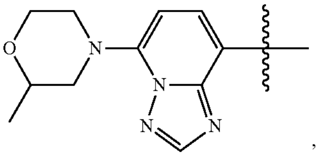,
-continued
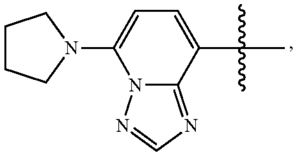,
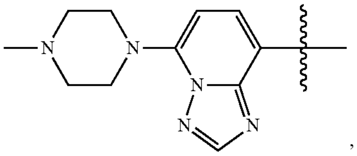,
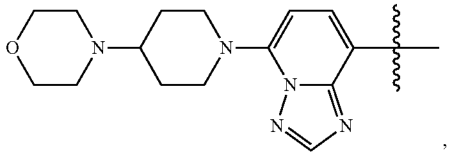,
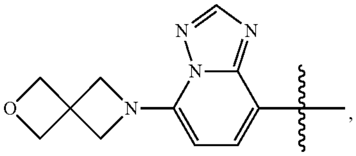,
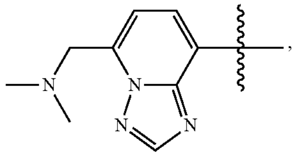,
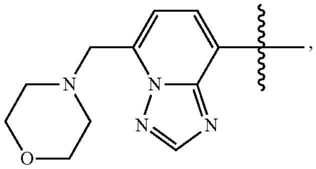,
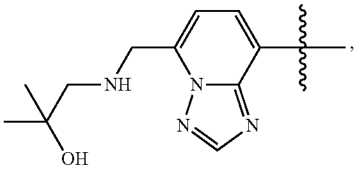,
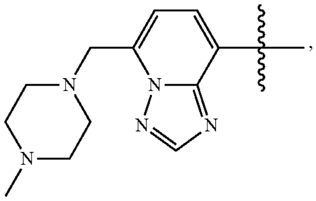,
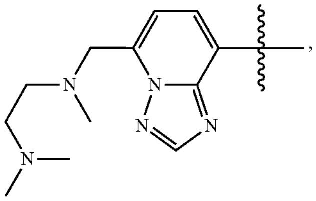,
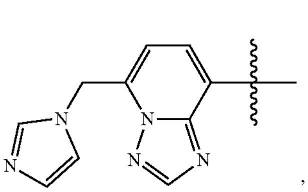,
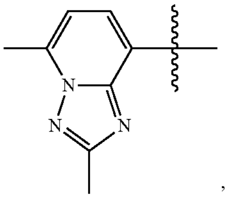, -continued
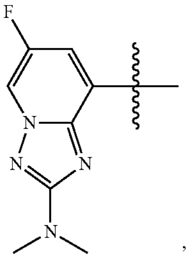
,
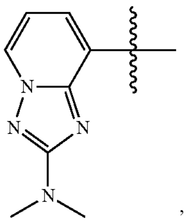
,
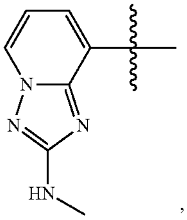
,
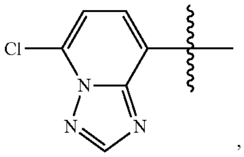
,
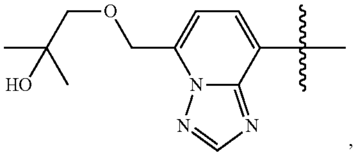
,
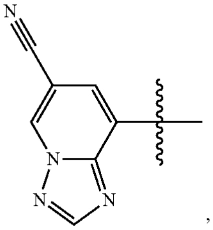
,
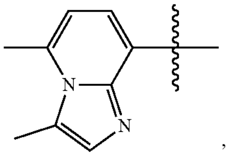
,
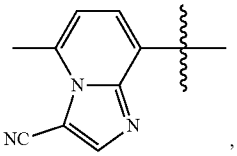
,
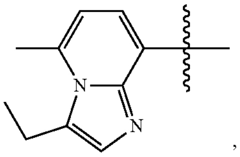
,
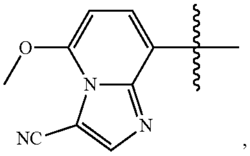
,
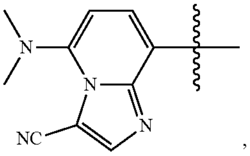
,
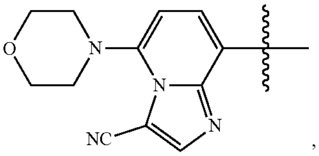
,
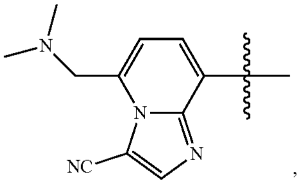
,
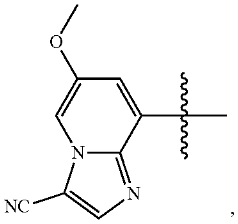
,
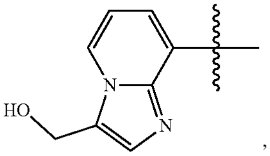
,
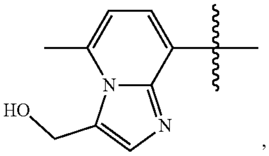
,
-continued
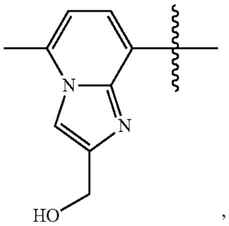
,
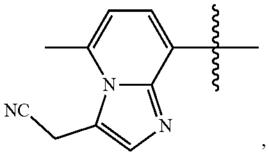
,
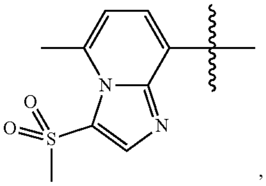
,
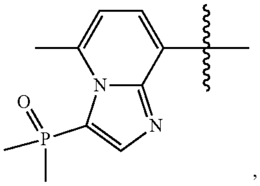
,
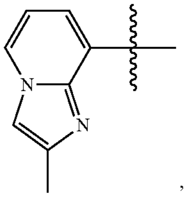
,
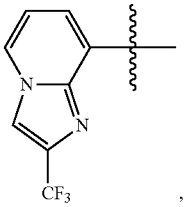
,
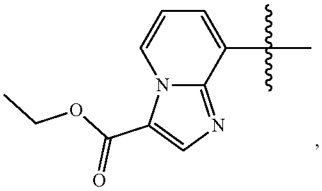
,
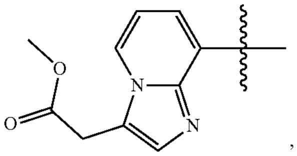
,
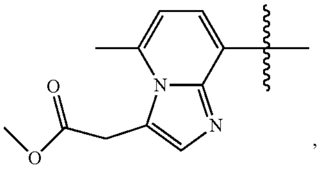
,
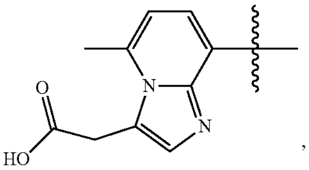
,
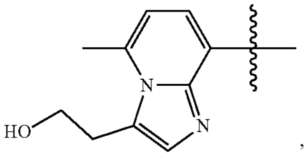
,
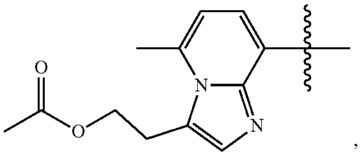
, -continued
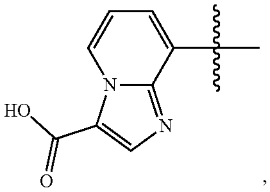,
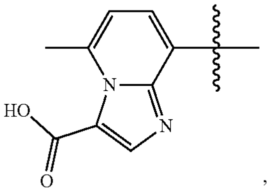,
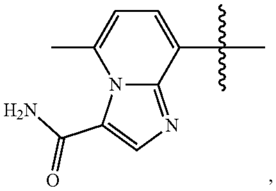,
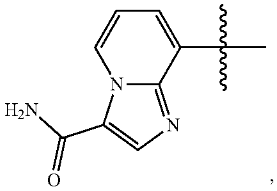,
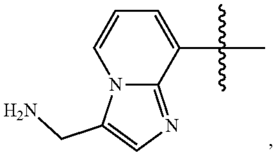,
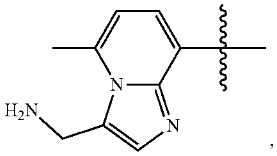,
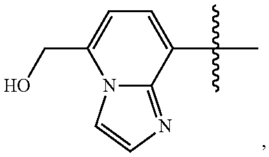,
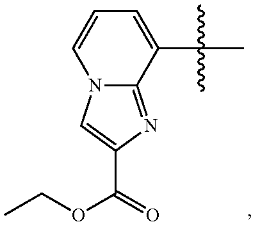,
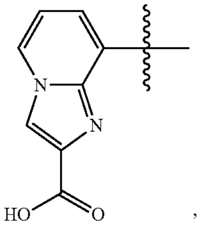,
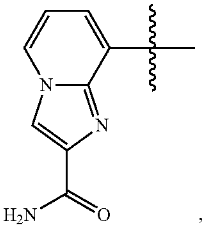,
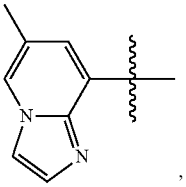,
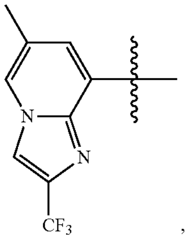,
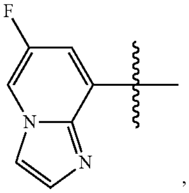,
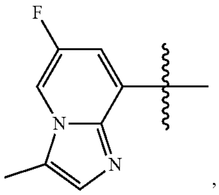,
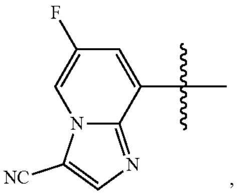,
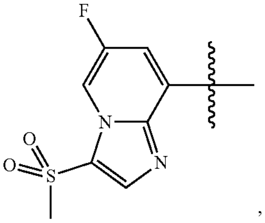,
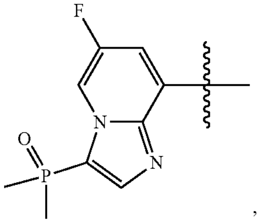,
-continued
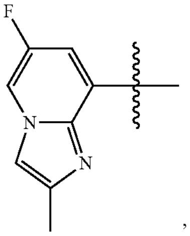,
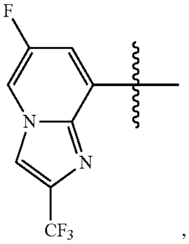,
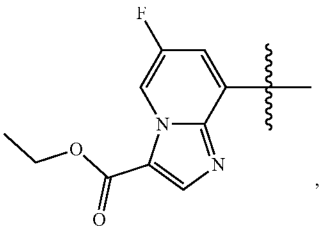,
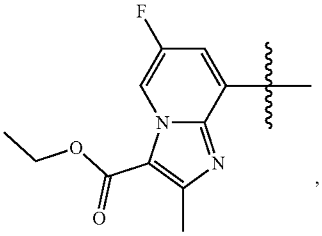,
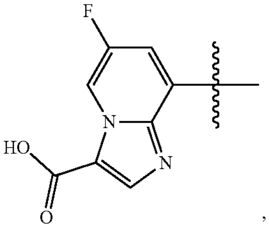,
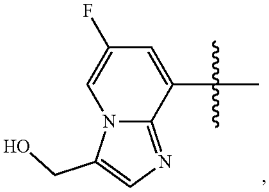,
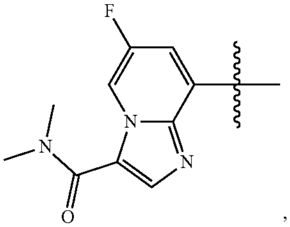,
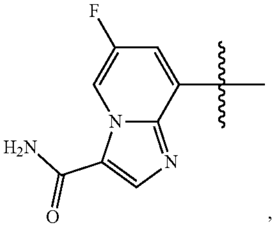,
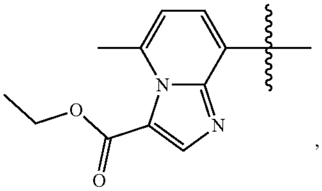,
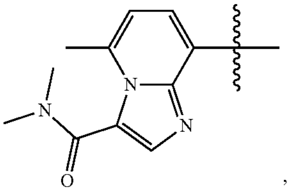,
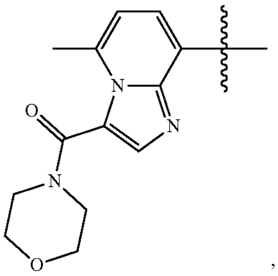, -continued
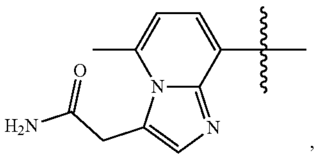,
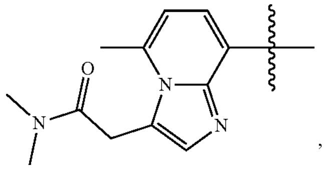,
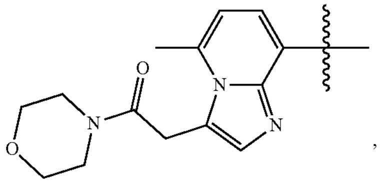,
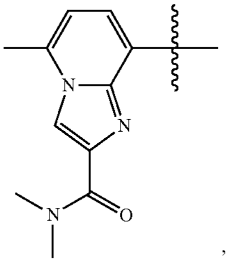,
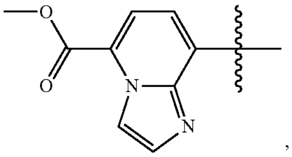,
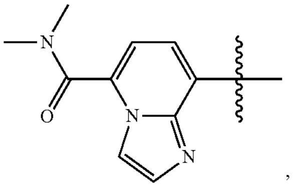,
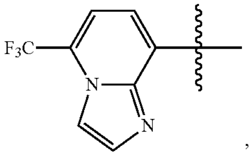,
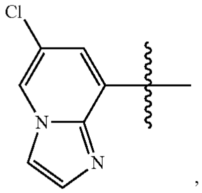,
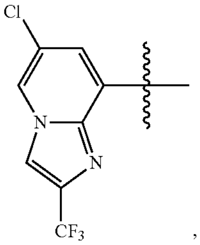,
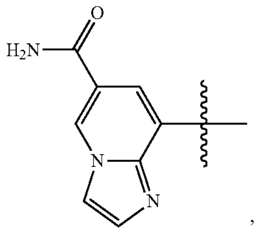,
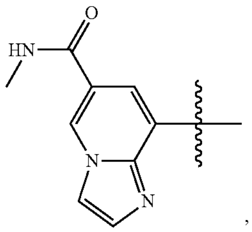,
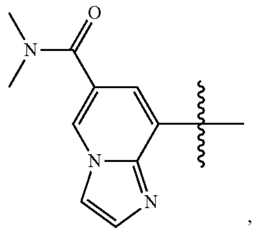,
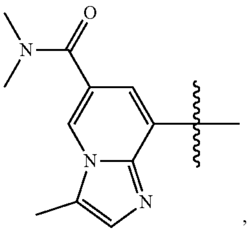,
-continued
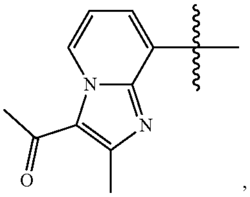,
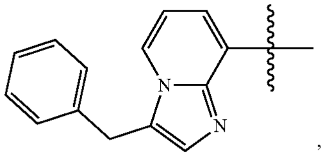,
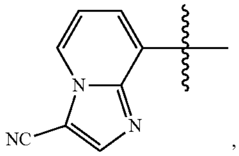,
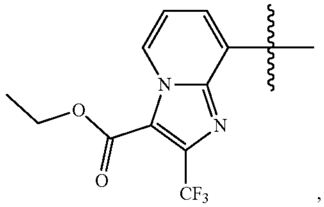,
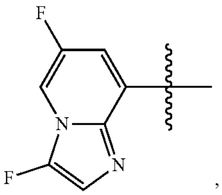,
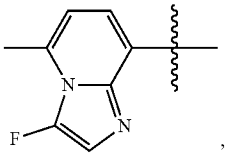,
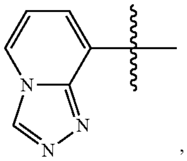,
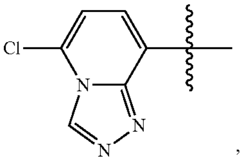,
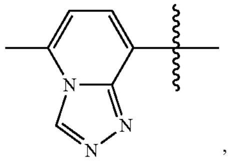,
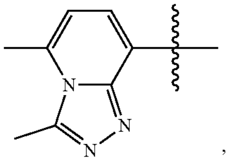,
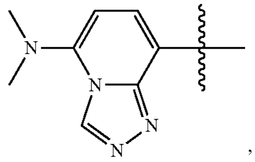,
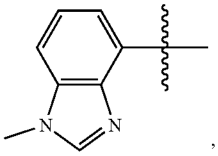,
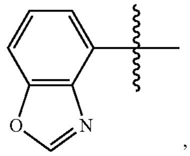,
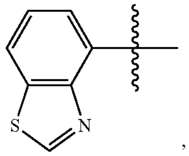,
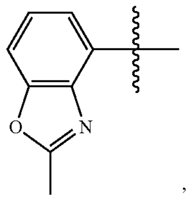,
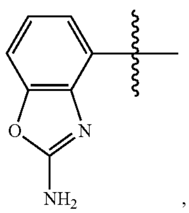,
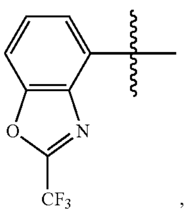,
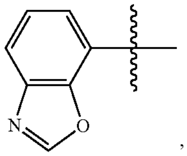,
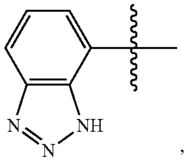,
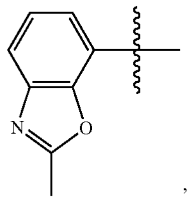,
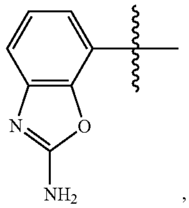, -continued
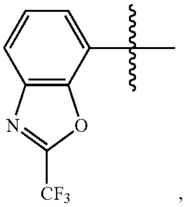 , 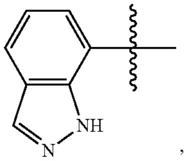 , 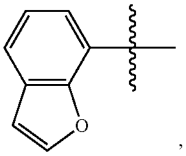 ,
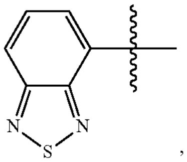 , 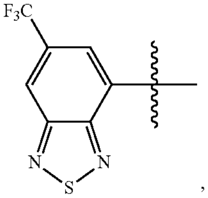 ,
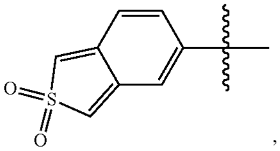 , 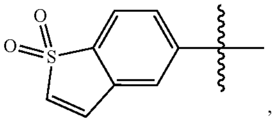 ,
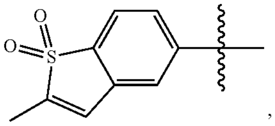 , 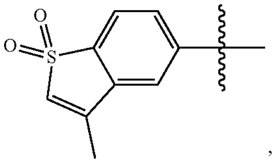 ,
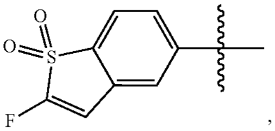 , 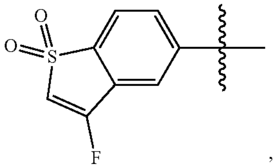 ,
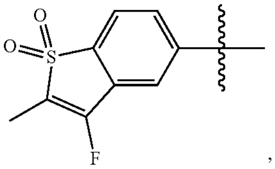 , 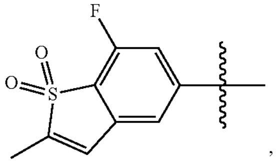 ,
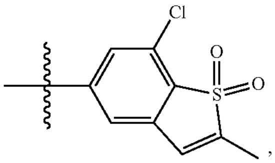 , 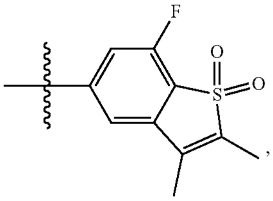 ,
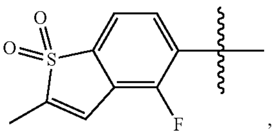 , 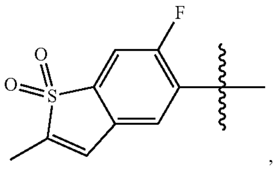 ,
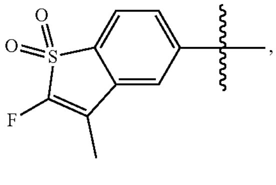 , 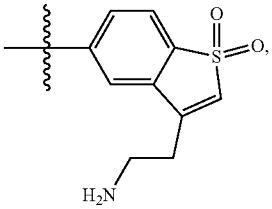
-continued
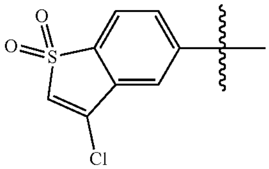 , 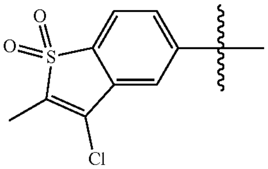 ,
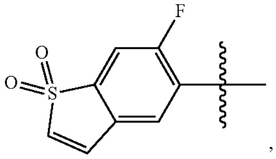 , 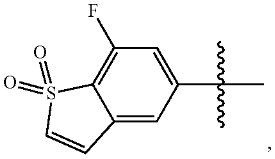 ,
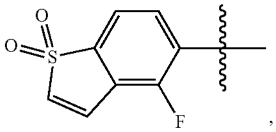 , 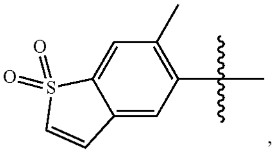 ,
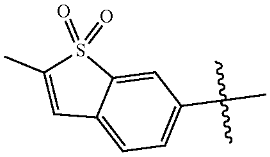 , 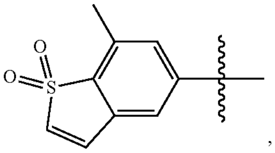 ,
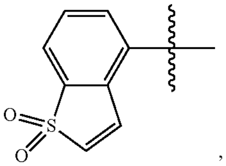 , 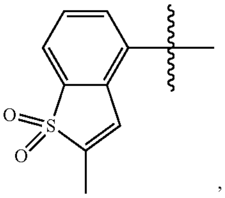 ,
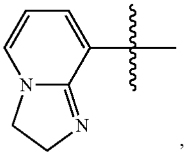 , or 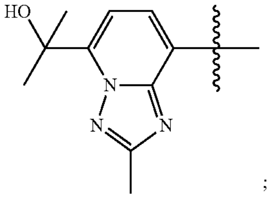 ;
or, $R^2$ is H, —$CH_3$, —$CF_3$, —$OCH_3$,
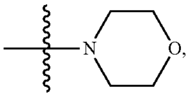 [SMILES: *N1CCOCC1]
—$N(CH_3)_2$,
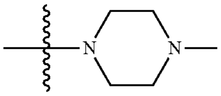 ,
—$CH_2OCH_2C(CH_3)_2OH$, —$CH_2N(CH_3)_2$,
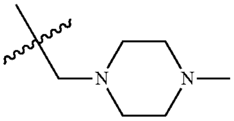 , $—CH_2NHCH_2C(CH_3)_2OH$,

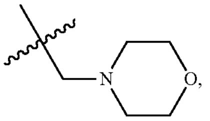
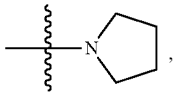
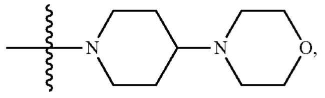
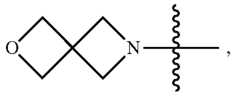

$—CH_2N(CH_3)\ CH_2CH_2N(CH_3)_2$,

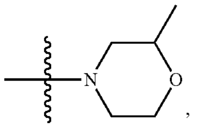
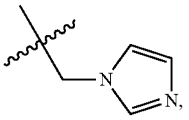

$—C(CH_3)_2OH$, $—CHF_2$, $—CO_2CH_3$, $—CH_2OH$, $—CON(CH_3)_2$, $—CH_2N(CH_3)_2$, —CN, or —Cl;

or, $R^3$ is H, $—OCH_3$, —F, —CN, —Cl, $—CH_3$, $—CONH_2$, $—CF_3$, $—CONHCH_3$, or $—CON(CH_3)_2$;

or, $R^4$ is H, —F, or $—CH_3$;

or, $R^6$ is H, $—COOCH_2CH_3$, —COOH, $—CONH_2$, $—CH_3$, $—COCH_3$,

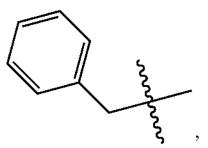 [SMILES: *Cc1ccccc1]

$—CH_2CH_3$, —F, —CN, $—CH(CH_3)_2$, $—CH_2CONH_2$, $—CH_2CH_2OH$, $—CH_2OH$, $—CH_2NH_2$, $—CH_2COOCH_3$, $—CH_2COOH$, $—CH_2CON(CH_3)_2$, $—CH_2CH_2OCOCH_3$, $—CH_2NHCOCH_3$, $—CON(CH_3)_2$, —CN,

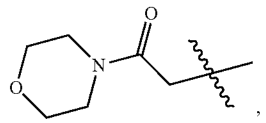
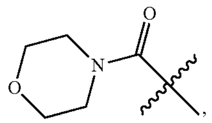

$—CONH_2$, $—CH_2CN$, $—SO_2Me$, or $—PO(CH_3)_2$;

or, $R^7$ is H, $—NH(CH_3)$, $—N(CH_3)_2$, $—CH_3$, $—CF_3$, —OH, $—CH_2OH$, $—COOCH_2CH_3$, —COOH, $—CONH_2$, $—CON(CH_3)_2$, or $—NH_2$;

or, $R^8$ is H;

or, $R^9$ is H, —F, —Cl, or $—CH_3$;

or, $R^{10}$ is H, $—CH_3$, $—CH_2CH_2NH_2$, —F, or —Cl;

or, $R^{11}$ is H, $—CH_3$, or —F;

or, $R^{12}$, $R^{13}$, $R^{14}$, and $R^{15}$ are H.

11. The compound as shown in formula (I), the pharmaceutically acceptable salt, hydrate, stereoisomer, or solvate thereof according to claim 1, wherein the compound as shown in formula (I) is selected from the compounds as shown below:

(Ia-1)

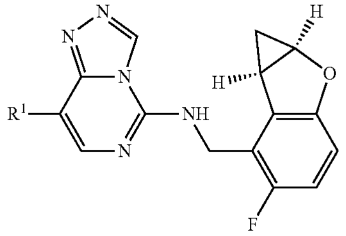

(Ia-2)

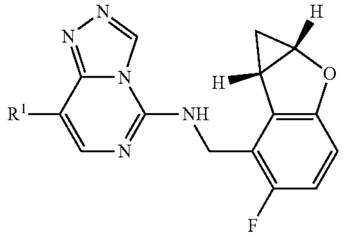

(Ia-3)

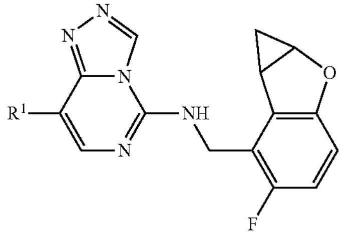

(Ia-4)

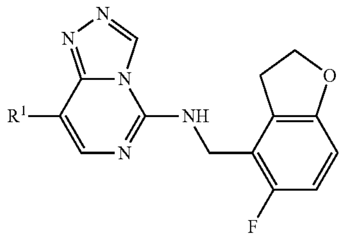

(Ia-5)

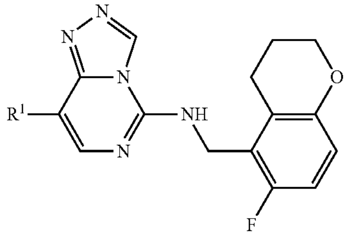

(Ia-6)

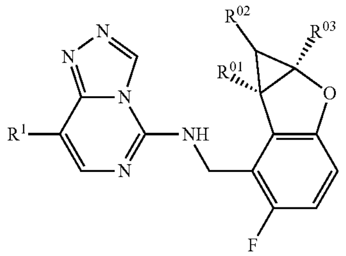

-continued
(Ia-7)
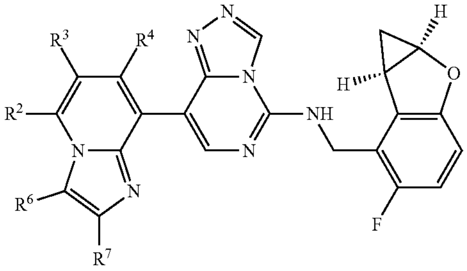
(Ia-8)
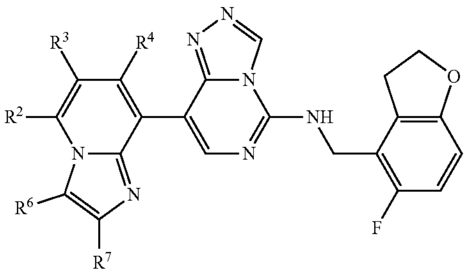
(Ia-9)
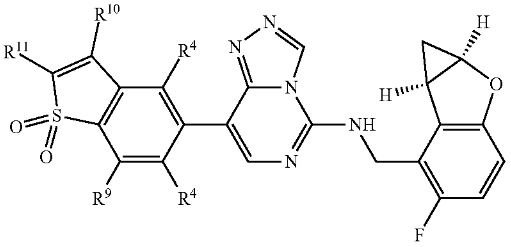
(Ia-10)
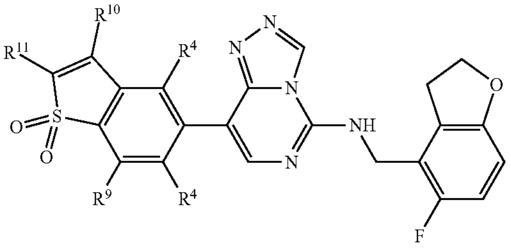
(Ia-11)
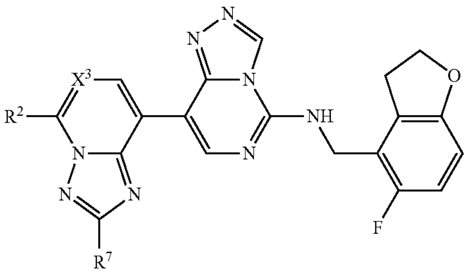
-continued
(Ib)
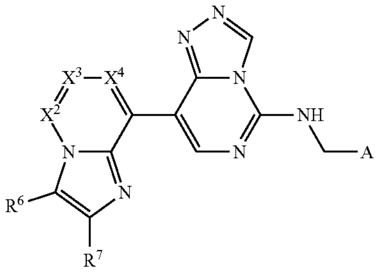
(Ic)
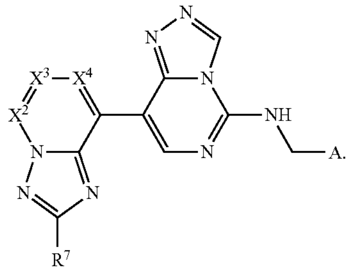
12. The compound as shown in formula (I), the pharmaceutically acceptable salt, hydrate, stereoisomer, or solvate thereof according to claim 1, wherein the compound as shown in formula (I) is selected from any one of the following compounds:
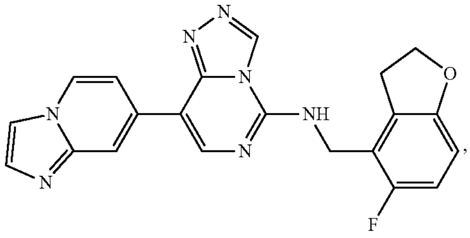
,
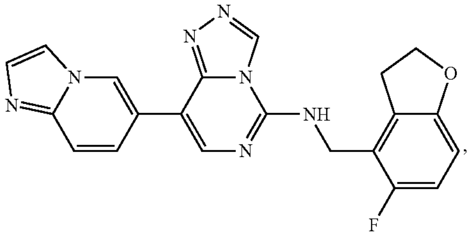
,
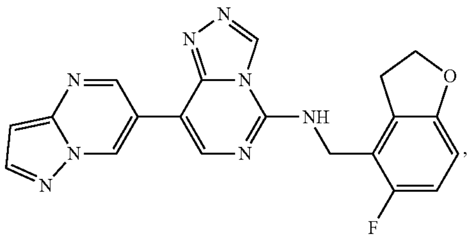
, -continued
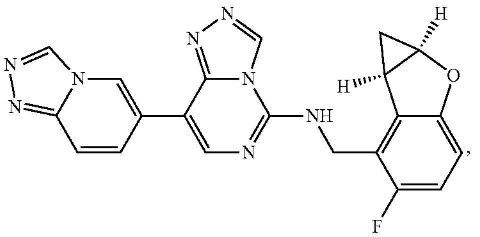
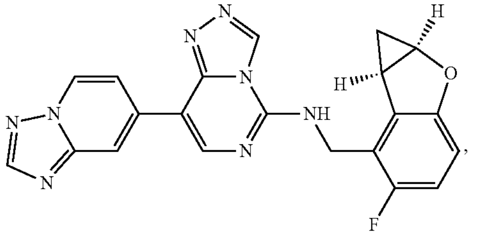
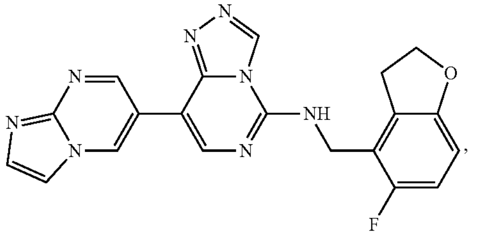
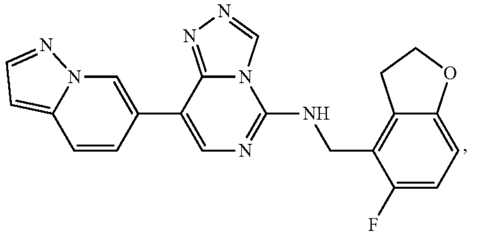
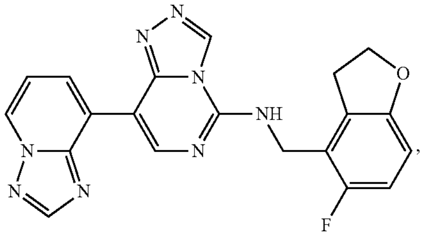
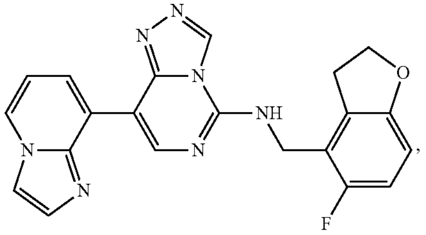
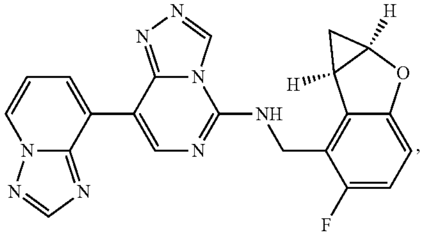
-continued
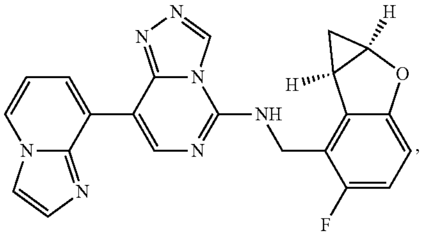
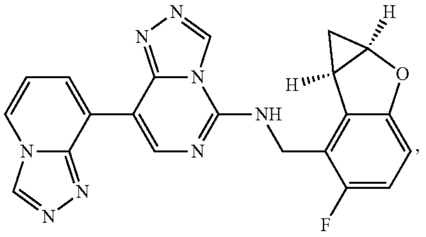
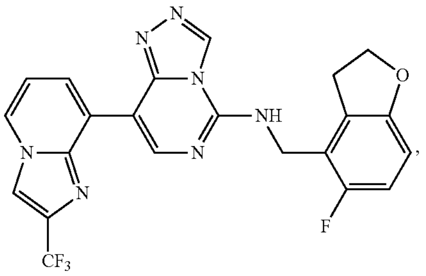
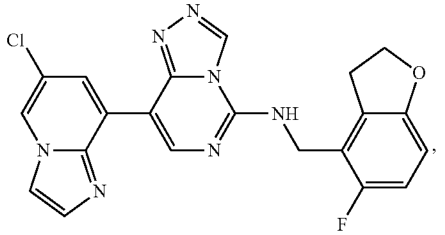
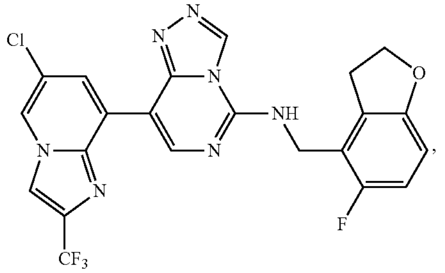
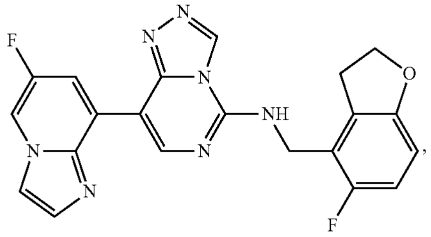

-continued
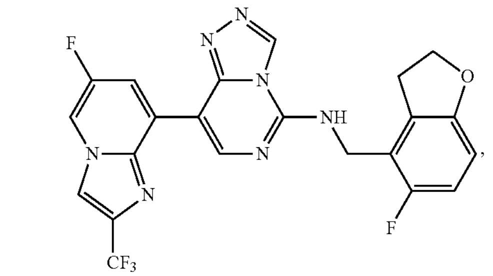
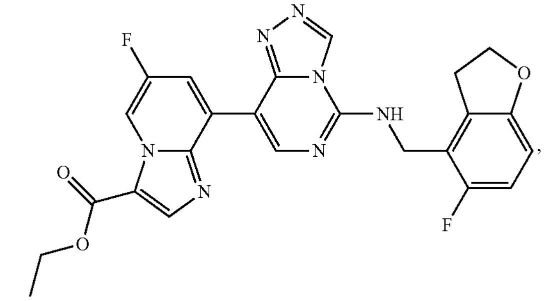
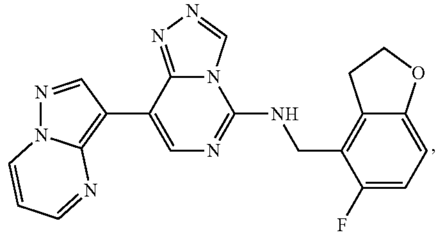
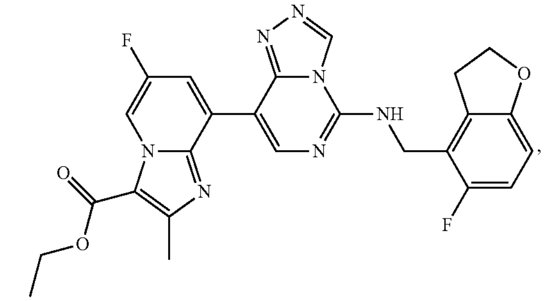
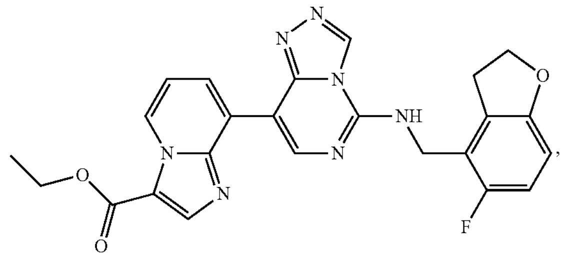
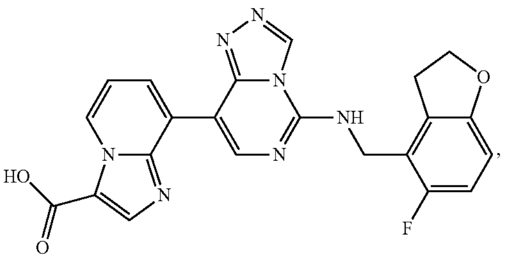
-continued
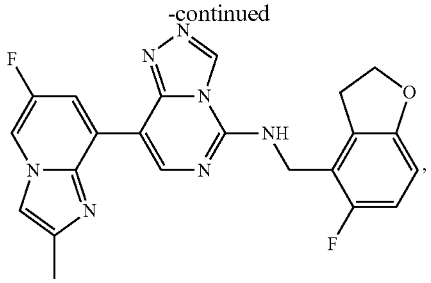
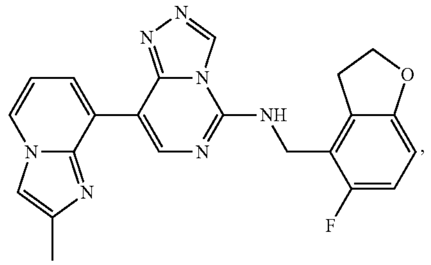
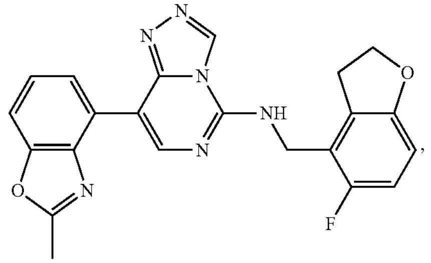
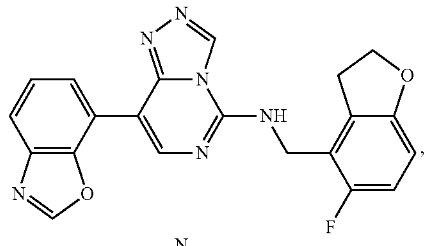
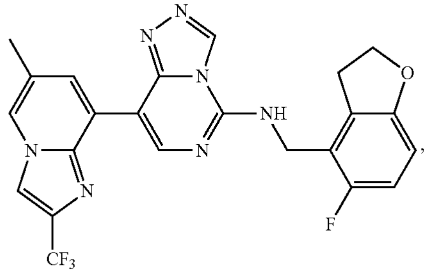
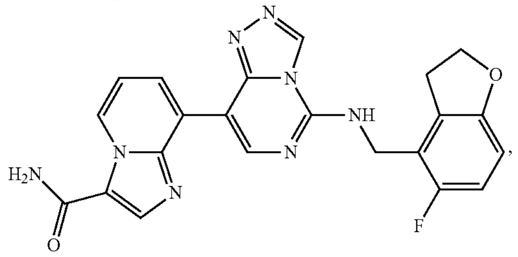

-continued
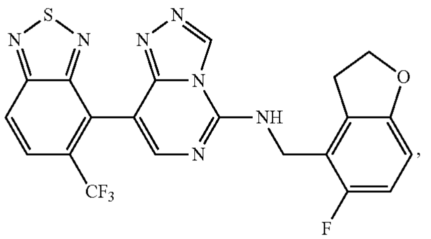,
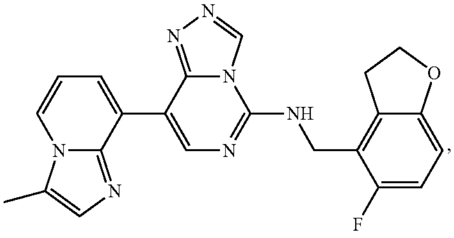,
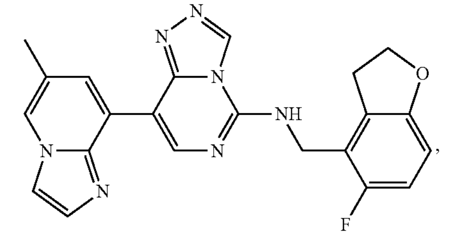,
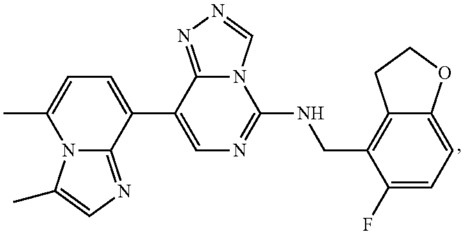,
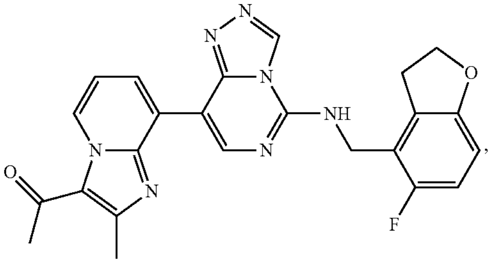,
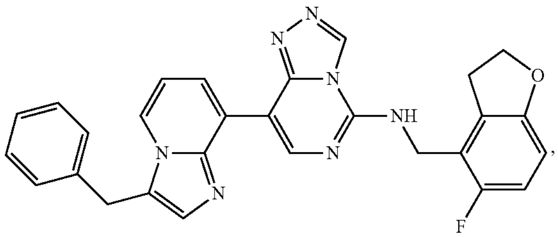,
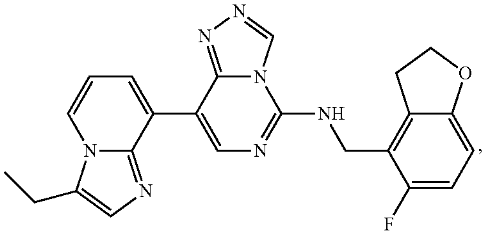,
-continued
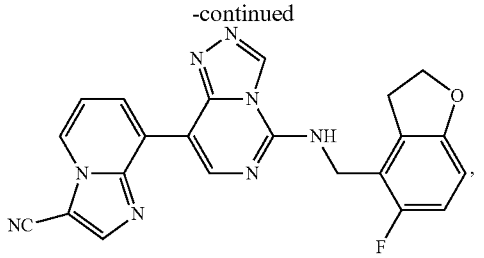,
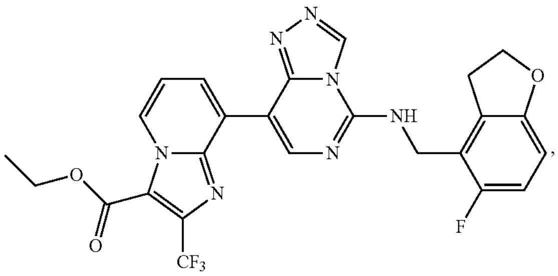,
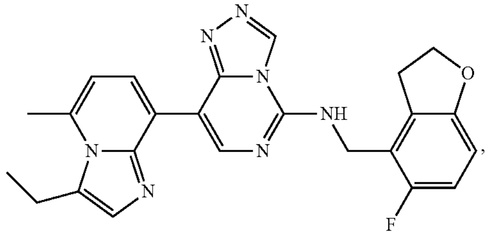,
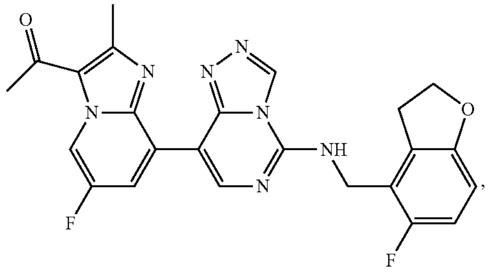,
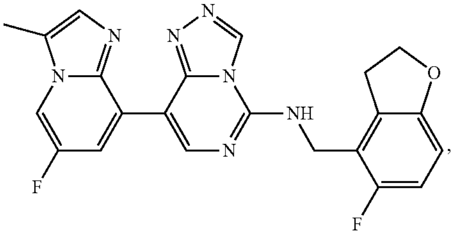,
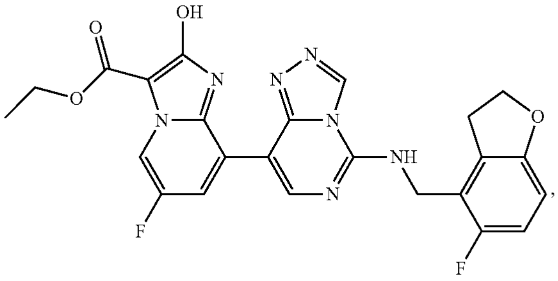, -continued
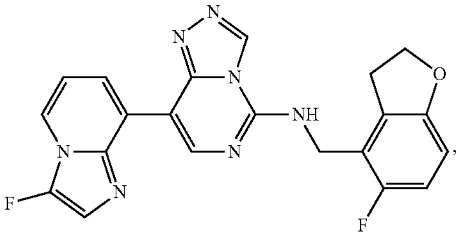
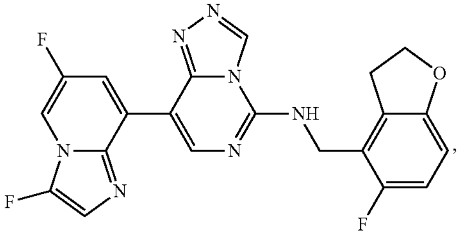
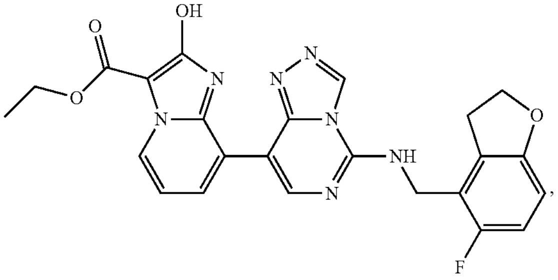
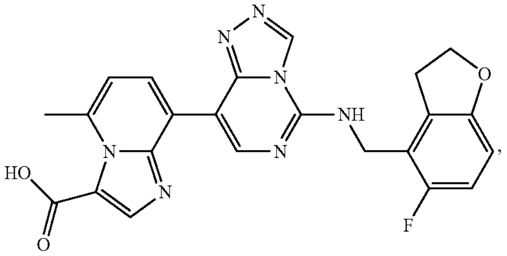
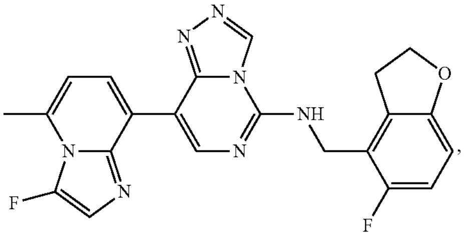
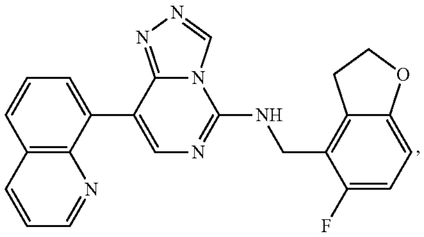
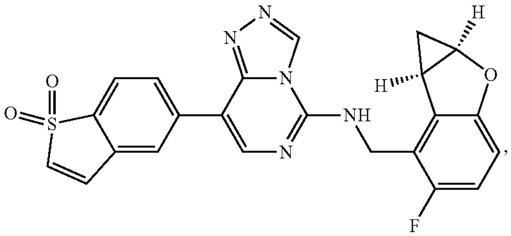
-continued
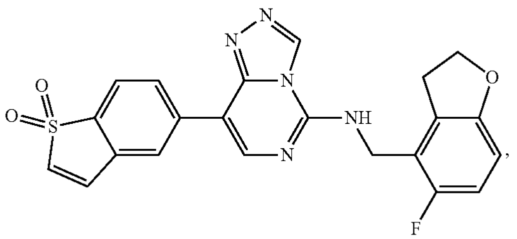
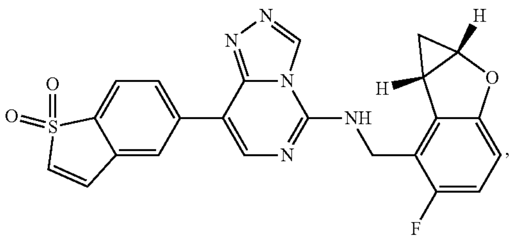
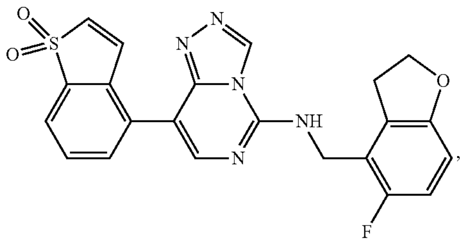
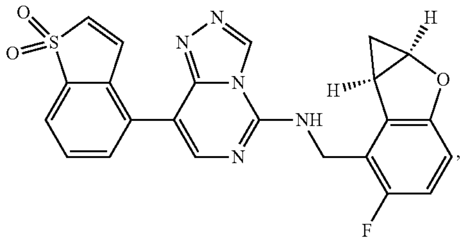
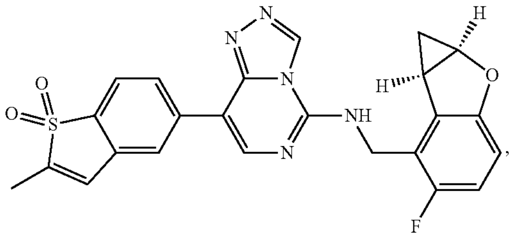
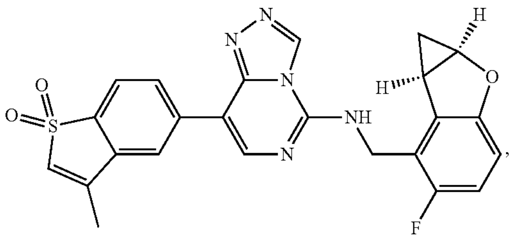
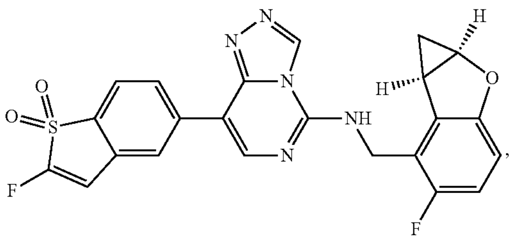

-continued
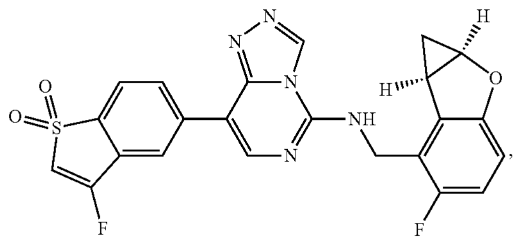,
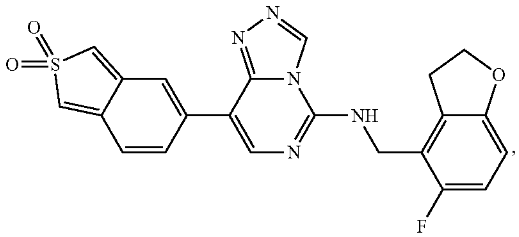,
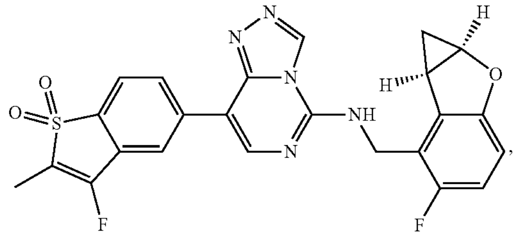,
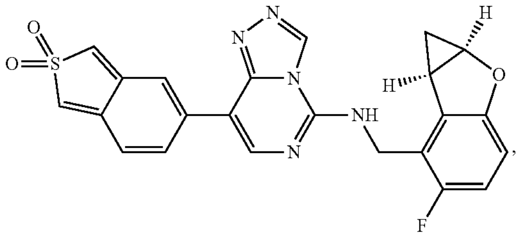,
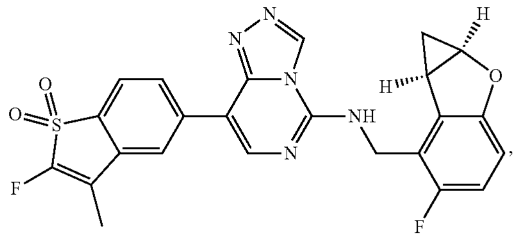,
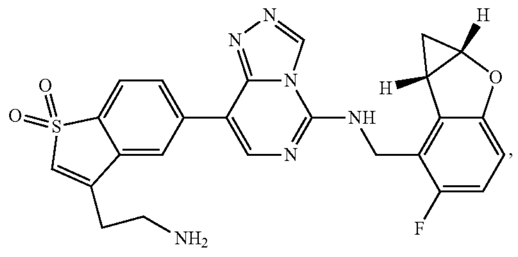,
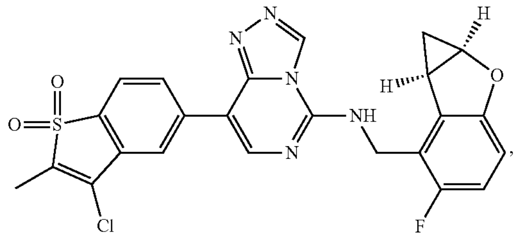,
-continued
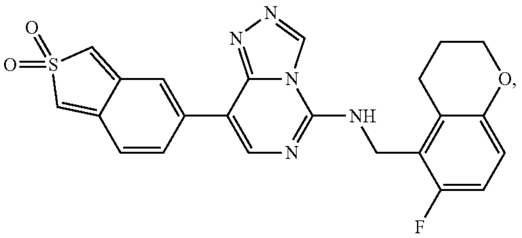,
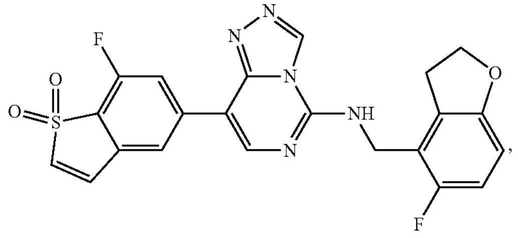,
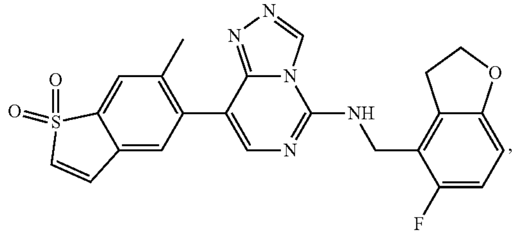,
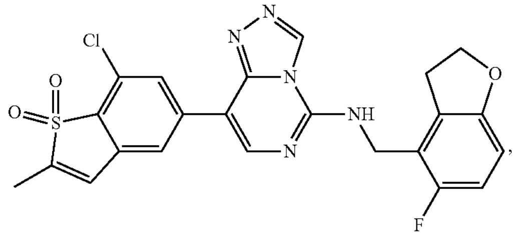,
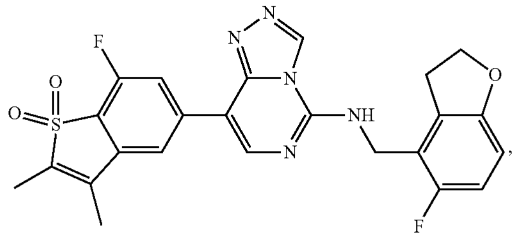,
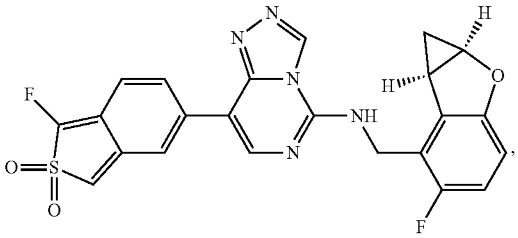,
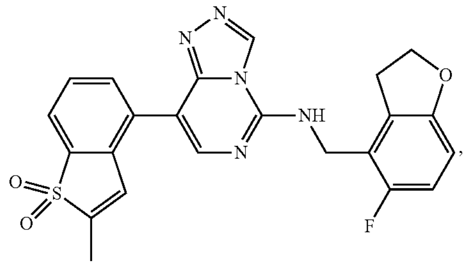, -continued
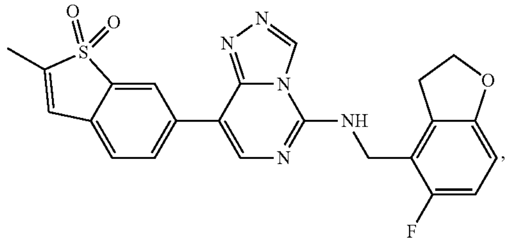
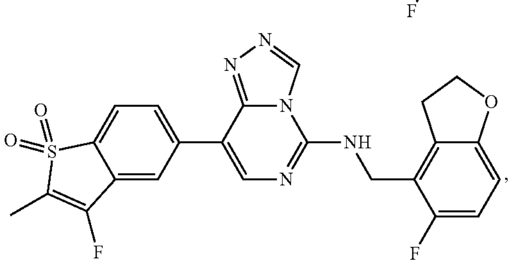
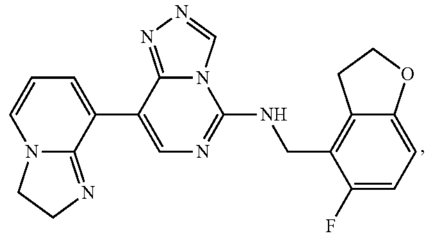
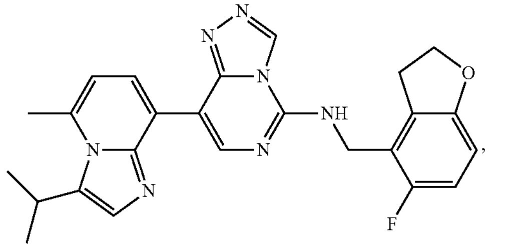
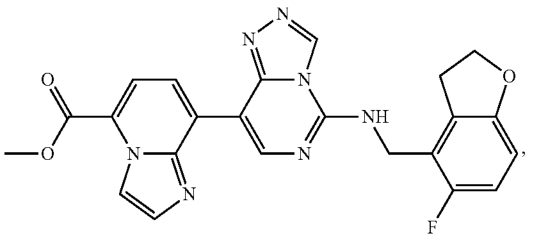
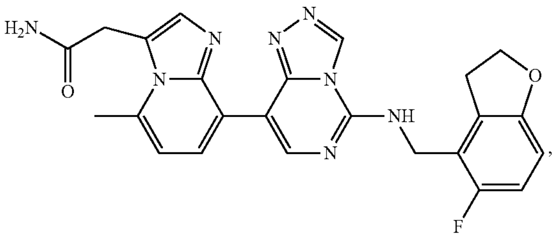
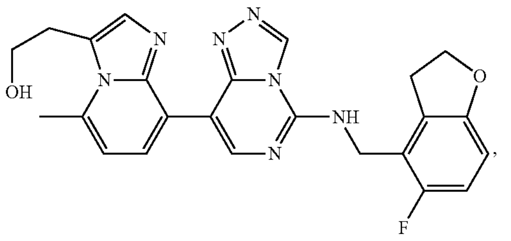
-continued
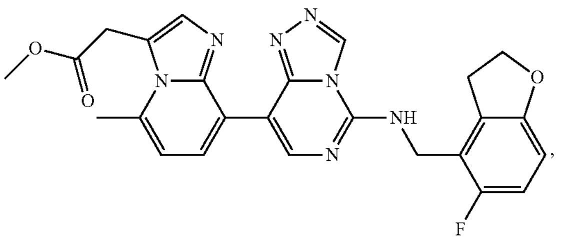
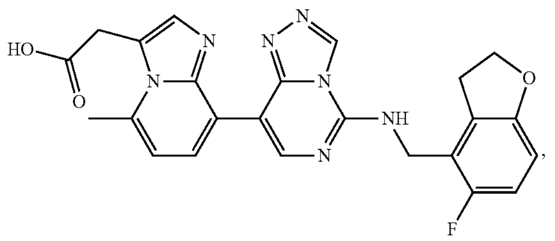
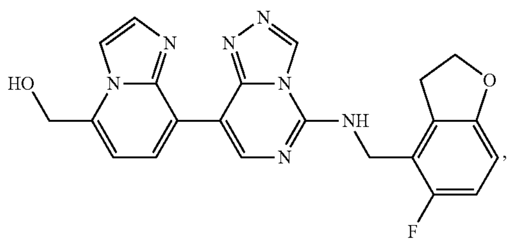
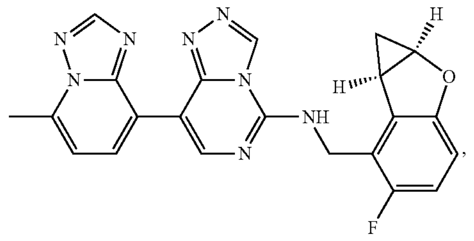
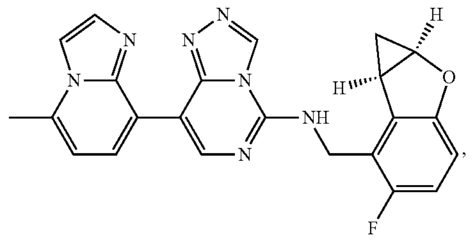
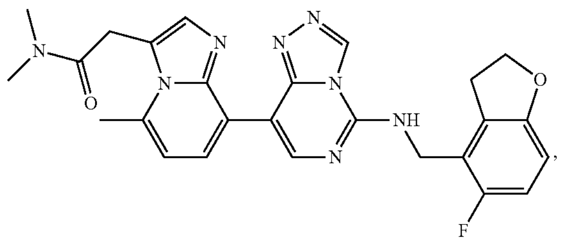
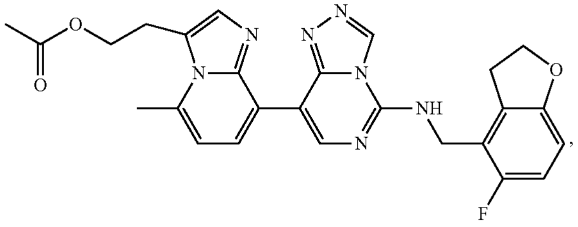

-continued
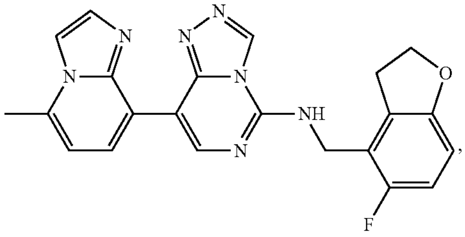
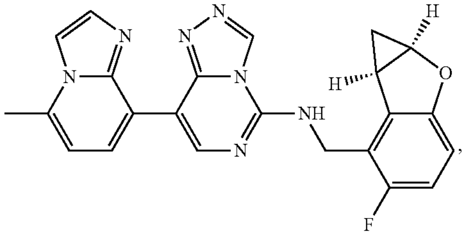
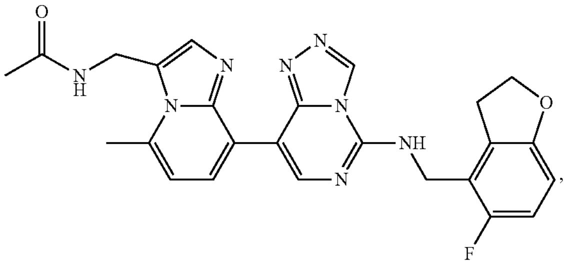
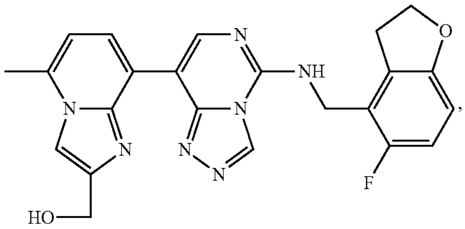
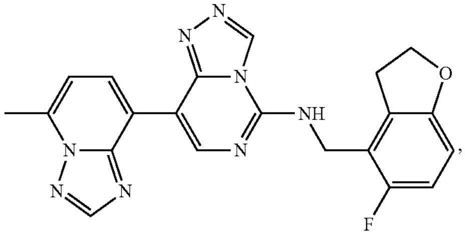
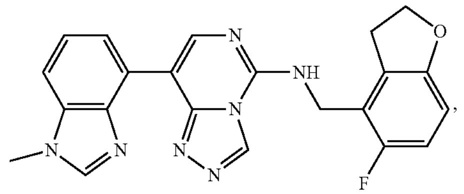
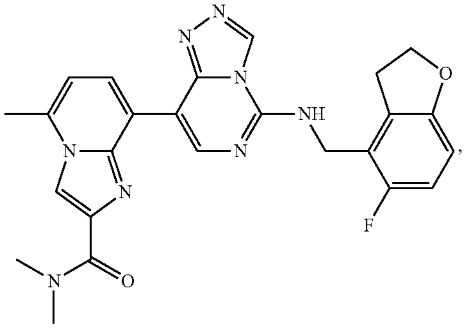
-continued
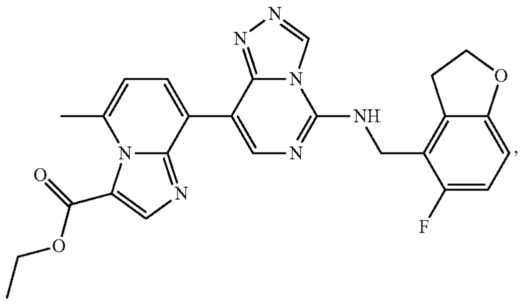
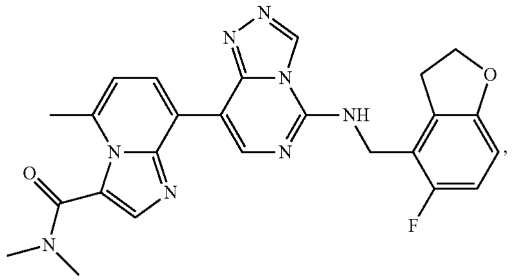
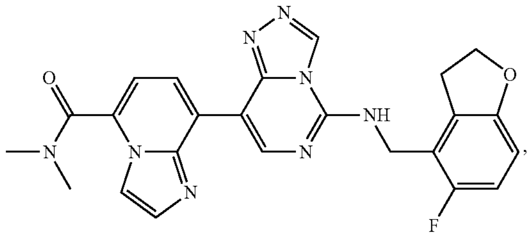
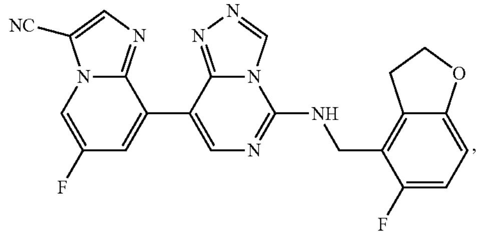
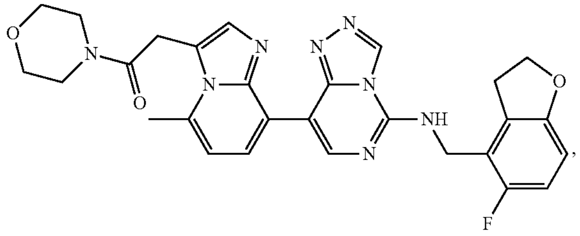
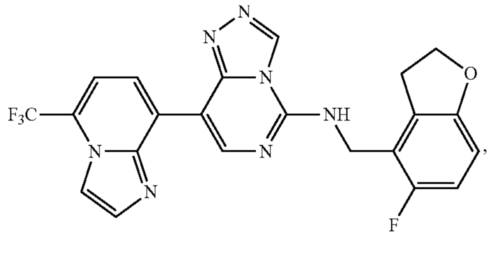

-continued
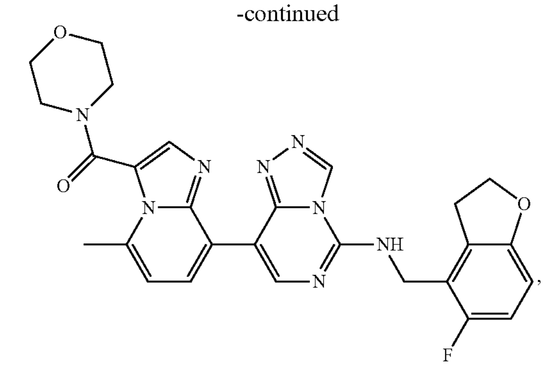
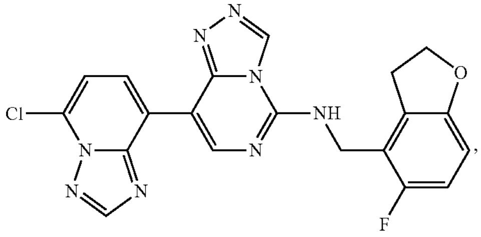
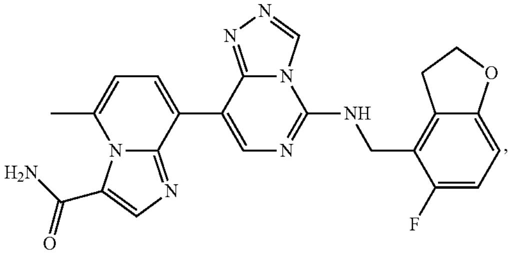
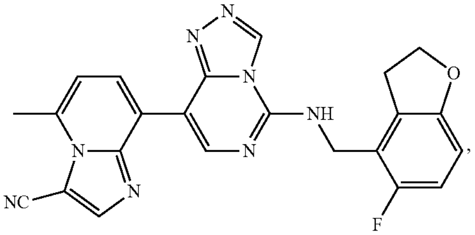
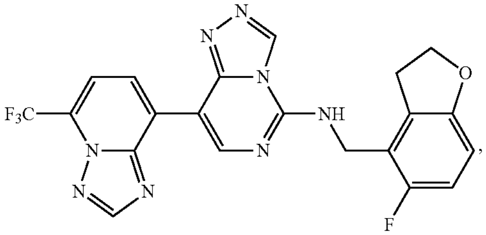
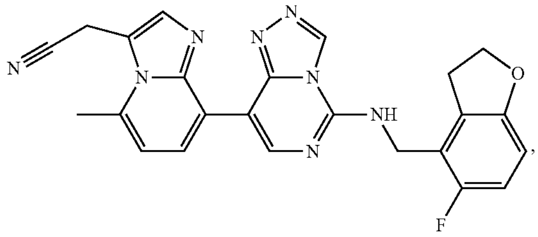
-continued
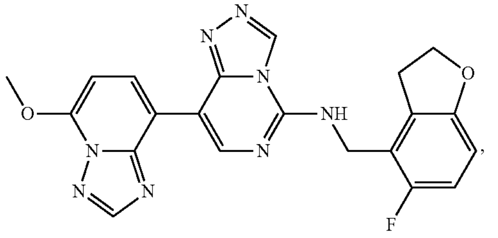
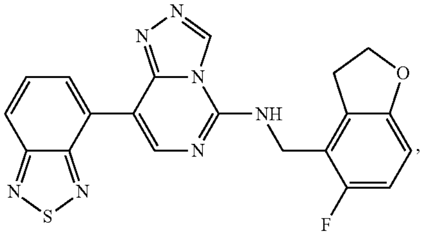
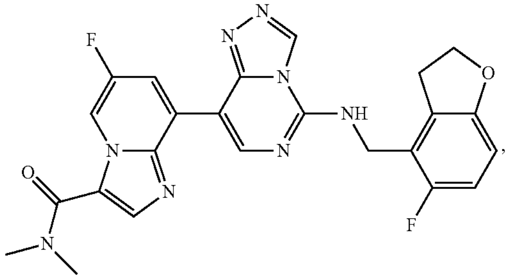
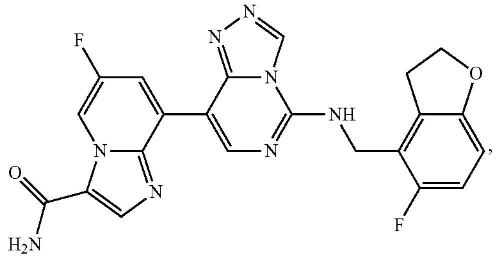
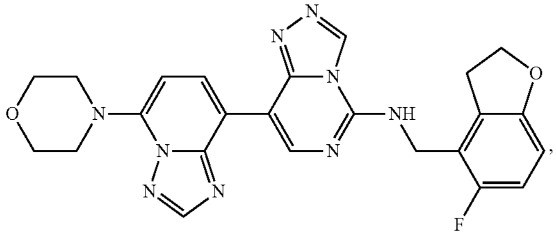
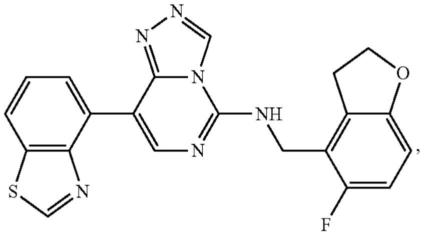
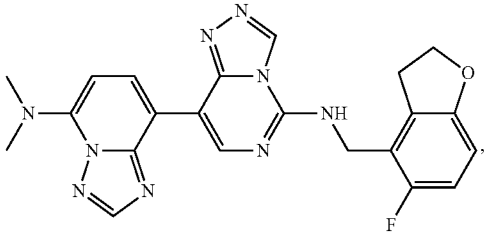

-continued
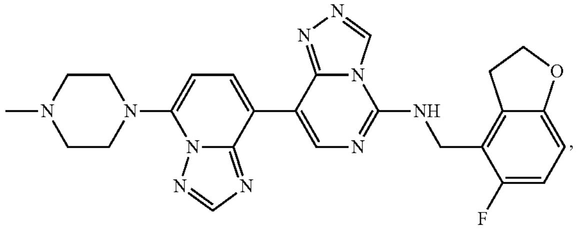
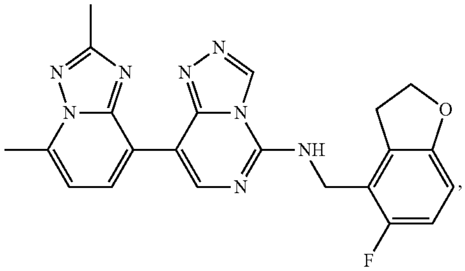
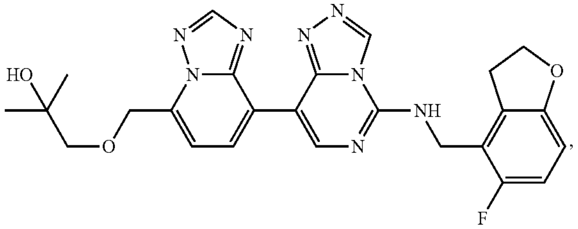
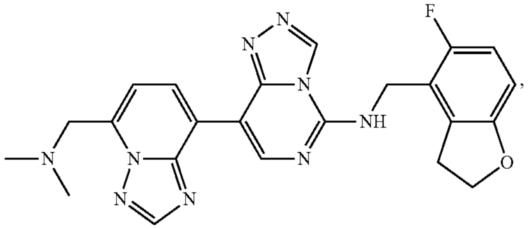
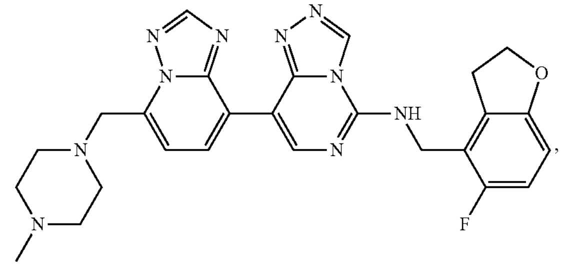
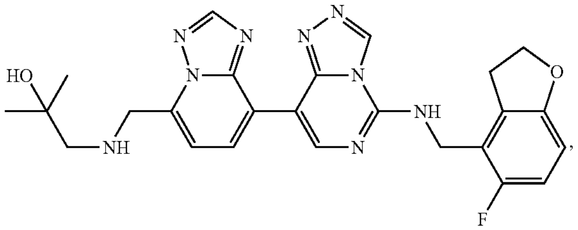
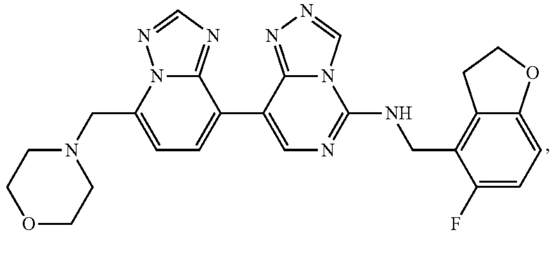
-continued
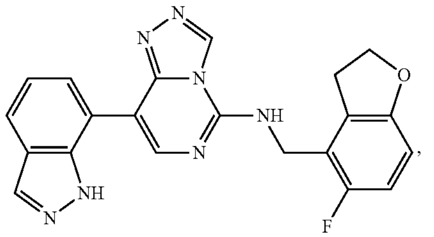
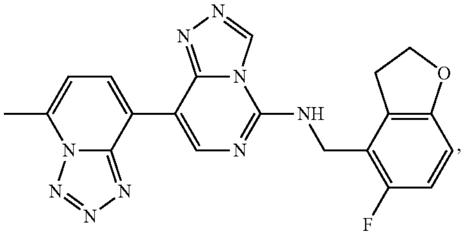
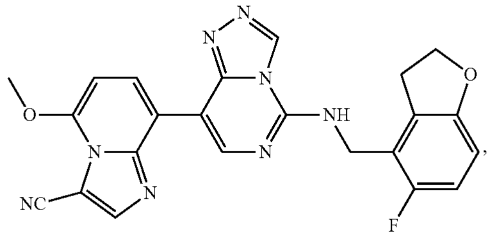
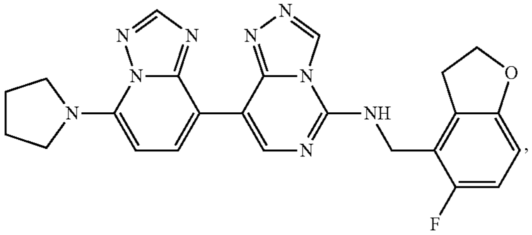
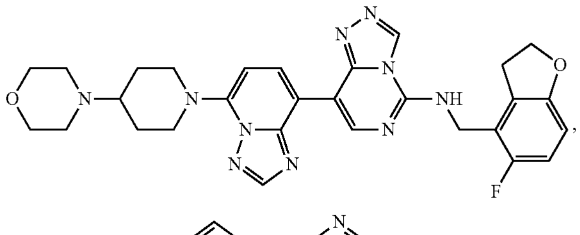
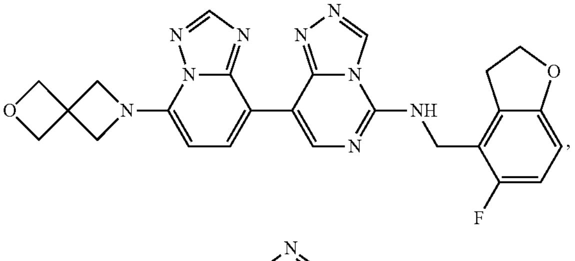
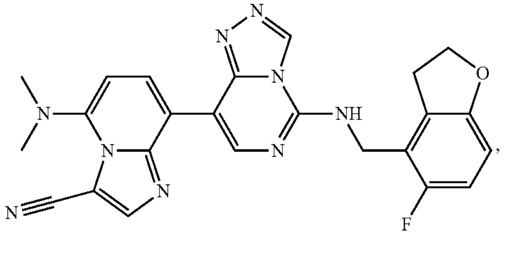

-continued
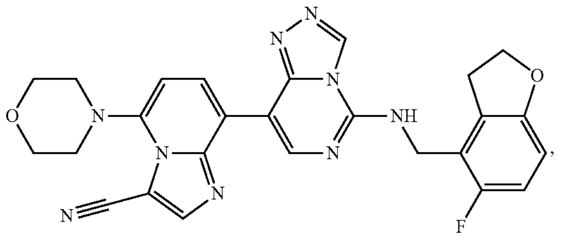
,
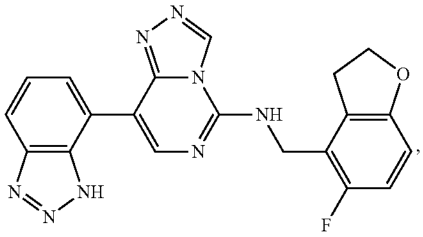
,
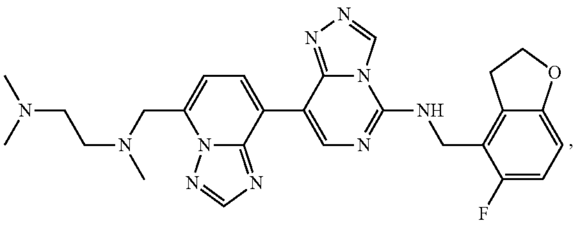
,
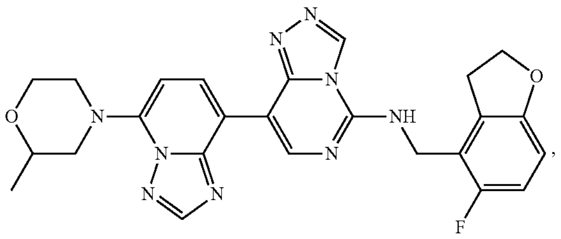
,
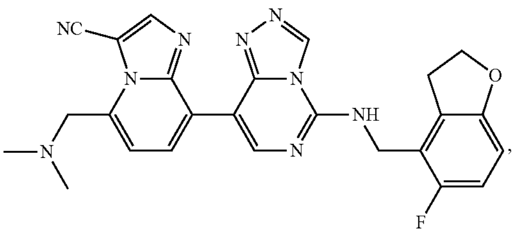
,
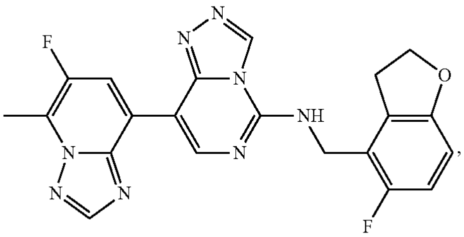
,
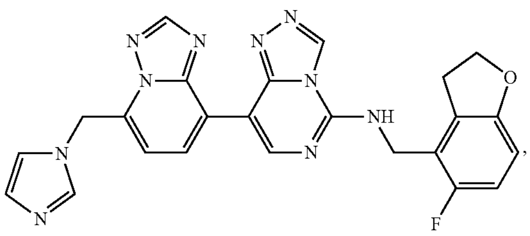
,
-continued
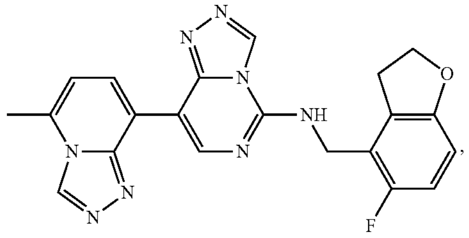
,
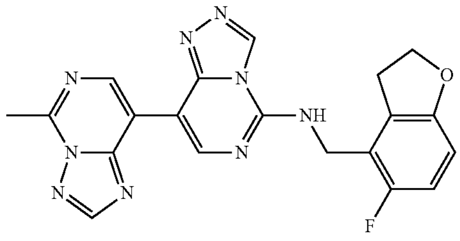
,
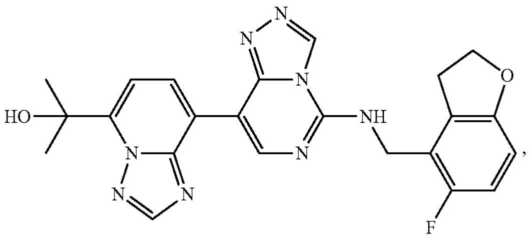
,
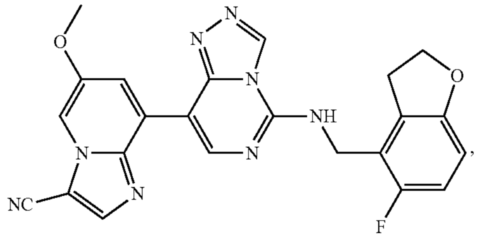
,
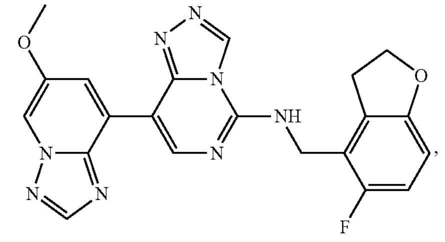
,
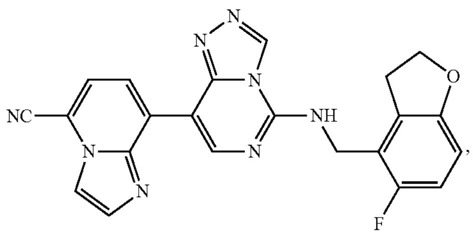
,
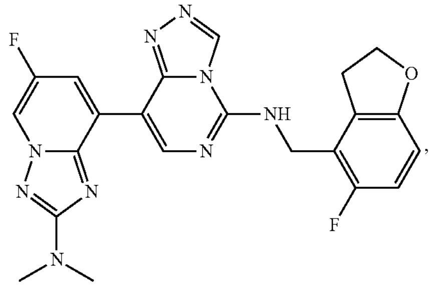
, -continued
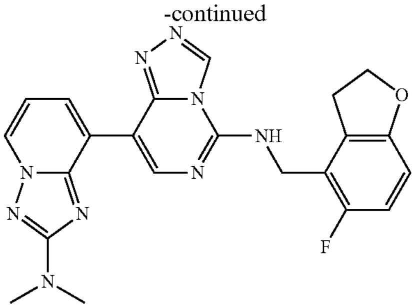
,
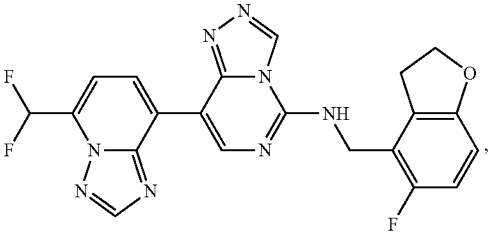
,
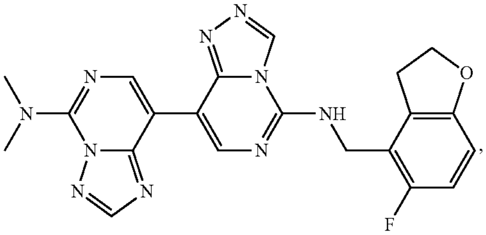
,
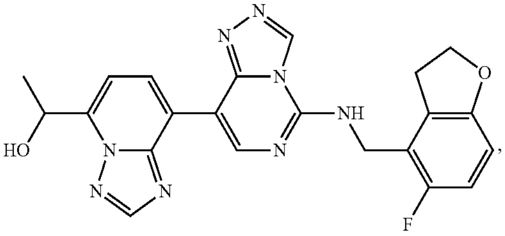
,
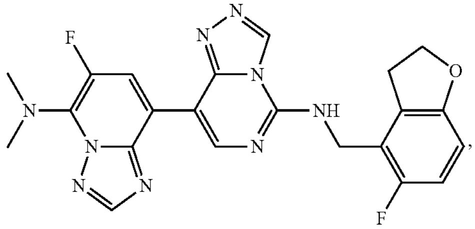
,
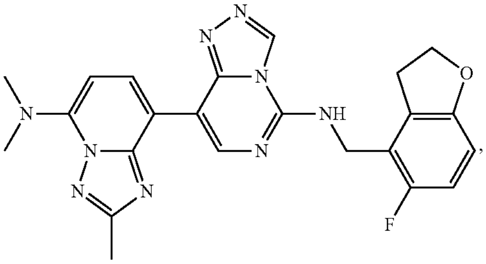
,
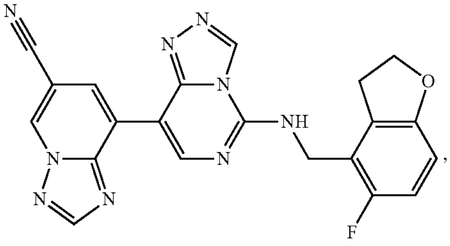
,
-continued
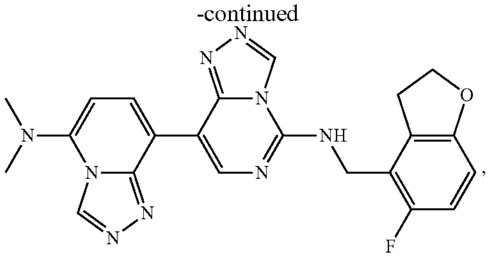
,
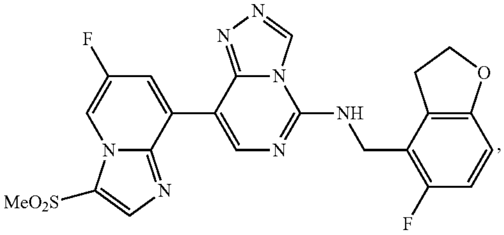
,
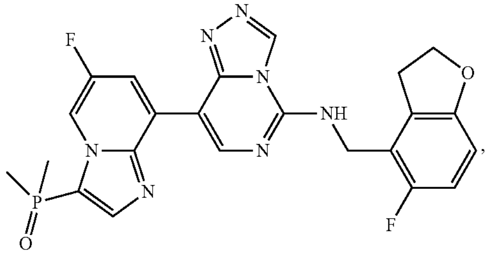
,
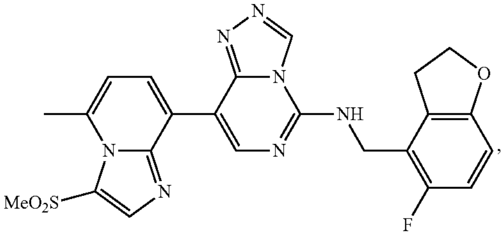
,
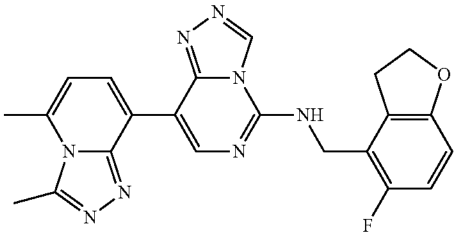
and
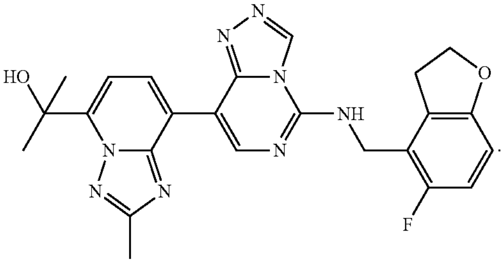
.
13. A method for preparing the compound as shown in formula (I) according to claim 1, comprising the step of:
subjecting halo intermediate $B_0$ and intermediate $E_0$ to a coupling reaction so as to obtain the compound as shown in formula (I),

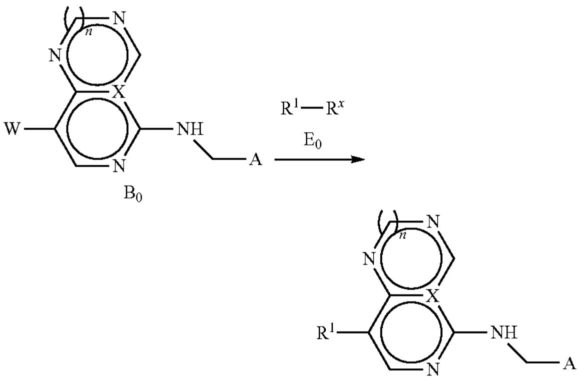

(I)

wherein W represents halogen; $R^x$ is —$B(OH)_2$ or

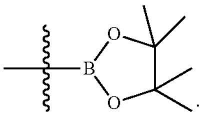 [SMILES: *B1OC(C)(C)C(C)(C)O1]

14. A method for preparing the compounds as shown in formulae I-A, (Ib) or (Ic), wherein the method for preparing the compound as shown in formula I-A includes the step of: subjecting halo intermediate compound B and intermediate $E_0$ to a coupling reaction as shown below so as to obtain the compound as shown in formula I-A;

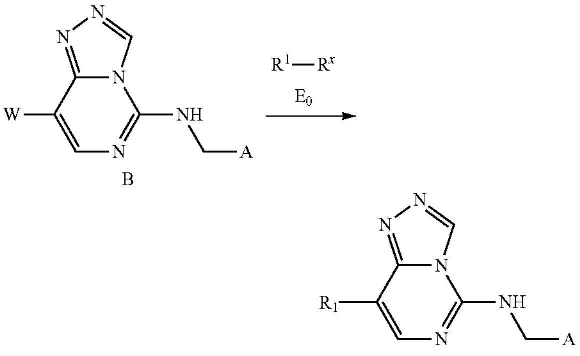

or, the method for preparing the compound as shown in formula (Ib) includes the step of: subjecting intermediate B-1 to a ring closure reaction as shown below so as to obtain the compound as shown in formula (Ib);

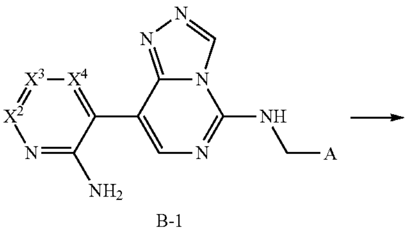

-continued

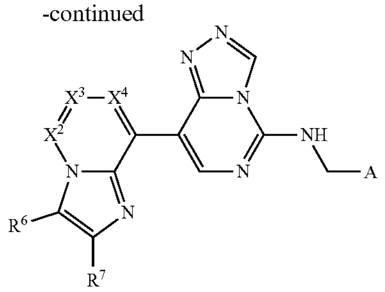

(Ib)

or, the method for preparing the compound as shown in formula (Ic) comprises the step of: subjecting halo intermediate compound B and intermediate $E_{01}$ to a coupling reaction as shown below so as to obtain the compound as shown in formula (Ic);

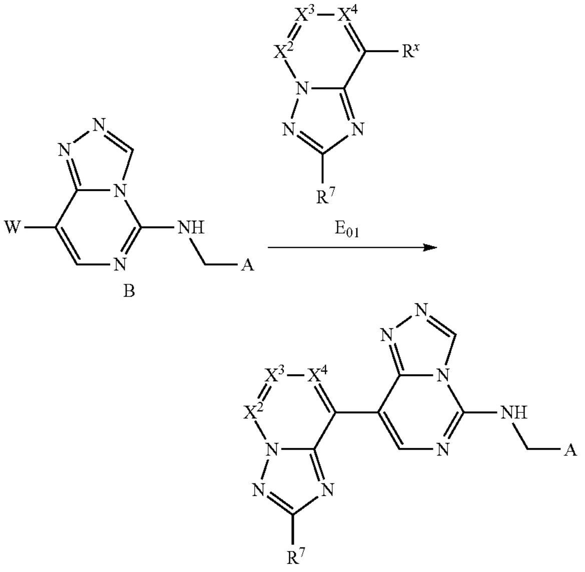

(Ic)

wherein in the compounds described above, W represents halogen; $R^x$ is —$B(OH)_2$ or

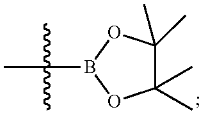 [SMILES: *B1OC(C)(C)C(C)(C)O1]

the definitions of A, $R^1$, $X^2$, $X^3$, $X^4$, $R^6$, and $R^7$ are according to claim 1.

15. A pharmaceutical composition, comprising the compound as shown in formula (I), the pharmaceutically acceptable salt, hydrate, stereoisomer thereof, or solvate thereof according to claim 1, and a pharmaceutically acceptable excipient.

16. A pharmaceutical preparation, comprising the compound as shown in formula (I), the pharmaceutically acceptable salt, hydrate, stereoisomer thereof, or solvate thereof according to claim 1, wherein the pharmaceutical preparation is in the form of tablets, capsules, pills, powders, granules, elixirs, tinctures, suspensions, syrups, emulsions, or solutions; the mode of administration of the pharmaceutical preparation is oral administration, sublingual administration, subcutaneous injection, intravenous injection, intramuscular injection, intrasternal injection, nasal administration, local topical administration, or rectal administration.

17. A method for treating cancer in a subject in need thereof, comprising: administrating the compound as shown in formula (I), the pharmaceutically acceptable salt, hydrate, stereoisomer, or solvate thereof according to claim 1 to the subject in need thereof; the compound as shown in formula (I), the pharmaceutically acceptable salt, hydrate, stereoisomer, or solvate thereof can be used alone or in combination with an additional drug; the additional drug is an anti-cancer drug, an immuno-oncology drug, an antiallergic drug, an antiemetic, an analgesic, or a cell protective drug; the cancer is B-cell non-Hodgkin lymphoma or malignant rhabdoid tumor.

18. The method according to claim 17, wherein the B-cell non-Hodgkin lymphoma is diffuse large B-cell lymphoma or follicular lymphoma.

* * * * *